United States Patent
Flohr et al.

(10) Patent No.: US 8,309,596 B2
(45) Date of Patent: Nov. 13, 2012

(54) KALLIKREIN 7 MODULATORS

(75) Inventors: Stefanie Flohr, Lörrach (DE); Stefan Andreas Randl, Basel (CH); Nils Ostermann, Binzen (DE); Ulrich Hassiepen, Lörrach (DE); Frederic Berst, Altkirch (FR); Ursula Bodendorf, Basel (CH); Bernd Gerhartz, Lörrach (DE); Andreas Marzinzik, Weil (DE); Claus Ehrhardt, Lörrach (DE); Josef Gottfried Meingassner, Vienna (AT)

(73) Assignee: Novartis AG, Basel (CH)

( * ) Notice: Subject to any disclaimer, the term of this patent is extended or adjusted under 35 U.S.C. 154(b) by 191 days.

(21) Appl. No.: 12/665,892

(22) PCT Filed: Jun. 26, 2008

(86) PCT No.: PCT/EP2008/058139
§ 371 (c)(1),
(2), (4) Date: Jun. 16, 2010

(87) PCT Pub. No.: WO2009/000878
PCT Pub. Date: Dec. 31, 2008

(65) Prior Publication Data
US 2010/0256144 A1  Oct. 7, 2010

(30) Foreign Application Priority Data

Jun. 28, 2007 (EP) .................... 07111316
Aug. 29, 2007 (EP) .................... 07115197

(51) Int. Cl.
| | |
|---|---|
| A61K 31/5377 | (2006.01) |
| A61K 31/496 | (2006.01) |
| A61K 31/454 | (2006.01) |
| A61K 31/437 | (2006.01) |
| A61K 31/4375 | (2006.01) |
| A61K 31/404 | (2006.01) |
| A61K 31/4035 | (2006.01) |
| A61K 31/403 | (2006.01) |
| A61K 31/4025 | (2006.01) |
| A61K 31/40 | (2006.01) |
| C07D 413/12 | (2006.01) |
| C07D 409/12 | (2006.01) |
| C07D 405/12 | (2006.01) |
| C07D 401/12 | (2006.01) |
| C07D 403/12 | (2006.01) |
| C07D 217/26 | (2006.01) |
| C07D 211/60 | (2006.01) |
| C07D 209/42 | (2006.01) |
| C07D 209/44 | (2006.01) |
| C07D 209/52 | (2006.01) |
| C07D 207/16 | (2006.01) |

(52) U.S. Cl. ... 514/423; 514/343; 514/326; 514/254.01; 514/235.5; 514/422; 514/318; 514/339; 514/412; 514/307; 514/354; 546/279.1; 546/208; 546/196; 546/245; 546/276.7; 546/278.1; 546/277.1; 546/146; 548/538; 548/525; 548/452; 544/372; 544/141

(58) Field of Classification Search .................. 514/343, 514/423, 326, 254.01, 235.5, 422, 318, 339, 514/412, 307, 354; 544/372, 141; 546/279.1, 546/208, 196, 245, 276.7, 278.1, 277.1, 146; 548/538, 525, 452
See application file for complete search history.

(56) References Cited

U.S. PATENT DOCUMENTS 3,905,870 A   9/1975 Kutzbach et al.

FOREIGN PATENT DOCUMENTS

| | | |
|---|---|---|
| DE | 3843226 A1 | 6/1990 |
| WO | 98/03537 A | 1/1998 |
| WO | 01/47886 A | 7/2001 |
| WO | WO 0147886 A1 * | 7/2001 |
| WO | WO 02/00651 A2 | 1/2002 |
| WO | WO 02/70510 A2 | 9/2002 |
| WO | WO 03/062392 A2 | 7/2003 |
| WO | WO 2004/058747 A1 | 7/2004 |
| WO | 2004/094372 A | 11/2004 |
| WO | 2004/110433 A | 12/2004 |
| WO | 2005/058817 A | 6/2005 |
| WO | WO 2005/075667 A1 | 8/2005 |
| WO | 2005/092849 A | 10/2005 |
| WO | WO 2006/010750 A1 | 2/2006 |

OTHER PUBLICATIONS

Wanner et al.; "Asymmetrische Synthesen mit chiralen 1,4-0xazin-2,5-dionen: Darstellung enantiomerenreiner 2-substituierter Pipecolinsaurederivate"; Liebigs Ann. Chem.; 477-484 (1993).
Debela, Mekdes et al: "Specificity Profiling of Seven Human Tissue Kallikreins Reveals Individual Subsite Preferences" Journal of Biological Chemistry 6, vol. 281, No. 35, 2006, pp. 25678-25688, XP002491508 p. 25680.
Diamandis, Eleftherios P. et al: "New nomenclature for the human tissue kallikrein gene family" Clinical Chemistry, vol. 46, No. 11, 2000, pp. 1855-1858, XP002491509.
Yousef, G. M. et al: "The KLK7 (PRSS6) gene, encoding for the stratum corneum chymotryptic enzyme is a new member of the human kalllikrein gene family—genomic characterization, mapping, tissue expression and hormonal regulation" Gene, vol. 254, No. 1,2, 2000, pp. 119-128, XP002491510.
Katz, Bradley A. et al: "Crystal structure of recombinant human tissue kallikrein at 2.0 .ANG. resolution" Protein Science, vol. 7, No. 4, 1998, pp. 875-885, XP002491511.

(Continued)

Primary Examiner — Joseph Kosack
Assistant Examiner — Matthew Coughlin
(74) Attorney, Agent, or Firm — John B. Alexander

(57) ABSTRACT

The present invention relates to the crystal structure of the serine protease kallikrein 7 and to the use of this crystal structure in drug discovery. The present invention also relates to compounds binding specifically to this active site of kallikrein 7.

6 Claims, No Drawings

OTHER PUBLICATIONS

Hansson, Lennart et al: "Cloning, expression, and characterization of stratum corneum chymotryptic enzyme. A skin-specific human serine proteinase" Journal of Biological Chemistry, vol. 269, No. 30, 1994, pp. 19420-19426, XP002491512.

Lesk, Arthur M. et al: "Conservation and variability in the structures of serine proteinases of the chymotrypsin family" Journal of Molecular Biology, vol. 258, No. 3, 1996, pp. 501-537, XP002491513.

Debela, Medes et al: "Chymotryptic specificity determinants i n the 1.O.ANG. structure of the zinc-inhibited human tissue kallikrein 7" Proceedings of the National Academy of Sciences of the United States of America, vol. 104, No. 41, 2007, pp. 16086-16091, XP002491514.

Fernandez, Israel S. et al: "Crystallization and preliminary crystallographic studies of human kallikrein 7, a serine protease of the multigene kallikrein family" Acta Cry Stallographica, Section F : Structural Biology and Crystallization Communications, vol. F63, No. 8, 2007, pp. 669-672, XP002491515.

Database CA [Online] Chemical Abstracts Service, Columbus, Ohio, US; Egorova, T. P. et al: "Amino acid composition, structural features, and substrate specificity of rabbit plasma kininogen" XP002491516 retrieved from STN Database accession No. 1975:402758 abstract & Biokhimiya (Moscow) , 40(1), 158-65 Coden: BIOHAO; ISSN: 0320-9725, 1975.

* cited by examiner

SEQUENCE LISTING

<160> NUMBER OF SEQ ID NOS: 1

<210> SEQ ID NO 1
<211> LENGTH: 43
<212> TYPE: DNA
<213> ORGANISM: Artificial
<220> FEATURE:
<223> OTHER INFORMATION: artificial primer

<400> SEQUENCE: 1
gactgcacga aggttcgcaa ggacttactg gaaaattcca tgc         43

KALLIKREIN 7 MODULATORS

This application is the National Stage of Application No. PCT/EP2008/058139, filed on Jun. 26, 2008, which claims benefit under 35 U.S.C. §119(a)-(d) or (f) or 365(b) of EP Application No. 07111316.1, filed Jun. 28, 2007, and EP Application No. 07115197.1, filed Aug. 29, 2007, the contents of which are incorporated herein by reference in their entirety.

FIELD OF THE INVENTION

The present invention relates to the crystal structure of the serine protease kallikrein 7 and to the use of this crystal structure in drug discovery. The present invention also relates to compounds binding specifically to this active site of kallikrein 7.

BACKGROUND OF THE INVENTION

Kallikrein 7 is a S1 serine protease of the kallikrein gene family displaying a chymotrypsin like activity. Human kallikrein 7 (hK7, KLK7 or stratum corneum chymotryptic enzyme (SCCE), Swissprot P49862) is mainly expressed in the skin and appears to play an important role in skin physiology (1, 2, 3). hK7 is involved in the degradation of the intercellular cohesive structure in cornified squamous epithelia in the process of desquamation. The desquamation process is well regulated and delicately balanced with the de novo production of corneocytes to maintain a constant thickness of the stratum corneum. In this regard, hK7 is reported to be able to cleave the corneodesmosomal proteins corneodesmosin and desmocollin 1 (4, 5, 6). In addition, recently it has been shown that the two lipid processing enzymes β-glucocerebrosidase and acidic sphingomyelinase can be degraded by hK7 (7). Both lipid processing enzymes are co-secreted with their substrates glucosylceramides and sphingomyelin and process these polar lipid precursors into their more non-polar products e.g. ceramides, which are subsequently incorporated into the extracellular lamellar membranes. The lamellar membrane architecture is critical for a functional skin barrier. Finally, hK7 has been shown to activate the pro-inflammatory cytokine Pro-interleukin-1β (IL-1β) (8) and to (in)activate cathelicidines (hCAP18) which regulate an important defense mechanism to prevent infections against a wide variety of microbial pathogens (34).

Recent studies link an increased activity of hK7 to inflammatory skin diseases like atopic dermatitis, psoriasis or Netherton's syndrome. An increased hK7 activity might lead to an uncontrolled degradation of corneodesmosomes resulting in a miss-regulated desquamation, an enhanced degradation of lipid processing enzymes resulting in a disturbed lamellar membrane architecture or an uncontrolled (in)activation of the pro-inflammatory cytokine IL-1β or the cathilicidin hCAP18. The net result could lead to an impaired skin barrier function and inflammation (see also WO-A-2004/108139).

The hK7 activity is controlled on several levels. Various factors might be responsible for an increased hK7 activity in inflammatory skin diseases. Firstly, the amount of protease being expressed might be influenced by genetic factors. Such a genetic link, a polymorphism in the 3'-UTR in the hK7 gene, was recently described (9). The authors hypothesis that the described 4 base pair insertion in the 3'-UTR of the kallikrein 7 gene stabilizes the hK7 mRNA and results in an overexpression of hK7. Secondly, since hK7 is secreted via lamellar bodies to the stratum corneum extracellular space as zymogen and it is not able to autoactivate, it needs to be activated by another protease e.g. kallikrein 5 (5). Uncontrolled activity of such an activating enzyme might result in an overactivation of hK7. Thirdly, activated hK7 can be inhibited by natural inhibitors like LEKTI, ALP or elafin (10, 11). The decreased expression or the lack of such inhibitors might result in an enhanced activity of hK7. Recently it was found, that mutations in the spink5 gene, coding for LEKTI, are causative for Netherton's syndrome (12) and a single point mutation in the gene is linked to atopic dermatitis (13, 14). Finally, another level of controlling the activity of hK7 is the pH. hK7 has a neutral to slightly alkaline pH optimum (2) and there is a pH gradient from neutral to acidic from the innermost to the outermost layers in the skin. Environmental factors like soap might result in a pH increase in the outermost layers of the stratum corneum towards the pH optimum of hK7 thereby increasing the hK7 activity.

The hypothesis that an increased activity of hK7 is linked to inflammatory skin diseases is supported by the following studies: Firstly, Netherton's syndrome patients show a phenotype dependent increase in serine protease activity, a decrease in corneodesmosomes, a decrease in the lipid processing enzymes β-glucocerebrosidase and acidic sphingomyelinase, and an impaired barrier function (15, 16). Secondly, a transgenic mice overexpressing human kallikrein 7 shows a skin phenotype similar to that found in patients with atopic dermatitis (17, 18, 19). Thirdly, in the skin of atopic dermatitis and psoriasis patients elevated levels of hK7 were described (17, 20).

Therefore, hK7 is considered to be a potential target for the treatment of inflammatory skin diseases like atopic dermatitis, psoriasis or Netherton's syndrome and there is a need for specific modulators (agonists or inhibitors) thereof.

In order to fulfill this need, the present inventors have developed methods for cloning, expression, purification and crystallization of hK7, and have been able to obtain for the first time the structure of human kallikrein 7 at a very high resolution.

This structure of human kallikrein 7 at a very high resolution has allowed for the identification of the active site of the enzyme, and compounds binding specifically to said active site of kallikrein 7.

SUMMARY OF THE INVENTION

In order to fulfill the needs identified herein-above, the present inventors have developed methods for cloning, expression, purification and crystallization of hK7, and have been able to obtain for the first time the structure of human kallikrein 7 at a very high resolution. The obtained structure of human kallikrein 7 at a very high resolution has allowed to identify the active site of the enzyme and compounds binding specifically to said active site of kallikrein 7. The present inventors have furthermore been able to confirm that these compounds have a modulatory effect on kallikrein 7.

The present invention thus pertains to a crystal of human kallikrein 7 comprising the binding pocket having a three-dimensional structure characterized by the structure coordinates of Table 3 below. This crystal can also comprise a co-crystallised ligand.

The present invention also pertains to a computer readable medium comprising data storage material encoded with computer readable data wherein said data comprises the structure coordinates of a crystal according to the invention, and to the use of this crystal for the generation of crystal structure data.

Another embodiment of the present invention is a method of identifying a ligand that binds to kallikrein 7, this method comprising the steps of (i) using the three dimensional structure data generated according to the invention to select and/or design a potential ligand that binds to kallikrein 7, and (ii) identifying among the potential ligand selected in step (i), those ligands that bind to kallikrein 7 in an in vitro, in vivo or cell-based assay.

Yet another embodiment of the present invention relates to a modulator of kallikrein 7 characterised in that it binds in the binding pocket having a three-dimensional structure characterized by the structure coordinates of Table 3. This modulator of kallikrein 7 can be a compound of formula

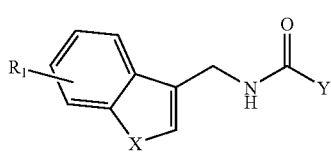

(I)

wherein
$R_1$ is hydrogen, cyano, $(C_{1-8})$alkyl, $(C_{2-8})$alkenyl, $(C_{2-8})$alkynyl, halogen, $(C_{1-8})$alkylamino, $(C_{1-8})$alkylamino$(C_{1-8})$alkyl, $(C_{1-8})$alkoxy, halo$(C_{1-8})$alkyl,
X is CH=CH, NH, N=CH, O or S,
Y is a group of formula

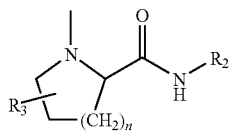

(II)

wherein
the N-containing ring system is optionally annelated with $(C_{3-8})$cycloalkyl, $(C_{6-18})$aryl or heterocyclyl having 5 to 6 ring members and 1 to 4 heteroatoms selected from N, O, S,
n is 1, 2 or 3,
$R_2$ is
$(C_{1-8})$alkyl, $(C_{1-8})$alkylamino, $(C_{1-8})$alkylamino$(C_{1-8})$alkyl, di$(C_{1-8})$alkylamino$(C_{1-8})$alkyl, halo$(C_{1-8})$alkyl, $(C_{1-8})$alkoxy, $(C_{1-8})$alkoxy$(C_{1-8})$alkyl, or
$(CH_2)_m$—Z, wherein Z is unsubstituted or substituted $(C_{3-8})$cycloalkyl, $(C_{6-18})$aryl or heterocyclyl having 5 to 6 ring members and 1 to 4 heteroatoms selected from N, O, S and m is 0, 1 or 2,
$R_3$ is hydrogen, $(C_{1-8})$alkyl, $(C_{1-8})$alkoxy, $(C_{6-18})$aryl or heterocyclyl having 5 to 6 ring members and 1 to 4 heteroatoms selected from N, O, S.

In particular, this modulator can be a compound, wherein $R_1$ is hydrogen, ethynyl, chloro or bromo,
X is CH=CH or S,
Y is a group of formula (II), wherein
the N-containing ring system is optionally annelated with cyclopropyl, cyclopentyl or phenyl,
n is 1 or 2,
$R_2$ is $(C_{1-8})$alkyl, $(C_{1-4})$alkylamino, di$(C_{1-4})$alkylamino$(C_{1-4})$alkyl, $(C_{1-4})$alkoxy, $(C_{1-4})$alkoxy$(C_{1-4})$alkyl or a group $(CH_2)_m$—Z, wherein Z is unsubstituted cyclohexyl, unsubstituted phenyl, phenyl substituted by $(C_{1-4})$alkoxy, phenyl substituted by heterocyclyl having 6 ring members and 1 or 2 heteroatoms selected from N, O, or unsubstituted or substituted heterocyclyl having 6 ring members and 1 or 2 heteroatoms selected from N, O;
m is 1 or 2,
$R_3$ is hydrogen or $(C_{1-4})$alkoxy.

In another embodiment of such a modulator, Y can be a group of formula (II), wherein
the N-containing ring system is optionally annelated with cyclopropyl, cyclopentyl or phenyl,
$R_2$ is methyl, dimethylaminoethyl, methoxyethyl, or a group $(CH_2)_m$—Z, wherein Z is unsubstituted cyclohexyl, unsubstituted phenyl, phenyl substituted by methoxy, piperazinyl or morpholinyl;
pyridinyl, piperidinyl, tetrahydrofuranyl, unsubstituted piperazinyl or piperazinyl substituted by methyl or phenyl,
and m, n, $R_1$, $R_3$ and X are as defined above.

The compounds of the invention can be in the form of a salt and/or for use as a pharmaceutical. The present invention hence also relates to a pharmaceutical composition comprising a compound as described herein-above in association with at least one pharmaceutical excipient, and to a method of treating disorders mediated by kallikrein-7 activity, which treatment comprises administering to a subject in need of such treatment an effective amount of a compound of the invention.

According to the present invention, a disorder which is mediated by kallikrein-7 activity can be selected from the group consisting of inflammatory and/or hyperproliferative and pruritic skin diseases such as keloids, hypertrophic scars, acne, atopic dermatitis, psoriasis, pustular psoriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer.

DETAILED DESCRIPTION OF THE INVENTION

List of Abbreviations

| Abbreviation | Description |
|---|---|
| DMSO | dimethylsulfoxide |
| hK7 | human kallikrein 7 |
| UTR | untranslated region |
| LEKTI | lympho-epithelial Kazal-type related inhibitor |
| Spink5 | serine protease inhibitor Kazal-type 5 |
| ALP | antileukoprotease |
| HPLC | high performance liquid chromatography |
| GluHCl | glucosamine hydrochloride |
| pro-hK7 | pro-human kallikrein 7 |
| PEG | polyethylene glycol |
| SDS | sodium dodecyl sulfate |
| Tris | tris-(hydroxymethyl)-amino methane |
| IPTG | isopropyl-β-D-thiogalactoside |
| GSH | Glutathion or γ-L-Glutamyl-L-cysteinylglycin |
| GSSH | oxidized form of glutathion |
| EDTA | ethylenediaminetetraacitic acid |
| DMSO | dimethylsulfoxide |
| HCl | hydrochloric acid |
| SLS | Swiss Light Source |
| a.u. | asymmetric unit |
| DTT | D,L-dithiothreitol |

Kallikrein 7 is a S1 serine protease of the kallikrein gene family displaying a chymotrypsin like activity. Human kallikrein 7 (hK7, KLK7 or stratum corneum chymotryptic enzyme (SCCE), Swissprot P49862) plays an important role in skin physiology (1, 2, 3).

The present invention provides a crystal of human kallikrein 7 comprising the binding pocket having a three-dimensional structure characterized by the structure coordinates of Table 3 below. The present invention also provides to a computer readable medium comprising data storage material encoded with computer readable data wherein said data comprises the structure coordinates of a crystal according to the invention, and the use of this crystal for the generation of crystal structure data. Moreover, the present invention provides a method of identifying a ligand that binds to kallikrein 7, this method comprising the steps of (i) using the three dimensional structure data generated according to the invention to select and/or design a potential ligand that binds to kallikrein 7, and (ii) identifying among the potential ligand selected in step (i), those ligands that bind to kallikrein 7 in an in vitro, in vivo or cell-based assay. Modulator of kallikrein 7 according to the present invention are characterised in that it binds in the binding pocket having a three-dimensional structure characterized by the structure coordinates of Table 3 and can be a compound of formula

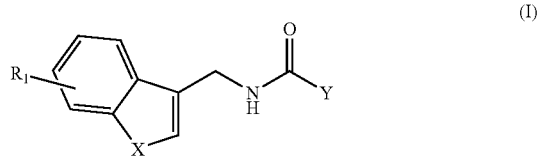

(I)

wherein
R$_1$ is hydrogen, cyano, (C$_{1-8}$)alkyl, (C$_{2-8}$)alkenyl, (C$_{2-8}$)alkynyl, halogen, (C$_{1-8}$)alkylamino, (C$_{1-8}$)alkylamino (C$_{1-8}$)alkyl, (C$_{1-8}$)alkoxy, halo(C$_{1-8}$)alkyl,
X is CH=CH, NH, N=CH, O or S,
Y is a group of formula

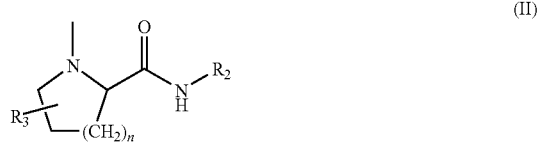

(II)

wherein
the N-containing ring system is optionally annelated with (C$_{3-8}$)cycloalkyl, (C$_{6-18}$)aryl or heterocyclyl having 5 to 6 ring members and 1 to 4 heteroatoms selected from N, O, S,
n is 1, 2 or 3,
R$_2$ is
(C$_{1-8}$)alkyl, (C$_{1-8}$)alkylamino, (C$_{1-8}$)alkylamino (C$_{1-8}$)alkyl, di(C$_{1-8}$)alkylamino(C$_{1-8}$)alkyl, halo (C$_{1-8}$)alkyl, (C$_{1-8}$)alkoxy, (C$_{1-8}$)alkoxy(C$_{1-8}$) alkyl, or
(CH$_2$)$_m$—Z, wherein Z is unsubstituted or substituted (C$_{3-8}$)cycloalkyl, (C$_{6-18}$)aryl or heterocyclyl having 5 to 6 ring members and 1 to 4 heteroatoms selected from N, O, S and m is 0, 1 or 2,
R$_3$ is hydrogen, (C$_{1-8}$)alkyl, (C$_{1-8}$)alkoxy, (C$_{6-18}$)aryl or heterocyclyl having 5 to 6 ring members and 1 to 4 heteroatoms selected from N, O, S.

The crystals according to the invention preferably belong to the orthorhombic space group P2$_1$2$_1$2$_1$ (triclinic). The crystals have 1 molecule per asymmetric unit.

Depending on the conditions used for crystallization, the parameters characterising the unit cell may vary with a limited range, at least within the range of the resolution. The resolution of the X-ray crystallography is typically ≦5 Ångstroms and by means of the purification method described therein, it is possible to provide crystals of such high internal order that a resolution of ≦2 Å can be achieved.

The term "unit cell" refers to the basic shape block. The entire volume of a crystal may be constructed by regular assembly of such blocks. Each unit cell comprises a complete representation of the unit of pattern, the repetition of which builds up the crystal.

The term "space group" according to the invention refers to the arrangement of symmetry elements of a crystal.

The term "structure coordinates" or "atomic coordinates" refers to mathematical coordinates derived from the mathematical equations related to the pattern obtained on diffraction of a monochromatic beam of X-rays by the atoms (scattering centers) of a crystal comprising hK7. The diffraction data are used to calculate an electron density map of the repeating unit of the crystal. The electron density maps are used to establish the positions of the individual atoms within the unit cell of the crystal. The structure coordinates of hK7 can be found in Table 3.

A "fragment" of Kallikrein 7 comprises more than 50% consecutive amino acids of the sequence of the Kallikrein 7.

As used herein, a "homologue" of that sequence shares at least 70% identity, preferably 80% identity, more preferably 90%, and even more preferably 95% identity with the corresponding sequence when performing optimal alignment. Optimal alignment of sequences for determining a comparison window may be conducted by the local homology algorithm of Smith and Waterman (*J. Theor. Biol.*, 91 (2) pgs. 370-380 (1981), by the homology alignment algorithm of Needleman and Wunsch, *J. Miol. Biol.*, 48(3) pgs. 443-453 (1972), by the search for similarity via the method of Pearson and Lipman, *PNAS, USA*, 85(5) pgs. 2444-2448 (1988) or by computerized implementations of these algorithms (GAP, BESTFIT, FASTA and TFASTA in the Wisconsin Genetics Software Package Release 7.0, Genetic Computer Group, 575, Science Drive, Madison, Wis.).

The best alignment (i.e., resulting in the highest percentage of identity over the comparison window) generated by the various methods is selected for determining percentage identity.

The terms "ligand" or "modulator", which are used interchangeably herein, refers to a molecule or group of molecules that bind to one or more specific sites of Kallikrein 7. A ligand according to the invention can be an agonist or an antagonist. In addition, ligands according to the invention are preferably low molecular weight molecules.

The term "low molecular weight molecules" according to the invention refers to preferably organic compounds generally having a molecular weight less than about 1000, more preferably less than about 500.

More preferably, said ligand inhibits kallikrein 7 biological activity. A compound is considered as an kallikrein 7 inhibitor if it has an IC$_{50}$ ranging from 0.001 nM to 1.0 μM.

Preferred modulators are organic compounds, e.g. 1,2-dicarboxylic acid amides of an N-containing ring system, such as e.g. pyrrolidine, e.g. which are antagonists of Kallikrein-7 activity.

In one aspect the present invention is a compound of formula

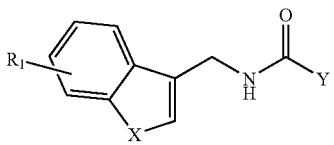

(I)

wherein
R$_1$ is hydrogen, cyano, alkyl, alkenyl, alkynyl, halogen, alkylamino, alkylaminoalkyl, alkoxy, haloalkyl,
X is CH=CH, NH, N=CH, O or S,
Y is a group of formula

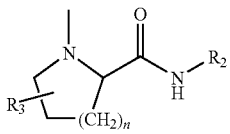

(II)

wherein
the N-containing ring system is optionally annelated with cycloalkyl, aryl or heterocyclyl having 5 to 6 ring members and 1 to 4 heteroatoms selected from N, O, S,
n is 1, 2 or 3,
R$_2$ is
  alkyl, alkylamino, alkylaminoalkyl, dialkylaminoalkyl, haloalkyl, alkoxy, alkoxyalkyl,
or
  (CH$_2$)$_m$—Z, wherein Z is unsubstituted or substituted cycloalkyl, aryl or heterocyclyl having 5 to 6 ring members and 1 to 4 heteroatoms selected from N, O, S and m is 0, 1 or 2,
R$_3$ is hydrogen, alkyl, alkoxy, aryl or heterocyclyl having 5 to 6 ring members and 1 to 4 heteroatoms selected from N, O, S.

Any group (substituent) defined herein may comprise 1 to 18 carbon atoms, for example
  alkyl e.g. includes (C1-12)alkyl, such as (C1-4)alkyl, e.g. methyl, ethyl, propyl, isopropyl, n-butyl, tert-butyl, sec-butyl, n-pentyl, neopentyl, n-hexyl;
  alkenyl e.g. includes (C2-12)alkenyl, such as ethenyl, propenyl, butenyl, 1-methyl-2-buten-1-yl, alkadienes and the like;
  alkynyl e.g. includes (C2-12)alkynyl, such as ethynyl;
  cycloalkyl e.g. includes (C3-12)cycloalkyl, such as cyclopropyl, cyclobutyl, cyclopentyl, cyclohexyl;
  alkoxy e.g. includes (C1-12)alkoxy, such as methoxy, ethoxy;
  aryl includes (C6-18)aryl, e.g. phenyl, naphtyl;
  aliphatic heterocyclyl and aromatic heterocyclyl;
  heterocyclyl having 1 to 4 heteroatoms selected from N, O, S; such as heterocyclyl having
    1 to 2 heteroatoms selected from N, O, e.g. including
    pyridinyl, e.g. pyridin-3-yl, pyridin-4-yl;
    piperidinyl, e.g. piperidin-4-yl;
    piperazinyl, e.g. piperazin-1-yl;
    morpholinyl, e.g. morpholin-4-yl;
    tetrahydrofuranyl, e.g. tetrahydrofuran-2-yl;
  halogen includes F, Cl, Br, I, such as chloro, bromo;

Any group defined herein may be unsubstituted or substituted, e.g. one or morefold.
Substituents include e.g. methyl, methoxy, ethynyl, chloro, bromo.

Alkyl, alkenyl, alkynyl, aryl and heterocyclyl include unsubstituted or substituted alkyl, aryl or heterocyclyl, e.g. substituted by groups which are conventional in organic chemistry.

In one aspect the present invention is a compound of formula (I) as defined above, wherein
R$_1$ is hydrogen, cyano, (C$_{1-8}$)alkyl, (C$_{2-8}$)alkenyl, (C$_{2-8}$)alkynyl or halogen
X is CH=CH, NH, N=CH, O or S,
Y is a group of formula

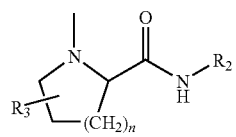

(II)

wherein
the N-containing ring system is optionally annelated with (C$_{3-8}$)cycloalkyl, (C$_{6-18}$)aryl or heterocyclyl having 5 to 6 ring members and 1 to 2 heteroatoms selected from N, O, S,
n is 1, 2 or 3,
R$_2$ is
  (C$_{1-8}$)alkyl, (C$_{1-8}$)alkylamino, (C$_{1-8}$)alkylamino(C$_{1-8}$)alkyl, di(C$_{1-8}$)alkylamino(C$_{1-8}$)alkyl, (C$_{1-8}$)alkoxy, (C$_{1-8}$)alkoxy(C$_{1-8}$)alkyl, or
  (CH$_2$)$_m$—Z, wherein Z is unsubstituted or substituted (C$_{3-8}$)cycloalkyl, (C$_{6-18}$)aryl or heterocyclyl having 5 to 6 ring members and 1 to 2 heteroatoms selected from N, O, S and m is 1 or 2,
R$_3$ is hydrogen, (C$_{1-8}$)alkyl or (C$_{1-8}$)alkoxy.

In one aspect the present invention is a compound of formula (I), wherein
R$_1$ is hydrogen, ethynyl, chloro or bromo,
X is CH=CH or S,
Y is a group of formula (II), wherein
  the N-containing ring system is optionally annelated with cyclopropyl, cyclopentyl or phenyl,
  n is 1 or 2,
  R$_2$ is (C$_{1-8}$)alkyl, (C$_{1-4}$)alkylamino, di(C$_{1-4}$)alkylamino(C$_{1-4}$)alkyl, (C$_{1-4}$)alkoxy, (C$_{1-4}$)alkoxy(C$_{1-4}$)alkyl or
    a group (CH$_2$)$_m$—Z, wherein Z is unsubstituted cyclohexyl, unsubstituted phenyl, phenyl substituted by (C$_{1-4}$)alkoxy, phenyl substituted by heterocyclyl having 6 ring members and 1 or 2 heteroatoms selected from N, O, or
  unsubstituted or substituted heterocyclyl having 6 ring members and 1 or 2 heteroatoms selected from N, O;
  m is 1 or 2,
  R$_3$ is hydrogen or (C$_{1-4}$)alkoxy.

In one aspect the present invention is a compound of formula (I) and Y is a group of formula (II), wherein
  the N-containing ring system is optionally annelated with cyclopropyl, cyclopentyl or phenyl,
  R$_2$ is methyl, dimethylaminoethyl, methoxyethyl, or a group (CH$_2$)$_m$—Z, wherein Z is unsubstituted cyclohexyl, unsubstituted phenyl, phenyl substituted by methoxy, piperazinyl or morpholinyl;
  pyridinyl, piperidinyl, tetrahydrofuranyl, unsubstituted piperazinyl or piperazinyl substituted by methyl or phenyl,
and m, n, R$_1$, R$_3$ and X are as defined above.

In one aspect the present invention is a compound of formula (I), wherein
X is CH=CH,
$R_1$ is ethynyl or chloro,
Y is a group of formula (II), wherein
n is 1,
$R_3$ is hydrogen,
$R_2$ is methyl, methoxyethyl, dimethylaminoethyl, pyridin-3-ylmethyl, pyridin-4-ylmethyl, pyridin-3-yl-ethyl, pyridin-4-yl-ethyl, 6-methoxy-pyridin-3-ylmethyl, (4-methoxy-phenyl)-ethyl, (4-methyl-piperazin-1-yl)ethyl, (4-benzyl-piperazin-1-yl)ethyl, 4-(4-methyl-piperazin-1-yl)-benzyl, 1-methyl-piperidin-4-ylmethyl, 2-(4-morpholin-4-ylmethyl)-benzyl.

In one aspect the present invention is a compound of formula (I), wherein
X is CH=CH,
$R_1$ is hydrogen,
Y is a group of formula (II), wherein
The N-containing ring system is optionally annelated with phenyl,
$R_3$ is hydrogen or phenyl,
n is 1 or 2,
$R_2$ is benzyl, phenethyl, cyclohexylmethyl, (4-methoxy-phenyl)-ethyl, 3-methyl-butyl, tetrahydrofuran-2-ylmethyl.

In one aspect the present invention is a compound of formula (I), wherein
X is CH=CH,
$R_1$ is ethynyl,
Y is a group of formula (II), wherein
The N-containing ring system is optionally annelated with cyclopropyl, cyclopentyl, phenyl,
$R_3$ is hydrogen,
n is 1,
$R_2$ is pyridin-3-ylmethyl.

In one aspect the present invention is a compound of formula (I), wherein
X is CH=CH
$R_1$ is ethynyl,
Y is a group of formula (II), wherein
$R_3$ is methoxy,
n is 1,
$R_2$ is pyridin-3-ylmethyl.

In one aspect the present invention is a compound of formula (I), wherein
X is CH=CH
$R_1$ is ethynyl,
Y is a group of formula (II), wherein
$R_3$ is hydrogen,
n is 2,
$R_2$ is pyridin-3-ylmethyl.

In one aspect the present invention is a compound of formula (I), wherein
X is S
$R_1$ is chloro or bromo,
Y is a group of formula (II), wherein
$R_3$ is hydrogen,
n is 1,
$R_2$ is (4-methoxy-phenyl)-ethyl.

In a compound of formula I each single defined substitutent may be a preferred substituent, e.g. independently of each other substitutent defined.

In another aspect the present invention provides a compound of formula I, selected from the group consisting of
(S)-Pyrrolidine-1,2-dicarboxylic acid 1-[(7-ethynyl-naphthalen-1-ylmethyl)-amide] 2-[(2-pyridin-3-yl-ethyl)-amide],
(S)-Pyrrolidine-1,2-dicarboxylic acid 2-[(2-dimethylamino-ethyl)-amide] 1-[(7-ethynyl-naphthalen-1-ylmethyl)-amide],
(S)-Pyrrolidine-1,2-dicarboxylic acid 1-[(7-ethynyl-naphthalen-1-ylmethyl)-amide] 2-[(2-pyridin-4-yl-ethyl)-amide],
(S)-Pyrrolidine-1,2-dicarboxylic acid 1-[(7-ethynyl-naphthalen-1-ylmethyl)-amide] 2-[(6-methoxy-pyridin-3-ylmethyl)-amide],
(S)-Pyrrolidine-1,2-dicarboxylic acid 1-[(7-ethynyl-naphthalen-1-ylmethyl)-amide] 2-[(1-methyl-piperidin-4-ylmethyl)-amide],
(S)-Pyrrolidine-1,2-dicarboxylic acid 1-[(7-ethynyl-naphthalen-1-ylmethyl)-amide] 2-[4-(4-methyl-piperazin-1-yl)-benzylamide],
(S)-Pyrrolidine-1,2-dicarboxylic acid 1-[(7-ethynyl-naphthalen-1-ylmethyl)-amide] 2-(4-morpholin-4-ylmethyl-benzylamide),
(S)-Pyrrolidine-1,2-dicarboxylic acid 1-[(7-ethynyl-naphthalen-1-ylmethyl)-amide] 2-methylamide,
(S)-Pyrrolidine-1,2-dicarboxylic acid 2-{[2-(4-benzyl-piperazin-1-yl)-ethyl]amide} 1-[(7-ethynyl-naphthalen-1-ylmethyl)-amide],
(S)-Pyrrolidine-1,2-dicarboxylic acid 1-[(7-ethynyl-naphthalen-1-ylmethyl)-amide] 2-[(2-methoxy-ethyl)-amide],
(S)-Pyrrolidine-1,2-dicarboxylic acid 1-[(7-ethynyl-naphthalen-1-ylmethyl)-amide] 2-[(pyridin-3-ylmethyl)-amide],
(S)-Pyrrolidine-1,2-dicarboxylic acid 1-[(7-ethynyl-naphthalen-1-ylmethyl)-amide] 2-[(pyridin-4-ylmethyl)-amide],
(S)-Pyrrolidine-1,2-dicarboxylic acid 1-[(7-ethynyl-naphthalen-1-ylmethyl)-amide] 2-{[2-(4-methyl-piperazin-1-yl)-ethyl]-amide},
(S)-Pyrrolidine-1,2-dicarboxylic acid 1-[(6-chloro-naphthalen-1-ylmethyl)-amide] 2-{[2-(4-methoxy-phenyl)-ethyl]-amide},
(S)-Pyrrolidine-1,2-dicarboxylic acid 1-[(7-chloro-naphthalen-1-ylmethyl)-amide] 2-{[2-(4-methoxy-phenyl)-ethyl]-amide},
(S)-Pyrrolidine-1,2-dicarboxylic acid 1-[(5-bromo-benzo[b]thiophen-3-ylmethyl)-amide] 2-{[2-(4-methoxy-phenyl)-ethyl]-amide},
(S)-Pyrrolidine-1,2-dicarboxylic acid 1-[(5-chloro-benzo[b]thiophen-3-ylmethyl)-amide] 2-{[2-(4-methoxy-phenyl)-ethyl]-amide},
(S)-Pyrrolidine-1,2-dicarboxylic acid 1-[(7-ethynyl-naphthalen-1-ylmethyl)-amide] 2-{[2-(4-methoxy-phenyl)-ethyl]-amide},
(2S,4R)-4-Methoxy-pyrrolidine-1,2-dicarboxylic acid 1-[(7-ethynyl-naphthalen-1-ylmethyl)-amide] 2-[(pyridin-3-ylmethyl)-amide],
(S)-Piperidine-1,2-dicarboxylic acid 1-[(7-ethynyl-naphthalen-1-ylmethyl)-amide] 2-[(pyridin-3-ylmethyl)-amide],
(S)-Hexahydro-cyclopenta[c]pyrrole-1,2-dicarboxylic acid 2-[(7-ethynyl-naphthalen-1-ylmethyl)-amide] 1-[(pyridin-3-ylmethyl)-amide],
(S)-2,3-Dihydro-indole-1,2-dicarboxylic acid 1-[(7-ethynyl-naphthalen-1-ylmethyl)-amide] 2-[(pyridin-3-ylmethyl)-amide],
(S)-1,3-Dihydro-isoindole-1,2-dicarboxylic acid 2-[(7-ethynyl-naphthalen-1-ylmethyl)-amide] 1-[(pyridin-3-ylmethyl)-amide],
(1R,2S,5S)-3-Aza-bicyclo[3.1.0]hexane-2,3-dicarboxylic acid 3-[(7-ethynyl-naphthalen-1-ylmethyl)-amide] 2-[(pyridin-3-ylmethyl)-amide], (1S,2S,5R)-3-Aza-bicyclo[3.1.0]hexane-2,3-dicarboxylic acid 3-[(7-ethynyl-naphthalen-1-ylmethyl)-amide] 2-[(pyridin-3-ylmethyl)-amide],
(S)-Pyrrolidine-1,2-dicarboxylic acid 1-[(naphthalen-1-ylmethyl)-amide] 2-(phenethyl-amide),
(2S,4S)-4-Phenyl-pyrrolidine-1,2-dicarboxylic acid 1-[(naphthalen-1-ylmethyl)-amide] 2-(phenethyl-amide),
(2S,4R)-4-Phenyl-pyrrolidine-1,2-dicarboxylic acid 1-[(naphthalen-1-ylmethyl)-amide] 2-(phenethyl-amide),
(S)-3,4-Dihydro-1H-isoquinoline-2,3-dicarboxylic acid 2-[(naphthalen-1-ylmethyl)-amide] 3-(phenethyl-amide),
(S)-Piperidine-1,2-dicarboxylic acid 1-[(naphthalen-1-ylmethyl)-amide] 2-(phenethyl-amide),
(S)-Pyrrolidine-1,2-dicarboxylic acid 2-{[2-(4-methoxyphenyl)-ethyl]-amide} 1-[(naphthalen-1-ylmethyl)-amide],
(S)-Pyrrolidine-1,2-dicarboxylic acid 2-benzylamide 1-[(naphthalen-1-ylmethyl)-amide],
(S)-Pyrrolidine-1,2-dicarboxylic acid 2-cyclohexylmethylamide 1-[(naphthalen-1-ylmethyl)-amide],
(S)-Pyrrolidine-1,2-dicarboxylic acid 2-[(3-methyl-butyl)-amide] 1-[(naphthalen-1-ylmethyl)-amide],
(S)-Pyrrolidine-1,2-dicarboxylic acid 1-[(naphthalen-1-ylmethyl)-amide] 2-[(tetrahydro-furan-2-ylmethyl)-amide],
(1S,2S,5R)-3-aza-bicyclo[3.1.0]hexane-2,3-dicarboxylic acid 3-[(7-chloro-naphthalen-1-ylmethyl)-amide] 2-[(pyridin-3-ylmethyl)-amide], and
(1S,2S,5R)-3-aza-bicyclo[3.1.0]hexane-2,3-dicarboxylic acid 3-[(7-chloro-naphthalen-1-ylmethyl)-amide] 2-{[2-(4-methoxy-phenyl)-ethyl]-amide}.

The chemical names of the compounds of the present invention as indicated herein are copied from ISIS, version 2.5 (AutoNom 2000 Name).

Compounds provided by the present invention are hereinafter designated as "compound(s) of (according to) the present invention". A compound of the present invention includes a compound in any form, e.g. in free form, in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention may exist in the form of isomers and mixtures thereof; e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates. A compound of the present invention may be present in the (R)-, (S)- or (R,S)-configuration preferably in the (R)- or (S)-configuration regarding specified positions in the compound of the present invention.

A compound provided by the present invention may be in the (R)- and in the (S)-configuration, e.g. including mixtures thereof, in a compound of formula I, and is preferably in the (R)- or in the (S)-configuration.

Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of the present invention, where tautomers can exist.

In another aspect the present invention provides a process for the production of a compound of the present invention, e.g. of formula I, comprising the steps
A. reacting a compound of formula

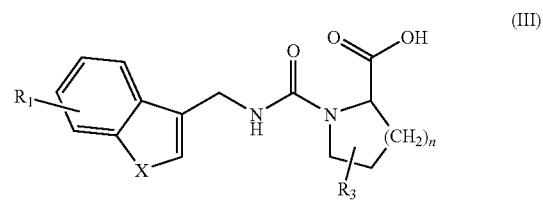

wherein $R_1$ and $R_3$ are as defined above, with a compound of formula

wherein $R_2$ is as defined above, under appropriate conditions, e.g. in the presence of N-(3-dimethylamino-propyl)-N-carbodiimide-HCl, N,N-diisopropylethylamine, $CH_2Cl_2$, trifluoroacetic acid, acetonitril, at appropriate temperatures, e.g. room temperature, for an appropriate time, e.g. over night;
OR
B) reacting a compound of formula

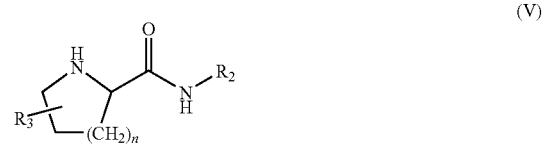

wherein $R_2$, $R_3$ and n are as defined above, with a compound of formula

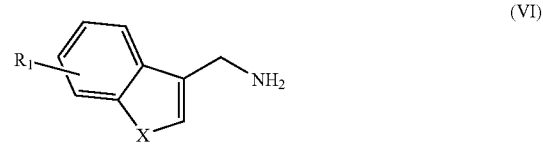

wherein $R_1$ and X are as defined above, under appropriate conditions, e.g. in the presence of 4-nitrophenylchloroformate, pyridine, N,N-diisopropylethylamine, $CH_2Cl_2$, at appropriate temperatures, e.g. room temperature, for an appropriate time, e.g. over night;
and isolating a compound of formula I obtained from the reaction mixture.

In an intermediate of formulae (III), (IV), (V) or (VI) (starting materials), functional groups, if present, optionally may be in protected form or in the form of a salt, if a salt-forming group is present. Protecting groups, optionally present, may be removed at an appropriate stage, e.g. according, e.g. analogously, to a method as conventional A compound of formula I thus obtained may be converted into another compound of formula I, e.g. or a compound of formula I obtained in free form may be converted into a salt of a compound of formula I and vice versa.

Intermediates (starting materials) of formulae (III), (IV), (V) or (VI) are known or may be prepared according, e.g. analogously, to a method as conventional or as specified herein.

Any compound described herein, e.g. a compound of the present invention and intermediates of formulae (III), (IV), (V) or (VI) may be prepared as appropriate, e.g. according, e.g. analogously, to a method as conventional, e.g. or as specified herein.

The compounds of the present invention, e.g. including a compound of formula I, exhibit pharmacological activity and are therefore useful as pharmaceuticals. E.g., the compounds of the present invention are found to inhibit Kallikrein-7 activity.

Compounds of the present invention have $IC_{50}$ values between 1 nM and 10 µM e.g. determined in the following assay:

Materials and Buffers

The fluorescence-quenched substrate Ac-Glu-Asp (EDANS)-Lys-Pro-Ile-Leu-Phe^Arg-Leu-Gly-Lys(DAB-CYL)-Glu-$NH_2$ (where ^ indicates the scissile bond, identified by MS analysis) is purchased from Biosyntan (Berlin, Germany) and kept as a 5 mM stock solution in DMSO at −20° C. All other chemicals are of analytical grade.

Enzymatic reactions are conducted in 50 mM sodium citrate buffer at pH 5.6 containing 150 mM NaCl and 0.05% (w/v) CHAPS.

All protein and peptide containing solutions are handled in siliconized tubes (Life Systems Design, Merenschwand, Switzerland). The compound solutions as well as the enzyme and the substrate solutions are transferred to the 384-well plates (black Cliniplate; cat. no. 95040020 Labsystems Oy, Finland) by means of a CyBi-Well 96-channel pipettor (CyBio AG, Jena, Germany).

Instrumentation for FI Measurements

For fluorescence intensity (FI) measurements an Ultra Evolution reader (TECAN, Maennedorf, Switzerland) is used. The instrument is equipped with a combination of a 350 nm (20 nm bandwidth) and a 500 nm (25 nm bandwidth) bandpath filter for fluorescence excitation and emission acquisition, respectively. To increase the signal:background ratio, an appropriate dichroic mirror is employed. The optical filters and the dichroic mirror are purchased from TECAN. The fluorophores in each well are excited by three flashes per measurement.

Determination of $IC_{50}$ Values

For the determination of $IC_{50}$ values the assay is performed at room temperature in 384-well plates. All final assay volumes were 30 µl. Test compounds are dissolved in 90% (v/v) DMSO/water and diluted in water (containing 0.05% (w/v) CHAPS) to 3-times the desired assay concentration. The 11 final compound concentrations are: 0.3 nM, 1 nM, 3 nM, 10 nM, 30 nM, 100 nM, 300 nM, 1 µM, 3 µM, 10 µM and 30 µM. For each assay, 10 µl water/CHAPS (±test compound) are added per well, followed by 10 µl protease solution (diluted with 1.5× assay buffer). The protease concentration in final assay solution is 0.2 nM (according to the enzyme concentrations determined by the Bradford method). After 1 hour of incubation at room temperature, the reaction is started by addition of 10 µl substrate solution (substrate dissolved in 1.5× assay buffer, final concentration was 2 µM). The effect of the compound on the enzymatic activity is obtained from the linear progress curves and determined from two readings, the first one taken directly after the addition of substrate and the second one after 1 hour. The $IC_{50}$ value is calculated from the plot of percentage of inhibition vs. inhibitor concentration using non-linear regression analysis software (XLfit, Vers. 4.0; ID Business Solution Ltd., Guildford, Surrey, UK).

The compounds of the present invention show activity in that ASSAY and are therefore indicated for the treatment of disorders (diseases) mediated by Kallikrein-7 activity. $IC_{50}$ values for compounds of the present invention are in the range of below 10 µM, preferably below 10 nM, e.g. the compound of example 36 has an $IC_{50}$ value of 3 nM.

Disorders, e.g. including diseases, mediated by Kallikrein-7 activity and which are prone to be successfully treated with Kallikrein-7 antagonists, e.g. with compounds of the present invention, include disorders, wherein the activity of Kallikrein-7 play a causal or contributory role, e.g. diseases involved with epithelial dysfunction such as inflammatory and/or hyperproliferative and pruritic skin diseases like e.g. atopic dermatitis, psoriasis, Netherton syndrome or other pruritic dermatoses such as prurigo nodularis, unspecified itch as well as other diseases with epithelial barrier dysfunction such as inflammatory bowel disease or Crohn's disease.

In another aspect the present invention provides
a compound of the present invention for use as a pharmaceutical,
the use of a compound of the present invention as a pharmaceutical,
the use of a compound of the present invention for the manufacture of a medicament, e.g. for the treatment of disorders mediated by Kallikrein-7 activity.

For pharmaceutical use one or more compounds of the present invention may be used, e.g. one, or a combination of two or more compounds of the present invention, preferably one compound of the present invention is used.

A compound of the present invention may be used as a pharmaceutical in the form of a pharmaceutical composition.

In another aspect the present invention provides a pharmaceutical composition comprising a compound of the present invention in association with at least one pharmaceutically acceptable excipient, e.g. appropriate carrier and/or diluent, e.g. including fillers, binders, disintegrants, flow conditioners, lubricants, sugars or sweeteners, fragrances, preservatives, stabilizers, wetting agents and/or emulsifiers, solubilizers, salts for regulating osmotic pressure and/or buffers.

In another aspect the present invention provides
a pharmaceutical composition of the present invention for use of treating disorders which are mediated by Kallikrein-7 activity.
the use of a pharmaceutical composition of the present invention for treating disorders which are mediated by Kallikrein-7 activity.

In a further aspect the present invention provides a method of treating disorders which are mediated by Kallikrein-7 activity, e.g. including disorders as specified above, which treatment comprises administering to a subject in need of such treatment an effective amount of a compound of the present invention; e.g. in the form of a pharmaceutical composition.

In another aspect the present invention provides
a compound of the present invention for the manufacture of a medicament,
the use of a compound of the present invention for the manufacture of a medicament, e.g. a pharmaceutical composition, for the treatment of disorders, which are mediated by Kallikrein-7 activity, e.g. for the treatment of skin diseases like e.g. atopic dermatitis, psoriasis, Netherton syndrome or other pruritic dermatoses such as prurigo nodularis, unspecified itch.

Treatment includes treatment and prophylaxis (prevention). Treatment can be by local or systemic application such as e.g. creams, ointments or suppositories or by oral, sc or iv application, respectively.

For such treatment, the appropriate dosage will, of course, vary depending upon, for example, the chemical nature and the pharmakokinetic data of a compound of the present invention used, the individual host, the mode of administration and the nature and severity of the conditions being treated. However, in general, for satisfactory results in larger mammals, for example humans, an indicated daily dosage includes a range from about 0.001 g to about 1.5 g, such as 0.001 g to 1.5 g;
from about 0.01 mg/kg body weight to about 20 mg/kg body weight, such as 0.01 mg/kg body weight to 20 mg/kg body weight, for example administered in divided doses up to four times a day.

A compound of the present invention may be administered to larger mammals, for example humans, by similar modes of administration than conventionally used with other mediators, e.g. low molecular weight inhibitors, of Kallikrein-7 activity.

A compound of the present invention may be administered by any conventional route, for example enterally, e.g. including nasal, buccal, rectal, oral, administration; parenterally, e.g. including intravenous, intraarterial, intramuscular, intracardiac, subcutaneous, intraosseous infusion, transdermal (diffusion through the intact skin), transmucosal (diffusion through a mucous membrane), inhalational administration; topically; e.g. including epicutaneous, intranasal, intratracheal administration; intraperitoneal (infusion or injection into the peritoneal cavity); epidural (peridural) (injection or infusion into the epidural space); intrathecal (injection or infusion into the cerebrospinal fluid); intravitreal (administration via the eye); e.g. in form of coated or uncoated tablets, capsules, (injectable) solutions, infusion solutions, solid solutions, suspensions, dispersions, solid dispersions; e.g. in the form of ampoules, vials, in the form of creams, gels, pastes, inhaler powder, foams, tinctures, lip sticks, drops, sprays, or in the form of suppositories. Preferably a compound of the present invention is applied topically.

For topical use, e.g. including administration to the eye, satisfactory results may be obtained with local administration of a 0.5-10%, such as 1-3% concentration of active substance several times daily, e.g. 2 to 5 times daily.

The compounds of the present invention may be administered in the form of a pharmaceutically acceptable salt, or in free form; optionally in the form of a solvate. A compound of the present invention in the form of a salt and/or in the form of a solvate exhibit the same order of activity as a compound of the present invention in free form.

A compound of the present invention may be used for any method or use as described herein alone or in combination with one or more, at least one, other, second drug substance.

In another aspect the present invention provides

A combination of a compound of the present invention with at least one second drug substance;

A pharmaceutical combination comprising a compound of the present invention in combination with at least one second drug substance;

A pharmaceutical composition comprising a compound of the present invention in combination with at least one second drug substance and one or more pharmaceutically acceptable excipient(s);

A compound of the present invention in combination with at least one second drug substance, e.g. in the form of a pharmaceutical combination or composition, for use in any method as defined herein, e.g.

A combination, a pharmaceutical combination or a pharmaceutical composition, comprising a compound of the present invention and at least one second drug substance for use as a pharmaceutical;

The use as a pharmaceutical of a compound of the present invention in combination with at least one second drug substance, e.g. in the form of a pharmaceutical combination or composition;

The use of a compound of the present invention for the manufacture of a medicament for use in combination with a second drug substance A method for treating disorders mediated by Kallikrein-7 activity in a subject in need thereof, comprising co-administering, concomitantly or in sequence, a therapeutically effective amount of a compound of the present invention and at least one second drug substance, e.g. in the form of a pharmaceutical combination or composition;

A compound of the present invention in combination with at least one second drug substance, e.g. in the form of a pharmaceutical combination or composition, for use in the preparation of a medicament for use in disorders mediated by Kallikrein-7 activity.

Combinations include fixed combinations, in which a compound of the present invention and at least one second drug substance are in the same formulation; kits, in which a compound of the present invention and at least one second drug substance in separate formulations are provided in the same package, e.g. with instruction for co-administration; and free combinations in which a compound of the present invention and at least one second drug substance are packaged separately, but instruction for concomitant or sequential administration are given.

In another aspect the present invention provides

A pharmaceutical package comprising a first drug substance which is a compound of the present invention and at least one second drug substance, beside instructions for combined administration;

A pharmaceutical package comprising a compound of the present invention beside instructions for combined administration with at least one second drug substance;

A pharmaceutical package comprising at least one second drug substance beside instructions for combined administration with a compound of the present invention.

Treatment with combinations according to the present invention may provide improvements compared with single treatment.

In another aspect the present invention provides

A pharmaceutical combination comprising an amount of a compound of the present invention and an amount of a second drug substance, wherein the amounts are appropriate to produce a synergistic therapeutic effect;

A method for improving the therapeutic utility of a compound of the present invention comprising co-administering, e.g. concomitantly or in sequence, of a therapeutically effective amount of a compound of the present invention and a second drug substance.

A method for improving the therapeutic utility of a second drug substance comprising co-administering, e.g. concomitantly or in sequence, of a therapeutically effective amount of a compound of the present invention and a second drug substance.

A combination of the present invention and a second drug substance as a combination partner may be administered by any conventional route, for example as set out above for a compound of the present invention. A second drug may be administered in dosages as appropriate, e.g. in dosage ranges which are similar to those used for single treatment, or, e.g. in case of synergy, even below conventional dosage ranges.

Pharmaceutical compositions according to the present invention may be manufactured according, e.g. analogously, to a method as conventional, e.g. by mixing, granulating, coating, dissolving or lyophilizing processes. Unit dosage forms may contain, for example, from about 0.1 mg to about 1500 mg, such as 1 mg to about 1000 mg. Pharmaceutical compositions comprising a combination of the present invention and pharmaceutical compositions comprising a second drug as described herein, may be provided as appropriate, e.g. according, e.g. analogously, to a method as conventional, or as described herein for a pharmaceutical composition of the present invention.

By the term "second drug substance" is meant an anti-inflammatory, immunomodulatory drug, anticancer drug, anesthetic drug or chemotherapeutic drug. A "second drug substance" can also be a compound having Kallikrein-7 activity, but not being a compound of the present invention.

If the compounds of the present invention are administered in combination with other drugs dosages of the co-administered second drug will of course vary depending on the type of co-drug employed, on the specific drug employed, on the condition being treated, as in case of a compound of the present invention. In general dosages similar than those as provided by the second drug supplier may be appropriate In the following Examples all temperatures indicated are in degree Celsius (°).

The following abbreviations are also used:
aq. aqueous
Ac$_2$O acetic anhydride
AcOH acetic acid
CH$_2$Cl$_2$ dichloromethane
DCE 1,2-dichloroethane
DIPEA N,N-diisopropylethylamine
DMA N,N-dimethylacetamide
EtOAc ethylacetate
HATU O-(7-azabenzotriazol-1-yl)-N,N,N',N'-tetramethyluronium hexafluorophosphate
NMP N-methylpyrrolidinone
rt room temperature
TFA trifluoroacetic acid
THF tetrahydrofuran
TLC thin layer chromatography
TMOF trimethylorthoformate A kallikrein 7 inhibitor can also be a "peptide" or a "peptide derivative", which terms are intended to embrace a "peptidomimetic" or "peptide analogue" which complement the three-dimensional structure of the binding pocket of kallikrein 7 or can be designed with improved physical or chemical properties to bind with the three-dimensional binding pocket of the kallikrein 7 as provided in the present invention.

The term "mutant" refers to a mutated sequence by deletion, insertion or preferably replacement of one or more selected amino acids, provided that such mutant sequence shares at least 90% identity, more preferably 95%, and even more preferably 99% identity with the corresponding fragment sequence when performing optimal alignment.

Methods for the preparation of protein mutants are commonly known in the art. For example, kallikrein 7 mutants may be prepared by expression of kallikrein 7 DNA previously modified in its coding region by oligonucleotide directed mutagenesis.

As used herein, the term "binding pocket" refers to the region of kallikrein 7 that, as a result of its shape and physicochemical properties favorably associates with another chemical entity or compound and is defined in by the coordinates of Table 3.

The kallikrein 7 protein to be used for crystallization may be biologically active or inactive. Such ability may be determined by morphological, biochemical or viability analysis well-known in the art.

Expression of recombinant kallikrein 7 or fragment thereof is achievable in eukaryotic or prokaryotic systems or in vitro expression systems.

According to a preferred embodiment, kallikrein 7 is bound to at least one ligand at any step prior to crystallization.

Kallikrein 7 may be expressed as a fusion protein, e.g. a glutathione-S-transferase (GST) or histidine-tagged fusion protein. If desired, the fusion partner is removed before crystallization.

For carrying out the step of crystallization of the method for making a crystal, various methods can be used including vapour diffusion, dialysis or batch crystallization according to methods known in the art ("Crystallization of Biological Macromolecules", A. McPherson, Cold Spring Harbor Laboratory Press, Cold Spring Harbor, N.Y., USA).

In vapour diffusion crystallization, a small volume (i.e., a few microliters) of protein solution is mixed with a solution containing a precipitant. This mixed volume is suspended over a well containing a small amount, i.e. about 1 ml, of precipitant. Vapour diffusion from the drop to the well will result in crystal formation in the drop.

The dialysis method of crystallization utilizes a semipermeable size-exclusion membrane that retains the protein but allows small molecules (i.e. buffers and precipitants) to diffuse in and out. In dialysis, rather than concentrating the protein and the precipitant by evaporation, the precipitant is allowed to slowly diffuse through the membrane and reduce the solubility of the protein while keeping the protein concentration fixed.

The batch method generally involves the slow addition of a precipitant to an aqueous solution of protein until the solution just becomes turbid, at this point the container can be sealed and left undisturbed for a period of time until crystallization occurs. In the batch technique the precipitant and the target molecule solution are simply mixed. Supersaturation is achieved directly rather than by diffusion. Often the batch technique is performed under oil. The oil prevents evaporation and extremely small drops can be used. For this, the term "microbatch" is used. A modification of this technique is not to use paraffin oil (which prevents evaporation completely) but rather use silicone oil or a mixture of silicone and paraffin oils so that a slow evaporation is possible.

The claimed invention can encompass any and all methods of crystallization. One skilled in the art can choose any of such methods and vary the parameters such that the chosen method results in the desired crystals.

One preferred method of crystallization of kallikrein 7 involves mixing a kallikrein 7 solution with a "reservoir buffer". For crystal formation, the concentration of the precipitating agent in the mixture has to be increased, e.g. by addition of precipitating agent, for example by titration, or by allowing the concentration of precipitating agent to balance by diffusion between the crystallization buffer and a reservoir buffer (not necessarily the same as the original reservoir buffer). Under suitable conditions such diffusion of precipitating agent occurs along the gradient of precipitating agent, e.g. from the reservoir buffer having a higher concentration of precipitating agent into the crystallization buffer having a lower concentration of precipitating agent. Diffusion may be achieved e.g. by vapour diffusion techniques allowing diffusion of water in the common gas phase. Known techniques are e.g. vapour diffusion methods, such as the "hanging drop" or the "sitting drop" method. In the vapour diffusion method a drop of crystallization buffer containing the protein is hanging above or sitting beside a much larger pool of reservoir buffer. Alternatively, the balancing of the precipitating agent can be achieved through a semipermeable membrane that separates the crystallization buffer from the reservoir buffer and prevents dilution of the protein into the reservoir buffer.

Formation of kallikrein 7 can be achieved under various conditions which are essentially determined by the following parameters: pH, presence of salts and additives, precipitating agent, protein concentration and temperature. The pH may range, for example, from about 4.0 to 9.0.

In another specific embodiment, the invention relates to a method for making a co-crystal of kallikrein 7 in complex with a ligand.

The crystal form of kallikrein 7 crystal may also be used for exchanging the ligand by soaking compounds of interest, for example, for compound optimization, or for the discovery of novel scaffolds in fragment based screening approaches.

Structure coordinates of a crystalline composition of this invention may be stored in a machine-readable form on a machine-readable storage medium, e.g. a computer hard drive, diskette, DAT tape, etc., for display as a three-dimensional shape or for other uses involving computer-assisted manipulation of, or computation based on, the structural coordinates or the three-dimensional structures they define. For example, data defining the three dimensional structure of a protein of the kallikrein family, or portions or structurally similar homologues of such proteins, may be stored in a machine-readable storage medium, and may be displayed as a graphical three-dimensional representation of the protein structure, typically using a computer capable of reading the data from said storage medium and programmed with instructions for creating the representation from such data.

According to the present invention, a three-dimensional kallikrein 7 model is obtainable from a kallikrein 7 crystal comprising the kallikrein 7, fragment or homologue thereof.

The present invention also relates to a computer readable medium having stored a model of the kallikrein 7 crystal structure. In a preferred embodiment, said model is built from all or a selected portion of it, of the atomic coordinates of Table 3 derived from the X-ray diffraction data.

By "selected portion", it is meant the structure coordinates of at least 10 consecutive amino acids shown in Table 3 and preferably at least 50 amino acids, and more preferably at least 100 consecutive amino acids.

The knowledge obtained from the three-dimensional model of kallikrein 7 can be used in various ways. For example, it can be used to identify chemical entities, for example, small organic and bioorganic molecules such as peptidomimetics and synthetic organic molecules that bind to kallikrein 7 and preferably block or prevent a kallikrein 7-mediated or associated process or event, or that act as kallikrein 7 agonists. Furthermore, this information can be used to design and prepare kallikrein 7 mutants, e.g. mutants with altered catalytic activity, model the three-dimensional structure and solve the crystal structure of proteins, such as kallikrein 7 homologues, kallikrein 7 mutants or kallikrein 7 co-complexes, involving e.g. molecular replacement or homology modeling.

The term "molecular replacement" refers to a method that involves generating a preliminary structural model of a crystal whose structural coordinates are unknown, by orienting and positioning a molecule whose structural coordinates are known, e.g., the kallikrein 7 coordinates within the unit cell of the unknown crystal, so as to best account for the observed diffraction pattern of the unknown crystal. Phases can then be calculated from this model, and combined with the observed amplitudes to give an approximated Fourier synthesis of the structure whose coordinates are unknown. This in turn can be subject to any of the several forms of refinement to provide a final accurate structure of the unknown crystal. Using the structural coordinates provided by this invention, molecular replacement may be used to determine the structural coordinates of a crystalline co complex, unknown ligand, mutant, or homolog, or of a different crystalline form of kallikrein 7. Additionally, the claimed crystal and its coordinates may be used to determine the structural coordinates of a chemical entity that associates with kallikrein 7.

"Homology modeling" according to the invention involves constructing a model of an unknown structure using structural coordinates of one or more related proteins, protein domains and/or one subdomains such as kallikrein 7. Homology modeling may be conducted by fitting common or homologous portions of the protein or peptide whose three dimensional structure is to be solved to the three dimensional structure of homologous structural elements. Homology modeling can include rebuilding part or all of a three dimensional structure with replace of amino acids or other components by those of the related structure to be solved.

Based on the three-dimensional structure of kallikrein 7 as provided in the present invention and using the atomic coordinates of Table 3, or a selected portion of it, the effects of site-specific mutations can be predicted. More specifically, the structural information provided herein permits the identification of desirable sites for amino acid modification, particularly amino acid mutation resulting in substitutional, insertional or deletional variants. Such variants may be designed to have special properties, particularly properties distinct from wild-type kallikrein 7, such as altered catalytic activity. Substitutions, deletions and insertions may be combined to arrive at a desired variant. Such variants can be prepared by methods well-known in the art, e.g. starting from wild-type kallikrein 7 or by de novo synthesis.

The kallikrein 7 structural information provided herein is useful for the design of ligands which are capable of selectively interacting with kallikrein 7, but not other proteases other than Kallikrein 7, and thereby specifically modulating the biological activity of kallikrein 7 and not other kallikrein 7 proteases.

Chemical entities that have a surface that mimics the accessible surface of the binding pocket of kallikrein 7 can be constructed by those skilled in the art. By way of example, the skilled artisan can screen three-dimensional structural databases of compounds to identify those compounds that position appropriate functional groups in similar three dimensional structural arrangement, then build combinatorial chemistry libraries around such chemical entities to identify those with high affinity to the binding pocket of kallikrein 7.

In a specific embodiment of the invention, a cell-based assay is designed to identify ligands which inhibit the biological activity of kallikrein 7.

Ligands, such as small molecular weight compounds can be identified from screening compound databases or libraries and using a computational means to form a fitting operation to a binding site on the kallikrein 7. The three dimensional structure of kallikrein 7 as provided in the present invention by the structure coordinates of Table 3 or a selected portion of it, can be used together with various docking programs.

The potential inhibitory or binding effect of a chemical entity on kallikrein 7 may be analyzed prior to its actual synthesis and testing by the use of computer-modeling techniques. If the theoretical structure of the given chemical entity suggests insufficient interaction and association between it and Kallikrein 7, the need for synthesis and testing of the chemical entity is obviated. However, if computer modeling indicates a strong interaction, the molecule may then be synthesized and tested for its ability to bind to kallikrein 7. Thus, expensive and time-consuming synthesis of inoperative compounds may be avoided.

This "in silico" analysis may begin by visual inspection of, for example, the binding pocket on a computer screen based on the structural coordinates of Table 3 in whole or in part. Selected fragments or chemical entities may then be positioned in a variety of orientations, or "docked," within the binding pocket of kallikrein 7. Docking may be accomplished using software such as Quanta and SYBYL, followed by energy minimization and molecular dynamics with standard molecular mechanics force fields, such as CHARMM and AMBER. Specialized computer programs may be of use for selecting interesting fragments or chemical entities. These programs include, for example, GRID, available from Oxford University, Oxford, UK; 5 MOSS or CATALYST, available from Molecular Simulations, Burlington, Mass.; AUTODOCK, available from Scripps Research Institute, La Jolla, Calif.; DOCK, available from University of California, San Francisco, Calif., and XSITE, available from University College of London, UK.

Preferred is a method for designing a kallikrein 7 inhibitor which interacts at the substrate binding site of kallikrein 7 or any other binding sites. One approach enabled by this invention is the use of the structure coordinates of kallikrein 7 to design chemical entities that bind to or associate with Kallikrein 7 and alter the physical properties of the chemical entities in different ways. Thus, properties such as, for example, solubility, affinity, specificity, potency, on/off rates, or other binding characteristics may all be altered and/or maximized. One may design desired chemical entities by probing a kallikrein 7 comprising the binding pocket of the invention with a library of different entities to determine optimal sites for interaction between candidate chemical entities and kallikrein 7. For example, high-resolution X-ray diffraction data collected from crystals saturated with solvent allows the determination of where each type of solvent molecule adheres. Small molecules that bind tightly to those sites can then be designed and synthesized and tested for the desired activity. Once the desired activity is obtained, the molecules can be further altered to maximize desirable properties.

Once a compound has been designed or selected by the above methods, the efficiency with which that compound may bind to kallikrein 7 may be tested and modified for the maximum desired characteristic(s) using computational or experimental evaluation. Various parameters can be maximized depending on the desired result. These include, but are not limited to, specificity, affinity, on/off rates, hydrophobicity, solubility, and other characteristics readily identifiable by the skilled artisan.

In a preferred embodiment, the structure coordinates of Table 3 of kallikrein 7 is used in the above computer-based design step.

The invention further relates to a method for selecting a ligand that binds to kallikrein 7, comprising:
a. co-crystallizing or incubating a candidate compound or mix of compounds with kallikrein 7 under appropriate conditions,
b. determining by X-ray or NMR methods the amino acids of kallikrein 7 which interacts with the candidate compound,
c. selecting the compound which interacts at least with one or more amino acids of the binding pocket.

For carrying out step b., mapping of the binding site of ligand is usually performed by recording NMR spectra with and without the candidate compound, and identifying those resonances of the protein that are affected by ligand binding. This requires assignment of the protein resonance prior to the analysis, or comparison with the pattern of chemical shift changes that occur upon binding of ligands with known binding sites. Alternatively, competition experiments using said ligands with known binding sites can yield equivalent information.

The present invention further provides methods to design novel ligands of kallikrein 7, using fragment linking approaches. Compounds binding to different binding regions of Kallikrein 7 are first selected. The ligands are linked together based on the spatial orientation, so that the designed novel compounds fits within the two binding sites.

The invention thus relates to a method to design ligands to kallikrein 7, wherein said method comprises:
a. providing a first ligand that binds to one or more amino acids of a first binding region of kallikrein 7,
b. providing a second ligand that binds to one or more amino amino acids of a second binding region of Kallikrein 7, and,
c. linking said first ligand to said second ligand to design a ligand that binds to the first and second binding pockets of kallikrein 7.

The selection of an appropriate linking group is made by maintaining the spatial orientation of the ligands to one another and to kallikrein 7 based upon principles of bond angle and bond length information well known in the organic chemical art.

In addition, antagonists of kallikrein 7 can be used to treat patients, or for the manufacture of a medicament to treat, for inflammatory and/or hyperproliferative and pruritic skin diseases such as keloids, hypertrophic scars, acne, atopic dermatitis, psoriasis, pustular psoriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer.

The following examples serve to illustrate the present invention but should not be construed as a limitation thereof. The invention particularly relates to the specific embodiments described in these examples.

EXAMPLES

Cloning

To prevent autocleavage of hK7, the autocleavage site at position Tyr180 (numbering according to Swiss-Prot entry P49862) has been mutated to Arg by site-directed mutagenesis according to the standard protocol using pET24_His-Pro-EK-KLK7(aa37-253) as template (QuickChange site-directed mutagenesis kit; Stratagene; mutagenesis primer: 5' GACTGCACGAAGGTTCGCAAGGACT-TACTGGAAAATTCCATGC). Cloning of vector pET24_His-Pro-EK-KLK7(aa37-253) has been in a manner usual in the art. The final vector was named pET24c-His-ProKLK7-Enterok-KLK7(aa37-253)_Y180R.

Expression and Purification

*E. coli* strain BL21(DE3) harboring the expression plasmid for pro-hK7 was cultivated at 37 C in LB medium containing 34 µg/ml chloramphenicol and 30 µg/ml kanamycin. Induction was started with 0.4 mM IPTG at an $OD_{600}$ of 1.0 for 4 hours at 37° C. Subsequently, the cells were harvested by centrifugation. All purification steps were done at 4 C, unless stated otherwise. Cells from 10 liter *E. coli* cell culture (25 g cell pellet) were resuspended in 200 ml 50 mM Tris/HCl buffer, pH 8.0 containing 1 mM $MgCl_2$ and stored at -20° C. overnight. After thawing, 1 µl Benzonase (ROCHE) was added and the sample was incubated for 10 min at 37° C. The cells were ruptured by sonication (4 times 20 seconds at 70% amplitude; Branson Digital Sonifier W-450D) and the homogenate was centrifuged at 7000 g for 15 min. The inclusion body-containing pellet was washed three times with 50 mM Tris pH 8.0 buffer containing 25% sucrose, 1% Triton 100 and 1 µl Benzonase and finally two times with $H_2O$ containing 1 mM $MgCl_2$. The inclusion bodies were further purified by HPLC using a reverse phase column. For this, the inclusion bodies were dissolved in 6 M GuHCl (10 mg/ml) and 100 mM DTT and applied to a GE Source RPC column (Fine line 35S) equilibrated with 0.1% TFA and 10% acetonitrile. The protein was eluted by an increasing acetonitrile concentration from 10-100%. Fractions containing the protease were pooled and lyophilized. The dried protein was diluted to a final concentration of 50 µg/ml in 50 mM Tris/HCl pH 8.0 buffer (10° C. cold) containing 2 M urea, 500 mM NaCl, 10 mM $CaCl_2$, 0.1 M $NH_4Cl$, 1 mM EDTA, 1.25 mM GSH and 0.5 mM GSSG. Subsequently, the sample was dialyzed against 10 mM Tris pH 8.0 buffer and loaded on a Q-sepharose column (50 ml). The protein was eluted by an increasing salt concentration from 0-0.5 M NaCl and fractions containing pro-hK7 were pooled and concentrated to approx. 5 ml. Subsequently, the sample was activated by the addition of enterokinase (1:100) for 24 h at 8° C. Finally, hK7 was applied to a size exclusion chromatography column (Superdex 75, HiLoad 26/60, Amersham) equilibrated with 50 mM Tris, 100 mM NaCl, pH 8 at a flow rate of 2.5 ml/min. For crystallization trials the protein buffer was exchanged by dialysis against 50 mM sodium acetate at pH 5.6 and 100 mM sodium chloride and the protein was stored at 4° C.

Crystallization hK7 was concentrated to 24.6 mg/ml and crystallized at 20° C. by the vapor diffusion method in hanging drops. 0.5 µl protein solution containing 50 mM sodium acetate at pH 5.6, 100 mM sodium chloride, 2 mM inhibitor and 1.8% (v/v) DMSO was mixed with 0.5 µl reservoir solution composed of 35% (w/v) PEG 3350, 200 mM calcium chloride and 100 mM sodium acetate at pH 4.8. The drops were equilibrated against 1 ml of the reservoir solution. Diffracting quality crystals appeared within 1-3 days.

Data Collection

For X-ray data collection a crystal was flash frozen in liquid nitrogen without additional cryoprotectant. The X-ray diffraction data were collected from a single crystal for the hK7-inhibitor complex at 95 K at the beamline X10SA of the Swiss Light Source with a MAR225 mosaic CCD detector at a wavelength of 0.9799 Å. For the crystals of hK7 in complex with inhibitors, 299 or 300 images were collected, with 0.5° oscillation each. The exposure time was between 0.5 s and 1 s per image. The crystal-to-detector distance was between 100 mm and 120 mm. The raw diffraction data were processed and scaled with the HKL program suite version 1.98.0 (21) or with XDS/XSCALE (22) using the APRV (23) interface. The crystal data and data collection statistics are summarized in Table 1.

TABLE 1

Data collection statistics

| Modulator | Compound 1 |
|---|---|
| X-ray source | SLS/X10SA |
| date of data collection | 23.03.2006 |
| Wavelength (Å) | 0.979908 |
| Detector | MARCCD 225 |
| Temperature (K) | 100 |
| Number of crystals | 1 |
| Space group | $P2_12_12_1$ |
| Unit cell dimensions: a, b, c (Å) | 42.61, 60.34, 80.63 |
| Number of monomers/a.u. | 1 |
| Packing coefficient (Å 3/Da) | 2.1 |
| Solvent content (%) | 41.5 |
| Resolution range (Å) | 33.5-1.1 |
| Number of observations | 312326 |
| Number of unique reflections | 81660 |
| Overall | 3.8 |
| Data redundancy | |
| Data completeness (%) | 96.0% |
| $<I/\sigma(I)>$ | 34.7 |
| Rmerge | 0.087 |
| Highest resolution shell | 1.14-1.10 Å |
| Resolution range | |
| Completeness for shell | 73.9% |
| $<I/\sigma(I)>$ | 2.2 |
| Rmerge for shell | 0.334 |

$Rmerge = \Sigma|Io-<I>|/\Sigma<I>$

Structure Determination and Structure Refinement

The hK7 structure in complex with compound 1 was solved by molecular replacement with the program MOLREP version 9.2.10 (24), using the coordinates of human kallikrein 1 (pdb code 1SPJ, refined to 1.7 Å resolution (25)) as a search model. With a high resolution data cut-off of 4.0 Å an unambiguous solution was found in space group $P2_12_12_1$ with one protein-modulator complex in the asymmetric unit (correlation coefficient of 0.34, R-factor of 0.48). An initial refinement cycle was applied using the rigid-body, simulated-annealing and bindividual refinement protocols of the program CNX version 2005 (26) and a high resolution data cut-off of 1.5 Å. The hK7 structure was build and refined by alternating cycles of manual model (re)building using the program O version 9 (27) and automated refinement using the minimize and bindividual protocols of the program CNX version 2005. Subsequently, the resolution was extended to 1.2 Å, 209 water molecules were added using the water-pick protocol of the program CNX version 2005 and finally the modulator was added. Anisotropic displacement parameters were included for the final refinement cycles at 1.2 Å resolution using the adp protocol of CNX 2005. The refinement target was the maximum likelihood function with the parameters described by Engh and Huber (28) using amplitudes. Cross validation was used throughout the refinement process, using 9.8% of the reflections which were excluded from the refinement. The quality of the final model was assessed with the programs CNX 2005 and PROCHECK (29). The refinement statistics are summarized in Table 2.

TABLE 2

Refinement statistics

| Inhibitor | Compound 1 |
|---|---|
| Data used in refinement | |
| resolution range | 33.5-1.2 Å |
| intensity cutoff (Sigma(F)) | 0.0 |

TABLE 2-continued

Refinement statistics

| Inhibitor | Compound 1 |
|---|---|
| number of reflections (working/test set) | 58820/6415 |
| completeness (working + test set) | 89.5% |
| test set | 9.8% |
| Fit to data used in refinement | |
| overall Rcryst | 0.181 |
| overall Rfree | 0.197 |
| Fit in the highest resolution bin | |
| resolution range | 1.28-1.20 Å |
| bin completeness (working + test set) | 99.5% |
| bin Rcryst | 0.182 |
| bin Rfree | 0.195 |
| Number of non-hydrogen atoms | |
| protein atoms | 1785 |
| inhibitor atoms | 32 |
| waters | 209 |
| Overall B value from Wilson plot | 12.5 Å$^2$ |
| Overall mean B value | 16.4 Å$^2$ |
| protein atoms | 17.5 Å$^2$ |
| inhibitor atoms | 14.8 Å$^2$ |
| water molecules | 27.9 Å$^2$ |
| Cross-validated estimated coordinate error | |
| from Luzzati plot | 0.13 Å |
| from σA | 0.01 Å |
| Rms deviations from ideal values | |
| bond lengths | 0.018 Å |
| bond angles | 1.7° |
| dihedral angles | 21.5° |
| improper angles | 1.3° |
| Ramachandran plot | |
| residues in most favorable regions | 90.6% |
| residues in additional allowed regions | 9.4% |

Rcryst=Σ|Fo−Fc|/ΣFo 219 of the 224 amino acids could be traced in the high quality electron density map. Amino acids $^{166}$RKDLL$^{170}$ (amino acid numbering according to the chymotrypsinogen numbering scheme (30) is used throughout the document unless stated otherwise) lack electron density and were not included into the final structures. The arginine residue of this disordered loop is mutated in the construct used for crystallization (according to Swiss-Prot numbering entry P49862 this residue is Tyr180). The wild type tyrosine residue was prone to autocatalytic cleavage, which is not the case for the arginine mutant as was demonstrated by MS analysis.

As expected, six disulfide bonds were found between residues Cys22-Cys157, Cys42-Cys58, Cys129-Cys232, Cys136-Cys201, Cys168-Cys182 and Cys191-Cys220 and cis-peptide bonds were build for amino acids Pro147 and Pro219. Due to the high resolution of the structure the side chains of amino acids 30, 38, 39, 49, 50, 84, 90, 110, 138, 153, 161, 164, 187, 192 and 200 were build in two conformations Structure of hK7

The structure of hK7 resembles the overall architecture of hK1, hK6 and hK8 (25, 31, 32) and follows the classical chymotrypsin like fold, composed of two β-barrels and a C-terminal α-helix. The active site, including the catalytic triad composed of His57, Asp102 and Ser195 is located at the interface of the two β-barrels.

Similar to hK5 and hK6 and in contrast to hK1, hK7 lacks the so called kallikrein loop. The kallikrein loop is an insertion of up to 11 amino acid residues between Thr96 and Gln97 characteristic for some of the kallikreins, especially the classical ones. It protrudes over the non-primed binding site like a lid. hK7 has no amino acid insertion in this region and is indistinguishable in length compared to trypsin or chymotrypsin.

Despite the overall structural similarity to other kallikreins, the S1 pocket of hK7 differs from the trypsin-like specificity of e.g. hK1, hK5, hK6 and hK8 in that the polar Asn189 replaces the negatively charged Asp at the bottom of the pocket and the hydrophobic Ala190 substitutes the polar Ser/Thr residues. These specific structural features of the S1 pocket are well in agreement with the observed chymotrypsin-like specificity of hK7 with a preference for medium to large sized S1 residues with a polar tip. hK7 has a preferred specificity for Tyr over Ala, Met and Phe in P1 (1, 33).

A disordered loop is located at the far end of the S3/S4 substrate binding pocket. In other S1 serine proteases complexed with inhibitors binding from S1 to S3, the homologous loop is ordered and folds back forming part of the S3/S4 binding pocket, thereby contributing to inhibitor binding. Therefore, it might be possible that this part of the kallikrein 7 structure gets ordered upon binding of inhibitors that occupy the S3/S4 pockets. In addition, due to the autocleavage after the tyrosine residue of this loop during purification, this tyrosine has been replaced by an arginine residue, which might also influence the conformation of this loop.

Our modulators bind to the active site of kallikrein 7 adopting an unexpected binding mode spanning from S1 towards the primed binding site.

For compound 1 the naphthyl and methoxyphenyl moieties bind to the S1 and S2' pockets, respectively. The central pyrrolidine ring binds to the S1' pocket and induces a conformational change of the His57 side chain, thereby disturbing the catalytic triad composed of His57, Asp102 and Ser195. Upon inhibitor binding, the His57 side chain swings towards the S2 pocket (rotation around chi1 by 120° and around chi2 by 90° compared to the structure of hK6 pdb code 1L2E) and forms together with the disulfide bond between Cys42 and Cys58 a hydrophobic pocket occupied by the pyrrolidine ring of the inhibitor. The carbonyl oxygen atom of the inhibitor's urea moiety occupies the oxyanion hole and is in H-bonding distance to the backbone nitrogen atoms of Gly193 and Ser195. One urea nitrogen atom makes water mediated interactions to the side chain of His57 and the backbone carbonyl group of Ser214. The inhibitor amide nitrogen atom interacts with the backbone carbonyl oxygen atom of His41. The methoxyphenyl moiety is in Van-der-Waals distance to Val149 and Phe151 with the phenyl ring making an edge-to-face interaction to the side chain of Phe151.

Within the crystal environment a symmetry related hK7 molecule packs in close proximity to the active site of hK7. As previously mentioned, the modulator binding induces a movement of the catalytic His57 side chain. One nitrogen atom of this displaced His57 side chain is in H-bonding distance to the backbone carbonyl group of Phe151 of the symmetry related molecule. In addition, the primed site moieties of the modulators are in contact with the side chains of Pro21 and Asp154 of the same symmetry related molecule. Therefore, an influence on the binding modes of the modulators by the crystal contacts cannot be totally excluded. However, the crystal contact does not prevent binding of different prime site scaffolds in different prime site pockets.

TABLE 3

Three-dimensional structure of the new binding pocket of kallikrein 7

| | | | | | | | | | | | | |
|---|---|---|---|---|---|---|---|---|---|---|---|---|
| CRYST1 | 42.611 | | 60.343 | | 80.633 | 90.00 | 90.00 | 90.00 | P 21 21 21 | 4 | | |
| ORIGX1 | | 1.000000 | 0.000000 | | 0.000000 | | 0.00000 | | | | | |
| ORIGX2 | | 0.000000 | 1.000000 | | 0.000000 | | 0.00000 | | | | | |
| ORIGX3 | | 0.000000 | 0.000000 | | 1.000000 | | 0.00000 | | | | | |
| SCALE1 | | 0.023468 | 0.000000 | | 0.000000 | | 0.00000 | | | | | |
| SCALE2 | | 0.000000 | 0.016572 | | 0.000000 | | 0.00000 | | | | | |
| SCALE3 | | 0.000000 | 0.000000 | | 0.012402 | | 0.00000 | | | | | |
| ATOM | 1 | CB | ILE | A | 16 | 5.077 | 12.746 | 32.116 | 1.00 | 10.74 | A | C |
| ANISOU | 1 | CB | ILE | A | 16 | 1357 | 1177 | 1385 | 9 | 1 | 0 A | C |
| SIGUIJ | 1 | CB | ILE | A | 16 | 22 | 18 | 18 | 999999 | 999999 | 999999 A | C |
| ATOM | 2 | CG2 | ILE | A | 16 | 4.414 | 12.703 | 30.717 | 1.00 | 11.43 | A | C |
| ANISOU | 2 | CG2 | ILE | A | 16 | 1373 | 1474 | 1390 | 7 | -2 | 0 A | C |
| SIGUIJ | 2 | CG2 | ILE | A | 16 | 22 | 13 | 13 | 999999 | 852 | 999999 A | C |
| ATOM | 3 | CG1 | ILE | A | 16 | 5.646 | 11.351 | 32.538 | 1.00 | 10.15 | A | C |
| ANISOU | 3 | CG1 | ILE | A | 16 | 1298 | 1167 | 1395 | -13 | -4 | 0 A | C |
| SIGUIJ | 3 | CG1 | ILE | A | 16 | 15 | 11 | 11 | 999999 | 999999 | 999999 A | C |
| ATOM | 4 | CD1 | ILE | A | 16 | 6.590 | 10.689 | 31.560 | 1.00 | 10.76 | A | C |
| ANISOU | 4 | CD1 | ILE | A | 16 | 1346 | 1238 | 1417 | 29 | 5 | -1 A | C |
| SIGUIJ | 4 | CD1 | ILE | A | 16 | 15 | 22 | 10 | 999999 | 999999 | 999999 A | C |
| ATOM | 5 | C | ILE | A | 16 | 5.552 | 15.206 | 31.787 | 1.00 | 10.91 | A | C |
| ANISOU | 5 | C | ILE | A | 16 | 1183 | 1092 | 1440 | 4 | -108 | -3 A | C |
| SIGUIJ | 5 | C | ILE | A | 16 | 12 | 15 | 9 | 999999 | 999999 | 999999 A | C |
| ATOM | 6 | O | ILE | A | 16 | 4.774 | 15.767 | 32.532 | 1.00 | 10.79 | A | O |
| ANISOU | 6 | O | ILE | A | 16 | 1286 | 1171 | 1507 | 63 | -57 | -6 A | O |
| SIGUIJ | 6 | O | ILE | A | 16 | 1 | 0 | 0 | 221 | 57 | 289 A | O |
| ATOM | 7 | N | ILE | A | 16 | 6.698 | 13.966 | 33.589 | 1.00 | 9.90 | A | N |
| ANISOU | 7 | N | ILE | A | 16 | 1283 | 1064 | 1282 | 59 | 0 | 1 A | N |
| SIGUIJ | 7 | N | ILE | A | 16 | 1 | 0 | 0 | 221 | 66 | 290 A | N |
| ATOM | 8 | CA | ILE | A | 16 | 6.169 | 13.847 | 32.184 | 1.00 | 10.55 | A | C |
| ANISOU | 8 | CA | ILE | A | 16 | 1283 | 1114 | 1281 | 81 | 0 | -1 A | C |
| SIGUIJ | 8 | CA | ILE | A | 16 | 14 | 13 | 21 | 0 | 265989 | 999999 A | C |
| ATOM | 9 | N | ILE | A | 17 | 5.926 | 15.671 | 30.585 | 1.00 | 11.18 | A | N |
| ANISOU | 9 | N | ILE | A | 17 | 1446 | 1153 | 1477 | 56 | 2 | -2 A | N |
| SIGUIJ | 9 | N | ILE | A | 17 | 1 | 0 | 0 | 221 | 66 | 290 A | N |
| ATOM | 10 | CA | ILE | A | 17 | 5.417 | 16.952 | 30.064 | 1.00 | 12.10 | A | C |
| ANISOU | 10 | CA | ILE | A | 17 | 1450 | 1172 | 1618 | 57 | -64 | 8 A | C |
| SIGUIJ | 10 | CA | ILE | A | 17 | 8 | 9 | 12 | 156 | 1511 | 999999 A | C |
| ATOM | 11 | CB | ILE | A | 17 | 6.529 | 17.735 | 29.350 | 1.00 | 12.26 | A | C |
| ANISOU | 11 | CB | ILE | A | 17 | 1537 | 1234 | 1787 | 48 | 55 | 9 A | C |
| SIGUIJ | 11 | CB | ILE | A | 17 | 8 | 8 | 10 | 180 | 6 | 999999 A | C |
| ATOM | 12 | CG2 | ILE | A | 17 | 5.941 | 19.119 | 28.872 | 1.00 | 12.53 | A | C |
| ANISOU | 12 | CG2 | ILE | A | 17 | 1893 | 1304 | 1900 | 189 | 2 | 15 A | C |
| SIGUIJ | 12 | CG2 | ILE | A | 17 | 8 | 8 | 8 | 191 | 617 | 999999 A | C |
| ATOM | 13 | CG1 | ILE | A | 17 | 7.750 | 17.957 | 30.263 | 1.00 | 12.96 | A | C |
| ANISOU | 13 | CG1 | ILE | A | 17 | 1634 | 1643 | 1921 | 0 | -58 | -1 A | C |
| SIGUIJ | 13 | CG1 | ILE | A | 17 | 8 | 7 | 7 | 197 | 676 | 999999 A | C |
| ATOM | 14 | CD1 | ILE | A | 17 | 7.426 | 18.712 | 31.538 | 1.00 | 13.60 | A | C |
| ANISOU | 14 | CD1 | ILE | A | 17 | 1963 | 1656 | 1929 | 44 | 2 | 1 A | C |
| SIGUIJ | 14 | CD1 | ILE | A | 17 | 8 | 7 | 6 | 201 | 676 | 999999 A | C |
| ATOM | 15 | C | ILE | A | 17 | 4.313 | 16.687 | 29.037 | 1.00 | 12.56 | A | C |
| ANISOU | 15 | C | ILE | A | 17 | 1402 | 1257 | 1586 | 32 | -21 | 0 A | C |
| SIGUIJ | 15 | C | ILE | A | 17 | 8 | 5 | 5 | 204 | 659 | 988023 A | C |
| ATOM | 16 | O | ILE | A | 17 | 4.516 | 15.889 | 28.122 | 1.00 | 12.36 | A | O |
| ANISOU | 16 | O | ILE | A | 17 | 1497 | 1275 | 1591 | 49 | -5 | 1 A | O |
| SIGUIJ | 16 | O | ILE | A | 17 | 1 | 0 | 0 | 221 | 57 | 289 A | O |
| ATOM | 17 | N | ASP | A | 18 | 3.150 | 17.343 | 29.232 | 1.00 | 13.27 | A | N |
| ANISOU | 17 | N | ASP | A | 18 | 1416 | 1360 | 1685 | 89 | -34 | -3 A | N |
| SIGUIJ | 17 | N | ASP | A | 18 | 1 | 0 | 0 | 221 | 66 | 290 A | N |
| ATOM | 18 | CA | ASP | A | 18 | 2.007 | 17.349 | 28.291 | 1.00 | 14.05 | A | C |
| ANISOU | 18 | CA | ASP | A | 18 | 1544 | 1613 | 1897 | 46 | -212 | 60 A | C |
| SIGUIJ | 18 | CA | ASP | A | 18 | 7 | 7 | 4 | 206 | 638 | 855653 A | C |
| ATOM | 19 | CB | ASP | A | 18 | 2.386 | 17.918 | 26.913 | 1.00 | 15.58 | A | C |
| ANISOU | 19 | CB | ASP | A | 18 | 2263 | 1479 | 1926 | 68 | -18 | -3 A | C |
| SIGUIJ | 19 | CB | ASP | A | 18 | 7 | 7 | 4 | 208 | 617 | 754615 A | C |
| ATOM | 20 | CG | ASP | A | 18 | 1.151 | 18.251 | 26.055 | 1.00 | 16.60 | A | C |
| ANISOU | 20 | CG | ASP | A | 18 | 2333 | 1838 | 1991 | 172 | -63 | -25 A | C |
| SIGUIJ | 20 | CG | ASP | A | 18 | 7 | 7 | 3 | 209 | 596 | 674948 A | C |
| ATOM | 21 | OD1 | ASP | A | 18 | 0.112 | 18.577 | 26.628 | 1.00 | 18.23 | A | O |
| ANISOU | 21 | OD1 | ASP | A | 18 | 2635 | 4119 | 2133 | 945 | 30 | 51 A | O |
| SIGUIJ | 21 | OD1 | ASP | A | 18 | 1 | 0 | 0 | 221 | 57 | 289 A | O |
| ATOM | 22 | OD2 | ASP | A | 18 | 1.233 | 18.185 | 24.829 | 1.00 | 17.67 | A | O |
| ANISOU | 22 | OD2 | ASP | A | 18 | 2389 | 3156 | 1991 | 483 | -53 | -40 A | O |
| SIGUIJ | 22 | OD2 | ASP | A | 18 | 1 | 0 | 0 | 221 | 57 | 289 A | O |
| ATOM | 23 | C | ASP | A | 18 | 1.403 | 15.964 | 28.130 | 1.00 | 14.19 | A | C |
| ANISOU | 23 | C | ASP | A | 18 | 1588 | 1641 | 1795 | -3 | -25 | -1 A | C |
| SIGUIJ | 23 | C | ASP | A | 18 | 7 | 7 | 3 | 210 | 576 | 610513 A | C |
| ATOM | 24 | O | ASP | A | 18 | 0.895 | 15.606 | 27.045 | 1.00 | 14.18 | A | O |
| ANISOU | 24 | O | ASP | A | 18 | 1730 | 1957 | 1807 | -162 | -32 | -33 A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 24 | O | ASP | A | 18 | 1 | 0 | 0 | 221 | 57 | 289 | A | O |
| ATOM | 25 | N | GLY | A | 19 | 1.416 | 15.209 | 29.232 | 1.00 | 14.20 | | A | N |
| ANISOU | 25 | N | GLY | A | 19 | 1512 | 1612 | 1803 | −41 | −23 | −6 | A | N |
| SIGUIJ | 25 | N | GLY | A | 19 | 1 | 0 | 0 | 221 | 66 | 290 | A | N |
| ATOM | 26 | CA | GLY | A | 19 | 0.676 | 13.954 | 29.260 | 1.00 | 14.43 | | A | C |
| ANISOU | 26 | CA | GLY | A | 19 | 1470 | 1590 | 2177 | −13 | −3 | 0 | A | C |
| SIGUIJ | 26 | CA | GLY | A | 19 | 7 | 7 | 2 | 16 | 2131 | 13262 | A | C |
| ATOM | 27 | C | GLY | A | 19 | −0.615 | 14.053 | 30.048 | 1.00 | 14.46 | | A | C |
| ANISOU | 27 | C | GLY | A | 19 | 1325 | 1580 | 1798 | −38 | −240 | −26 | A | C |
| SIGUIJ | 27 | C | GLY | A | 19 | 7 | 8 | 2 | 156 | 1509 | 13262 | A | C |
| ATOM | 28 | O | GLY | A | 19 | −1.228 | 15.140 | 30.140 | 1.00 | 15.36 | | A | O |
| ANISOU | 28 | O | GLY | A | 19 | 1457 | 1603 | 3368 | 13 | 40 | −1 | A | O |
| SIGUIJ | 28 | O | GLY | A | 19 | 1 | 0 | 0 | 221 | 57 | 289 | A | O |
| ATOM | 29 | N | ALA | A | 20 | −1.039 | 12.931 | 30.604 | 1.00 | 14.61 | | A | N |
| ANISOU | 29 | N | ALA | A | 20 | 1411 | 1582 | 1989 | 6 | −73 | 2 | A | N |
| SIGUIJ | 29 | N | ALA | A | 20 | 1 | 0 | 0 | 221 | 66 | 290 | A | N |
| ATOM | 30 | CA | ALA | A | 20 | −2.330 | 12.843 | 31.298 | 1.00 | 14.42 | | A | C |
| ANISOU | 30 | CA | ALA | A | 20 | 1426 | 1559 | 2026 | 28 | −54 | 5 | A | C |
| SIGUIJ | 30 | CA | ALA | A | 20 | 7 | 8 | 2 | 180 | 1232 | 13262 | A | C |
| ATOM | 31 | CB | ALA | A | 20 | −3.444 | 12.549 | 30.291 | 1.00 | 15.24 | | A | C |
| ANISOU | 31 | CB | ALA | A | 20 | 1603 | 2578 | 2199 | −195 | −182 | −43 | A | C |
| SIGUIJ | 31 | CB | ALA | A | 20 | 7 | 9 | 1 | 191 | 1068 | 13262 | A | C |
| ATOM | 32 | C | ALA | A | 20 | −2.215 | 11.693 | 32.256 | 1.00 | 14.43 | | A | C |
| ANISOU | 32 | C | ALA | A | 20 | 1227 | 1549 | 1982 | 77 | 13 | −2 | A | C |
| SIGUIJ | 32 | C | ALA | A | 20 | 6 | 9 | 1 | 197 | 955 | 13262 | A | C |
| ATOM | 33 | O | ALA | A | 20 | −1.402 | 10.791 | 32.055 | 1.00 | 13.98 | | A | O |
| ANISOU | 33 | O | ALA | A | 20 | 1331 | 1642 | 1760 | 183 | −31 | 14 | A | O |
| SIGUIJ | 33 | O | ALA | A | 20 | 1 | 0 | 0 | 221 | 57 | 289 | A | O |
| ATOM | 34 | N | PRO | A | 21 | −3.043 | 11.661 | 33.301 | 1.00 | 14.48 | | A | N |
| ANISOU | 34 | N | PRO | A | 21 | 1288 | 1632 | 2007 | 39 | 59 | −5 | A | N |
| SIGUIJ | 34 | N | PRO | A | 21 | 1 | 0 | 0 | 221 | 66 | 290 | A | N |
| ATOM | 35 | CD | PRO | A | 21 | −4.048 | 12.644 | 33.756 | 1.00 | 14.83 | | A | C |
| ANISOU | 35 | CD | PRO | A | 21 | 1541 | 1800 | 2794 | 175 | 325 | −92 | A | C |
| SIGUIJ | 35 | CD | PRO | A | 21 | 7 | 11 | 1 | 201 | 872 | 13263 | A | C |
| ATOM | 36 | CA | PRO | A | 21 | −2.941 | 10.505 | 34.219 | 1.00 | 14.80 | | A | C |
| ANISOU | 36 | CA | PRO | A | 21 | 1375 | 1626 | 1987 | 3 | 4 | 0 | A | C |
| SIGUIJ | 36 | CA | PRO | A | 21 | 7 | 13 | 1 | 204 | 807 | 13263 | A | C |
| ATOM | 37 | CB | PRO | A | 21 | −4.067 | 10.765 | 35.243 | 1.00 | 14.78 | | A | C |
| ANISOU | 37 | CB | PRO | A | 21 | 1626 | 2137 | 2270 | 87 | 260 | −36 | A | C |
| SIGUIJ | 37 | CB | PRO | A | 21 | 9 | 20 | 0 | 206 | 755 | 13263 | A | C |
| ATOM | 38 | CG | PRO | A | 21 | −4.249 | 12.306 | 35.208 | 1.00 | 15.02 | | A | C |
| ANISOU | 38 | CG | PRO | A | 21 | 1710 | 2137 | 2810 | 95 | 340 | −30 | A | C |
| SIGUIJ | 38 | CG | PRO | A | 21 | 5 | 0 | 0 | 208 | 712 | 13264 | A | C |
| ATOM | 39 | C | PRO | A | 21 | −3.124 | 9.168 | 33.462 | 1.00 | 15.07 | | A | C |
| ANISOU | 39 | C | PRO | A | 21 | 1444 | 1620 | 1929 | −40 | 41 | 6 | A | C |
| SIGUIJ | 39 | C | PRO | A | 21 | 5 | 1 | 1 | 209 | 675 | 13264 | A | C |
| ATOM | 40 | O | PRO | A | 21 | −4.000 | 9.040 | 32.592 | 1.00 | 15.55 | | A | O |
| ANISOU | 40 | O | PRO | A | 21 | 1692 | 2259 | 2177 | −91 | −215 | −34 | A | O |
| SIGUIJ | 40 | O | PRO | A | 21 | 1 | 0 | 0 | 221 | 57 | 289 | A | O |
| ATOM | 41 | N | CYS | A | 22 | −2.296 | 8.185 | 33.761 | 1.00 | 15.39 | | A | N |
| ANISOU | 41 | N | CYS | A | 22 | 1549 | 1659 | 2056 | 23 | −11 | 1 | A | N |
| SIGUIJ | 41 | N | CYS | A | 22 | 1 | 0 | 0 | 221 | 66 | 290 | A | N |
| ATOM | 42 | CA | CYS | A | 22 | −2.418 | 6.865 | 33.130 | 1.00 | 15.88 | | A | C |
| ANISOU | 42 | CA | CYS | A | 22 | 1853 | 1653 | 2100 | 10 | −75 | −3 | A | C |
| SIGUIJ | 42 | CA | CYS | A | 22 | 5 | 1 | 1 | 210 | 644 | 13265 | A | C |
| ATOM | 43 | C | CYS | A | 22 | −3.697 | 6.228 | 33.607 | 1.00 | 16.58 | | A | C |
| ANISOU | 43 | C | CYS | A | 22 | 1864 | 1719 | 2307 | −16 | −27 | 0 | A | C |
| SIGUIJ | 43 | C | CYS | A | 22 | 5 | 1 | 1 | 211 | 617 | 13265 | A | C |
| ATOM | 44 | O | CYS | A | 22 | −4.105 | 6.448 | 34.723 | 1.00 | 16.62 | | A | O |
| ANISOU | 44 | O | CYS | A | 22 | 2051 | 1809 | 2331 | −14 | 49 | −2 | A | O |
| SIGUIJ | 44 | O | CYS | A | 22 | 1 | 0 | 0 | 221 | 57 | 289 | A | O |
| ATOM | 45 | CB | CYS | A | 22 | −1.259 | 5.925 | 33.523 | 1.00 | 15.41 | | A | C |
| ANISOU | 45 | CB | CYS | A | 22 | 1802 | 1480 | 2278 | −117 | −147 | 4 | A | C |
| SIGUIJ | 45 | CB | CYS | A | 22 | 5 | 1 | 1 | 212 | 592 | 13266 | A | C |
| ATOM | 46 | SG | CYS | A | 22 | 0.421 | 6.523 | 33.162 | 1.00 | 14.69 | | A | S |
| ANISOU | 46 | SG | CYS | A | 22 | 1822 | 1696 | 1955 | −194 | −224 | 61 | A | S |
| SIGUIJ | 46 | SG | CYS | A | 22 | 1 | 0 | 0 | 221 | 49 | 289 | A | S |
| ATOM | 47 | N | ALA | A | 23 | −4.321 | 5.433 | 32.759 | 1.00 | 17.74 | | A | N |
| ANISOU | 47 | N | ALA | A | 23 | 2277 | 1732 | 2634 | 5 | −394 | −34 | A | N |
| SIGUIJ | 47 | N | ALA | A | 23 | 1 | 0 | 0 | 221 | 66 | 290 | A | N |
| ATOM | 48 | CA | ALA | A | 23 | −5.508 | 4.669 | 33.194 | 1.00 | 18.55 | | A | C |
| ANISOU | 48 | CA | ALA | A | 23 | 2391 | 1809 | 3463 | −41 | −135 | −3 | A | C |
| SIGUIJ | 48 | CA | ALA | A | 23 | 5 | 1 | 1 | 213 | 571 | 13267 | A | C |
| ATOM | 49 | CB | ALA | A | 23 | −6.037 | 3.781 | 32.042 | 1.00 | 18.86 | | A | C |
| ANISOU | 49 | CB | ALA | A | 23 | 2965 | 2068 | 3487 | −401 | −128 | −35 | A | C |
| SIGUIJ | 49 | CB | ALA | A | 23 | 5 | 1 | 1 | 213 | 552 | 13268 | A | C |
| ATOM | 50 | C | ALA | A | 23 | −5.166 | 3.804 | 34.407 | 1.00 | 19.23 | | A | C |
| ANISOU | 50 | C | ALA | A | 23 | 1845 | 1832 | 3427 | 1 | 37 | 1 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 50 | C | ALA | A | 23 | 5 | 1 | 1 | 214 | 534 | 13269 | A | C |
| ATOM | 51 | O | ALA | A | 23 | −4.112 | 3.144 | 34.461 | 1.00 | 18.85 | | A | O |
| ANISOU | 51 | O | ALA | A | 23 | 1841 | 1831 | 3120 | 0 | 48 | 1 | A | O |
| SIGUIJ | 51 | O | ALA | A | 23 | 1 | 0 | 0 | 221 | 57 | 289 | A | O |
| ATOM | 52 | N | ARG | A | 24 | −6.032 | 3.816 | 35.411 | 1.00 | 20.08 | | A | N |
| ANISOU | 52 | N | ARG | A | 24 | 1882 | 2804 | 3472 | 5 | 75 | −1 | A | N |
| SIGUIJ | 52 | N | ARG | A | 24 | 1 | 0 | 0 | 221 | 65 | 290 | A | N |
| ATOM | 53 | CA | ARG | A | 24 | −5.697 | 3.207 | 36.691 | 1.00 | 20.80 | | A | C |
| ANISOU | 53 | CA | ARG | A | 24 | 1855 | 2815 | 3452 | 129 | 140 | −15 | A | C |
| SIGUIJ | 53 | CA | ARG | A | 24 | 5 | 1 | 1 | 214 | 518 | 13269 | A | C |
| ATOM | 54 | CB | ARG | A | 24 | −6.822 | 3.458 | 37.694 | 1.00 | 22.17 | | A | C |
| ANISOU | 54 | CB | ARG | A | 24 | 3555 | 4746 | 5612 | 306 | 2004 | −298 | A | C |
| SIGUIJ | 54 | CB | ARG | A | 24 | 5 | 1 | 1 | 214 | 504 | 13270 | A | C |
| ATOM | 55 | CG | ARG | A | 24 | −6.871 | 4.917 | 38.104 | 1.00 | 24.04 | | A | C |
| ANISOU | 55 | CG | ARG | A | 24 | 7566 | 4653 | 3991 | 894 | 390 | 104 | A | C |
| SIGUIJ | 55 | CG | ARG | A | 24 | 5 | 1 | 1 | 215 | 490 | 13271 | A | C |
| ATOM | 56 | CD | ARG | A | 24 | −5.651 | 5.348 | 38.911 | 1.00 | 25.58 | | A | C |
| ANISOU | 56 | CD | ARG | A | 24 | 8395 | 7383 | 5215 | −3 | −385 | 2 | A | C |
| SIGUIJ | 56 | CD | ARG | A | 24 | 5 | 1 | 1 | 215 | 478 | 13273 | A | C |
| ATOM | 57 | NE | ARG | A | 24 | −6.074 | 5.585 | 40.291 | 1.00 | 27.17 | | A | N |
| ANISOU | 57 | NE | ARG | A | 24 | 10414 | 8862 | 5354 | 905 | 77 | 25 | A | N |
| SIGUIJ | 57 | NE | ARG | A | 24 | 1 | 0 | 0 | 221 | 65 | 290 | A | N |
| ATOM | 58 | CZ | ARG | A | 24 | −6.285 | 6.793 | 40.812 | 1.00 | 27.52 | | A | C |
| ANISOU | 58 | CZ | ARG | A | 24 | 6679 | 8752 | 5430 | 224 | 147 | 4 | A | C |
| SIGUIJ | 58 | CZ | ARG | A | 24 | 5 | 1 | 1 | 215 | 466 | 13274 | A | C |
| ATOM | 59 | NH1 | ARG | A | 24 | −6.098 | 7.887 | 40.064 | 1.00 | 28.32 | | A | N |
| ANISOU | 59 | NH1 | ARG | A | 24 | 6831 | 8764 | 5428 | 172 | 118 | 4 | A | N |
| SIGUIJ | 59 | NH1 | ARG | A | 24 | 1 | 0 | 0 | 221 | 65 | 290 | A | N |
| ATOM | 60 | NH2 | ARG | A | 24 | −6.731 | 6.923 | 42.060 | 1.00 | 28.06 | | A | N |
| ANISOU | 60 | NH2 | ARG | A | 24 | 5890 | 11495 | 5319 | 752 | −191 | −109 | A | N |
| SIGUIJ | 60 | NH2 | ARG | A | 24 | 1 | 0 | 0 | 221 | 65 | 290 | A | N |
| ATOM | 61 | C | ARG | A | 24 | −5.476 | 1.724 | 36.489 | 1.00 | 20.46 | | A | C |
| ANISOU | 61 | C | ARG | A | 24 | 1964 | 2810 | 3539 | 158 | 110 | −16 | A | C |
| SIGUIJ | 61 | C | ARG | A | 24 | 5 | 1 | 1 | 216 | 455 | 13275 | A | C |
| ATOM | 62 | O | ARG | A | 24 | −6.252 | 1.056 | 35.774 | 1.00 | 21.02 | | A | O |
| ANISOU | 62 | O | ARG | A | 24 | 2562 | 3150 | 3998 | −121 | −294 | −37 | A | O |
| SIGUIJ | 62 | O | ARG | A | 24 | 1 | 0 | 0 | 221 | 57 | 289 | A | O |
| ATOM | 63 | N | GLY | A | 25 | −4.405 | 1.185 | 37.066 | 1.00 | 19.77 | | A | N |
| ANISOU | 63 | N | GLY | A | 25 | 1694 | 2152 | 3266 | −187 | 298 | 55 | A | N |
| SIGUIJ | 63 | N | GLY | A | 25 | 1 | 0 | 0 | 221 | 65 | 290 | A | N |
| ATOM | 64 | CA | GLY | A | 25 | −4.142 | −0.252 | 36.960 | 1.00 | 19.02 | | A | C |
| ANISOU | 64 | CA | GLY | A | 25 | 2494 | 2178 | 3788 | −31 | 221 | −4 | A | C |
| SIGUIJ | 64 | CA | GLY | A | 25 | 5 | 1 | 1 | 216 | 445 | 13276 | A | C |
| ATOM | 65 | C | GLY | A | 25 | −3.455 | −0.704 | 35.691 | 1.00 | 18.44 | | A | C |
| ANISOU | 65 | C | GLY | A | 25 | 1599 | 2043 | 3543 | −102 | −238 | −3 | A | C |
| SIGUIJ | 65 | C | GLY | A | 25 | 5 | 1 | 1 | 216 | 436 | 13277 | A | C |
| ATOM | 66 | O | GLY | A | 25 | −3.197 | −1.879 | 35.566 | 1.00 | 18.78 | | A | O |
| ANISOU | 66 | O | GLY | A | 25 | 2182 | 2069 | 3909 | 1 | −69 | −1 | A | O |
| SIGUIJ | 66 | O | GLY | A | 25 | 1 | 0 | 0 | 221 | 57 | 289 | A | O |
| ATOM | 67 | N | SER | A | 26 | −3.101 | 0.199 | 34.775 | 1.00 | 17.58 | | A | N |
| ANISOU | 67 | N | SER | A | 26 | 1637 | 1926 | 3293 | −297 | −416 | −184 | A | N |
| SIGUIJ | 67 | N | SER | A | 26 | 1 | 0 | 0 | 221 | 65 | 290 | A | N |
| ATOM | 68 | CA | SER | A | 26 | −2.521 | −0.204 | 33.539 | 1.00 | 16.76 | | A | C |
| ANISOU | 68 | CA | SER | A | 26 | 1639 | 1828 | 3224 | −141 | −487 | −92 | A | C |
| SIGUIJ | 68 | CA | SER | A | 26 | 5 | 1 | 1 | 216 | 427 | 13279 | A | C |
| ATOM | 69 | CB | SER | A | 26 | −2.959 | 0.744 | 32.420 | 1.00 | 17.50 | | A | C |
| ANISOU | 69 | CB | SER | A | 26 | 2341 | 1960 | 3304 | 23 | −634 | −58 | A | C |
| SIGUIJ | 69 | CB | SER | A | 26 | 5 | 1 | 1 | 216 | 419 | 13280 | A | C |
| ATOM | 70 | OG | SER | A | 26 | −2.523 | 2.081 | 32.633 | 1.00 | 17.84 | | A | O |
| ANISOU | 70 | OG | SER | A | 26 | 2705 | 1973 | 2835 | −62 | −851 | 69 | A | O |
| SIGUIJ | 70 | OG | SER | A | 26 | 1 | 0 | 0 | 221 | 57 | 289 | A | O |
| ATOM | 71 | C | SER | A | 26 | −0.983 | −0.267 | 33.562 | 1.00 | 15.79 | | A | C |
| ANISOU | 71 | C | SER | A | 26 | 1642 | 1901 | 2649 | −132 | −475 | −100 | A | C |
| SIGUIJ | 71 | C | SER | A | 26 | 4 | 1 | 1 | 216 | 411 | 13282 | A | C |
| ATOM | 72 | O | SER | A | 26 | −0.388 | −0.642 | 32.569 | 1.00 | 15.91 | | A | O |
| ANISOU | 72 | O | SER | A | 26 | 1789 | 1923 | 2633 | 5 | −449 | −18 | A | O |
| SIGUIJ | 72 | O | SER | A | 26 | 1 | 0 | 0 | 221 | 57 | 289 | A | O |
| ATOM | 73 | N | HIS | A | 27 | −0.404 | 0.093 | 34.705 | 1.00 | 14.85 | | A | N |
| ANISOU | 73 | N | HIS | A | 27 | 1597 | 1233 | 2583 | −97 | −450 | 88 | A | N |
| SIGUIJ | 73 | N | HIS | A | 27 | 1 | 0 | 0 | 221 | 65 | 290 | A | N |
| ATOM | 74 | CA | HIS | A | 27 | 1.073 | 0.045 | 34.891 | 1.00 | 14.13 | | A | C |
| ANISOU | 74 | CA | HIS | A | 27 | 1596 | 1182 | 2242 | −107 | −396 | 104 | A | C |
| SIGUIJ | 74 | CA | HIS | A | 27 | 4 | 1 | 1 | 217 | 404 | 13283 | A | C |
| ATOM | 75 | CB | HIS | A | 27 | 1.648 | 1.471 | 34.961 | 1.00 | 14.38 | | A | C |
| ANISOU | 75 | CB | HIS | A | 27 | 1622 | 1194 | 2354 | −125 | −156 | −12 | A | C |
| SIGUIJ | 75 | CB | HIS | A | 27 | 4 | 1 | 1 | 217 | 397 | 13285 | A | C |
| ATOM | 76 | CG | HIS | A | 27 | 1.495 | 2.179 | 33.679 | 1.00 | 15.00 | | A | C |
| ANISOU | 76 | CG | HIS | A | 27 | 1758 | 1278 | 2360 | −48 | −128 | −2 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 76 | CG | HIS | A | 27 | 4 | 1 | 1 | 217 | 390 | 13286 | A | C |
| ATOM | 77 | CD2 | HIS | A | 27 | 2.337 | 2.364 | 32.656 | 1.00 | 15.85 | | A | C |
| ANISOU | 77 | CD2 | HIS | A | 27 | 2142 | 1369 | 2619 | 15 | 183 | 34 | A | C |
| SIGUIJ | 77 | CD2 | HIS | A | 27 | 4 | 1 | 1 | 217 | 384 | 13288 | A | C |
| ATOM | 78 | ND1 | HIS | A | 27 | 0.259 | 2.638 | 33.259 | 1.00 | 15.70 | | A | N |
| ANISOU | 78 | ND1 | HIS | A | 27 | 1802 | 1462 | 2672 | 0 | −210 | 2 | A | N |
| SIGUIJ | 78 | ND1 | HIS | A | 27 | 1 | 0 | 0 | 221 | 65 | 290 | A | N |
| ATOM | 79 | CE1 | HIS | A | 27 | 0.339 | 3.050 | 32.017 | 1.00 | 15.87 | | A | C |
| ANISOU | 79 | CE1 | HIS | A | 27 | 2573 | 1650 | 2706 | 234 | −53 | 63 | A | C |
| SIGUIJ | 79 | CE1 | HIS | A | 27 | 4 | 1 | 1 | 217 | 378 | 13290 | A | C |
| ATOM | 80 | NE2 | HIS | A | 27 | 1.584 | 2.889 | 31.613 | 1.00 | 15.97 | | A | N |
| ANISOU | 80 | NE2 | HIS | A | 27 | 2579 | 1630 | 2756 | 223 | −27 | 16 | A | N |
| SIGUIJ | 80 | NE2 | HIS | A | 27 | 1 | 0 | 0 | 221 | 65 | 290 | A | N |
| ATOM | 81 | C | HIS | A | 27 | 1.499 | −0.711 | 36.103 | 1.00 | 13.41 | | A | C |
| ANISOU | 81 | C | HIS | A | 27 | 1335 | 1030 | 2120 | −38 | −247 | −16 | A | C |
| SIGUIJ | 81 | C | HIS | A | 27 | 4 | 1 | 1 | 217 | 372 | 13292 | A | C |
| ATOM | 82 | O | HIS | A | 27 | 2.230 | −0.213 | 36.943 | 1.00 | 12.83 | | A | O |
| ANISOU | 82 | O | HIS | A | 27 | 1319 | 1289 | 1972 | −233 | −109 | 9 | A | O |
| SIGUIJ | 82 | O | HIS | A | 27 | 1 | 0 | 0 | 221 | 57 | 289 | A | O |
| ATOM | 83 | N | PRO | A | 28 | 1.059 | −1.976 | 36.227 | 1.00 | 12.88 | | A | N |
| ANISOU | 83 | N | PRO | A | 28 | 1587 | 1063 | 2237 | −143 | −402 | 36 | A | N |
| SIGUIJ | 83 | N | PRO | A | 28 | 1 | 0 | 0 | 221 | 65 | 290 | A | N |
| ATOM | 84 | CD | PRO | A | 28 | 0.178 | −2.764 | 35.323 | 1.00 | 13.22 | | A | C |
| ANISOU | 84 | CD | PRO | A | 28 | 1835 | 1215 | 2589 | −167 | −633 | −88 | A | C |
| SIGUIJ | 84 | CD | PRO | A | 28 | 4 | 1 | 1 | 217 | 366 | 13294 | A | C |
| ATOM | 85 | CA | PRO | A | 28 | 1.373 | −2.734 | 37.452 | 1.00 | 12.51 | | A | C |
| ANISOU | 85 | CA | PRO | A | 28 | 1385 | 1110 | 2197 | −28 | −278 | 24 | A | C |
| SIGUIJ | 85 | CA | PRO | A | 28 | 4 | 1 | 1 | 217 | 361 | 13296 | A | C |
| ATOM | 86 | CB | PRO | A | 28 | 0.454 | −3.952 | 37.370 | 1.00 | 13.00 | | A | C |
| ANISOU | 86 | CB | PRO | A | 28 | 1841 | 1359 | 2863 | −369 | −419 | 98 | A | C |
| SIGUIJ | 86 | CB | PRO | A | 28 | 4 | 1 | 1 | 218 | 356 | 13298 | A | C |
| ATOM | 87 | CG | PRO | A | 28 | 0.220 | −4.146 | 35.990 | 1.00 | 13.60 | | A | C |
| ANISOU | 87 | CG | PRO | A | 28 | 1975 | 1284 | 2883 | −96 | −481 | 53 | A | C |
| SIGUIJ | 87 | CG | PRO | A | 28 | 4 | 1 | 1 | 218 | 351 | 13300 | A | C |
| ATOM | 88 | C | PRO | A | 28 | 2.842 | −3.139 | 37.575 | 1.00 | 12.04 | | A | C |
| ANISOU | 88 | C | PRO | A | 28 | 1377 | 1099 | 1824 | −36 | −239 | 19 | A | C |
| SIGUIJ | 88 | C | PRO | A | 28 | 4 | 1 | 1 | 218 | 347 | 13302 | A | C |
| ATOM | 89 | O | PRO | A | 28 | 3.260 | −3.581 | 38.616 | 1.00 | 11.68 | | A | O |
| ANISOU | 89 | O | PRO | A | 28 | 1326 | 1114 | 1831 | −80 | −229 | 36 | A | O |
| SIGUIJ | 89 | O | PRO | A | 28 | 1 | 0 | 0 | 221 | 57 | 289 | A | O |
| ATOM | 90 | N | TRP | A | 29 | 3.566 | −2.991 | 36.501 | 1.00 | 11.90 | | A | N |
| ANISOU | 90 | N | TRP | A | 29 | 1528 | 1241 | 1911 | −72 | −107 | −4 | A | N |
| SIGUIJ | 90 | N | TRP | A | 29 | 1 | 0 | 0 | 221 | 65 | 290 | A | N |
| ATOM | 91 | CA | TRP | A | 29 | 4.996 | −3.300 | 36.496 | 1.00 | 12.18 | | A | C |
| ANISOU | 91 | CA | TRP | A | 29 | 1523 | 1332 | 1800 | −64 | −101 | 15 | A | C |
| SIGUIJ | 91 | CA | TRP | A | 29 | 4 | 1 | 1 | 218 | 342 | 13304 | A | C |
| ATOM | 92 | CB | TRP | A | 29 | 5.462 | −3.949 | 35.170 | 1.00 | 13.13 | | A | C |
| ANISOU | 92 | CB | TRP | A | 29 | 2014 | 1545 | 1850 | 145 | −35 | −22 | A | C |
| SIGUIJ | 92 | CB | TRP | A | 29 | 4 | 1 | 1 | 218 | 338 | 13306 | A | C |
| ATOM | 93 | CG | TRP | A | 29 | 4.557 | −3.677 | 34.063 | 1.00 | 14.19 | | A | C |
| ANISOU | 93 | CG | TRP | A | 29 | 1935 | 1421 | 1840 | 59 | 5 | 2 | A | C |
| SIGUIJ | 93 | CG | TRP | A | 29 | 4 | 1 | 1 | 218 | 334 | 13309 | A | C |
| ATOM | 94 | CD2 | TRP | A | 29 | 4.456 | −2.468 | 33.269 | 1.00 | 14.61 | | A | C |
| ANISOU | 94 | CD2 | TRP | A | 29 | 1678 | 1431 | 1845 | 15 | −7 | 0 | A | C |
| SIGUIJ | 94 | CD2 | TRP | A | 29 | 4 | 1 | 1 | 218 | 330 | 13311 | A | C |
| ATOM | 95 | CE2 | TRP | A | 29 | 3.367 | −2.647 | 32.397 | 1.00 | 14.65 | | A | C |
| ANISOU | 95 | CE2 | TRP | A | 29 | 1668 | 2320 | 1813 | −130 | 26 | 14 | A | C |
| SIGUIJ | 95 | CE2 | TRP | A | 29 | 4 | 1 | 1 | 218 | 326 | 13313 | A | C |
| ATOM | 96 | CE3 | TRP | A | 29 | 5.164 | −1.260 | 33.223 | 1.00 | 14.33 | | A | C |
| ANISOU | 96 | CE3 | TRP | A | 29 | 1697 | 1435 | 1778 | 16 | 3 | 0 | A | C |
| SIGUIJ | 96 | CE3 | TRP | A | 29 | 4 | 1 | 1 | 218 | 322 | 13316 | A | C |
| ATOM | 97 | CD1 | TRP | A | 29 | 3.550 | −4.500 | 33.613 | 1.00 | 15.11 | | A | C |
| ANISOU | 97 | CD1 | TRP | A | 29 | 2761 | 2440 | 1961 | −856 | −156 | 143 | A | C |
| SIGUIJ | 97 | CD1 | TRP | A | 29 | 4 | 1 | 1 | 218 | 319 | 13318 | A | C |
| ATOM | 98 | NE1 | TRP | A | 29 | 2.846 | −3.888 | 32.651 | 1.00 | 15.86 | | A | N |
| ANISOU | 98 | NE1 | TRP | A | 29 | 2881 | 2580 | 1940 | −698 | −148 | 114 | A | N |
| SIGUIJ | 98 | NE1 | TRP | A | 29 | 1 | 0 | 0 | 221 | 65 | 290 | A | N |
| ATOM | 99 | CZ2 | TRP | A | 29 | 2.979 | −1.691 | 31.498 | 1.00 | 15.40 | | A | C |
| ANISOU | 99 | CZ2 | TRP | A | 29 | 2058 | 2335 | 1811 | −28 | 17 | 0 | A | C |
| SIGUIJ | 99 | CZ2 | TRP | A | 29 | 4 | 1 | 1 | 218 | 315 | 13321 | A | C |
| ATOM | 100 | CZ3 | TRP | A | 29 | 4.756 | −0.305 | 32.310 | 1.00 | 14.89 | | A | C |
| ANISOU | 100 | CZ3 | TRP | A | 29 | 1979 | 1524 | 1775 | 179 | 30 | 17 | A | C |
| SIGUIJ | 100 | CZ3 | TRP | A | 29 | 4 | 1 | 1 | 218 | 312 | 13324 | A | C |
| ATOM | 101 | CH2 | TRP | A | 29 | 3.670 | −0.537 | 31.460 | 1.00 | 14.79 | | A | C |
| ANISOU | 101 | CH2 | TRP | A | 29 | 2012 | 2299 | 1774 | 13 | 28 | 0 | A | C |
| SIGUIJ | 101 | CH2 | TRP | A | 29 | 4 | 1 | 1 | 218 | 308 | 13326 | A | C |
| ATOM | 102 | C | TRP | A | 29 | 5.828 | −2.043 | 36.737 | 1.00 | 12.02 | | A | C |
| ANISOU | 102 | C | TRP | A | 29 | 1359 | 1288 | 1518 | 12 | 23 | 1 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 102 | C | TRP | A | 29 | 3 | 1 | 1 | 218 | 305 | 13329 | A | C |
| ATOM | 103 | O | TRP | A | 29 | 7.069 | −2.125 | 36.796 | 1.00 | 12.59 | | A | O |
| ANISOU | 103 | O | TRP | A | 29 | 1355 | 1715 | 2100 | 60 | 1 | 0 | A | O |
| SIGUIJ | 103 | O | TRP | A | 29 | 1 | 0 | 0 | 221 | 57 | 289 | A | O |
| ATOM | 104 | N | AGLN | A | 30 | 5.205 | −0.863 | 36.830 | 0.50 | 11.35 | | A | N |
| ANISOU | 104 | N | AGLN | A | 30 | 1329 | 1275 | 1273 | −2 | −1 | 0 | A | N |
| SIGUIJ | 104 | N | AGLN | A | 30 | 1 | 0 | 0 | 221 | 65 | 290 | A | N |
| ATOM | 105 | N | BGLN | A | 30 | 5.203 | −0.881 | 36.850 | 0.50 | 13.54 | | A | N |
| ANISOU | 105 | N | BGLN | A | 30 | 1323 | 1291 | 1407 | 0 | 0 | 0 | A | N |
| SIGUIJ | 105 | N | BGLN | A | 30 | 1 | 0 | 0 | 221 | 65 | 290 | A | N |
| ATOM | 106 | CA | AGLN | A | 30 | 5.894 | 0.403 | 37.181 | 0.50 | 11.36 | | A | C |
| ANISOU | 106 | CA | AGLN | A | 30 | 1320 | 1267 | 1269 | 0 | −2 | 0 | A | C |
| SIGUIJ | 106 | CA | AGLN | A | 30 | 3 | 1 | 1 | 218 | 302 | 13332 | A | C |
| ATOM | 107 | CA | BGLN | A | 30 | 5.970 | 0.313 | 37.155 | 0.50 | 13.55 | | A | C |
| ANISOU | 107 | CA | BGLN | A | 30 | 1312 | 1301 | 1399 | 0 | −2 | 0 | A | C |
| SIGUIJ | 107 | CA | BGLN | A | 30 | 3 | 1 | 1 | 218 | 299 | 13335 | A | C |
| ATOM | 108 | CB | AGLN | A | 30 | 5.001 | 1.609 | 36.822 | 0.50 | 12.26 | | A | C |
| ANISOU | 108 | CB | AGLN | A | 30 | 1333 | 1253 | 1305 | −2 | 0 | 0 | A | C |
| SIGUIJ | 108 | CB | AGLN | A | 30 | 3 | 1 | 1 | 218 | 296 | 13338 | A | C |
| ATOM | 109 | CB | BGLN | A | 30 | 5.267 | 1.540 | 36.592 | 0.50 | 14.45 | | A | C |
| ANISOU | 109 | CB | BGLN | A | 30 | 1335 | 1312 | 1452 | 0 | −6 | 0 | A | C |
| SIGUIJ | 109 | CB | BGLN | A | 30 | 3 | 1 | 2 | 219 | 294 | 13341 | A | C |
| ATOM | 110 | CG | AGLN | A | 30 | 5.508 | 3.025 | 37.334 | 0.50 | 14.52 | | A | C |
| ANISOU | 110 | CG | AGLN | A | 30 | 1371 | 1241 | 1278 | −7 | 1 | 0 | A | C |
| SIGUIJ | 110 | CG | AGLN | A | 30 | 3 | 1 | 2 | 219 | 291 | 13344 | A | C |
| ATOM | 111 | CG | BGLN | A | 30 | 6.161 | 2.794 | 36.722 | 0.50 | 16.71 | | A | C |
| ANISOU | 111 | CG | BGLN | A | 30 | 1348 | 1315 | 1580 | 0 | −35 | 0 | A | C |
| SIGUIJ | 111 | CG | BGLN | A | 30 | 3 | 1 | 2 | 219 | 288 | 13347 | A | C |
| ATOM | 112 | CD | AGLN | A | 30 | 6.288 | 3.795 | 36.261 | 0.50 | 14.95 | | A | C |
| ANISOU | 112 | CD | AGLN | A | 30 | 1351 | 1153 | 1282 | 37 | 5 | 2 | A | C |
| SIGUIJ | 112 | CD | AGLN | A | 30 | 3 | 1 | 1 | 219 | 286 | 13350 | A | C |
| ATOM | 113 | CD | BGLN | A | 30 | 6.013 | 3.746 | 35.560 | 0.50 | 17.14 | | A | C |
| ANISOU | 113 | CD | BGLN | A | 30 | 2113 | 1379 | 1582 | 255 | 76 | 29 | A | C |
| SIGUIJ | 113 | CD | BGLN | A | 30 | 3 | 1 | 1 | 35 | 2109 | 290 | A | C |
| ATOM | 114 | OE1 | AGLN | A | 30 | 5.876 | 3.821 | 35.118 | 0.50 | 16.06 | | A | O |
| ANISOU | 114 | OE1 | AGLN | A | 30 | 1451 | 2071 | 1288 | 196 | −24 | −17 | A | O |
| SIGUIJ | 114 | OE1 | AGLN | A | 30 | 1 | 0 | 0 | 221 | 57 | 289 | A | O |
| ATOM | 115 | OE1 | BGLN | A | 30 | 5.231 | 3.488 | 34.662 | 0.50 | 18.25 | | A | O |
| ANISOU | 115 | OE1 | BGLN | A | 30 | 2203 | 1420 | 1669 | 292 | −14 | −6 | A | O |
| SIGUIJ | 115 | OE1 | BGLN | A | 30 | 1 | 0 | 0 | 221 | 57 | 289 | A | O |
| ATOM | 116 | NE2 | AGLN | A | 30 | 7.403 | 4.428 | 36.640 | 0.50 | 16.36 | | A | N |
| ANISOU | 116 | NE2 | AGLN | A | 30 | 1381 | 1242 | 1350 | −6 | 0 | 0 | A | N |
| SIGUIJ | 116 | NE2 | AGLN | A | 30 | 1 | 0 | 0 | 221 | 65 | 289 | A | N |
| ATOM | 117 | NE2 | BGLN | A | 30 | 6.748 | 4.850 | 35.586 | 0.50 | 18.55 | | A | N |
| ANISOU | 117 | NE2 | BGLN | A | 30 | 1820 | 1249 | 1612 | 450 | 53 | 57 | A | N |
| SIGUIJ | 117 | NE2 | BGLN | A | 30 | 1 | 0 | 0 | 221 | 65 | 289 | A | N |
| ATOM | 118 | C | AGLN | A | 30 | 6.208 | 0.473 | 38.664 | 0.50 | 10.74 | | A | C |
| ANISOU | 118 | C | AGLN | A | 30 | 1091 | 1125 | 1264 | −1 | 15 | 0 | A | C |
| SIGUIJ | 118 | C | AGLN | A | 30 | 3 | 1 | 1 | 157 | 1501 | 290 | A | C |
| ATOM | 119 | C | BGLN | A | 30 | 6.210 | 0.474 | 38.651 | 0.50 | 12.93 | | A | C |
| ANISOU | 119 | C | BGLN | A | 30 | 1098 | 1088 | 1390 | 0 | 1 | 0 | A | C |
| SIGUIJ | 119 | C | BGLN | A | 30 | 3 | 1 | 1 | 181 | 1228 | 290 | A | C |
| ATOM | 120 | O | AGLN | A | 30 | 5.337 | 0.147 | 39.489 | 0.50 | 10.87 | | A | O |
| ANISOU | 120 | O | AGLN | A | 30 | 1106 | 1331 | 1279 | −50 | 25 | 6 | A | O |
| SIGUIJ | 120 | O | AGLN | A | 30 | 1 | 0 | 0 | 221 | 57 | 289 | A | O |
| ATOM | 121 | O | BGLN | A | 30 | 5.317 | 0.188 | 39.463 | 0.50 | 13.06 | | A | O |
| ANISOU | 121 | O | BGLN | A | 30 | 1169 | 1313 | 1472 | −63 | 66 | 19 | A | O |
| SIGUIJ | 121 | O | BGLN | A | 30 | 1 | 0 | 0 | 221 | 57 | 289 | A | O |
| ATOM | 122 | N | VAL | A | 31 | 7.422 | 0.905 | 39.005 | 1.00 | 9.60 | | A | N |
| ANISOU | 122 | N | VAL | A | 31 | 1089 | 1057 | 1213 | 5 | 14 | 1 | A | N |
| SIGUIJ | 122 | N | VAL | A | 31 | 1 | 0 | 0 | 221 | 65 | 289 | A | N |
| ATOM | 123 | CA | VAL | A | 31 | 7.763 | 1.199 | 40.367 | 1.00 | 9.54 | | A | C |
| ANISOU | 123 | CA | VAL | A | 31 | 1166 | 1082 | 1207 | −8 | 1 | 0 | A | C |
| SIGUIJ | 123 | CA | VAL | A | 31 | 3 | 1 | 1 | 191 | 1065 | 290 | A | C |
| ATOM | 124 | CB | VAL | A | 31 | 8.754 | 0.156 | 40.963 | 1.00 | 9.53 | | A | C |
| ANISOU | 124 | CB | VAL | A | 31 | 1198 | 1106 | 1235 | 11 | −1 | 0 | A | C |
| SIGUIJ | 124 | CB | VAL | A | 31 | 3 | 1 | 1 | 197 | 953 | 290 | A | C |
| ATOM | 125 | CG1 | VAL | A | 31 | 8.192 | −1.238 | 40.888 | 1.00 | 10.19 | | A | C |
| ANISOU | 125 | CG1 | VAL | A | 31 | 1457 | 1140 | 1524 | −82 | −5 | −3 | A | C |
| SIGUIJ | 125 | CG1 | VAL | A | 31 | 3 | 1 | 1 | 201 | 870 | 290 | A | C |
| ATOM | 126 | CG2 | VAL | A | 31 | 10.134 | 0.266 | 40.296 | 1.00 | 9.91 | | A | C |
| ANISOU | 126 | CG2 | VAL | A | 31 | 1206 | 1164 | 1260 | 3 | 4 | 0 | A | C |
| SIGUIJ | 126 | CG2 | VAL | A | 31 | 3 | 1 | 1 | 204 | 806 | 290 | A | C |
| ATOM | 127 | C | VAL | A | 31 | 8.337 | 2.615 | 40.423 | 1.00 | 9.25 | | A | C |
| ANISOU | 127 | C | VAL | A | 31 | 1145 | 1079 | 1094 | 12 | 1 | 0 | A | C |
| SIGUIJ | 127 | C | VAL | A | 31 | 3 | 1 | 1 | 206 | 754 | 290 | A | C |
| ATOM | 128 | O | VAL | A | 31 | 8.676 | 3.230 | 39.417 | 1.00 | 9.42 | | A | O |
| ANISOU | 128 | O | VAL | A | 31 | 1235 | 1123 | 1098 | 8 | 18 | 1 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 128 | O | VAL | A | 31 | 1 | 0 | 0 | 221 | 57 | 289 | A | O |
| ATOM | 129 | N | ALA | A | 32 | 8.436 | 3.153 | 41.652 | 1.00 | 9.37 | | A | N |
| ANISOU | 129 | N | ALA | A | 32 | 1272 | 1099 | 1098 | −23 | 16 | −2 | A | N |
| SIGUIJ | 129 | N | ALA | A | 32 | 1 | 0 | 0 | 221 | 65 | 289 | A | N |
| ATOM | 130 | CA | ALA | A | 32 | 9.210 | 4.366 | 41.898 | 1.00 | 9.78 | | A | C |
| ANISOU | 130 | CA | ALA | A | 32 | 1249 | 1094 | 1197 | −13 | −1 | 0 | A | C |
| SIGUIJ | 130 | CA | ALA | A | 32 | 3 | 1 | 0 | 208 | 711 | 290 | A | C |
| ATOM | 131 | CB | ALA | A | 32 | 8.351 | 5.460 | 42.481 | 1.00 | 9.76 | | A | C |
| ANISOU | 131 | CB | ALA | A | 32 | 1359 | 1149 | 1201 | 66 | 10 | 3 | A | C |
| SIGUIJ | 131 | CB | ALA | A | 32 | 3 | 1 | 0 | 209 | 675 | 290 | A | C |
| ATOM | 132 | C | ALA | A | 32 | 10.330 | 4.050 | 42.873 | 1.00 | 10.12 | | A | C |
| ANISOU | 132 | C | ALA | A | 32 | 1242 | 1129 | 1199 | −11 | −1 | 0 | A | C |
| SIGUIJ | 132 | C | ALA | A | 32 | 3 | 1 | 0 | 210 | 643 | 290 | A | C |
| ATOM | 133 | O | ALA | A | 32 | 10.139 | 3.271 | 43.844 | 1.00 | 10.36 | | A | O |
| ANISOU | 133 | O | ALA | A | 32 | 1456 | 1231 | 1233 | −165 | −69 | 41 | A | O |
| SIGUIJ | 133 | O | ALA | A | 32 | 1 | 0 | 0 | 221 | 57 | 289 | A | O |
| ATOM | 134 | N | LEU | A | 33 | 11.476 | 4.682 | 42.664 | 1.00 | 10.54 | | A | N |
| ANISOU | 134 | N | LEU | A | 33 | 1224 | 1112 | 1226 | 3 | 0 | 0 | A | N |
| SIGUIJ | 134 | N | LEU | A | 33 | 1 | 0 | 0 | 221 | 65 | 289 | A | N |
| ATOM | 135 | CA | LEU | A | 33 | 12.560 | 4.613 | 43.607 | 1.00 | 11.11 | | A | C |
| ANISOU | 135 | CA | LEU | A | 33 | 1222 | 1142 | 1244 | 7 | −3 | 0 | A | C |
| SIGUIJ | 135 | CA | LEU | A | 33 | 3 | 1 | 0 | 211 | 616 | 290 | A | C |
| ATOM | 136 | CB | LEU | A | 33 | 13.898 | 4.466 | 42.877 | 1.00 | 12.76 | | A | C |
| ANISOU | 136 | CB | LEU | A | 33 | 1307 | 1723 | 1534 | 78 | 145 | −32 | A | C |
| SIGUIJ | 136 | CB | LEU | A | 33 | 3 | 1 | 0 | 212 | 592 | 290 | A | C |
| ATOM | 137 | CG | LEU | A | 33 | 14.013 | 3.133 | 42.096 | 1.00 | 13.82 | | A | C |
| ANISOU | 137 | CG | LEU | A | 33 | 2005 | 1782 | 1606 | 316 | −131 | −94 | A | C |
| SIGUIJ | 137 | CG | LEU | A | 33 | 3 | 1 | 0 | 213 | 570 | 290 | A | C |
| ATOM | 138 | CD1 | LEU | A | 33 | 15.339 | 3.077 | 41.298 | 1.00 | 15.26 | | A | C |
| ANISOU | 138 | CD1 | LEU | A | 33 | 2152 | 3310 | 1943 | 551 | 89 | 191 | A | C |
| SIGUIJ | 138 | CD1 | LEU | A | 33 | 3 | 1 | 0 | 213 | 551 | 290 | A | C |
| ATOM | 139 | CD2 | LEU | A | 33 | 13.824 | 1.976 | 43.017 | 1.00 | 14.92 | | A | C |
| ANISOU | 139 | CD2 | LEU | A | 33 | 3327 | 1868 | 1759 | 214 | 9 | 1 | A | C |
| SIGUIJ | 139 | CD2 | LEU | A | 33 | 3 | 1 | 0 | 214 | 534 | 290 | A | C |
| ATOM | 140 | C | LEU | A | 33 | 12.540 | 5.910 | 44.392 | 1.00 | 11.52 | | A | C |
| ANISOU | 140 | C | LEU | A | 33 | 1208 | 1140 | 1249 | −7 | −1 | 0 | A | C |
| SIGUIJ | 140 | C | LEU | A | 33 | 3 | 1 | 0 | 214 | 518 | 290 | A | C |
| ATOM | 141 | O | LEU | A | 33 | 12.664 | 7.004 | 43.780 | 1.00 | 10.87 | | A | O |
| ANISOU | 141 | O | LEU | A | 33 | 1395 | 1137 | 1241 | −18 | 13 | −1 | A | O |
| SIGUIJ | 141 | O | LEU | A | 33 | 1 | 0 | 0 | 221 | 57 | 289 | A | O |
| ATOM | 142 | N | LEU | A | 34 | 12.396 | 5.788 | 45.715 | 1.00 | 11.68 | | A | N |
| ANISOU | 142 | N | LEU | A | 34 | 1170 | 1376 | 1248 | 15 | 3 | 0 | A | N |
| SIGUIJ | 142 | N | LEU | A | 34 | 1 | 0 | 0 | 221 | 65 | 289 | A | N |
| ATOM | 143 | CA | LEU | A | 34 | 12.314 | 6.943 | 46.604 | 1.00 | 12.60 | | A | C |
| ANISOU | 143 | CA | LEU | A | 34 | 1479 | 1370 | 1243 | 7 | 73 | 3 | A | C |
| SIGUIJ | 143 | CA | LEU | A | 34 | 3 | 1 | 0 | 214 | 503 | 290 | A | C |
| ATOM | 144 | CB | LEU | A | 34 | 11.081 | 6.842 | 47.541 | 1.00 | 12.95 | | A | C |
| ANISOU | 144 | CB | LEU | A | 34 | 1514 | 1734 | 1296 | −17 | 119 | 10 | A | C |
| SIGUIJ | 144 | CB | LEU | A | 34 | 3 | 1 | 0 | 215 | 490 | 290 | A | C |
| ATOM | 145 | CG | LEU | A | 34 | 9.777 | 6.385 | 46.830 | 1.00 | 12.96 | | A | C |
| ANISOU | 145 | CG | LEU | A | 34 | 1607 | 1906 | 1508 | −69 | −3 | 1 | A | C |
| SIGUIJ | 145 | CG | LEU | A | 34 | 3 | 1 | 0 | 215 | 477 | 290 | A | C |
| ATOM | 146 | CD1 | LEU | A | 34 | 8.650 | 6.238 | 47.872 | 1.00 | 13.74 | | A | C |
| ANISOU | 146 | CD1 | LEU | A | 34 | 1687 | 2206 | 1548 | −130 | 51 | −19 | A | C |
| SIGUIJ | 146 | CD1 | LEU | A | 34 | 3 | 1 | 0 | 215 | 466 | 290 | A | C |
| ATOM | 147 | CD2 | LEU | A | 34 | 9.357 | 7.365 | 45.767 | 1.00 | 13.15 | | A | C |
| ANISOU | 147 | CD2 | LEU | A | 34 | 1786 | 1933 | 1514 | 11 | −1 | 0 | A | C |
| SIGUIJ | 147 | CD2 | LEU | A | 34 | 3 | 1 | 0 | 216 | 455 | 290 | A | C |
| ATOM | 148 | C | LEU | A | 34 | 13.565 | 7.002 | 47.468 | 1.00 | 13.57 | | A | C |
| ANISOU | 148 | C | LEU | A | 34 | 1511 | 1624 | 1306 | −12 | 30 | 1 | A | C |
| SIGUIJ | 148 | C | LEU | A | 34 | 3 | 1 | 0 | 216 | 445 | 290 | A | C |
| ATOM | 149 | O | LEU | A | 34 | 14.159 | 5.987 | 47.850 | 1.00 | 13.68 | | A | O |
| ANISOU | 149 | O | LEU | A | 34 | 1564 | 1637 | 1416 | 2 | −11 | 0 | A | O |
| SIGUIJ | 149 | O | LEU | A | 34 | 1 | 0 | 0 | 221 | 57 | 289 | A | O |
| ATOM | 150 | N | SER | A | 35 | 13.936 | 8.232 | 47.793 | 1.00 | 14.73 | | A | N |
| ANISOU | 150 | N | SER | A | 35 | 1898 | 1654 | 1350 | −116 | −70 | 21 | A | N |
| SIGUIJ | 150 | N | SER | A | 35 | 1 | 0 | 0 | 221 | 65 | 289 | A | N |
| ATOM | 151 | CA | SER | A | 35 | 14.881 | 8.464 | 48.857 | 1.00 | 16.41 | | A | C |
| ANISOU | 151 | CA | SER | A | 35 | 2180 | 2469 | 1578 | −157 | −305 | −116 | A | C |
| SIGUIJ | 151 | CA | SER | A | 35 | 3 | 1 | 0 | 216 | 436 | 290 | A | C |
| ATOM | 152 | CB | SER | A | 35 | 15.753 | 9.660 | 48.459 | 1.00 | 17.26 | | A | C |
| ANISOU | 152 | CB | SER | A | 35 | 2216 | 2459 | 2653 | −95 | 0 | 0 | A | C |
| SIGUIJ | 152 | CB | SER | A | 35 | 3 | 1 | 0 | 216 | 427 | 290 | A | C |
| ATOM | 153 | OG | SER | A | 35 | 16.663 | 9.949 | 49.532 | 1.00 | 19.50 | | A | O |
| ANISOU | 153 | OG | SER | A | 35 | 2541 | 5015 | 2800 | −738 | −110 | −149 | A | O |
| SIGUIJ | 153 | OG | SER | A | 35 | 1 | 0 | 0 | 221 | 57 | 289 | A | O |
| ATOM | 154 | C | SER | A | 35 | 14.032 | 8.785 | 50.083 | 1.00 | 16.90 | | A | C |
| ANISOU | 154 | C | SER | A | 35 | 2398 | 2366 | 1625 | −6 | −193 | 2 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 154 | C | SER | A | 35 | 3 | 1 | 0 | 216 | 419 | 290 | A | C |
| ATOM | 155 | O | SER | A | 35 | 13.521 | 9.891 | 50.175 | 1.00 | 16.99 | | A | O |
| ANISOU | 155 | O | SER | A | 35 | 2400 | 2365 | 1781 | 0 | −161 | −2 | A | O |
| SIGUIJ | 155 | O | SER | A | 35 | 1 | 0 | 0 | 221 | 57 | 289 | A | O |
| ATOM | 156 | N | GLY | A | 36 | 13.870 | 7.816 | 50.996 | 1.00 | 17.66 | | A | N |
| ANISOU | 156 | N | GLY | A | 36 | 2457 | 2401 | 1660 | −24 | −183 | 29 | A | N |
| SIGUIJ | 156 | N | GLY | A | 36 | 1 | 0 | 0 | 221 | 65 | 289 | A | N |
| ATOM | 157 | CA | GLY | A | 36 | 12.902 | 7.996 | 52.076 | 1.00 | 18.35 | | A | C |
| ANISOU | 157 | CA | GLY | A | 36 | 2983 | 2300 | 2129 | −149 | 320 | −62 | A | C |
| SIGUIJ | 157 | CA | GLY | A | 36 | 3 | 1 | 0 | 217 | 411 | 290 | A | C |
| ATOM | 158 | C | GLY | A | 36 | 11.499 | 8.004 | 51.475 | 1.00 | 18.74 | | A | C |
| ANISOU | 158 | C | GLY | A | 36 | 2927 | 2453 | 1870 | −152 | 436 | −76 | A | C |
| SIGUIJ | 158 | C | GLY | A | 36 | 3 | 1 | 0 | 217 | 404 | 290 | A | C |
| ATOM | 159 | O | GLY | A | 36 | 11.031 | 6.959 | 50.980 | 1.00 | 19.36 | | A | O |
| ANISOU | 159 | O | GLY | A | 36 | 3305 | 2782 | 2182 | −526 | 835 | −406 | A | O |
| SIGUIJ | 159 | O | GLY | A | 36 | 1 | 0 | 0 | 221 | 57 | 289 | A | O |
| ATOM | 160 | N | AASN | A | 38 | 10.841 | 9.156 | 51.477 | 0.50 | 19.21 | | A | N |
| ANISOU | 160 | N | AASN | A | 38 | 2998 | 2481 | 1260 | −106 | 463 | −60 | A | N |
| SIGUIJ | 160 | N | AASN | A | 38 | 1 | 0 | 0 | 221 | 65 | 289 | A | N |
| ATOM | 161 | N | BASN | A | 38 | 10.837 | 9.161 | 51.484 | 0.50 | 21.40 | | A | N |
| ANISOU | 161 | N | BASN | A | 38 | 2935 | 2451 | 1681 | −163 | 415 | −91 | A | N |
| SIGUIJ | 161 | N | BASN | A | 38 | 1 | 0 | 0 | 221 | 65 | 289 | A | N |
| ATOM | 162 | CA | AASN | A | 38 | 9.525 | 9.292 | 50.867 | 0.50 | 19.45 | | A | C |
| ANISOU | 162 | CA | AASN | A | 38 | 3071 | 2625 | 1630 | −86 | 299 | −37 | A | C |
| SIGUIJ | 162 | CA | AASN | A | 38 | 3 | 1 | 0 | 217 | 397 | 290 | A | C |
| ATOM | 163 | CA | BASN | A | 38 | 9.584 | 9.336 | 50.746 | 0.50 | 21.64 | | A | C |
| ANISOU | 163 | CA | BASN | A | 38 | 3238 | 2455 | 2604 | −245 | −109 | 36 | A | C |
| SIGUIJ | 163 | CA | BASN | A | 38 | 3 | 1 | 0 | 217 | 390 | 290 | A | C |
| ATOM | 164 | CB | AASN | A | 38 | 8.565 | 9.931 | 51.867 | 0.50 | 21.32 | | A | C |
| ANISOU | 164 | CB | AASN | A | 38 | 3969 | 3097 | 1906 | 520 | 779 | 254 | A | C |
| SIGUIJ | 164 | CB | AASN | A | 38 | 3 | 1 | 0 | 217 | 384 | 290 | A | C |
| ATOM | 165 | CB | BASN | A | 38 | 8.446 | 9.760 | 51.678 | 0.50 | 23.51 | | A | C |
| ANISOU | 165 | CB | BASN | A | 38 | 3600 | 3504 | 2904 | 159 | 143 | 64 | A | C |
| SIGUIJ | 165 | CB | BASN | A | 38 | 3 | 1 | 0 | 217 | 378 | 290 | A | C |
| ATOM | 166 | CG | AASN | A | 38 | 9.047 | 11.305 | 52.305 | 0.50 | 22.29 | | A | C |
| ANISOU | 166 | CG | AASN | A | 38 | 4334 | 3158 | 2340 | 437 | 629 | 163 | A | C |
| SIGUIJ | 166 | CG | AASN | A | 38 | 3 | 1 | 0 | 217 | 372 | 290 | A | C |
| ATOM | 167 | CG | BASN | A | 38 | 7.797 | 8.601 | 52.331 | 0.50 | 24.48 | | A | C |
| ANISOU | 167 | CG | BASN | A | 38 | 3999 | 3561 | 3006 | 25 | 316 | 14 | A | C |
| SIGUIJ | 167 | CG | BASN | A | 38 | 3 | 1 | 0 | 217 | 366 | 290 | A | C |
| ATOM | 168 | OD1 | AASN | A | 38 | 9.518 | 11.483 | 53.418 | 0.50 | 23.94 | | A | O |
| ANISOU | 168 | OD1 | AASN | A | 38 | 13642 | 4902 | 4099 | 786 | −3366 | −264 | A | O |
| SIGUIJ | 168 | OD1 | AASN | A | 38 | 1 | 0 | 0 | 221 | 57 | 289 | A | O |
| ATOM | 169 | OD1 | BASN | A | 38 | 7.643 | 8.557 | 53.549 | 0.50 | 26.13 | | A | O |
| ANISOU | 169 | OD1 | BASN | A | 38 | 4651 | 7786 | 3014 | −907 | 366 | 32 | A | O |
| SIGUIJ | 169 | OD1 | BASN | A | 38 | 1 | 0 | 0 | 221 | 57 | 289 | A | O |
| ATOM | 170 | ND2 | AASN | A | 38 | 8.954 | 12.272 | 51.420 | 0.50 | 23.58 | | A | N |
| ANISOU | 170 | ND2 | AASN | A | 38 | 3506 | 2961 | 2202 | −23 | 218 | −6 | A | N |
| SIGUIJ | 170 | ND2 | AASN | A | 38 | 1 | 0 | 0 | 221 | 65 | 289 | A | N |
| ATOM | 171 | ND2 | BASN | A | 38 | 7.399 | 7.631 | 51.525 | 0.50 | 25.77 | | A | N |
| ANISOU | 171 | ND2 | BASN | A | 38 | 5305 | 3691 | 3182 | −249 | −8 | 1 | A | N |
| SIGUIJ | 171 | ND2 | BASN | A | 38 | 1 | 0 | 0 | 221 | 65 | 289 | A | N |
| ATOM | 172 | C | AASN | A | 38 | 9.587 | 10.171 | 49.609 | 0.50 | 18.94 | | A | C |
| ANISOU | 172 | C | AASN | A | 38 | 2703 | 2575 | 1608 | −86 | 266 | −69 | A | C |
| SIGUIJ | 172 | C | AASN | A | 38 | 3 | 1 | 0 | 217 | 361 | 290 | A | C |
| ATOM | 173 | C | BASN | A | 38 | 9.640 | 10.322 | 49.580 | 0.50 | 21.13 | | A | C |
| ANISOU | 173 | C | BASN | A | 38 | 2703 | 2394 | 2572 | −42 | 49 | −10 | A | C |
| SIGUIJ | 173 | C | BASN | A | 38 | 3 | 1 | 0 | 218 | 356 | 290 | A | C |
| ATOM | 174 | O | AASN | A | 38 | 8.557 | 10.475 | 49.008 | 0.50 | 19.09 | | A | O |
| ANISOU | 174 | O | AASN | A | 38 | 2944 | 2973 | 2298 | −1 | −114 | −3 | A | O |
| SIGUIJ | 174 | O | AASN | A | 38 | 1 | 0 | 0 | 221 | 57 | 289 | A | O |
| ATOM | 175 | O | BASN | A | 38 | 8.597 | 10.687 | 49.032 | 0.50 | 21.28 | | A | O |
| ANISOU | 175 | O | BASN | A | 38 | 2746 | 2555 | 2688 | 7 | −5 | 0 | A | O |
| SIGUIJ | 175 | O | BASN | A | 38 | 1 | 0 | 0 | 221 | 57 | 289 | A | O |
| ATOM | 176 | N | AGLN | A | 39 | 10.789 | 10.602 | 49.221 | 0.50 | 17.84 | | A | N |
| ANISOU | 176 | N | AGLN | A | 39 | 2564 | 1698 | 1697 | 277 | 233 | 69 | A | N |
| SIGUIJ | 176 | N | AGLN | A | 39 | 1 | 0 | 0 | 221 | 65 | 289 | A | N |
| ATOM | 177 | N | BGLN | A | 39 | 10.842 | 10.756 | 49.195 | 0.50 | 20.03 | | A | N |
| ANISOU | 177 | N | BGLN | A | 39 | 2585 | 2227 | 1629 | 17 | −247 | −9 | A | N |
| SIGUIJ | 177 | N | BGLN | A | 39 | 1 | 0 | 0 | 221 | 65 | 289 | A | N |
| ATOM | 178 | CA | AGLN | A | 39 | 10.911 | 11.552 | 48.118 | 0.50 | 16.87 | | A | C |
| ANISOU | 178 | CA | AGLN | A | 39 | 2168 | 1642 | 1636 | 149 | 59 | 16 | A | C |
| SIGUIJ | 178 | CA | AGLN | A | 39 | 3 | 1 | 0 | 218 | 351 | 290 | A | C |
| ATOM | 179 | CA | BGLN | A | 39 | 10.968 | 11.684 | 48.078 | 0.50 | 19.06 | | A | C |
| ANISOU | 179 | CA | BGLN | A | 39 | 2140 | 2182 | 1656 | 365 | −2 | −1 | A | C |
| SIGUIJ | 179 | CA | BGLN | A | 39 | 3 | 1 | 0 | 218 | 346 | 290 | A | C |
| ATOM | 180 | CB | AGLN | A | 39 | 12.010 | 12.556 | 48.439 | 0.50 | 18.21 | | A | C |
| ANISOU | 180 | CB | AGLN | A | 39 | 2485 | 2055 | 1554 | −214 | 134 | −43 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 180 | CB | AGLN | A | 39 | 3 | 1 | 0 | 218 | 342 | 290 | A | C |
| ATOM | 181 | CB | BGLN | A | 39 | 12.119 | 12.679 | 48.323 | 0.50 | 20.40 | | A | C |
| ANISOU | 181 | CB | BGLN | A | 39 | 2467 | 2609 | 1793 | −4 | −34 | 2 | A | C |
| SIGUIJ | 181 | CB | BGLN | A | 39 | 3 | 1 | 0 | 218 | 338 | 290 | A | C |
| ATOM | 182 | CG | AGLN | A | 39 | 11.590 | 13.519 | 49.543 | 0.50 | 20.94 | | A | C |
| ANISOU | 182 | CG | AGLN | A | 39 | 4813 | 2247 | 1558 | 498 | 400 | 67 | A | C |
| SIGUIJ | 182 | CG | AGLN | A | 39 | 3 | 1 | 0 | 218 | 334 | 290 | A | C |
| ATOM | 183 | CG | BGLN | A | 39 | 12.162 | 13.856 | 47.333 | 0.50 | 23.13 | | A | C |
| ANISOU | 183 | CG | BGLN | A | 39 | 6609 | 2671 | 1942 | 540 | 793 | 97 | A | C |
| SIGUIJ | 183 | CG | BGLN | A | 39 | 3 | 1 | 0 | 218 | 330 | 290 | A | C |
| ATOM | 184 | CD | AGLN | A | 39 | 10.530 | 14.487 | 49.057 | 0.50 | 22.09 | | A | C |
| ANISOU | 184 | CD | AGLN | A | 39 | 4844 | 1804 | 3110 | 132 | −396 | −23 | A | C |
| SIGUIJ | 184 | CD | AGLN | A | 39 | 3 | 1 | 0 | 218 | 326 | 290 | A | C |
| ATOM | 185 | CD | BGLN | A | 39 | 13.249 | 14.884 | 47.642 | 0.50 | 24.28 | | A | C |
| ANISOU | 185 | CD | BGLN | A | 39 | 7887 | 3880 | 5011 | −575 | 13 | −2 | A | C |
| SIGUIJ | 185 | CD | BGLN | A | 39 | 3 | 1 | 0 | 218 | 322 | 290 | A | C |
| ATOM | 186 | OE1 | AGLN | A | 39 | 10.757 | 15.244 | 48.122 | 0.50 | 23.85 | | A | O |
| ANISOU | 186 | OE1 | AGLN | A | 39 | 7952 | 1817 | 3362 | 285 | 481 | 26 | A | O |
| SIGUIJ | 186 | OE1 | AGLN | A | 39 | 1 | 0 | 0 | 221 | 57 | 289 | A | O |
| ATOM | 187 | OE1 | BGLN | A | 39 | 14.098 | 14.668 | 48.508 | 0.50 | 26.04 | | A | O |
| ANISOU | 187 | OE1 | BGLN | A | 39 | 9118 | 6539 | 6004 | 151 | −1012 | −51 | A | O |
| SIGUIJ | 187 | OE1 | BGLN | A | 39 | 1 | 0 | 0 | 221 | 57 | 289 | A | O |
| ATOM | 188 | NE2 | AGLN | A | 39 | 9.365 | 14.454 | 49.682 | 0.50 | 23.39 | | A | N |
| ANISOU | 188 | NE2 | AGLN | A | 39 | 5096 | 5212 | 3983 | 41 | 71 | −10 | A | N |
| SIGUIJ | 188 | NE2 | AGLN | A | 39 | 1 | 0 | 0 | 221 | 65 | 289 | A | N |
| ATOM | 189 | NE2 | BGLN | A | 39 | 13.221 | 16.010 | 46.939 | 0.50 | 25.58 | | A | N |
| ANISOU | 189 | NE2 | BGLN | A | 39 | 6178 | 3851 | 4926 | −526 | 159 | −50 | A | N |
| SIGUIJ | 189 | NE2 | BGLN | A | 39 | 1 | 0 | 0 | 221 | 65 | 289 | A | N |
| ATOM | 190 | C | AGLN | A | 39 | 11.215 | 10.869 | 46.777 | 0.50 | 15.25 | | A | C |
| ANISOU | 190 | C | AGLN | A | 39 | 1586 | 1583 | 1636 | 0 | 0 | 0 | A | C |
| SIGUIJ | 190 | C | AGLN | A | 39 | 3 | 1 | 0 | 218 | 318 | 290 | A | C |
| ATOM | 191 | C | BGLN | A | 39 | 11.231 | 10.914 | 46.773 | 0.50 | 17.44 | | A | C |
| ANISOU | 191 | C | BGLN | A | 39 | 1636 | 2081 | 1649 | 161 | −1 | 3 | A | C |
| SIGUIJ | 191 | C | BGLN | A | 39 | 3 | 1 | 0 | 218 | 315 | 290 | A | C |
| ATOM | 192 | O | AGLN | A | 39 | 12.145 | 10.050 | 46.676 | 0.50 | 14.48 | | A | O |
| ANISOU | 192 | O | AGLN | A | 39 | 1594 | 1581 | 1457 | 0 | −14 | 0 | A | O |
| SIGUIJ | 192 | O | AGLN | A | 39 | 1 | 0 | 0 | 221 | 57 | 289 | A | O |
| ATOM | 193 | O | BGLN | A | 39 | 12.138 | 10.069 | 46.696 | 0.50 | 16.67 | | A | O |
| ANISOU | 193 | O | BGLN | A | 39 | 1674 | 2111 | 1542 | 191 | −4 | −4 | A | O |
| SIGUIJ | 193 | O | BGLN | A | 39 | 1 | 0 | 0 | 221 | 57 | 289 | A | O |
| ATOM | 194 | N | LEU | A | 40 | 10.460 | 11.236 | 45.742 | 1.00 | 13.93 | | A | N |
| ANISOU | 194 | N | LEU | A | 40 | 1491 | 1582 | 1598 | −2 | 66 | 1 | A | N |
| SIGUIJ | 194 | N | LEU | A | 40 | 1 | 0 | 0 | 221 | 65 | 289 | A | N |
| ATOM | 195 | CA | LEU | A | 40 | 10.683 | 10.606 | 44.410 | 1.00 | 12.92 | | A | C |
| ANISOU | 195 | CA | LEU | A | 40 | 1356 | 1524 | 1597 | −31 | 53 | 8 | A | C |
| SIGUIJ | 195 | CA | LEU | A | 40 | 3 | 1 | 0 | 218 | 312 | 290 | A | C |
| ATOM | 196 | CB | LEU | A | 40 | 9.769 | 11.223 | 43.394 | 1.00 | 12.72 | | A | C |
| ANISOU | 196 | CB | LEU | A | 40 | 1493 | 1494 | 1694 | −1 | −55 | −8 | A | C |
| SIGUIJ | 196 | CB | LEU | A | 40 | 3 | 1 | 0 | 218 | 308 | 290 | A | C |
| ATOM | 197 | CG | LEU | A | 40 | 10.039 | 10.715 | 41.963 | 1.00 | 12.55 | | A | C |
| ANISOU | 197 | CG | LEU | A | 40 | 1722 | 1387 | 1706 | −5 | 0 | 0 | A | C |
| SIGUIJ | 197 | CG | LEU | A | 40 | 3 | 1 | 0 | 218 | 305 | 290 | A | C |
| ATOM | 198 | CD1 | LEU | A | 40 | 9.679 | 9.246 | 41.850 | 1.00 | 12.53 | | A | C |
| ANISOU | 198 | CD1 | LEU | A | 40 | 1609 | 1377 | 1747 | 14 | 2 | 0 | A | C |
| SIGUIJ | 198 | CD1 | LEU | A | 40 | 3 | 1 | 0 | 218 | 302 | 290 | A | C |
| ATOM | 199 | CD2 | LEU | A | 40 | 9.166 | 11.497 | 40.989 | 1.00 | 12.87 | | A | C |
| ANISOU | 199 | CD2 | LEU | A | 40 | 2090 | 1780 | 1721 | 377 | −27 | −22 | A | C |
| SIGUIJ | 199 | CD2 | LEU | A | 40 | 3 | 1 | 0 | 218 | 299 | 290 | A | C |
| ATOM | 200 | C | LEU | A | 40 | 12.119 | 10.859 | 43.997 | 1.00 | 12.46 | | A | C |
| ANISOU | 200 | C | LEU | A | 40 | 1335 | 1197 | 1424 | 25 | 5 | 0 | A | C |
| SIGUIJ | 200 | C | LEU | A | 40 | 3 | 1 | 0 | 218 | 296 | 290 | A | C |
| ATOM | 201 | O | LEU | A | 40 | 12.604 | 12.013 | 44.012 | 1.00 | 12.88 | | A | O |
| ANISOU | 201 | O | LEU | A | 40 | 1625 | 1248 | 1672 | −94 | 3 | 3 | A | O |
| SIGUIJ | 201 | O | LEU | A | 40 | 1 | 0 | 0 | 221 | 57 | 289 | A | O |
| ATOM | 202 | N | HIS | A | 41 | 12.788 | 9.810 | 43.565 | 1.00 | 11.50 | | A | N |
| ANISOU | 202 | N | HIS | A | 41 | 1248 | 1160 | 1302 | −24 | 1 | 0 | A | N |
| SIGUIJ | 202 | N | HIS | A | 41 | 1 | 0 | 0 | 221 | 65 | 289 | A | N |
| ATOM | 203 | CA | HIS | A | 41 | 14.095 | 9.947 | 42.933 | 1.00 | 10.71 | | A | C |
| ANISOU | 203 | CA | HIS | A | 41 | 1249 | 1155 | 1274 | −28 | 0 | 0 | A | C |
| SIGUIJ | 203 | CA | HIS | A | 41 | 3 | 1 | 0 | 219 | 293 | 290 | A | C |
| ATOM | 204 | CB | HIS | A | 41 | 15.128 | 9.142 | 43.722 | 1.00 | 10.98 | | A | C |
| ANISOU | 204 | CB | HIS | A | 41 | 1266 | 1209 | 1307 | −4 | −1 | 0 | A | C |
| SIGUIJ | 204 | CB | HIS | A | 41 | 3 | 1 | 0 | 219 | 291 | 290 | A | C |
| ATOM | 205 | CG | HIS | A | 41 | 16.523 | 9.500 | 43.347 | 1.00 | 10.96 | | A | C |
| ANISOU | 205 | CG | HIS | A | 41 | 1281 | 1429 | 1279 | −91 | 2 | 6 | A | C |
| SIGUIJ | 205 | CG | HIS | A | 41 | 2 | 1 | 0 | 219 | 288 | 290 | A | C |
| ATOM | 206 | CD2 | HIS | A | 41 | 17.517 | 8.800 | 42.755 | 1.00 | 10.94 | | A | C |
| ANISOU | 206 | CD2 | HIS | A | 41 | 1306 | 1513 | 1249 | −42 | −1 | 0 | A | C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 206 | CD2 | HIS | A | 41 | 2 | 1 | 0 | 219 | 285 | 290 | A | C |
| ATOM | 207 | ND1 | HIS | A | 41 | 17.048 | 10.749 | 43.618 | 1.00 | 11.76 | | A | N |
| ANISOU | 207 | ND1 | HIS | A | 41 | 1482 | 1474 | 1696 | −178 | −65 | −59 | A | N |
| SIGUIJ | 207 | ND1 | HIS | A | 41 | 1 | 0 | 0 | 221 | 65 | 289 | A | N |
| ATOM | 208 | CE1 | HIS | A | 41 | 18.293 | 10.801 | 43.195 | 1.00 | 11.42 | | A | C |
| ANISOU | 208 | CE1 | HIS | A | 41 | 1480 | 1707 | 1745 | −159 | −40 | −22 | A | C |
| SIGUIJ | 208 | CE1 | HIS | A | 41 | 2 | 1 | 0 | 219 | 283 | 290 | A | C |
| ATOM | 209 | NE2 | HIS | A | 41 | 18.614 | 9.642 | 42.680 | 1.00 | 11.19 | | A | N |
| ANISOU | 209 | NE2 | HIS | A | 41 | 1406 | 1687 | 1633 | −183 | 13 | 8 | A | N |
| SIGUIJ | 209 | NE2 | HIS | A | 41 | 1 | 0 | 0 | 221 | 65 | 289 | A | N |
| ATOM | 210 | C | HIS | A | 41 | 14.067 | 9.523 | 41.444 | 1.00 | 10.29 | | A | C |
| ANISOU | 210 | C | HIS | A | 41 | 1182 | 1050 | 1269 | −7 | −3 | 0 | A | C |
| SIGUIJ | 210 | C | HIS | A | 41 | 2 | 1 | 0 | 219 | 280 | 290 | A | C |
| ATOM | 211 | O | HIS | A | 41 | 14.590 | 10.273 | 40.588 | 1.00 | 10.52 | | A | O |
| ANISOU | 211 | O | HIS | A | 41 | 1447 | 1068 | 1291 | −92 | 77 | −27 | A | O |
| SIGUIJ | 211 | O | HIS | A | 41 | 1 | 0 | 0 | 221 | 57 | 289 | A | O |
| ATOM | 212 | N | CYS | A | 42 | 13.481 | 8.354 | 41.138 | 1.00 | 9.76 | | A | N |
| ANISOU | 212 | N | CYS | A | 42 | 1233 | 1063 | 1149 | −34 | 10 | −3 | A | N |
| SIGUIJ | 212 | N | CYS | A | 42 | 1 | 0 | 0 | 221 | 64 | 289 | A | N |
| ATOM | 213 | CA | CYS | A | 42 | 13.458 | 7.885 | 39.760 | 1.00 | 9.65 | | A | C |
| ANISOU | 213 | CA | CYS | A | 42 | 1222 | 1113 | 1149 | −30 | 1 | 0 | A | C |
| SIGUIJ | 213 | CA | CYS | A | 42 | 2 | 1 | 0 | 219 | 278 | 290 | A | C |
| ATOM | 214 | C | CYS | A | 42 | 12.287 | 6.932 | 39.567 | 1.00 | 9.15 | | A | C |
| ANISOU | 214 | C | CYS | A | 42 | 1079 | 897 | 1150 | 151 | 1 | −2 | A | C |
| SIGUIJ | 214 | C | CYS | A | 42 | 2 | 1 | 0 | 219 | 276 | 290 | A | C |
| ATOM | 215 | O | CYS | A | 42 | 11.652 | 6.457 | 40.545 | 1.00 | 9.16 | | A | O |
| ANISOU | 215 | O | CYS | A | 42 | 1210 | 1144 | 1141 | −8 | 3 | 0 | A | O |
| SIGUIJ | 215 | O | CYS | A | 42 | 1 | 0 | 0 | 221 | 57 | 289 | A | O |
| ATOM | 216 | CB | CYS | A | 42 | 14.705 | 7.106 | 39.423 | 1.00 | 10.11 | | A | C |
| ANISOU | 216 | CB | CYS | A | 42 | 1254 | 1211 | 1236 | 16 | 1 | 1 | A | C |
| SIGUIJ | 216 | CB | CYS | A | 42 | 2 | 1 | 0 | 219 | 273 | 290 | A | C |
| ATOM | 217 | SG | CYS | A | 42 | 16.187 | 8.081 | 39.076 | 1.00 | 10.44 | | A | S |
| ANISOU | 217 | SG | CYS | A | 42 | 1259 | 1262 | 1221 | 0 | 5 | 0 | A | S |
| SIGUIJ | 217 | SG | CYS | A | 42 | 1 | 0 | 0 | 221 | 49 | 289 | A | S |
| ATOM | 218 | N | GLY | A | 43 | 11.981 | 6.644 | 38.326 | 1.00 | 9.41 | | A | N |
| ANISOU | 218 | N | GLY | A | 43 | 1123 | 916 | 1162 | 72 | 2 | −2 | A | N |
| SIGUIJ | 218 | N | GLY | A | 43 | 1 | 0 | 0 | 221 | 64 | 289 | A | N |
| ATOM | 219 | CA | GLY | A | 43 | 11.122 | 5.525 | 38.028 | 1.00 | 9.14 | | A | C |
| ANISOU | 219 | CA | GLY | A | 43 | 1184 | 946 | 1182 | 23 | 0 | 0 | A | C |
| SIGUIJ | 219 | CA | GLY | A | 43 | 2 | 1 | 0 | 219 | 271 | 290 | A | C |
| ATOM | 220 | C | GLY | A | 43 | 11.888 | 4.246 | 37.848 | 1.00 | 9.24 | | A | C |
| ANISOU | 220 | C | GLY | A | 43 | 1222 | 956 | 1143 | 35 | 7 | 2 | A | C |
| SIGUIJ | 220 | C | GLY | A | 43 | 2 | 1 | 0 | 219 | 269 | 290 | A | C |
| ATOM | 221 | O | GLY | A | 43 | 13.118 | 4.214 | 37.889 | 1.00 | 9.94 | | A | O |
| ANISOU | 221 | O | GLY | A | 43 | 1219 | 1071 | 1587 | 27 | 5 | 0 | A | O |
| SIGUIJ | 221 | O | GLY | A | 43 | 1 | 0 | 0 | 221 | 56 | 289 | A | O |
| ATOM | 222 | N | GLY | A | 44 | 11.154 | 3.165 | 37.568 | 1.00 | 9.21 | | A | N |
| ANISOU | 222 | N | GLY | A | 44 | 1227 | 951 | 1241 | 46 | 0 | 0 | A | N |
| SIGUIJ | 222 | N | GLY | A | 44 | 1 | 0 | 0 | 221 | 64 | 289 | A | N |
| ATOM | 223 | CA | GLY | A | 44 | 11.759 | 1.840 | 37.297 | 1.00 | 9.38 | | A | C |
| ANISOU | 223 | CA | GLY | A | 44 | 1195 | 949 | 1269 | 42 | −2 | 0 | A | C |
| SIGUIJ | 223 | CA | GLY | A | 44 | 2 | 1 | 0 | 219 | 267 | 290 | A | C |
| ATOM | 224 | C | GLY | A | 44 | 10.670 | 0.881 | 36.925 | 1.00 | 9.47 | | A | C |
| ANISOU | 224 | C | GLY | A | 44 | 1167 | 935 | 1090 | 60 | 8 | 4 | A | C |
| SIGUIJ | 224 | C | GLY | A | 44 | 2 | 1 | 0 | 219 | 265 | 290 | A | C |
| ATOM | 225 | O | GLY | A | 44 | 9.475 | 1.226 | 36.894 | 1.00 | 9.28 | | A | O |
| ANISOU | 225 | O | GLY | A | 44 | 1154 | 1005 | 1272 | 64 | 11 | −2 | A | O |
| SIGUIJ | 225 | O | GLY | A | 44 | 1 | 0 | 0 | 221 | 56 | 289 | A | O |
| ATOM | 226 | N | VAL | A | 45 | 11.109 | −0.343 | 36.641 | 1.00 | 9.57 | | A | N |
| ANISOU | 226 | N | VAL | A | 45 | 1228 | 939 | 1165 | 63 | 9 | 5 | A | N |
| SIGUIJ | 226 | N | VAL | A | 45 | 1 | 0 | 0 | 221 | 64 | 289 | A | N |
| ATOM | 227 | CA | VAL | A | 45 | 10.162 | −1.428 | 36.379 | 1.00 | 10.47 | | A | C |
| ANISOU | 227 | CA | VAL | A | 45 | 1349 | 1042 | 1480 | −33 | −43 | −3 | A | C |
| SIGUIJ | 227 | CA | VAL | A | 45 | 2 | 1 | 0 | 219 | 263 | 290 | A | C |
| ATOM | 228 | CB | VAL | A | 45 | 10.067 | −1.867 | 34.895 | 1.00 | 11.25 | | A | C |
| ANISOU | 228 | CB | VAL | A | 45 | 1934 | 1227 | 1484 | 57 | −100 | −12 | A | C |
| SIGUIJ | 228 | CB | VAL | A | 45 | 2 | 1 | 0 | 219 | 261 | 290 | A | C |
| ATOM | 229 | CG1 | VAL | A | 45 | 9.505 | −0.699 | 34.079 | 1.00 | 12.17 | | A | C |
| ANISOU | 229 | CG1 | VAL | A | 45 | 2443 | 1284 | 1519 | 201 | −199 | −37 | A | C |
| SIGUIJ | 229 | CG1 | VAL | A | 45 | 2 | 1 | 0 | 219 | 259 | 290 | A | C |
| ATOM | 230 | CG2 | VAL | A | 45 | 11.426 | −2.314 | 34.385 | 1.00 | 11.84 | | A | C |
| ANISOU | 230 | CG2 | VAL | A | 45 | 1964 | 1327 | 1651 | 79 | −23 | −4 | A | C |
| SIGUIJ | 230 | CG2 | VAL | A | 45 | 2 | 1 | 0 | 219 | 257 | 290 | A | C |
| ATOM | 231 | C | VAL | A | 45 | 10.536 | −2.640 | 37.193 | 1.00 | 10.59 | | A | C |
| ANISOU | 231 | C | VAL | A | 45 | 1193 | 1043 | 1477 | −72 | −27 | 1 | A | C |
| SIGUIJ | 231 | C | VAL | A | 45 | 2 | 1 | 0 | 219 | 255 | 290 | A | C |
| ATOM | 232 | O | VAL | A | 45 | 11.695 | −2.926 | 37.505 | 1.00 | 10.74 | | A | O |
| ANISOU | 232 | O | VAL | A | 45 | 1202 | 1061 | 1805 | −105 | −120 | 41 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 232 | O | VAL | A | 45 | 1 | 0 | 0 | 221 | 56 | 289 | A | O |
| ATOM | 233 | N | LEU | A | 46 | 9.494 | −3.408 | 37.539 | 1.00 | 10.71 | | A | N |
| ANISOU | 233 | N | LEU | A | 46 | 1168 | 973 | 1575 | −10 | 4 | 0 | A | N |
| SIGUIJ | 233 | N | LEU | A | 46 | 1 | 0 | 0 | 221 | 64 | 289 | A | N |
| ATOM | 234 | CA | LEU | A | 46 | 9.719 | −4.660 | 38.256 | 1.00 | 10.83 | | A | C |
| ANISOU | 234 | CA | LEU | A | 46 | 1417 | 991 | 1583 | 23 | 7 | 0 | A | C |
| SIGUIJ | 234 | CA | LEU | A | 46 | 2 | 1 | 0 | 219 | 253 | 290 | A | C |
| ATOM | 235 | CB | LEU | A | 46 | 8.469 | −5.021 | 39.052 | 1.00 | 11.09 | | A | C |
| ANISOU | 235 | CB | LEU | A | 46 | 1450 | 1269 | 1572 | −64 | 6 | 1 | A | C |
| SIGUIJ | 235 | CB | LEU | A | 46 | 2 | 1 | 0 | 219 | 252 | 290 | A | C |
| ATOM | 236 | CG | LEU | A | 46 | 8.600 | −6.228 | 39.986 | 1.00 | 11.03 | | A | C |
| ANISOU | 236 | CG | LEU | A | 46 | 1562 | 1272 | 1562 | −60 | 0 | −2 | A | C |
| SIGUIJ | 236 | CG | LEU | A | 46 | 2 | 1 | 0 | 219 | 250 | 290 | A | C |
| ATOM | 237 | CD1 | LEU | A | 46 | 9.556 | −5.869 | 41.099 | 1.00 | 11.37 | | A | C |
| ANISOU | 237 | CD1 | LEU | A | 46 | 1540 | 1181 | 1562 | −1 | 0 | 0 | A | C |
| SIGUIJ | 237 | CD1 | LEU | A | 46 | 2 | 1 | 0 | 219 | 248 | 290 | A | C |
| ATOM | 238 | CD2 | LEU | A | 46 | 7.237 | −6.661 | 40.502 | 1.00 | 12.42 | | A | C |
| ANISOU | 238 | CD2 | LEU | A | 46 | 1663 | 1418 | 2039 | −113 | 194 | −12 | A | C |
| SIGUIJ | 238 | CD2 | LEU | A | 46 | 2 | 1 | 0 | 219 | 247 | 290 | A | C |
| ATOM | 239 | C | LEU | A | 46 | 10.037 | −5.762 | 37.279 | 1.00 | 11.25 | | A | C |
| ANISOU | 239 | C | LEU | A | 46 | 1508 | 1024 | 1604 | 63 | 4 | −1 | A | C |
| SIGUIJ | 239 | C | LEU | A | 46 | 2 | 1 | 0 | 219 | 245 | 290 | A | C |
| ATOM | 240 | O | LEU | A | 46 | 9.172 | −6.116 | 36.443 | 1.00 | 11.54 | | A | O |
| ANISOU | 240 | O | LEU | A | 46 | 1554 | 1295 | 1635 | −16 | −8 | −1 | A | O |
| SIGUIJ | 240 | O | LEU | A | 46 | 1 | 0 | 0 | 221 | 56 | 289 | A | O |
| ATOM | 241 | N | VAL | A | 47 | 11.218 | −6.360 | 37.374 | 1.00 | 11.33 | | A | N |
| ANISOU | 241 | N | VAL | A | 47 | 1473 | 917 | 1721 | −1 | −8 | 0 | A | N |
| SIGUIJ | 241 | N | VAL | A | 47 | 1 | 0 | 0 | 221 | 64 | 289 | A | N |
| ATOM | 242 | CA | VAL | A | 47 | 11.617 | −7.457 | 36.456 | 1.00 | 12.20 | | A | C |
| ANISOU | 242 | CA | VAL | A | 47 | 1589 | 944 | 1749 | 22 | 8 | 0 | A | C |
| SIGUIJ | 242 | CA | VAL | A | 47 | 2 | 1 | 0 | 219 | 243 | 290 | A | C |
| ATOM | 243 | CB | VAL | A | 47 | 13.132 | −7.531 | 36.319 | 1.00 | 11.95 | | A | C |
| ANISOU | 243 | CB | VAL | A | 47 | 1588 | 1116 | 2027 | 27 | 27 | −1 | A | C |
| SIGUIJ | 243 | CB | VAL | A | 47 | 2 | 1 | 0 | 219 | 242 | 290 | A | C |
| ATOM | 244 | CG1 | VAL | A | 47 | 13.524 | −8.722 | 35.459 | 1.00 | 12.53 | | A | C |
| ANISOU | 244 | CG1 | VAL | A | 47 | 1881 | 1165 | 2043 | 135 | 24 | −11 | A | C |
| SIGUIJ | 244 | CG1 | VAL | A | 47 | 2 | 1 | 0 | 219 | 240 | 290 | A | C |
| ATOM | 245 | CG2 | VAL | A | 47 | 13.676 | −6.210 | 35.700 | 1.00 | 12.70 | | A | C |
| ANISOU | 245 | CG2 | VAL | A | 47 | 1707 | 1139 | 2103 | −9 | 56 | 3 | A | C |
| SIGUIJ | 245 | CG2 | VAL | A | 47 | 2 | 1 | 0 | 219 | 239 | 290 | A | C |
| ATOM | 246 | C | VAL | A | 47 | 11.094 | −8.792 | 37.019 | 1.00 | 12.39 | | A | C |
| ANISOU | 246 | C | VAL | A | 47 | 1511 | 945 | 1769 | 46 | 17 | −1 | A | C |
| SIGUIJ | 246 | C | VAL | A | 47 | 2 | 1 | 0 | 219 | 237 | 290 | A | C |
| ATOM | 247 | O | VAL | A | 47 | 10.525 | −9.641 | 36.298 | 1.00 | 13.11 | | A | O |
| ANISOU | 247 | O | VAL | A | 47 | 1875 | 1153 | 1846 | −200 | 9 | −29 | A | O |
| SIGUIJ | 247 | O | VAL | A | 47 | 1 | 0 | 0 | 221 | 56 | 289 | A | O |
| ATOM | 248 | N | ASN | A | 48 | 11.274 | −8.986 | 38.310 | 1.00 | 12.97 | | A | N |
| ANISOU | 248 | N | ASN | A | 48 | 1610 | 1093 | 1767 | 10 | −9 | 1 | A | N |
| SIGUIJ | 248 | N | ASN | A | 48 | 1 | 0 | 0 | 221 | 64 | 289 | A | N |
| ATOM | 249 | CA | ASN | A | 48 | 10.692 | −10.197 | 38.940 | 1.00 | 13.56 | | A | C |
| ANISOU | 249 | CA | ASN | A | 48 | 1881 | 1184 | 1765 | −143 | −30 | 21 | A | C |
| SIGUIJ | 249 | CA | ASN | A | 48 | 2 | 1 | 0 | 219 | 236 | 290 | A | C |
| ATOM | 250 | CB | ASN | A | 48 | 11.514 | −11.465 | 38.691 | 1.00 | 13.95 | | A | C |
| ANISOU | 250 | CB | ASN | A | 48 | 1980 | 1232 | 1875 | −85 | −22 | 3 | A | C |
| SIGUIJ | 250 | CB | ASN | A | 48 | 2 | 1 | 0 | 219 | 234 | 290 | A | C |
| ATOM | 251 | CG | ASN | A | 48 | 12.949 | −11.323 | 39.128 | 1.00 | 14.48 | | A | C |
| ANISOU | 251 | CG | ASN | A | 48 | 2032 | 1624 | 2353 | −125 | −178 | 8 | A | C |
| SIGUIJ | 251 | CG | ASN | A | 48 | 2 | 1 | 0 | 219 | 233 | 290 | A | C |
| ATOM | 252 | OD1 | ASN | A | 48 | 13.236 | −10.802 | 40.234 | 1.00 | 14.80 | | A | O |
| ANISOU | 252 | OD1 | ASN | A | 48 | 1744 | 1578 | 2355 | 13 | −166 | −9 | A | O |
| SIGUIJ | 252 | OD1 | ASN | A | 48 | 1 | 0 | 0 | 221 | 56 | 289 | A | O |
| ATOM | 253 | ND2 | ASN | A | 48 | 13.863 | −11.736 | 38.267 | 1.00 | 15.49 | | A | N |
| ANISOU | 253 | ND2 | ASN | A | 48 | 2331 | 2029 | 2614 | 46 | 56 | −4 | A | N |
| SIGUIJ | 253 | ND2 | ASN | A | 48 | 1 | 0 | 0 | 221 | 64 | 289 | A | N |
| ATOM | 254 | C | ASN | A | 48 | 10.591 | −9.863 | 40.432 | 1.00 | 14.01 | | A | C |
| ANISOU | 254 | C | ASN | A | 48 | 1938 | 1259 | 1777 | −307 | 26 | −25 | A | C |
| SIGUIJ | 254 | C | ASN | A | 48 | 2 | 1 | 0 | 219 | 232 | 290 | A | C |
| ATOM | 255 | O | ASN | A | 48 | 10.777 | −8.674 | 40.833 | 1.00 | 13.61 | | A | O |
| ANISOU | 255 | O | ASN | A | 48 | 1850 | 1230 | 1641 | −252 | −44 | 32 | A | O |
| SIGUIJ | 255 | O | ASN | A | 48 | 1 | 0 | 0 | 221 | 56 | 289 | A | O |
| ATOM | 256 | N | AGLU | A | 49 | 10.232 | −10.835 | 41.275 | 0.50 | 14.78 | | A | N |
| ANISOU | 256 | N | AGLU | A | 49 | 1993 | 1342 | 1824 | −383 | −31 | 33 | A | N |
| SIGUIJ | 256 | N | AGLU | A | 49 | 1 | 0 | 0 | 221 | 64 | 289 | A | N |
| ATOM | 257 | N | BGLU | A | 49 | 10.279 | −10.868 | 41.259 | 0.50 | 16.97 | | A | N |
| ANISOU | 257 | N | BGLU | A | 49 | 2692 | 1451 | 1833 | −668 | −125 | 73 | A | N |
| SIGUIJ | 257 | N | BGLU | A | 49 | 1 | 0 | 0 | 221 | 64 | 289 | A | N |
| ATOM | 258 | CA | AGLU | A | 49 | 9.895 | −10.519 | 42.670 | 0.50 | 15.14 | | A | C |
| ANISOU | 258 | CA | AGLU | A | 49 | 1953 | 1282 | 1836 | −526 | −10 | 14 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 258 | CA | AGLU | A | 49 | 2 | 1 | 0 | 219 | 230 | 290 | A | C |
| ATOM | 259 | CA | BGLU | A | 49 | 9.970 | −10.660 | 42.680 | 0.50 | 17.33 | | A | C |
| ANISOU | 259 | CA | BGLU | A | 49 | 2140 | 2923 | 1801 | −131 | −322 | −14 | A | C |
| SIGUIJ | 259 | CA | BGLU | A | 49 | 2 | 1 | 0 | 219 | 229 | 290 | A | C |
| ATOM | 260 | CB | AGLU | A | 49 | 9.299 | −11.753 | 43.388 | 0.50 | 16.48 | | A | C |
| ANISOU | 260 | CB | AGLU | A | 49 | 2320 | 1346 | 1820 | −689 | 41 | −34 | A | C |
| SIGUIJ | 260 | CB | AGLU | A | 49 | 2 | 1 | 0 | 219 | 228 | 290 | A | C |
| ATOM | 261 | CB | BGLU | A | 49 | 9.618 | −12.009 | 43.367 | 0.50 | 18.67 | | A | C |
| ANISOU | 261 | CB | BGLU | A | 49 | 5735 | 2899 | 2972 | 33 | 1843 | 23 | A | C |
| SIGUIJ | 261 | CB | BGLU | A | 49 | 2 | 1 | 0 | 219 | 226 | 290 | A | C |
| ATOM | 262 | CG | AGLU | A | 49 | 8.105 | −12.394 | 42.692 | 0.50 | 18.70 | | A | C |
| ANISOU | 262 | CG | AGLU | A | 49 | 2626 | 2154 | 1929 | −1165 | −48 | 54 | A | C |
| SIGUIJ | 262 | CG | AGLU | A | 49 | 2 | 1 | 0 | 219 | 225 | 290 | A | C |
| ATOM | 263 | CG | BGLU | A | 49 | 8.504 | −12.838 | 42.715 | 0.50 | 20.89 | | A | C |
| ANISOU | 263 | CG | BGLU | A | 49 | 6858 | 2850 | 6466 | 104 | −162 | −36 | A | C |
| SIGUIJ | 263 | CG | BGLU | A | 49 | 2 | 1 | 0 | 219 | 224 | 290 | A | C |
| ATOM | 264 | CD | AGLU | A | 49 | 8.468 | −13.544 | 41.739 | 0.50 | 19.66 | | A | C |
| ANISOU | 264 | CD | AGLU | A | 49 | 3022 | 2158 | 1755 | −883 | −230 | 149 | A | C |
| SIGUIJ | 264 | CD | AGLU | A | 49 | 2 | 1 | 0 | 219 | 223 | 290 | A | C |
| ATOM | 265 | CD | BGLU | A | 49 | 7.906 | −13.862 | 43.655 | 0.50 | 21.85 | | A | C |
| ANISOU | 265 | CD | BGLU | A | 49 | 6242 | 2697 | 6614 | 528 | −98 | 69 | A | C |
| SIGUIJ | 265 | CD | BGLU | A | 49 | 2 | 1 | 0 | 219 | 222 | 290 | A | C |
| ATOM | 266 | OE1 | AGLU | A | 49 | 9.352 | −13.404 | 40.878 | 0.50 | 20.29 | | A | O |
| ANISOU | 266 | OE1 | AGLU | A | 49 | 3300 | 1254 | 2020 | −905 | 54 | −28 | A | O |
| SIGUIJ | 266 | OE1 | AGLU | A | 49 | 1 | 0 | 0 | 221 | 56 | 289 | A | O |
| ATOM | 267 | OE1 | BGLU | A | 49 | 8.685 | −14.452 | 44.415 | 0.50 | 22.48 | | A | O |
| ANISOU | 267 | OE1 | BGLU | A | 49 | 5760 | 1973 | 6434 | 47 | 22 | 0 | A | O |
| SIGUIJ | 267 | OE1 | BGLU | A | 49 | 1 | 0 | 0 | 221 | 56 | 289 | A | O |
| ATOM | 268 | OE2 | AGLU | A | 49 | 7.836 | −14.615 | 41.842 | 0.50 | 21.02 | | A | O |
| ANISOU | 268 | OE2 | AGLU | A | 49 | 2538 | 1944 | 1986 | −562 | −21 | 16 | A | O |
| SIGUIJ | 268 | OE2 | AGLU | A | 49 | 1 | 0 | 0 | 221 | 56 | 289 | A | O |
| ATOM | 269 | OE2 | BGLU | A | 49 | 6.671 | −14.055 | 43.646 | 0.50 | 23.21 | | A | O |
| ANISOU | 269 | OE2 | BGLU | A | 49 | 6326 | 6186 | 4560 | −14 | −65 | 3 | A | O |
| SIGUIJ | 269 | OE2 | BGLU | A | 49 | 1 | 0 | 0 | 221 | 56 | 289 | A | O |
| ATOM | 270 | C | AGLU | A | 49 | 11.092 | −9.977 | 43.471 | 0.50 | 14.59 | | A | C |
| ANISOU | 270 | C | AGLU | A | 49 | 1877 | 959 | 1825 | −364 | −1 | 3 | A | C |
| SIGUIJ | 270 | C | AGLU | A | 49 | 2 | 1 | 0 | 219 | 220 | 290 | A | C |
| ATOM | 271 | C | BGLU | A | 49 | 11.117 | −10.003 | 43.452 | 0.50 | 16.78 | | A | C |
| ANISOU | 271 | C | BGLU | A | 49 | 1898 | 2721 | 1417 | −13 | −68 | 2 | A | C |
| SIGUIJ | 271 | C | BGLU | A | 49 | 2 | 1 | 0 | 219 | 219 | 290 | A | C |
| ATOM | 272 | O | AGLU | A | 49 | 10.911 | −9.406 | 44.538 | 0.50 | 14.43 | | A | O |
| ANISOU | 272 | O | AGLU | A | 49 | 1617 | 968 | 1833 | −452 | −2 | −5 | A | O |
| SIGUIJ | 272 | O | AGLU | A | 49 | 1 | 0 | 0 | 221 | 56 | 289 | A | O |
| ATOM | 273 | O | BGLU | A | 49 | 10.903 | −9.403 | 44.497 | 0.50 | 16.62 | | A | O |
| ANISOU | 273 | O | BGLU | A | 49 | 2607 | 2738 | 1454 | 3 | 81 | −1 | A | O |
| SIGUIJ | 273 | O | BGLU | A | 49 | 1 | 0 | 0 | 221 | 56 | 289 | A | O |
| ATOM | 274 | N | AARG | A | 50 | 12.298 | −10.150 | 42.935 | 0.50 | 14.49 | | A | N |
| ANISOU | 274 | N | AARG | A | 50 | 1891 | 1588 | 1752 | −249 | −23 | 23 | A | N |
| SIGUIJ | 274 | N | AARG | A | 50 | 1 | 0 | 0 | 221 | 64 | 289 | A | N |
| ATOM | 275 | N | BARG | A | 50 | 12.324 | −10.137 | 42.917 | 0.50 | 16.68 | | A | N |
| ANISOU | 275 | N | BARG | A | 50 | 1933 | 1479 | 1657 | −163 | 39 | −17 | A | N |
| SIGUIJ | 275 | N | BARG | A | 50 | 1 | 0 | 0 | 221 | 64 | 289 | A | N |
| ATOM | 276 | CA | AARG | A | 50 | 13.500 | −9.681 | 43.606 | 0.50 | 14.49 | | A | C |
| ANISOU | 276 | CA | AARG | A | 50 | 1818 | 1271 | 1701 | −88 | 17 | −7 | A | C |
| SIGUIJ | 276 | CA | AARG | A | 50 | 2 | 1 | 0 | 219 | 218 | 290 | A | C |
| ATOM | 277 | CA | BARG | A | 50 | 13.521 | −9.691 | 43.604 | 0.50 | 16.68 | | A | C |
| ANISOU | 277 | CA | BARG | A | 50 | 1925 | 1261 | 1694 | −78 | 21 | −5 | A | C |
| SIGUIJ | 277 | CA | BARG | A | 50 | 2 | 1 | 0 | 219 | 217 | 290 | A | C |
| ATOM | 278 | CB | AARG | A | 50 | 14.485 | −10.854 | 43.733 | 0.50 | 16.52 | | A | C |
| ANISOU | 278 | CB | AARG | A | 50 | 2045 | 1410 | 2763 | 76 | −144 | −3 | A | C |
| SIGUIJ | 278 | CB | AARG | A | 50 | 2 | 1 | 0 | 219 | 216 | 290 | A | C |
| ATOM | 279 | CB | BARG | A | 50 | 14.511 | −10.863 | 43.682 | 0.50 | 18.71 | | A | C |
| ANISOU | 279 | CB | BARG | A | 50 | 2233 | 1459 | 2243 | 166 | 0 | 15 | A | C |
| SIGUIJ | 279 | CB | BARG | A | 50 | 2 | 1 | 0 | 220 | 215 | 290 | A | C |
| ATOM | 280 | CG | AARG | A | 50 | 14.078 | −11.827 | 44.830 | 0.50 | 19.27 | | A | C |
| ANISOU | 280 | CG | AARG | A | 50 | 2668 | 1491 | 2900 | 48 | 68 | 56 | A | C |
| SIGUIJ | 280 | CG | AARG | A | 50 | 2 | 1 | 0 | 220 | 214 | 290 | A | C |
| ATOM | 281 | CG | BARG | A | 50 | 15.776 | −10.563 | 44.436 | 0.50 | 21.46 | | A | C |
| ANISOU | 281 | CG | BARG | A | 50 | 2299 | 2636 | 2258 | −105 | 5 | −9 | A | C |
| SIGUIJ | 281 | CG | BARG | A | 50 | 2 | 1 | 0 | 220 | 213 | 290 | A | C |
| ATOM | 282 | CD | AARG | A | 50 | 14.453 | −11.226 | 46.145 | 0.50 | 21.50 | | A | C |
| ANISOU | 282 | CD | AARG | A | 50 | 4009 | 2861 | 2974 | −1194 | 251 | −214 | A | C |
| SIGUIJ | 282 | CD | AARG | A | 50 | 2 | 1 | 0 | 220 | 212 | 290 | A | C |
| ATOM | 283 | CD | BARG | A | 50 | 15.496 | −10.244 | 45.904 | 0.50 | 23.69 | | A | C |
| ANISOU | 283 | CD | BARG | A | 50 | 1961 | 2702 | 2258 | −105 | −36 | −9 | A | C |
| SIGUIJ | 283 | CD | BARG | A | 50 | 2 | 1 | 0 | 220 | 210 | 290 | A | C |
| ATOM | 284 | NE | AARG | A | 50 | 14.330 | −12.163 | 47.243 | 0.50 | 23.77 | | A | N |
| ANISOU | 284 | NE | AARG | A | 50 | 10900 | 2957 | 3100 | −1335 | 899 | −149 | A | N |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 284 | NE | AARG | A | 50 | 1 | 0 | 0 | 221 | 64 | 289 | A | N |
| ATOM | 285 | NE | BARG | A | 50 | 15.178 | −11.468 | 46.633 | 0.50 | 25.96 | | A | N |
| ANISOU | 285 | NE | BARG | A | 50 | 3268 | 2753 | 2278 | −366 | 95 | −42 | A | N |
| SIGUIJ | 285 | NE | BARG | A | 50 | 1 | 0 | 0 | 221 | 64 | 289 | A | N |
| ATOM | 286 | CZ | AARG | A | 50 | 14.812 | −11.933 | 48.455 | 0.50 | 24.33 | | A | C |
| ANISOU | 286 | CZ | AARG | A | 50 | 13002 | 3449 | 3369 | −1870 | 159 | −30 | A | C |
| SIGUIJ | 286 | CZ | AARG | A | 50 | 2 | 1 | 0 | 220 | 209 | 290 | A | C |
| ATOM | 287 | CZ | BARG | A | 50 | 14.845 | −11.524 | 47.916 | 0.50 | 26.52 | | A | C |
| ANISOU | 287 | CZ | BARG | A | 50 | 6401 | 1896 | 2492 | −303 | 909 | −62 | A | C |
| SIGUIJ | 287 | CZ | BARG | A | 50 | 2 | 1 | 0 | 220 | 208 | 290 | A | C |
| ATOM | 288 | NH1 | AARG | A | 50 | 15.452 | −10.794 | 48.688 | 0.50 | 24.98 | | A | N |
| ANISOU | 288 | NH1 | AARG | A | 50 | 7444 | 1672 | 5139 | 1342 | −320 | −124 | A | N |
| SIGUIJ | 288 | NH1 | AARG | A | 50 | 1 | 0 | 0 | 221 | 64 | 289 | A | N |
| ATOM | 289 | NH1 | BARG | A | 50 | 14.778 | −10.419 | 48.644 | 0.50 | 27.17 | | A | N |
| ANISOU | 289 | NH1 | BARG | A | 50 | 2982 | 1878 | 2323 | 88 | −2 | 0 | A | N |
| SIGUIJ | 289 | NH1 | BARG | A | 50 | 1 | 0 | 0 | 221 | 64 | 289 | A | N |
| ATOM | 290 | NH2 | AARG | A | 50 | 14.635 | −12.813 | 49.432 | 0.50 | 25.28 | | A | N |
| ANISOU | 290 | NH2 | AARG | A | 50 | 10903 | 3280 | 3376 | −1231 | 350 | −56 | A | N |
| SIGUIJ | 290 | NH2 | AARG | A | 50 | 1 | 0 | 0 | 221 | 64 | 289 | A | N |
| ATOM | 291 | NH2 | BARG | A | 50 | 14.585 | −12.699 | 48.471 | 0.50 | 27.47 | | A | N |
| ANISOU | 291 | NH2 | BARG | A | 50 | 5043 | 1978 | 2193 | −488 | −128 | 21 | A | N |
| SIGUIJ | 291 | NH2 | BARG | A | 50 | 1 | 0 | 0 | 221 | 64 | 289 | A | N |
| ATOM | 292 | C | AARG | A | 50 | 14.230 | −8.472 | 42.996 | 0.50 | 13.60 | | A | C |
| ANISOU | 292 | C | AARG | A | 50 | 1610 | 1207 | 1674 | 40 | 4 | −1 | A | C |
| SIGUIJ | 292 | C | AARG | A | 50 | 2 | 1 | 0 | 220 | 207 | 290 | A | C |
| ATOM | 293 | C | BARG | A | 50 | 14.234 | −8.472 | 42.995 | 0.50 | 15.79 | | A | C |
| ANISOU | 293 | C | BARG | A | 50 | 1663 | 1187 | 1666 | 69 | 0 | −8 | A | C |
| SIGUIJ | 293 | C | BARG | A | 50 | 2 | 1 | 0 | 220 | 207 | 290 | A | C |
| ATOM | 294 | O | AARG | A | 50 | 15.150 | −7.938 | 43.635 | 0.50 | 13.67 | | A | O |
| ANISOU | 294 | O | AARG | A | 50 | 1658 | 1339 | 1681 | −26 | 1 | 1 | A | O |
| SIGUIJ | 294 | O | AARG | A | 50 | 1 | 0 | 0 | 221 | 56 | 289 | A | O |
| ATOM | 295 | O | BARG | A | 50 | 15.147 | −7.928 | 43.630 | 0.50 | 15.86 | | A | O |
| ANISOU | 295 | O | BARG | A | 50 | 1742 | 1370 | 1670 | −36 | −9 | 3 | A | O |
| SIGUIJ | 295 | O | BARG | A | 50 | 1 | 0 | 0 | 221 | 56 | 289 | A | O |
| ATOM | 296 | N | TRP | A | 51 | 13.850 | −8.067 | 41.779 | 1.00 | 12.29 | | A | N |
| ANISOU | 296 | N | TRP | A | 51 | 1505 | 1152 | 1666 | −23 | 12 | 1 | A | N |
| SIGUIJ | 296 | N | TRP | A | 51 | 1 | 0 | 0 | 221 | 64 | 289 | A | N |
| ATOM | 297 | CA | TRP | A | 51 | 14.687 | −7.155 | 41.015 | 1.00 | 11.48 | | A | C |
| ANISOU | 297 | CA | TRP | A | 51 | 1322 | 1088 | 1578 | 80 | −57 | 4 | A | C |
| SIGUIJ | 297 | CA | TRP | A | 51 | 2 | 1 | 0 | 220 | 206 | 290 | A | C |
| ATOM | 298 | CB | TRP | A | 51 | 15.438 | −7.960 | 39.942 | 1.00 | 11.69 | | A | C |
| ANISOU | 298 | CB | TRP | A | 51 | 1512 | 1196 | 1650 | 156 | 29 | −17 | A | C |
| SIGUIJ | 298 | CB | TRP | A | 51 | 2 | 1 | 0 | 220 | 205 | 290 | A | C |
| ATOM | 299 | CG | TRP | A | 51 | 16.522 | −8.845 | 40.509 | 1.00 | 12.06 | | A | C |
| ANISOU | 299 | CG | TRP | A | 51 | 1546 | 1244 | 1789 | 172 | −23 | 4 | A | C |
| SIGUIJ | 299 | CG | TRP | A | 51 | 2 | 1 | 0 | 220 | 204 | 290 | A | C |
| ATOM | 300 | CD2 | TRP | A | 51 | 17.836 | −8.423 | 40.881 | 1.00 | 12.06 | | A | C |
| ANISOU | 300 | CD2 | TRP | A | 51 | 1547 | 1134 | 2005 | 202 | −63 | 2 | A | C |
| SIGUIJ | 300 | CD2 | TRP | A | 51 | 2 | 1 | 0 | 220 | 203 | 290 | A | C |
| ATOM | 301 | CE2 | TRP | A | 51 | 18.523 | −9.572 | 41.358 | 1.00 | 12.45 | | A | C |
| ANISOU | 301 | CE2 | TRP | A | 51 | 1614 | 1123 | 2069 | 211 | −80 | 5 | A | C |
| SIGUIJ | 301 | CE2 | TRP | A | 51 | 2 | 1 | 0 | 220 | 202 | 290 | A | C |
| ATOM | 302 | CE3 | TRP | A | 51 | 18.514 | −7.191 | 40.859 | 1.00 | 12.45 | | A | C |
| ANISOU | 302 | CE3 | TRP | A | 51 | 1580 | 1160 | 2082 | 175 | −53 | −2 | A | C |
| SIGUIJ | 302 | CE3 | TRP | A | 51 | 2 | 1 | 0 | 220 | 201 | 290 | A | C |
| ATOM | 303 | CD1 | TRP | A | 51 | 16.465 | −10.197 | 40.765 | 1.00 | 12.45 | | A | C |
| ANISOU | 303 | CD1 | TRP | A | 51 | 1555 | 1255 | 2117 | 201 | 136 | 36 | A | C |
| SIGUIJ | 303 | CD1 | TRP | A | 51 | 2 | 1 | 0 | 220 | 200 | 290 | A | C |
| ATOM | 304 | NE1 | TRP | A | 51 | 17.655 | −10.617 | 41.271 | 1.00 | 12.82 | | A | N |
| ANISOU | 304 | NE1 | TRP | A | 51 | 1665 | 1140 | 2779 | 176 | −147 | 22 | A | N |
| SIGUIJ | 304 | NE1 | TRP | A | 51 | 1 | 0 | 0 | 221 | 64 | 289 | A | N |
| ATOM | 305 | CZ2 | TRP | A | 51 | 19.835 | −9.530 | 41.785 | 1.00 | 12.49 | | A | C |
| ANISOU | 305 | CZ2 | TRP | A | 51 | 1611 | 1163 | 2023 | 200 | −56 | 7 | A | C |
| SIGUIJ | 305 | CZ2 | TRP | A | 51 | 2 | 1 | 0 | 220 | 199 | 290 | A | C |
| ATOM | 306 | CZ3 | TRP | A | 51 | 19.811 | −7.153 | 41.280 | 1.00 | 12.11 | | A | C |
| ANISOU | 306 | CZ3 | TRP | A | 51 | 1560 | 1152 | 1987 | 177 | −12 | 1 | A | C |
| SIGUIJ | 306 | CZ3 | TRP | A | 51 | 2 | 1 | 0 | 220 | 198 | 290 | A | C |
| ATOM | 307 | CH2 | TRP | A | 51 | 20.475 | −8.318 | 41.738 | 1.00 | 12.39 | | A | C |
| ANISOU | 307 | CH2 | TRP | A | 51 | 1622 | 1161 | 2100 | 192 | −45 | 3 | A | C |
| SIGUIJ | 307 | CH2 | TRP | A | 51 | 2 | 1 | 0 | 220 | 197 | 290 | A | C |
| ATOM | 308 | C | TRP | A | 51 | 13.891 | −6.072 | 40.335 | 1.00 | 10.92 | | A | C |
| ANISOU | 308 | C | TRP | A | 51 | 1176 | 1024 | 1481 | −8 | 7 | 0 | A | C |
| SIGUIJ | 308 | C | TRP | A | 51 | 2 | 1 | 0 | 220 | 197 | 290 | A | C |
| ATOM | 309 | O | TRP | A | 51 | 12.875 | −6.331 | 39.672 | 1.00 | 10.75 | | A | O |
| ANISOU | 309 | O | TRP | A | 51 | 1253 | 1057 | 1624 | −29 | −90 | 2 | A | O |
| SIGUIJ | 309 | O | TRP | A | 51 | 1 | 0 | 0 | 221 | 56 | 289 | A | O |
| ATOM | 310 | N | VAL | A | 52 | 14.461 | −4.863 | 40.420 | 1.00 | 9.93 | | A | N |
| ANISOU | 310 | N | VAL | A | 52 | 1180 | 1012 | 1381 | 3 | 5 | 0 | A | N |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 310 | N | VAL | A | 52 | 1 | 0 | 0 | 221 | 64 | 289 | A | N |
| ATOM | 311 | CA | VAL | A | 52 | 13.946 | −3.683 | 39.687 | 1.00 | 10.04 | | A | C |
| ANISOU | 311 | CA | VAL | A | 52 | 1260 | 1029 | 1401 | 35 | −8 | 1 | A | C |
| SIGUIJ | 311 | CA | VAL | A | 52 | 2 | 1 | 0 | 220 | 196 | 290 | A | C |
| ATOM | 312 | CB | VAL | A | 52 | 13.646 | −2.570 | 40.742 | 1.00 | 10.01 | | A | C |
| ANISOU | 312 | CB | VAL | A | 52 | 1267 | 1028 | 1421 | 8 | 5 | 0 | A | C |
| SIGUIJ | 312 | CB | VAL | A | 52 | 2 | 1 | 0 | 220 | 195 | 290 | A | C |
| ATOM | 313 | CG1 | VAL | A | 52 | 13.540 | −1.174 | 40.086 | 1.00 | 10.49 | | A | C |
| ANISOU | 313 | CG1 | VAL | A | 52 | 1519 | 1027 | 1429 | 22 | 8 | 1 | A | C |
| SIGUIJ | 313 | CG1 | VAL | A | 52 | 2 | 1 | 0 | 220 | 194 | 290 | A | C |
| ATOM | 314 | CG2 | VAL | A | 52 | 12.358 | −2.904 | 41.442 | 1.00 | 10.41 | | A | C |
| ANISOU | 314 | CG2 | VAL | A | 52 | 1315 | 1176 | 1577 | −25 | 66 | −2 | A | C |
| SIGUIJ | 314 | CG2 | VAL | A | 52 | 2 | 1 | 0 | 220 | 193 | 290 | A | C |
| ATOM | 315 | C | VAL | A | 52 | 14.986 | −3.249 | 38.695 | 1.00 | 9.93 | | A | C |
| ANISOU | 315 | C | VAL | A | 52 | 1213 | 950 | 1395 | 98 | −18 | 3 | A | C |
| SIGUIJ | 315 | C | VAL | A | 52 | 2 | 1 | 0 | 220 | 193 | 290 | A | C |
| ATOM | 316 | O | VAL | A | 52 | 16.193 | −3.210 | 39.022 | 1.00 | 10.38 | | A | O |
| ANISOU | 316 | O | VAL | A | 52 | 1200 | 1474 | 1279 | 89 | 3 | −2 | A | O |
| SIGUIJ | 316 | O | VAL | A | 52 | 1 | 0 | 0 | 221 | 56 | 289 | A | O |
| ATOM | 317 | N | LEU | A | 53 | 14.537 | −2.834 | 37.532 | 1.00 | 9.71 | | A | N |
| ANISOU | 317 | N | LEU | A | 53 | 1220 | 933 | 1395 | 84 | −2 | 0 | A | N |
| SIGUIJ | 317 | N | LEU | A | 53 | 1 | 0 | 0 | 221 | 64 | 289 | A | N |
| ATOM | 318 | CA | LEU | A | 53 | 15.414 | −2.262 | 36.504 | 1.00 | 9.85 | | A | C |
| ANISOU | 318 | CA | LEU | A | 53 | 1255 | 969 | 1420 | 69 | 14 | 0 | A | C |
| SIGUIJ | 318 | CA | LEU | A | 53 | 2 | 1 | 0 | 220 | 192 | 290 | A | C |
| ATOM | 319 | CB | LEU | A | 53 | 15.126 | −2.913 | 35.149 | 1.00 | 10.62 | | A | C |
| ANISOU | 319 | CB | LEU | A | 53 | 1407 | 1063 | 1430 | 18 | 3 | −3 | A | C |
| SIGUIJ | 319 | CB | LEU | A | 53 | 2 | 1 | 0 | 220 | 191 | 290 | A | C |
| ATOM | 320 | CG | LEU | A | 53 | 15.952 | −2.426 | 33.945 | 1.00 | 11.41 | | A | C |
| ANISOU | 320 | CG | LEU | A | 53 | 1564 | 1285 | 1460 | −109 | 58 | −30 | A | C |
| SIGUIJ | 320 | CG | LEU | A | 53 | 2 | 1 | 0 | 220 | 190 | 290 | A | C |
| ATOM | 321 | CD1 | LEU | A | 53 | 17.413 | −2.811 | 34.144 | 1.00 | 11.99 | | A | C |
| ANISOU | 321 | CD1 | LEU | A | 53 | 1598 | 1740 | 1791 | 0 | 14 | 0 | A | C |
| SIGUIJ | 321 | CD1 | LEU | A | 53 | 2 | 1 | 0 | 220 | 190 | 290 | A | C |
| ATOM | 322 | CD2 | LEU | A | 53 | 15.368 | −3.099 | 32.683 | 1.00 | 12.17 | | A | C |
| ANISOU | 322 | CD2 | LEU | A | 53 | 1834 | 1300 | 1485 | −176 | −27 | 11 | A | C |
| SIGUIJ | 322 | CD2 | LEU | A | 53 | 2 | 1 | 0 | 220 | 189 | 290 | A | C |
| ATOM | 323 | C | LEU | A | 53 | 15.139 | −0.749 | 36.447 | 1.00 | 9.78 | | A | C |
| ANISOU | 323 | C | LEU | A | 53 | 1161 | 957 | 1161 | 42 | 0 | 0 | A | C |
| SIGUIJ | 323 | C | LEU | A | 53 | 2 | 1 | 0 | 220 | 188 | 290 | A | C |
| ATOM | 324 | O | LEU | A | 53 | 13.987 | −0.283 | 36.434 | 1.00 | 9.80 | | A | O |
| ANISOU | 324 | O | LEU | A | 53 | 1161 | 1023 | 1414 | 59 | −19 | −2 | A | O |
| SIGUIJ | 324 | O | LEU | A | 53 | 1 | 0 | 0 | 221 | 56 | 289 | A | O |
| ATOM | 325 | N | THR | A | 54 | 16.206 | 0.054 | 36.393 | 1.00 | 9.36 | | A | N |
| ANISOU | 325 | N | THR | A | 54 | 1186 | 980 | 1366 | 15 | 5 | 0 | A | N |
| SIGUIJ | 325 | N | THR | A | 54 | 1 | 0 | 0 | 221 | 64 | 289 | A | N |
| ATOM | 326 | CA | THR | A | 54 | 16.127 | 1.504 | 36.372 | 1.00 | 8.84 | | A | C |
| ANISOU | 326 | CA | THR | A | 54 | 1075 | 983 | 1311 | 1 | 13 | 0 | A | C |
| SIGUIJ | 326 | CA | THR | A | 54 | 2 | 1 | 0 | 220 | 187 | 290 | A | C |
| ATOM | 327 | CB | THR | A | 54 | 16.005 | 2.003 | 37.822 | 1.00 | 9.07 | | A | C |
| ANISOU | 327 | CB | THR | A | 54 | 1303 | 1023 | 1315 | 63 | 0 | 0 | A | C |
| SIGUIJ | 327 | CB | THR | A | 54 | 2 | 1 | 0 | 220 | 187 | 290 | A | C |
| ATOM | 328 | OG1 | THR | A | 54 | 15.735 | 3.395 | 37.800 | 1.00 | 9.46 | | A | O |
| ANISOU | 328 | OG1 | THR | A | 54 | 1233 | 1021 | 1316 | 33 | 2 | 0 | A | O |
| SIGUIJ | 328 | OG1 | THR | A | 54 | 1 | 0 | 0 | 221 | 56 | 289 | A | O |
| ATOM | 329 | CG2 | THR | A | 54 | 17.246 | 1.746 | 38.680 | 1.00 | 9.74 | | A | C |
| ANISOU | 329 | CG2 | THR | A | 54 | 1317 | 1192 | 1327 | 102 | 0 | 2 | A | C |
| SIGUIJ | 329 | CG2 | THR | A | 54 | 2 | 1 | 0 | 220 | 186 | 290 | A | C |
| ATOM | 330 | C | THR | A | 54 | 17.386 | 2.042 | 35.672 | 1.00 | 8.45 | | A | C |
| ANISOU | 330 | C | THR | A | 54 | 1059 | 1008 | 1241 | 0 | −14 | 0 | A | C |
| SIGUIJ | 330 | C | THR | A | 54 | 2 | 1 | 0 | 220 | 185 | 290 | A | C |
| ATOM | 331 | O | THR | A | 54 | 18.135 | 1.279 | 35.019 | 1.00 | 8.67 | | A | O |
| ANISOU | 331 | O | THR | A | 54 | 1116 | 1041 | 1232 | 19 | 11 | 0 | A | O |
| SIGUIJ | 331 | O | THR | A | 54 | 1 | 0 | 0 | 221 | 56 | 289 | A | O |
| ATOM | 332 | N | ALA | A | 55 | 17.617 | 3.347 | 35.762 | 1.00 | 7.93 | | A | N |
| ANISOU | 332 | N | ALA | A | 55 | 1049 | 1005 | 1170 | −2 | −7 | 0 | A | N |
| SIGUIJ | 332 | N | ALA | A | 55 | 1 | 0 | 0 | 221 | 64 | 289 | A | N |
| ATOM | 333 | CA | ALA | A | 55 | 18.795 | 3.977 | 35.147 | 1.00 | 8.32 | | A | C |
| ANISOU | 333 | CA | ALA | A | 55 | 1069 | 1011 | 1176 | −7 | 12 | 0 | A | C |
| SIGUIJ | 333 | CA | ALA | A | 55 | 2 | 1 | 0 | 220 | 185 | 290 | A | C |
| ATOM | 334 | CB | ALA | A | 55 | 18.411 | 5.409 | 34.690 | 1.00 | 8.36 | | A | C |
| ANISOU | 334 | CB | ALA | A | 55 | 1358 | 1036 | 1190 | 63 | 5 | 1 | A | C |
| SIGUIJ | 334 | CB | ALA | A | 55 | 2 | 1 | 0 | 220 | 184 | 290 | A | C |
| ATOM | 335 | C | ALA | A | 55 | 19.957 | 4.000 | 36.103 | 1.00 | 8.62 | | A | C |
| ANISOU | 335 | C | ALA | A | 55 | 1091 | 1008 | 1198 | −13 | −14 | 0 | A | C |
| SIGUIJ | 335 | C | ALA | A | 55 | 2 | 0 | 0 | 220 | 183 | 290 | A | C |
| ATOM | 336 | O | ALA | A | 55 | 19.779 | 4.158 | 37.313 | 1.00 | 9.17 | | A | O |
| ANISOU | 336 | O | ALA | A | 55 | 1214 | 1103 | 1202 | −8 | 0 | 0 | A | O |

TABLE 3-continued

Three-dimensional structure of the new binding pocket of kallikrein 7

| SIGUIJ | 336 | O | ALA | A | 55 | 1 | 0 | 0 | 221 | 56 | 289 | A | O |
|---|---|---|---|---|---|---|---|---|---|---|---|---|---|
| ATOM | 337 | N | ALA | A | 56 | 21.161 | 3.886 | 35.553 | 1.00 | 8.88 | | A | N |
| ANISOU | 337 | N | ALA | A | 56 | 1095 | 1072 | 1255 | 2 | 0 | 0 | A | N |
| SIGUIJ | 337 | N | ALA | A | 56 | 1 | 0 | 0 | 221 | 64 | 289 | A | N |
| ATOM | 338 | CA | ALA | A | 56 | 22.391 | 4.022 | 36.349 | 1.00 | 9.13 | | A | C |
| ANISOU | 338 | CA | ALA | A | 56 | 1104 | 1100 | 1268 | 0 | −8 | 0 | A | C |
| SIGUIJ | 338 | CA | ALA | A | 56 | 2 | 0 | 0 | 220 | 183 | 290 | A | C |
| ATOM | 339 | CB | ALA | A | 56 | 23.610 | 3.713 | 35.508 | 1.00 | 9.18 | | A | C |
| ANISOU | 339 | CB | ALA | A | 56 | 1170 | 1355 | 1368 | 54 | 68 | −18 | A | C |
| SIGUIJ | 339 | CB | ALA | A | 56 | 2 | 0 | 0 | 220 | 182 | 290 | A | C |
| ATOM | 340 | C | ALA | A | 56 | 22.554 | 5.400 | 37.029 | 1.00 | 9.29 | | A | C |
| ANISOU | 340 | C | ALA | A | 56 | 1031 | 1098 | 1243 | −5 | 28 | 1 | A | C |
| SIGUIJ | 340 | C | ALA | A | 56 | 2 | 0 | 0 | 220 | 181 | 290 | A | C |
| ATOM | 341 | O | ALA | A | 56 | 23.143 | 5.504 | 38.109 | 1.00 | 9.43 | | A | O |
| ANISOU | 341 | O | ALA | A | 56 | 1154 | 1208 | 1275 | 1 | −41 | 0 | A | O |
| SIGUIJ | 341 | O | ALA | A | 56 | 1 | 0 | 0 | 221 | 56 | 289 | A | O |
| ATOM | 342 | N | HIS | A | 57 | 21.994 | 6.440 | 36.418 | 1.00 | 9.29 | | A | N |
| ANISOU | 342 | N | HIS | A | 57 | 957 | 1083 | 1231 | −43 | 84 | 18 | A | N |
| SIGUIJ | 342 | N | HIS | A | 57 | 1 | 0 | 0 | 221 | 64 | 289 | A | N |
| ATOM | 343 | CA | HIS | A | 57 | 22.040 | 7.794 | 36.980 | 1.00 | 9.88 | | A | C |
| ANISOU | 343 | CA | HIS | A | 57 | 1219 | 1096 | 1260 | −30 | 0 | 0 | A | C |
| SIGUIJ | 343 | CA | HIS | A | 57 | 2 | 0 | 0 | 220 | 181 | 290 | A | C |
| ATOM | 344 | CB | HIS | A | 57 | 21.411 | 8.781 | 35.963 | 1.00 | 10.96 | | A | C |
| ANISOU | 344 | CB | HIS | A | 57 | 1419 | 1251 | 1271 | 138 | 58 | 39 | A | C |
| SIGUIJ | 344 | CB | HIS | A | 57 | 2 | 0 | 0 | 220 | 180 | 290 | A | C |
| ATOM | 345 | CG | HIS | A | 57 | 21.862 | 10.199 | 36.174 | 1.00 | 12.51 | | A | C |
| ANISOU | 345 | CG | HIS | A | 57 | 1737 | 1288 | 1898 | 38 | −5 | 0 | A | C |
| SIGUIJ | 345 | CG | HIS | A | 57 | 2 | 0 | 0 | 220 | 179 | 290 | A | C |
| ATOM | 346 | CD2 | HIS | A | 57 | 22.606 | 10.741 | 37.162 | 1.00 | 13.42 | | A | C |
| ANISOU | 346 | CD2 | HIS | A | 57 | 1862 | 1514 | 1884 | −127 | 0 | 3 | A | C |
| SIGUIJ | 346 | CD2 | HIS | A | 57 | 2 | 0 | 0 | 220 | 179 | 290 | A | C |
| ATOM | 347 | ND1 | HIS | A | 57 | 21.560 | 11.229 | 35.324 | 1.00 | 14.09 | | A | N |
| ANISOU | 347 | ND1 | HIS | A | 57 | 2608 | 1322 | 1981 | 155 | −147 | −10 | A | N |
| SIGUIJ | 347 | ND1 | HIS | A | 57 | 1 | 0 | 0 | 221 | 64 | 289 | A | N |
| ATOM | 348 | CE1 | HIS | A | 57 | 22.111 | 12.339 | 35.771 | 1.00 | 13.23 | | A | C |
| ANISOU | 348 | CE1 | HIS | A | 57 | 2744 | 1480 | 1458 | −159 | 453 | −54 | A | C |
| SIGUIJ | 348 | CE1 | HIS | A | 57 | 2 | 0 | 0 | 220 | 178 | 290 | A | C |
| ATOM | 349 | NE2 | HIS | A | 57 | 22.758 | 12.076 | 36.880 | 1.00 | 14.35 | | A | N |
| ANISOU | 349 | NE2 | HIS | A | 57 | 3163 | 1518 | 1641 | −219 | 192 | −26 | A | N |
| SIGUIJ | 349 | NE2 | HIS | A | 57 | 1 | 0 | 0 | 221 | 64 | 289 | A | N |
| ATOM | 350 | C | HIS | A | 57 | 21.270 | 7.859 | 38.294 | 1.00 | 9.53 | | A | C |
| ANISOU | 350 | C | HIS | A | 57 | 1189 | 1089 | 1252 | −5 | 1 | 0 | A | C |
| SIGUIJ | 350 | C | HIS | A | 57 | 2 | 0 | 0 | 220 | 177 | 290 | A | C |
| ATOM | 351 | O | HIS | A | 57 | 21.458 | 8.814 | 39.087 | 1.00 | 10.26 | | A | O |
| ANISOU | 351 | O | HIS | A | 57 | 1338 | 1104 | 1272 | −37 | 1 | 0 | A | O |
| SIGUIJ | 351 | O | HIS | A | 57 | 1 | 0 | 0 | 221 | 56 | 289 | A | O |
| ATOM | 352 | N | CYS | A | 58 | 20.425 | 6.851 | 38.554 | 1.00 | 9.49 | | A | N |
| ANISOU | 352 | N | CYS | A | 58 | 1141 | 1056 | 1135 | 30 | 0 | 0 | A | N |
| SIGUIJ | 352 | N | CYS | A | 58 | 1 | 0 | 0 | 221 | 64 | 289 | A | N |
| ATOM | 353 | CA | CYS | A | 58 | 19.571 | 6.827 | 39.746 | 1.00 | 9.52 | | A | C |
| ANISOU | 353 | CA | CYS | A | 58 | 1135 | 1174 | 1134 | 1 | 0 | 0 | A | C |
| SIGUIJ | 353 | CA | CYS | A | 58 | 2 | 0 | 0 | 220 | 177 | 290 | A | C |
| ATOM | 354 | C | CYS | A | 58 | 20.272 | 6.262 | 40.960 | 1.00 | 9.45 | | A | C |
| ANISOU | 354 | C | CYS | A | 58 | 1145 | 1141 | 1148 | 0 | 0 | 0 | A | C |
| SIGUIJ | 354 | C | CYS | A | 58 | 2 | 0 | 0 | 220 | 176 | 290 | A | C |
| ATOM | 355 | O | CYS | A | 58 | 19.644 | 6.126 | 42.034 | 1.00 | 9.93 | | A | O |
| ANISOU | 355 | O | CYS | A | 58 | 1175 | 1346 | 1160 | −85 | 0 | −2 | A | O |
| SIGUIJ | 355 | O | CYS | A | 58 | 1 | 0 | 0 | 221 | 56 | 289 | A | O |
| ATOM | 356 | CB | CYS | A | 58 | 18.255 | 6.019 | 39.504 | 1.00 | 9.74 | | A | C |
| ANISOU | 356 | CB | CYS | A | 58 | 1142 | 1223 | 1171 | −10 | −1 | 0 | A | C |
| SIGUIJ | 356 | CB | CYS | A | 58 | 2 | 0 | 0 | 220 | 176 | 290 | A | C |
| ATOM | 357 | SG | CYS | A | 58 | 17.343 | 6.738 | 38.109 | 1.00 | 10.15 | | A | S |
| ANISOU | 357 | SG | CYS | A | 58 | 1255 | 1365 | 1167 | 73 | −21 | −8 | A | S |
| SIGUIJ | 357 | SG | CYS | A | 58 | 1 | 0 | 0 | 221 | 49 | 289 | A | S |
| ATOM | 358 | N | LYS | A | 59 | 21.545 | 5.879 | 40.830 | 1.00 | 9.63 | | A | N |
| ANISOU | 358 | N | LYS | A | 59 | 1153 | 1158 | 1143 | 0 | 0 | 0 | A | N |
| SIGUIJ | 358 | N | LYS | A | 59 | 1 | 0 | 0 | 221 | 64 | 289 | A | N |
| ATOM | 359 | CA | LYS | A | 59 | 22.295 | 5.248 | 41.932 | 1.00 | 10.30 | | A | C |
| ANISOU | 359 | CA | LYS | A | 59 | 1207 | 1213 | 1158 | 0 | −5 | 0 | A | C |
| SIGUIJ | 359 | CA | LYS | A | 59 | 2 | 0 | 0 | 220 | 175 | 290 | A | C |
| ATOM | 360 | CB | LYS | A | 59 | 23.780 | 5.188 | 41.566 | 1.00 | 10.96 | | A | C |
| ANISOU | 360 | CB | LYS | A | 59 | 1230 | 1351 | 1404 | 13 | 59 | −5 | A | C |
| SIGUIJ | 360 | CB | LYS | A | 59 | 2 | 0 | 0 | 220 | 174 | 290 | A | C |
| ATOM | 361 | CG | LYS | A | 59 | 24.660 | 4.440 | 42.551 | 1.00 | 11.83 | | A | C |
| ANISOU | 361 | CG | LYS | A | 59 | 1373 | 1413 | 1556 | 26 | −75 | 22 | A | C |
| SIGUIJ | 361 | CG | LYS | A | 59 | 2 | 0 | 0 | 220 | 174 | 290 | A | C |
| ATOM | 362 | CD | LYS | A | 59 | 24.533 | 2.938 | 42.481 | 1.00 | 12.32 | | A | C |
| ANISOU | 362 | CD | LYS | A | 59 | 1496 | 1416 | 1989 | 5 | −20 | 0 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 362 | CD | LYS | A | 59 | 2 | 0 | 0 | 220 | 173 | 290 | A | C |
| ATOM | 363 | CE | LYS | A | 59 | 25.438 | 2.259 | 43.495 | 1.00 | 13.78 | | A | C |
| ANISOU | 363 | CE | LYS | A | 59 | 1943 | 1448 | 2351 | 32 | −400 | 22 | A | C |
| SIGUIJ | 363 | CE | LYS | A | 59 | 2 | 0 | 0 | 220 | 173 | 290 | A | C |
| ATOM | 364 | NZ | LYS | A | 59 | 25.395 | 0.771 | 43.306 | 1.00 | 14.23 | | A | N |
| ANISOU | 364 | NZ | LYS | A | 59 | 1869 | 1446 | 2495 | 2 | −88 | −1 | A | N |
| SIGUIJ | 364 | NZ | LYS | A | 59 | 1 | 0 | 0 | 221 | 64 | 289 | A | N |
| ATOM | 365 | C | LYS | A | 59 | 22.162 | 5.994 | 43.235 | 1.00 | 10.26 | | A | C |
| ANISOU | 365 | C | LYS | A | 59 | 1250 | 1239 | 1163 | 0 | −3 | 0 | A | C |
| SIGUIJ | 365 | C | LYS | A | 59 | 2 | 0 | 0 | 220 | 172 | 290 | A | C |
| ATOM | 366 | O | LYS | A | 59 | 22.388 | 7.236 | 43.300 | 1.00 | 10.37 | | A | O |
| ANISOU | 366 | O | LYS | A | 59 | 1272 | 1239 | 1294 | −6 | 0 | 0 | A | O |
| SIGUIJ | 366 | O | LYS | A | 59 | 1 | 0 | 0 | 221 | 56 | 289 | A | O |
| ATOM | 367 | N | MET | A | 60 | 21.881 | 5.232 | 44.286 | 1.00 | 10.70 | | A | N |
| ANISOU | 367 | N | MET | A | 60 | 1336 | 1275 | 1175 | −9 | −15 | 2 | A | N |
| SIGUIJ | 367 | N | MET | A | 60 | 1 | 0 | 0 | 221 | 64 | 289 | A | N |
| ATOM | 368 | CA | MET | A | 60 | 21.897 | 5.745 | 45.657 | 1.00 | 11.34 | | A | C |
| ANISOU | 368 | CA | MET | A | 60 | 1248 | 1409 | 1190 | −70 | 5 | −4 | A | C |
| SIGUIJ | 368 | CA | MET | A | 60 | 2 | 0 | 0 | 220 | 172 | 290 | A | C |
| ATOM | 369 | CB | MET | A | 60 | 20.485 | 6.153 | 46.160 | 1.00 | 11.40 | | A | C |
| ANISOU | 369 | CB | MET | A | 60 | 1260 | 1508 | 1141 | −54 | 5 | −1 | A | C |
| SIGUIJ | 369 | CB | MET | A | 60 | 2 | 0 | 0 | 220 | 171 | 290 | A | C |
| ATOM | 370 | CG | MET | A | 60 | 19.864 | 7.316 | 45.370 | 1.00 | 11.47 | | A | C |
| ANISOU | 370 | CG | MET | A | 60 | 1539 | 1552 | 1210 | 0 | −88 | 1 | A | C |
| SIGUIJ | 370 | CG | MET | A | 60 | 2 | 0 | 0 | 220 | 170 | 290 | A | C |
| ATOM | 371 | SD | MET | A | 60 | 18.429 | 8.017 | 46.154 | 1.00 | 12.13 | | A | S |
| ANISOU | 371 | SD | MET | A | 60 | 1617 | 1619 | 1416 | 0 | 32 | −4 | A | S |
| SIGUIJ | 371 | SD | MET | A | 60 | 1 | 0 | 0 | 221 | 49 | 289 | A | S |
| ATOM | 372 | CE | MET | A | 60 | 17.335 | 6.674 | 45.953 | 1.00 | 12.68 | | A | C |
| ANISOU | 372 | CE | MET | A | 60 | 1631 | 1618 | 1685 | 0 | −1 | 0 | A | C |
| SIGUIJ | 372 | CE | MET | A | 60 | 2 | 0 | 0 | 220 | 170 | 290 | A | C |
| ATOM | 373 | C | MET | A | 60 | 22.473 | 4.642 | 46.538 | 1.00 | 11.97 | | A | C |
| ANISOU | 373 | C | MET | A | 60 | 1349 | 1454 | 1244 | −22 | −15 | 1 | A | C |
| SIGUIJ | 373 | C | MET | A | 60 | 2 | 0 | 0 | 220 | 169 | 290 | A | C |
| ATOM | 374 | O | MET | A | 60 | 22.558 | 3.468 | 46.135 | 1.00 | 11.95 | | A | O |
| ANISOU | 374 | O | MET | A | 60 | 1622 | 1458 | 1361 | 6 | −42 | −1 | A | O |
| SIGUIJ | 374 | O | MET | A | 60 | 1 | 0 | 0 | 221 | 56 | 289 | A | O |
| ATOM | 375 | N | ASN | A | 61 | 22.845 | 5.046 | 47.770 | 1.00 | 12.35 | | A | N |
| ANISOU | 375 | N | ASN | A | 61 | 1484 | 1681 | 1245 | −258 | 9 | −7 | A | N |
| SIGUIJ | 375 | N | ASN | A | 61 | 1 | 0 | 0 | 221 | 64 | 289 | A | N |
| ATOM | 376 | CA | ASN | A | 61 | 23.360 | 4.027 | 48.734 | 1.00 | 13.41 | | A | C |
| ANISOU | 376 | CA | ASN | A | 61 | 1617 | 1771 | 1319 | −213 | −53 | 15 | A | C |
| SIGUIJ | 376 | CA | ASN | A | 61 | 2 | 0 | 0 | 220 | 169 | 290 | A | C |
| ATOM | 377 | CB | ASN | A | 61 | 23.892 | 4.694 | 50.038 | 1.00 | 14.86 | | A | C |
| ANISOU | 377 | CB | ASN | A | 61 | 3266 | 1779 | 1457 | −502 | −580 | 159 | A | C |
| SIGUIJ | 377 | CB | ASN | A | 61 | 2 | 0 | 0 | 220 | 168 | 290 | A | C |
| ATOM | 378 | CG | ASN | A | 61 | 22.813 | 5.445 | 50.823 | 1.00 | 16.38 | | A | C |
| ANISOU | 378 | CG | ASN | A | 61 | 3335 | 1441 | 1982 | −792 | −221 | 101 | A | C |
| SIGUIJ | 378 | CG | ASN | A | 61 | 2 | 0 | 0 | 220 | 168 | 290 | A | C |
| ATOM | 379 | OD1 | ASN | A | 61 | 22.045 | 6.213 | 50.270 | 1.00 | 18.80 | | A | O |
| ANISOU | 379 | OD1 | ASN | A | 61 | 4072 | 2068 | 1933 | −106 | −272 | 14 | A | O |
| SIGUIJ | 379 | OD1 | ASN | A | 61 | 1 | 0 | 0 | 221 | 56 | 289 | A | O |
| ATOM | 380 | ND2 | ASN | A | 61 | 22.736 | 5.213 | 52.150 | 1.00 | 16.96 | | A | N |
| ANISOU | 380 | ND2 | ASN | A | 61 | 3563 | 3835 | 2029 | −1706 | −396 | 422 | A | N |
| SIGUIJ | 380 | ND2 | ASN | A | 61 | 1 | 0 | 0 | 221 | 64 | 289 | A | N |
| ATOM | 381 | C | ASN | A | 61 | 22.285 | 3.003 | 49.077 | 1.00 | 13.01 | | A | C |
| ANISOU | 381 | C | ASN | A | 61 | 1424 | 1571 | 1372 | −3 | −7 | 0 | A | C |
| SIGUIJ | 381 | C | ASN | A | 61 | 2 | 0 | 0 | 220 | 167 | 290 | A | C |
| ATOM | 382 | O | ASN | A | 61 | 22.608 | 1.872 | 49.349 | 1.00 | 13.50 | | A | O |
| ANISOU | 382 | O | ASN | A | 61 | 1675 | 1609 | 1932 | 9 | −255 | 91 | A | O |
| SIGUIJ | 382 | O | ASN | A | 61 | 1 | 0 | 0 | 221 | 56 | 289 | A | O |
| ATOM | 383 | N | GLU | A | 63 | 21.023 | 3.431 | 49.090 | 1.00 | 12.53 | | A | N |
| ANISOU | 383 | N | GLU | A | 63 | 1385 | 1471 | 1537 | −62 | −3 | −1 | A | N |
| SIGUIJ | 383 | N | GLU | A | 63 | 1 | 0 | 0 | 221 | 63 | 289 | A | N |
| ATOM | 384 | CA | GLU | A | 63 | 19.913 | 2.513 | 49.306 | 1.00 | 12.71 | | A | C |
| ANISOU | 384 | CA | GLU | A | 63 | 1326 | 1471 | 1544 | −29 | −20 | −3 | A | C |
| SIGUIJ | 384 | CA | GLU | A | 63 | 2 | 0 | 0 | 220 | 167 | 290 | A | C |
| ATOM | 385 | CB | GLU | A | 63 | 19.736 | 2.165 | 50.795 | 1.00 | 14.43 | | A | C |
| ANISOU | 385 | CB | GLU | A | 63 | 2200 | 1709 | 1562 | −81 | 64 | −8 | A | C |
| SIGUIJ | 385 | CB | GLU | A | 63 | 2 | 0 | 0 | 220 | 166 | 290 | A | C |
| ATOM | 386 | CG | GLU | A | 63 | 19.298 | 3.358 | 51.617 | 1.00 | 16.54 | | A | C |
| ANISOU | 386 | CG | GLU | A | 63 | 2343 | 1765 | 1556 | 27 | −22 | −1 | A | C |
| SIGUIJ | 386 | CG | GLU | A | 63 | 2 | 0 | 0 | 220 | 166 | 290 | A | C |
| ATOM | 387 | CD | GLU | A | 63 | 19.201 | 3.109 | 53.132 | 1.00 | 18.20 | | A | C |
| ANISOU | 387 | CD | GLU | A | 63 | 2750 | 3194 | 1587 | −794 | −150 | 148 | A | C |
| SIGUIJ | 387 | CD | GLU | A | 63 | 2 | 0 | 0 | 220 | 165 | 290 | A | C |
| ATOM | 388 | OE1 | GLU | A | 63 | 19.523 | 1.977 | 53.567 | 1.00 | 19.99 | | A | O |
| ANISOU | 388 | OE1 | GLU | A | 63 | 4498 | 3286 | 1741 | −416 | −449 | 110 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 388 | OE1 | GLU | A | 63 | 1 | 0 | 0 | 221 | 56 | 289 | A | O |
| ATOM | 389 | OE2 | GLU | A | 63 | 18.818 | 4.060 | 53.865 | 1.00 | 19.97 | | A | O |
| ANISOU | 389 | OE2 | GLU | A | 63 | 4058 | 3563 | 1631 | −98 | −368 | 37 | A | O |
| SIGUIJ | 389 | OE2 | GLU | A | 63 | 1 | 0 | 0 | 221 | 56 | 289 | A | O |
| ATOM | 390 | C | GLU | A | 63 | 18.664 | 3.191 | 48.763 | 1.00 | 12.29 | | A | C |
| ANISOU | 390 | C | GLU | A | 63 | 1309 | 1487 | 1482 | −25 | −4 | −1 | A | C |
| SIGUIJ | 390 | C | GLU | A | 63 | 2 | 0 | 0 | 220 | 165 | 290 | A | C |
| ATOM | 391 | O | GLU | A | 63 | 18.691 | 4.408 | 48.431 | 1.00 | 11.91 | | A | O |
| ANISOU | 391 | O | GLU | A | 63 | 1594 | 1484 | 1449 | −48 | −8 | 3 | A | O |
| SIGUIJ | 391 | O | GLU | A | 63 | 1 | 0 | 0 | 221 | 56 | 289 | A | O |
| ATOM | 392 | N | TYR | A | 64 | 17.566 | 2.423 | 48.707 | 1.00 | 11.40 | | A | N |
| ANISOU | 392 | N | TYR | A | 64 | 1302 | 1504 | 1269 | −33 | 0 | 0 | A | N |
| SIGUIJ | 392 | N | TYR | A | 64 | 1 | 0 | 0 | 221 | 63 | 289 | A | N |
| ATOM | 393 | CA | TYR | A | 64 | 16.342 | 2.920 | 48.090 | 1.00 | 11.01 | | A | C |
| ANISOU | 393 | CA | TYR | A | 64 | 1304 | 1529 | 1246 | −17 | 2 | 0 | A | C |
| SIGUIJ | 393 | CA | TYR | A | 64 | 2 | 0 | 0 | 220 | 164 | 290 | A | C |
| ATOM | 394 | CB | TYR | A | 64 | 16.171 | 2.369 | 46.649 | 1.00 | 11.12 | | A | C |
| ANISOU | 394 | CB | TYR | A | 64 | 1399 | 1577 | 1236 | −31 | 12 | 0 | A | C |
| SIGUIJ | 394 | CB | TYR | A | 64 | 2 | 0 | 0 | 220 | 164 | 290 | A | C |
| ATOM | 395 | CG | TYR | A | 64 | 17.429 | 2.395 | 45.795 | 1.00 | 10.88 | | A | C |
| ANISOU | 395 | CG | TYR | A | 64 | 1406 | 1299 | 1206 | −27 | 9 | −2 | A | C |
| SIGUIJ | 395 | CG | TYR | A | 64 | 2 | 0 | 0 | 220 | 163 | 290 | A | C |
| ATOM | 396 | CD1 | TYR | A | 64 | 17.623 | 3.388 | 44.817 | 1.00 | 10.36 | | A | C |
| ANISOU | 396 | CD1 | TYR | A | 64 | 1236 | 1307 | 1181 | −10 | −2 | 0 | A | C |
| SIGUIJ | 396 | CD1 | TYR | A | 64 | 2 | 0 | 0 | 220 | 163 | 290 | A | C |
| ATOM | 397 | CE1 | TYR | A | 64 | 18.785 | 3.425 | 44.042 | 1.00 | 11.12 | | A | C |
| ANISOU | 397 | CE1 | TYR | A | 64 | 1251 | 1400 | 1198 | −52 | 3 | −1 | A | C |
| SIGUIJ | 397 | CE1 | TYR | A | 64 | 2 | 0 | 0 | 220 | 162 | 290 | A | C |
| ATOM | 398 | CD2 | TYR | A | 64 | 18.418 | 1.456 | 45.983 | 1.00 | 10.39 | | A | C |
| ANISOU | 398 | CD2 | TYR | A | 64 | 1401 | 1279 | 1269 | −37 | 18 | −5 | A | C |
| SIGUIJ | 398 | CD2 | TYR | A | 64 | 2 | 0 | 0 | 220 | 162 | 290 | A | C |
| ATOM | 399 | CE2 | TYR | A | 64 | 19.572 | 1.461 | 45.226 | 1.00 | 11.07 | | A | C |
| ANISOU | 399 | CE2 | TYR | A | 64 | 1382 | 1442 | 1213 | −5 | −6 | 0 | A | C |
| SIGUIJ | 399 | CE2 | TYR | A | 64 | 2 | 0 | 0 | 220 | 161 | 290 | A | C |
| ATOM | 400 | CZ | TYR | A | 64 | 19.744 | 2.465 | 44.251 | 1.00 | 10.47 | | A | C |
| ANISOU | 400 | CZ | TYR | A | 64 | 1314 | 1434 | 1196 | −10 | −10 | 0 | A | C |
| SIGUIJ | 400 | CZ | TYR | A | 64 | 2 | 0 | 0 | 220 | 161 | 290 | A | C |
| ATOM | 401 | OH | TYR | A | 64 | 20.920 | 2.531 | 43.518 | 1.00 | 10.97 | | A | O |
| ANISOU | 401 | OH | TYR | A | 64 | 1338 | 1250 | 1217 | −13 | 11 | −1 | A | O |
| SIGUIJ | 401 | OH | TYR | A | 64 | 1 | 0 | 0 | 221 | 56 | 289 | A | O |
| ATOM | 402 | C | TYR | A | 64 | 15.140 | 2.452 | 48.882 | 1.00 | 10.76 | | A | C |
| ANISOU | 402 | C | TYR | A | 64 | 1295 | 1450 | 1252 | −5 | 1 | 0 | A | C |
| SIGUIJ | 402 | C | TYR | A | 64 | 2 | 0 | 0 | 220 | 161 | 290 | A | C |
| ATOM | 403 | O | TYR | A | 64 | 15.215 | 1.388 | 49.500 | 1.00 | 11.00 | | A | O |
| ANISOU | 403 | O | TYR | A | 64 | 1447 | 1447 | 1285 | 0 | 5 | 0 | A | O |
| SIGUIJ | 403 | O | TYR | A | 64 | 1 | 0 | 0 | 221 | 56 | 289 | A | O |
| ATOM | 404 | N | THR | A | 65 | 14.050 | 3.184 | 48.808 | 1.00 | 10.90 | | A | N |
| ANISOU | 404 | N | THR | A | 65 | 1263 | 1414 | 1312 | −42 | 2 | 1 | A | N |
| SIGUIJ | 404 | N | THR | A | 65 | 1 | 0 | 0 | 221 | 63 | 289 | A | N |
| ATOM | 405 | CA | THR | A | 65 | 12.729 | 2.613 | 49.160 | 1.00 | 10.94 | | A | C |
| ANISOU | 405 | CA | THR | A | 65 | 1275 | 1602 | 1189 | −104 | −15 | 10 | A | C |
| SIGUIJ | 405 | CA | THR | A | 65 | 2 | 0 | 0 | 220 | 160 | 290 | A | C |
| ATOM | 406 | CB | THR | A | 65 | 12.010 | 3.507 | 50.169 | 1.00 | 11.44 | | A | C |
| ANISOU | 406 | CB | THR | A | 65 | 1538 | 1758 | 1222 | 54 | 28 | −1 | A | C |
| SIGUIJ | 406 | CB | THR | A | 65 | 2 | 0 | 0 | 220 | 160 | 290 | A | C |
| ATOM | 407 | OG1 | THR | A | 65 | 12.804 | 3.542 | 51.378 | 1.00 | 12.76 | | A | O |
| ANISOU | 407 | OG1 | THR | A | 65 | 1686 | 2183 | 1274 | 26 | −63 | −3 | A | O |
| SIGUIJ | 407 | OG1 | THR | A | 65 | 1 | 0 | 0 | 221 | 56 | 289 | A | O |
| ATOM | 408 | CG2 | THR | A | 65 | 10.601 | 2.977 | 50.484 | 1.00 | 12.54 | | A | C |
| ANISOU | 408 | CG2 | THR | A | 65 | 1620 | 2247 | 1409 | −129 | 71 | −9 | A | C |
| SIGUIJ | 408 | CG2 | THR | A | 65 | 2 | 0 | 0 | 220 | 159 | 290 | A | C |
| ATOM | 409 | C | THR | A | 65 | 11.968 | 2.489 | 47.860 | 1.00 | 10.48 | | A | C |
| ANISOU | 409 | C | THR | A | 65 | 1234 | 1247 | 1178 | 1 | 4 | 0 | A | C |
| SIGUIJ | 409 | C | THR | A | 65 | 2 | 0 | 0 | 220 | 159 | 290 | A | C |
| ATOM | 410 | O | THR | A | 65 | 11.754 | 3.485 | 47.143 | 1.00 | 10.45 | | A | O |
| ANISOU | 410 | O | THR | A | 65 | 1626 | 1261 | 1260 | −28 | −151 | 11 | A | O |
| SIGUIJ | 410 | O | THR | A | 65 | 1 | 0 | 0 | 221 | 56 | 289 | A | O |
| ATOM | 411 | N | VAL | A | 66 | 11.531 | 1.285 | 47.556 | 1.00 | 10.31 | | A | N |
| ANISOU | 411 | N | VAL | A | 66 | 1269 | 1245 | 1202 | −1 | 5 | 0 | A | N |
| SIGUIJ | 411 | N | VAL | A | 66 | 1 | 0 | 0 | 221 | 63 | 289 | A | N |
| ATOM | 412 | CA | VAL | A | 66 | 10.826 | 1.050 | 46.318 | 1.00 | 10.41 | | A | C |
| ANISOU | 412 | CA | VAL | A | 66 | 1283 | 1255 | 1218 | 0 | 0 | 0 | A | C |
| SIGUIJ | 412 | CA | VAL | A | 66 | 2 | 0 | 0 | 220 | 158 | 290 | A | C |
| ATOM | 413 | CB | VAL | A | 66 | 11.278 | −0.305 | 45.707 | 1.00 | 10.27 | | A | C |
| ANISOU | 413 | CB | VAL | A | 66 | 1308 | 1252 | 1283 | 4 | 2 | 0 | A | C |
| SIGUIJ | 413 | CB | VAL | A | 66 | 2 | 0 | 0 | 220 | 158 | 290 | A | C |
| ATOM | 414 | CG1 | VAL | A | 66 | 10.536 | −0.512 | 44.365 | 1.00 | 11.03 | | A | C |
| ANISOU | 414 | CG1 | VAL | A | 66 | 1336 | 1294 | 1294 | −1 | −2 | 0 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 414 | CG1 | VAL | A | 66 | 2 | 0 | 0 | 220 | 157 | 290 | A | C |
| ATOM | 415 | CG2 | VAL | A | 66 | 12.791 | −0.328 | 45.524 | 1.00 | 11.29 | | A | C |
| ANISOU | 415 | CG2 | VAL | A | 66 | 1317 | 1501 | 2141 | 14 | 95 | −6 | A | C |
| SIGUIJ | 415 | CG2 | VAL | A | 66 | 2 | 0 | 0 | 220 | 157 | 290 | A | C |
| ATOM | 416 | C | VAL | A | 66 | 9.323 | 1.056 | 46.549 | 1.00 | 10.46 | | A | C |
| ANISOU | 416 | C | VAL | A | 66 | 1281 | 1388 | 1207 | 29 | −3 | 0 | A | C |
| SIGUIJ | 416 | C | VAL | A | 66 | 2 | 0 | 0 | 220 | 157 | 290 | A | C |
| ATOM | 417 | O | VAL | A | 66 | 8.809 | 0.338 | 47.437 | 1.00 | 10.81 | | A | O |
| ANISOU | 417 | O | VAL | A | 66 | 1451 | 1425 | 1233 | 4 | 54 | 6 | A | O |
| SIGUIJ | 417 | O | VAL | A | 66 | 1 | 0 | 0 | 221 | 56 | 289 | A | O |
| ATOM | 418 | N | HIS | A | 67 | 8.607 | 1.884 | 45.793 | 1.00 | 10.18 | | A | N |
| ANISOU | 418 | N | HIS | A | 67 | 1194 | 1341 | 1212 | −9 | 0 | 0 | A | N |
| SIGUIJ | 418 | N | HIS | A | 67 | 1 | 0 | 0 | 221 | 63 | 289 | A | N |
| ATOM | 419 | CA | HIS | A | 67 | 7.143 | 1.919 | 45.767 | 1.00 | 10.17 | | A | C |
| ANISOU | 419 | CA | HIS | A | 67 | 1196 | 1244 | 1298 | −1 | −5 | 0 | A | C |
| SIGUIJ | 419 | CA | HIS | A | 67 | 2 | 0 | 0 | 220 | 156 | 290 | A | C |
| ATOM | 420 | CB | HIS | A | 67 | 6.708 | 3.371 | 45.496 | 1.00 | 10.26 | | A | C |
| ANISOU | 420 | CB | HIS | A | 67 | 1232 | 1246 | 1435 | 0 | 2 | 0 | A | C |
| SIGUIJ | 420 | CB | HIS | A | 67 | 2 | 0 | 0 | 220 | 156 | 290 | A | C |
| ATOM | 421 | CG | HIS | A | 67 | 5.308 | 3.503 | 44.984 | 1.00 | 10.76 | | A | C |
| ANISOU | 421 | CG | HIS | A | 67 | 1245 | 1194 | 1533 | −2 | −28 | 1 | A | C |
| SIGUIJ | 421 | CG | HIS | A | 67 | 2 | 0 | 0 | 220 | 155 | 290 | A | C |
| ATOM | 422 | CD2 | HIS | A | 67 | 4.768 | 3.234 | 43.783 | 1.00 | 10.31 | | A | C |
| ANISOU | 422 | CD2 | HIS | A | 67 | 1216 | 1250 | 1538 | −1 | −17 | 0 | A | C |
| SIGUIJ | 422 | CD2 | HIS | A | 67 | 2 | 0 | 0 | 220 | 155 | 290 | A | C |
| ATOM | 423 | ND1 | HIS | A | 67 | 4.294 | 4.012 | 45.769 | 1.00 | 11.12 | | A | N |
| ANISOU | 423 | ND1 | HIS | A | 67 | 1360 | 1233 | 1686 | 3 | 107 | 3 | A | N |
| SIGUIJ | 423 | ND1 | HIS | A | 67 | 1 | 0 | 0 | 221 | 63 | 289 | A | N |
| ATOM | 424 | CE1 | HIS | A | 67 | 3.182 | 4.034 | 45.061 | 1.00 | 10.85 | | A | C |
| ANISOU | 424 | CE1 | HIS | A | 67 | 1383 | 1465 | 1735 | 17 | 71 | −9 | A | C |
| SIGUIJ | 424 | CE1 | HIS | A | 67 | 2 | 0 | 0 | 220 | 155 | 290 | A | C |
| ATOM | 425 | NE2 | HIS | A | 67 | 3.436 | 3.561 | 43.858 | 1.00 | 10.92 | | A | N |
| ANISOU | 425 | NE2 | HIS | A | 67 | 1229 | 1417 | 1718 | 61 | 2 | 0 | A | N |
| SIGUIJ | 425 | NE2 | HIS | A | 67 | 1 | 0 | 0 | 221 | 63 | 289 | A | N |
| ATOM | 426 | C | HIS | A | 67 | 6.627 | 1.015 | 44.664 | 1.00 | 10.07 | | A | C |
| ANISOU | 426 | C | HIS | A | 67 | 1158 | 1224 | 1269 | 1 | 3 | 0 | A | C |
| SIGUIJ | 426 | C | HIS | A | 67 | 2 | 0 | 0 | 220 | 154 | 290 | A | C |
| ATOM | 427 | O | HIS | A | 67 | 7.046 | 1.167 | 43.504 | 1.00 | 10.01 | | A | O |
| ANISOU | 427 | O | HIS | A | 67 | 1205 | 1245 | 1268 | 0 | 7 | 0 | A | O |
| SIGUIJ | 427 | O | HIS | A | 67 | 1 | 0 | 0 | 221 | 56 | 289 | A | O |
| ATOM | 428 | N | LEU | A | 68 | 5.689 | 0.115 | 45.004 | 1.00 | 9.85 | | A | N |
| ANISOU | 428 | N | LEU | A | 68 | 1174 | 1220 | 1400 | 0 | 48 | 0 | A | N |
| SIGUIJ | 428 | N | LEU | A | 68 | 1 | 0 | 0 | 221 | 63 | 289 | A | N |
| ATOM | 429 | CA | LEU | A | 68 | 5.041 | −0.761 | 44.009 | 1.00 | 10.06 | | A | C |
| ANISOU | 429 | CA | LEU | A | 68 | 1254 | 1218 | 1423 | −5 | 8 | 0 | A | C |
| SIGUIJ | 429 | CA | LEU | A | 68 | 2 | 0 | 0 | 220 | 154 | 290 | A | C |
| ATOM | 430 | CB | LEU | A | 68 | 5.539 | −2.229 | 44.129 | 1.00 | 11.11 | | A | C |
| ANISOU | 430 | CB | LEU | A | 68 | 1414 | 1239 | 1632 | 55 | −12 | 0 | A | C |
| SIGUIJ | 430 | CB | LEU | A | 68 | 2 | 0 | 0 | 220 | 153 | 290 | A | C |
| ATOM | 431 | CG | LEU | A | 68 | 7.056 | −2.399 | 44.241 | 1.00 | 10.33 | | A | C |
| ANISOU | 431 | CG | LEU | A | 68 | 1408 | 1250 | 1460 | 60 | 1 | −1 | A | C |
| SIGUIJ | 431 | CG | LEU | A | 68 | 2 | 0 | 0 | 220 | 153 | 290 | A | C |
| ATOM | 432 | CD1 | LEU | A | 68 | 7.481 | −2.431 | 45.695 | 1.00 | 11.37 | | A | C |
| ANISOU | 432 | CD1 | LEU | A | 68 | 1457 | 1613 | 1458 | −5 | 0 | 0 | A | C |
| SIGUIJ | 432 | CD1 | LEU | A | 68 | 2 | 0 | 0 | 220 | 153 | 290 | A | C |
| ATOM | 433 | CD2 | LEU | A | 68 | 7.459 | −3.723 | 43.526 | 1.00 | 11.32 | | A | C |
| ANISOU | 433 | CD2 | LEU | A | 68 | 1607 | 1255 | 1485 | 112 | 4 | 2 | A | C |
| SIGUIJ | 433 | CD2 | LEU | A | 68 | 2 | 0 | 0 | 220 | 152 | 290 | A | C |
| ATOM | 434 | C | LEU | A | 68 | 3.539 | −0.772 | 44.264 | 1.00 | 10.57 | | A | C |
| ANISOU | 434 | C | LEU | A | 68 | 1264 | 1284 | 1304 | 0 | −2 | 0 | A | C |
| SIGUIJ | 434 | C | LEU | A | 68 | 2 | 0 | 0 | 220 | 152 | 290 | A | C |
| ATOM | 435 | O | LEU | A | 68 | 3.091 | −0.494 | 45.394 | 1.00 | 10.51 | | A | O |
| ANISOU | 435 | O | LEU | A | 68 | 1309 | 1276 | 1306 | 3 | 0 | 0 | A | O |
| SIGUIJ | 435 | O | LEU | A | 68 | 1 | 0 | 0 | 221 | 56 | 289 | A | O |
| ATOM | 436 | N | GLY | A | 69 | 2.783 | −1.092 | 43.229 | 1.00 | 10.50 | | A | N |
| ANISOU | 436 | N | GLY | A | 69 | 1270 | 1244 | 1298 | 0 | 0 | 0 | A | N |
| SIGUIJ | 436 | N | GLY | A | 69 | 1 | 0 | 0 | 221 | 63 | 289 | A | N |
| ATOM | 437 | CA | GLY | A | 69 | 1.403 | −1.483 | 43.461 | 1.00 | 10.99 | | A | C |
| ANISOU | 437 | CA | GLY | A | 69 | 1293 | 1231 | 1709 | 0 | 86 | 1 | A | C |
| SIGUIJ | 437 | CA | GLY | A | 69 | 1 | 0 | 0 | 220 | 151 | 290 | A | C |
| ATOM | 438 | C | GLY | A | 69 | 0.398 | −0.368 | 43.576 | 1.00 | 11.51 | | A | C |
| ANISOU | 438 | C | GLY | A | 69 | 1328 | 1234 | 1649 | 2 | 110 | 4 | A | C |
| SIGUIJ | 438 | C | GLY | A | 69 | 1 | 0 | 0 | 220 | 151 | 290 | A | C |
| ATOM | 439 | O | GLY | A | 69 | −0.713 | −0.611 | 44.076 | 1.00 | 12.48 | | A | O |
| ANISOU | 439 | O | GLY | A | 69 | 1428 | 1370 | 2142 | 27 | 322 | 166 | A | O |
| SIGUIJ | 439 | O | GLY | A | 69 | 1 | 0 | 0 | 221 | 56 | 289 | A | O |
| ATOM | 440 | N | SER | A | 70 | 0.747 | 0.848 | 43.134 | 1.00 | 11.57 | | A | N |
| ANISOU | 440 | N | SER | A | 70 | 1235 | 1236 | 1574 | 0 | 24 | 0 | A | N |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 440 | N | SER | A | 70 | 1 | 0 | 0 | 221 | 63 | 289 | A | N |
| ATOM | 441 | CA | SER | A | 70 | −0.237 | 1.925 | 43.056 | 1.00 | 11.55 | | A | C |
| ANISOU | 441 | CA | SER | A | 70 | 1239 | 1251 | 1429 | 0 | 21 | 0 | A | C |
| SIGUIJ | 441 | CA | SER | A | 70 | 1 | 0 | 0 | 220 | 151 | 290 | A | C |
| ATOM | 442 | CB | SER | A | 70 | −0.441 | 2.619 | 44.423 | 1.00 | 11.96 | | A | C |
| ANISOU | 442 | CB | SER | A | 70 | 1738 | 1285 | 1450 | −46 | 94 | −11 | A | C |
| SIGUIJ | 442 | CB | SER | A | 70 | 1 | 0 | 0 | 220 | 150 | 290 | A | C |
| ATOM | 443 | OG | SER | A | 70 | −1.443 | 3.618 | 44.270 | 1.00 | 12.98 | | A | O |
| ANISOU | 443 | OG | SER | A | 70 | 1764 | 1288 | 1593 | −48 | 22 | −4 | A | O |
| SIGUIJ | 443 | OG | SER | A | 70 | 1 | 0 | 0 | 221 | 56 | 289 | A | O |
| ATOM | 444 | C | SER | A | 70 | 0.204 | 2.965 | 42.058 | 1.00 | 11.53 | | A | C |
| ANISOU | 444 | C | SER | A | 70 | 1228 | 1259 | 1420 | 3 | 43 | −2 | A | C |
| SIGUIJ | 444 | C | SER | A | 70 | 1 | 0 | 0 | 220 | 150 | 290 | A | C |
| ATOM | 445 | O | SER | A | 70 | 1.350 | 3.343 | 41.990 | 1.00 | 11.37 | | A | O |
| ANISOU | 445 | O | SER | A | 70 | 1239 | 1366 | 1663 | −21 | 49 | 5 | A | O |
| SIGUIJ | 445 | O | SER | A | 70 | 1 | 0 | 0 | 221 | 56 | 289 | A | O |
| ATOM | 446 | N | ASP | A | 71 | −0.770 | 3.521 | 41.354 | 1.00 | 11.71 | | A | N |
| ANISOU | 446 | N | ASP | A | 71 | 1281 | 1265 | 1534 | 0 | −31 | 0 | A | N |
| SIGUIJ | 446 | N | ASP | A | 71 | 1 | 0 | 0 | 221 | 63 | 289 | A | N |
| ATOM | 447 | CA | ASP | A | 71 | −0.489 | 4.711 | 40.534 | 1.00 | 12.03 | | A | C |
| ANISOU | 447 | CA | ASP | A | 71 | 1427 | 1275 | 1596 | 9 | 48 | 6 | A | C |
| SIGUIJ | 447 | CA | ASP | A | 71 | 1 | 0 | 0 | 220 | 150 | 290 | A | C |
| ATOM | 448 | CB | ASP | A | 71 | −1.604 | 4.894 | 39.509 | 1.00 | 13.40 | | A | C |
| ANISOU | 448 | CB | ASP | A | 71 | 1546 | 1920 | 1725 | 110 | −53 | 22 | A | C |
| SIGUIJ | 448 | CB | ASP | A | 71 | 1 | 0 | 0 | 220 | 149 | 290 | A | C |
| ATOM | 449 | CG | ASP | A | 71 | −1.791 | 3.679 | 38.665 | 1.00 | 14.52 | | A | C |
| ANISOU | 449 | CG | ASP | A | 71 | 1903 | 1952 | 1767 | 18 | 12 | −1 | A | C |
| SIGUIJ | 449 | CG | ASP | A | 71 | 1 | 0 | 0 | 220 | 149 | 290 | A | C |
| ATOM | 450 | OD1 | ASP | A | 71 | −0.769 | 3.147 | 38.164 | 1.00 | 14.88 | | A | O |
| ANISOU | 450 | OD1 | ASP | A | 71 | 1891 | 1928 | 1789 | −5 | 18 | 1 | A | O |
| SIGUIJ | 450 | OD1 | ASP | A | 71 | 1 | 0 | 0 | 221 | 56 | 289 | A | O |
| ATOM | 451 | OD2 | ASP | A | 71 | −2.933 | 3.147 | 38.541 | 1.00 | 16.44 | | A | O |
| ANISOU | 451 | OD2 | ASP | A | 71 | 2055 | 2638 | 2741 | −297 | −69 | −29 | A | O |
| SIGUIJ | 451 | OD2 | ASP | A | 71 | 1 | 0 | 0 | 221 | 56 | 289 | A | O |
| ATOM | 452 | C | ASP | A | 71 | −0.334 | 5.983 | 41.366 | 1.00 | 12.00 | | A | C |
| ANISOU | 452 | C | ASP | A | 71 | 1593 | 1286 | 1589 | 18 | 0 | 0 | A | C |
| SIGUIJ | 452 | C | ASP | A | 71 | 1 | 0 | 0 | 220 | 148 | 290 | A | C |
| ATOM | 453 | O | ASP | A | 71 | 0.092 | 7.014 | 40.822 | 1.00 | 11.57 | | A | O |
| ANISOU | 453 | O | ASP | A | 71 | 1416 | 1223 | 1748 | 205 | 222 | 23 | A | O |
| SIGUIJ | 453 | O | ASP | A | 71 | 1 | 0 | 0 | 221 | 56 | 289 | A | O |
| ATOM | 454 | N | THR | A | 72 | −0.589 | 5.932 | 42.678 | 1.00 | 11.84 | | A | N |
| ANISOU | 454 | N | THR | A | 72 | 1627 | 1334 | 1591 | 167 | 1 | 2 | A | N |
| SIGUIJ | 454 | N | THR | A | 72 | 1 | 0 | 0 | 221 | 63 | 289 | A | N |
| ATOM | 455 | CA | THR | A | 72 | −0.466 | 7.136 | 43.527 | 1.00 | 11.99 | | A | C |
| ANISOU | 455 | CA | THR | A | 72 | 1268 | 1356 | 1575 | −7 | 322 | 0 | A | C |
| SIGUIJ | 455 | CA | THR | A | 72 | 1 | 0 | 0 | 220 | 148 | 290 | A | C |
| ATOM | 456 | CB | THR | A | 72 | −1.802 | 7.379 | 44.280 | 1.00 | 12.04 | | A | C |
| ANISOU | 456 | CB | THR | A | 72 | 1289 | 1617 | 1621 | 29 | 345 | −17 | A | C |
| SIGUIJ | 456 | CB | THR | A | 72 | 1 | 0 | 0 | 220 | 148 | 290 | A | C |
| ATOM | 457 | OG1 | THR | A | 72 | −2.851 | 7.509 | 43.306 | 1.00 | 12.69 | | A | O |
| ANISOU | 457 | OG1 | THR | A | 72 | 1472 | 1832 | 1826 | 116 | 159 | −45 | A | O |
| SIGUIJ | 457 | OG1 | THR | A | 72 | 1 | 0 | 0 | 221 | 56 | 289 | A | O |
| ATOM | 458 | CG2 | THR | A | 72 | −1.690 | 8.607 | 45.139 | 1.00 | 12.47 | | A | C |
| ANISOU | 458 | CG2 | THR | A | 72 | 1869 | 1575 | 1577 | 163 | 78 | 38 | A | C |
| SIGUIJ | 458 | CG2 | THR | A | 72 | 1 | 0 | 0 | 220 | 147 | 290 | A | C |
| ATOM | 459 | C | THR | A | 72 | 0.680 | 6.999 | 44.523 | 1.00 | 12.26 | | A | C |
| ANISOU | 459 | C | THR | A | 72 | 1391 | 1326 | 1778 | 0 | 167 | −1 | A | C |
| SIGUIJ | 459 | C | THR | A | 72 | 1 | 0 | 0 | 220 | 147 | 290 | A | C |
| ATOM | 460 | O | THR | A | 72 | 0.670 | 6.113 | 45.375 | 1.00 | 12.26 | | A | O |
| ANISOU | 460 | O | THR | A | 72 | 1528 | 1340 | 1812 | 14 | 190 | 14 | A | O |
| SIGUIJ | 460 | O | THR | A | 72 | 1 | 0 | 0 | 221 | 56 | 289 | A | O |
| ATOM | 461 | N | LEU | A | 73 | 1.680 | 7.883 | 44.462 | 1.00 | 12.60 | | A | N |
| ANISOU | 461 | N | LEU | A | 73 | 1402 | 1339 | 1916 | −10 | 225 | −38 | A | N |
| SIGUIJ | 461 | N | LEU | A | 73 | 1 | 0 | 0 | 221 | 63 | 289 | A | N |
| ATOM | 462 | CA | LEU | A | 73 | 2.735 | 7.884 | 45.504 | 1.00 | 13.57 | | A | C |
| ANISOU | 462 | CA | LEU | A | 73 | 1418 | 1628 | 1928 | −59 | 214 | 36 | A | C |
| SIGUIJ | 462 | CA | LEU | A | 73 | 1 | 0 | 0 | 220 | 147 | 290 | A | C |
| ATOM | 463 | CB | LEU | A | 73 | 3.846 | 8.880 | 45.130 | 1.00 | 14.14 | | A | C |
| ANISOU | 463 | CB | LEU | A | 73 | 1465 | 1597 | 2415 | −28 | 407 | 22 | A | C |
| SIGUIJ | 463 | CB | LEU | A | 73 | 1 | 0 | 0 | 220 | 146 | 290 | A | C |
| ATOM | 464 | CG | LEU | A | 73 | 4.664 | 8.540 | 43.867 | 1.00 | 13.84 | | A | C |
| ANISOU | 464 | CG | LEU | A | 73 | 1301 | 1722 | 2343 | 0 | 289 | 3 | A | C |
| SIGUIJ | 464 | CG | LEU | A | 73 | 1 | 0 | 0 | 220 | 146 | 290 | A | C |
| ATOM | 465 | CD1 | LEU | A | 73 | 5.730 | 9.650 | 43.616 | 1.00 | 14.45 | | A | C |
| ANISOU | 465 | CD1 | LEU | A | 73 | 1792 | 2224 | 2208 | −505 | 131 | 111 | A | C |
| SIGUIJ | 465 | CD1 | LEU | A | 73 | 1 | 0 | 0 | 220 | 146 | 290 | A | C |
| ATOM | 466 | CD2 | LEU | A | 73 | 5.275 | 7.165 | 43.926 | 1.00 | 13.66 | | A | C |
| ANISOU | 466 | CD2 | LEU | A | 73 | 1572 | 1774 | 1998 | 116 | 193 | −65 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 466 | CD2 | LEU | A | 73 | 1 | 0 | 0 | 220 | 145 | 290 | A | C |
| ATOM | 467 | C | LEU | A | 73 | 2.146 | 8.248 | 46.864 | 1.00 | 14.07 | | A | C |
| ANISOU | 467 | C | LEU | A | 73 | 1415 | 1764 | 1928 | −28 | 196 | 10 | A | C |
| SIGUIJ | 467 | C | LEU | A | 73 | 1 | 0 | 0 | 220 | 145 | 290 | A | C |
| ATOM | 468 | O | LEU | A | 73 | 1.291 | 9.145 | 46.949 | 1.00 | 14.84 | | A | O |
| ANISOU | 468 | O | LEU | A | 73 | 1604 | 1916 | 2178 | 129 | 180 | −51 | A | O |
| SIGUIJ | 468 | O | LEU | A | 73 | 1 | 0 | 0 | 221 | 56 | 289 | A | O |
| ATOM | 469 | N | GLY | A | 76 | 2.573 | 7.558 | 47.894 | 1.00 | 14.43 | | A | N |
| ANISOU | 469 | N | GLY | A | 76 | 1813 | 1793 | 1988 | 0 | 31 | 0 | A | N |
| SIGUIJ | 469 | N | GLY | A | 76 | 1 | 0 | 0 | 221 | 63 | 289 | A | N |
| ATOM | 470 | CA | GLY | A | 76 | 2.029 | 7.757 | 49.227 | 1.00 | 14.66 | | A | C |
| ANISOU | 470 | CA | GLY | A | 76 | 1744 | 1834 | 1985 | −30 | 8 | 2 | A | C |
| SIGUIJ | 470 | CA | GLY | A | 76 | 1 | 0 | 0 | 220 | 145 | 290 | A | C |
| ATOM | 471 | C | GLY | A | 76 | 0.747 | 6.990 | 49.509 | 1.00 | 14.25 | | A | C |
| ANISOU | 471 | C | GLY | A | 76 | 1721 | 1756 | 1856 | −5 | −26 | −3 | A | C |
| SIGUIJ | 471 | C | GLY | A | 76 | 1 | 0 | 0 | 220 | 144 | 290 | A | C |
| ATOM | 472 | O | GLY | A | 76 | 0.269 | 7.028 | 50.633 | 1.00 | 14.94 | | A | O |
| ANISOU | 472 | O | GLY | A | 76 | 1824 | 2245 | 1875 | 36 | 13 | −5 | A | O |
| SIGUIJ | 472 | O | GLY | A | 76 | 1 | 0 | 0 | 221 | 56 | 289 | A | O |
| ATOM | 473 | N | ASP | A | 77 | 0.159 | 6.340 | 48.523 | 1.00 | 13.69 | | A | N |
| ANISOU | 473 | N | ASP | A | 77 | 1317 | 1637 | 1787 | 112 | 135 | −36 | A | N |
| SIGUIJ | 473 | N | ASP | A | 77 | 1 | 0 | 0 | 221 | 63 | 289 | A | N |
| ATOM | 474 | CA | ASP | A | 77 | −1.065 | 5.558 | 48.748 | 1.00 | 13.68 | | A | C |
| ANISOU | 474 | CA | ASP | A | 77 | 1253 | 1499 | 1497 | 188 | 60 | −38 | A | C |
| SIGUIJ | 474 | CA | ASP | A | 77 | 1 | 0 | 0 | 220 | 144 | 290 | A | C |
| ATOM | 475 | CB | ASP | A | 77 | −1.328 | 4.788 | 47.449 | 1.00 | 13.39 | | A | C |
| ANISOU | 475 | CB | ASP | A | 77 | 1275 | 1491 | 1499 | 144 | 77 | −42 | A | C |
| SIGUIJ | 475 | CB | ASP | A | 77 | 1 | 0 | 0 | 220 | 144 | 290 | A | C |
| ATOM | 476 | CG | ASP | A | 77 | −2.624 | 3.983 | 47.429 | 1.00 | 13.49 | | A | C |
| ANISOU | 476 | CG | ASP | A | 77 | 1298 | 1594 | 1652 | 81 | 69 | −17 | A | C |
| SIGUIJ | 476 | CG | ASP | A | 77 | 1 | 0 | 0 | 220 | 143 | 290 | A | C |
| ATOM | 477 | OD1 | ASP | A | 77 | −3.249 | 3.763 | 48.497 | 1.00 | 13.62 | | A | O |
| ANISOU | 477 | OD1 | ASP | A | 77 | 1608 | 1673 | 1756 | 27 | 252 | −26 | A | O |
| SIGUIJ | 477 | OD1 | ASP | A | 77 | 1 | 0 | 0 | 221 | 56 | 289 | A | O |
| ATOM | 478 | OD2 | ASP | A | 77 | −3.016 | 3.557 | 46.318 | 1.00 | 14.34 | | A | O |
| ANISOU | 478 | OD2 | ASP | A | 77 | 1858 | 1927 | 1673 | −312 | −4 | 14 | A | O |
| SIGUIJ | 478 | OD2 | ASP | A | 77 | 1 | 0 | 0 | 221 | 56 | 289 | A | O |
| ATOM | 479 | C | ASP | A | 77 | −0.798 | 4.565 | 49.902 | 1.00 | 14.30 | | A | C |
| ANISOU | 479 | C | ASP | A | 77 | 1373 | 1544 | 1509 | 164 | 23 | −19 | A | C |
| SIGUIJ | 479 | C | ASP | A | 77 | 1 | 0 | 0 | 220 | 143 | 290 | A | C |
| ATOM | 480 | O | ASP | A | 77 | 0.222 | 3.792 | 49.856 | 1.00 | 14.35 | | A | O |
| ANISOU | 480 | O | ASP | A | 77 | 1562 | 1823 | 1918 | 397 | 35 | −31 | A | O |
| SIGUIJ | 480 | O | ASP | A | 77 | 1 | 0 | 0 | 221 | 56 | 289 | A | O |
| ATOM | 481 | N | ARG | A | 78 | −1.655 | 4.557 | 50.920 | 1.00 | 14.71 | | A | N |
| ANISOU | 481 | N | ARG | A | 78 | 1452 | 1639 | 1527 | 128 | 77 | −58 | A | N |
| SIGUIJ | 481 | N | ARG | A | 78 | 1 | 0 | 0 | 221 | 63 | 289 | A | N |
| ATOM | 482 | CA | ARG | A | 78 | −1.464 | 3.618 | 52.022 | 1.00 | 16.17 | | A | C |
| ANISOU | 482 | CA | ARG | A | 78 | 2269 | 1750 | 1601 | 287 | 65 | 28 | A | C |
| SIGUIJ | 482 | CA | ARG | A | 78 | 1 | 0 | 0 | 220 | 143 | 290 | A | C |
| ATOM | 483 | CB | ARG | A | 78 | −2.529 | 3.871 | 53.099 | 1.00 | 17.47 | | A | C |
| ANISOU | 483 | CB | ARG | A | 78 | 2312 | 2487 | 1606 | 464 | 61 | 16 | A | C |
| SIGUIJ | 483 | CB | ARG | A | 78 | 1 | 0 | 0 | 220 | 142 | 290 | A | C |
| ATOM | 484 | CG | ARG | A | 78 | −2.395 | 5.237 | 53.737 | 1.00 | 19.88 | | A | C |
| ANISOU | 484 | CG | ARG | A | 78 | 4181 | 2508 | 1646 | 282 | 71 | 10 | A | C |
| SIGUIJ | 484 | CG | ARG | A | 78 | 1 | 0 | 0 | 220 | 142 | 290 | A | C |
| ATOM | 485 | CD | ARG | A | 78 | −2.622 | 5.235 | 55.222 | 1.00 | 22.19 | | A | C |
| ANISOU | 485 | CD | ARG | A | 78 | 9298 | 12495 | 1770 | 143 | 854 | 5 | A | C |
| SIGUIJ | 485 | CD | ARG | A | 78 | 1 | 0 | 0 | 220 | 142 | 290 | A | C |
| ATOM | 486 | NE | ARG | A | 78 | −2.002 | 6.444 | 55.777 | 1.00 | 24.36 | | A | N |
| ANISOU | 486 | NE | ARG | A | 78 | 12217 | 12616 | 5189 | −25 | −2043 | −76 | A | N |
| SIGUIJ | 486 | NE | ARG | A | 78 | 1 | 0 | 0 | 221 | 63 | 289 | A | N |
| ATOM | 487 | CZ | ARG | A | 78 | −2.465 | 7.108 | 56.841 | 1.00 | 24.83 | | A | C |
| ANISOU | 487 | CZ | ARG | A | 78 | 12396 | 12449 | 5150 | 1 | −1980 | 33 | A | C |
| SIGUIJ | 487 | CZ | ARG | A | 78 | 1 | 0 | 0 | 220 | 141 | 290 | A | C |
| ATOM | 488 | NH1 | ARG | A | 78 | −3.552 | 6.670 | 57.451 | 1.00 | 25.75 | | A | N |
| ANISOU | 488 | NH1 | ARG | A | 78 | 13703 | 12469 | 9248 | −20 | 334 | −1 | A | N |
| SIGUIJ | 488 | NH1 | ARG | A | 78 | 1 | 0 | 0 | 221 | 63 | 289 | A | N |
| ATOM | 489 | NH2 | ARG | A | 78 | −1.838 | 8.192 | 57.300 | 1.00 | 25.77 | | A | N |
| ANISOU | 489 | NH2 | ARG | A | 78 | 10587 | 12383 | 2300 | 134 | 175 | −3 | A | N |
| SIGUIJ | 489 | NH2 | ARG | A | 78 | 1 | 0 | 0 | 221 | 63 | 289 | A | N |
| ATOM | 490 | C | ARG | A | 78 | −1.544 | 2.178 | 51.552 | 1.00 | 16.15 | | A | C |
| ANISOU | 490 | C | ARG | A | 78 | 1423 | 1795 | 2007 | 264 | 272 | −124 | A | C |
| SIGUIJ | 490 | C | ARG | A | 78 | 1 | 0 | 0 | 220 | 141 | 290 | A | C |
| ATOM | 491 | O | ARG | A | 78 | −1.031 | 1.267 | 52.269 | 1.00 | 16.98 | | A | O |
| ANISOU | 491 | O | ARG | A | 78 | 2446 | 2180 | 2451 | 659 | 47 | 112 | A | O |
| SIGUIJ | 491 | O | ARG | A | 78 | 1 | 0 | 0 | 221 | 56 | 289 | A | O |
| ATOM | 492 | N | ARG | A | 79 | −2.172 | 1.901 | 50.414 | 1.00 | 16.20 | | A | N |
| ANISOU | 492 | N | ARG | A | 79 | 1402 | 1810 | 1951 | −7 | 327 | 19 | A | N |

TABLE 3-continued

Three-dimensional structure of the new binding pocket of kallikrein 7

| | | | | | | | | | | | | | | |
|---|---|---|---|---|---|---|---|---|---|---|---|---|---|---|
| SIGUIJ | 492 | N | ARG | A | 79 | 1 | 0 | 0 | 221 | 63 | 289 | A | N | |
| ATOM | 493 | CA | ARG | A | 79 | −2.289 | 0.528 | 49.913 | 1.00 | 16.42 | | A | C | |
| ANISOU | 493 | CA | ARG | A | 79 | 1569 | 1827 | 2088 | 26 | 234 | −31 | A | C | |
| SIGUIJ | 493 | CA | ARG | A | 79 | 1 | 0 | 0 | 220 | 141 | 290 | A | C | |
| ATOM | 494 | CB | ARG | A | 79 | −3.446 | 0.379 | 48.938 | 1.00 | 17.75 | | A | C | |
| ANISOU | 494 | CB | ARG | A | 79 | 2015 | 2016 | 2694 | −8 | −291 | −5 | A | C | |
| SIGUIJ | 494 | CB | ARG | A | 79 | 1 | 0 | 0 | 220 | 141 | 290 | A | C | |
| ATOM | 495 | CG | ARG | A | 79 | −4.772 | 0.900 | 49.454 | 1.00 | 19.73 | | A | C | |
| ANISOU | 495 | CG | ARG | A | 79 | 2352 | 2502 | 4693 | 128 | 447 | −122 | A | C | |
| SIGUIJ | 495 | CG | ARG | A | 79 | 1 | 0 | 0 | 220 | 140 | 290 | A | C | |
| ATOM | 496 | CD | ARG | A | 79 | −5.852 | 0.878 | 48.382 | 1.00 | 21.61 | | A | C | |
| ANISOU | 496 | CD | ARG | A | 79 | 2995 | 3034 | 5338 | −6 | −194 | −6 | A | C | |
| SIGUIJ | 496 | CD | ARG | A | 79 | 1 | 0 | 0 | 220 | 140 | 290 | A | C | |
| ATOM | 497 | NE | ARG | A | 79 | −5.728 | 1.918 | 47.348 | 1.00 | 23.13 | | A | N | |
| ANISOU | 497 | NE | ARG | A | 79 | 2535 | 3036 | 5331 | −8 | −269 | −3 | A | N | |
| SIGUIJ | 497 | NE | ARG | A | 79 | 1 | 0 | 0 | 221 | 63 | 289 | A | N | |
| ATOM | 498 | CZ | ARG | A | 79 | −5.263 | 1.690 | 46.132 | 1.00 | 22.93 | | A | C | |
| ANISOU | 498 | CZ | ARG | A | 79 | 3535 | 2972 | 5475 | −31 | 109 | −1 | A | C | |
| SIGUIJ | 498 | CZ | ARG | A | 79 | 1 | 0 | 0 | 220 | 140 | 290 | A | C | |
| ATOM | 499 | NH1 | ARG | A | 79 | −4.840 | 0.456 | 45.833 | 1.00 | 24.17 | | A | N | |
| ANISOU | 499 | NH1 | ARG | A | 79 | 13175 | 4146 | 5369 | 3344 | −187 | −71 | A | N | |
| SIGUIJ | 499 | NH1 | ARG | A | 79 | 1 | 0 | 0 | 221 | 63 | 289 | A | N | |
| ATOM | 500 | NH2 | ARG | A | 79 | −5.275 | 2.636 | 45.196 | 1.00 | 23.78 | | A | N | |
| ANISOU | 500 | NH2 | ARG | A | 79 | 2347 | 2953 | 5443 | 101 | 254 | −27 | A | N | |
| SIGUIJ | 500 | NH2 | ARG | A | 79 | 1 | 0 | 0 | 221 | 63 | 289 | A | N | |
| ATOM | 501 | C | ARG | A | 79 | −1.034 | 0.098 | 49.130 | 1.00 | 15.58 | | A | C | |
| ANISOU | 501 | C | ARG | A | 79 | 1606 | 1618 | 2236 | 0 | 327 | 12 | A | C | |
| SIGUIJ | 501 | C | ARG | A | 79 | 1 | 0 | 0 | 220 | 139 | 290 | A | C | |
| ATOM | 502 | O | ARG | A | 79 | −0.912 | −1.087 | 48.742 | 1.00 | 15.65 | | A | O | |
| ANISOU | 502 | O | ARG | A | 79 | 1870 | 1615 | 2332 | 2 | 464 | 5 | A | O | |
| SIGUIJ | 502 | O | ARG | A | 79 | 1 | 0 | 0 | 221 | 55 | 289 | A | O | |
| ATOM | 503 | N | ALA | A | 80 | −0.142 | 1.027 | 48.813 | 1.00 | 14.69 | | A | N | |
| ANISOU | 503 | N | ALA | A | 80 | 1528 | 1554 | 1949 | 42 | 261 | −52 | A | N | |
| SIGUIJ | 503 | N | ALA | A | 80 | 1 | 0 | 0 | 221 | 63 | 289 | A | N | |
| ATOM | 504 | CA | ALA | A | 80 | 1.055 | 0.671 | 48.028 | 1.00 | 13.83 | | A | C | |
| ANISOU | 504 | CA | ALA | A | 80 | 1362 | 1539 | 1466 | 101 | −41 | 26 | A | C | |
| SIGUIJ | 504 | CA | ALA | A | 80 | 1 | 0 | 0 | 220 | 139 | 290 | A | C | |
| ATOM | 505 | CB | ALA | A | 80 | 1.820 | 1.914 | 47.622 | 1.00 | 14.11 | | A | C | |
| ANISOU | 505 | CB | ALA | A | 80 | 1648 | 1594 | 1901 | 3 | 210 | 16 | A | C | |
| SIGUIJ | 505 | CB | ALA | A | 80 | 1 | 0 | 0 | 220 | 139 | 290 | A | C | |
| ATOM | 506 | C | ALA | A | 80 | 1.967 | −0.207 | 48.880 | 1.00 | 13.53 | | A | C | |
| ANISOU | 506 | C | ALA | A | 80 | 1254 | 1447 | 1366 | 57 | 32 | −12 | A | C | |
| SIGUIJ | 506 | C | ALA | A | 80 | 1 | 0 | 0 | 220 | 138 | 290 | A | C | |
| ATOM | 507 | O | ALA | A | 80 | 1.945 | −0.152 | 50.133 | 1.00 | 14.15 | | A | O | |
| ANISOU | 507 | O | ALA | A | 80 | 1894 | 2156 | 1364 | 533 | 24 | 17 | A | O | |
| SIGUIJ | 507 | O | ALA | A | 80 | 1 | 0 | 0 | 221 | 55 | 289 | A | O | |
| ATOM | 508 | N | GLN | A | 81 | 2.777 | −1.007 | 48.211 | 1.00 | 12.88 | | A | N | |
| ANISOU | 508 | N | GLN | A | 81 | 1164 | 1353 | 1355 | −3 | 17 | 0 | A | N | |
| SIGUIJ | 508 | N | GLN | A | 81 | 1 | 0 | 0 | 221 | 63 | 289 | A | N | |
| ATOM | 509 | CA | GLN | A | 81 | 3.903 | −1.702 | 48.858 | 1.00 | 12.88 | | A | C | |
| ANISOU | 509 | CA | GLN | A | 81 | 1258 | 1538 | 1457 | 117 | −31 | 15 | A | C | |
| SIGUIJ | 509 | CA | GLN | A | 81 | 1 | 0 | 0 | 220 | 138 | 290 | A | C | |
| ATOM | 510 | CB | GLN | A | 81 | 4.243 | −2.974 | 48.113 | 1.00 | 13.68 | | A | C | |
| ANISOU | 510 | CB | GLN | A | 81 | 1628 | 1557 | 1580 | 178 | −15 | −23 | A | C | |
| SIGUIJ | 510 | CB | GLN | A | 81 | 1 | 0 | 0 | 220 | 138 | 290 | A | C | |
| ATOM | 511 | CG | GLN | A | 81 | 3.280 | −4.094 | 48.365 | 1.00 | 14.30 | | A | C | |
| ANISOU | 511 | CG | GLN | A | 81 | 2118 | 1938 | 1820 | −259 | 12 | −9 | A | C | |
| SIGUIJ | 511 | CG | GLN | A | 81 | 1 | 0 | 0 | 220 | 138 | 290 | A | C | |
| ATOM | 512 | CD | GLN | A | 81 | 3.665 | −5.304 | 47.553 | 1.00 | 14.78 | | A | C | |
| ANISOU | 512 | CD | GLN | A | 81 | 2410 | 1963 | 1852 | −203 | 54 | −20 | A | C | |
| SIGUIJ | 512 | CD | GLN | A | 81 | 1 | 0 | 0 | 220 | 137 | 290 | A | C | |
| ATOM | 513 | OE1 | GLN | A | 81 | 4.755 | −5.840 | 47.685 | 1.00 | 14.65 | | A | O | |
| ANISOU | 513 | OE1 | GLN | A | 81 | 2285 | 1532 | 1692 | −435 | 53 | −31 | A | O | |
| SIGUIJ | 513 | OE1 | GLN | A | 81 | 1 | 0 | 0 | 221 | 55 | 289 | A | O | |
| ATOM | 514 | NE2 | GLN | A | 81 | 2.772 | −5.731 | 46.694 | 1.00 | 15.20 | | A | N | |
| ANISOU | 514 | NE2 | GLN | A | 81 | 2594 | 1610 | 2068 | −72 | −186 | 19 | A | N | |
| SIGUIJ | 514 | NE2 | GLN | A | 81 | 1 | 0 | 0 | 221 | 63 | 289 | A | N | |
| ATOM | 515 | C | GLN | A | 81 | 5.107 | −0.798 | 48.860 | 1.00 | 12.83 | | A | C | |
| ANISOU | 515 | C | GLN | A | 81 | 1272 | 1621 | 1317 | 87 | 1 | −1 | A | C | |
| SIGUIJ | 515 | C | GLN | A | 81 | 1 | 0 | 0 | 220 | 137 | 290 | A | C | |
| ATOM | 516 | O | GLN | A | 81 | 5.399 | −0.130 | 47.854 | 1.00 | 13.03 | | A | O | |
| ANISOU | 516 | O | GLN | A | 81 | 1658 | 1744 | 1347 | −33 | 49 | 8 | A | O | |
| SIGUIJ | 516 | O | GLN | A | 81 | 1 | 0 | 0 | 221 | 55 | 289 | A | O | |
| ATOM | 517 | N | ARG | A | 82 | 5.822 | −0.751 | 49.982 | 1.00 | 12.82 | | A | N | |
| ANISOU | 517 | N | ARG | A | 82 | 1266 | 1962 | 1310 | 69 | 0 | 0 | A | N | |
| SIGUIJ | 517 | N | ARG | A | 82 | 1 | 0 | 0 | 221 | 63 | 289 | A | N | |
| ATOM | 518 | CA | ARG | A | 82 | 7.114 | −0.102 | 50.076 | 1.00 | 13.15 | | A | C | |
| ANISOU | 518 | CA | ARG | A | 82 | 1298 | 2122 | 1292 | −4 | 1 | 19 | A | C | |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 518 | CA | ARG | A | 82 | 1 | 0 | 0 | 220 | 137 | 290 | A | C |
| ATOM | 519 | CB | ARG | A | 82 | 7.102 | 1.055 | 51.076 | 1.00 | 13.97 | | A | C |
| ANISOU | 519 | CB | ARG | A | 82 | 1542 | 2195 | 1404 | −74 | 89 | −71 | A | C |
| SIGUIJ | 519 | CB | ARG | A | 82 | 1 | 0 | 0 | 220 | 136 | 290 | A | C |
| ATOM | 520 | CG | ARG | A | 82 | 6.258 | 2.217 | 50.605 | 1.00 | 15.61 | | A | C |
| ANISOU | 520 | CG | ARG | A | 82 | 1860 | 2364 | 1795 | 128 | −3 | −4 | A | C |
| SIGUIJ | 520 | CG | ARG | A | 82 | 1 | 0 | 0 | 220 | 136 | 290 | A | C |
| ATOM | 521 | CD | ARG | A | 82 | 5.972 | 3.220 | 51.759 | 1.00 | 17.78 | | A | C |
| ANISOU | 521 | CD | ARG | A | 82 | 3912 | 2325 | 1887 | 147 | 488 | 37 | A | C |
| SIGUIJ | 521 | CD | ARG | A | 82 | 1 | 0 | 0 | 220 | 136 | 290 | A | C |
| ATOM | 522 | NE | ARG | A | 82 | 7.152 | 3.801 | 52.439 | 1.00 | 20.13 | | A | N |
| ANISOU | 522 | NE | ARG | A | 82 | 4477 | 3200 | 2961 | −273 | −130 | 25 | A | N |
| SIGUIJ | 522 | NE | ARG | A | 82 | 1 | 0 | 0 | 221 | 63 | 289 | A | N |
| ATOM | 523 | CZ | ARG | A | 82 | 7.612 | 3.635 | 53.704 | 1.00 | 20.42 | | A | C |
| ANISOU | 523 | CZ | ARG | A | 82 | 3283 | 3539 | 2778 | 21 | 351 | −15 | A | C |
| SIGUIJ | 523 | CZ | ARG | A | 82 | 1 | 0 | 0 | 220 | 136 | 290 | A | C |
| ATOM | 524 | NH1 | ARG | A | 82 | 7.071 | 2.836 | 54.659 | 1.00 | 21.72 | | A | N |
| ANISOU | 524 | NH1 | ARG | A | 82 | 2666 | 3558 | 2587 | 15 | −6 | 0 | A | N |
| SIGUIJ | 524 | NH1 | ARG | A | 82 | 1 | 0 | 0 | 221 | 63 | 289 | A | N |
| ATOM | 525 | NH2 | ARG | A | 82 | 8.667 | 4.345 | 54.040 | 1.00 | 21.55 | | A | N |
| ANISOU | 525 | NH2 | ARG | A | 82 | 3396 | 3567 | 3679 | −3 | 60 | 1 | A | N |
| SIGUIJ | 525 | NH2 | ARG | A | 82 | 1 | 0 | 0 | 221 | 63 | 289 | A | N |
| ATOM | 526 | C | ARG | A | 82 | 8.125 | −1.142 | 50.520 | 1.00 | 12.58 | | A | C |
| ANISOU | 526 | C | ARG | A | 82 | 1406 | 2256 | 1072 | 133 | 74 | 4 | A | C |
| SIGUIJ | 526 | C | ARG | A | 82 | 1 | 0 | 0 | 220 | 135 | 290 | A | C |
| ATOM | 527 | O | ARG | A | 82 | 7.855 | −1.914 | 51.507 | 1.00 | 13.16 | | A | O |
| ANISOU | 527 | O | ARG | A | 82 | 1450 | 2400 | 1172 | 188 | 134 | 113 | A | O |
| SIGUIJ | 527 | O | ARG | A | 82 | 1 | 0 | 0 | 221 | 55 | 289 | A | O |
| ATOM | 528 | N | ILE | A | 83 | 9.274 | −1.267 | 49.827 | 1.00 | 11.91 | | A | N |
| ANISOU | 528 | N | ILE | A | 83 | 1409 | 1711 | 1104 | 68 | 86 | 1 | A | N |
| SIGUIJ | 528 | N | ILE | A | 83 | 1 | 0 | 0 | 221 | 63 | 289 | A | N |
| ATOM | 529 | CA | ILE | A | 83 | 10.267 | −2.294 | 50.147 | 1.00 | 11.49 | | A | C |
| ANISOU | 529 | CA | ILE | A | 83 | 1349 | 1609 | 1387 | −26 | 0 | 0 | A | C |
| SIGUIJ | 529 | CA | ILE | A | 83 | 1 | 0 | 0 | 220 | 135 | 290 | A | C |
| ATOM | 530 | CB | ILE | A | 83 | 10.238 | −3.458 | 49.116 | 1.00 | 11.87 | | A | C |
| ANISOU | 530 | CB | ILE | A | 83 | 1459 | 1615 | 1407 | −37 | 7 | −2 | A | C |
| SIGUIJ | 530 | CB | ILE | A | 83 | 1 | 0 | 0 | 220 | 135 | 290 | A | C |
| ATOM | 531 | CG2 | ILE | A | 83 | 11.302 | −4.507 | 49.456 | 1.00 | 12.03 | | A | C |
| ANISOU | 531 | CG2 | ILE | A | 83 | 1493 | 1636 | 1501 | −11 | 0 | 0 | A | C |
| SIGUIJ | 531 | CG2 | ILE | A | 83 | 1 | 0 | 0 | 220 | 135 | 290 | A | C |
| ATOM | 532 | CG1 | ILE | A | 83 | 8.827 | −4.068 | 49.036 | 1.00 | 11.90 | | A | C |
| ANISOU | 532 | CG1 | ILE | A | 83 | 1477 | 1764 | 1850 | −95 | 21 | 6 | A | C |
| SIGUIJ | 532 | CG1 | ILE | A | 83 | 1 | 0 | 0 | 220 | 134 | 290 | A | C |
| ATOM | 533 | CD1 | ILE | A | 83 | 8.669 | −5.109 | 47.983 | 1.00 | 12.03 | | A | C |
| ANISOU | 533 | CD1 | ILE | A | 83 | 1593 | 1763 | 1886 | −7 | −62 | −2 | A | C |
| SIGUIJ | 533 | CD1 | ILE | A | 83 | 1 | 0 | 0 | 220 | 134 | 290 | A | C |
| ATOM | 534 | C | ILE | A | 83 | 11.635 | −1.625 | 50.099 | 1.00 | 11.35 | | A | C |
| ANISOU | 534 | C | ILE | A | 83 | 1318 | 1448 | 1310 | 49 | 0 | 0 | A | C |
| SIGUIJ | 534 | C | ILE | A | 83 | 1 | 0 | 0 | 220 | 134 | 290 | A | C |
| ATOM | 535 | O | ILE | A | 83 | 12.039 | −0.953 | 49.109 | 1.00 | 11.54 | | A | O |
| ANISOU | 535 | O | ILE | A | 83 | 1387 | 1486 | 1327 | 7 | 6 | 0 | A | O |
| SIGUIJ | 535 | O | ILE | A | 83 | 1 | 0 | 0 | 221 | 55 | 289 | A | O |
| ATOM | 536 | N | ALYS | A | 84 | 12.412 | −1.875 | 51.155 | 0.50 | 11.01 | | A | N |
| ANISOU | 536 | N | ALYS | A | 84 | 1311 | 1305 | 1306 | 0 | 0 | 0 | A | N |
| SIGUIJ | 536 | N | ALYS | A | 84 | 1 | 0 | 0 | 221 | 63 | 289 | A | N |
| ATOM | 537 | N | BLYS | A | 84 | 12.408 | −1.860 | 51.162 | 0.50 | 13.20 | | A | N |
| ANISOU | 537 | N | BLYS | A | 84 | 1313 | 1284 | 1307 | 0 | 0 | 0 | A | N |
| SIGUIJ | 537 | N | BLYS | A | 84 | 1 | 0 | 0 | 221 | 63 | 289 | A | N |
| ATOM | 538 | CA | ALYS | A | 84 | 13.788 | −1.375 | 51.216 | 0.50 | 11.28 | | A | C |
| ANISOU | 538 | CA | ALYS | A | 84 | 1318 | 1319 | 1231 | 0 | 2 | 0 | A | C |
| SIGUIJ | 538 | CA | ALYS | A | 84 | 1 | 0 | 0 | 220 | 134 | 290 | A | C |
| ATOM | 539 | CA | BLYS | A | 84 | 13.787 | −1.365 | 51.222 | 0.50 | 13.47 | | A | C |
| ANISOU | 539 | CA | BLYS | A | 84 | 1322 | 1300 | 1256 | −1 | 3 | 0 | A | C |
| SIGUIJ | 539 | CA | BLYS | A | 84 | 1 | 0 | 0 | 220 | 133 | 290 | A | C |
| ATOM | 540 | CB | ALYS | A | 84 | 14.322 | −1.576 | 52.631 | 0.50 | 12.09 | | A | C |
| ANISOU | 540 | CB | ALYS | A | 84 | 1460 | 1737 | 1232 | 119 | −21 | −2 | A | C |
| SIGUIJ | 540 | CB | ALYS | A | 84 | 1 | 0 | 0 | 220 | 133 | 290 | A | C |
| ATOM | 541 | CB | BLYS | A | 84 | 14.312 | −1.526 | 52.654 | 0.50 | 14.28 | | A | C |
| ANISOU | 541 | CB | BLYS | A | 84 | 1368 | 1464 | 1254 | 25 | 4 | 0 | A | C |
| SIGUIJ | 541 | CB | BLYS | A | 84 | 1 | 0 | 0 | 220 | 133 | 290 | A | C |
| ATOM | 542 | CG | ALYS | A | 84 | 15.582 | −0.808 | 52.931 | 0.50 | 13.81 | | A | C |
| ANISOU | 542 | CG | ALYS | A | 84 | 1596 | 2052 | 1371 | −78 | −71 | 18 | A | C |
| SIGUIJ | 542 | CG | ALYS | A | 84 | 1 | 0 | 0 | 220 | 132 | 290 | A | C |
| ATOM | 543 | CG | BLYS | A | 84 | 15.719 | −0.993 | 52.907 | 0.50 | 16.00 | | A | C |
| ANISOU | 543 | CG | BLYS | A | 84 | 1422 | 1806 | 1303 | −104 | 3 | −1 | A | C |
| SIGUIJ | 543 | CG | BLYS | A | 84 | 1 | 0 | 0 | 220 | 132 | 290 | A | C |
| ATOM | 544 | CD | ALYS | A | 84 | 15.272 | 0.692 | 53.048 | 0.50 | 15.76 | | A | C |
| ANISOU | 544 | CD | ALYS | A | 84 | 1770 | 2063 | 1729 | −42 | −5 | 2 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 544 | CD | ALYS | A | 84 | 1 | 0 | 0 | 220 | 132 | 290 | A | C |
| ATOM | 545 | CD | BLYS | A | 84 | 15.824 | 0.519 | 52.707 | 0.50 | 17.95 | | A | C |
| ANISOU | 545 | CD | BLYS | A | 84 | 2138 | 1820 | 1735 | −173 | −167 | 68 | A | C |
| SIGUIJ | 545 | CD | BLYS | A | 84 | 1 | 0 | 0 | 220 | 132 | 290 | A | C |
| ATOM | 546 | CE | ALYS | A | 84 | 16.490 | 1.520 | 53.380 | 0.50 | 17.29 | | A | C |
| ANISOU | 546 | CE | ALYS | A | 84 | 1795 | 1956 | 2589 | 26 | −257 | 21 | A | C |
| SIGUIJ | 546 | CE | ALYS | A | 84 | 1 | 0 | 0 | 220 | 131 | 290 | A | C |
| ATOM | 547 | CE | BLYS | A | 84 | 14.820 | 1.325 | 53.515 | 0.50 | 19.48 | | A | C |
| ANISOU | 547 | CE | BLYS | A | 84 | 2552 | 2209 | 2096 | 105 | 75 | 19 | A | C |
| SIGUIJ | 547 | CE | BLYS | A | 84 | 1 | 0 | 0 | 220 | 131 | 290 | A | C |
| ATOM | 548 | NZ | ALYS | A | 84 | 16.029 | 2.817 | 53.936 | 0.50 | 18.71 | | A | N |
| ANISOU | 548 | NZ | ALYS | A | 84 | 2335 | 1993 | 2853 | 103 | 11 | 0 | A | N |
| SIGUIJ | 548 | NZ | ALYS | A | 84 | 1 | 0 | 0 | 221 | 63 | 289 | A | N |
| ATOM | 549 | NZ | BLYS | A | 84 | 15.068 | 1.396 | 54.997 | 0.50 | 20.90 | | A | N |
| ANISOU | 549 | NZ | BLYS | A | 84 | 3179 | 3141 | 2119 | 1 | −31 | −1 | A | N |
| SIGUIJ | 549 | NZ | BLYS | A | 84 | 1 | 0 | 0 | 221 | 63 | 289 | A | N |
| ATOM | 550 | C | ALYS | A | 84 | 14.654 | −2.177 | 50.232 | 0.50 | 10.91 | | A | C |
| ANISOU | 550 | C | ALYS | A | 84 | 1313 | 1314 | 1240 | 0 | −1 | 0 | A | C |
| SIGUIJ | 550 | C | ALYS | A | 84 | 1 | 0 | 0 | 220 | 131 | 290 | A | C |
| ATOM | 551 | C | BLYS | A | 84 | 14.659 | −2.175 | 50.245 | 0.50 | 13.10 | | A | C |
| ANISOU | 551 | C | BLYS | A | 84 | 1316 | 1304 | 1255 | 0 | 0 | 0 | A | C |
| SIGUIJ | 551 | C | BLYS | A | 84 | 1 | 0 | 0 | 220 | 131 | 290 | A | C |
| ATOM | 552 | O | ALYS | A | 84 | 14.506 | −3.403 | 50.098 | 0.50 | 11.25 | | A | O |
| ANISOU | 552 | O | ALYS | A | 84 | 1365 | 1314 | 1304 | −1 | 2 | 0 | A | O |
| SIGUIJ | 552 | O | ALYS | A | 84 | 1 | 0 | 0 | 221 | 55 | 289 | A | O |
| ATOM | 553 | O | BLYS | A | 84 | 14.502 | −3.395 | 50.108 | 0.50 | 13.44 | | A | O |
| ANISOU | 553 | O | BLYS | A | 84 | 1409 | 1305 | 1320 | −4 | 2 | 0 | A | O |
| SIGUIJ | 553 | O | BLYS | A | 84 | 1 | 0 | 0 | 221 | 55 | 289 | A | O |
| ATOM | 554 | N | ALA | A | 85 | 15.588 | −1.496 | 49.575 | 1.00 | 10.86 | | A | N |
| ANISOU | 554 | N | ALA | A | 85 | 1309 | 1307 | 1236 | 0 | −6 | 0 | A | N |
| SIGUIJ | 554 | N | ALA | A | 85 | 1 | 0 | 0 | 221 | 63 | 289 | A | N |
| ATOM | 555 | CA | ALA | A | 85 | 16.554 | −2.127 | 48.697 | 1.00 | 10.85 | | A | C |
| ANISOU | 555 | CA | ALA | A | 85 | 1332 | 1285 | 1263 | −5 | 20 | −2 | A | C |
| SIGUIJ | 555 | CA | ALA | A | 85 | 1 | 0 | 0 | 220 | 130 | 290 | A | C |
| ATOM | 556 | CB | ALA | A | 85 | 16.188 | −1.868 | 47.212 | 1.00 | 10.61 | | A | C |
| ANISOU | 556 | CB | ALA | A | 85 | 1545 | 1376 | 1277 | −32 | −40 | 6 | A | C |
| SIGUIJ | 556 | CB | ALA | A | 85 | 1 | 0 | 0 | 220 | 130 | 290 | A | C |
| ATOM | 557 | C | ALA | A | 85 | 17.920 | −1.574 | 49.010 | 1.00 | 11.52 | | A | C |
| ANISOU | 557 | C | ALA | A | 85 | 1340 | 1278 | 1472 | −15 | −6 | 0 | A | C |
| SIGUIJ | 557 | C | ALA | A | 85 | 1 | 0 | 0 | 220 | 130 | 290 | A | C |
| ATOM | 558 | O | ALA | A | 85 | 18.180 | −0.367 | 48.811 | 1.00 | 11.81 | | A | O |
| ANISOU | 558 | O | ALA | A | 85 | 1423 | 1289 | 1607 | −36 | 8 | 0 | A | O |
| SIGUIJ | 558 | O | ALA | A | 85 | 1 | 0 | 0 | 221 | 55 | 289 | A | O |
| ATOM | 559 | N | SER | A | 86 | 18.835 | −2.432 | 49.461 | 1.00 | 11.89 | | A | N |
| ANISOU | 559 | N | SER | A | 86 | 1430 | 1388 | 1488 | 81 | −1 | 1 | A | N |
| SIGUIJ | 559 | N | SER | A | 86 | 1 | 0 | 0 | 221 | 63 | 289 | A | N |
| ATOM | 560 | CA | SER | A | 86 | 20.157 | −1.979 | 49.872 | 1.00 | 12.90 | | A | C |
| ANISOU | 560 | CA | SER | A | 86 | 1476 | 1777 | 1455 | −50 | 1 | −1 | A | C |
| SIGUIJ | 560 | CA | SER | A | 86 | 1 | 0 | 0 | 220 | 130 | 290 | A | C |
| ATOM | 561 | CB | SER | A | 86 | 20.636 | −2.820 | 51.051 | 1.00 | 13.15 | | A | C |
| ANISOU | 561 | CB | SER | A | 86 | 1981 | 1880 | 1582 | −59 | −228 | 63 | A | C |
| SIGUIJ | 561 | CB | SER | A | 86 | 1 | 0 | 0 | 220 | 130 | 290 | A | C |
| ATOM | 562 | OG | SER | A | 86 | 19.800 | −2.651 | 52.157 | 1.00 | 14.64 | | A | O |
| ANISOU | 562 | OG | SER | A | 86 | 2186 | 2107 | 1678 | −37 | −97 | 22 | A | O |
| SIGUIJ | 562 | OG | SER | A | 86 | 1 | 0 | 0 | 221 | 55 | 289 | A | O |
| ATOM | 563 | C | SER | A | 86 | 21.190 | −2.062 | 48.745 | 1.00 | 13.37 | | A | C |
| ANISOU | 563 | C | SER | A | 86 | 1473 | 1707 | 1453 | −43 | 0 | 0 | A | C |
| SIGUIJ | 563 | C | SER | A | 86 | 1 | 0 | 0 | 220 | 129 | 290 | A | C |
| ATOM | 564 | O | SER | A | 86 | 22.076 | −1.207 | 48.664 | 1.00 | 14.89 | | A | O |
| ANISOU | 564 | O | SER | A | 86 | 1823 | 2110 | 2787 | −408 | 86 | 46 | A | O |
| SIGUIJ | 564 | O | SER | A | 86 | 1 | 0 | 0 | 221 | 55 | 289 | A | O |
| ATOM | 565 | N | LYS | A | 87 | 21.103 | −3.048 | 47.876 | 1.00 | 13.17 | | A | N |
| ANISOU | 565 | N | LYS | A | 87 | 1507 | 1678 | 1442 | −30 | 0 | 0 | A | N |
| SIGUIJ | 565 | N | LYS | A | 87 | 1 | 0 | 0 | 221 | 62 | 289 | A | N |
| ATOM | 566 | CA | LYS | A | 87 | 22.134 | −3.292 | 46.848 | 1.00 | 13.39 | | A | C |
| ANISOU | 566 | CA | LYS | A | 87 | 1513 | 1739 | 1433 | 22 | −3 | 0 | A | C |
| SIGUIJ | 566 | CA | LYS | A | 87 | 1 | 0 | 0 | 220 | 129 | 290 | A | C |
| ATOM | 567 | CB | LYS | A | 87 | 22.532 | −4.783 | 46.793 | 1.00 | 15.31 | | A | C |
| ANISOU | 567 | CB | LYS | A | 87 | 1588 | 1756 | 1988 | 34 | 46 | −8 | A | C |
| SIGUIJ | 567 | CB | LYS | A | 87 | 1 | 0 | 0 | 220 | 129 | 290 | A | C |
| ATOM | 568 | CG | LYS | A | 87 | 23.052 | −5.301 | 48.119 | 1.00 | 16.98 | | A | C |
| ANISOU | 568 | CG | LYS | A | 87 | 1980 | 2174 | 2064 | 209 | −66 | 66 | A | C |
| SIGUIJ | 568 | CG | LYS | A | 87 | 1 | 0 | 0 | 220 | 129 | 290 | A | C |
| ATOM | 569 | CD | LYS | A | 87 | 23.352 | −6.794 | 47.948 | 1.00 | 19.00 | | A | C |
| ANISOU | 569 | CD | LYS | A | 87 | 3261 | 2229 | 2866 | 465 | −27 | −20 | A | C |
| SIGUIJ | 569 | CD | LYS | A | 87 | 1 | 0 | 0 | 220 | 128 | 290 | A | C |
| ATOM | 570 | CE | LYS | A | 87 | 23.903 | −7.405 | 49.195 | 1.00 | 20.42 | | A | C |
| ANISOU | 570 | CE | LYS | A | 87 | 3382 | 3215 | 2904 | 1007 | 191 | 243 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 570 | CE | LYS | A | 87 | 1 | 0 | 0 | 220 | 128 | 290 | A | C |
| ATOM | 571 | NZ | LYS | A | 87 | 23.646 | −8.865 | 49.145 | 1.00 | 22.25 | | A | N |
| ANISOU | 571 | NZ | LYS | A | 87 | 8485 | 3389 | 5651 | 92 | 1139 | −70 | A | N |
| SIGUIJ | 571 | NZ | LYS | A | 87 | 1 | 0 | 0 | 221 | 62 | 289 | A | N |
| ATOM | 572 | C | LYS | A | 87 | 21.668 | −2.897 | 45.446 | 1.00 | 12.69 | | A | C |
| ANISOU | 572 | C | LYS | A | 87 | 1309 | 1533 | 1428 | −82 | 19 | 9 | A | C |
| SIGUIJ | 572 | C | LYS | A | 87 | 1 | 0 | 0 | 220 | 128 | 290 | A | C |
| ATOM | 573 | O | LYS | A | 87 | 20.487 | −3.076 | 45.072 | 1.00 | 12.42 | | A | O |
| ANISOU | 573 | O | LYS | A | 87 | 1335 | 1510 | 1674 | −77 | −56 | −16 | A | O |
| SIGUIJ | 573 | O | LYS | A | 87 | 1 | 0 | 0 | 221 | 55 | 289 | A | O |
| ATOM | 574 | N | SER | A | 88 | 22.603 | −2.427 | 44.641 | 1.00 | 11.85 | | A | N |
| ANISOU | 574 | N | SER | A | 88 | 1231 | 1293 | 1400 | 33 | 5 | −2 | A | N |
| SIGUIJ | 574 | N | SER | A | 88 | 1 | 0 | 0 | 221 | 62 | 289 | A | N |
| ATOM | 575 | CA | SER | A | 88 | 22.302 | −2.157 | 43.242 | 1.00 | 11.82 | | A | C |
| ANISOU | 575 | CA | SER | A | 88 | 1310 | 1266 | 1405 | 0 | −4 | 0 | A | C |
| SIGUIJ | 575 | CA | SER | A | 88 | 1 | 0 | 0 | 220 | 128 | 290 | A | C |
| ATOM | 576 | CB | SER | A | 88 | 21.699 | −0.751 | 43.109 | 1.00 | 11.87 | | A | C |
| ANISOU | 576 | CB | SER | A | 88 | 1411 | 1273 | 1611 | 29 | −17 | 0 | A | C |
| SIGUIJ | 576 | CB | SER | A | 88 | 1 | 0 | 0 | 220 | 127 | 290 | A | C |
| ATOM | 577 | OG | SER | A | 88 | 22.490 | 0.270 | 43.706 | 1.00 | 11.43 | | A | O |
| ANISOU | 577 | OG | SER | A | 88 | 1456 | 1288 | 1576 | −5 | −6 | 0 | A | O |
| SIGUIJ | 577 | OG | SER | A | 88 | 1 | 0 | 0 | 221 | 55 | 289 | A | O |
| ATOM | 578 | C | SER | A | 88 | 23.561 | −2.295 | 42.397 | 1.00 | 11.83 | | A | C |
| ANISOU | 578 | C | SER | A | 88 | 1310 | 1405 | 1435 | 14 | 5 | −1 | A | C |
| SIGUIJ | 578 | C | SER | A | 88 | 1 | 0 | 0 | 220 | 127 | 290 | A | C |
| ATOM | 579 | O | SER | A | 88 | 24.684 | −2.165 | 42.928 | 1.00 | 11.99 | | A | C |
| ANISOU | 579 | O | SER | A | 88 | 1354 | 1687 | 1594 | −27 | −86 | −8 | A | C |
| SIGUIJ | 579 | O | SER | A | 88 | 1 | 0 | 0 | 221 | 55 | 289 | A | C |
| ATOM | 580 | N | PHE | A | 89 | 23.369 | −2.558 | 41.108 | 1.00 | 11.41 | | A | N |
| ANISOU | 580 | N | PHE | A | 89 | 1224 | 1344 | 1444 | 31 | 8 | −2 | A | N |
| SIGUIJ | 580 | N | PHE | A | 89 | 1 | 0 | 0 | 221 | 62 | 289 | A | N |
| ATOM | 581 | CA | PHE | A | 89 | 24.457 | −2.972 | 40.208 | 1.00 | 11.41 | | A | C |
| ANISOU | 581 | CA | PHE | A | 89 | 1236 | 1359 | 1516 | 51 | 26 | −7 | A | C |
| SIGUIJ | 581 | CA | PHE | A | 89 | 1 | 0 | 0 | 220 | 127 | 290 | A | C |
| ATOM | 582 | CB | PHE | A | 89 | 24.433 | −4.489 | 40.002 | 1.00 | 12.08 | | A | C |
| ANISOU | 582 | CB | PHE | A | 89 | 1854 | 1348 | 1848 | 58 | 0 | −2 | A | C |
| SIGUIJ | 582 | CB | PHE | A | 89 | 1 | 0 | 0 | 220 | 127 | 290 | A | C |
| ATOM | 583 | CG | PHE | A | 89 | 24.452 | −5.264 | 41.298 | 1.00 | 12.41 | | A | C |
| ANISOU | 583 | CG | PHE | A | 89 | 1977 | 1324 | 1856 | 87 | −10 | −4 | A | C |
| SIGUIJ | 583 | CG | PHE | A | 89 | 1 | 0 | 0 | 220 | 127 | 290 | A | C |
| ATOM | 584 | CD1 | PHE | A | 89 | 23.290 | −5.587 | 41.963 | 1.00 | 13.24 | | A | C |
| ANISOU | 584 | CD1 | PHE | A | 89 | 2000 | 1457 | 1919 | 49 | 4 | 1 | A | C |
| SIGUIJ | 584 | CD1 | PHE | A | 89 | 1 | 0 | 0 | 220 | 126 | 290 | A | C |
| ATOM | 585 | CD2 | PHE | A | 89 | 25.664 | −5.585 | 41.911 | 1.00 | 13.13 | | A | C |
| ANISOU | 585 | CD2 | PHE | A | 89 | 2036 | 1910 | 1891 | 269 | −31 | −35 | A | C |
| SIGUIJ | 585 | CD2 | PHE | A | 89 | 1 | 0 | 0 | 220 | 126 | 290 | A | C |
| ATOM | 586 | CE1 | PHE | A | 89 | 23.316 | −6.181 | 43.191 | 1.00 | 13.82 | | A | C |
| ANISOU | 586 | CE1 | PHE | A | 89 | 2540 | 1477 | 1932 | 170 | 45 | 10 | A | C |
| SIGUIJ | 586 | CE1 | PHE | A | 89 | 1 | 0 | 0 | 220 | 126 | 290 | A | C |
| ATOM | 587 | CE2 | PHE | A | 89 | 25.653 | −6.191 | 43.178 | 1.00 | 13.75 | | A | C |
| ANISOU | 587 | CE2 | PHE | A | 89 | 2563 | 1950 | 1900 | 194 | −63 | −18 | A | C |
| SIGUIJ | 587 | CE2 | PHE | A | 89 | 1 | 0 | 0 | 220 | 126 | 290 | A | C |
| ATOM | 588 | CZ | PHE | A | 89 | 24.517 | −6.464 | 43.779 | 1.00 | 13.84 | | A | C |
| ANISOU | 588 | CZ | PHE | A | 89 | 2582 | 1757 | 2030 | 251 | 1 | 0 | A | C |
| SIGUIJ | 588 | CZ | PHE | A | 89 | 1 | 0 | 0 | 220 | 125 | 290 | A | C |
| ATOM | 589 | C | PHE | A | 89 | 24.226 | −2.252 | 38.903 | 1.00 | 11.62 | | A | C |
| ANISOU | 589 | C | PHE | A | 89 | 1222 | 1245 | 1445 | 252 | 138 | −127 | A | C |
| SIGUIJ | 589 | C | PHE | A | 89 | 1 | 0 | 0 | 220 | 125 | 290 | A | C |
| ATOM | 590 | O | PHE | A | 89 | 23.326 | −2.590 | 38.108 | 1.00 | 11.21 | | A | O |
| ANISOU | 590 | O | PHE | A | 89 | 1301 | 1248 | 1491 | 213 | 85 | −90 | A | O |
| SIGUIJ | 590 | O | PHE | A | 89 | 1 | 0 | 0 | 221 | 55 | 289 | A | O |
| ATOM | 591 | N | AARG | A | 90 | 25.105 | −1.294 | 38.630 | 0.50 | 12.01 | | A | N |
| ANISOU | 591 | N | AARG | A | 90 | 1452 | 1515 | 1438 | −8 | 0 | 0 | A | N |
| SIGUIJ | 591 | N | AARG | A | 90 | 1 | 0 | 0 | 221 | 62 | 289 | A | N |
| ATOM | 592 | N | BARG | A | 90 | 25.097 | −1.280 | 38.633 | 0.50 | 14.20 | | A | N |
| ANISOU | 592 | N | BARG | A | 90 | 1474 | 1529 | 1451 | −17 | 1 | 0 | A | N |
| SIGUIJ | 592 | N | BARG | A | 90 | 1 | 0 | 0 | 221 | 62 | 289 | A | N |
| ATOM | 593 | CA | AARG | A | 90 | 25.103 | −0.574 | 37.349 | 0.50 | 13.07 | | A | C |
| ANISOU | 593 | CA | AARG | A | 90 | 1337 | 1515 | 1436 | −7 | 2 | 0 | A | C |
| SIGUIJ | 593 | CA | AARG | A | 90 | 1 | 0 | 0 | 220 | 125 | 290 | A | C |
| ATOM | 594 | CA | BARG | A | 90 | 25.092 | −0.536 | 37.359 | 0.50 | 15.26 | | A | C |
| ANISOU | 594 | CA | BARG | A | 90 | 1311 | 1551 | 1448 | 4 | 4 | 0 | A | C |
| SIGUIJ | 594 | CA | BARG | A | 90 | 1 | 0 | 0 | 220 | 125 | 290 | A | C |
| ATOM | 595 | CB | AARG | A | 90 | 25.964 | 0.653 | 37.398 | 0.50 | 13.27 | | A | C |
| ANISOU | 595 | CB | AARG | A | 90 | 1359 | 1530 | 1493 | −22 | 0 | 0 | A | C |
| SIGUIJ | 595 | CB | AARG | A | 90 | 1 | 0 | 0 | 220 | 125 | 290 | A | C |
| ATOM | 596 | CB | BARG | A | 90 | 25.879 | 0.766 | 37.474 | 0.50 | 15.46 | | A | C |
| ANISOU | 596 | CB | BARG | A | 90 | 1415 | 1599 | 3073 | −44 | −208 | −23 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 596 | CB | BARG | A | 90 | 1 | 0 | 0 | 220 | 124 | 290 | A | C |
| ATOM | 597 | CG | AARG | A | 90 | 25.363 | 1.765 | 38.207 | 0.50 | 14.09 | | A | C |
| ANISOU | 597 | CG | AARG | A | 90 | 1315 | 1506 | 1503 | −57 | 3 | 1 | A | C |
| SIGUIJ | 597 | CG | AARG | A | 90 | 1 | 0 | 0 | 220 | 124 | 290 | A | C |
| ATOM | 598 | CG | BARG | A | 90 | 25.238 | 1.764 | 38.451 | 0.50 | 16.28 | | A | C |
| ANISOU | 598 | CG | BARG | A | 90 | 1597 | 1623 | 3101 | −3 | −141 | −7 | A | C |
| SIGUIJ | 598 | CG | BARG | A | 90 | 1 | 0 | 0 | 220 | 124 | 290 | A | C |
| ATOM | 599 | CD | AARG | A | 90 | 26.399 | 2.861 | 38.297 | 0.50 | 15.12 | | A | C |
| ANISOU | 599 | CD | AARG | A | 90 | 1180 | 1377 | 1504 | 72 | 7 | −2 | A | C |
| SIGUIJ | 599 | CD | AARG | A | 90 | 1 | 0 | 0 | 220 | 124 | 290 | A | C |
| ATOM | 600 | CD | BARG | A | 90 | 26.049 | 3.043 | 38.668 | 0.50 | 17.31 | | A | C |
| ANISOU | 600 | CD | BARG | A | 90 | 1713 | 1622 | 4341 | −7 | −565 | 48 | A | C |
| SIGUIJ | 600 | CD | BARG | A | 90 | 1 | 0 | 0 | 220 | 124 | 290 | A | C |
| ATOM | 601 | NE | AARG | A | 90 | 25.790 | 4.161 | 38.571 | 0.50 | 15.48 | | A | N |
| ANISOU | 601 | NE | AARG | A | 90 | 1129 | 1362 | 1352 | 52 | −16 | 3 | A | N |
| SIGUIJ | 601 | NE | AARG | A | 90 | 1 | 0 | 0 | 221 | 62 | 289 | A | N |
| ATOM | 602 | NE | BARG | A | 90 | 27.405 | 2.748 | 39.094 | 0.50 | 17.67 | | A | N |
| ANISOU | 602 | NE | BARG | A | 90 | 1618 | 2442 | 3049 | 156 | −166 | 24 | A | N |
| SIGUIJ | 602 | NE | BARG | A | 90 | 1 | 0 | 0 | 221 | 62 | 289 | A | N |
| ATOM | 603 | CZ | AARG | A | 90 | 26.464 | 5.249 | 38.929 | 0.50 | 15.12 | | A | C |
| ANISOU | 603 | CZ | AARG | A | 90 | 1156 | 1371 | 1291 | 30 | 21 | −4 | A | C |
| SIGUIJ | 603 | CZ | AARG | A | 90 | 1 | 0 | 0 | 220 | 123 | 290 | A | C |
| ATOM | 604 | CZ | BARG | A | 90 | 28.397 | 3.628 | 39.073 | 0.50 | 17.31 | | A | C |
| ANISOU | 604 | CZ | BARG | A | 90 | 1654 | 2495 | 3133 | 110 | −154 | 16 | A | C |
| SIGUIJ | 604 | CZ | BARG | A | 90 | 1 | 0 | 0 | 220 | 123 | 290 | A | C |
| ATOM | 605 | NH1 | AARG | A | 90 | 27.789 | 5.187 | 39.088 | 0.50 | 15.97 | | A | N |
| ANISOU | 605 | NH1 | AARG | A | 90 | 1171 | 1391 | 2259 | 29 | −89 | 6 | A | N |
| SIGUIJ | 605 | NH1 | AARG | A | 90 | 1 | 0 | 0 | 221 | 62 | 289 | A | N |
| ATOM | 606 | NH1 | BARG | A | 90 | 28.185 | 4.878 | 38.667 | 0.50 | 18.16 | | A | N |
| ANISOU | 606 | NH1 | BARG | A | 90 | 1573 | 2490 | 3114 | 82 | −178 | 12 | A | N |
| SIGUIJ | 606 | NH1 | BARG | A | 90 | 1 | 0 | 0 | 221 | 62 | 289 | A | N |
| ATOM | 607 | NH2 | AARG | A | 90 | 25.818 | 6.401 | 39.026 | 0.50 | 14.36 | | A | N |
| ANISOU | 607 | NH2 | AARG | A | 90 | 780 | 1244 | 886 | −183 | 9 | 8 | A | N |
| SIGUIJ | 607 | NH2 | AARG | A | 90 | 1 | 0 | 0 | 221 | 62 | 289 | A | N |
| ATOM | 608 | NH2 | BARG | A | 90 | 29.620 | 3.219 | 39.394 | 0.50 | 16.55 | | A | N |
| ANISOU | 608 | NH2 | BARG | A | 90 | 1599 | 2618 | 2127 | 159 | 98 | −22 | A | N |
| SIGUIJ | 608 | NH2 | BARG | A | 90 | 1 | 0 | 0 | 221 | 62 | 289 | A | N |
| ATOM | 609 | C | AARG | A | 90 | 25.703 | −1.419 | 36.246 | 0.50 | 13.71 | | A | C |
| ANISOU | 609 | C | AARG | A | 90 | 1376 | 1535 | 1437 | 19 | 13 | −3 | A | C |
| SIGUIJ | 609 | C | AARG | A | 90 | 1 | 0 | 0 | 220 | 123 | 290 | A | C |
| ATOM | 610 | C | BARG | A | 90 | 25.739 | −1.352 | 36.246 | 0.50 | 15.90 | | A | C |
| ANISOU | 610 | C | BARG | A | 90 | 1375 | 1581 | 1444 | 51 | 8 | −4 | A | C |
| SIGUIJ | 610 | C | BARG | A | 90 | 1 | 0 | 0 | 220 | 123 | 290 | A | C |
| ATOM | 611 | O | AARG | A | 90 | 26.568 | −2.275 | 36.492 | 0.50 | 13.91 | | A | O |
| ANISOU | 611 | O | AARG | A | 90 | 1717 | 1882 | 1575 | 358 | 3 | 36 | A | O |
| SIGUIJ | 611 | O | AARG | A | 90 | 1 | 0 | 0 | 221 | 55 | 289 | A | O |
| ATOM | 612 | O | BARG | A | 90 | 26.653 | −2.145 | 36.490 | 0.50 | 16.10 | | A | O |
| ANISOU | 612 | O | BARG | A | 90 | 1656 | 1911 | 2112 | 331 | −111 | 76 | A | O |
| SIGUIJ | 612 | O | BARG | A | 90 | 1 | 0 | 0 | 221 | 55 | 289 | A | O |
| ATOM | 613 | N | HIS | A | 91 | 25.256 | −1.184 | 35.020 | 1.00 | 14.41 | | A | N |
| ANISOU | 613 | N | HIS | A | 91 | 1453 | 1903 | 1440 | 182 | −1 | 5 | A | N |
| SIGUIJ | 613 | N | HIS | A | 91 | 1 | 0 | 0 | 221 | 62 | 289 | A | N |
| ATOM | 614 | CA | HIS | A | 91 | 25.955 | −1.767 | 33.871 | 1.00 | 15.48 | | A | C |
| ANISOU | 614 | CA | HIS | A | 91 | 1577 | 2114 | 1439 | 328 | 2 | 8 | A | C |
| SIGUIJ | 614 | CA | HIS | A | 91 | 1 | 0 | 0 | 220 | 123 | 290 | A | C |
| ATOM | 615 | CB | HIS | A | 91 | 25.243 | −1.342 | 32.609 | 1.00 | 15.53 | | A | C |
| ANISOU | 615 | CB | HIS | A | 91 | 1692 | 2116 | 1439 | 400 | −21 | −23 | A | C |
| SIGUIJ | 615 | CB | HIS | A | 91 | 1 | 0 | 0 | 220 | 122 | 290 | A | C |
| ATOM | 616 | CG | HIS | A | 91 | 25.732 | −2.054 | 31.364 | 1.00 | 16.17 | | A | C |
| ANISOU | 616 | CG | HIS | A | 91 | 2080 | 2039 | 1478 | 403 | 112 | 14 | A | C |
| SIGUIJ | 616 | CG | HIS | A | 91 | 1 | 0 | 0 | 220 | 122 | 290 | A | C |
| ATOM | 617 | CD2 | HIS | A | 91 | 25.170 | −3.049 | 30.632 | 1.00 | 16.53 | | A | C |
| ANISOU | 617 | CD2 | HIS | A | 91 | 2575 | 2179 | 1489 | 112 | 120 | 22 | A | C |
| SIGUIJ | 617 | CD2 | HIS | A | 91 | 1 | 0 | 0 | 220 | 122 | 290 | A | C |
| ATOM | 618 | ND1 | HIS | A | 91 | 26.940 | −1.752 | 30.760 | 1.00 | 16.33 | | A | N |
| ANISOU | 618 | ND1 | HIS | A | 91 | 2208 | 2709 | 1805 | 237 | 296 | −14 | A | N |
| SIGUIJ | 618 | ND1 | HIS | A | 91 | 1 | 0 | 0 | 221 | 62 | 289 | A | N |
| ATOM | 619 | CE1 | HIS | A | 91 | 27.098 | −2.551 | 29.707 | 1.00 | 16.71 | | A | C |
| ANISOU | 619 | CE1 | HIS | A | 91 | 3168 | 2580 | 1781 | 149 | 530 | 68 | A | C |
| SIGUIJ | 619 | CE1 | HIS | A | 91 | 1 | 0 | 0 | 220 | 122 | 290 | A | C |
| ATOM | 620 | NE2 | HIS | A | 91 | 26.049 | −3.343 | 29.609 | 1.00 | 16.79 | | A | N |
| ANISOU | 620 | NE2 | HIS | A | 91 | 3036 | 2323 | 1757 | 343 | 466 | 148 | A | N |
| SIGUIJ | 620 | NE2 | HIS | A | 91 | 1 | 0 | 0 | 221 | 62 | 289 | A | N |
| ATOM | 621 | C | HIS | A | 91 | 27.399 | −1.213 | 33.878 | 1.00 | 16.12 | | A | C |
| ANISOU | 621 | C | HIS | A | 91 | 1549 | 1980 | 1755 | 379 | 51 | −52 | A | C |
| SIGUIJ | 621 | C | HIS | A | 91 | 1 | 0 | 0 | 220 | 122 | 290 | A | C |
| ATOM | 622 | O | HIS | A | 91 | 27.633 | −0.033 | 34.149 | 1.00 | 15.90 | | A | O |
| ANISOU | 622 | O | HIS | A | 91 | 1630 | 2027 | 2064 | 291 | 356 | −175 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 622 | O | HIS | A | 91 | 1 | 0 | 0 | 221 | 55 | 289 | A | O |
| ATOM | 623 | N | PRO | A | 92 | 28.377 | −2.096 | 33.568 | 1.00 | 17.08 | | A | N |
| ANISOU | 623 | N | PRO | A | 92 | 1599 | 1960 | 2747 | 346 | 307 | −122 | A | N |
| SIGUIJ | 623 | N | PRO | A | 92 | 1 | 0 | 0 | 221 | 62 | 289 | A | N |
| ATOM | 624 | CD | PRO | A | 92 | 28.200 | −3.528 | 33.228 | 1.00 | 17.34 | | A | C |
| ANISOU | 624 | CD | PRO | A | 92 | 1555 | 1964 | 2959 | 352 | 421 | −171 | A | C |
| SIGUIJ | 624 | CD | PRO | A | 92 | 1 | 0 | 0 | 220 | 121 | 290 | A | C |
| ATOM | 625 | CA | PRO | A | 92 | 29.789 | −1.732 | 33.662 | 1.00 | 18.05 | | A | C |
| ANISOU | 625 | CA | PRO | A | 92 | 1637 | 2575 | 3230 | 178 | 267 | −45 | A | C |
| SIGUIJ | 625 | CA | PRO | A | 92 | 1 | 0 | 0 | 220 | 121 | 290 | A | C |
| ATOM | 626 | CB | PRO | A | 92 | 30.523 | −3.039 | 33.352 | 1.00 | 18.03 | | A | C |
| ANISOU | 626 | CB | PRO | A | 92 | 2147 | 2595 | 5347 | 238 | 1218 | −26 | A | C |
| SIGUIJ | 626 | CB | PRO | A | 92 | 1 | 0 | 0 | 220 | 121 | 290 | A | C |
| ATOM | 627 | CG | PRO | A | 92 | 29.595 | −3.943 | 32.745 | 1.00 | 17.85 | | A | C |
| ANISOU | 627 | CG | PRO | A | 92 | 1886 | 2564 | 5684 | 469 | 1307 | −351 | A | C |
| SIGUIJ | 627 | CG | PRO | A | 92 | 1 | 0 | 0 | 220 | 121 | 290 | A | C |
| ATOM | 628 | C | PRO | A | 92 | 30.261 | −0.614 | 32.741 | 1.00 | 18.73 | | A | C |
| ANISOU | 628 | C | PRO | A | 92 | 2870 | 2518 | 3323 | 60 | 795 | −195 | A | C |
| SIGUIJ | 628 | C | PRO | A | 92 | 1 | 0 | 0 | 220 | 121 | 290 | A | C |
| ATOM | 629 | O | PRO | A | 92 | 31.335 | 0.019 | 32.997 | 1.00 | 19.68 | | A | O |
| ANISOU | 629 | O | PRO | A | 92 | 3289 | 3223 | 3753 | −484 | 378 | 338 | A | O |
| SIGUIJ | 629 | O | PRO | A | 92 | 1 | 0 | 0 | 221 | 55 | 289 | A | O |
| ATOM | 630 | N | GLY | A | 93 | 29.503 | −0.367 | 31.687 | 1.00 | 19.18 | | A | N |
| ANISOU | 630 | N | GLY | A | 93 | 2405 | 2455 | 3056 | 209 | 1157 | −308 | A | N |
| SIGUIJ | 630 | N | GLY | A | 93 | 1 | 0 | 0 | 221 | 62 | 289 | A | N |
| ATOM | 631 | CA | GLY | A | 93 | 29.954 | 0.623 | 30.716 | 1.00 | 19.61 | | A | C |
| ANISOU | 631 | CA | GLY | A | 93 | 2978 | 2883 | 3679 | 249 | 1468 | 152 | A | C |
| SIGUIJ | 631 | CA | GLY | A | 93 | 1 | 0 | 0 | 220 | 120 | 290 | A | C |
| ATOM | 632 | C | GLY | A | 93 | 29.473 | 2.046 | 30.978 | 1.00 | 19.41 | | A | C |
| ANISOU | 632 | C | GLY | A | 93 | 2053 | 2902 | 1983 | 215 | −4 | −11 | A | C |
| SIGUIJ | 632 | C | GLY | A | 93 | 1 | 0 | 0 | 220 | 120 | 290 | A | C |
| ATOM | 633 | O | GLY | A | 93 | 29.597 | 2.921 | 30.112 | 1.00 | 19.30 | | A | O |
| ANISOU | 633 | O | GLY | A | 93 | 1718 | 2790 | 1916 | 404 | 188 | −106 | A | O |
| SIGUIJ | 633 | O | GLY | A | 93 | 1 | 0 | 0 | 221 | 55 | 289 | A | O |
| ATOM | 634 | N | TYR | A | 94 | 28.871 | 2.295 | 32.157 | 1.00 | 19.65 | | A | N |
| ANISOU | 634 | N | TYR | A | 94 | 2158 | 3387 | 1987 | 465 | −3 | −8 | A | N |
| SIGUIJ | 634 | N | TYR | A | 94 | 1 | 0 | 0 | 221 | 62 | 289 | A | N |
| ATOM | 635 | CA | TYR | A | 94 | 28.106 | 3.547 | 32.315 | 1.00 | 19.52 | | A | C |
| ANISOU | 635 | CA | TYR | A | 94 | 1425 | 3106 | 1812 | 5 | 30 | 4 | A | C |
| SIGUIJ | 635 | CA | TYR | A | 94 | 1 | 0 | 0 | 220 | 120 | 290 | A | C |
| ATOM | 636 | CB | TYR | A | 94 | 27.215 | 3.525 | 33.587 | 1.00 | 18.03 | | A | C |
| ANISOU | 636 | CB | TYR | A | 94 | 1488 | 2218 | 1833 | 0 | 63 | 0 | A | C |
| SIGUIJ | 636 | CB | TYR | A | 94 | 1 | 0 | 0 | 220 | 120 | 290 | A | C |
| ATOM | 637 | CG | TYR | A | 94 | 26.540 | 4.842 | 33.886 | 1.00 | 16.64 | | A | C |
| ANISOU | 637 | CG | TYR | A | 94 | 1190 | 2118 | 1697 | −176 | 81 | 21 | A | C |
| SIGUIJ | 637 | CG | TYR | A | 94 | 1 | 0 | 0 | 220 | 120 | 290 | A | C |
| ATOM | 638 | CD1 | TYR | A | 94 | 25.670 | 5.431 | 32.967 | 1.00 | 16.20 | | A | C |
| ANISOU | 638 | CD1 | TYR | A | 94 | 1200 | 1798 | 1785 | −351 | −38 | −20 | A | C |
| SIGUIJ | 638 | CD1 | TYR | A | 94 | 1 | 0 | 0 | 220 | 119 | 290 | A | C |
| ATOM | 639 | CE1 | TYR | A | 94 | 25.003 | 6.633 | 33.222 | 1.00 | 15.88 | | A | C |
| ANISOU | 639 | CE1 | TYR | A | 94 | 1296 | 1798 | 1741 | −327 | 89 | 53 | A | C |
| SIGUIJ | 639 | CE1 | TYR | A | 94 | 1 | 0 | 0 | 220 | 119 | 290 | A | C |
| ATOM | 640 | CD2 | TYR | A | 94 | 26.765 | 5.484 | 35.089 | 1.00 | 16.08 | | A | C |
| ANISOU | 640 | CD2 | TYR | A | 94 | 1683 | 2145 | 1718 | −218 | 4 | 7 | A | C |
| SIGUIJ | 640 | CD2 | TYR | A | 94 | 1 | 0 | 0 | 220 | 119 | 290 | A | C |
| ATOM | 641 | CE2 | TYR | A | 94 | 26.156 | 6.678 | 35.380 | 1.00 | 15.75 | | A | C |
| ANISOU | 641 | CE2 | TYR | A | 94 | 1824 | 2177 | 1776 | −145 | 0 | 0 | A | C |
| SIGUIJ | 641 | CE2 | TYR | A | 94 | 1 | 0 | 0 | 220 | 119 | 290 | A | C |
| ATOM | 642 | CZ | TYR | A | 94 | 25.269 | 7.255 | 34.455 | 1.00 | 15.56 | | A | C |
| ANISOU | 642 | CZ | TYR | A | 94 | 1649 | 1854 | 1770 | −374 | 23 | 31 | A | C |
| SIGUIJ | 642 | CZ | TYR | A | 94 | 1 | 0 | 0 | 220 | 119 | 290 | A | C |
| ATOM | 643 | OH | TYR | A | 94 | 24.616 | 8.431 | 34.713 | 1.00 | 16.26 | | A | O |
| ANISOU | 643 | OH | TYR | A | 94 | 2237 | 2035 | 1910 | −48 | 22 | −4 | A | O |
| SIGUIJ | 643 | OH | TYR | A | 94 | 1 | 0 | 0 | 221 | 55 | 289 | A | O |
| ATOM | 644 | C | TYR | A | 94 | 28.994 | 4.752 | 32.342 | 1.00 | 20.49 | | A | C |
| ANISOU | 644 | C | TYR | A | 94 | 1698 | 3273 | 2675 | −205 | 15 | 2 | A | C |
| SIGUIJ | 644 | C | TYR | A | 94 | 1 | 0 | 0 | 220 | 119 | 290 | A | C |
| ATOM | 645 | O | TYR | A | 94 | 29.967 | 4.779 | 33.096 | 1.00 | 20.98 | | A | O |
| ANISOU | 645 | O | TYR | A | 94 | 1824 | 4079 | 2897 | −213 | −149 | −19 | A | O |
| SIGUIJ | 645 | O | TYR | A | 94 | 1 | 0 | 0 | 221 | 55 | 289 | A | O |
| ATOM | 646 | N | SER | A | 95 | 28.623 | 5.734 | 31.536 | 1.00 | 21.52 | | A | N |
| ANISOU | 646 | N | SER | A | 95 | 1637 | 3332 | 2624 | −119 | 145 | 13 | A | N |
| SIGUIJ | 646 | N | SER | A | 95 | 1 | 0 | 0 | 221 | 62 | 289 | A | N |
| ATOM | 647 | CA | SER | A | 95 | 29.362 | 6.989 | 31.443 | 1.00 | 22.67 | | A | C |
| ANISOU | 647 | CA | SER | A | 95 | 2089 | 3501 | 3158 | −388 | 156 | 47 | A | C |
| SIGUIJ | 647 | CA | SER | A | 95 | 1 | 0 | 0 | 220 | 118 | 290 | A | C |
| ATOM | 648 | CB | SER | A | 95 | 29.691 | 7.323 | 29.984 | 1.00 | 22.92 | | A | C |
| ANISOU | 648 | CB | SER | A | 95 | 2562 | 2915 | 3189 | −9 | 350 | −2 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 648 | CB | SER | A | 95 | 1 | 0 | 0 | 220 | 118 | 290 | A | C |
| ATOM | 649 | OG | SER | A | 95 | 30.349 | 8.587 | 29.868 | 1.00 | 23.39 | | A | O |
| ANISOU | 649 | OG | SER | A | 95 | 2664 | 2945 | 3663 | −58 | 370 | 36 | A | O |
| SIGUIJ | 649 | OG | SER | A | 95 | 1 | 0 | 0 | 221 | 55 | 289 | A | O |
| ATOM | 650 | C | SER | A | 95 | 28.503 | 8.103 | 31.972 | 1.00 | 23.35 | | A | C |
| ANISOU | 650 | C | SER | A | 95 | 2613 | 3917 | 2845 | 123 | −66 | 22 | A | C |
| SIGUIJ | 650 | C | SER | A | 95 | 1 | 0 | 0 | 220 | 118 | 290 | A | C |
| ATOM | 651 | O | SER | A | 95 | 27.447 | 8.418 | 31.383 | 1.00 | 23.22 | | A | O |
| ANISOU | 651 | O | SER | A | 95 | 2406 | 2721 | 2567 | −271 | 111 | 96 | A | O |
| SIGUIJ | 651 | O | SER | A | 95 | 1 | 0 | 0 | 221 | 55 | 289 | A | O |
| ATOM | 652 | N | THR | A | 96 | 28.986 | 8.760 | 33.015 | 1.00 | 24.40 | | A | N |
| ANISOU | 652 | N | THR | A | 96 | 2502 | 3902 | 2847 | 184 | −57 | 18 | A | N |
| SIGUIJ | 652 | N | THR | A | 96 | 1 | 0 | 0 | 221 | 62 | 289 | A | N |
| ATOM | 653 | CA | THR | A | 96 | 28.311 | 9.981 | 33.445 | 1.00 | 25.35 | | A | C |
| ANISOU | 653 | CA | THR | A | 96 | 3199 | 4099 | 4076 | 423 | 382 | −155 | A | C |
| SIGUIJ | 653 | CA | THR | A | 96 | 1 | 0 | 0 | 220 | 118 | 290 | A | C |
| ATOM | 654 | CB | THR | A | 96 | 28.954 | 10.613 | 34.718 | 1.00 | 25.49 | | A | C |
| ANISOU | 654 | CB | THR | A | 96 | 4324 | 4243 | 4194 | 7 | 9 | 1 | A | C |
| SIGUIJ | 654 | CB | THR | A | 96 | 1 | 0 | 0 | 220 | 118 | 290 | A | C |
| ATOM | 655 | OG1 | THR | A | 96 | 30.207 | 11.246 | 34.389 | 1.00 | 26.34 | | A | O |
| ANISOU | 655 | OG1 | THR | A | 96 | 4383 | 4266 | 5130 | 8 | 242 | 12 | A | O |
| SIGUIJ | 655 | OG1 | THR | A | 96 | 1 | 0 | 0 | 221 | 55 | 289 | A | O |
| ATOM | 656 | CG2 | THR | A | 96 | 29.150 | 9.564 | 35.786 | 1.00 | 25.75 | | A | C |
| ANISOU | 656 | CG2 | THR | A | 96 | 4300 | 4244 | 4201 | 5 | −6 | 0 | A | C |
| SIGUIJ | 656 | CG2 | THR | A | 96 | 1 | 0 | 0 | 220 | 117 | 290 | A | C |
| ATOM | 657 | C | THR | A | 96 | 28.271 | 11.064 | 32.364 | 1.00 | 25.73 | | A | C |
| ANISOU | 657 | C | THR | A | 96 | 3284 | 4232 | 4245 | −37 | −73 | −3 | A | C |
| SIGUIJ | 657 | C | THR | A | 96 | 1 | 0 | 0 | 220 | 117 | 290 | A | C |
| ATOM | 658 | O | THR | A | 96 | 27.348 | 11.863 | 32.334 | 1.00 | 26.22 | | A | O |
| ANISOU | 658 | O | THR | A | 96 | 3374 | 4343 | 5847 | 63 | −110 | 5 | A | O |
| SIGUIJ | 658 | O | THR | A | 96 | 1 | 0 | 0 | 221 | 55 | 289 | A | O |
| ATOM | 659 | N | GLN | A | 97 | 29.223 | 11.086 | 31.438 | 1.00 | 25.95 | | A | N |
| ANISOU | 659 | N | GLN | A | 97 | 3446 | 2803 | 4422 | −4 | 98 | 0 | A | N |
| SIGUIJ | 659 | N | GLN | A | 97 | 1 | 0 | 0 | 221 | 62 | 289 | A | N |
| ATOM | 660 | CA | GLN | A | 97 | 29.316 | 12.202 | 30.515 | 1.00 | 26.11 | | A | C |
| ANISOU | 660 | CA | GLN | A | 97 | 4352 | 2818 | 4419 | −155 | 4 | 5 | A | C |
| SIGUIJ | 660 | CA | GLN | A | 97 | 1 | 0 | 0 | 220 | 117 | 290 | A | C |
| ATOM | 661 | CB | GLN | A | 97 | 30.759 | 12.402 | 30.099 | 1.00 | 26.98 | | A | C |
| ANISOU | 661 | CB | GLN | A | 97 | 4370 | 3746 | 4402 | −291 | 2 | −12 | A | C |
| SIGUIJ | 661 | CB | GLN | A | 97 | 1 | 0 | 0 | 220 | 117 | 290 | A | C |
| ATOM | 662 | CG | GLN | A | 97 | 30.868 | 13.209 | 28.809 | 1.00 | 28.30 | | A | C |
| ANISOU | 662 | CG | GLN | A | 97 | 7564 | 3747 | 4466 | 113 | 518 | 18 | A | C |
| SIGUIJ | 662 | CG | GLN | A | 97 | 1 | 0 | 0 | 220 | 117 | 290 | A | C |
| ATOM | 663 | CD | GLN | A | 97 | 32.287 | 13.304 | 28.275 | 1.00 | 28.85 | | A | C |
| ANISOU | 663 | CD | GLN | A | 97 | 7752 | 12170 | 5505 | −481 | 913 | −68 | A | C |
| SIGUIJ | 663 | CD | GLN | A | 97 | 1 | 0 | 0 | 220 | 117 | 290 | A | C |
| ATOM | 664 | OE1 | GLN | A | 97 | 33.062 | 12.322 | 28.317 | 1.00 | 29.55 | | A | O |
| ANISOU | 664 | OE1 | GLN | A | 97 | 7610 | 12063 | 21148 | −623 | 173 | 18 | A | O |
| SIGUIJ | 664 | OE1 | GLN | A | 97 | 1 | 0 | 0 | 221 | 55 | 289 | A | O |
| ATOM | 665 | NE2 | GLN | A | 97 | 32.643 | 14.484 | 27.760 | 1.00 | 29.45 | | A | N |
| ANISOU | 665 | NE2 | GLN | A | 97 | 8173 | 12295 | 5335 | −805 | 457 | −5 | A | N |
| SIGUIJ | 665 | NE2 | GLN | A | 97 | 1 | 0 | 0 | 221 | 62 | 289 | A | N |
| ATOM | 666 | C | GLN | A | 97 | 28.464 | 11.981 | 29.254 | 1.00 | 25.48 | | A | C |
| ANISOU | 666 | C | GLN | A | 97 | 4377 | 3209 | 4425 | −221 | −1 | −4 | A | C |
| SIGUIJ | 666 | C | GLN | A | 97 | 1 | 0 | 0 | 220 | 116 | 290 | A | C |
| ATOM | 667 | O | GLN | A | 97 | 27.764 | 12.899 | 28.770 | 1.00 | 25.97 | | A | O |
| ANISOU | 667 | O | GLN | A | 97 | 4438 | 3244 | 4429 | −178 | 0 | −1 | A | O |
| SIGUIJ | 667 | O | GLN | A | 97 | 1 | 0 | 0 | 221 | 55 | 289 | A | O |
| ATOM | 668 | N | THR | A | 98 | 28.517 | 10.768 | 28.709 | 1.00 | 24.71 | | A | N |
| ANISOU | 668 | N | THR | A | 98 | 2139 | 3129 | 4134 | −535 | 501 | 154 | A | N |
| SIGUIJ | 668 | N | THR | A | 98 | 1 | 0 | 0 | 221 | 62 | 289 | A | N |
| ATOM | 669 | CA | THR | A | 98 | 27.845 | 10.474 | 27.448 | 1.00 | 23.55 | | A | C |
| ANISOU | 669 | CA | THR | A | 98 | 2234 | 2397 | 4212 | −131 | 363 | 126 | A | C |
| SIGUIJ | 669 | CA | THR | A | 98 | 1 | 0 | 0 | 220 | 116 | 290 | A | C |
| ATOM | 670 | CB | THR | A | 98 | 28.672 | 9.553 | 26.535 | 1.00 | 24.14 | | A | C |
| ANISOU | 670 | CB | THR | A | 98 | 2923 | 2652 | 4789 | 8 | 855 | −11 | A | C |
| SIGUIJ | 670 | CB | THR | A | 98 | 1 | 0 | 0 | 220 | 116 | 290 | A | C |
| ATOM | 671 | OG1 | THR | A | 98 | 28.693 | 8.242 | 27.090 | 1.00 | 25.41 | | A | O |
| ANISOU | 671 | OG1 | THR | A | 98 | 2682 | 2630 | 4677 | 18 | 885 | −60 | A | O |
| SIGUIJ | 671 | OG1 | THR | A | 98 | 1 | 0 | 0 | 221 | 55 | 289 | A | O |
| ATOM | 672 | CG2 | THR | A | 98 | 30.139 | 10.013 | 26.443 | 1.00 | 24.07 | | A | C |
| ANISOU | 672 | CG2 | THR | A | 98 | 2936 | 2641 | 10007 | 22 | 1164 | 50 | A | C |
| SIGUIJ | 672 | CG2 | THR | A | 98 | 1 | 0 | 0 | 220 | 116 | 290 | A | C |
| ATOM | 673 | C | THR | A | 98 | 26.474 | 9.803 | 27.646 | 1.00 | 22.30 | | A | C |
| ANISOU | 673 | C | THR | A | 98 | 2155 | 2072 | 2681 | 3 | 206 | 9 | A | C |
| SIGUIJ | 673 | C | THR | A | 98 | 1 | 0 | 0 | 220 | 116 | 290 | A | C |
| ATOM | 674 | O | THR | A | 98 | 25.704 | 9.655 | 26.689 | 1.00 | 22.13 | | A | O |
| ANISOU | 674 | O | THR | A | 98 | 2401 | 3340 | 2810 | −247 | 48 | 20 | A | O |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 674 | O | THR | A | 98 | 1 | 0 | 0 | 221 | 55 | 289 | A O |
| ATOM | 675 | N | HIS | A | 99 | 26.193 | 9.360 | 28.868 | 1.00 | 20.81 | | A N |
| ANISOU | 675 | N | HIS | A | 99 | 1992 | 1996 | 2663 | 1 | 155 | −3 | A N |
| SIGUIJ | 675 | N | HIS | A | 99 | 1 | 0 | 0 | 221 | 62 | 289 | A N |
| ATOM | 676 | CA | HIS | A | 99 | 24.951 | 8.634 | 29.168 | 1.00 | 19.34 | | A C |
| ANISOU | 676 | CA | HIS | A | 99 | 1983 | 1987 | 2190 | −2 | 56 | 0 | A C |
| SIGUIJ | 676 | CA | HIS | A | 99 | 1 | 0 | 0 | 220 | 116 | 290 | A C |
| ATOM | 677 | CB | HIS | A | 99 | 23.715 | 9.438 | 28.729 | 1.00 | 19.79 | | A C |
| ANISOU | 677 | CB | HIS | A | 99 | 2185 | 2005 | 3747 | 4 | −484 | 19 | A C |
| SIGUIJ | 677 | CB | HIS | A | 99 | 1 | 0 | 0 | 220 | 115 | 290 | A C |
| ATOM | 678 | CG | HIS | A | 99 | 23.728 | 10.846 | 29.213 | 1.00 | 20.14 | | A C |
| ANISOU | 678 | CG | HIS | A | 99 | 2351 | 2015 | 3830 | −96 | −197 | −2 | A C |
| SIGUIJ | 678 | CG | HIS | A | 99 | 1 | 0 | 0 | 220 | 115 | 290 | A C |
| ATOM | 679 | CD2 | HIS | A | 99 | 24.036 | 11.996 | 28.581 | 1.00 | 20.41 | | A C |
| ANISOU | 679 | CD2 | HIS | A | 99 | 2203 | 2017 | 3899 | −57 | −203 | 33 | A C |
| SIGUIJ | 679 | CD2 | HIS | A | 99 | 1 | 0 | 0 | 220 | 115 | 290 | A C |
| ATOM | 680 | ND1 | HIS | A | 99 | 23.382 | 11.190 | 30.501 | 1.00 | 20.50 | | A N |
| ANISOU | 680 | ND1 | HIS | A | 99 | 2303 | 1993 | 3822 | −68 | −213 | 25 | A N |
| SIGUIJ | 680 | ND1 | HIS | A | 99 | 1 | 0 | 0 | 221 | 62 | 289 | A N |
| ATOM | 681 | CE1 | HIS | A | 99 | 23.466 | 12.501 | 30.641 | 1.00 | 20.81 | | A C |
| ANISOU | 681 | CE1 | HIS | A | 99 | 3146 | 2005 | 4017 | −152 | 95 | −5 | A C |
| SIGUIJ | 681 | CE1 | HIS | A | 99 | 1 | 0 | 0 | 220 | 115 | 290 | A C |
| ATOM | 682 | NE2 | HIS | A | 99 | 23.862 | 13.012 | 29.487 | 1.00 | 20.46 | | A N |
| ANISOU | 682 | NE2 | HIS | A | 99 | 2633 | 2027 | 3964 | −118 | −62 | 3 | A N |
| SIGUIJ | 682 | NE2 | HIS | A | 99 | 1 | 0 | 0 | 221 | 62 | 289 | A N |
| ATOM | 683 | C | HIS | A | 99 | 24.866 | 7.234 | 28.583 | 1.00 | 18.13 | | A C |
| ANISOU | 683 | C | HIS | A | 99 | 1816 | 1980 | 2160 | 34 | 45 | −7 | A C |
| SIGUIJ | 683 | C | HIS | A | 99 | 1 | 0 | 0 | 220 | 115 | 290 | A C |
| ATOM | 684 | O | HIS | A | 99 | 23.823 | 6.602 | 28.685 | 1.00 | 17.56 | | A O |
| ANISOU | 684 | O | HIS | A | 99 | 1823 | 2014 | 1995 | 16 | 39 | −3 | A O |
| SIGUIJ | 684 | O | HIS | A | 99 | 1 | 0 | 0 | 221 | 55 | 289 | A O |
| ATOM | 685 | N | VAL | A | 100 | 25.945 | 6.723 | 27.986 | 1.00 | 16.94 | | A N |
| ANISOU | 685 | N | VAL | A | 100 | 1769 | 1861 | 2023 | −14 | −8 | −1 | A N |
| SIGUIJ | 685 | N | VAL | A | 100 | 1 | 0 | 0 | 221 | 62 | 289 | A N |
| ATOM | 686 | CA | VAL | A | 100 | 25.868 | 5.369 | 27.479 | 1.00 | 15.87 | | A C |
| ANISOU | 686 | CA | VAL | A | 100 | 2252 | 1850 | 1935 | −47 | 6 | −1 | A C |
| SIGUIJ | 686 | CA | VAL | A | 100 | 1 | 0 | 0 | 220 | 115 | 290 | A C |
| ATOM | 687 | CB | VAL | A | 100 | 27.067 | 5.027 | 26.514 | 1.00 | 16.42 | | A C |
| ANISOU | 687 | CB | VAL | A | 100 | 2363 | 2101 | 2040 | 27 | 102 | 9 | A C |
| SIGUIJ | 687 | CB | VAL | A | 100 | 1 | 0 | 0 | 220 | 114 | 290 | A C |
| ATOM | 688 | CG1 | VAL | A | 100 | 27.048 | 5.936 | 25.329 | 1.00 | 17.26 | | A C |
| ANISOU | 688 | CG1 | VAL | A | 100 | 5438 | 3054 | 2562 | 1740 | 1368 | 709 | A C |
| SIGUIJ | 688 | CG1 | VAL | A | 100 | 1 | 0 | 0 | 220 | 114 | 290 | A C |
| ATOM | 689 | CG2 | VAL | A | 100 | 28.328 | 5.041 | 27.227 | 1.00 | 17.69 | | A C |
| ANISOU | 689 | CG2 | VAL | A | 100 | 2424 | 2757 | 2236 | 10 | −1 | 0 | A C |
| SIGUIJ | 689 | CG2 | VAL | A | 100 | 1 | 0 | 0 | 220 | 114 | 290 | A C |
| ATOM | 690 | C | VAL | A | 100 | 25.769 | 4.380 | 28.619 | 1.00 | 14.72 | | A C |
| ANISOU | 690 | C | VAL | A | 100 | 1790 | 1813 | 1929 | −4 | 3 | 0 | A C |
| SIGUIJ | 690 | C | VAL | A | 100 | 1 | 0 | 0 | 220 | 114 | 290 | A C |
| ATOM | 691 | O | VAL | A | 100 | 26.243 | 4.597 | 29.731 | 1.00 | 13.86 | | A O |
| ANISOU | 691 | O | VAL | A | 100 | 1438 | 1838 | 1841 | −123 | 192 | 52 | A O |
| SIGUIJ | 691 | O | VAL | A | 100 | 1 | 0 | 0 | 221 | 55 | 289 | A O |
| ATOM | 692 | N | ASN | A | 101 | 25.088 | 3.291 | 28.328 | 1.00 | 14.10 | | A N |
| ANISOU | 692 | N | ASN | A | 101 | 1521 | 1758 | 1671 | 104 | 276 | −91 | A N |
| SIGUIJ | 692 | N | ASN | A | 101 | 1 | 0 | 0 | 221 | 62 | 289 | A N |
| ATOM | 693 | CA | ASN | A | 101 | 24.902 | 2.223 | 29.310 | 1.00 | 13.56 | | A C |
| ANISOU | 693 | CA | ASN | A | 101 | 1559 | 1763 | 1689 | 87 | 245 | −77 | A C |
| SIGUIJ | 693 | CA | ASN | A | 101 | 1 | 0 | 0 | 220 | 114 | 290 | A C |
| ATOM | 694 | CB | ASN | A | 101 | 26.234 | 1.525 | 29.592 | 1.00 | 14.79 | | A C |
| ANISOU | 694 | CB | ASN | A | 101 | 1609 | 1960 | 2094 | 186 | 184 | −71 | A C |
| SIGUIJ | 694 | CB | ASN | A | 101 | 1 | 0 | 0 | 220 | 114 | 290 | A C |
| ATOM | 695 | CG | ASN | A | 101 | 26.820 | 0.963 | 28.306 | 1.00 | 15.68 | | A C |
| ANISOU | 695 | CG | ASN | A | 101 | 1696 | 2225 | 2125 | 340 | 181 | −106 | A C |
| SIGUIJ | 695 | CG | ASN | A | 101 | 1 | 0 | 0 | 220 | 113 | 290 | A C |
| ATOM | 696 | OD1 | ASN | A | 101 | 26.100 | 0.323 | 27.515 | 1.00 | 16.85 | | A O |
| ANISOU | 696 | OD1 | ASN | A | 101 | 1850 | 2274 | 2189 | 254 | 114 | −66 | A O |
| SIGUIJ | 696 | OD1 | ASN | A | 101 | 1 | 0 | 0 | 221 | 55 | 289 | A O |
| ATOM | 697 | ND2 | ASN | A | 101 | 28.091 | 1.260 | 28.064 | 1.00 | 17.12 | | A N |
| ANISOU | 697 | ND2 | ASN | A | 101 | 1754 | 3141 | 2634 | 138 | 263 | −32 | A N |
| SIGUIJ | 697 | ND2 | ASN | A | 101 | 1 | 0 | 0 | 221 | 62 | 289 | A N |
| ATOM | 698 | C | ASN | A | 101 | 24.208 | 2.657 | 30.602 | 1.00 | 12.67 | | A C |
| ANISOU | 698 | C | ASN | A | 101 | 1176 | 1390 | 1549 | −9 | 34 | 1 | A C |
| SIGUIJ | 698 | C | ASN | A | 101 | 1 | 0 | 0 | 220 | 113 | 290 | A C |
| ATOM | 699 | O | ASN | A | 101 | 24.582 | 2.223 | 31.707 | 1.00 | 12.12 | | A O |
| ANISOU | 699 | O | ASN | A | 101 | 1255 | 1474 | 1494 | 236 | 113 | −82 | A O |
| SIGUIJ | 699 | O | ASN | A | 101 | 1 | 0 | 0 | 221 | 55 | 289 | A O |
| ATOM | 700 | N | ASP | A | 102 | 23.206 | 3.509 | 30.439 | 1.00 | 11.51 | | A N |
| ANISOU | 700 | N | ASP | A | 102 | 1197 | 1369 | 1286 | −5 | 3 | 0 | A N |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 700 | N | ASP | A | 102 | 1 | 0 | 0 | 221 | 62 | 289 | A | N |
| ATOM | 701 | CA | ASP | A | 102 | 22.522 | 4.095 | 31.589 | 1.00 | 11.50 | | A | C |
| ANISOU | 701 | CA | ASP | A | 102 | 1226 | 1317 | 1276 | −19 | 0 | 0 | A | C |
| SIGUIJ | 701 | CA | ASP | A | 102 | 1 | 0 | 0 | 220 | 113 | 290 | A | C |
| ATOM | 702 | CB | ASP | A | 102 | 21.924 | 5.449 | 31.192 | 1.00 | 11.19 | | A | C |
| ANISOU | 702 | CB | ASP | A | 102 | 1327 | 1329 | 1286 | 0 | −1 | 0 | A | C |
| SIGUIJ | 702 | CB | ASP | A | 102 | 1 | 0 | 0 | 220 | 113 | 290 | A | C |
| ATOM | 703 | CG | ASP | A | 102 | 21.442 | 6.269 | 32.400 | 1.00 | 11.45 | | A | C |
| ANISOU | 703 | CG | ASP | A | 102 | 1369 | 1344 | 1283 | 0 | −2 | 0 | A | C |
| SIGUIJ | 703 | CG | ASP | A | 102 | 1 | 0 | 0 | 220 | 113 | 290 | A | C |
| ATOM | 704 | OD1 | ASP | A | 102 | 21.673 | 5.856 | 33.563 | 1.00 | 11.51 | | A | O |
| ANISOU | 704 | OD1 | ASP | A | 102 | 1251 | 1347 | 1283 | −10 | 2 | 0 | A | O |
| SIGUIJ | 704 | OD1 | ASP | A | 102 | 1 | 0 | 0 | 221 | 55 | 289 | A | O |
| ATOM | 705 | OD2 | ASP | A | 102 | 20.801 | 7.313 | 32.169 | 1.00 | 11.08 | | A | O |
| ANISOU | 705 | OD2 | ASP | A | 102 | 1421 | 1354 | 1220 | 9 | 8 | 1 | A | O |
| SIGUIJ | 705 | OD2 | ASP | A | 102 | 1 | 0 | 0 | 221 | 55 | 289 | A | O |
| ATOM | 706 | C | ASP | A | 102 | 21.455 | 3.144 | 32.131 | 1.00 | 11.59 | | A | C |
| ANISOU | 706 | C | ASP | A | 102 | 1223 | 1280 | 1252 | 2 | 0 | 0 | A | C |
| SIGUIJ | 706 | C | ASP | A | 102 | 1 | 0 | 0 | 220 | 113 | 290 | A | C |
| ATOM | 707 | O | ASP | A | 102 | 20.245 | 3.459 | 32.084 | 1.00 | 12.68 | | A | O |
| ANISOU | 707 | O | ASP | A | 102 | 1258 | 1687 | 1990 | 120 | −29 | 6 | A | O |
| SIGUIJ | 707 | O | ASP | A | 102 | 1 | 0 | 0 | 221 | 55 | 289 | A | O |
| ATOM | 708 | N | LEU | A | 103 | 21.891 | 2.007 | 32.676 | 1.00 | 11.50 | | A | N |
| ANISOU | 708 | N | LEU | A | 103 | 1270 | 1269 | 1266 | 0 | 0 | 0 | A | N |
| SIGUIJ | 708 | N | LEU | A | 103 | 1 | 0 | 0 | 221 | 62 | 289 | A | N |
| ATOM | 709 | CA | LEU | A | 103 | 20.952 | 1.083 | 33.286 | 1.00 | 11.53 | | A | C |
| ANISOU | 709 | CA | LEU | A | 103 | 1278 | 1263 | 1325 | 3 | 4 | 0 | A | C |
| SIGUIJ | 709 | CA | LEU | A | 103 | 1 | 0 | 0 | 220 | 112 | 290 | A | C |
| ATOM | 710 | CB | LEU | A | 103 | 20.328 | 0.088 | 32.300 | 1.00 | 13.13 | | A | C |
| ANISOU | 710 | CB | LEU | A | 103 | 1965 | 1515 | 1359 | −384 | −11 | 7 | A | C |
| SIGUIJ | 710 | CB | LEU | A | 103 | 1 | 0 | 0 | 220 | 112 | 290 | A | C |
| ATOM | 711 | CG | LEU | A | 103 | 21.231 | −1.005 | 31.756 | 1.00 | 13.55 | | A | C |
| ANISOU | 711 | CG | LEU | A | 103 | 2312 | 1741 | 1668 | −140 | 116 | −26 | A | C |
| SIGUIJ | 711 | CG | LEU | A | 103 | 1 | 0 | 0 | 220 | 112 | 290 | A | C |
| ATOM | 712 | CD1 | LEU | A | 103 | 20.335 | −2.057 | 30.957 | 1.00 | 14.38 | | A | C |
| ANISOU | 712 | CD1 | LEU | A | 103 | 2180 | 1679 | 1605 | −68 | 167 | −20 | A | C |
| SIGUIJ | 712 | CD1 | LEU | A | 103 | 1 | 0 | 0 | 220 | 112 | 290 | A | C |
| ATOM | 713 | CD2 | LEU | A | 103 | 22.241 | −0.489 | 30.744 | 1.00 | 14.48 | | A | C |
| ANISOU | 713 | CD2 | LEU | A | 103 | 2282 | 1609 | 1715 | −26 | 149 | −6 | A | C |
| SIGUIJ | 713 | CD2 | LEU | A | 103 | 1 | 0 | 0 | 220 | 112 | 290 | A | C |
| ATOM | 714 | C | LEU | A | 103 | 21.563 | 0.405 | 34.495 | 1.00 | 10.75 | | A | C |
| ANISOU | 714 | C | LEU | A | 103 | 1217 | 1210 | 1320 | −1 | 9 | −1 | A | C |
| SIGUIJ | 714 | C | LEU | A | 103 | 1 | 0 | 0 | 220 | 112 | 290 | A | C |
| ATOM | 715 | O | LEU | A | 103 | 22.807 | 0.317 | 34.647 | 1.00 | 10.74 | | A | O |
| ANISOU | 715 | O | LEU | A | 103 | 1212 | 1289 | 1464 | 5 | 0 | 0 | A | O |
| SIGUIJ | 715 | O | LEU | A | 103 | 1 | 0 | 0 | 221 | 55 | 289 | A | O |
| ATOM | 716 | N | MET | A | 104 | 20.688 | −0.027 | 35.400 | 1.00 | 10.28 | | A | N |
| ANISOU | 716 | N | MET | A | 104 | 1183 | 1062 | 1306 | 86 | 12 | −3 | A | N |
| SIGUIJ | 716 | N | MET | A | 104 | 1 | 0 | 0 | 221 | 62 | 289 | A | N |
| ATOM | 717 | CA | MET | A | 104 | 21.074 | −0.508 | 36.711 | 1.00 | 9.73 | | A | C |
| ANISOU | 717 | CA | MET | A | 104 | 1188 | 1015 | 1310 | 2 | −12 | 0 | A | C |
| SIGUIJ | 717 | CA | MET | A | 104 | 1 | 0 | 0 | 220 | 112 | 290 | A | C |
| ATOM | 718 | CB | MET | A | 104 | 21.242 | 0.689 | 37.670 | 1.00 | 9.60 | | A | C |
| ANISOU | 718 | CB | MET | A | 104 | 1156 | 1018 | 1297 | −47 | 20 | 0 | A | C |
| SIGUIJ | 718 | CB | MET | A | 104 | 1 | 0 | 0 | 220 | 111 | 290 | A | C |
| ATOM | 719 | CG | MET | A | 104 | 21.621 | 0.322 | 39.100 | 1.00 | 9.22 | | A | C |
| ANISOU | 719 | CG | MET | A | 104 | 1309 | 1117 | 1294 | 25 | 1 | 0 | A | C |
| SIGUIJ | 719 | CG | MET | A | 104 | 1 | 0 | 0 | 220 | 111 | 290 | A | C |
| ATOM | 720 | SD | MET | A | 104 | 21.934 | 1.769 | 40.144 | 1.00 | 10.10 | | A | S |
| ANISOU | 720 | SD | MET | A | 104 | 1365 | 1162 | 1408 | 92 | −113 | −79 | A | S |
| SIGUIJ | 720 | SD | MET | A | 104 | 1 | 0 | 0 | 221 | 48 | 289 | A | S |
| ATOM | 721 | CE | MET | A | 104 | 20.275 | 2.461 | 40.318 | 1.00 | 9.48 | | A | C |
| ANISOU | 721 | CE | MET | A | 104 | 1365 | 1153 | 1527 | 95 | −27 | 5 | A | C |
| SIGUIJ | 721 | CE | MET | A | 104 | 1 | 0 | 0 | 220 | 111 | 290 | A | C |
| ATOM | 722 | C | MET | A | 104 | 19.992 | −1.444 | 37.231 | 1.00 | 9.69 | | A | C |
| ANISOU | 722 | C | MET | A | 104 | 1168 | 965 | 1359 | 60 | 28 | −1 | A | C |
| SIGUIJ | 722 | C | MET | A | 104 | 1 | 0 | 0 | 220 | 111 | 290 | A | C |
| ATOM | 723 | O | MET | A | 104 | 18.798 | −1.172 | 37.066 | 1.00 | 10.37 | | A | O |
| ANISOU | 723 | O | MET | A | 104 | 1184 | 1080 | 1646 | 87 | 4 | 1 | A | O |
| SIGUIJ | 723 | O | MET | A | 104 | 1 | 0 | 0 | 221 | 55 | 289 | A | O |
| ATOM | 724 | N | LEU | A | 105 | 20.411 | −2.514 | 37.907 | 1.00 | 9.28 | | A | N |
| ANISOU | 724 | N | LEU | A | 105 | 1116 | 966 | 1347 | 39 | 1 | 0 | A | N |
| SIGUIJ | 724 | N | LEU | A | 105 | 1 | 0 | 0 | 221 | 62 | 289 | A | N |
| ATOM | 725 | CA | LEU | A | 105 | 19.499 | −3.414 | 38.580 | 1.00 | 9.44 | | A | C |
| ANISOU | 725 | CA | LEU | A | 105 | 1032 | 926 | 1390 | 124 | 14 | 1 | A | C |
| SIGUIJ | 725 | CA | LEU | A | 105 | 1 | 0 | 0 | 220 | 111 | 290 | A | C |
| ATOM | 726 | CB | LEU | A | 105 | 19.892 | −4.877 | 38.263 | 1.00 | 10.10 | | A | C |
| ANISOU | 726 | CB | LEU | A | 105 | 1389 | 953 | 1640 | 202 | 53 | −30 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 726 | CB | LEU | A | 105 | 1 | 0 | 0 | 220 | 111 | 290 | A | C |
| ATOM | 727 | CG | LEU | A | 105 | 19.402 | −5.290 | 36.891 | 1.00 | 10.37 | | A | C |
| ANISOU | 727 | CG | LEU | A | 105 | 1620 | 1043 | 1658 | 20 | −1 | 0 | A | C |
| SIGUIJ | 727 | CG | LEU | A | 105 | 1 | 0 | 0 | 220 | 110 | 290 | A | C |
| ATOM | 728 | CD1 | LEU | A | 105 | 20.243 | −6.494 | 36.416 | 1.00 | 11.78 | | A | C |
| ANISOU | 728 | CD1 | LEU | A | 105 | 2116 | 1331 | 1753 | 403 | −62 | −49 | A | C |
| SIGUIJ | 728 | CD1 | LEU | A | 105 | 1 | 0 | 0 | 220 | 110 | 290 | A | C |
| ATOM | 729 | CD2 | LEU | A | 105 | 17.882 | −5.623 | 36.914 | 1.00 | 11.41 | | A | C |
| ANISOU | 729 | CD2 | LEU | A | 105 | 1642 | 1495 | 1676 | −87 | 0 | −1 | A | C |
| SIGUIJ | 729 | CD2 | LEU | A | 105 | 1 | 0 | 0 | 220 | 110 | 290 | A | C |
| ATOM | 730 | C | LEU | A | 105 | 19.553 | −3.168 | 40.074 | 1.00 | 9.78 | | A | C |
| ANISOU | 730 | C | LEU | A | 105 | 1222 | 1045 | 1390 | 44 | 19 | −1 | A | C |
| SIGUIJ | 730 | C | LEU | A | 105 | 1 | 0 | 0 | 220 | 110 | 290 | A | C |
| ATOM | 731 | O | LEU | A | 105 | 20.639 | −3.056 | 40.668 | 1.00 | 10.06 | | A | O |
| ANISOU | 731 | O | LEU | A | 105 | 1251 | 1567 | 1485 | −8 | −34 | −1 | A | O |
| SIGUIJ | 731 | O | LEU | A | 105 | 1 | 0 | 0 | 221 | 55 | 289 | A | O |
| ATOM | 732 | N | VAL | A | 106 | 18.376 | −3.053 | 40.700 | 1.00 | 9.72 | | A | N |
| ANISOU | 732 | N | VAL | A | 106 | 1211 | 1073 | 1326 | 60 | −6 | 1 | A | N |
| SIGUIJ | 732 | N | VAL | A | 106 | 1 | 0 | 0 | 221 | 62 | 289 | A | N |
| ATOM | 733 | CA | VAL | A | 106 | 18.253 | −2.806 | 42.118 | 1.00 | 9.98 | | A | C |
| ANISOU | 733 | CA | VAL | A | 106 | 1165 | 997 | 1333 | −15 | −2 | 0 | A | C |
| SIGUIJ | 733 | CA | VAL | A | 106 | 1 | 0 | 0 | 220 | 110 | 290 | A | C |
| ATOM | 734 | CB | VAL | A | 106 | 17.319 | −1.592 | 42.401 | 1.00 | 9.38 | | A | C |
| ANISOU | 734 | CB | VAL | A | 106 | 1195 | 1027 | 1322 | 18 | −11 | 0 | A | C |
| SIGUIJ | 734 | CB | VAL | A | 106 | 1 | 0 | 0 | 220 | 110 | 290 | A | C |
| ATOM | 735 | CG1 | VAL | A | 106 | 17.014 | −1.470 | 43.855 | 1.00 | 10.46 | | A | C |
| ANISOU | 735 | CG1 | VAL | A | 106 | 1714 | 1079 | 1335 | 127 | 79 | 19 | A | C |
| SIGUIJ | 735 | CG1 | VAL | A | 106 | 1 | 0 | 0 | 220 | 110 | 290 | A | C |
| ATOM | 736 | CG2 | VAL | A | 106 | 17.961 | −0.326 | 41.839 | 1.00 | 10.19 | | A | C |
| ANISOU | 736 | CG2 | VAL | A | 106 | 1372 | 1081 | 1382 | −80 | 0 | 3 | A | C |
| SIGUIJ | 736 | CG2 | VAL | A | 106 | 1 | 0 | 0 | 220 | 109 | 290 | A | C |
| ATOM | 737 | C | VAL | A | 106 | 17.652 | −4.046 | 42.767 | 1.00 | 9.99 | | A | C |
| ANISOU | 737 | C | VAL | A | 106 | 1187 | 973 | 1384 | 17 | 69 | 0 | A | C |
| SIGUIJ | 737 | C | VAL | A | 106 | 1 | 0 | 0 | 220 | 109 | 290 | A | C |
| ATOM | 738 | O | VAL | A | 106 | 16.621 | −4.558 | 42.315 | 1.00 | 10.40 | | A | O |
| ANISOU | 738 | O | VAL | A | 106 | 1257 | 1052 | 1559 | −27 | −37 | 2 | A | O |
| SIGUIJ | 738 | O | VAL | A | 106 | 1 | 0 | 0 | 221 | 55 | 289 | A | O |
| ATOM | 739 | N | LYS | A | 107 | 18.348 | −4.591 | 43.770 | 1.00 | 10.39 | | A | N |
| ANISOU | 739 | N | LYS | A | 107 | 1370 | 1019 | 1447 | 76 | −6 | 3 | A | N |
| SIGUIJ | 739 | N | LYS | A | 107 | 1 | 0 | 0 | 221 | 62 | 289 | A | N |
| ATOM | 740 | CA | LYS | A | 107 | 17.914 | −5.842 | 44.388 | 1.00 | 10.98 | | A | C |
| ANISOU | 740 | CA | LYS | A | 107 | 1397 | 1005 | 1459 | 101 | 3 | −2 | A | C |
| SIGUIJ | 740 | CA | LYS | A | 107 | 1 | 0 | 0 | 220 | 109 | 290 | A | C |
| ATOM | 741 | CB | LYS | A | 107 | 19.106 | −6.668 | 44.803 | 1.00 | 11.90 | | A | C |
| ANISOU | 741 | CB | LYS | A | 107 | 1601 | 1250 | 1934 | 297 | −164 | 11 | A | C |
| SIGUIJ | 741 | CB | LYS | A | 107 | 1 | 0 | 0 | 220 | 109 | 290 | A | C |
| ATOM | 742 | CG | LYS | A | 107 | 18.732 | −8.049 | 45.245 | 1.00 | 13.32 | | A | C |
| ANISOU | 742 | CG | LYS | A | 107 | 1830 | 1239 | 2066 | 316 | 18 | −9 | A | C |
| SIGUIJ | 742 | CG | LYS | A | 107 | 1 | 0 | 0 | 220 | 109 | 290 | A | C |
| ATOM | 743 | CD | LYS | A | 107 | 19.993 | −8.863 | 45.608 | 1.00 | 14.98 | | A | C |
| ANISOU | 743 | CD | LYS | A | 107 | 2079 | 1905 | 2194 | 715 | 85 | 171 | A | C |
| SIGUIJ | 743 | CD | LYS | A | 107 | 1 | 0 | 0 | 220 | 109 | 290 | A | C |
| ATOM | 744 | CE | LYS | A | 107 | 19.721 | −10.362 | 45.772 | 1.00 | 16.42 | | A | C |
| ANISOU | 744 | CE | LYS | A | 107 | 2713 | 1921 | 3605 | 647 | 435 | 263 | A | C |
| SIGUIJ | 744 | CE | LYS | A | 107 | 1 | 0 | 0 | 220 | 109 | 290 | A | C |
| ATOM | 745 | NZ | LYS | A | 107 | 21.008 | −11.032 | 46.297 | 1.00 | 17.72 | | A | N |
| ANISOU | 745 | NZ | LYS | A | 107 | 3026 | 2306 | 4028 | 981 | 93 | −57 | A | N |
| SIGUIJ | 745 | NZ | LYS | A | 107 | 1 | 0 | 0 | 221 | 62 | 289 | A | N |
| ATOM | 746 | C | LYS | A | 107 | 17.065 | −5.531 | 45.604 | 1.00 | 11.00 | | A | C |
| ANISOU | 746 | C | LYS | A | 107 | 1395 | 1032 | 1450 | 71 | −1 | 1 | A | C |
| SIGUIJ | 746 | C | LYS | A | 107 | 1 | 0 | 0 | 220 | 108 | 290 | A | C |
| ATOM | 747 | O | LYS | A | 107 | 17.547 | −4.887 | 46.553 | 1.00 | 11.19 | | A | O |
| ANISOU | 747 | O | LYS | A | 107 | 1567 | 1170 | 1442 | −78 | 5 | −2 | A | O |
| SIGUIJ | 747 | O | LYS | A | 107 | 1 | 0 | 0 | 221 | 55 | 289 | A | O |
| ATOM | 748 | N | LEU | A | 108 | 15.802 | −5.981 | 45.603 | 1.00 | 11.24 | | A | N |
| ANISOU | 748 | N | LEU | A | 108 | 1422 | 1231 | 1342 | 2 | 0 | 0 | A | N |
| SIGUIJ | 748 | N | LEU | A | 108 | 1 | 0 | 0 | 221 | 62 | 289 | A | N |
| ATOM | 749 | CA | LEU | A | 108 | 14.907 | −5.711 | 46.740 | 1.00 | 11.85 | | A | C |
| ANISOU | 749 | CA | LEU | A | 108 | 1465 | 1277 | 1352 | 9 | 22 | 1 | A | C |
| SIGUIJ | 749 | CA | LEU | A | 108 | 1 | 0 | 0 | 220 | 108 | 290 | A | C |
| ATOM | 750 | CB | LEU | A | 108 | 13.474 | −6.132 | 46.387 | 1.00 | 12.01 | | A | C |
| ANISOU | 750 | CB | LEU | A | 108 | 1478 | 1343 | 1502 | −20 | −1 | 0 | A | C |
| SIGUIJ | 750 | CB | LEU | A | 108 | 1 | 0 | 0 | 220 | 108 | 290 | A | C |
| ATOM | 751 | CG | LEU | A | 108 | 12.919 | −5.418 | 45.167 | 1.00 | 11.86 | | A | C |
| ANISOU | 751 | CG | LEU | A | 108 | 1536 | 1382 | 1505 | 24 | −4 | −2 | A | C |
| SIGUIJ | 751 | CG | LEU | A | 108 | 1 | 0 | 0 | 220 | 108 | 290 | A | C |
| ATOM | 752 | CD1 | LEU | A | 108 | 11.513 | −5.984 | 44.837 | 1.00 | 12.58 | | A | C |
| ANISOU | 752 | CD1 | LEU | A | 108 | 1614 | 1501 | 2352 | −35 | −229 | 51 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 752 | CD1 | LEU | A | 108 | 1 | 0 | 0 | 220 | 108 | 290 | A | C |
| ATOM | 753 | CD2 | LEU | A | 108 | 12.846 | −3.926 | 45.399 | 1.00 | 12.88 | | A | C |
| ANISOU | 753 | CD2 | LEU | A | 108 | 2113 | 1389 | 1608 | 57 | −30 | −3 | A | C |
| SIGUIJ | 753 | CD2 | LEU | A | 108 | 1 | 0 | 0 | 220 | 108 | 290 | A | C |
| ATOM | 754 | C | LEU | A | 108 | 15.392 | −6.546 | 47.952 | 1.00 | 12.20 | | A | C |
| ANISOU | 754 | C | LEU | A | 108 | 1519 | 1267 | 1374 | −32 | −25 | 5 | A | C |
| SIGUIJ | 754 | C | LEU | A | 108 | 1 | 0 | 0 | 220 | 108 | 290 | A | C |
| ATOM | 755 | O | LEU | A | 108 | 15.854 | −7.685 | 47.786 | 1.00 | 12.60 | | A | O |
| ANISOU | 755 | O | LEU | A | 108 | 1852 | 1313 | 1599 | 91 | 70 | 18 | A | O |
| SIGUIJ | 755 | O | LEU | A | 108 | 1 | 0 | 0 | 221 | 55 | 289 | A | O |
| ATOM | 756 | N | ASN | A | 109 | 15.259 | −6.006 | 49.139 | 1.00 | 12.92 | | A | N |
| ANISOU | 756 | N | ASN | A | 109 | 1573 | 1345 | 1374 | −40 | −4 | 1 | A | N |
| SIGUIJ | 756 | N | ASN | A | 109 | 1 | 0 | 0 | 221 | 62 | 289 | A | N |
| ATOM | 757 | CA | ASN | A | 109 | 15.681 | −6.757 | 50.345 | 1.00 | 13.41 | | A | C |
| ANISOU | 757 | CA | ASN | A | 109 | 1847 | 1426 | 1378 | 46 | −54 | −5 | A | C |
| SIGUIJ | 757 | CA | ASN | A | 109 | 1 | 0 | 0 | 220 | 107 | 290 | A | C |
| ATOM | 758 | CB | ASN | A | 109 | 15.811 | −5.836 | 51.542 | 1.00 | 13.05 | | A | C |
| ANISOU | 758 | CB | ASN | A | 109 | 1687 | 1456 | 1376 | 40 | −37 | −5 | A | C |
| SIGUIJ | 758 | CB | ASN | A | 109 | 1 | 0 | 0 | 220 | 107 | 290 | A | C |
| ATOM | 759 | CG | ASN | A | 109 | 17.005 | −4.891 | 51.431 | 1.00 | 12.98 | | A | C |
| ANISOU | 759 | CG | ASN | A | 109 | 1680 | 1476 | 1525 | 43 | −12 | −3 | A | C |
| SIGUIJ | 759 | CG | ASN | A | 109 | 1 | 0 | 0 | 220 | 107 | 290 | A | C |
| ATOM | 760 | OD1 | ASN | A | 109 | 17.785 | −4.886 | 50.442 | 1.00 | 12.94 | | A | O |
| ANISOU | 760 | OD1 | ASN | A | 109 | 1730 | 1565 | 1552 | 32 | 28 | 5 | A | O |
| SIGUIJ | 760 | OD1 | ASN | A | 109 | 1 | 0 | 0 | 221 | 55 | 289 | A | O |
| ATOM | 761 | ND2 | ASN | A | 109 | 17.173 | −4.096 | 52.470 | 1.00 | 13.30 | | A | N |
| ANISOU | 761 | ND2 | ASN | A | 109 | 1687 | 1502 | 1533 | 28 | −5 | −1 | A | N |
| SIGUIJ | 761 | ND2 | ASN | A | 109 | 1 | 0 | 0 | 221 | 61 | 289 | A | N |
| ATOM | 762 | C | ASN | A | 109 | 14.724 | −7.859 | 50.719 | 1.00 | 14.69 | | A | C |
| ANISOU | 762 | C | ASN | A | 109 | 2099 | 1588 | 1559 | −140 | 26 | −7 | A | C |
| SIGUIJ | 762 | C | ASN | A | 109 | 1 | 0 | 0 | 220 | 107 | 290 | A | C |
| ATOM | 763 | O | ASN | A | 109 | 15.098 | −8.816 | 51.433 | 1.00 | 14.91 | | A | O |
| ANISOU | 763 | O | ASN | A | 109 | 2374 | 1641 | 1909 | −293 | −314 | 134 | A | O |
| SIGUIJ | 763 | O | ASN | A | 109 | 1 | 0 | 0 | 221 | 55 | 289 | A | O |
| ATOM | 764 | N | ASER | A | 110 | 13.476 | −7.736 | 50.267 | 0.50 | 15.29 | | A | N |
| ANISOU | 764 | N | ASER | A | 110 | 2135 | 1762 | 1816 | −127 | −63 | 22 | A | N |
| SIGUIJ | 764 | N | ASER | A | 110 | 1 | 0 | 0 | 221 | 61 | 289 | A | N |
| ATOM | 765 | N | BSER | A | 110 | 13.510 | −7.789 | 50.203 | 0.50 | 17.48 | | A | N |
| ANISOU | 765 | N | BSER | A | 110 | 2143 | 1640 | 1822 | −165 | −84 | 33 | A | N |
| SIGUIJ | 765 | N | BSER | A | 110 | 1 | 0 | 0 | 221 | 61 | 289 | A | N |
| ATOM | 766 | CA | ASER | A | 110 | 12.395 | −8.696 | 50.529 | 0.50 | 16.79 | | A | C |
| ANISOU | 766 | CA | ASER | A | 110 | 2341 | 2020 | 1933 | −347 | −38 | 28 | A | C |
| SIGUIJ | 766 | CA | ASER | A | 110 | 1 | 0 | 0 | 220 | 107 | 290 | A | C |
| ATOM | 767 | CA | BSER | A | 110 | 12.531 | −8.835 | 50.409 | 0.50 | 18.98 | | A | C |
| ANISOU | 767 | CA | BSER | A | 110 | 2251 | 1710 | 2035 | −244 | −20 | 14 | A | C |
| SIGUIJ | 767 | CA | BSER | A | 110 | 1 | 0 | 0 | 220 | 107 | 290 | A | C |
| ATOM | 768 | CB | ASER | A | 110 | 11.484 | −8.210 | 51.703 | 0.50 | 17.69 | | A | C |
| ANISOU | 768 | CB | ASER | A | 110 | 2668 | 2689 | 2019 | −1 | 64 | 1 | A | C |
| SIGUIJ | 768 | CB | ASER | A | 110 | 1 | 0 | 0 | 220 | 107 | 290 | A | C |
| ATOM | 769 | CB | BSER | A | 110 | 11.640 | −8.504 | 51.614 | 0.50 | 19.88 | | A | C |
| ANISOU | 769 | CB | BSER | A | 110 | 2409 | 2429 | 2071 | 2 | 24 | −1 | A | C |
| SIGUIJ | 769 | CB | BSER | A | 110 | 1 | 0 | 0 | 220 | 107 | 290 | A | C |
| ATOM | 770 | OG | ASER | A | 110 | 10.860 | −6.950 | 51.498 | 0.50 | 19.99 | | A | O |
| ANISOU | 770 | OG | ASER | A | 110 | 2698 | 2686 | 2036 | 1 | 23 | 1 | A | O |
| SIGUIJ | 770 | OG | ASER | A | 110 | 1 | 0 | 0 | 221 | 55 | 289 | A | O |
| ATOM | 771 | OG | BSER | A | 110 | 12.411 | −8.427 | 52.800 | 0.50 | 22.18 | | A | O |
| ANISOU | 771 | OG | BSER | A | 110 | 2462 | 2576 | 2090 | −34 | −7 | −1 | A | O |
| SIGUIJ | 771 | OG | BSER | A | 110 | 1 | 0 | 0 | 221 | 55 | 289 | A | O |
| ATOM | 772 | C | ASER | A | 110 | 11.603 | −8.807 | 49.216 | 0.50 | 17.01 | | A | C |
| ANISOU | 772 | C | ASER | A | 110 | 2432 | 1844 | 1956 | −290 | −74 | 37 | A | C |
| SIGUIJ | 772 | C | ASER | A | 110 | 1 | 0 | 0 | 220 | 106 | 290 | A | C |
| ATOM | 773 | C | BSER | A | 110 | 11.713 | −8.885 | 49.138 | 0.50 | 19.20 | | A | C |
| ANISOU | 773 | C | BSER | A | 110 | 2224 | 1826 | 2022 | −206 | −2 | 1 | A | C |
| SIGUIJ | 773 | C | BSER | A | 110 | 1 | 0 | 0 | 220 | 106 | 290 | A | C |
| ATOM | 774 | O | ASER | A | 110 | 11.619 | −7.866 | 48.392 | 0.50 | 16.63 | | A | O |
| ANISOU | 774 | O | ASER | A | 110 | 1439 | 1829 | 1952 | −117 | 96 | 24 | A | O |
| SIGUIJ | 774 | O | ASER | A | 110 | 1 | 0 | 0 | 221 | 55 | 289 | A | O |
| ATOM | 775 | O | BSER | A | 110 | 11.771 | −7.974 | 48.291 | 0.50 | 18.82 | | A | O |
| ANISOU | 775 | O | BSER | A | 110 | 2693 | 1817 | 2024 | −219 | −7 | 2 | A | O |
| SIGUIJ | 775 | O | BSER | A | 110 | 1 | 0 | 0 | 221 | 55 | 289 | A | O |
| ATOM | 776 | N | GLN | A | 111 | 10.933 | −9.932 | 48.996 | 1.00 | 17.12 | | A | N |
| ANISOU | 776 | N | GLN | A | 111 | 1988 | 1698 | 1958 | −28 | 0 | 0 | A | N |
| SIGUIJ | 776 | N | GLN | A | 111 | 1 | 0 | 0 | 221 | 61 | 289 | A | N |
| ATOM | 777 | CA | GLN | A | 111 | 10.229 | −10.117 | 47.737 | 1.00 | 18.12 | | A | C |
| ANISOU | 777 | CA | GLN | A | 111 | 2166 | 1970 | 1991 | −137 | −72 | 43 | A | C |
| SIGUIJ | 777 | CA | GLN | A | 111 | 1 | 0 | 0 | 220 | 106 | 290 | A | C |
| ATOM | 778 | CB | GLN | A | 111 | 9.766 | −11.557 | 47.579 | 1.00 | 19.48 | | A | C |
| ANISOU | 778 | CB | GLN | A | 111 | 2371 | 1998 | 2746 | −187 | −160 | −30 | A | C |

TABLE 3-continued

Three-dimensional structure of the new binding pocket of kallikrein 7

| SIGUIJ | 778 | CB | GLN | A | 111 | 1 | 0 | 0 | 220 | 106 | 290 | A | C |
|---|---|---|---|---|---|---|---|---|---|---|---|---|---|
| ATOM | 779 | CG | GLN | A | 111 | 10.845 | −12.568 | 47.392 | 1.00 | 22.14 | | A | C |
| ANISOU | 779 | CG | GLN | A | 111 | 2793 | 2264 | 7919 | 80 | 852 | 92 | A | C |
| SIGUIJ | 779 | CG | GLN | A | 111 | 1 | 0 | 0 | 220 | 106 | 290 | A | C |
| ATOM | 780 | CD | GLN | A | 111 | 10.308 | −13.819 | 46.758 | 1.00 | 23.28 | | A | C |
| ANISOU | 780 | CD | GLN | A | 111 | 6731 | 2748 | 9230 | −935 | −488 | −3 | A | C |
| SIGUIJ | 780 | CD | GLN | A | 111 | 1 | 0 | 0 | 220 | 106 | 290 | A | C |
| ATOM | 781 | OE1 | GLN | A | 111 | 10.959 | −14.434 | 45.907 | 1.00 | 24.92 | | A | O |
| ANISOU | 781 | OE1 | GLN | A | 111 | 9238 | 4863 | 9655 | 1005 | 29 | −45 | A | O |
| SIGUIJ | 781 | OE1 | GLN | A | 111 | 1 | 0 | 0 | 221 | 55 | 289 | A | O |
| ATOM | 782 | NE2 | GLN | A | 111 | 9.103 | −14.201 | 47.157 | 1.00 | 24.43 | | A | N |
| ANISOU | 782 | NE2 | GLN | A | 111 | 6765 | 2621 | 9593 | −908 | −357 | −33 | A | N |
| SIGUIJ | 782 | NE2 | GLN | A | 111 | 1 | 0 | 0 | 221 | 61 | 289 | A | N |
| ATOM | 783 | C | GLN | A | 111 | 9.019 | −9.201 | 47.593 | 1.00 | 17.61 | | A | C |
| ANISOU | 783 | C | GLN | A | 111 | 2163 | 1938 | 1772 | −146 | −57 | 24 | A | C |
| SIGUIJ | 783 | C | GLN | A | 111 | 1 | 0 | 0 | 220 | 106 | 290 | A | C |
| ATOM | 784 | O | GLN | A | 111 | 8.280 | −8.956 | 48.526 | 1.00 | 18.10 | | A | O |
| ANISOU | 784 | O | GLN | A | 111 | 2463 | 2452 | 1934 | 2 | 144 | 9 | A | O |
| SIGUIJ | 784 | O | GLN | A | 111 | 1 | 0 | 0 | 221 | 55 | 289 | A | O |
| ATOM | 785 | N | ALA | A | 112 | 8.811 | −8.718 | 46.377 | 1.00 | 17.05 | | A | N |
| ANISOU | 785 | N | ALA | A | 112 | 2003 | 1853 | 1753 | −48 | 14 | −4 | A | N |
| SIGUIJ | 785 | N | ALA | A | 112 | 1 | 0 | 0 | 221 | 61 | 289 | A | N |
| ATOM | 786 | CA | ALA | A | 112 | 7.570 | −8.041 | 46.057 | 1.00 | 16.69 | | A | C |
| ANISOU | 786 | CA | ALA | A | 112 | 1968 | 1731 | 1752 | −118 | 9 | −4 | A | C |
| SIGUIJ | 786 | CA | ALA | A | 112 | 1 | 0 | 0 | 220 | 106 | 290 | A | C |
| ATOM | 787 | CB | ALA | A | 112 | 7.670 | −7.434 | 44.679 | 1.00 | 16.65 | | A | C |
| ANISOU | 787 | CB | ALA | A | 112 | 2000 | 1744 | 1751 | −188 | −5 | 3 | A | C |
| SIGUIJ | 787 | CB | ALA | A | 112 | 1 | 0 | 0 | 220 | 105 | 290 | A | C |
| ATOM | 788 | C | ALA | A | 112 | 6.462 | −9.070 | 46.059 | 1.00 | 16.29 | | A | C |
| ANISOU | 788 | C | ALA | A | 112 | 1843 | 1588 | 2130 | 17 | 8 | 0 | A | C |
| SIGUIJ | 788 | C | ALA | A | 112 | 1 | 0 | 0 | 220 | 105 | 290 | A | C |
| ATOM | 789 | O | ALA | A | 112 | 6.640 | −10.181 | 45.548 | 1.00 | 16.84 | | A | O |
| ANISOU | 789 | O | ALA | A | 112 | 1983 | 1611 | 2562 | −162 | 436 | −121 | A | O |
| SIGUIJ | 789 | O | ALA | A | 112 | 1 | 0 | 0 | 221 | 55 | 289 | A | O |
| ATOM | 790 | N | ARG | A | 113 | 5.317 | −8.648 | 46.555 | 1.00 | 15.89 | | A | N |
| ANISOU | 790 | N | ARG | A | 113 | 1770 | 1310 | 2014 | −103 | −46 | 3 | A | N |
| SIGUIJ | 790 | N | ARG | A | 113 | 1 | 0 | 0 | 221 | 61 | 289 | A | N |
| ATOM | 791 | CA | ARG | A | 113 | 4.134 | −9.498 | 46.561 | 1.00 | 16.10 | | A | C |
| ANISOU | 791 | CA | ARG | A | 113 | 1809 | 1395 | 2123 | −170 | −36 | −3 | A | C |
| SIGUIJ | 791 | CA | ARG | A | 113 | 1 | 0 | 0 | 220 | 105 | 290 | A | C |
| ATOM | 792 | CB | ARG | A | 113 | 3.307 | −9.105 | 47.789 | 1.00 | 16.85 | | A | C |
| ANISOU | 792 | CB | ARG | A | 113 | 1921 | 1804 | 2139 | 10 | −9 | 0 | A | C |
| SIGUIJ | 792 | CB | ARG | A | 113 | 1 | 0 | 0 | 220 | 105 | 290 | A | C |
| ATOM | 793 | CG | ARG | A | 113 | 2.029 | −9.912 | 47.973 | 1.00 | 18.15 | | A | C |
| ANISOU | 793 | CG | ARG | A | 113 | 2179 | 2462 | 2531 | −397 | 25 | 63 | A | C |
| SIGUIJ | 793 | CG | ARG | A | 113 | 1 | 0 | 0 | 220 | 105 | 290 | A | C |
| ATOM | 794 | CD | ARG | A | 113 | 1.363 | −9.577 | 49.279 | 1.00 | 19.35 | | A | C |
| ANISOU | 794 | CD | ARG | A | 113 | 2480 | 3481 | 2568 | 4 | 76 | 9 | A | C |
| SIGUIJ | 794 | CD | ARG | A | 113 | 1 | 0 | 0 | 220 | 105 | 290 | A | C |
| ATOM | 795 | NE | ARG | A | 113 | 0.698 | −8.280 | 49.188 | 1.00 | 21.35 | | A | N |
| ANISOU | 795 | NE | ARG | A | 113 | 3765 | 3821 | 3177 | 658 | 33 | 35 | A | N |
| SIGUIJ | 795 | NE | ARG | A | 113 | 1 | 0 | 0 | 221 | 61 | 289 | A | N |
| ATOM | 796 | CZ | ARG | A | 113 | 1.124 | −7.145 | 49.720 | 1.00 | 21.76 | | A | C |
| ANISOU | 796 | CZ | ARG | A | 113 | 4752 | 4010 | 2907 | 147 | 339 | 40 | A | C |
| SIGUIJ | 796 | CZ | ARG | A | 113 | 1 | 0 | 0 | 220 | 105 | 290 | A | C |
| ATOM | 797 | NH1 | ARG | A | 113 | 2.263 | −7.116 | 50.403 | 1.00 | 22.87 | | A | N |
| ANISOU | 797 | NH1 | ARG | A | 113 | 4831 | 9256 | 3113 | 35 | 215 | 4 | A | N |
| SIGUIJ | 797 | NH1 | ARG | A | 113 | 1 | 0 | 0 | 221 | 61 | 289 | A | N |
| ATOM | 798 | NH2 | ARG | A | 113 | 0.407 | −6.033 | 49.560 | 1.00 | 22.28 | | A | N |
| ANISOU | 798 | NH2 | ARG | A | 113 | 4317 | 3819 | 2073 | −127 | 387 | −52 | A | N |
| SIGUIJ | 798 | NH2 | ARG | A | 113 | 1 | 0 | 0 | 221 | 61 | 289 | A | N |
| ATOM | 799 | C | ARG | A | 113 | 3.379 | −9.243 | 45.280 | 1.00 | 16.20 | | A | C |
| ANISOU | 799 | C | ARG | A | 113 | 1605 | 1249 | 2069 | −215 | 83 | 13 | A | C |
| SIGUIJ | 799 | C | ARG | A | 113 | 1 | 0 | 0 | 220 | 104 | 290 | A | C |
| ATOM | 800 | O | ARG | A | 113 | 2.898 | −8.126 | 45.043 | 1.00 | 15.52 | | A | O |
| ANISOU | 800 | O | ARG | A | 113 | 1821 | 1271 | 2200 | −140 | −20 | −2 | A | O |
| SIGUIJ | 800 | O | ARG | A | 113 | 1 | 0 | 0 | 221 | 55 | 289 | A | O |
| ATOM | 801 | N | LEU | A | 114 | 3.248 | −10.255 | 44.430 | 1.00 | 16.44 | | A | N |
| ANISOU | 801 | N | LEU | A | 114 | 1747 | 1247 | 2127 | −113 | −55 | 1 | A | N |
| SIGUIJ | 801 | N | LEU | A | 114 | 1 | 0 | 0 | 221 | 61 | 289 | A | N |
| ATOM | 802 | CA | LEU | A | 114 | 2.613 | −10.095 | 43.145 | 1.00 | 17.11 | | A | C |
| ANISOU | 802 | CA | LEU | A | 114 | 1733 | 1504 | 2137 | −27 | −60 | −2 | A | C |
| SIGUIJ | 802 | CA | LEU | A | 114 | 1 | 0 | 0 | 220 | 104 | 290 | A | C |
| ATOM | 803 | CB | LEU | A | 114 | 3.090 | −11.177 | 42.160 | 1.00 | 16.77 | | A | C |
| ANISOU | 803 | CB | LEU | A | 114 | 1677 | 1500 | 2110 | −15 | −116 | 2 | A | C |
| SIGUIJ | 803 | CB | LEU | A | 114 | 1 | 0 | 0 | 220 | 104 | 290 | A | C |
| ATOM | 804 | CG | LEU | A | 114 | 4.604 | −11.244 | 41.936 | 1.00 | 16.57 | | A | C |
| ANISOU | 804 | CG | LEU | A | 114 | 1686 | 1414 | 2554 | −26 | −58 | 2 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 804 | CG | LEU | A | 114 | 1 | 0 | 0 | 220 | 104 | 290 | A | C |
| ATOM | 805 | CD1 | LEU | A | 114 | 4.934 | −12.344 | 40.931 | 1.00 | 16.95 | | A | C |
| ANISOU | 805 | CD1 | LEU | A | 114 | 2302 | 1465 | 2569 | 124 | −15 | 2 | A | C |
| SIGUIJ | 805 | CD1 | LEU | A | 114 | 1 | 0 | 0 | 220 | 104 | 290 | A | C |
| ATOM | 806 | CD2 | LEU | A | 114 | 5.114 | −9.909 | 41.432 | 1.00 | 17.11 | | A | C |
| ANISOU | 806 | CD2 | LEU | A | 114 | 2276 | 1462 | 3081 | −108 | 329 | 44 | A | C |
| SIGUIJ | 806 | CD2 | LEU | A | 114 | 1 | 0 | 0 | 220 | 104 | 290 | A | C |
| ATOM | 807 | C | LEU | A | 114 | 1.097 | −10.149 | 43.285 | 1.00 | 18.00 | | A | C |
| ANISOU | 807 | C | LEU | A | 114 | 1728 | 1573 | 2995 | −6 | 15 | 0 | A | C |
| SIGUIJ | 807 | C | LEU | A | 114 | 1 | 0 | 0 | 220 | 104 | 290 | A | C |
| ATOM | 808 | O | LEU | A | 114 | 0.577 | −10.827 | 44.215 | 1.00 | 18.24 | | A | O |
| ANISOU | 808 | O | LEU | A | 114 | 2536 | 1872 | 3167 | −325 | 254 | 55 | A | O |
| SIGUIJ | 808 | O | LEU | A | 114 | 1 | 0 | 0 | 221 | 55 | 289 | A | O |
| ATOM | 809 | N | SER | A | 115 | 0.408 | −9.482 | 42.337 | 1.00 | 18.77 | | A | N |
| ANISOU | 809 | N | SER | A | 115 | 1763 | 1552 | 3043 | −36 | −49 | 4 | A | N |
| SIGUIJ | 809 | N | SER | A | 115 | 1 | 0 | 0 | 221 | 61 | 289 | A | N |
| ATOM | 810 | CA | SER | A | 115 | −1.055 | −9.364 | 42.358 | 1.00 | 19.64 | | A | C |
| ANISOU | 810 | CA | SER | A | 115 | 1766 | 2476 | 3337 | 46 | −53 | 3 | A | C |
| SIGUIJ | 810 | CA | SER | A | 115 | 1 | 0 | 0 | 220 | 104 | 290 | A | C |
| ATOM | 811 | CB | SER | A | 115 | −1.452 | −8.523 | 43.539 | 1.00 | 20.16 | | A | C |
| ANISOU | 811 | CB | SER | A | 115 | 2626 | 2474 | 3445 | 12 | 261 | −3 | A | C |
| SIGUIJ | 811 | CB | SER | A | 115 | 1 | 0 | 0 | 220 | 104 | 290 | A | C |
| ATOM | 812 | OG | SER | A | 115 | −1.140 | −7.162 | 43.223 | 1.00 | 21.32 | | A | O |
| ANISOU | 812 | OG | SER | A | 115 | 3340 | 2498 | 4640 | 27 | 979 | 112 | A | O |
| SIGUIJ | 812 | OG | SER | A | 115 | 1 | 0 | 0 | 221 | 55 | 289 | A | O |
| ATOM | 813 | C | SER | A | 115 | −1.528 | −8.645 | 41.083 | 1.00 | 19.90 | | A | C |
| ANISOU | 813 | C | SER | A | 115 | 1763 | 2272 | 3371 | −161 | −175 | −32 | A | C |
| SIGUIJ | 813 | C | SER | A | 115 | 1 | 0 | 0 | 220 | 103 | 290 | A | C |
| ATOM | 814 | O | SER | A | 115 | −0.753 | −8.325 | 40.227 | 1.00 | 20.05 | | A | O |
| ANISOU | 814 | O | SER | A | 115 | 1816 | 1909 | 3486 | 9 | −71 | 3 | A | O |
| SIGUIJ | 814 | O | SER | A | 115 | 1 | 0 | 0 | 221 | 54 | 289 | A | O |
| ATOM | 815 | N | SER | A | 116 | −2.838 | −8.428 | 40.931 | 1.00 | 20.69 | | A | N |
| ANISOU | 815 | N | SER | A | 116 | 1795 | 2418 | 5718 | −141 | −452 | −36 | A | N |
| SIGUIJ | 815 | N | SER | A | 116 | 1 | 0 | 0 | 221 | 61 | 289 | A | N |
| ATOM | 816 | CA | SER | A | 116 | −3.329 | −7.557 | 39.857 | 1.00 | 20.69 | | A | C |
| ANISOU | 816 | CA | SER | A | 116 | 1953 | 2455 | 5706 | −48 | −455 | −54 | A | C |
| SIGUIJ | 816 | CA | SER | A | 116 | 1 | 0 | 0 | 220 | 103 | 290 | A | C |
| ATOM | 817 | CB | SER | A | 116 | −4.865 | −7.371 | 39.972 | 1.00 | 21.19 | | A | C |
| ANISOU | 817 | CB | SER | A | 116 | 1986 | 3668 | 8877 | 97 | −207 | 8 | A | C |
| SIGUIJ | 817 | CB | SER | A | 116 | 1 | 0 | 0 | 220 | 103 | 290 | A | C |
| ATOM | 818 | OG | SER | A | 116 | −5.215 | −6.768 | 41.202 | 1.00 | 22.45 | | A | O |
| ANISOU | 818 | OG | SER | A | 116 | 2138 | 3815 | 8778 | 623 | −419 | 88 | A | O |
| SIGUIJ | 818 | OG | SER | A | 116 | 1 | 0 | 0 | 221 | 54 | 289 | A | O |
| ATOM | 819 | C | SER | A | 116 | −2.644 | −6.171 | 39.784 | 1.00 | 20.42 | | A | C |
| ANISOU | 819 | C | SER | A | 116 | 2214 | 2521 | 4640 | −172 | −509 | −96 | A | C |
| SIGUIJ | 819 | C | SER | A | 116 | 1 | 0 | 0 | 220 | 103 | 290 | A | C |
| ATOM | 820 | O | SER | A | 116 | −2.550 | −5.610 | 38.697 | 1.00 | 21.05 | | A | O |
| ANISOU | 820 | O | SER | A | 116 | 2131 | 2640 | 4675 | −95 | −490 | −34 | A | O |
| SIGUIJ | 820 | O | SER | A | 116 | 1 | 0 | 0 | 221 | 54 | 289 | A | O |
| ATOM | 821 | N | MET | A | 117 | −2.153 | −5.667 | 40.921 | 1.00 | 19.82 | | A | N |
| ANISOU | 821 | N | MET | A | 117 | 1407 | 1770 | 4466 | 182 | −306 | 96 | A | N |
| SIGUIJ | 821 | N | MET | A | 117 | 1 | 0 | 0 | 221 | 61 | 289 | A | N |
| ATOM | 822 | CA | MET | A | 117 | −1.520 | −4.350 | 40.929 | 1.00 | 19.03 | | A | C |
| ANISOU | 822 | CA | MET | A | 117 | 1729 | 1849 | 3850 | 32 | −57 | 7 | A | C |
| SIGUIJ | 822 | CA | MET | A | 117 | 1 | 0 | 0 | 220 | 103 | 290 | A | C |
| ATOM | 823 | CB | MET | A | 117 | −1.943 | −3.547 | 42.132 | 1.00 | 20.66 | | A | C |
| ANISOU | 823 | CB | MET | A | 117 | 2266 | 1946 | 3895 | 138 | 61 | 7 | A | C |
| SIGUIJ | 823 | CB | MET | A | 117 | 1 | 0 | 0 | 220 | 103 | 290 | A | C |
| ATOM | 824 | CG | MET | A | 117 | −3.379 | −2.897 | 41.980 | 1.00 | 22.36 | | A | C |
| ANISOU | 824 | CG | MET | A | 117 | 2554 | 3281 | 5392 | 737 | −96 | 42 | A | C |
| SIGUIJ | 824 | CG | MET | A | 117 | 1 | 0 | 0 | 220 | 103 | 290 | A | C |
| ATOM | 825 | SD | MET | A | 117 | −3.694 | −2.019 | 40.387 | 1.00 | 24.64 | | A | S |
| ANISOU | 825 | SD | MET | A | 117 | 2679 | 3265 | 5461 | 451 | −289 | 102 | A | S |
| SIGUIJ | 825 | SD | MET | A | 117 | 1 | 0 | 0 | 221 | 48 | 289 | A | S |
| ATOM | 826 | CE | MET | A | 117 | −3.179 | −0.412 | 40.861 | 1.00 | 23.83 | | A | C |
| ANISOU | 826 | CE | MET | A | 117 | 3978 | 3438 | 5677 | −2 | −189 | 3 | A | C |
| SIGUIJ | 826 | CE | MET | A | 117 | 1 | 0 | 0 | 220 | 103 | 290 | A | C |
| ATOM | 827 | C | MET | A | 117 | 0.001 | −4.376 | 40.899 | 1.00 | 17.74 | | A | C |
| ANISOU | 827 | C | MET | A | 117 | 1732 | 1355 | 2342 | 25 | −74 | 1 | A | C |
| SIGUIJ | 827 | C | MET | A | 117 | 1 | 0 | 0 | 220 | 102 | 290 | A | C |
| ATOM | 828 | O | MET | A | 117 | 0.612 | −3.307 | 40.805 | 1.00 | 17.16 | | A | O |
| ANISOU | 828 | O | MET | A | 117 | 1737 | 1336 | 2063 | 38 | −73 | −2 | A | O |
| SIGUIJ | 828 | O | MET | A | 117 | 1 | 0 | 0 | 221 | 54 | 289 | A | O |
| ATOM | 829 | N | VAL | A | 118 | 0.611 | −5.574 | 41.004 | 1.00 | 16.28 | | A | N |
| ANISOU | 829 | N | VAL | A | 118 | 1624 | 1330 | 2554 | −26 | −76 | 3 | A | N |
| SIGUIJ | 829 | N | VAL | A | 118 | 1 | 0 | 0 | 221 | 61 | 289 | A | N |
| ATOM | 830 | CA | VAL | A | 118 | 2.095 | −5.723 | 40.950 | 1.00 | 15.27 | | A | C |
| ANISOU | 830 | CA | VAL | A | 118 | 1629 | 1193 | 2104 | −36 | −94 | 1 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 830 | CA | VAL | A | 118 | 1 | 0 | 0 | 220 | 102 | 290 | A | C |
| ATOM | 831 | CB | VAL | A | 118 | 2.649 | −5.931 | 42.377 | 1.00 | 14.08 | | A | C |
| ANISOU | 831 | CB | VAL | A | 118 | 1405 | 1263 | 2061 | 3 | 12 | 0 | A | C |
| SIGUIJ | 831 | CB | VAL | A | 118 | 1 | 0 | 0 | 220 | 102 | 290 | A | C |
| ATOM | 832 | CG1 | VAL | A | 118 | 4.176 | −6.145 | 42.338 | 1.00 | 13.42 | | A | C |
| ANISOU | 832 | CG1 | VAL | A | 118 | 1408 | 1247 | 2297 | −1 | 22 | 0 | A | C |
| SIGUIJ | 832 | CG1 | VAL | A | 118 | 1 | 0 | 0 | 220 | 102 | 290 | A | C |
| ATOM | 833 | CG2 | VAL | A | 118 | 2.304 | −4.722 | 43.232 | 1.00 | 14.26 | | A | C |
| ANISOU | 833 | CG2 | VAL | A | 118 | 1562 | 1269 | 2099 | 11 | 76 | 1 | A | C |
| SIGUIJ | 833 | CG2 | VAL | A | 118 | 1 | 0 | 0 | 220 | 102 | 290 | A | C |
| ATOM | 834 | C | VAL | A | 118 | 2.414 | −6.890 | 40.055 | 1.00 | 15.11 | | A | C |
| ANISOU | 834 | C | VAL | A | 118 | 1434 | 1161 | 2121 | −131 | −60 | 1 | A | C |
| SIGUIJ | 834 | C | VAL | A | 118 | 1 | 0 | 0 | 220 | 102 | 290 | A | C |
| ATOM | 835 | O | VAL | A | 118 | 2.127 | −8.060 | 40.396 | 1.00 | 14.71 | | A | O |
| ANISOU | 835 | O | VAL | A | 118 | 1814 | 1179 | 2218 | −232 | −43 | −2 | A | O |
| SIGUIJ | 835 | O | VAL | A | 118 | 1 | 0 | 0 | 221 | 54 | 289 | A | O |
| ATOM | 836 | N | LYS | A | 119 | 2.949 | −6.593 | 38.882 | 1.00 | 15.20 | | A | N |
| ANISOU | 836 | N | LYS | A | 119 | 1746 | 1300 | 2172 | −183 | 63 | 7 | A | N |
| SIGUIJ | 836 | N | LYS | A | 119 | 1 | 0 | 0 | 221 | 61 | 289 | A | N |
| ATOM | 837 | CA | LYS | A | 119 | 3.202 | −7.592 | 37.838 | 1.00 | 15.90 | | A | C |
| ANISOU | 837 | CA | LYS | A | 119 | 1689 | 1303 | 2175 | −188 | 65 | 3 | A | C |
| SIGUIJ | 837 | CA | LYS | A | 119 | 1 | 0 | 0 | 220 | 102 | 290 | A | C |
| ATOM | 838 | CB | LYS | A | 119 | 2.212 | −7.325 | 36.693 | 1.00 | 17.02 | | A | C |
| ANISOU | 838 | CB | LYS | A | 119 | 2159 | 1934 | 2519 | −57 | −311 | 59 | A | C |
| SIGUIJ | 838 | CB | LYS | A | 119 | 1 | 0 | 0 | 220 | 102 | 290 | A | C |
| ATOM | 839 | CG | LYS | A | 119 | 2.221 | −8.230 | 35.431 | 1.00 | 18.86 | | A | C |
| ANISOU | 839 | CG | LYS | A | 119 | 2605 | 2223 | 2673 | −541 | 42 | −144 | A | C |
| SIGUIJ | 839 | CG | LYS | A | 119 | 1 | 0 | 0 | 220 | 102 | 290 | A | C |
| ATOM | 840 | CD | LYS | A | 119 | 1.015 | −7.886 | 34.493 | 1.00 | 20.61 | | A | C |
| ANISOU | 840 | CD | LYS | A | 119 | 2753 | 4116 | 2776 | −120 | 4 | 9 | A | C |
| SIGUIJ | 840 | CD | LYS | A | 119 | 1 | 0 | 0 | 220 | 101 | 290 | A | C |
| ATOM | 841 | CE | LYS | A | 119 | 1.219 | −6.625 | 33.566 | 1.00 | 21.72 | | A | C |
| ANISOU | 841 | CE | LYS | A | 119 | 12388 | 4128 | 2918 | −702 | 1335 | −104 | A | C |
| SIGUIJ | 841 | CE | LYS | A | 119 | 1 | 0 | 0 | 220 | 101 | 290 | A | C |
| ATOM | 842 | NZ | LYS | A | 119 | 0.012 | −6.188 | 32.720 | 1.00 | 22.83 | | A | N |
| ANISOU | 842 | NZ | LYS | A | 119 | 15093 | 9430 | 6830 | 1341 | −1471 | −282 | A | N |
| SIGUIJ | 842 | NZ | LYS | A | 119 | 1 | 0 | 0 | 221 | 61 | 289 | A | N |
| ATOM | 843 | C | LYS | A | 119 | 4.607 | −7.439 | 37.305 | 1.00 | 15.59 | | A | C |
| ANISOU | 843 | C | LYS | A | 119 | 1648 | 1253 | 1821 | −207 | −51 | −38 | A | C |
| SIGUIJ | 843 | C | LYS | A | 119 | 1 | 0 | 0 | 220 | 101 | 290 | A | C |
| ATOM | 844 | O | LYS | A | 119 | 5.169 | −6.306 | 37.257 | 1.00 | 15.70 | | A | O |
| ANISOU | 844 | O | LYS | A | 119 | 1822 | 1301 | 2500 | −310 | −73 | −4 | A | O |
| SIGUIJ | 844 | O | LYS | A | 119 | 1 | 0 | 0 | 221 | 54 | 289 | A | O |
| ATOM | 845 | N | LYS | A | 120 | 5.202 | −8.532 | 36.877 | 1.00 | 14.95 | | A | N |
| ANISOU | 845 | N | LYS | A | 120 | 1615 | 1235 | 1756 | −241 | −16 | −21 | A | N |
| SIGUIJ | 845 | N | LYS | A | 120 | 1 | 0 | 0 | 221 | 61 | 289 | A | N |
| ATOM | 846 | CA | LYS | A | 120 | 6.481 | −8.482 | 36.187 | 1.00 | 15.06 | | A | C |
| ANISOU | 846 | CA | LYS | A | 120 | 1640 | 1387 | 1823 | −226 | 23 | 20 | A | C |
| SIGUIJ | 846 | CA | LYS | A | 120 | 1 | 0 | 0 | 220 | 101 | 290 | A | C |
| ATOM | 847 | CB | LYS | A | 120 | 7.023 | −9.919 | 36.034 | 1.00 | 15.87 | | A | C |
| ANISOU | 847 | CB | LYS | A | 120 | 2003 | 1450 | 2116 | −80 | 13 | −2 | A | C |
| SIGUIJ | 847 | CB | LYS | A | 120 | 1 | 0 | 0 | 220 | 101 | 290 | A | C |
| ATOM | 848 | CG | LYS | A | 120 | 7.214 | −10.634 | 37.396 | 1.00 | 17.11 | | A | C |
| ANISOU | 848 | CG | LYS | A | 120 | 2185 | 1579 | 2148 | −69 | −15 | 47 | A | C |
| SIGUIJ | 848 | CG | LYS | A | 120 | 1 | 0 | 0 | 220 | 101 | 290 | A | C |
| ATOM | 849 | CD | LYS | A | 120 | 7.903 | −12.032 | 37.231 | 1.00 | 19.27 | | A | C |
| ANISOU | 849 | CD | LYS | A | 120 | 2483 | 1637 | 3342 | 40 | 265 | 32 | A | C |
| SIGUIJ | 849 | CD | LYS | A | 120 | 1 | 0 | 0 | 220 | 101 | 290 | A | C |
| ATOM | 850 | CE | LYS | A | 120 | 7.005 | −13.100 | 36.616 | 1.00 | 20.80 | | A | C |
| ANISOU | 850 | CE | LYS | A | 120 | 3181 | 2025 | 3841 | −384 | −22 | −5 | A | C |
| SIGUIJ | 850 | CE | LYS | A | 120 | 1 | 0 | 0 | 220 | 101 | 290 | A | C |
| ATOM | 851 | NZ | LYS | A | 120 | 7.677 | −14.431 | 36.757 | 1.00 | 22.64 | | A | N |
| ANISOU | 851 | NZ | LYS | A | 120 | 4052 | 2242 | 5342 | 35 | −275 | 13 | A | N |
| SIGUIJ | 851 | NZ | LYS | A | 120 | 1 | 0 | 0 | 221 | 61 | 289 | A | N |
| ATOM | 852 | C | LYS | A | 120 | 6.322 | −7.836 | 34.835 | 1.00 | 14.75 | | A | C |
| ANISOU | 852 | C | LYS | A | 120 | 1766 | 1360 | 1821 | −282 | −1 | 14 | A | C |
| SIGUIJ | 852 | C | LYS | A | 120 | 1 | 0 | 0 | 220 | 100 | 290 | A | C |
| ATOM | 853 | O | LYS | A | 120 | 5.385 | −8.141 | 34.071 | 1.00 | 14.75 | | A | O |
| ANISOU | 853 | O | LYS | A | 120 | 1794 | 1689 | 1830 | −381 | 1 | −4 | A | O |
| SIGUIJ | 853 | O | LYS | A | 120 | 1 | 0 | 0 | 221 | 54 | 289 | A | O |
| ATOM | 854 | N | VAL | A | 121 | 7.278 | −6.993 | 34.497 | 1.00 | 13.48 | | A | N |
| ANISOU | 854 | N | VAL | A | 121 | 1616 | 1143 | 1653 | −106 | −1 | −3 | A | N |
| SIGUIJ | 854 | N | VAL | A | 121 | 1 | 0 | 0 | 221 | 61 | 289 | A | N |
| ATOM | 855 | CA | VAL | A | 121 | 7.253 | −6.364 | 33.174 | 1.00 | 13.91 | | A | C |
| ANISOU | 855 | CA | VAL | A | 121 | 1816 | 1210 | 1670 | −227 | −55 | 38 | A | C |
| SIGUIJ | 855 | CA | VAL | A | 121 | 1 | 0 | 0 | 220 | 100 | 290 | A | C |
| ATOM | 856 | CB | VAL | A | 121 | 8.314 | −5.209 | 33.126 | 1.00 | 13.56 | | A | C |
| ANISOU | 856 | CB | VAL | A | 121 | 1770 | 1166 | 1874 | −183 | −1 | −1 | A | C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 856 | CB | VAL | A | 121 | 1 | 0 | 0 | 220 | 100 | 290 | A C |
| ATOM | 857 | CG1 | VAL | A | 121 | 9.753 | −5.773 | 32.994 | 1.00 | 13.96 | | A C |
| ANISOU | 857 | CG1 | VAL | A | 121 | 1784 | 1184 | 2409 | −164 | 50 | 1 | A C |
| SIGUIJ | 857 | CG1 | VAL | A | 121 | 1 | 0 | 0 | 220 | 100 | 290 | A C |
| ATOM | 858 | CG2 | VAL | A | 121 | 7.983 | −4.239 | 32.010 | 1.00 | 13.81 | | A C |
| ANISOU | 858 | CG2 | VAL | A | 121 | 1908 | 1183 | 1879 | −146 | −1 | 3 | A C |
| SIGUIJ | 858 | CG2 | VAL | A | 121 | 1 | 0 | 0 | 220 | 100 | 290 | A C |
| ATOM | 859 | C | VAL | A | 121 | 7.593 | −7.395 | 32.072 | 1.00 | 14.19 | | A C |
| ANISOU | 859 | C | VAL | A | 121 | 1805 | 1241 | 1751 | −314 | 16 | −26 | A C |
| SIGUIJ | 859 | C | VAL | A | 121 | 1 | 0 | 0 | 220 | 100 | 290 | A C |
| ATOM | 860 | O | VAL | A | 121 | 8.297 | −8.355 | 32.317 | 1.00 | 14.22 | | A O |
| ANISOU | 860 | O | VAL | A | 121 | 1970 | 1332 | 1922 | −204 | −9 | 12 | A O |
| SIGUIJ | 860 | O | VAL | A | 121 | 1 | 0 | 0 | 221 | 54 | 289 | A O |
| ATOM | 861 | N | ARG | A | 122 | 7.115 | −7.145 | 30.859 | 1.00 | 15.04 | | A N |
| ANISOU | 861 | N | ARG | A | 122 | 1902 | 1439 | 1781 | −380 | −36 | 47 | A N |
| SIGUIJ | 861 | N | ARG | A | 122 | 1 | 0 | 0 | 221 | 61 | 289 | A N |
| ATOM | 862 | CA | ARG | A | 122 | 7.471 | −7.987 | 29.718 | 1.00 | 16.06 | | A C |
| ANISOU | 862 | CA | ARG | A | 122 | 2015 | 1586 | 1913 | −475 | 71 | −103 | A C |
| SIGUIJ | 862 | CA | ARG | A | 122 | 1 | 0 | 0 | 220 | 100 | 290 | A C |
| ATOM | 863 | CB | ARG | A | 122 | 6.305 | −8.073 | 28.739 | 1.00 | 17.68 | | A C |
| ANISOU | 863 | CB | ARG | A | 122 | 2071 | 2635 | 1977 | −651 | 6 | 24 | A C |
| SIGUIJ | 863 | CB | ARG | A | 122 | 1 | 0 | 0 | 220 | 100 | 290 | A C |
| ATOM | 864 | CG | ARG | A | 122 | 6.544 | −9.094 | 27.666 | 1.00 | 20.19 | | A C |
| ANISOU | 864 | CG | ARG | A | 122 | 3512 | 2743 | 2006 | −306 | 3 | −1 | A C |
| SIGUIJ | 864 | CG | ARG | A | 122 | 1 | 0 | 0 | 220 | 100 | 290 | A C |
| ATOM | 865 | CD | ARG | A | 122 | 5.253 | −9.413 | 26.867 | 1.00 | 22.38 | | A C |
| ANISOU | 865 | CD | ARG | A | 122 | 4419 | 9397 | 2928 | −2250 | −689 | 483 | A C |
| SIGUIJ | 865 | CD | ARG | A | 122 | 1 | 0 | 0 | 220 | 99 | 290 | A C |
| ATOM | 866 | NE | ARG | A | 122 | 5.370 | −10.389 | 25.762 | 1.00 | 24.54 | | A N |
| ANISOU | 866 | NE | ARG | A | 122 | 16521 | 10017 | 3336 | −1114 | −402 | 52 | A N |
| SIGUIJ | 866 | NE | ARG | A | 122 | 1 | 0 | 0 | 221 | 61 | 289 | A N |
| ATOM | 867 | CZ | ARG | A | 122 | 5.921 | −11.604 | 25.812 | 1.00 | 25.24 | | A C |
| ANISOU | 867 | CZ | ARG | A | 122 | 19802 | 10702 | 6450 | 339 | −866 | −27 | A C |
| SIGUIJ | 867 | CZ | ARG | A | 122 | 1 | 0 | 0 | 220 | 99 | 290 | A C |
| ATOM | 868 | NH1 | ARG | A | 122 | 6.484 | −12.073 | 26.931 | 1.00 | 26.18 | | A N |
| ANISOU | 868 | NH1 | ARG | A | 122 | 14276 | 11218 | 5120 | 412 | 1934 | 164 | A N |
| SIGUIJ | 868 | NH1 | ARG | A | 122 | 1 | 0 | 0 | 221 | 61 | 289 | A N |
| ATOM | 869 | NH2 | ARG | A | 122 | 5.850 | −12.387 | 24.728 | 1.00 | 25.97 | | A N |
| ANISOU | 869 | NH2 | ARG | A | 122 | 5520 | 10676 | 6376 | 380 | 43 | −11 | A N |
| SIGUIJ | 869 | NH2 | ARG | A | 122 | 1 | 0 | 0 | 221 | 61 | 289 | A N |
| ATOM | 870 | C | ARG | A | 122 | 8.683 | −7.361 | 29.040 | 1.00 | 15.84 | | A C |
| ANISOU | 870 | C | ARG | A | 122 | 1947 | 1450 | 1847 | −377 | 11 | −15 | A C |
| SIGUIJ | 870 | C | ARG | A | 122 | 1 | 0 | 0 | 220 | 99 | 290 | A C |
| ATOM | 871 | O | ARG | A | 122 | 8.602 | −6.251 | 28.425 | 1.00 | 15.65 | | A O |
| ANISOU | 871 | O | ARG | A | 122 | 2349 | 1468 | 1918 | −374 | −36 | 21 | A O |
| SIGUIJ | 871 | O | ARG | A | 122 | 1 | 0 | 0 | 221 | 54 | 289 | A O |
| ATOM | 872 | N | LEU | A | 123 | 9.801 | −8.051 | 29.159 | 1.00 | 15.39 | | A N |
| ANISOU | 872 | N | LEU | A | 123 | 2119 | 1866 | 1765 | −115 | 15 | −5 | A N |
| SIGUIJ | 872 | N | LEU | A | 123 | 1 | 0 | 0 | 221 | 61 | 289 | A N |
| ATOM | 873 | CA | LEU | A | 123 | 11.038 | −7.618 | 28.518 | 1.00 | 15.70 | | A C |
| ANISOU | 873 | CA | LEU | A | 123 | 2100 | 1663 | 1771 | −34 | 16 | −1 | A C |
| SIGUIJ | 873 | CA | LEU | A | 123 | 1 | 0 | 0 | 220 | 99 | 290 | A C |
| ATOM | 874 | CB | LEU | A | 123 | 12.221 | −8.340 | 29.185 | 1.00 | 15.74 | | A C |
| ANISOU | 874 | CB | LEU | A | 123 | 2196 | 1845 | 1826 | 79 | −20 | −4 | A C |
| SIGUIJ | 874 | CB | LEU | A | 123 | 1 | 0 | 0 | 220 | 99 | 290 | A C |
| ATOM | 875 | CG | LEU | A | 123 | 12.488 | −7.891 | 30.640 | 1.00 | 15.65 | | A C |
| ANISOU | 875 | CG | LEU | A | 123 | 2233 | 1901 | 1819 | −18 | −3 | 0 | A C |
| SIGUIJ | 875 | CG | LEU | A | 123 | 1 | 0 | 0 | 220 | 99 | 290 | A C |
| ATOM | 876 | CD1 | LEU | A | 123 | 13.577 | −8.783 | 31.226 | 1.00 | 16.72 | | A C |
| ANISOU | 876 | CD1 | LEU | A | 123 | 3489 | 3126 | 2116 | 1193 | −488 | −401 | A C |
| SIGUIJ | 876 | CD1 | LEU | A | 123 | 1 | 0 | 0 | 220 | 99 | 290 | A C |
| ATOM | 877 | CD2 | LEU | A | 123 | 12.911 | −6.437 | 30.715 | 1.00 | 16.26 | | A C |
| ANISOU | 877 | CD2 | LEU | A | 123 | 2186 | 1902 | 2056 | −19 | −2 | 0 | A C |
| SIGUIJ | 877 | CD2 | LEU | A | 123 | 1 | 0 | 0 | 220 | 99 | 290 | A C |
| ATOM | 878 | C | LEU | A | 123 | 10.950 | −7.937 | 27.023 | 1.00 | 16.09 | | A C |
| ANISOU | 878 | C | LEU | A | 123 | 1925 | 1611 | 1775 | 59 | 8 | 2 | A C |
| SIGUIJ | 878 | C | LEU | A | 123 | 1 | 0 | 0 | 220 | 99 | 290 | A C |
| ATOM | 879 | O | LEU | A | 123 | 10.185 | −8.833 | 26.592 | 1.00 | 16.40 | | A O |
| ANISOU | 879 | O | LEU | A | 123 | 2612 | 2183 | 1779 | −574 | 96 | −66 | A O |
| SIGUIJ | 879 | O | LEU | A | 123 | 1 | 0 | 0 | 221 | 54 | 289 | A O |
| ATOM | 880 | N | PRO | A | 124 | 11.700 | −7.220 | 26.206 | 1.00 | 16.35 | | A N |
| ANISOU | 880 | N | PRO | A | 124 | 1978 | 1672 | 1766 | −4 | −4 | 0 | A N |
| SIGUIJ | 880 | N | PRO | A | 124 | 1 | 0 | 0 | 221 | 61 | 289 | A N |
| ATOM | 881 | CD | PRO | A | 124 | 12.624 | −6.128 | 26.560 | 1.00 | 15.91 | | A C |
| ANISOU | 881 | CD | PRO | A | 124 | 2031 | 1734 | 1615 | −73 | 78 | −16 | A C |
| SIGUIJ | 881 | CD | PRO | A | 124 | 1 | 0 | 0 | 220 | 99 | 290 | A C |
| ATOM | 882 | CA | PRO | A | 124 | 11.586 | −7.385 | 24.754 | 1.00 | 17.20 | | A C |
| ANISOU | 882 | CA | PRO | A | 124 | 2443 | 1676 | 1767 | −42 | −34 | 2 | A C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 882 | CA | PRO | A | 124 | 1 | 0 | 0 | 220 | 98 | 290 | A C |
| ATOM | 883 | CB | PRO | A | 124 | 12.208 | −6.094 | 24.205 | 1.00 | 16.17 | | A C |
| ANISOU | 883 | CB | PRO | A | 124 | 2152 | 1605 | 1773 | 101 | −16 | −4 | A C |
| SIGUIJ | 883 | CB | PRO | A | 124 | 1 | 0 | 0 | 220 | 98 | 290 | A C |
| ATOM | 884 | CG | PRO | A | 124 | 13.248 | −5.750 | 25.256 | 1.00 | 15.99 | | A C |
| ANISOU | 884 | CG | PRO | A | 124 | 2019 | 1617 | 1641 | 84 | 110 | 22 | A C |
| SIGUIJ | 884 | CG | PRO | A | 124 | 1 | 0 | 0 | 220 | 98 | 290 | A C |
| ATOM | 885 | C | PRO | A | 124 | 12.337 | −8.618 | 24.267 | 1.00 | 18.28 | | A C |
| ANISOU | 885 | C | PRO | A | 124 | 3163 | 1858 | 1998 | 300 | 192 | 45 | A C |
| SIGUIJ | 885 | C | PRO | A | 124 | 1 | 0 | 0 | 220 | 98 | 290 | A C |
| ATOM | 886 | O | PRO | A | 124 | 13.386 | −8.981 | 24.829 | 1.00 | 18.87 | | A O |
| ANISOU | 886 | O | PRO | A | 124 | 3346 | 1649 | 2602 | 279 | −159 | −43 | A O |
| SIGUIJ | 886 | O | PRO | A | 124 | 1 | 0 | 0 | 221 | 54 | 289 | A O |
| ATOM | 887 | N | SER | A | 125 | 11.791 | −9.243 | 23.222 | 1.00 | 19.66 | | A N |
| ANISOU | 887 | N | SER | A | 125 | 3843 | 2018 | 2171 | 175 | −77 | −8 | A N |
| SIGUIJ | 887 | N | SER | A | 125 | 1 | 0 | 0 | 221 | 61 | 289 | A N |
| ATOM | 888 | CA | SER | A | 125 | 12.571 | −10.203 | 22.419 | 1.00 | 20.69 | | A C |
| ANISOU | 888 | CA | SER | A | 125 | 4056 | 1869 | 2511 | 35 | 286 | 9 | A C |
| SIGUIJ | 888 | CA | SER | A | 125 | 1 | 0 | 0 | 220 | 98 | 290 | A C |
| ATOM | 889 | CB | SER | A | 125 | 11.778 | −11.476 | 22.152 | 1.00 | 21.47 | | A C |
| ANISOU | 889 | CB | SER | A | 125 | 5812 | 2535 | 3271 | −1022 | 117 | −40 | A C |
| SIGUIJ | 889 | CB | SER | A | 125 | 1 | 0 | 0 | 220 | 98 | 290 | A C |
| ATOM | 890 | OG | SER | A | 125 | 10.598 | −11.193 | 21.456 | 1.00 | 23.27 | | A O |
| ANISOU | 890 | OG | SER | A | 125 | 6259 | 3583 | 4621 | −942 | −609 | 247 | A O |
| SIGUIJ | 890 | OG | SER | A | 125 | 1 | 0 | 0 | 221 | 54 | 289 | A O |
| ATOM | 891 | C | SER | A | 125 | 13.076 | −9.643 | 21.077 | 1.00 | 20.70 | | A C |
| ANISOU | 891 | C | SER | A | 125 | 4813 | 1956 | 2566 | −188 | 474 | −34 | A C |
| SIGUIJ | 891 | C | SER | A | 125 | 1 | 0 | 0 | 220 | 98 | 290 | A C |
| ATOM | 892 | O | SER | A | 125 | 13.944 | −10.244 | 20.430 | 1.00 | 21.30 | | A O |
| ANISOU | 892 | O | SER | A | 125 | 4931 | 1911 | 2914 | −268 | 699 | −84 | A O |
| SIGUIJ | 892 | O | SER | A | 125 | 1 | 0 | 0 | 221 | 54 | 289 | A O |
| ATOM | 893 | N | ARG | A | 128 | 12.552 | −8.492 | 20.667 | 1.00 | 20.62 | | A N |
| ANISOU | 893 | N | ARG | A | 128 | 4284 | 1853 | 2191 | −355 | 662 | −99 | A N |
| SIGUIJ | 893 | N | ARG | A | 128 | 1 | 0 | 0 | 221 | 61 | 289 | A N |
| ATOM | 894 | CA | ARG | A | 128 | 13.031 | −7.806 | 19.477 | 1.00 | 20.32 | | A C |
| ANISOU | 894 | CA | ARG | A | 128 | 3194 | 1797 | 2110 | −112 | 365 | −34 | A C |
| SIGUIJ | 894 | CA | ARG | A | 128 | 1 | 0 | 0 | 220 | 98 | 290 | A C |
| ATOM | 895 | CB | ARG | A | 128 | 12.083 | −8.091 | 18.318 | 1.00 | 21.53 | | A C |
| ANISOU | 895 | CB | ARG | A | 128 | 4473 | 2586 | 2833 | −575 | −573 | 171 | A C |
| SIGUIJ | 895 | CB | ARG | A | 128 | 1 | 0 | 0 | 220 | 98 | 290 | A C |
| ATOM | 896 | CG | ARG | A | 128 | 11.995 | −9.586 | 17.993 | 1.00 | 23.54 | | A C |
| ANISOU | 896 | CG | ARG | A | 128 | 15334 | 2629 | 3423 | −1034 | −1494 | 123 | A C |
| SIGUIJ | 896 | CG | ARG | A | 128 | 1 | 0 | 0 | 220 | 98 | 290 | A C |
| ATOM | 897 | CD | ARG | A | 128 | 10.802 | −9.845 | 17.097 | 1.00 | 24.98 | | A C |
| ANISOU | 897 | CD | ARG | A | 128 | 18087 | 12399 | 6545 | −4248 | −4147 | 1621 | A C |
| SIGUIJ | 897 | CD | ARG | A | 128 | 1 | 0 | 0 | 220 | 97 | 290 | A C |
| ATOM | 898 | NE | ARG | A | 128 | 10.637 | −8.686 | 16.229 | 1.00 | 26.43 | | A N |
| ANISOU | 898 | NE | ARG | A | 128 | 19357 | 11868 | 3343 | 286 | 1652 | 51 | A N |
| SIGUIJ | 898 | NE | ARG | A | 128 | 1 | 0 | 0 | 221 | 61 | 289 | A N |
| ATOM | 899 | CZ | ARG | A | 128 | 11.441 | −8.423 | 15.203 | 1.00 | 26.81 | | A C |
| ANISOU | 899 | CZ | ARG | A | 128 | 16526 | 8558 | 1782 | 1274 | −336 | −33 | A C |
| SIGUIJ | 899 | CZ | ARG | A | 128 | 1 | 0 | 0 | 220 | 97 | 290 | A C |
| ATOM | 900 | NH1 | ARG | A | 128 | 12.441 | −9.269 | 14.965 | 1.00 | 27.32 | | A N |
| ANISOU | 900 | NH1 | ARG | A | 128 | 16054 | 7639 | 4806 | 508 | 437 | 23 | A N |
| SIGUIJ | 900 | NH1 | ARG | A | 128 | 1 | 0 | 0 | 221 | 61 | 289 | A N |
| ATOM | 901 | NH2 | ARG | A | 128 | 11.249 | −7.338 | 14.434 | 1.00 | 26.86 | | A N |
| ANISOU | 901 | NH2 | ARG | A | 128 | 4057 | 8229 | 1749 | −729 | −40 | 3 | A N |
| SIGUIJ | 901 | NH2 | ARG | A | 128 | 1 | 0 | 0 | 221 | 61 | 289 | A N |
| ATOM | 902 | C | ARG | A | 128 | 13.053 | −6.304 | 19.747 | 1.00 | 19.30 | | A C |
| ANISOU | 902 | C | ARG | A | 128 | 2695 | 1789 | 1719 | −36 | 33 | −1 | A C |
| SIGUIJ | 902 | C | ARG | A | 128 | 1 | 0 | 0 | 220 | 97 | 290 | A C |
| ATOM | 903 | O | ARG | A | 128 | 12.416 | −5.831 | 20.708 | 1.00 | 19.07 | | A O |
| ANISOU | 903 | O | ARG | A | 128 | 2890 | 2004 | 1722 | 150 | 62 | 9 | A O |
| SIGUIJ | 903 | O | ARG | A | 128 | 1 | 0 | 0 | 221 | 54 | 289 | A O |
| ATOM | 904 | N | CYS | A | 129 | 13.757 | −5.588 | 18.894 | 1.00 | 18.42 | | A N |
| ANISOU | 904 | N | CYS | A | 129 | 2557 | 1768 | 1672 | 7 | −39 | 0 | A N |
| SIGUIJ | 904 | N | CYS | A | 129 | 1 | 0 | 0 | 221 | 61 | 289 | A N |
| ATOM | 905 | CA | CYS | A | 129 | 13.825 | −4.124 | 18.956 | 1.00 | 17.61 | | A C |
| ANISOU | 905 | CA | CYS | A | 129 | 2220 | 1775 | 1665 | 23 | −62 | −3 | A C |
| SIGUIJ | 905 | CA | CYS | A | 129 | 1 | 0 | 0 | 220 | 97 | 290 | A C |
| ATOM | 906 | C | CYS | A | 129 | 12.751 | −3.513 | 18.078 | 1.00 | 17.14 | | A C |
| ANISOU | 906 | C | CYS | A | 129 | 2128 | 1964 | 1479 | 75 | 88 | 28 | A C |
| SIGUIJ | 906 | C | CYS | A | 129 | 1 | 0 | 0 | 220 | 97 | 290 | A C |
| ATOM | 907 | O | CYS | A | 129 | 12.690 | −3.773 | 16.860 | 1.00 | 17.35 | | A O |
| ANISOU | 907 | O | CYS | A | 129 | 2814 | 2211 | 1492 | 197 | 16 | 3 | A O |
| SIGUIJ | 907 | O | CYS | A | 129 | 1 | 0 | 0 | 221 | 54 | 289 | A O |
| ATOM | 908 | CB | CYS | A | 129 | 15.170 | −3.684 | 18.428 | 1.00 | 17.49 | | A C |
| ANISOU | 908 | CB | CYS | A | 129 | 2202 | 1672 | 1772 | 57 | −59 | −7 | A C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 908 | CB  | CYS | A | 129 | 1      | 0      | 0      | 220 | 97   | 290  | A | C |
| ATOM   | 909 | SG  | CYS | A | 129 | 16.567 | −4.357 | 19.370 | 1.00 | 17.33 |     | A | S |
| ANISOU | 909 | SG  | CYS | A | 129 | 2527   | 2258   | 1937   | 480 | −253 | −185 | A | S |
| SIGUIJ | 909 | SG  | CYS | A | 129 | 1      | 0      | 0      | 221 | 48   | 289  | A | S |
| ATOM   | 910 | N   | GLU | A | 130 | 11.875 | −2.719 | 18.655 | 1.00 | 16.42 |     | A | N |
| ANISOU | 910 | N   | GLU | A | 130 | 1991   | 1922   | 1399   | −6  | 22   | −1   | A | N |
| SIGUIJ | 910 | N   | GLU | A | 130 | 1      | 0      | 0      | 221 | 61   | 289  | A | N |
| ATOM   | 911 | CA  | GLU | A | 130 | 10.879 | −2.008 | 17.822 | 1.00 | 16.19 |     | A | C |
| ANISOU | 911 | CA  | GLU | A | 130 | 2000   | 1988   | 1415   | −1  | −3   | 0    | A | C |
| SIGUIJ | 911 | CA  | GLU | A | 130 | 1      | 0      | 0      | 220 | 97   | 290  | A | C |
| ATOM   | 912 | CB  | GLU | A | 130 | 9.741  | −1.429 | 18.687 | 1.00 | 16.86 |     | A | C |
| ANISOU | 912 | CB  | GLU | A | 130 | 2205   | 2773   | 1438   | 392 | 14   | 2    | A | C |
| SIGUIJ | 912 | CB  | GLU | A | 130 | 1      | 0      | 0      | 220 | 97   | 290  | A | C |
| ATOM   | 913 | CG  | GLU | A | 130 | 8.808  | −2.483 | 19.317 | 1.00 | 19.01 |     | A | C |
| ANISOU | 913 | CG  | GLU | A | 130 | 2557   | 3102   | 1342   | 33  | −56  | −6   | A | C |
| SIGUIJ | 913 | CG  | GLU | A | 130 | 1      | 0      | 0      | 220 | 97   | 290  | A | C |
| ATOM   | 914 | CD  | GLU | A | 130 | 7.994  | −3.328 | 18.339 | 1.00 | 19.91 |     | A | C |
| ANISOU | 914 | CD  | GLU | A | 130 | 3068   | 3337   | 1719   | −65 | −404 | −104 | A | C |
| SIGUIJ | 914 | CD  | GLU | A | 130 | 1      | 0      | 0      | 220 | 97   | 290  | A | C |
| ATOM   | 915 | OE1 | GLU | A | 130 | 7.833  | −2.865 | 17.179 | 1.00 | 20.94 |     | A | O |
| ANISOU | 915 | OE1 | GLU | A | 130 | 2710   | 3803   | 1799   | −221 | −414 | 82  | A | O |
| SIGUIJ | 915 | OE1 | GLU | A | 130 | 1      | 0      | 0      | 221 | 54   | 289  | A | O |
| ATOM   | 916 | OE2 | GLU | A | 130 | 7.530  | −4.438 | 18.743 | 1.00 | 21.75 |     | A | O |
| ANISOU | 916 | OE2 | GLU | A | 130 | 4740   | 3706   | 2415   | −733 | −335 | 139 | A | O |
| SIGUIJ | 916 | OE2 | GLU | A | 130 | 1      | 0      | 0      | 221 | 54   | 289  | A | O |
| ATOM   | 917 | C   | GLU | A | 130 | 11.549 | −0.890 | 17.037 | 1.00 | 15.24 |     | A | C |
| ANISOU | 917 | C   | GLU | A | 130 | 1918   | 1991   | 1348   | 10  | −50  | 3    | A | C |
| SIGUIJ | 917 | C   | GLU | A | 130 | 1      | 0      | 0      | 220 | 96   | 290  | A | C |
| ATOM   | 918 | O   | GLU | A | 130 | 12.429 | −0.227 | 17.555 | 1.00 | 15.46 |     | A | O |
| ANISOU | 918 | O   | GLU | A | 130 | 1999   | 2010   | 1554   | 0   | −184 | 11   | A | O |
| SIGUIJ | 918 | O   | GLU | A | 130 | 1      | 0      | 0      | 221 | 54   | 289  | A | O |
| ATOM   | 919 | N   | PRO | A | 131 | 11.143 | −0.677 | 15.749 | 1.00 | 14.49 |     | A | N |
| ANISOU | 919 | N   | PRO | A | 131 | 1826   | 2049   | 1323   | 37  | −4   | 0    | A | N |
| SIGUIJ | 919 | N   | PRO | A | 131 | 1      | 0      | 0      | 221 | 61   | 289  | A | N |
| ATOM   | 920 | CD  | PRO | A | 131 | 10.218 | −1.515 | 14.966 | 1.00 | 14.56 |     | A | C |
| ANISOU | 920 | CD  | PRO | A | 131 | 1943   | 2110   | 1393   | −15 | −84  | −2   | A | C |
| SIGUIJ | 920 | CD  | PRO | A | 131 | 1      | 0      | 0      | 220 | 96   | 290  | A | C |
| ATOM   | 921 | CA  | PRO | A | 131 | 11.842 | 0.294  | 14.898 | 1.00 | 13.90 |     | A | C |
| ANISOU | 921 | CA  | PRO | A | 131 | 1928   | 2069   | 1341   | 14  | 47   | −3   | A | C |
| SIGUIJ | 921 | CA  | PRO | A | 131 | 1      | 0      | 0      | 220 | 96   | 290  | A | C |
| ATOM   | 922 | CB  | PRO | A | 131 | 11.461 | −0.116 | 13.495 | 1.00 | 14.54 |     | A | C |
| ANISOU | 922 | CB  | PRO | A | 131 | 2366   | 1951   | 1375   | 130 | −87  | −18  | A | C |
| SIGUIJ | 922 | CB  | PRO | A | 131 | 1      | 0      | 0      | 220 | 96   | 290  | A | C |
| ATOM   | 923 | CG  | PRO | A | 131 | 10.119 | −0.726 | 13.664 | 1.00 | 14.36 |     | A | C |
| ANISOU | 923 | CG  | PRO | A | 131 | 2401   | 2105   | 1378   | 58  | −81  | −11  | A | C |
| SIGUIJ | 923 | CG  | PRO | A | 131 | 1      | 0      | 0      | 220 | 96   | 290  | A | C |
| ATOM   | 924 | C   | PRO | A | 131 | 11.405 | 1.728  | 15.135 | 1.00 | 13.68 |     | A | C |
| ANISOU | 924 | C   | PRO | A | 131 | 1793   | 2075   | 1235   | 7   | −59  | −1   | A | C |
| SIGUIJ | 924 | C   | PRO | A | 131 | 1      | 0      | 0      | 220 | 96   | 290  | A | C |
| ATOM   | 925 | O   | PRO | A | 131 | 10.293 | 1.971  | 15.604 | 1.00 | 13.49 |     | A | O |
| ANISOU | 925 | O   | PRO | A | 131 | 1786   | 2141   | 1185   | 17  | −73  | −7   | A | O |
| SIGUIJ | 925 | O   | PRO | A | 131 | 1      | 0      | 0      | 221 | 54   | 289  | A | O |
| ATOM   | 926 | N   | PRO | A | 132 | 12.236 | 2.678  | 14.727 | 1.00 | 13.65 |     | A | N |
| ANISOU | 926 | N   | PRO | A | 132 | 1761   | 2065   | 1241   | 31  | −62  | 1    | A | N |
| SIGUIJ | 926 | N   | PRO | A | 132 | 1      | 0      | 0      | 221 | 61   | 289  | A | N |
| ATOM   | 927 | CD  | PRO | A | 132 | 13.662 | 2.507  | 14.308 | 1.00 | 13.98 |     | A | C |
| ANISOU | 927 | CD  | PRO | A | 132 | 1800   | 2434   | 1629   | 75  | 49   | 2    | A | C |
| SIGUIJ | 927 | CD  | PRO | A | 132 | 1      | 0      | 0      | 220 | 96   | 290  | A | C |
| ATOM   | 928 | CA  | PRO | A | 132 | 11.820 | 4.055  | 14.586 | 1.00 | 13.24 |     | A | C |
| ANISOU | 928 | CA  | PRO | A | 132 | 1713   | 2054   | 1338   | 9   | −165 | −9   | A | C |
| SIGUIJ | 928 | CA  | PRO | A | 132 | 1      | 0      | 0      | 220 | 96   | 290  | A | C |
| ATOM   | 929 | CB  | PRO | A | 132 | 12.975 | 4.692  | 13.777 | 1.00 | 13.98 |     | A | C |
| ANISOU | 929 | CB  | PRO | A | 132 | 1910   | 2297   | 1630   | −115 | 22  | −1   | A | C |
| SIGUIJ | 929 | CB  | PRO | A | 132 | 1      | 0      | 0      | 220 | 96   | 290  | A | C |
| ATOM   | 930 | CG  | PRO | A | 132 | 14.175 | 3.851  | 14.183 | 1.00 | 13.59 |     | A | C |
| ANISOU | 930 | CG  | PRO | A | 132 | 1983   | 2462   | 1533   | 0   | 47   | −1   | A | C |
| SIGUIJ | 930 | CG  | PRO | A | 132 | 1      | 0      | 0      | 220 | 96   | 290  | A | C |
| ATOM   | 931 | C   | PRO | A | 132 | 10.480 | 4.149  | 13.876 | 1.00 | 13.22 |     | A | C |
| ANISOU | 931 | C   | PRO | A | 132 | 1672   | 1663   | 1185   | 0   | −83  | −1   | A | C |
| SIGUIJ | 931 | C   | PRO | A | 132 | 1      | 0      | 0      | 220 | 95   | 290  | A | C |
| ATOM   | 932 | O   | PRO | A | 132 | 10.202 | 3.377  | 12.911 | 1.00 | 12.65 |     | A | O |
| ANISOU | 932 | O   | PRO | A | 132 | 1839   | 1675   | 1185   | −16 | −117 | 3    | A | O |
| SIGUIJ | 932 | O   | PRO | A | 132 | 1      | 0      | 0      | 221 | 54   | 289  | A | O |
| ATOM   | 933 | N   | GLY | A | 133 | 9.649  | 5.097  | 14.310 | 1.00 | 12.65 |     | A | N |
| ANISOU | 933 | N   | GLY | A | 133 | 1647   | 1646   | 1150   | 0   | −123 | −6   | A | N |
| SIGUIJ | 933 | N   | GLY | A | 133 | 1      | 0      | 0      | 221 | 61   | 289  | A | N |
| ATOM   | 934 | CA  | GLY | A | 133 | 8.320  | 5.258  | 13.755 | 1.00 | 12.67 |     | A | C |
| ANISOU | 934 | CA  | GLY | A | 133 | 1649   | 1779   | 1108   | 20  | −106 | 8    | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 934 | CA | GLY | A | 133 | 1 | 0 | 0 | 220 | 95 | 290 | A | C |
| ATOM | 935 | C | GLY | A | 133 | 7.225 | 4.581 | 14.547 | 1.00 | 12.73 | | A | C |
| ANISOU | 935 | C | GLY | A | 133 | 1724 | 1811 | 1198 | −9 | −33 | −1 | A | C |
| SIGUIJ | 935 | C | GLY | A | 133 | 1 | 0 | 0 | 220 | 95 | 290 | A | C |
| ATOM | 936 | O | GLY | A | 133 | 6.042 | 4.877 | 14.319 | 1.00 | 13.38 | | A | O |
| ANISOU | 936 | O | GLY | A | 133 | 1756 | 2135 | 1334 | 80 | −53 | −1 | A | O |
| SIGUIJ | 936 | O | GLY | A | 133 | 1 | 0 | 0 | 221 | 54 | 289 | A | O |
| ATOM | 937 | N | THR | A | 134 | 7.600 | 3.704 | 15.477 | 1.00 | 13.30 | | A | N |
| ANISOU | 937 | N | THR | A | 134 | 1756 | 1820 | 1198 | −2 | −27 | −1 | A | N |
| SIGUIJ | 937 | N | THR | A | 134 | 1 | 0 | 0 | 221 | 61 | 289 | A | N |
| ATOM | 938 | CA | THR | A | 134 | 6.617 | 3.030 | 16.301 | 1.00 | 13.30 | | A | C |
| ANISOU | 938 | CA | THR | A | 134 | 1731 | 1806 | 1200 | 3 | −37 | 1 | A | C |
| SIGUIJ | 938 | CA | THR | A | 134 | 1 | 0 | 0 | 220 | 95 | 290 | A | C |
| ATOM | 939 | CB | THR | A | 134 | 7.235 | 1.798 | 16.938 | 1.00 | 13.36 | | A | C |
| ANISOU | 939 | CB | THR | A | 134 | 1759 | 1787 | 1244 | −6 | −84 | −12 | A | C |
| SIGUIJ | 939 | CB | THR | A | 134 | 1 | 0 | 0 | 220 | 95 | 290 | A | C |
| ATOM | 940 | OG1 | THR | A | 134 | 7.779 | 0.970 | 15.916 | 1.00 | 13.52 | | A | O |
| ANISOU | 940 | OG1 | THR | A | 134 | 2156 | 1751 | 1418 | −86 | 199 | −33 | A | O |
| SIGUIJ | 940 | OG1 | THR | A | 134 | 1 | 0 | 0 | 221 | 54 | 289 | A | O |
| ATOM | 941 | CG2 | THR | A | 134 | 6.197 | 0.987 | 17.718 | 1.00 | 14.12 | | A | C |
| ANISOU | 941 | CG2 | THR | A | 134 | 2547 | 2022 | 1879 | −383 | 580 | −260 | A | C |
| SIGUIJ | 941 | CG2 | THR | A | 134 | 1 | 0 | 0 | 220 | 95 | 290 | A | C |
| ATOM | 942 | C | THR | A | 134 | 6.095 | 3.992 | 17.394 | 1.00 | 13.61 | | A | C |
| ANISOU | 942 | C | THR | A | 134 | 1677 | 1805 | 1200 | −4 | −46 | −1 | A | C |
| SIGUIJ | 942 | C | THR | A | 134 | 1 | 0 | 0 | 220 | 95 | 290 | A | C |
| ATOM | 943 | O | THR | A | 134 | 6.886 | 4.678 | 18.065 | 1.00 | 12.95 | | A | O |
| ANISOU | 943 | O | THR | A | 134 | 1695 | 1805 | 1240 | −11 | −73 | −6 | A | O |
| SIGUIJ | 943 | O | THR | A | 134 | 1 | 0 | 0 | 221 | 54 | 289 | A | O |
| ATOM | 944 | N | THR | A | 135 | 4.776 | 4.050 | 17.591 | 1.00 | 13.92 | | A | N |
| ANISOU | 944 | N | THR | A | 135 | 1678 | 2130 | 1187 | 2 | −57 | −5 | A | N |
| SIGUIJ | 944 | N | THR | A | 135 | 1 | 0 | 0 | 221 | 61 | 289 | A | N |
| ATOM | 945 | CA | THR | A | 135 | 4.168 | 4.738 | 18.736 | 1.00 | 14.83 | | A | C |
| ANISOU | 945 | CA | THR | A | 135 | 1958 | 2083 | 1256 | −16 | 104 | 9 | A | C |
| SIGUIJ | 945 | CA | THR | A | 135 | 1 | 0 | 0 | 220 | 95 | 290 | A | C |
| ATOM | 946 | CB | THR | A | 135 | 2.654 | 4.998 | 18.466 | 1.00 | 15.90 | | A | C |
| ANISOU | 946 | CB | THR | A | 135 | 2026 | 3624 | 1838 | 264 | −17 | −14 | A | C |
| SIGUIJ | 946 | CB | THR | A | 135 | 1 | 0 | 0 | 220 | 95 | 290 | A | C |
| ATOM | 947 | OG1 | THR | A | 135 | 2.510 | 5.931 | 17.384 | 1.00 | 18.22 | | A | O |
| ANISOU | 947 | OG1 | THR | A | 135 | 3170 | 3640 | 1940 | −12 | −413 | 38 | A | O |
| SIGUIJ | 947 | OG1 | THR | A | 135 | 1 | 0 | 0 | 221 | 54 | 289 | A | O |
| ATOM | 948 | CG2 | THR | A | 135 | 1.994 | 5.573 | 19.688 | 1.00 | 17.09 | | A | C |
| ANISOU | 948 | CG2 | THR | A | 135 | 2150 | 3585 | 1851 | 292 | 31 | 13 | A | C |
| SIGUIJ | 948 | CG2 | THR | A | 135 | 1 | 0 | 0 | 220 | 95 | 290 | A | C |
| ATOM | 949 | C | THR | A | 135 | 4.320 | 3.966 | 20.031 | 1.00 | 14.33 | | A | C |
| ANISOU | 949 | C | THR | A | 135 | 1624 | 1974 | 1241 | −200 | 52 | −19 | A | C |
| SIGUIJ | 949 | C | THR | A | 135 | 1 | 0 | 0 | 220 | 95 | 290 | A | C |
| ATOM | 950 | O | THR | A | 135 | 4.113 | 2.746 | 20.078 | 1.00 | 14.51 | | A | O |
| ANISOU | 950 | O | THR | A | 135 | 2619 | 2002 | 1444 | −383 | 77 | −31 | A | O |
| SIGUIJ | 950 | O | THR | A | 135 | 1 | 0 | 0 | 221 | 54 | 289 | A | O |
| ATOM | 951 | N | CYS | A | 136 | 4.776 | 4.666 | 21.062 | 1.00 | 13.59 | | A | N |
| ANISOU | 951 | N | CYS | A | 136 | 1558 | 1773 | 1249 | −12 | −20 | −1 | A | N |
| SIGUIJ | 951 | N | CYS | A | 136 | 1 | 0 | 0 | 221 | 61 | 289 | A | N |
| ATOM | 952 | CA | CYS | A | 136 | 5.015 | 4.065 | 22.378 | 1.00 | 13.33 | | A | C |
| ANISOU | 952 | CA | CYS | A | 136 | 1554 | 1725 | 1237 | 101 | 28 | −5 | A | C |
| SIGUIJ | 952 | CA | CYS | A | 136 | 1 | 0 | 0 | 220 | 94 | 290 | A | C |
| ATOM | 953 | C | CYS | A | 136 | 4.471 | 4.964 | 23.473 | 1.00 | 12.46 | | A | C |
| ANISOU | 953 | C | CYS | A | 136 | 1464 | 1601 | 1229 | 0 | 37 | 2 | A | C |
| SIGUIJ | 953 | C | CYS | A | 136 | 1 | 0 | 0 | 220 | 94 | 290 | A | C |
| ATOM | 954 | O | CYS | A | 136 | 4.032 | 6.090 | 23.209 | 1.00 | 12.45 | | A | O |
| ANISOU | 954 | O | CYS | A | 136 | 1879 | 1656 | 1331 | 157 | 112 | 44 | A | O |
| SIGUIJ | 954 | O | CYS | A | 136 | 1 | 0 | 0 | 221 | 54 | 289 | A | O |
| ATOM | 955 | CB | CYS | A | 136 | 6.509 | 3.869 | 22.590 | 1.00 | 14.29 | | A | C |
| ANISOU | 955 | CB | CYS | A | 136 | 1573 | 2489 | 1431 | 233 | 0 | 0 | A | C |
| SIGUIJ | 955 | CB | CYS | A | 136 | 1 | 0 | 0 | 220 | 94 | 290 | A | C |
| ATOM | 956 | SG | CYS | A | 136 | 7.367 | 3.000 | 21.237 | 1.00 | 16.81 | | A | S |
| ANISOU | 956 | SG | CYS | A | 136 | 2525 | 2969 | 1554 | 833 | 250 | 66 | A | S |
| SIGUIJ | 956 | SG | CYS | A | 136 | 1 | 0 | 0 | 221 | 48 | 289 | A | S |
| ATOM | 957 | N | THR | A | 137 | 4.529 | 4.464 | 24.723 | 1.00 | 11.20 | | A | N |
| ANISOU | 957 | N | THR | A | 137 | 1477 | 1553 | 1216 | −9 | 18 | 1 | A | N |
| SIGUIJ | 957 | N | THR | A | 137 | 1 | 0 | 0 | 221 | 61 | 289 | A | N |
| ATOM | 958 | CA | THR | A | 137 | 4.042 | 5.275 | 25.863 | 1.00 | 11.13 | | A | C |
| ANISOU | 958 | CA | THR | A | 137 | 1388 | 1566 | 1178 | −4 | −44 | −4 | A | C |
| SIGUIJ | 958 | CA | THR | A | 137 | 1 | 0 | 0 | 220 | 94 | 290 | A | C |
| ATOM | 959 | CB | THR | A | 137 | 2.808 | 4.631 | 26.475 | 1.00 | 11.38 | | A | C |
| ANISOU | 959 | CB | THR | A | 137 | 1492 | 1805 | 1290 | −120 | 28 | −6 | A | C |
| SIGUIJ | 959 | CB | THR | A | 137 | 1 | 0 | 0 | 220 | 94 | 290 | A | C |
| ATOM | 960 | OG1 | THR | A | 137 | 1.772 | 4.518 | 25.474 | 1.00 | 12.96 | | A | O |
| ANISOU | 960 | OG1 | THR | A | 137 | 1690 | 2319 | 1457 | −189 | −148 | 9 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 960 | OG1 | THR | A | 137 | 1 | 0 | 0 | 221 | 54 | 289 | A | O |
| ATOM | 961 | CG2 | THR | A | 137 | 2.294 | 5.460 | 27.644 | 1.00 | 12.06 | | A | C |
| ANISOU | 961 | CG2 | THR | A | 137 | 1591 | 1848 | 1280 | −27 | 3 | 0 | A | C |
| SIGUIJ | 961 | CG2 | THR | A | 137 | 1 | 0 | 0 | 220 | 94 | 290 | A | C |
| ATOM | 962 | C | THR | A | 137 | 5.114 | 5.316 | 26.922 | 1.00 | 10.72 | | A | C |
| ANISOU | 962 | C | THR | A | 137 | 1358 | 1288 | 1131 | −10 | −4 | 0 | A | C |
| SIGUIJ | 962 | C | THR | A | 137 | 1 | 0 | 0 | 220 | 94 | 290 | A | C |
| ATOM | 963 | O | THR | A | 137 | 5.701 | 4.302 | 27.259 | 1.00 | 10.60 | | A | O |
| ANISOU | 963 | O | THR | A | 137 | 1439 | 1299 | 1274 | 23 | −53 | −8 | A | O |
| SIGUIJ | 963 | O | THR | A | 137 | 1 | 0 | 0 | 221 | 54 | 289 | A | O |
| ATOM | 964 | N | AVAL | A | 138 | 5.393 | 6.508 | 27.426 | 0.50 | 10.12 | | A | N |
| ANISOU | 964 | N | AVAL | A | 138 | 1211 | 1281 | 1094 | 8 | −3 | 0 | A | N |
| SIGUIJ | 964 | N | AVAL | A | 138 | 1 | 0 | 0 | 221 | 60 | 289 | A | N |
| ATOM | 965 | N | BVAL | A | 138 | 5.385 | 6.512 | 27.428 | 0.50 | 12.31 | | A | N |
| ANISOU | 965 | N | BVAL | A | 138 | 1443 | 1286 | 1103 | −4 | −40 | 1 | A | N |
| SIGUIJ | 965 | N | BVAL | A | 138 | 1 | 0 | 0 | 221 | 60 | 289 | A | N |
| ATOM | 966 | CA | AVAL | A | 138 | 6.324 | 6.704 | 28.549 | 0.50 | 10.10 | | A | C |
| ANISOU | 966 | CA | AVAL | A | 138 | 1182 | 1254 | 1073 | 6 | 9 | 0 | A | C |
| SIGUIJ | 966 | CA | AVAL | A | 138 | 1 | 0 | 0 | 220 | 94 | 290 | A | C |
| ATOM | 967 | CA | BVAL | A | 138 | 6.312 | 6.716 | 28.551 | 0.50 | 12.29 | | A | C |
| ANISOU | 967 | CA | BVAL | A | 138 | 1531 | 1444 | 1157 | 15 | −118 | −14 | A | C |
| SIGUIJ | 967 | CA | BVAL | A | 138 | 1 | 0 | 0 | 220 | 94 | 290 | A | C |
| ATOM | 968 | CB | AVAL | A | 138 | 7.508 | 7.655 | 28.165 | 0.50 | 10.53 | | A | C |
| ANISOU | 968 | CB | AVAL | A | 138 | 1183 | 1243 | 957 | 10 | −16 | 1 | A | C |
| SIGUIJ | 968 | CB | AVAL | A | 138 | 1 | 0 | 0 | 220 | 94 | 290 | A | C |
| ATOM | 969 | CB | BVAL | A | 138 | 7.386 | 7.752 | 28.218 | 0.50 | 12.72 | | A | C |
| ANISOU | 969 | CB | BVAL | A | 138 | 1606 | 1489 | 1617 | −11 | 0 | 0 | A | C |
| SIGUIJ | 969 | CB | BVAL | A | 138 | 1 | 0 | 0 | 220 | 94 | 290 | A | C |
| ATOM | 970 | CG1 | AVAL | A | 138 | 7.015 | 9.028 | 27.740 | 0.50 | 12.13 | | A | C |
| ANISOU | 970 | CG1 | AVAL | A | 138 | 842 | 1196 | 916 | −110 | −4 | −3 | A | C |
| SIGUIJ | 970 | CG1 | AVAL | A | 138 | 1 | 0 | 0 | 220 | 93 | 290 | A | C |
| ATOM | 971 | CG1 | BVAL | A | 138 | 8.402 | 7.849 | 29.353 | 0.50 | 14.32 | | A | C |
| ANISOU | 971 | CG1 | BVAL | A | 138 | 1610 | 1933 | 1620 | −51 | 0 | 0 | A | C |
| SIGUIJ | 971 | CG1 | BVAL | A | 138 | 1 | 0 | 0 | 220 | 93 | 290 | A | C |
| ATOM | 972 | CG2 | AVAL | A | 138 | 8.490 | 7.746 | 29.329 | 0.50 | 11.37 | | A | C |
| ANISOU | 972 | CG2 | AVAL | A | 138 | 1172 | 1688 | 941 | −47 | 5 | 0 | A | C |
| SIGUIJ | 972 | CG2 | AVAL | A | 138 | 1 | 0 | 0 | 220 | 93 | 290 | A | C |
| ATOM | 973 | CG2 | BVAL | A | 138 | 8.073 | 7.365 | 26.963 | 0.50 | 13.56 | | A | C |
| ANISOU | 973 | CG2 | BVAL | A | 138 | 1626 | 1632 | 1622 | 1 | 0 | 0 | A | C |
| SIGUIJ | 973 | CG2 | BVAL | A | 138 | 1 | 0 | 0 | 220 | 93 | 290 | A | C |
| ATOM | 974 | C | AVAL | A | 138 | 5.531 | 7.206 | 29.743 | 0.50 | 9.50 | | A | C |
| ANISOU | 974 | C | AVAL | A | 138 | 1136 | 1216 | 1080 | −7 | 6 | 0 | A | C |
| SIGUIJ | 974 | C | AVAL | A | 138 | 1 | 0 | 0 | 220 | 93 | 290 | A | C |
| ATOM | 975 | C | BVAL | A | 138 | 5.507 | 7.183 | 29.746 | 0.50 | 11.69 | | A | C |
| ANISOU | 975 | C | BVAL | A | 138 | 1477 | 1210 | 1138 | −57 | −117 | 21 | A | C |
| SIGUIJ | 975 | C | BVAL | A | 138 | 1 | 0 | 0 | 220 | 93 | 290 | A | C |
| ATOM | 976 | O | AVAL | A | 138 | 4.578 | 7.983 | 29.589 | 0.50 | 9.79 | | A | O |
| ANISOU | 976 | O | AVAL | A | 138 | 1151 | 1246 | 1524 | 11 | −36 | 3 | A | O |
| SIGUIJ | 976 | O | AVAL | A | 138 | 1 | 0 | 0 | 221 | 54 | 289 | A | O |
| ATOM | 977 | O | BVAL | A | 138 | 4.527 | 7.927 | 29.600 | 0.50 | 11.98 | | A | O |
| ANISOU | 977 | O | BVAL | A | 138 | 1549 | 1334 | 1002 | 40 | −111 | −13 | A | O |
| SIGUIJ | 977 | O | BVAL | A | 138 | 1 | 0 | 0 | 221 | 54 | 289 | A | O |
| ATOM | 978 | N | SER | A | 139 | 5.937 | 6.742 | 30.928 | 1.00 | 9.56 | | A | N |
| ANISOU | 978 | N | SER | A | 139 | 1291 | 1221 | 1099 | −1 | −38 | 0 | A | N |
| SIGUIJ | 978 | N | SER | A | 139 | 1 | 0 | 0 | 221 | 60 | 289 | A | N |
| ATOM | 979 | CA | SER | A | 139 | 5.170 | 7.005 | 32.131 | 1.00 | 9.54 | | A | C |
| ANISOU | 979 | CA | SER | A | 139 | 1324 | 1237 | 1118 | 8 | −24 | −2 | A | C |
| SIGUIJ | 979 | CA | SER | A | 139 | 1 | 0 | 0 | 220 | 93 | 290 | A | C |
| ATOM | 980 | CB | SER | A | 139 | 4.269 | 5.812 | 32.461 | 1.00 | 10.03 | | A | C |
| ANISOU | 980 | CB | SER | A | 139 | 1401 | 1270 | 1287 | −34 | 10 | −3 | A | C |
| SIGUIJ | 980 | CB | SER | A | 139 | 1 | 0 | 0 | 220 | 93 | 290 | A | C |
| ATOM | 981 | OG | SER | A | 139 | 5.003 | 4.617 | 32.481 | 1.00 | 11.51 | | A | O |
| ANISOU | 981 | OG | SER | A | 139 | 1459 | 1292 | 1644 | −1 | 33 | 1 | A | O |
| SIGUIJ | 981 | OG | SER | A | 139 | 1 | 0 | 0 | 221 | 54 | 289 | A | O |
| ATOM | 982 | C | SER | A | 139 | 6.078 | 7.354 | 33.297 | 1.00 | 9.22 | | A | C |
| ANISOU | 982 | C | SER | A | 139 | 1253 | 1054 | 1087 | 66 | 23 | 8 | A | C |
| SIGUIJ | 982 | C | SER | A | 139 | 1 | 0 | 0 | 220 | 93 | 290 | A | C |
| ATOM | 983 | O | SER | A | 139 | 7.224 | 6.867 | 33.392 | 1.00 | 9.85 | | A | O |
| ANISOU | 983 | O | SER | A | 139 | 1281 | 1163 | 1307 | 117 | 0 | 4 | A | O |
| SIGUIJ | 983 | O | SER | A | 139 | 1 | 0 | 0 | 221 | 54 | 289 | A | O |
| ATOM | 984 | N | GLY | A | 140 | 5.572 | 8.185 | 34.207 | 1.00 | 9.08 | | A | N |
| ANISOU | 984 | N | GLY | A | 140 | 1119 | 1029 | 1087 | −4 | −2 | 0 | A | N |
| SIGUIJ | 984 | N | GLY | A | 140 | 1 | 0 | 0 | 221 | 60 | 289 | A | N |
| ATOM | 985 | CA | GLY | A | 140 | 6.380 | 8.522 | 35.357 | 1.00 | 8.65 | | A | C |
| ANISOU | 985 | CA | GLY | A | 140 | 1095 | 1033 | 1083 | −2 | 1 | 0 | A | C |
| SIGUIJ | 985 | CA | GLY | A | 140 | 1 | 0 | 0 | 220 | 93 | 290 | A | C |
| ATOM | 986 | C | GLY | A | 140 | 5.665 | 9.494 | 36.268 | 1.00 | 8.84 | | A | C |
| ANISOU | 986 | C | GLY | A | 140 | 1080 | 1012 | 1076 | 13 | 0 | 0 | A | C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 986 | C | GLY | A | 140 | 1 | 0 | 0 | 220 | 93 | 290 | A | C |
| ATOM | 987 | O | GLY | A | 140 | 4.631 | 10.083 | 35.912 | 1.00 | 9.20 | | A | O |
| ANISOU | 987 | O | GLY | A | 140 | 1154 | 1180 | 1100 | 132 | 0 | 2 | A | O |
| SIGUIJ | 987 | O | GLY | A | 140 | 1 | 0 | 0 | 221 | 54 | 289 | A | O |
| ATOM | 988 | N | TRP | A | 141 | 6.298 | 9.713 | 37.416 | 1.00 | 8.37 | | A | N |
| ANISOU | 988 | N | TRP | A | 141 | 1068 | 998 | 1071 | 1 | 0 | 0 | A | N |
| SIGUIJ | 988 | N | TRP | A | 141 | 1 | 0 | 0 | 221 | 60 | 289 | A | N |
| ATOM | 989 | CA | TRP | A | 141 | 5.861 | 10.711 | 38.419 | 1.00 | 8.42 | | A | C |
| ANISOU | 989 | CA | TRP | A | 141 | 1159 | 1028 | 1085 | 39 | 2 | 1 | A | C |
| SIGUIJ | 989 | CA | TRP | A | 141 | 1 | 0 | 0 | 220 | 92 | 290 | A | C |
| ATOM | 990 | CB | TRP | A | 141 | 5.863 | 10.071 | 39.821 | 1.00 | 8.68 | | A | C |
| ANISOU | 990 | CB | TRP | A | 141 | 1235 | 1071 | 1094 | −6 | −19 | 1 | A | C |
| SIGUIJ | 990 | CB | TRP | A | 141 | 1 | 0 | 0 | 220 | 92 | 290 | A | C |
| ATOM | 991 | CG | TRP | A | 141 | 4.815 | 9.037 | 40.046 | 1.00 | 9.31 | | A | C |
| ANISOU | 991 | CG | TRP | A | 141 | 1259 | 1093 | 1260 | −23 | 0 | 0 | A | C |
| SIGUIJ | 991 | CG | TRP | A | 141 | 1 | 0 | 0 | 220 | 92 | 290 | A | C |
| ATOM | 992 | CD2 | TRP | A | 141 | 4.973 | 7.599 | 40.033 | 1.00 | 9.94 | | A | C |
| ANISOU | 992 | CD2 | TRP | A | 141 | 1400 | 1092 | 1238 | −27 | −19 | 2 | A | C |
| SIGUIJ | 992 | CD2 | TRP | A | 141 | 1 | 0 | 0 | 220 | 92 | 290 | A | C |
| ATOM | 993 | CE2 | TRP | A | 141 | 3.721 | 7.036 | 40.431 | 1.00 | 10.38 | | A | C |
| ANISOU | 993 | CE2 | TRP | A | 141 | 1454 | 1293 | 1265 | −130 | −3 | 2 | A | C |
| SIGUIJ | 993 | CE2 | TRP | A | 141 | 1 | 0 | 0 | 220 | 92 | 290 | A | C |
| ATOM | 994 | CE3 | TRP | A | 141 | 6.041 | 6.729 | 39.721 | 1.00 | 10.05 | | A | C |
| ANISOU | 994 | CE3 | TRP | A | 141 | 1450 | 1194 | 1146 | 55 | −80 | −15 | A | C |
| SIGUIJ | 994 | CE3 | TRP | A | 141 | 1 | 0 | 0 | 220 | 92 | 290 | A | C |
| ATOM | 995 | CD1 | TRP | A | 141 | 3.527 | 9.252 | 40.428 | 1.00 | 10.23 | | A | C |
| ANISOU | 995 | CD1 | TRP | A | 141 | 1255 | 1266 | 1297 | −1 | −2 | 0 | A | C |
| SIGUIJ | 995 | CD1 | TRP | A | 141 | 1 | 0 | 0 | 220 | 92 | 290 | A | C |
| ATOM | 996 | NE1 | TRP | A | 141 | 2.851 | 8.071 | 40.672 | 1.00 | 10.13 | | A | N |
| ANISOU | 996 | NE1 | TRP | A | 141 | 1458 | 1320 | 1352 | −122 | 21 | −17 | A | N |
| SIGUIJ | 996 | NE1 | TRP | A | 141 | 1 | 0 | 0 | 221 | 60 | 289 | A | N |
| ATOM | 997 | CZ2 | TRP | A | 141 | 3.529 | 5.643 | 40.519 | 1.00 | 10.92 | | A | C |
| ANISOU | 997 | CZ2 | TRP | A | 141 | 1913 | 1299 | 1413 | −192 | −119 | 38 | A | C |
| SIGUIJ | 997 | CZ2 | TRP | A | 141 | 1 | 0 | 0 | 220 | 92 | 290 | A | C |
| ATOM | 998 | CZ3 | TRP | A | 141 | 5.811 | 5.348 | 39.810 | 1.00 | 10.75 | | A | C |
| ANISOU | 998 | CZ3 | TRP | A | 141 | 1928 | 1208 | 1483 | −30 | −130 | 8 | A | C |
| SIGUIJ | 998 | CZ3 | TRP | A | 141 | 1 | 0 | 0 | 220 | 92 | 290 | A | C |
| ATOM | 999 | CH2 | TRP | A | 141 | 4.561 | 4.850 | 40.207 | 1.00 | 11.25 | | A | C |
| ANISOU | 999 | CH2 | TRP | A | 141 | 1969 | 1395 | 1465 | −113 | −126 | 25 | A | C |
| SIGUIJ | 999 | CH2 | TRP | A | 141 | 1 | 0 | 0 | 220 | 92 | 290 | A | C |
| ATOM | 1000 | C | TRP | A | 141 | 6.775 | 11.907 | 38.430 | 1.00 | 9.04 | | A | C |
| ANISOU | 1000 | C | TRP | A | 141 | 1142 | 1016 | 1281 | 54 | −4 | 0 | A | C |
| SIGUIJ | 1000 | C | TRP | A | 141 | 1 | 0 | 0 | 220 | 92 | 290 | A | C |
| ATOM | 1001 | O | TRP | A | 141 | 6.708 | 12.694 | 39.416 | 1.00 | 9.10 | | A | O |
| ANISOU | 1001 | O | TRP | A | 141 | 1424 | 1075 | 1289 | 135 | −48 | −30 | A | O |
| SIGUIJ | 1001 | O | TRP | A | 141 | 1 | 0 | 0 | 221 | 54 | 289 | A | O |
| ATOM | 1002 | N | GLY | A | 142 | 7.582 | 12.103 | 37.387 | 1.00 | 8.85 | | A | N |
| ANISOU | 1002 | N | GLY | A | 142 | 1106 | 950 | 1270 | 30 | −28 | −1 | A | N |
| SIGUIJ | 1002 | N | GLY | A | 142 | 1 | 0 | 0 | 221 | 60 | 289 | A | N |
| ATOM | 1003 | CA | GLY | A | 142 | 8.438 | 13.273 | 37.308 | 1.00 | 9.39 | | A | C |
| ANISOU | 1003 | CA | GLY | A | 142 | 1130 | 971 | 1490 | 7 | −14 | 0 | A | C |
| SIGUIJ | 1003 | CA | GLY | A | 142 | 1 | 0 | 0 | 220 | 92 | 290 | A | C |
| ATOM | 1004 | C | GLY | A | 142 | 7.624 | 14.567 | 37.182 | 1.00 | 9.80 | | A | C |
| ANISOU | 1004 | C | GLY | A | 142 | 1139 | 988 | 1262 | 15 | 4 | 0 | A | C |
| SIGUIJ | 1004 | C | GLY | A | 142 | 1 | 0 | 0 | 220 | 91 | 290 | A | C |
| ATOM | 1005 | O | GLY | A | 142 | 6.425 | 14.609 | 37.001 | 1.00 | 9.72 | | A | O |
| ANISOU | 1005 | O | GLY | A | 142 | 1138 | 1093 | 1291 | 4 | −6 | 0 | A | O |
| SIGUIJ | 1005 | O | GLY | A | 142 | 1 | 0 | 0 | 221 | 54 | 289 | A | O |
| ATOM | 1006 | N | THR | A | 143 | 8.368 | 15.669 | 37.165 | 1.00 | 9.84 | | A | N |
| ANISOU | 1006 | N | THR | A | 143 | 1165 | 993 | 1462 | 11 | 17 | 0 | A | N |
| SIGUIJ | 1006 | N | THR | A | 143 | 1 | 0 | 0 | 221 | 60 | 289 | A | N |
| ATOM | 1007 | CA | THR | A | 143 | 7.699 | 16.969 | 37.095 | 1.00 | 10.27 | | A | C |
| ANISOU | 1007 | CA | THR | A | 143 | 1258 | 1018 | 1345 | 54 | 3 | −1 | A | C |
| SIGUIJ | 1007 | CA | THR | A | 143 | 1 | 0 | 0 | 220 | 91 | 290 | A | C |
| ATOM | 1008 | CB | THR | A | 143 | 8.746 | 18.084 | 37.231 | 1.00 | 10.32 | | A | C |
| ANISOU | 1008 | CB | THR | A | 143 | 1204 | 970 | 1652 | 102 | −17 | 0 | A | C |
| SIGUIJ | 1008 | CB | THR | A | 143 | 1 | 0 | 0 | 220 | 91 | 290 | A | C |
| ATOM | 1009 | OG1 | THR | A | 143 | 8.063 | 19.358 | 37.259 | 1.00 | 9.98 | | A | O |
| ANISOU | 1009 | OG1 | THR | A | 143 | 1329 | 1005 | 1727 | 174 | −10 | 1 | A | O |
| SIGUIJ | 1009 | OG1 | THR | A | 143 | 1 | 0 | 0 | 221 | 54 | 289 | A | O |
| ATOM | 1010 | CG2 | THR | A | 143 | 9.814 | 18.077 | 36.102 | 1.00 | 11.20 | | A | C |
| ANISOU | 1010 | CG2 | THR | A | 143 | 1556 | 1474 | 1984 | −12 | 329 | −83 | A | C |
| SIGUIJ | 1010 | CG2 | THR | A | 143 | 1 | 0 | 0 | 220 | 91 | 290 | A | C |
| ATOM | 1011 | C | THR | A | 143 | 6.907 | 17.091 | 35.796 | 1.00 | 9.85 | | A | C |
| ANISOU | 1011 | C | THR | A | 143 | 1261 | 1021 | 1340 | 16 | −3 | 0 | A | C |
| SIGUIJ | 1011 | C | THR | A | 143 | 1 | 0 | 0 | 220 | 91 | 290 | A | C |
| ATOM | 1012 | O | THR | A | 143 | 7.319 | 16.587 | 34.723 | 1.00 | 10.01 | | A | O |
| ANISOU | 1012 | O | THR | A | 143 | 1366 | 1051 | 1335 | 64 | 2 | 2 | A | O |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1012 | O | THR | A | 143 | 1 | 0 | 0 | 221 | 54 | 289 | A O |
| ATOM | 1013 | N | THR | A | 144 | 5.791 | 17.825 | 35.914 | 1.00 | 10.36 | | A N |
| ANISOU | 1013 | N | THR | A | 144 | 1238 | 1002 | 1364 | −10 | 6 | 0 | A N |
| SIGUIJ | 1013 | N | THR | A | 144 | 1 | 0 | 0 | 221 | 60 | 289 | A N |
| ATOM | 1014 | CA | THR | A | 144 | 4.945 | 18.147 | 34.775 | 1.00 | 10.86 | | A C |
| ANISOU | 1014 | CA | THR | A | 144 | 1287 | 1167 | 1390 | 23 | −21 | 1 | A C |
| SIGUIJ | 1014 | CA | THR | A | 144 | 1 | 0 | 0 | 220 | 91 | 290 | A C |
| ATOM | 1015 | CB | THR | A | 144 | 3.454 | 17.993 | 35.145 | 1.00 | 10.86 | | A C |
| ANISOU | 1015 | CB | THR | A | 144 | 1301 | 1280 | 1505 | 2 | 14 | 0 | A C |
| SIGUIJ | 1015 | CB | THR | A | 144 | 1 | 0 | 0 | 220 | 91 | 290 | A C |
| ATOM | 1016 | OG1 | THR | A | 144 | 3.194 | 18.895 | 36.245 | 1.00 | 11.34 | | A O |
| ANISOU | 1016 | OG1 | THR | A | 144 | 1482 | 1318 | 1493 | 112 | 0 | −2 | A O |
| SIGUIJ | 1016 | OG1 | THR | A | 144 | 1 | 0 | 0 | 221 | 54 | 289 | A O |
| ATOM | 1017 | CG2 | THR | A | 144 | 3.171 | 16.582 | 35.580 | 1.00 | 11.09 | | A C |
| ANISOU | 1017 | CG2 | THR | A | 144 | 1458 | 1289 | 1506 | −29 | 2 | 0 | A C |
| SIGUIJ | 1017 | CG2 | THR | A | 144 | 1 | 0 | 0 | 220 | 91 | 290 | A C |
| ATOM | 1018 | C | THR | A | 144 | 5.183 | 19.524 | 34.244 | 1.00 | 11.05 | | A C |
| ANISOU | 1018 | C | THR | A | 144 | 1315 | 1164 | 1433 | 14 | −2 | 0 | A C |
| SIGUIJ | 1018 | C | THR | A | 144 | 1 | 0 | 0 | 220 | 91 | 290 | A C |
| ATOM | 1019 | O | THR | A | 144 | 4.545 | 19.931 | 33.272 | 1.00 | 11.42 | | A O |
| ANISOU | 1019 | O | THR | A | 144 | 1681 | 1258 | 1494 | 202 | −153 | −83 | A O |
| SIGUIJ | 1019 | O | THR | A | 144 | 1 | 0 | 0 | 221 | 54 | 289 | A O |
| ATOM | 1020 | N | THR | A | 145 | 6.052 | 20.279 | 34.904 | 1.00 | 11.43 | | A N |
| ANISOU | 1020 | N | THR | A | 145 | 1298 | 1103 | 1471 | 30 | 1 | 0 | A N |
| SIGUIJ | 1020 | N | THR | A | 145 | 1 | 0 | 0 | 221 | 60 | 289 | A N |
| ATOM | 1021 | CA | THR | A | 145 | 6.405 | 21.640 | 34.524 | 1.00 | 12.02 | | A C |
| ANISOU | 1021 | CA | THR | A | 145 | 1643 | 1128 | 1554 | −73 | 3 | −1 | A C |
| SIGUIJ | 1021 | CA | THR | A | 145 | 1 | 0 | 0 | 220 | 91 | 290 | A C |
| ATOM | 1022 | CB | THR | A | 145 | 5.840 | 22.676 | 35.533 | 1.00 | 11.75 | | A C |
| ANISOU | 1022 | CB | THR | A | 145 | 1687 | 1177 | 1583 | 0 | −1 | 0 | A C |
| SIGUIJ | 1022 | CB | THR | A | 145 | 1 | 0 | 0 | 220 | 91 | 290 | A C |
| ATOM | 1023 | OG1 | THR | A | 145 | 6.301 | 22.372 | 36.851 | 1.00 | 12.15 | | A O |
| ANISOU | 1023 | OG1 | THR | A | 145 | 1658 | 1383 | 1594 | 119 | 2 | 2 | A O |
| SIGUIJ | 1023 | OG1 | THR | A | 145 | 1 | 0 | 0 | 221 | 54 | 289 | A O |
| ATOM | 1024 | CG2 | THR | A | 145 | 4.316 | 22.694 | 35.480 | 1.00 | 12.43 | | A C |
| ANISOU | 1024 | CG2 | THR | A | 145 | 1686 | 1575 | 2121 | 14 | −22 | −1 | A C |
| SIGUIJ | 1024 | CG2 | THR | A | 145 | 1 | 0 | 0 | 220 | 91 | 290 | A C |
| ATOM | 1025 | C | THR | A | 145 | 7.915 | 21.777 | 34.499 | 1.00 | 13.22 | | A C |
| ANISOU | 1025 | C | THR | A | 145 | 1651 | 1148 | 1958 | −98 | 35 | 2 | A C |
| SIGUIJ | 1025 | C | THR | A | 145 | 1 | 0 | 0 | 220 | 90 | 290 | A C |
| ATOM | 1026 | O | THR | A | 145 | 8.640 | 21.001 | 35.108 | 1.00 | 12.96 | | A O |
| ANISOU | 1026 | O | THR | A | 145 | 1572 | 1279 | 1698 | 39 | 312 | 39 | A O |
| SIGUIJ | 1026 | O | THR | A | 145 | 1 | 0 | 0 | 221 | 54 | 289 | A O |
| ATOM | 1027 | N | SER | A | 146 | 8.396 | 22.805 | 33.789 | 1.00 | 14.32 | | A N |
| ANISOU | 1027 | N | SER | A | 146 | 2081 | 1240 | 1923 | −316 | 13 | −12 | A N |
| SIGUIJ | 1027 | N | SER | A | 146 | 1 | 0 | 0 | 221 | 60 | 289 | A N |
| ATOM | 1028 | CA | SER | A | 146 | 9.827 | 23.078 | 33.778 | 1.00 | 15.69 | | A C |
| ANISOU | 1028 | CA | SER | A | 146 | 2077 | 1369 | 2390 | −354 | 29 | 5 | A C |
| SIGUIJ | 1028 | CA | SER | A | 146 | 1 | 0 | 0 | 220 | 90 | 290 | A C |
| ATOM | 1029 | CB | SER | A | 146 | 10.531 | 22.074 | 32.828 | 1.00 | 15.13 | | A C |
| ANISOU | 1029 | CB | SER | A | 146 | 1955 | 1414 | 2348 | −341 | −53 | −21 | A C |
| SIGUIJ | 1029 | CB | SER | A | 146 | 1 | 0 | 0 | 220 | 90 | 290 | A C |
| ATOM | 1030 | OG | SER | A | 146 | 11.947 | 22.136 | 32.948 | 1.00 | 15.26 | | A O |
| ANISOU | 1030 | OG | SER | A | 146 | 1947 | 1494 | 1868 | −352 | −10 | 15 | A O |
| SIGUIJ | 1030 | OG | SER | A | 146 | 1 | 0 | 0 | 221 | 54 | 289 | A O |
| ATOM | 1031 | C | SER | A | 146 | 10.016 | 24.529 | 33.296 | 1.00 | 16.96 | | A C |
| ANISOU | 1031 | C | SER | A | 146 | 2270 | 1385 | 2791 | −317 | 274 | 89 | A C |
| SIGUIJ | 1031 | C | SER | A | 146 | 1 | 0 | 0 | 220 | 90 | 290 | A C |
| ATOM | 1032 | O | SER | A | 146 | 9.317 | 24.943 | 32.402 | 1.00 | 17.83 | | A O |
| ANISOU | 1032 | O | SER | A | 146 | 2835 | 1765 | 2966 | 26 | −7 | 1 | A O |
| SIGUIJ | 1032 | O | SER | A | 146 | 1 | 0 | 0 | 221 | 54 | 289 | A O |
| ATOM | 1033 | N | PRO | A | 147 | 10.984 | 25.281 | 33.888 | 1.00 | 18.13 | | A N |
| ANISOU | 1033 | N | PRO | A | 147 | 2614 | 1723 | 3238 | −579 | 48 | 25 | A N |
| SIGUIJ | 1033 | N | PRO | A | 147 | 1 | 0 | 0 | 221 | 60 | 289 | A N |
| ATOM | 1034 | CD | PRO | A | 147 | 11.203 | 26.695 | 33.477 | 1.00 | 18.57 | | A C |
| ANISOU | 1034 | CD | PRO | A | 147 | 3321 | 1758 | 3547 | −694 | 35 | 114 | A C |
| SIGUIJ | 1034 | CD | PRO | A | 147 | 1 | 0 | 0 | 220 | 90 | 290 | A C |
| ATOM | 1035 | CA | PRO | A | 147 | 11.935 | 24.865 | 34.919 | 1.00 | 18.91 | | A C |
| ANISOU | 1035 | CA | PRO | A | 147 | 2366 | 1635 | 3105 | −710 | 235 | 100 | A C |
| SIGUIJ | 1035 | CA | PRO | A | 147 | 1 | 0 | 0 | 220 | 90 | 290 | A C |
| ATOM | 1036 | CB | PRO | A | 147 | 13.038 | 25.941 | 34.860 | 1.00 | 18.92 | | A C |
| ANISOU | 1036 | CB | PRO | A | 147 | 2746 | 2035 | 3761 | −1103 | 220 | 172 | A C |
| SIGUIJ | 1036 | CB | PRO | A | 147 | 1 | 0 | 0 | 220 | 90 | 290 | A C |
| ATOM | 1037 | CG | PRO | A | 147 | 12.247 | 27.120 | 34.449 | 1.00 | 19.82 | | A C |
| ANISOU | 1037 | CG | PRO | A | 147 | 3386 | 2206 | 3649 | −752 | −3 | −16 | A C |
| SIGUIJ | 1037 | CG | PRO | A | 147 | 1 | 0 | 0 | 220 | 90 | 290 | A C |
| ATOM | 1038 | C | PRO | A | 147 | 11.384 | 24.714 | 36.329 | 1.00 | 19.36 | | A C |
| ANISOU | 1038 | C | PRO | A | 147 | 2281 | 1841 | 3094 | −744 | 184 | 101 | A C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1038 | C | PRO | A | 147 | 1 | 0 | 0 | 220 | 90 | 290 | A | C |
| ATOM | 1039 | O | PRO | A | 147 | 12.027 | 24.088 | 37.151 | 1.00 | 20.21 | | A | O |
| ANISOU | 1039 | O | PRO | A | 147 | 3189 | 2435 | 3163 | −54 | 1 | −1 | A | O |
| SIGUIJ | 1039 | O | PRO | A | 147 | 1 | 0 | 0 | 221 | 54 | 289 | A | O |
| ATOM | 1040 | N | ASP | A | 148 | 10.199 | 25.273 | 36.593 | 1.00 | 19.73 | | A | N |
| ANISOU | 1040 | N | ASP | A | 148 | 2484 | 2886 | 2571 | −251 | 4 | 5 | A | N |
| SIGUIJ | 1040 | N | ASP | A | 148 | 1 | 0 | 0 | 221 | 60 | 289 | A | N |
| ATOM | 1041 | CA | ASP | A | 148 | 9.538 | 25.134 | 37.886 | 1.00 | 19.78 | | A | C |
| ANISOU | 1041 | CA | ASP | A | 148 | 2418 | 2110 | 2565 | −14 | −6 | 0 | A | C |
| SIGUIJ | 1041 | CA | ASP | A | 148 | 1 | 0 | 0 | 220 | 90 | 290 | A | C |
| ATOM | 1042 | CB | ASP | A | 148 | 8.234 | 25.937 | 37.938 | 1.00 | 21.32 | | A | C |
| ANISOU | 1042 | CB | ASP | A | 148 | 2480 | 2280 | 3978 | 85 | 55 | 10 | A | C |
| SIGUIJ | 1042 | CB | ASP | A | 148 | 1 | 0 | 0 | 220 | 90 | 290 | A | C |
| ATOM | 1043 | CG | ASP | A | 148 | 8.457 | 27.414 | 38.112 | 1.00 | 22.69 | | A | C |
| ANISOU | 1043 | CG | ASP | A | 148 | 3800 | 2314 | 4254 | −113 | 3 | 0 | A | C |
| SIGUIJ | 1043 | CG | ASP | A | 148 | 1 | 0 | 0 | 220 | 90 | 290 | A | C |
| ATOM | 1044 | OD1 | ASP | A | 148 | 9.587 | 27.828 | 38.379 | 1.00 | 24.07 | | A | O |
| ANISOU | 1044 | OD1 | ASP | A | 148 | 3948 | 2897 | 5492 | −327 | −284 | −8 | A | O |
| SIGUIJ | 1044 | OD1 | ASP | A | 148 | 1 | 0 | 0 | 221 | 54 | 289 | A | O |
| ATOM | 1045 | OD2 | ASP | A | 148 | 7.483 | 28.188 | 37.967 | 1.00 | 24.12 | | A | O |
| ANISOU | 1045 | OD2 | ASP | A | 148 | 4594 | 3226 | 11473 | 650 | −1275 | −255 | A | O |
| SIGUIJ | 1045 | OD2 | ASP | A | 148 | 1 | 0 | 0 | 221 | 54 | 289 | A | O |
| ATOM | 1046 | C | ASP | A | 148 | 9.206 | 23.661 | 38.078 | 1.00 | 18.72 | | A | C |
| ANISOU | 1046 | C | ASP | A | 148 | 1599 | 2068 | 2271 | 180 | 104 | −31 | A | C |
| SIGUIJ | 1046 | C | ASP | A | 148 | 1 | 0 | 0 | 220 | 89 | 290 | A | C |
| ATOM | 1047 | O | ASP | A | 148 | 8.798 | 22.986 | 37.114 | 1.00 | 18.78 | | A | O |
| ANISOU | 1047 | O | ASP | A | 148 | 2096 | 2187 | 2285 | −13 | 21 | 2 | A | O |
| SIGUIJ | 1047 | O | ASP | A | 148 | 1 | 0 | 0 | 221 | 54 | 289 | A | O |
| ATOM | 1048 | N | VAL | A | 149 | 9.477 | 23.118 | 39.260 | 1.00 | 17.60 | | A | N |
| ANISOU | 1048 | N | VAL | A | 149 | 1685 | 1907 | 2307 | −149 | −66 | −24 | A | N |
| SIGUIJ | 1048 | N | VAL | A | 149 | 1 | 0 | 0 | 221 | 60 | 289 | A | N |
| ATOM | 1049 | CA | VAL | A | 149 | 9.117 | 21.723 | 39.475 | 1.00 | 16.98 | | A | C |
| ANISOU | 1049 | CA | VAL | A | 149 | 1519 | 1886 | 2609 | −52 | 235 | −23 | A | C |
| SIGUIJ | 1049 | CA | VAL | A | 149 | 1 | 0 | 0 | 220 | 89 | 290 | A | C |
| ATOM | 1050 | CB | VAL | A | 149 | 10.223 | 20.909 | 40.221 | 1.00 | 18.14 | | A | C |
| ANISOU | 1050 | CB | VAL | A | 149 | 2361 | 3066 | 3460 | 690 | −224 | 136 | A | C |
| SIGUIJ | 1050 | CB | VAL | A | 149 | 1 | 0 | 0 | 220 | 89 | 290 | A | C |
| ATOM | 1051 | CG1 | VAL | A | 149 | 11.607 | 21.415 | 39.780 | 1.00 | 19.42 | | A | C |
| ANISOU | 1051 | CG1 | VAL | A | 149 | 2784 | 4089 | 5840 | 250 | 613 | −77 | A | C |
| SIGUIJ | 1051 | CG1 | VAL | A | 149 | 1 | 0 | 0 | 220 | 89 | 290 | A | C |
| ATOM | 1052 | CG2 | VAL | A | 149 | 10.157 | 21.071 | 41.655 | 1.00 | 18.89 | | A | C |
| ANISOU | 1052 | CG2 | VAL | A | 149 | 2410 | 4172 | 3483 | −116 | −129 | −11 | A | C |
| SIGUIJ | 1052 | CG2 | VAL | A | 149 | 1 | 0 | 0 | 220 | 89 | 290 | A | C |
| ATOM | 1053 | C | VAL | A | 149 | 7.747 | 21.548 | 40.152 | 1.00 | 15.68 | | A | C |
| ANISOU | 1053 | C | VAL | A | 149 | 1353 | 1601 | 1887 | −25 | −116 | −11 | A | C |
| SIGUIJ | 1053 | C | VAL | A | 149 | 1 | 0 | 0 | 220 | 89 | 290 | A | C |
| ATOM | 1054 | O | VAL | A | 149 | 7.386 | 22.235 | 41.125 | 1.00 | 15.49 | | A | O |
| ANISOU | 1054 | O | VAL | A | 149 | 1800 | 1636 | 1937 | 7 | 18 | −1 | A | O |
| SIGUIJ | 1054 | O | VAL | A | 149 | 1 | 0 | 0 | 221 | 54 | 289 | A | O |
| ATOM | 1055 | N | THR | A | 150 | 6.961 | 20.639 | 39.577 | 1.00 | 14.24 | | A | N |
| ANISOU | 1055 | N | THR | A | 150 | 1201 | 1560 | 1574 | −12 | 94 | 3 | A | N |
| SIGUIJ | 1055 | N | THR | A | 150 | 1 | 0 | 0 | 221 | 60 | 289 | A | N |
| ATOM | 1056 | CA | THR | A | 150 | 5.613 | 20.336 | 40.083 | 1.00 | 13.97 | | A | C |
| ANISOU | 1056 | CA | THR | A | 150 | 1203 | 1419 | 1588 | 9 | 92 | −3 | A | C |
| SIGUIJ | 1056 | CA | THR | A | 150 | 1 | 0 | 0 | 220 | 89 | 290 | A | C |
| ATOM | 1057 | CB | THR | A | 150 | 4.525 | 21.015 | 39.233 | 1.00 | 13.75 | | A | C |
| ANISOU | 1057 | CB | THR | A | 150 | 1382 | 1432 | 1892 | 16 | −125 | 25 | A | C |
| SIGUIJ | 1057 | CB | THR | A | 150 | 1 | 0 | 0 | 220 | 89 | 290 | A | C |
| ATOM | 1058 | OG1 | THR | A | 150 | 4.809 | 22.402 | 39.136 | 1.00 | 13.44 | | A | O |
| ANISOU | 1058 | OG1 | THR | A | 150 | 1530 | 1432 | 1779 | 3 | 22 | 0 | A | O |
| SIGUIJ | 1058 | OG1 | THR | A | 150 | 1 | 0 | 0 | 221 | 54 | 289 | A | O |
| ATOM | 1059 | CG2 | THR | A | 150 | 3.156 | 20.866 | 39.871 | 1.00 | 14.02 | | A | C |
| ANISOU | 1059 | CG2 | THR | A | 150 | 1500 | 2153 | 2403 | −76 | 116 | 11 | A | C |
| SIGUIJ | 1059 | CG2 | THR | A | 150 | 1 | 0 | 0 | 220 | 89 | 290 | A | C |
| ATOM | 1060 | C | THR | A | 150 | 5.466 | 18.807 | 39.947 | 1.00 | 13.95 | | A | C |
| ANISOU | 1060 | C | THR | A | 150 | 1396 | 1421 | 1565 | −4 | 26 | 2 | A | C |
| SIGUIJ | 1060 | C | THR | A | 150 | 1 | 0 | 0 | 220 | 89 | 290 | A | C |
| ATOM | 1061 | O | THR | A | 150 | 5.425 | 18.253 | 38.819 | 1.00 | 13.25 | | A | O |
| ANISOU | 1061 | O | THR | A | 150 | 1375 | 1439 | 1553 | 2 | 22 | 0 | A | O |
| SIGUIJ | 1061 | O | THR | A | 150 | 1 | 0 | 0 | 221 | 54 | 289 | A | O |
| ATOM | 1062 | N | PHE | A | 151 | 5.438 | 18.123 | 41.069 | 1.00 | 14.35 | | A | N |
| ANISOU | 1062 | N | PHE | A | 151 | 2376 | 1402 | 1568 | −85 | 18 | −2 | A | N |
| SIGUIJ | 1062 | N | PHE | A | 151 | 1 | 0 | 0 | 221 | 60 | 289 | A | N |
| ATOM | 1063 | CA | PHE | A | 151 | 5.479 | 16.635 | 41.088 | 1.00 | 14.74 | | A | C |
| ANISOU | 1063 | CA | PHE | A | 151 | 2104 | 1402 | 1576 | −90 | 106 | −15 | A | C |
| SIGUIJ | 1063 | CA | PHE | A | 151 | 1 | 0 | 0 | 220 | 89 | 290 | A | C |
| ATOM | 1064 | CB | PHE | A | 151 | 6.448 | 16.168 | 42.184 | 1.00 | 15.42 | | A | C |
| ANISOU | 1064 | CB | PHE | A | 151 | 2535 | 1967 | 1768 | 224 | −141 | −45 | A | C |

TABLE 3-continued

Three-dimensional structure of the new binding pocket of kallikrein 7

| SIGUIJ | 1064 | CB | PHE | A | 151 | 1 | 0 | 0 | 220 | 89 | 290 | A | C |
|---|---|---|---|---|---|---|---|---|---|---|---|---|---|
| ATOM | 1065 | CG | PHE | A | 151 | 7.876 | 16.302 | 41.822 | 1.00 | 16.52 | | A | C |
| ANISOU | 1065 | CG | PHE | A | 151 | 2575 | 1771 | 2398 | 252 | 9 | 7 | A | C |
| SIGUIJ | 1065 | CG | PHE | A | 151 | 1 | 0 | 0 | 220 | 89 | 290 | A | C |
| ATOM | 1066 | CD1 | PHE | A | 151 | 8.715 | 17.164 | 42.537 | 1.00 | 17.26 | | A | C |
| ANISOU | 1066 | CD1 | PHE | A | 151 | 3798 | 2860 | 2442 | −887 | −54 | 34 | A | C |
| SIGUIJ | 1066 | CD1 | PHE | A | 151 | 1 | 0 | 0 | 220 | 88 | 290 | A | C |
| ATOM | 1067 | CD2 | PHE | A | 151 | 8.421 | 15.591 | 40.804 | 1.00 | 16.32 | | A | C |
| ANISOU | 1067 | CD2 | PHE | A | 151 | 2220 | 1574 | 2393 | 18 | −23 | 1 | A | C |
| SIGUIJ | 1067 | CD2 | PHE | A | 151 | 1 | 0 | 0 | 220 | 88 | 290 | A | C |
| ATOM | 1068 | CE1 | PHE | A | 151 | 10.046 | 17.272 | 42.212 | 1.00 | 17.77 | | A | C |
| ANISOU | 1068 | CE1 | PHE | A | 151 | 3814 | 3163 | 2595 | −917 | −4 | 3 | A | C |
| SIGUIJ | 1068 | CE1 | PHE | A | 151 | 1 | 0 | 0 | 220 | 88 | 290 | A | C |
| ATOM | 1069 | CE2 | PHE | A | 151 | 9.756 | 15.708 | 40.467 | 1.00 | 16.62 | | A | C |
| ANISOU | 1069 | CE2 | PHE | A | 151 | 2235 | 1615 | 2666 | 7 | 32 | 0 | A | C |
| SIGUIJ | 1069 | CE2 | PHE | A | 151 | 1 | 0 | 0 | 220 | 88 | 290 | A | C |
| ATOM | 1070 | CZ | PHE | A | 151 | 10.587 | 16.559 | 41.183 | 1.00 | 17.51 | | A | C |
| ANISOU | 1070 | CZ | PHE | A | 151 | 3519 | 3053 | 2754 | −1333 | 125 | −143 | A | C |
| SIGUIJ | 1070 | CZ | PHE | A | 151 | 1 | 0 | 0 | 220 | 88 | 290 | A | C |
| ATOM | 1071 | C | PHE | A | 151 | 4.084 | 16.083 | 41.317 | 1.00 | 14.71 | | A | C |
| ANISOU | 1071 | C | PHE | A | 151 | 2138 | 1651 | 1557 | −198 | 138 | −47 | A | C |
| SIGUIJ | 1071 | C | PHE | A | 151 | 1 | 0 | 0 | 220 | 88 | 290 | A | C |
| ATOM | 1072 | O | PHE | A | 151 | 3.495 | 16.307 | 42.380 | 1.00 | 14.96 | | A | O |
| ANISOU | 1072 | O | PHE | A | 151 | 2406 | 1832 | 1649 | −231 | 303 | −94 | A | O |
| SIGUIJ | 1072 | O | PHE | A | 151 | 1 | 0 | 0 | 221 | 54 | 289 | A | O |
| ATOM | 1073 | N | PRO | A | 152 | 3.497 | 15.385 | 40.340 | 1.00 | 14.27 | | A | N |
| ANISOU | 1073 | N | PRO | A | 152 | 1876 | 1307 | 1561 | 78 | 77 | 12 | A | N |
| SIGUIJ | 1073 | N | PRO | A | 152 | 1 | 0 | 0 | 221 | 60 | 289 | A | N |
| ATOM | 1074 | CD | PRO | A | 152 | 4.177 | 14.888 | 39.119 | 1.00 | 13.63 | | A | C |
| ANISOU | 1074 | CD | PRO | A | 152 | 1704 | 1335 | 1524 | 105 | −2 | −1 | A | C |
| SIGUIJ | 1074 | CD | PRO | A | 152 | 1 | 0 | 0 | 220 | 88 | 290 | A | C |
| ATOM | 1075 | CA | PRO | A | 152 | 2.168 | 14.843 | 40.478 | 1.00 | 14.57 | | A | C |
| ANISOU | 1075 | CA | PRO | A | 152 | 1912 | 1581 | 1682 | −23 | 48 | −4 | A | C |
| SIGUIJ | 1075 | CA | PRO | A | 152 | 1 | 0 | 0 | 220 | 88 | 290 | A | C |
| ATOM | 1076 | CB | PRO | A | 152 | 1.834 | 14.420 | 39.050 | 1.00 | 13.80 | | A | C |
| ANISOU | 1076 | CB | PRO | A | 152 | 1734 | 1470 | 1696 | 164 | −4 | −6 | A | C |
| SIGUIJ | 1076 | CB | PRO | A | 152 | 1 | 0 | 0 | 220 | 88 | 290 | A | C |
| ATOM | 1077 | CG | PRO | A | 152 | 3.207 | 13.884 | 38.561 | 1.00 | 13.60 | | A | C |
| ANISOU | 1077 | CG | PRO | A | 152 | 1709 | 1342 | 1615 | 106 | −9 | −6 | A | C |
| SIGUIJ | 1077 | CG | PRO | A | 152 | 1 | 0 | 0 | 220 | 88 | 290 | A | C |
| ATOM | 1078 | C | PRO | A | 152 | 2.094 | 13.623 | 41.416 | 1.00 | 14.68 | | A | C |
| ANISOU | 1078 | C | PRO | A | 152 | 1938 | 1582 | 1662 | −28 | 5 | 0 | A | C |
| SIGUIJ | 1078 | C | PRO | A | 152 | 1 | 0 | 0 | 220 | 88 | 290 | A | C |
| ATOM | 1079 | O | PRO | A | 152 | 3.014 | 12.759 | 41.387 | 1.00 | 14.95 | | A | O |
| ANISOU | 1079 | O | PRO | A | 152 | 2052 | 1731 | 1963 | 112 | 8 | 6 | A | O |
| SIGUIJ | 1079 | O | PRO | A | 152 | 1 | 0 | 0 | 221 | 54 | 289 | A | O |
| ATOM | 1080 | N | ASER | A | 153 | 1.037 | 13.452 | 42.177 | 0.50 | 14.75 | | A | N |
| ANISOU | 1080 | N | ASER | A | 153 | 1941 | 1271 | 1662 | 36 | 17 | 2 | A | N |
| SIGUIJ | 1080 | N | ASER | A | 153 | 1 | 0 | 0 | 221 | 60 | 289 | A | N |
| ATOM | 1081 | N | BSER | A | 153 | 1.027 | 13.449 | 42.165 | 0.50 | 16.94 | | A | N |
| ANISOU | 1081 | N | BSER | A | 153 | 1966 | 1686 | 1691 | −32 | 28 | −3 | A | N |
| SIGUIJ | 1081 | N | BSER | A | 153 | 1 | 0 | 0 | 221 | 60 | 289 | A | N |
| ATOM | 1082 | CA | ASER | A | 153 | 0.895 | 12.194 | 42.906 | 0.50 | 15.25 | | A | C |
| ANISOU | 1082 | CA | ASER | A | 153 | 1924 | 1273 | 1631 | 27 | 25 | 2 | A | C |
| SIGUIJ | 1082 | CA | ASER | A | 153 | 1 | 0 | 0 | 220 | 88 | 290 | A | C |
| ATOM | 1083 | CA | BSER | A | 153 | 0.874 | 12.194 | 42.901 | 0.50 | 17.44 | | A | C |
| ANISOU | 1083 | CA | BSER | A | 153 | 2666 | 1697 | 1679 | −100 | 53 | −5 | A | C |
| SIGUIJ | 1083 | CA | BSER | A | 153 | 1 | 0 | 0 | 220 | 88 | 290 | A | C |
| ATOM | 1084 | CB | ASER | A | 153 | −0.131 | 12.364 | 44.038 | 0.50 | 15.90 | | A | C |
| ANISOU | 1084 | CB | ASER | A | 153 | 1966 | 1581 | 1640 | 104 | 50 | 14 | A | C |
| SIGUIJ | 1084 | CB | ASER | A | 153 | 1 | 0 | 0 | 220 | 88 | 290 | A | C |
| ATOM | 1085 | CB | BSER | A | 153 | −0.203 | 12.347 | 43.970 | 0.50 | 18.09 | | A | C |
| ANISOU | 1085 | CB | BSER | A | 153 | 3327 | 2368 | 2346 | −33 | 714 | −24 | A | C |
| SIGUIJ | 1085 | CB | BSER | A | 153 | 1 | 0 | 0 | 220 | 87 | 290 | A | C |
| ATOM | 1086 | OG | ASER | A | 153 | 0.274 | 13.375 | 44.962 | 0.50 | 17.70 | | A | O |
| ANISOU | 1086 | OG | ASER | A | 153 | 2449 | 1707 | 1640 | −138 | 105 | −18 | A | O |
| SIGUIJ | 1086 | OG | ASER | A | 153 | 1 | 0 | 0 | 221 | 54 | 289 | A | O |
| ATOM | 1087 | OG | BSER | A | 153 | −1.393 | 12.819 | 43.378 | 0.50 | 19.89 | | A | O |
| ANISOU | 1087 | OG | BSER | A | 153 | 3692 | 2488 | 3783 | 1 | 7 | 0 | A | O |
| SIGUIJ | 1087 | OG | BSER | A | 153 | 1 | 0 | 0 | 221 | 54 | 289 | A | O |
| ATOM | 1088 | C | ASER | A | 153 | 0.491 | 11.031 | 42.001 | 0.50 | 14.78 | | A | C |
| ANISOU | 1088 | C | ASER | A | 153 | 2083 | 1334 | 1618 | −109 | 123 | −22 | A | C |
| SIGUIJ | 1088 | C | ASER | A | 153 | 1 | 0 | 0 | 220 | 87 | 290 | A | C |
| ATOM | 1089 | C | BSER | A | 153 | 0.498 | 11.033 | 41.995 | 0.50 | 16.97 | | A | C |
| ANISOU | 1089 | C | BSER | A | 153 | 2117 | 1650 | 1628 | 21 | 133 | 6 | A | C |
| SIGUIJ | 1089 | C | BSER | A | 153 | 1 | 0 | 0 | 220 | 87 | 290 | A | C |
| ATOM | 1090 | O | ASER | A | 153 | 0.821 | 9.878 | 42.297 | 0.50 | 14.89 | | A | O |
| ANISOU | 1090 | O | ASER | A | 153 | 2390 | 1392 | 1506 | 64 | 444 | 27 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1090 | O | ASER | A | 153 | 1 | 0 | 0 | 221 | 54 | 289 | A | O |
| ATOM | 1091 | O | BSER | A | 153 | 0.837 | 9.883 | 42.290 | 0.50 | 17.08 | | A | O |
| ANISOU | 1091 | O | BSER | A | 153 | 2077 | 1631 | 1788 | −18 | 54 | −3 | A | O |
| SIGUIJ | 1091 | O | BSER | A | 153 | 1 | 0 | 0 | 221 | 54 | 289 | A | O |
| ATOM | 1092 | N | ASP | A | 154 | −0.215 | 11.329 | 40.913 | 1.00 | 14.61 | | A | N |
| ANISOU | 1092 | N | ASP | A | 154 | 1867 | 1602 | 1507 | −21 | 292 | −15 | A | N |
| SIGUIJ | 1092 | N | ASP | A | 154 | 1 | 0 | 0 | 221 | 60 | 289 | A | N |
| ATOM | 1093 | CA | ASP | A | 154 | −0.716 | 10.259 | 40.073 | 1.00 | 14.15 | | A | C |
| ANISOU | 1093 | CA | ASP | A | 154 | 1829 | 1493 | 1506 | 129 | 111 | 39 | A | C |
| SIGUIJ | 1093 | CA | ASP | A | 154 | 1 | 0 | 0 | 220 | 87 | 290 | A | C |
| ATOM | 1094 | CB | ASP | A | 154 | −2.133 | 10.547 | 39.606 | 1.00 | 16.72 | | A | C |
| ANISOU | 1094 | CB | ASP | A | 154 | 2039 | 2560 | 3065 | 290 | −403 | 134 | A | C |
| SIGUIJ | 1094 | CB | ASP | A | 154 | 1 | 0 | 0 | 220 | 87 | 290 | A | C |
| ATOM | 1095 | CG | ASP | A | 154 | −3.149 | 10.212 | 40.698 | 1.00 | 18.51 | | A | C |
| ANISOU | 1095 | CG | ASP | A | 154 | 3092 | 3865 | 3820 | −195 | 421 | 100 | A | C |
| SIGUIJ | 1095 | CG | ASP | A | 154 | 1 | 0 | 0 | 220 | 87 | 290 | A | C |
| ATOM | 1096 | OD1 | ASP | A | 154 | −2.736 | 9.964 | 41.855 | 1.00 | 20.68 | | A | O |
| ANISOU | 1096 | OD1 | ASP | A | 154 | 5297 | 7688 | 3945 | 2014 | 103 | 129 | A | O |
| SIGUIJ | 1096 | OD1 | ASP | A | 154 | 1 | 0 | 0 | 221 | 54 | 289 | A | O |
| ATOM | 1097 | OD2 | ASP | A | 154 | −4.292 | 10.177 | 40.392 | 1.00 | 20.27 | | A | O |
| ANISOU | 1097 | OD2 | ASP | A | 154 | 3126 | 3468 | 4265 | −180 | 296 | 83 | A | O |
| SIGUIJ | 1097 | OD2 | ASP | A | 154 | 1 | 0 | 0 | 221 | 54 | 289 | A | O |
| ATOM | 1098 | C | ASP | A | 154 | 0.217 | 10.035 | 38.916 | 1.00 | 13.00 | | A | C |
| ANISOU | 1098 | C | ASP | A | 154 | 1619 | 1251 | 1396 | 54 | −30 | −6 | A | C |
| SIGUIJ | 1098 | C | ASP | A | 154 | 1 | 0 | 0 | 220 | 87 | 290 | A | C |
| ATOM | 1099 | O | ASP | A | 154 | 0.732 | 10.987 | 38.317 | 1.00 | 13.08 | | A | O |
| ANISOU | 1099 | O | ASP | A | 154 | 1725 | 1288 | 1483 | 35 | 25 | 3 | A | O |
| SIGUIJ | 1099 | O | ASP | A | 154 | 1 | 0 | 0 | 221 | 53 | 289 | A | O |
| ATOM | 1100 | N | LEU | A | 155 | 0.431 | 8.750 | 38.591 | 1.00 | 11.46 | | A | N |
| ANISOU | 1100 | N | LEU | A | 155 | 1268 | 1229 | 1300 | −2 | 1 | 0 | A | N |
| SIGUIJ | 1100 | N | LEU | A | 155 | 1 | 0 | 0 | 221 | 60 | 289 | A | N |
| ATOM | 1101 | CA | LEU | A | 155 | 1.333 | 8.396 | 37.482 | 1.00 | 10.69 | | A | C |
| ANISOU | 1101 | CA | LEU | A | 155 | 1278 | 1173 | 1299 | 9 | 0 | 0 | A | C |
| SIGUIJ | 1101 | CA | LEU | A | 155 | 1 | 0 | 0 | 220 | 87 | 290 | A | C |
| ATOM | 1102 | CB | LEU | A | 155 | 1.323 | 6.886 | 37.354 | 1.00 | 10.62 | | A | C |
| ANISOU | 1102 | CB | LEU | A | 155 | 1357 | 1170 | 1476 | 13 | 3 | 0 | A | C |
| SIGUIJ | 1102 | CB | LEU | A | 155 | 1 | 0 | 0 | 220 | 87 | 290 | A | C |
| ATOM | 1103 | CG | LEU | A | 155 | 2.321 | 6.294 | 36.341 | 1.00 | 10.20 | | A | C |
| ANISOU | 1103 | CG | LEU | A | 155 | 1369 | 1216 | 1468 | 42 | −1 | 0 | A | C |
| SIGUIJ | 1103 | CG | LEU | A | 155 | 1 | 0 | 0 | 220 | 87 | 290 | A | C |
| ATOM | 1104 | CD1 | LEU | A | 155 | 3.766 | 6.518 | 36.795 | 1.00 | 10.47 | | A | C |
| ANISOU | 1104 | CD1 | LEU | A | 155 | 1368 | 1430 | 1437 | 3 | 3 | 0 | A | C |
| SIGUIJ | 1104 | CD1 | LEU | A | 155 | 1 | 0 | 0 | 220 | 87 | 290 | A | C |
| ATOM | 1105 | CD2 | LEU | A | 155 | 2.044 | 4.778 | 36.195 | 1.00 | 10.77 | | A | C |
| ANISOU | 1105 | CD2 | LEU | A | 155 | 1559 | 1219 | 1641 | 13 | 0 | 0 | A | C |
| SIGUIJ | 1105 | CD2 | LEU | A | 155 | 1 | 0 | 0 | 220 | 87 | 290 | A | C |
| ATOM | 1106 | C | LEU | A | 155 | 0.811 | 9.022 | 36.189 | 1.00 | 10.49 | | A | C |
| ANISOU | 1106 | C | LEU | A | 155 | 1245 | 1164 | 1304 | −10 | 6 | 0 | A | C |
| SIGUIJ | 1106 | C | LEU | A | 155 | 1 | 0 | 0 | 220 | 87 | 290 | A | C |
| ATOM | 1107 | O | LEU | A | 155 | −0.371 | 8.882 | 35.838 | 1.00 | 11.28 | | A | O |
| ANISOU | 1107 | O | LEU | A | 155 | 1258 | 1519 | 1419 | −58 | −15 | −4 | A | O |
| SIGUIJ | 1107 | O | LEU | A | 155 | 1 | 0 | 0 | 221 | 53 | 289 | A | O |
| ATOM | 1108 | N | MET | A | 156 | 1.690 | 9.655 | 35.433 | 1.00 | 9.99 | | A | N |
| ANISOU | 1108 | N | MET | A | 156 | 1204 | 1082 | 1273 | 46 | 1 | 0 | A | N |
| SIGUIJ | 1108 | N | MET | A | 156 | 1 | 0 | 0 | 221 | 60 | 289 | A | N |
| ATOM | 1109 | CA | MET | A | 156 | 1.326 | 10.323 | 34.195 | 1.00 | 10.37 | | A | C |
| ANISOU | 1109 | CA | MET | A | 156 | 1254 | 1102 | 1270 | 11 | 0 | 0 | A | C |
| SIGUIJ | 1109 | CA | MET | A | 156 | 1 | 0 | 0 | 220 | 86 | 290 | A | C |
| ATOM | 1110 | CB | MET | A | 156 | 1.875 | 11.741 | 34.143 | 1.00 | 10.66 | | A | C |
| ANISOU | 1110 | CB | MET | A | 156 | 1241 | 1089 | 1358 | 18 | 15 | 0 | A | C |
| SIGUIJ | 1110 | CB | MET | A | 156 | 1 | 0 | 0 | 220 | 86 | 290 | A | C |
| ATOM | 1111 | CG | MET | A | 156 | 1.422 | 12.569 | 35.306 | 1.00 | 10.75 | | A | C |
| ANISOU | 1111 | CG | MET | A | 156 | 1467 | 1129 | 1354 | 172 | 19 | 16 | A | C |
| SIGUIJ | 1111 | CG | MET | A | 156 | 1 | 0 | 0 | 220 | 86 | 290 | A | C |
| ATOM | 1112 | SD | MET | A | 156 | −0.367 | 12.913 | 35.257 | 1.00 | 11.95 | | A | S |
| ANISOU | 1112 | SD | MET | A | 156 | 1475 | 1478 | 1716 | 248 | 47 | −47 | A | S |
| SIGUIJ | 1112 | SD | MET | A | 156 | 1 | 0 | 0 | 221 | 48 | 289 | A | S |
| ATOM | 1113 | CE | MET | A | 156 | −0.404 | 14.362 | 34.145 | 1.00 | 12.88 | | A | C |
| ANISOU | 1113 | CE | MET | A | 156 | 2145 | 1524 | 1792 | 231 | 6 | 3 | A | C |
| SIGUIJ | 1113 | CE | MET | A | 156 | 1 | 0 | 0 | 220 | 86 | 290 | A | C |
| ATOM | 1114 | C | MET | A | 156 | 1.926 | 9.535 | 33.003 | 1.00 | 10.18 | | A | C |
| ANISOU | 1114 | C | MET | A | 156 | 1229 | 1116 | 1253 | −4 | 0 | 0 | A | C |
| SIGUIJ | 1114 | C | MET | A | 156 | 1 | 0 | 0 | 220 | 86 | 290 | A | C |
| ATOM | 1115 | O | MET | A | 156 | 2.974 | 8.862 | 33.116 | 1.00 | 9.91 | | A | O |
| ANISOU | 1115 | O | MET | A | 156 | 1247 | 1152 | 1350 | 13 | −13 | 0 | A | O |
| SIGUIJ | 1115 | O | MET | A | 156 | 1 | 0 | 0 | 221 | 53 | 289 | A | O |
| ATOM | 1116 | N | CYS | A | 157 | 1.241 | 9.621 | 31.862 | 1.00 | 11.22 | | A | N |
| ANISOU | 1116 | N | CYS | A | 157 | 1250 | 1483 | 1243 | 112 | 2 | −8 | A | N |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1116 | N | CYS | A | 157 | 1 | 0 | 0 | 221 | 60 | 289 | A N |
| ATOM | 1117 | CA | CYS | A | 157 | 1.515 | 8.880 | 30.626 | 1.00 | 12.15 | | A C |
| ANISOU | 1117 | CA | CYS | A | 157 | 2256 | 1482 | 1236 | 275 | 149 | 44 | A C |
| SIGUIJ | 1117 | CA | CYS | A | 157 | 1 | 0 | 0 | 220 | 86 | 290 | A C |
| ATOM | 1118 | C | CYS | A | 157 | 1.524 | 9.860 | 29.448 | 1.00 | 11.80 | | A C |
| ANISOU | 1118 | C | CYS | A | 157 | 1292 | 1434 | 1196 | 50 | −9 | −1 | A C |
| SIGUIJ | 1118 | C | CYS | A | 157 | 1 | 0 | 0 | 220 | 86 | 290 | A C |
| ATOM | 1119 | O | CYS | A | 157 | 0.675 | 10.782 | 29.398 | 1.00 | 11.77 | | A O |
| ANISOU | 1119 | O | CYS | A | 157 | 1416 | 1540 | 1417 | 181 | −10 | 23 | A O |
| SIGUIJ | 1119 | O | CYS | A | 157 | 1 | 0 | 0 | 221 | 53 | 289 | A O |
| ATOM | 1120 | CB | CYS | A | 157 | 0.356 | 7.834 | 30.350 | 1.00 | 13.74 | | A C |
| ANISOU | 1120 | CB | CYS | A | 157 | 2508 | 1751 | 1748 | 47 | 47 | 3 | A C |
| SIGUIJ | 1120 | CB | CYS | A | 157 | 1 | 0 | 0 | 220 | 86 | 290 | A C |
| ATOM | 1121 | SG | CYS | A | 157 | 0.673 | 6.233 | 31.156 | 1.00 | 16.07 | | A S |
| ANISOU | 1121 | SG | CYS | A | 157 | 2211 | 1753 | 1968 | −138 | −181 | 62 | A S |
| SIGUIJ | 1121 | SG | CYS | A | 157 | 1 | 0 | 0 | 221 | 48 | 289 | A S |
| ATOM | 1122 | N | VAL | A | 158 | 2.415 | 9.642 | 28.483 | 1.00 | 11.72 | | A N |
| ANISOU | 1122 | N | VAL | A | 158 | 1299 | 1378 | 1182 | 5 | −8 | 0 | A N |
| SIGUIJ | 1122 | N | VAL | A | 158 | 1 | 0 | 0 | 221 | 60 | 289 | A N |
| ATOM | 1123 | CA | VAL | A | 158 | 2.293 | 10.363 | 27.243 | 1.00 | 12.28 | | A C |
| ANISOU | 1123 | CA | VAL | A | 158 | 1705 | 1408 | 1171 | 110 | 18 | 5 | A C |
| SIGUIJ | 1123 | CA | VAL | A | 158 | 1 | 0 | 0 | 220 | 86 | 290 | A C |
| ATOM | 1124 | CB | VAL | A | 158 | 3.136 | 11.684 | 27.278 | 1.00 | 13.24 | | A C |
| ANISOU | 1124 | CB | VAL | A | 158 | 1959 | 1516 | 1902 | −48 | −1 | 0 | A C |
| SIGUIJ | 1124 | CB | VAL | A | 158 | 1 | 0 | 0 | 220 | 86 | 290 | A C |
| ATOM | 1125 | CG1 | VAL | A | 158 | 4.608 | 11.418 | 27.296 | 1.00 | 13.74 | | A C |
| ANISOU | 1125 | CG1 | VAL | A | 158 | 1957 | 1569 | 1947 | −44 | 0 | 0 | A C |
| SIGUIJ | 1125 | CG1 | VAL | A | 158 | 1 | 0 | 0 | 220 | 86 | 290 | A C |
| ATOM | 1126 | CG2 | VAL | A | 158 | 2.745 | 12.647 | 26.178 | 1.00 | 14.77 | | A C |
| ANISOU | 1126 | CG2 | VAL | A | 158 | 4568 | 1691 | 1967 | 560 | −391 | −77 | A C |
| SIGUIJ | 1126 | CG2 | VAL | A | 158 | 1 | 0 | 0 | 220 | 86 | 290 | A C |
| ATOM | 1127 | C | VAL | A | 158 | 2.751 | 9.425 | 26.128 | 1.00 | 12.41 | | A C |
| ANISOU | 1127 | C | VAL | A | 158 | 1430 | 1350 | 1159 | −17 | 5 | −1 | A C |
| SIGUIJ | 1127 | C | VAL | A | 158 | 1 | 0 | 0 | 220 | 86 | 290 | A C |
| ATOM | 1128 | O | VAL | A | 158 | 3.652 | 8.600 | 26.272 | 1.00 | 12.16 | | A O |
| ANISOU | 1128 | O | VAL | A | 158 | 1502 | 1396 | 1358 | 35 | −88 | −21 | A O |
| SIGUIJ | 1128 | O | VAL | A | 158 | 1 | 0 | 0 | 221 | 53 | 289 | A O |
| ATOM | 1129 | N | ASP | A | 159 | 2.086 | 9.578 | 24.965 | 1.00 | 12.76 | | A N |
| ANISOU | 1129 | N | ASP | A | 159 | 1584 | 1656 | 1198 | 20 | −77 | 13 | A N |
| SIGUIJ | 1129 | N | ASP | A | 159 | 1 | 0 | 0 | 221 | 60 | 289 | A N |
| ATOM | 1130 | CA | ASP | A | 159 | 2.497 | 8.811 | 23.777 | 1.00 | 13.37 | | A C |
| ANISOU | 1130 | CA | ASP | A | 159 | 1598 | 1673 | 1204 | −8 | −52 | −2 | A C |
| SIGUIJ | 1130 | CA | ASP | A | 159 | 1 | 0 | 0 | 220 | 86 | 290 | A C |
| ATOM | 1131 | CB | ASP | A | 159 | 1.267 | 8.420 | 22.927 | 1.00 | 14.74 | | A C |
| ANISOU | 1131 | CB | ASP | A | 159 | 1857 | 2422 | 1533 | −246 | −301 | 42 | A C |
| SIGUIJ | 1131 | CB | ASP | A | 159 | 1 | 0 | 0 | 220 | 86 | 290 | A C |
| ATOM | 1132 | CG | ASP | A | 159 | 0.493 | 7.286 | 23.548 | 1.00 | 16.02 | | A C |
| ANISOU | 1132 | CG | ASP | A | 159 | 2007 | 2337 | 1862 | −160 | 34 | −15 | A C |
| SIGUIJ | 1132 | CG | ASP | A | 159 | 1 | 0 | 0 | 220 | 85 | 290 | A C |
| ATOM | 1133 | OD1 | ASP | A | 159 | 0.719 | 6.893 | 24.717 | 1.00 | 16.45 | | A O |
| ANISOU | 1133 | OD1 | ASP | A | 159 | 2215 | 2464 | 1870 | −62 | 17 | 0 | A O |
| SIGUIJ | 1133 | OD1 | ASP | A | 159 | 1 | 0 | 0 | 221 | 53 | 289 | A O |
| ATOM | 1134 | OD2 | ASP | A | 159 | −0.351 | 6.719 | 22.834 | 1.00 | 18.29 | | A O |
| ANISOU | 1134 | OD2 | ASP | A | 159 | 5074 | 4532 | 2734 | −2701 | −1569 | 1271 | A O |
| SIGUIJ | 1134 | OD2 | ASP | A | 159 | 1 | 0 | 0 | 221 | 53 | 289 | A O |
| ATOM | 1135 | C | ASP | A | 159 | 3.493 | 9.567 | 22.905 | 1.00 | 13.43 | | A C |
| ANISOU | 1135 | C | ASP | A | 159 | 1654 | 1629 | 1284 | 3 | 36 | 2 | A C |
| SIGUIJ | 1135 | C | ASP | A | 159 | 1 | 0 | 0 | 220 | 85 | 290 | A C |
| ATOM | 1136 | O | ASP | A | 159 | 3.303 | 10.759 | 22.627 | 1.00 | 13.53 | | A O |
| ANISOU | 1136 | O | ASP | A | 159 | 1965 | 1636 | 1365 | 27 | −70 | −4 | A O |
| SIGUIJ | 1136 | O | ASP | A | 159 | 1 | 0 | 0 | 221 | 53 | 289 | A O |
| ATOM | 1137 | N | VAL | A | 160 | 4.533 | 8.860 | 22.468 | 1.00 | 13.40 | | A N |
| ANISOU | 1137 | N | VAL | A | 160 | 1625 | 1614 | 1169 | 0 | 16 | 0 | A N |
| SIGUIJ | 1137 | N | VAL | A | 160 | 1 | 0 | 0 | 221 | 60 | 289 | A N |
| ATOM | 1138 | CA | VAL | A | 160 | 5.576 | 9.460 | 21.670 | 1.00 | 13.93 | | A C |
| ANISOU | 1138 | CA | VAL | A | 160 | 1688 | 1606 | 1314 | 7 | 131 | 10 | A C |
| SIGUIJ | 1138 | CA | VAL | A | 160 | 1 | 0 | 0 | 220 | 85 | 290 | A C |
| ATOM | 1139 | CB | VAL | A | 160 | 6.792 | 9.849 | 22.569 | 1.00 | 13.94 | | A C |
| ANISOU | 1139 | CB | VAL | A | 160 | 1836 | 1945 | 1543 | −94 | −38 | −4 | A C |
| SIGUIJ | 1139 | CB | VAL | A | 160 | 1 | 0 | 0 | 220 | 85 | 290 | A C |
| ATOM | 1140 | CG1 | VAL | A | 160 | 6.462 | 11.119 | 23.411 | 1.00 | 14.40 | | A C |
| ANISOU | 1140 | CG1 | VAL | A | 160 | 2351 | 2011 | 1859 | −197 | 319 | −127 | A C |
| SIGUIJ | 1140 | CG1 | VAL | A | 160 | 1 | 0 | 0 | 220 | 85 | 290 | A C |
| ATOM | 1141 | CG2 | VAL | A | 160 | 7.188 | 8.695 | 23.499 | 1.00 | 14.36 | | A C |
| ANISOU | 1141 | CG2 | VAL | A | 160 | 2235 | 1984 | 1618 | −33 | −139 | 13 | A C |
| SIGUIJ | 1141 | CG2 | VAL | A | 160 | 1 | 0 | 0 | 220 | 85 | 290 | A C |
| ATOM | 1142 | C | VAL | A | 160 | 6.039 | 8.422 | 20.663 | 1.00 | 14.44 | | A C |
| ANISOU | 1142 | C | VAL | A | 160 | 1886 | 1637 | 1361 | −2 | 225 | −19 | A C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1142 | C | VAL | A | 160 | 1 | 0 | 0 | 220 | 85 | 290 | A C |
| ATOM | 1143 | O | VAL | A | 160 | 5.843 | 7.199 | 20.854 | 1.00 | 14.89 | | A O |
| ANISOU | 1143 | O | VAL | A | 160 | 2763 | 1635 | 1732 | −86 | 614 | −37 | A O |
| SIGUIJ | 1143 | O | VAL | A | 160 | 1 | 0 | 0 | 221 | 53 | 289 | A O |
| ATOM | 1144 | N | ALYS | A | 161 | 6.709 | 8.880 | 19.616 | 0.50 | 14.82 | | A N |
| ANISOU | 1144 | N | ALYS | A | 161 | 1721 | 1923 | 1271 | −115 | 77 | 8 | A N |
| SIGUIJ | 1144 | N | ALYS | A | 161 | 1 | 0 | 0 | 221 | 60 | 289 | A N |
| ATOM | 1145 | N | BLYS | A | 161 | 6.739 | 8.891 | 19.639 | 0.50 | 17.01 | | A N |
| ANISOU | 1145 | N | BLYS | A | 161 | 1678 | 1944 | 1216 | −153 | 15 | 0 | A N |
| SIGUIJ | 1145 | N | BLYS | A | 161 | 1 | 0 | 0 | 221 | 60 | 289 | A N |
| ATOM | 1146 | CA | ALYS | A | 161 | 7.140 | 7.989 | 18.553 | 0.50 | 15.17 | | A C |
| ANISOU | 1146 | CA | ALYS | A | 161 | 1807 | 2002 | 1245 | 13 | 7 | −1 | A C |
| SIGUIJ | 1146 | CA | ALYS | A | 161 | 1 | 0 | 0 | 220 | 85 | 290 | A C |
| ATOM | 1147 | CA | BLYS | A | 161 | 7.167 | 8.044 | 18.538 | 0.50 | 17.36 | | A C |
| ANISOU | 1147 | CA | BLYS | A | 161 | 1866 | 2045 | 1191 | 22 | −24 | 1 | A C |
| SIGUIJ | 1147 | CA | BLYS | A | 161 | 1 | 0 | 0 | 220 | 85 | 290 | A C |
| ATOM | 1148 | CB | ALYS | A | 161 | 6.749 | 8.600 | 17.194 | 0.50 | 16.95 | | A C |
| ANISOU | 1148 | CB | ALYS | A | 161 | 2060 | 2058 | 1278 | −5 | −79 | 21 | A C |
| SIGUIJ | 1148 | CB | ALYS | A | 161 | 1 | 0 | 0 | 220 | 85 | 290 | A C |
| ATOM | 1149 | CB | BLYS | A | 161 | 6.826 | 8.764 | 17.223 | 0.50 | 19.14 | | A C |
| ANISOU | 1149 | CB | BLYS | A | 161 | 3838 | 2063 | 1294 | 108 | −494 | −25 | A C |
| SIGUIJ | 1149 | CB | BLYS | A | 161 | 1 | 0 | 0 | 220 | 85 | 290 | A C |
| ATOM | 1150 | CG | ALYS | A | 161 | 5.437 | 8.043 | 16.545 | 0.50 | 19.34 | | A C |
| ANISOU | 1150 | CG | ALYS | A | 161 | 2915 | 5131 | 1914 | −1480 | −539 | 360 | A C |
| SIGUIJ | 1150 | CG | ALYS | A | 161 | 1 | 0 | 0 | 220 | 85 | 290 | A C |
| ATOM | 1151 | CG | BLYS | A | 161 | 7.117 | 7.965 | 15.951 | 0.50 | 21.53 | | A C |
| ANISOU | 1151 | CG | BLYS | A | 161 | 3547 | 1785 | 1294 | −348 | −276 | 47 | A C |
| SIGUIJ | 1151 | CG | BLYS | A | 161 | 1 | 0 | 0 | 220 | 85 | 290 | A C |
| ATOM | 1152 | CD | ALYS | A | 161 | 5.332 | 8.488 | 15.063 | 0.50 | 20.76 | | A C |
| ANISOU | 1152 | CD | ALYS | A | 161 | 4366 | 4204 | 1772 | 34 | −188 | −25 | A C |
| SIGUIJ | 1152 | CD | ALYS | A | 161 | 1 | 0 | 0 | 220 | 85 | 290 | A C |
| ATOM | 1153 | CD | BLYS | A | 161 | 6.593 | 8.709 | 14.720 | 0.50 | 22.95 | | A C |
| ANISOU | 1153 | CD | BLYS | A | 161 | 4275 | 2216 | 1181 | 430 | −112 | −19 | A C |
| SIGUIJ | 1153 | CD | BLYS | A | 161 | 1 | 0 | 0 | 220 | 85 | 290 | A C |
| ATOM | 1154 | CE | ALYS | A | 161 | 5.716 | 9.966 | 14.901 | 0.50 | 22.03 | | A C |
| ANISOU | 1154 | CE | ALYS | A | 161 | 8184 | 4418 | 3039 | −842 | 864 | −158 | A C |
| SIGUIJ | 1154 | CE | ALYS | A | 161 | 1 | 0 | 0 | 220 | 84 | 290 | A C |
| ATOM | 1155 | CE | BLYS | A | 161 | 7.245 | 10.085 | 14.606 | 0.50 | 24.22 | | A C |
| ANISOU | 1155 | CE | BLYS | A | 161 | 4538 | 2268 | 2011 | 316 | 0 | 0 | A C |
| SIGUIJ | 1155 | CE | BLYS | A | 161 | 1 | 0 | 0 | 220 | 84 | 290 | A C |
| ATOM | 1156 | NZ | ALYS | A | 161 | 5.633 | 10.480 | 13.492 | 0.50 | 23.07 | | A N |
| ANISOU | 1156 | NZ | ALYS | A | 161 | 9802 | 5323 | 3110 | 434 | 1233 | 98 | A N |
| SIGUIJ | 1156 | NZ | ALYS | A | 161 | 1 | 0 | 0 | 221 | 60 | 289 | A N |
| ATOM | 1157 | NZ | BLYS | A | 161 | 7.093 | 10.747 | 13.285 | 0.50 | 25.26 | | A N |
| ANISOU | 1157 | NZ | BLYS | A | 161 | 3509 | 2200 | 2008 | 85 | 6 | 0 | A N |
| SIGUIJ | 1157 | NZ | BLYS | A | 161 | 1 | 0 | 0 | 221 | 60 | 289 | A N |
| ATOM | 1158 | C | ALYS | A | 161 | 8.652 | 7.771 | 18.618 | 0.50 | 14.88 | | A C |
| ANISOU | 1158 | C | ALYS | A | 161 | 1803 | 1893 | 1418 | −6 | 15 | 0 | A C |
| SIGUIJ | 1158 | C | ALYS | A | 161 | 1 | 0 | 0 | 220 | 84 | 290 | A C |
| ATOM | 1159 | C | BLYS | A | 161 | 8.672 | 7.780 | 18.617 | 0.50 | 17.07 | | A C |
| ANISOU | 1159 | C | BLYS | A | 161 | 1857 | 1895 | 1357 | 1 | −25 | 0 | A C |
| SIGUIJ | 1159 | C | BLYS | A | 161 | 1 | 0 | 0 | 220 | 84 | 290 | A C |
| ATOM | 1160 | O | ALYS | A | 161 | 9.407 | 8.730 | 18.907 | 0.50 | 14.76 | | A O |
| ANISOU | 1160 | O | ALYS | A | 161 | 1819 | 1897 | 1528 | −9 | −26 | −1 | A O |
| SIGUIJ | 1160 | O | ALYS | A | 161 | 1 | 0 | 0 | 221 | 53 | 289 | A O |
| ATOM | 1161 | O | BLYS | A | 161 | 9.444 | 8.716 | 18.909 | 0.50 | 16.95 | | A O |
| ANISOU | 1161 | O | BLYS | A | 161 | 1871 | 1904 | 1438 | −5 | −48 | −4 | A O |
| SIGUIJ | 1161 | O | BLYS | A | 161 | 1 | 0 | 0 | 221 | 53 | 289 | A O |
| ATOM | 1162 | N | LEU | A | 162 | 9.111 | 6.539 | 18.367 | 1.00 | 14.53 | | A N |
| ANISOU | 1162 | N | LEU | A | 162 | 1637 | 1883 | 1170 | −41 | −184 | −22 | A N |
| SIGUIJ | 1162 | N | LEU | A | 162 | 1 | 0 | 0 | 221 | 60 | 289 | A N |
| ATOM | 1163 | CA | LEU | A | 162 | 10.540 | 6.245 | 18.423 | 1.00 | 14.97 | | A C |
| ANISOU | 1163 | CA | LEU | A | 162 | 1641 | 1937 | 1336 | −28 | −196 | −30 | A C |
| SIGUIJ | 1163 | CA | LEU | A | 162 | 1 | 0 | 0 | 220 | 84 | 290 | A C |
| ATOM | 1164 | CB | LEU | A | 162 | 10.797 | 4.765 | 18.271 | 1.00 | 15.03 | | A C |
| ANISOU | 1164 | CB | LEU | A | 162 | 2006 | 1945 | 1331 | 30 | −92 | −19 | A C |
| SIGUIJ | 1164 | CB | LEU | A | 162 | 1 | 0 | 0 | 220 | 84 | 290 | A C |
| ATOM | 1165 | CG | LEU | A | 162 | 10.240 | 3.915 | 19.380 | 1.00 | 15.42 | | A C |
| ANISOU | 1165 | CG | LEU | A | 162 | 2416 | 2021 | 1397 | −68 | 36 | −4 | A C |
| SIGUIJ | 1165 | CG | LEU | A | 162 | 1 | 0 | 0 | 220 | 84 | 290 | A C |
| ATOM | 1166 | CD1 | LEU | A | 162 | 10.716 | 2.477 | 19.181 | 1.00 | 15.74 | | A C |
| ANISOU | 1166 | CD1 | LEU | A | 162 | 2552 | 2029 | 1560 | −38 | 114 | −6 | A C |
| SIGUIJ | 1166 | CD1 | LEU | A | 162 | 1 | 0 | 0 | 220 | 84 | 290 | A C |
| ATOM | 1167 | CD2 | LEU | A | 162 | 10.693 | 4.416 | 20.755 | 1.00 | 15.28 | | A C |
| ANISOU | 1167 | CD2 | LEU | A | 162 | 2820 | 1970 | 1440 | −3 | −127 | 0 | A C |
| SIGUIJ | 1167 | CD2 | LEU | A | 162 | 1 | 0 | 0 | 220 | 84 | 290 | A C |
| ATOM | 1168 | C | LEU | A | 162 | 11.304 | 6.935 | 17.295 | 1.00 | 15.37 | | A C |
| ANISOU | 1168 | C | LEU | A | 162 | 1833 | 1949 | 1447 | 5 | −48 | 0 | A C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1168 | C | LEU | A | 162 | 1 | 0 | 0 | 220 | 84 | 290 | A C |
| ATOM | 1169 | O | LEU | A | 162 | 10.794 | 7.015 | 16.148 | 1.00 | 15.52 | | A O |
| ANISOU | 1169 | O | LEU | A | 162 | 1829 | 2144 | 1445 | −15 | −39 | 0 | A O |
| SIGUIJ | 1169 | O | LEU | A | 162 | 1 | 0 | 0 | 221 | 53 | 289 | A O |
| ATOM | 1170 | N | ILE | A | 163 | 12.498 | 7.435 | 17.619 | 1.00 | 15.74 | | A N |
| ANISOU | 1170 | N | ILE | A | 163 | 1883 | 2260 | 1359 | −125 | −34 | −3 | A N |
| SIGUIJ | 1170 | N | ILE | A | 163 | 1 | 0 | 0 | 221 | 60 | 289 | A N |
| ATOM | 1171 | CA | ILE | A | 163 | 13.354 | 8.202 | 16.719 | 1.00 | 16.21 | | A C |
| ANISOU | 1171 | CA | ILE | A | 163 | 1862 | 2200 | 1390 | −53 | 2 | 0 | A C |
| SIGUIJ | 1171 | CA | ILE | A | 163 | 1 | 0 | 0 | 220 | 84 | 290 | A C |
| ATOM | 1172 | CB | ILE | A | 163 | 13.472 | 9.672 | 17.202 | 1.00 | 15.92 | | A C |
| ANISOU | 1172 | CB | ILE | A | 163 | 2120 | 2205 | 1412 | −20 | −124 | −15 | A C |
| SIGUIJ | 1172 | CB | ILE | A | 163 | 1 | 0 | 0 | 220 | 84 | 290 | A C |
| ATOM | 1173 | CG2 | ILE | A | 163 | 14.500 | 10.400 | 16.330 | 1.00 | 15.79 | | A C |
| ANISOU | 1173 | CG2 | ILE | A | 163 | 2191 | 2218 | 1522 | −2 | −32 | −1 | A C |
| SIGUIJ | 1173 | CG2 | ILE | A | 163 | 1 | 0 | 0 | 220 | 84 | 290 | A C |
| ATOM | 1174 | CG1 | ILE | A | 163 | 12.117 | 10.382 | 17.185 | 1.00 | 15.79 | | A C |
| ANISOU | 1174 | CG1 | ILE | A | 163 | 2130 | 2228 | 1603 | 0 | −121 | −1 | A C |
| SIGUIJ | 1174 | CG1 | ILE | A | 163 | 1 | 0 | 0 | 220 | 84 | 290 | A C |
| ATOM | 1175 | CD1 | ILE | A | 163 | 12.075 | 11.716 | 17.970 | 1.00 | 15.74 | | A C |
| ANISOU | 1175 | CD1 | ILE | A | 163 | 2539 | 2223 | 1621 | −69 | 39 | −6 | A C |
| SIGUIJ | 1175 | CD1 | ILE | A | 163 | 1 | 0 | 0 | 220 | 84 | 290 | A C |
| ATOM | 1176 | C | ILE | A | 163 | 14.720 | 7.506 | 16.806 | 1.00 | 16.73 | | A C |
| ANISOU | 1176 | C | ILE | A | 163 | 1831 | 2097 | 1548 | −115 | −3 | 0 | A C |
| SIGUIJ | 1176 | C | ILE | A | 163 | 1 | 0 | 0 | 220 | 83 | 290 | A C |
| ATOM | 1177 | O | ILE | A | 163 | 15.248 | 7.225 | 17.902 | 1.00 | 16.91 | | A O |
| ANISOU | 1177 | O | ILE | A | 163 | 1812 | 2195 | 1546 | −43 | 21 | −1 | A O |
| SIGUIJ | 1177 | O | ILE | A | 163 | 1 | 0 | 0 | 221 | 53 | 289 | A O |
| ATOM | 1178 | N | ASER | A | 164 | 15.283 | 7.166 | 15.649 | 0.50 | 17.54 | | A N |
| ANISOU | 1178 | N | ASER | A | 164 | 1955 | 2334 | 1556 | 13 | 11 | 0 | A N |
| SIGUIJ | 1178 | N | ASER | A | 164 | 1 | 0 | 0 | 221 | 60 | 289 | A N |
| ATOM | 1179 | N | BSER | A | 164 | 15.299 | 7.181 | 15.648 | 0.50 | 19.73 | | A N |
| ANISOU | 1179 | N | BSER | A | 164 | 2017 | 2399 | 1584 | −12 | 62 | −5 | A N |
| SIGUIJ | 1179 | N | BSER | A | 164 | 1 | 0 | 0 | 221 | 60 | 289 | A N |
| ATOM | 1180 | CA | ASER | A | 164 | 16.610 | 6.552 | 15.616 | 0.50 | 18.20 | | A C |
| ANISOU | 1180 | CA | ASER | A | 164 | 1927 | 2198 | 1631 | −47 | 11 | 0 | A C |
| SIGUIJ | 1180 | CA | ASER | A | 164 | 1 | 0 | 0 | 220 | 83 | 290 | A C |
| ATOM | 1181 | CA | BSER | A | 164 | 16.626 | 6.547 | 15.627 | 0.50 | 20.39 | | A C |
| ANISOU | 1181 | CA | BSER | A | 164 | 2009 | 2396 | 1594 | −21 | 53 | 1 | A C |
| SIGUIJ | 1181 | CA | BSER | A | 164 | 1 | 0 | 0 | 220 | 83 | 290 | A C |
| ATOM | 1182 | CB | ASER | A | 164 | 16.963 | 6.230 | 14.159 | 0.50 | 18.66 | | A C |
| ANISOU | 1182 | CB | ASER | A | 164 | 2509 | 2259 | 1665 | −37 | 143 | −14 | A C |
| SIGUIJ | 1182 | CB | ASER | A | 164 | 1 | 0 | 0 | 220 | 83 | 290 | A C |
| ATOM | 1183 | CB | BSER | A | 164 | 17.049 | 6.228 | 14.188 | 0.50 | 20.85 | | A C |
| ANISOU | 1183 | CB | BSER | A | 164 | 2339 | 3908 | 1573 | 918 | −59 | −42 | A C |
| SIGUIJ | 1183 | CB | BSER | A | 164 | 1 | 0 | 0 | 220 | 83 | 290 | A C |
| ATOM | 1184 | OG | ASER | A | 164 | 18.305 | 5.844 | 14.025 | 0.50 | 20.65 | | A O |
| ANISOU | 1184 | OG | ASER | A | 164 | 2516 | 2354 | 1592 | −9 | 137 | −6 | A O |
| SIGUIJ | 1184 | OG | ASER | A | 164 | 1 | 0 | 0 | 221 | 53 | 289 | A O |
| ATOM | 1185 | OG | BSER | A | 164 | 17.503 | 7.408 | 13.543 | 0.50 | 22.84 | | A O |
| ANISOU | 1185 | OG | BSER | A | 164 | 4086 | 4269 | 1212 | −25 | −553 | −49 | A O |
| SIGUIJ | 1185 | OG | BSER | A | 164 | 1 | 0 | 0 | 221 | 53 | 289 | A O |
| ATOM | 1186 | C | ASER | A | 164 | 17.670 | 7.497 | 16.218 | 0.50 | 18.34 | | A C |
| ANISOU | 1186 | C | ASER | A | 164 | 2095 | 2445 | 1585 | −265 | 48 | −6 | A C |
| SIGUIJ | 1186 | C | ASER | A | 164 | 1 | 0 | 0 | 220 | 83 | 290 | A C |
| ATOM | 1187 | C | BSER | A | 164 | 17.672 | 7.493 | 16.228 | 0.50 | 20.53 | | A C |
| ANISOU | 1187 | C | BSER | A | 164 | 2139 | 2579 | 1570 | −188 | 66 | −2 | A C |
| SIGUIJ | 1187 | C | BSER | A | 164 | 1 | 0 | 0 | 220 | 83 | 290 | A C |
| ATOM | 1188 | O | ASER | A | 164 | 17.544 | 8.711 | 16.080 | 0.50 | 18.24 | | A O |
| ANISOU | 1188 | O | ASER | A | 164 | 1689 | 2442 | 1801 | −325 | 9 | 11 | A O |
| SIGUIJ | 1188 | O | ASER | A | 164 | 1 | 0 | 0 | 221 | 53 | 289 | A O |
| ATOM | 1189 | O | BSER | A | 164 | 17.547 | 8.706 | 16.089 | 0.50 | 20.43 | | A O |
| ANISOU | 1189 | O | BSER | A | 164 | 1868 | 2576 | 1648 | −238 | −7 | 4 | A O |
| SIGUIJ | 1189 | O | BSER | A | 164 | 1 | 0 | 0 | 221 | 53 | 289 | A O |
| ATOM | 1190 | N | PRO | A | 165 | 18.726 | 6.936 | 16.871 | 1.00 | 18.81 | | A N |
| ANISOU | 1190 | N | PRO | A | 165 | 2149 | 2718 | 1539 | −112 | 89 | −4 | A N |
| SIGUIJ | 1190 | N | PRO | A | 165 | 1 | 0 | 0 | 221 | 60 | 289 | A N |
| ATOM | 1191 | CD | PRO | A | 165 | 18.987 | 5.525 | 17.213 | 1.00 | 18.76 | | A C |
| ANISOU | 1191 | CD | PRO | A | 165 | 2457 | 2721 | 1699 | −69 | −46 | −3 | A C |
| SIGUIJ | 1191 | CD | PRO | A | 165 | 1 | 0 | 0 | 220 | 83 | 290 | A C |
| ATOM | 1192 | CA | PRO | A | 165 | 19.775 | 7.824 | 17.374 | 1.00 | 19.57 | | A C |
| ANISOU | 1192 | CA | PRO | A | 165 | 2032 | 2668 | 1427 | −48 | 195 | −33 | A C |
| SIGUIJ | 1192 | CA | PRO | A | 165 | 1 | 0 | 0 | 220 | 83 | 290 | A C |
| ATOM | 1193 | CB | PRO | A | 165 | 20.786 | 6.876 | 18.018 | 1.00 | 19.09 | | A C |
| ANISOU | 1193 | CB | PRO | A | 165 | 2277 | 2742 | 1967 | 3 | −109 | 9 | A C |
| SIGUIJ | 1193 | CB | PRO | A | 165 | 1 | 0 | 0 | 220 | 83 | 290 | A C |
| ATOM | 1194 | CG | PRO | A | 165 | 20.466 | 5.504 | 17.491 | 1.00 | 19.35 | | A C |
| ANISOU | 1194 | CG | PRO | A | 165 | 2468 | 2765 | 2015 | −50 | −98 | −10 | A C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1194 | CG | PRO | A | 165 | 1 | 0 | 0 | 220 | 83 | 290 | A | C |
| ATOM | 1195 | C | PRO | A | 165 | 20.380 | 8.674 | 16.265 | 1.00 | 20.46 | | A | C |
| ANISOU | 1195 | C | PRO | A | 165 | 2709 | 3180 | 1499 | −561 | 189 | 70 | A | C |
| SIGUIJ | 1195 | C | PRO | A | 165 | 1 | 0 | 0 | 220 | 83 | 290 | A | C |
| ATOM | 1196 | O | PRO | A | 165 | 20.723 | 9.841 | 16.475 | 1.00 | 20.36 | | A | O |
| ANISOU | 1196 | O | PRO | A | 165 | 2254 | 3139 | 2103 | −399 | −6 | 15 | A | O |
| SIGUIJ | 1196 | O | PRO | A | 165 | 1 | 0 | 0 | 221 | 53 | 289 | A | O |
| ATOM | 1197 | N | GLN | A | 166 | 20.476 | 8.111 | 15.063 | 1.00 | 21.46 | | A | N |
| ANISOU | 1197 | N | GLN | A | 166 | 2181 | 3457 | 1534 | −440 | 99 | −28 | A | N |
| SIGUIJ | 1197 | N | GLN | A | 166 | 1 | 0 | 0 | 221 | 60 | 289 | A | N |
| ATOM | 1198 | CA | GLN | A | 166 | 21.083 | 8.867 | 13.962 | 1.00 | 22.39 | | A | C |
| ANISOU | 1198 | CA | GLN | A | 166 | 2032 | 3534 | 1614 | −301 | 112 | 82 | A | C |
| SIGUIJ | 1198 | CA | GLN | A | 166 | 1 | 0 | 0 | 220 | 83 | 290 | A | C |
| ATOM | 1199 | CB | GLN | A | 166 | 21.313 | 7.971 | 12.734 | 1.00 | 23.16 | | A | C |
| ANISOU | 1199 | CB | GLN | A | 166 | 3581 | 3767 | 1697 | 41 | 163 | −25 | A | C |
| SIGUIJ | 1199 | CB | GLN | A | 166 | 1 | 0 | 0 | 220 | 83 | 290 | A | C |
| ATOM | 1200 | CG | GLN | A | 166 | 22.377 | 6.908 | 12.923 | 1.00 | 24.35 | | A | C |
| ANISOU | 1200 | CG | GLN | A | 166 | 3512 | 3675 | 2572 | −51 | 33 | 4 | A | C |
| SIGUIJ | 1200 | CG | GLN | A | 166 | 1 | 0 | 0 | 220 | 83 | 290 | A | C |
| ATOM | 1201 | CD | GLN | A | 166 | 21.923 | 5.716 | 13.746 | 1.00 | 25.19 | | A | C |
| ANISOU | 1201 | CD | GLN | A | 166 | 5033 | 3707 | 2696 | −308 | 498 | −85 | A | C |
| SIGUIJ | 1201 | CD | GLN | A | 166 | 1 | 0 | 0 | 220 | 83 | 290 | A | C |
| ATOM | 1202 | OE1 | GLN | A | 166 | 20.727 | 5.479 | 13.912 | 1.00 | 25.85 | | A | O |
| ANISOU | 1202 | OE1 | GLN | A | 166 | 5129 | 6361 | 2617 | −825 | 467 | 14 | A | O |
| SIGUIJ | 1202 | OE1 | GLN | A | 166 | 1 | 0 | 0 | 221 | 53 | 289 | A | O |
| ATOM | 1203 | NE2 | GLN | A | 166 | 22.885 | 4.959 | 14.268 | 1.00 | 26.18 | | A | N |
| ANISOU | 1203 | NE2 | GLN | A | 166 | 7239 | 6079 | 4294 | 1731 | −609 | −394 | A | N |
| SIGUIJ | 1203 | NE2 | GLN | A | 166 | 1 | 0 | 0 | 221 | 60 | 289 | A | N |
| ATOM | 1204 | C | GLN | A | 166 | 20.221 | 10.037 | 13.575 | 1.00 | 22.75 | | A | C |
| ANISOU | 1204 | C | GLN | A | 166 | 2587 | 3802 | 1480 | 91 | 61 | −2 | A | C |
| SIGUIJ | 1204 | C | GLN | A | 166 | 1 | 0 | 0 | 220 | 82 | 290 | A | C |
| ATOM | 1205 | O | GLN | A | 166 | 20.709 | 10.983 | 12.975 | 1.00 | 23.16 | | A | O |
| ANISOU | 1205 | O | GLN | A | 166 | 4006 | 4222 | 3316 | 40 | 1137 | 617 | A | O |
| SIGUIJ | 1205 | O | GLN | A | 166 | 1 | 0 | 0 | 221 | 53 | 289 | A | O |
| ATOM | 1206 | N | ASP | A | 167 | 18.938 | 9.991 | 13.913 | 1.00 | 22.90 | | A | N |
| ANISOU | 1206 | N | ASP | A | 167 | 2602 | 3170 | 1754 | 108 | 135 | 0 | A | N |
| SIGUIJ | 1206 | N | ASP | A | 167 | 1 | 0 | 0 | 221 | 60 | 289 | A | N |
| ATOM | 1207 | CA | ASP | A | 167 | 18.056 | 11.093 | 13.579 | 1.00 | 23.15 | | A | C |
| ANISOU | 1207 | CA | ASP | A | 167 | 3064 | 3415 | 2305 | 420 | −80 | −10 | A | C |
| SIGUIJ | 1207 | CA | ASP | A | 167 | 1 | 0 | 0 | 220 | 82 | 290 | A | C |
| ATOM | 1208 | CB | ASP | A | 167 | 16.706 | 10.538 | 13.068 | 1.00 | 24.27 | | A | C |
| ANISOU | 1208 | CB | ASP | A | 167 | 3393 | 5992 | 1565 | −639 | 200 | −15 | A | C |
| SIGUIJ | 1208 | CB | ASP | A | 167 | 1 | 0 | 0 | 220 | 82 | 290 | A | C |
| ATOM | 1209 | CG | ASP | A | 167 | 16.877 | 9.635 | 11.810 | 1.00 | 25.43 | | A | C |
| ANISOU | 1209 | CG | ASP | A | 167 | 5659 | 6095 | 1537 | −5 | 55 | −1 | A | C |
| SIGUIJ | 1209 | CG | ASP | A | 167 | 1 | 0 | 0 | 220 | 82 | 290 | A | C |
| ATOM | 1210 | OD1 | ASP | A | 167 | 17.549 | 10.088 | 10.848 | 1.00 | 26.67 | | A | O |
| ANISOU | 1210 | OD1 | ASP | A | 167 | 6408 | 6339 | 1957 | −7 | 580 | 105 | A | O |
| SIGUIJ | 1210 | OD1 | ASP | A | 167 | 1 | 0 | 0 | 221 | 53 | 289 | A | O |
| ATOM | 1211 | OD2 | ASP | A | 167 | 16.381 | 8.468 | 11.749 | 1.00 | 26.53 | | A | O |
| ANISOU | 1211 | OD2 | ASP | A | 167 | 5637 | 6082 | 4197 | 23 | −291 | 5 | A | O |
| SIGUIJ | 1211 | OD2 | ASP | A | 167 | 1 | 0 | 0 | 221 | 53 | 289 | A | O |
| ATOM | 1212 | C | ASP | A | 167 | 17.849 | 12.040 | 14.763 | 1.00 | 22.74 | | A | C |
| ANISOU | 1212 | C | ASP | A | 167 | 2535 | 3302 | 2299 | 155 | 59 | 25 | A | C |
| SIGUIJ | 1212 | C | ASP | A | 167 | 1 | 0 | 0 | 220 | 82 | 290 | A | C |
| ATOM | 1213 | O | ASP | A | 167 | 17.058 | 12.949 | 14.672 | 1.00 | 23.11 | | A | O |
| ANISOU | 1213 | O | ASP | A | 167 | 5157 | 5350 | 2673 | 2471 | 408 | 362 | A | O |
| SIGUIJ | 1213 | O | ASP | A | 167 | 1 | 0 | 0 | 221 | 53 | 289 | A | O |
| ATOM | 1214 | N | CYS | A | 168 | 18.565 | 11.819 | 15.863 | 1.00 | 21.84 | | A | N |
| ANISOU | 1214 | N | CYS | A | 168 | 2657 | 2909 | 2338 | 110 | −25 | 0 | A | N |
| SIGUIJ | 1214 | N | CYS | A | 168 | 1 | 0 | 0 | 221 | 60 | 289 | A | N |
| ATOM | 1215 | CA | CYS | A | 168 | 18.455 | 12.574 | 17.109 | 1.00 | 21.29 | | A | C |
| ANISOU | 1215 | CA | CYS | A | 168 | 2458 | 2912 | 2337 | 10 | 18 | 1 | A | C |
| SIGUIJ | 1215 | CA | CYS | A | 168 | 1 | 0 | 0 | 220 | 82 | 290 | A | C |
| ATOM | 1216 | C | CYS | A | 168 | 19.744 | 13.356 | 17.349 | 1.00 | 21.19 | | A | C |
| ANISOU | 1216 | C | CYS | A | 168 | 2440 | 2839 | 2561 | 37 | −1 | 0 | A | C |
| SIGUIJ | 1216 | C | CYS | A | 168 | 1 | 0 | 0 | 220 | 82 | 290 | A | C |
| ATOM | 1217 | O | CYS | A | 168 | 20.753 | 12.779 | 17.774 | 1.00 | 21.33 | | A | O |
| ANISOU | 1217 | O | CYS | A | 168 | 2350 | 2590 | 2614 | −110 | −8 | −3 | A | O |
| SIGUIJ | 1217 | O | CYS | A | 168 | 1 | 0 | 0 | 221 | 53 | 289 | A | O |
| ATOM | 1218 | CB | CYS | A | 168 | 18.227 | 11.592 | 18.289 | 1.00 | 20.25 | | A | C |
| ANISOU | 1218 | CB | CYS | A | 168 | 2799 | 2942 | 2314 | 22 | 38 | 0 | A | C |
| SIGUIJ | 1218 | CB | CYS | A | 168 | 1 | 0 | 0 | 220 | 82 | 290 | A | C |
| ATOM | 1219 | SG | CYS | A | 168 | 17.637 | 12.381 | 19.813 | 1.00 | 19.44 | | A | S |
| ANISOU | 1219 | SG | CYS | A | 168 | 2305 | 2485 | 2228 | −371 | 51 | 139 | A | S |
| SIGUIJ | 1219 | SG | CYS | A | 168 | 1 | 0 | 0 | 221 | 48 | 289 | A | S |
| ATOM | 1220 | N | THR | A | 169 | 19.704 | 14.662 | 17.133 | 1.00 | 21.34 | | A | N |
| ANISOU | 1220 | N | THR | A | 169 | 2615 | 2832 | 2450 | 37 | 2 | 0 | A | N |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1220 | N | THR | A | 169 | 1 | 0 | 0 | 221 | 60 | 289 | A | N |
| ATOM | 1221 | CA | THR | A | 169 | 20.939 | 15.446 | 17.084 | 1.00 | 21.34 | | A | C |
| ANISOU | 1221 | CA | THR | A | 169 | 2648 | 2897 | 3004 | −8 | 26 | 1 | A | C |
| SIGUIJ | 1221 | CA | THR | A | 169 | 1 | 0 | 0 | 220 | 82 | 290 | A | C |
| ATOM | 1222 | CB | THR | A | 169 | 20.619 | 16.869 | 16.685 | 1.00 | 21.92 | | A | C |
| ANISOU | 1222 | CB | THR | A | 169 | 3516 | 2947 | 3132 | 191 | 37 | 15 | A | C |
| SIGUIJ | 1222 | CB | THR | A | 169 | 1 | 0 | 0 | 220 | 82 | 290 | A | C |
| ATOM | 1223 | OG1 | THR | A | 169 | 19.746 | 16.838 | 15.550 | 1.00 | 22.86 | | A | O |
| ANISOU | 1223 | OG1 | THR | A | 169 | 3587 | 3924 | 3179 | 159 | −15 | 0 | A | O |
| SIGUIJ | 1223 | OG1 | THR | A | 169 | 1 | 0 | 0 | 221 | 53 | 289 | A | O |
| ATOM | 1224 | CG2 | THR | A | 169 | 21.905 | 17.637 | 16.423 | 1.00 | 22.13 | | A | C |
| ANISOU | 1224 | CG2 | THR | A | 169 | 3660 | 3327 | 3109 | −45 | 39 | −4 | A | C |
| SIGUIJ | 1224 | CG2 | THR | A | 169 | 1 | 0 | 0 | 220 | 82 | 290 | A | C |
| ATOM | 1225 | C | THR | A | 169 | 21.691 | 15.465 | 18.390 | 1.00 | 21.07 | | A | C |
| ANISOU | 1225 | C | THR | A | 169 | 2190 | 2662 | 2837 | −67 | 302 | 33 | A | C |
| SIGUIJ | 1225 | C | THR | A | 169 | 1 | 0 | 0 | 220 | 82 | 290 | A | C |
| ATOM | 1226 | O | THR | A | 169 | 22.905 | 15.517 | 18.392 | 1.00 | 21.00 | | A | O |
| ANISOU | 1226 | O | THR | A | 169 | 2187 | 2828 | 3303 | −78 | 303 | 29 | A | O |
| SIGUIJ | 1226 | O | THR | A | 169 | 1 | 0 | 0 | 221 | 53 | 289 | A | O |
| ATOM | 1227 | N | LYS | A | 170 | 20.975 | 15.412 | 19.523 | 1.00 | 20.57 | | A | N |
| ANISOU | 1227 | N | LYS | A | 170 | 1891 | 2629 | 2700 | −119 | 96 | 14 | A | N |
| SIGUIJ | 1227 | N | LYS | A | 170 | 1 | 0 | 0 | 221 | 60 | 289 | A | N |
| ATOM | 1228 | CA | LYS | A | 170 | 21.672 | 15.507 | 20.806 | 1.00 | 20.13 | | A | C |
| ANISOU | 1228 | CA | LYS | A | 170 | 1876 | 2497 | 2697 | −38 | 92 | 5 | A | C |
| SIGUIJ | 1228 | CA | LYS | A | 170 | 1 | 0 | 0 | 220 | 82 | 290 | A | C |
| ATOM | 1229 | CB | LYS | A | 170 | 20.709 | 15.882 | 21.943 | 1.00 | 19.74 | | A | C |
| ANISOU | 1229 | CB | LYS | A | 170 | 1824 | 2107 | 2682 | −157 | 85 | 27 | A | C |
| SIGUIJ | 1229 | CB | LYS | A | 170 | 1 | 0 | 0 | 220 | 82 | 290 | A | C |
| ATOM | 1230 | CG | LYS | A | 170 | 19.604 | 14.816 | 22.229 | 1.00 | 18.85 | | A | C |
| ANISOU | 1230 | CG | LYS | A | 170 | 1779 | 2060 | 2249 | −125 | 1 | 0 | A | C |
| SIGUIJ | 1230 | CG | LYS | A | 170 | 1 | 0 | 0 | 220 | 82 | 290 | A | C |
| ATOM | 1231 | CD | LYS | A | 170 | 18.720 | 15.116 | 23.458 | 1.00 | 18.16 | | A | C |
| ANISOU | 1231 | CD | LYS | A | 170 | 1837 | 2256 | 2256 | −43 | 12 | 1 | A | C |
| SIGUIJ | 1231 | CD | LYS | A | 170 | 1 | 0 | 0 | 220 | 82 | 290 | A | C |
| ATOM | 1232 | CE | LYS | A | 170 | 17.997 | 16.462 | 23.389 | 1.00 | 17.62 | | A | C |
| ANISOU | 1232 | CE | LYS | A | 170 | 1895 | 2266 | 1848 | −17 | 3 | −1 | A | C |
| SIGUIJ | 1232 | CE | LYS | A | 170 | 1 | 0 | 0 | 220 | 82 | 290 | A | C |
| ATOM | 1233 | NZ | LYS | A | 170 | 16.968 | 16.452 | 22.315 | 1.00 | 16.88 | | A | N |
| ANISOU | 1233 | NZ | LYS | A | 170 | 1898 | 1875 | 1853 | −3 | 1 | 0 | A | N |
| SIGUIJ | 1233 | NZ | LYS | A | 170 | 1 | 0 | 0 | 221 | 60 | 289 | A | N |
| ATOM | 1234 | C | LYS | A | 170 | 22.412 | 14.201 | 21.174 | 1.00 | 20.06 | | A | C |
| ANISOU | 1234 | C | LYS | A | 170 | 1567 | 2434 | 2438 | −165 | 245 | 44 | A | C |
| SIGUIJ | 1234 | C | LYS | A | 170 | 1 | 0 | 0 | 220 | 81 | 290 | A | C |
| ATOM | 1235 | O | LYS | A | 170 | 23.217 | 14.193 | 22.112 | 1.00 | 20.45 | | A | O |
| ANISOU | 1235 | O | LYS | A | 170 | 1997 | 3070 | 2753 | −90 | −129 | −13 | A | O |
| SIGUIJ | 1235 | O | LYS | A | 170 | 1 | 0 | 0 | 221 | 53 | 289 | A | O |
| ATOM | 1236 | N | VAL | A | 171 | 22.152 | 13.098 | 20.470 | 1.00 | 20.14 | | A | N |
| ANISOU | 1236 | N | VAL | A | 171 | 1835 | 2415 | 2364 | −225 | 255 | 89 | A | N |
| SIGUIJ | 1236 | N | VAL | A | 171 | 1 | 0 | 0 | 221 | 60 | 289 | A | N |
| ATOM | 1237 | CA | VAL | A | 171 | 22.895 | 11.853 | 20.727 | 1.00 | 20.53 | | A | C |
| ANISOU | 1237 | CA | VAL | A | 171 | 2282 | 2522 | 2780 | −12 | −61 | −3 | A | C |
| SIGUIJ | 1237 | CA | VAL | A | 171 | 1 | 0 | 0 | 220 | 81 | 290 | A | C |
| ATOM | 1238 | CB | VAL | A | 171 | 22.084 | 10.556 | 20.310 | 1.00 | 20.49 | | A | C |
| ANISOU | 1238 | CB | VAL | A | 171 | 2207 | 2520 | 2482 | −16 | 71 | 4 | A | C |
| SIGUIJ | 1238 | CB | VAL | A | 171 | 1 | 0 | 0 | 220 | 81 | 290 | A | C |
| ATOM | 1239 | CG1 | VAL | A | 171 | 22.984 | 9.287 | 20.470 | 1.00 | 20.47 | | A | C |
| ANISOU | 1239 | CG1 | VAL | A | 171 | 2247 | 2537 | 2636 | 8 | 29 | −1 | A | C |
| SIGUIJ | 1239 | CG1 | VAL | A | 171 | 1 | 0 | 0 | 220 | 81 | 290 | A | C |
| ATOM | 1240 | CG2 | VAL | A | 171 | 20.770 | 10.419 | 21.143 | 1.00 | 20.58 | | A | C |
| ANISOU | 1240 | CG2 | VAL | A | 171 | 2165 | 3658 | 2337 | −151 | −17 | −8 | A | C |
| SIGUIJ | 1240 | CG2 | VAL | A | 171 | 1 | 0 | 0 | 220 | 81 | 290 | A | C |
| ATOM | 1241 | C | VAL | A | 171 | 24.187 | 11.930 | 19.884 | 1.00 | 20.83 | | A | C |
| ANISOU | 1241 | C | VAL | A | 171 | 2346 | 3732 | 2925 | −83 | 29 | 3 | A | C |
| SIGUIJ | 1241 | C | VAL | A | 171 | 1 | 0 | 0 | 220 | 81 | 290 | A | C |
| ATOM | 1242 | O | VAL | A | 171 | 24.131 | 12.259 | 18.675 | 1.00 | 21.72 | | A | O |
| ANISOU | 1242 | O | VAL | A | 171 | 2571 | 3750 | 2925 | 47 | 63 | −4 | A | O |
| SIGUIJ | 1242 | O | VAL | A | 171 | 1 | 0 | 0 | 221 | 53 | 289 | A | O |
| ATOM | 1243 | N | GLU | A | 177 | 24.714 | 6.144 | 22.061 | 1.00 | 30.45 | | A | N |
| ANISOU | 1243 | N | GLU | A | 177 | 15233 | 5567 | 7403 | 2183 | 1205 | 295 | A | N |
| SIGUIJ | 1243 | N | GLU | A | 177 | 1 | 0 | 0 | 221 | 59 | 289 | A | N |
| ATOM | 1244 | CA | GLU | A | 177 | 25.208 | 5.336 | 20.938 | 1.00 | 30.20 | | A | C |
| ANISOU | 1244 | CA | GLU | A | 177 | 6599 | 3692 | 7053 | −1437 | 11 | 52 | A | C |
| SIGUIJ | 1244 | CA | GLU | A | 177 | 1 | 0 | 0 | 220 | 81 | 290 | A | C |
| ATOM | 1245 | CB | GLU | A | 177 | 26.280 | 4.351 | 21.409 | 1.00 | 30.89 | | A | C |
| ANISOU | 1245 | CB | GLU | A | 177 | 8482 | 5844 | 7054 | 574 | −73 | −22 | A | C |
| SIGUIJ | 1245 | CB | GLU | A | 177 | 1 | 0 | 0 | 220 | 81 | 290 | A | C |
| ATOM | 1246 | CG | GLU | A | 177 | 27.548 | 4.940 | 22.022 | 1.00 | 31.90 | | A | C |
| ANISOU | 1246 | CG | GLU | A | 177 | 8808 | 7402 | 6935 | −165 | −36 | 4 | A | C |

TABLE 3-continued

Three-dimensional structure of the new binding pocket of kallikrein 7

| | | | | | | | | | | | | | | |
|---|---|---|---|---|---|---|---|---|---|---|---|---|---|---|
| SIGUIJ | 1246 | CG | GLU | A | 177 | 1 | 0 | 0 | 220 | 81 | 290 | A | C | |
| ATOM | 1247 | CD | GLU | A | 177 | 28.257 | 3.887 | 22.864 | 1.00 | 32.41 | | A | C | |
| ANISOU | 1247 | CD | GLU | A | 177 | 9329 | 7656 | 6884 | 219 | 11 | 1 | A | C | |
| SIGUIJ | 1247 | CD | GLU | A | 177 | 1 | 0 | 0 | 220 | 81 | 290 | A | C | |
| ATOM | 1248 | OE1 | GLU | A | 177 | 27.734 | 2.734 | 22.885 | 1.00 | 33.04 | | A | O | |
| ANISOU | 1248 | OE1 | GLU | A | 177 | 10051 | 7800 | 17802 | −100 | 605 | −45 | A | O | |
| SIGUIJ | 1248 | OE1 | GLU | A | 177 | 1 | 0 | 0 | 221 | 53 | 289 | A | O | |
| ATOM | 1249 | OE2 | GLU | A | 177 | 29.309 | 4.194 | 23.498 | 1.00 | 33.04 | | A | O | |
| ANISOU | 1249 | OE2 | GLU | A | 177 | 9204 | 7747 | 6480 | 175 | 243 | 22 | A | O | |
| SIGUIJ | 1249 | OE2 | GLU | A | 177 | 1 | 0 | 0 | 221 | 53 | 289 | A | O | |
| ATOM | 1250 | C | GLU | A | 177 | 24.084 | 4.530 | 20.269 | 1.00 | 29.54 | | A | C | |
| ANISOU | 1250 | C | GLU | A | 177 | 6277 | 2685 | 7931 | −641 | −409 | −78 | A | C | |
| SIGUIJ | 1250 | C | GLU | A | 177 | 1 | 0 | 0 | 220 | 81 | 290 | A | C | |
| ATOM | 1251 | O | GLU | A | 177 | 22.911 | 4.914 | 20.319 | 1.00 | 29.57 | | A | O | |
| ANISOU | 1251 | O | GLU | A | 177 | 6388 | 3811 | 3113 | −269 | −563 | 51 | A | O | |
| SIGUIJ | 1251 | O | GLU | A | 177 | 1 | 0 | 0 | 221 | 53 | 289 | A | O | |
| ATOM | 1252 | N | ASN | A | 178 | 24.479 | 3.419 | 19.638 | 1.00 | 28.62 | | A | N | |
| ANISOU | 1252 | N | ASN | A | 178 | 9088 | 2947 | 8004 | 196 | −131 | −24 | A | N | |
| SIGUIJ | 1252 | N | ASN | A | 178 | 1 | 0 | 0 | 221 | 59 | 289 | A | N | |
| ATOM | 1253 | CA | ASN | A | 178 | 23.571 | 2.477 | 18.981 | 1.00 | 27.24 | | A | C | |
| ANISOU | 1253 | CA | ASN | A | 178 | 7592 | 3769 | 4115 | −488 | 2926 | −271 | A | C | |
| SIGUIJ | 1253 | CA | ASN | A | 178 | 1 | 0 | 0 | 220 | 81 | 290 | A | C | |
| ATOM | 1254 | CB | ASN | A | 178 | 24.352 | 1.495 | 18.067 | 1.00 | 28.13 | | A | C | |
| ANISOU | 1254 | CB | ASN | A | 178 | 6290 | 3877 | 2567 | −101 | 1381 | −56 | A | C | |
| SIGUIJ | 1254 | CB | ASN | A | 178 | 1 | 0 | 0 | 220 | 81 | 290 | A | C | |
| ATOM | 1255 | CG | ASN | A | 178 | 25.745 | 1.119 | 18.625 | 1.00 | 28.73 | | A | C | |
| ANISOU | 1255 | CG | ASN | A | 178 | 6714 | 4665 | 4896 | 81 | 458 | 19 | A | C | |
| SIGUIJ | 1255 | CG | ASN | A | 178 | 1 | 0 | 0 | 220 | 81 | 290 | A | C | |
| ATOM | 1256 | OD1 | ASN | A | 178 | 26.192 | 1.636 | 19.666 | 1.00 | 29.72 | | A | O | |
| ANISOU | 1256 | OD1 | ASN | A | 178 | 8455 | 4754 | 5214 | 23 | −259 | −2 | A | O | |
| SIGUIJ | 1256 | OD1 | ASN | A | 178 | 1 | 0 | 0 | 221 | 53 | 289 | A | O | |
| ATOM | 1257 | ND2 | ASN | A | 178 | 26.448 | 0.220 | 17.914 | 1.00 | 29.42 | | A | N | |
| ANISOU | 1257 | ND2 | ASN | A | 178 | 7350 | 5001 | 4766 | 590 | 434 | 99 | A | N | |
| SIGUIJ | 1257 | ND2 | ASN | A | 178 | 1 | 0 | 0 | 221 | 59 | 289 | A | N | |
| ATOM | 1258 | C | ASN | A | 178 | 22.775 | 1.681 | 20.016 | 1.00 | 25.77 | | A | C | |
| ANISOU | 1258 | C | ASN | A | 178 | 3575 | 3705 | 2238 | −41 | 180 | 37 | A | C | |
| SIGUIJ | 1258 | C | ASN | A | 178 | 1 | 0 | 0 | 220 | 81 | 290 | A | C | |
| ATOM | 1259 | O | ASN | A | 178 | 22.065 | 0.768 | 19.660 | 1.00 | 26.06 | | A | O | |
| ANISOU | 1259 | O | ASN | A | 178 | 7055 | 7616 | 3835 | −3753 | 2759 | −2585 | A | O | |
| SIGUIJ | 1259 | O | ASN | A | 178 | 1 | 0 | 0 | 221 | 53 | 289 | A | O | |
| ATOM | 1260 | N | SER | A | 179 | 22.896 | 2.009 | 21.299 | 1.00 | 23.67 | | A | N | |
| ANISOU | 1260 | N | SER | A | 179 | 2304 | 2817 | 2162 | −205 | 341 | 260 | A | N | |
| SIGUIJ | 1260 | N | SER | A | 179 | 1 | 0 | 0 | 221 | 59 | 289 | A | N | |
| ATOM | 1261 | CA | SER | A | 179 | 21.988 | 1.398 | 22.278 | 1.00 | 21.65 | | A | C | |
| ANISOU | 1261 | CA | SER | A | 179 | 1937 | 1871 | 1752 | 31 | 149 | −112 | A | C | |
| SIGUIJ | 1261 | CA | SER | A | 179 | 1 | 0 | 0 | 220 | 81 | 290 | A | C | |
| ATOM | 1262 | CB | SER | A | 179 | 22.760 | 0.577 | 23.301 | 1.00 | 21.87 | | A | C | |
| ANISOU | 1262 | CB | SER | A | 179 | 2977 | 2792 | 1952 | 849 | 20 | 15 | A | C | |
| SIGUIJ | 1262 | CB | SER | A | 179 | 1 | 0 | 0 | 220 | 81 | 290 | A | C | |
| ATOM | 1263 | OG | SER | A | 179 | 23.751 | 1.382 | 23.877 | 1.00 | 22.51 | | A | O | |
| ANISOU | 1263 | OG | SER | A | 179 | 3828 | 3864 | 2467 | −1 | −265 | −14 | A | O | |
| SIGUIJ | 1263 | OG | SER | A | 179 | 1 | 0 | 0 | 221 | 53 | 289 | A | O | |
| ATOM | 1264 | C | SER | A | 179 | 21.163 | 2.461 | 22.981 | 1.00 | 20.58 | | A | C | |
| ANISOU | 1264 | C | SER | A | 179 | 1866 | 1786 | 1496 | 27 | 89 | 17 | A | C | |
| SIGUIJ | 1264 | C | SER | A | 179 | 1 | 0 | 0 | 220 | 80 | 290 | A | C | |
| ATOM | 1265 | O | SER | A | 179 | 20.666 | 2.225 | 24.082 | 1.00 | 19.04 | | A | O | |
| ANISOU | 1265 | O | SER | A | 179 | 1600 | 1802 | 1451 | −24 | −42 | −1 | A | O | |
| SIGUIJ | 1265 | O | SER | A | 179 | 1 | 0 | 0 | 221 | 53 | 289 | A | O | |
| ATOM | 1266 | N | MET | A | 180 | 21.010 | 3.603 | 22.317 | 1.00 | 19.80 | | A | N | |
| ANISOU | 1266 | N | MET | A | 180 | 2051 | 1818 | 1507 | 107 | 260 | 63 | A | N | |
| SIGUIJ | 1266 | N | MET | A | 180 | 1 | 0 | 0 | 221 | 59 | 289 | A | N | |
| ATOM | 1267 | CA | MET | A | 180 | 20.080 | 4.634 | 22.752 | 1.00 | 19.86 | | A | C | |
| ANISOU | 1267 | CA | MET | A | 180 | 2142 | 1852 | 1489 | 157 | 324 | 100 | A | C | |
| SIGUIJ | 1267 | CA | MET | A | 180 | 1 | 0 | 0 | 220 | 80 | 290 | A | C | |
| ATOM | 1268 | CB | MET | A | 180 | 20.877 | 5.887 | 23.100 | 1.00 | 21.09 | | A | C | |
| ANISOU | 1268 | CB | MET | A | 180 | 2439 | 2022 | 2291 | −55 | 297 | −47 | A | C | |
| SIGUIJ | 1268 | CB | MET | A | 180 | 1 | 0 | 0 | 220 | 80 | 290 | A | C | |
| ATOM | 1269 | CG | MET | A | 180 | 21.722 | 5.649 | 24.370 | 1.00 | 22.71 | | A | C | |
| ANISOU | 1269 | CG | MET | A | 180 | 2953 | 3089 | 2523 | 123 | −22 | 2 | A | C | |
| SIGUIJ | 1269 | CG | MET | A | 180 | 1 | 0 | 0 | 220 | 80 | 290 | A | C | |
| ATOM | 1270 | SD | MET | A | 180 | 22.740 | 6.968 | 25.045 | 1.00 | 25.89 | | A | S | |
| ANISOU | 1270 | SD | MET | A | 180 | 3687 | 3461 | 4056 | −155 | −668 | −263 | A | S | |
| SIGUIJ | 1270 | SD | MET | A | 180 | 1 | 0 | 0 | 221 | 48 | 289 | A | S | |
| ATOM | 1271 | CE | MET | A | 180 | 22.682 | 8.045 | 23.918 | 1.00 | 25.18 | | A | C | |
| ANISOU | 1271 | CE | MET | A | 180 | 2232 | 3732 | 4211 | 587 | 146 | −47 | A | C | |
| SIGUIJ | 1271 | CE | MET | A | 180 | 1 | 0 | 0 | 220 | 80 | 290 | A | C | |
| ATOM | 1272 | C | MET | A | 180 | 19.024 | 4.912 | 21.679 | 1.00 | 19.33 | | A | C | |
| ANISOU | 1272 | C | MET | A | 180 | 2299 | 2089 | 1567 | 219 | 212 | 98 | A | C | |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1272 | C | MET | A | 180 | 1 | 0 | 0 | 220 | 80 | 290 | A C |
| ATOM | 1273 | O | MET | A | 180 | 19.264 | 4.704 | 20.467 | 1.00 | 18.97 | | A O |
| ANISOU | 1273 | O | MET | A | 180 | 2263 | 2650 | 1587 | 50 | 250 | −36 | A O |
| SIGUIJ | 1273 | O | MET | A | 180 | 1 | 0 | 0 | 221 | 53 | 289 | A O |
| ATOM | 1274 | N | LEU | A | 181 | 17.860 | 5.385 | 22.110 | 1.00 | 18.49 | | A N |
| ANISOU | 1274 | N | LEU | A | 181 | 2227 | 1985 | 1333 | 141 | 80 | 24 | A N |
| SIGUIJ | 1274 | N | LEU | A | 181 | 1 | 0 | 0 | 221 | 59 | 289 | A N |
| ATOM | 1275 | CA | LEU | A | 181 | 16.721 | 5.725 | 21.257 | 1.00 | 18.17 | | A C |
| ANISOU | 1275 | CA | LEU | A | 181 | 2590 | 2084 | 1818 | 292 | −347 | −155 | A C |
| SIGUIJ | 1275 | CA | LEU | A | 181 | 1 | 0 | 0 | 220 | 80 | 290 | A C |
| ATOM | 1276 | CB | LEU | A | 181 | 15.499 | 4.782 | 21.584 | 1.00 | 19.17 | | A C |
| ANISOU | 1276 | CB | LEU | A | 181 | 2887 | 2534 | 3154 | −22 | −109 | −2 | A C |
| SIGUIJ | 1276 | CB | LEU | A | 181 | 1 | 0 | 0 | 220 | 80 | 290 | A C |
| ATOM | 1277 | CG | LEU | A | 181 | 15.488 | 3.297 | 21.162 | 1.00 | 20.31 | | A C |
| ANISOU | 1277 | CG | LEU | A | 181 | 8681 | 2536 | 3196 | 113 | −741 | −13 | A C |
| SIGUIJ | 1277 | CG | LEU | A | 181 | 1 | 0 | 0 | 220 | 80 | 290 | A C |
| ATOM | 1278 | CD1 | LEU | A | 181 | 14.409 | 2.548 | 21.904 | 1.00 | 20.65 | | A C |
| ANISOU | 1278 | CD1 | LEU | A | 181 | 8500 | 1489 | 3825 | 817 | −292 | −42 | A C |
| SIGUIJ | 1278 | CD1 | LEU | A | 181 | 1 | 0 | 0 | 220 | 80 | 290 | A C |
| ATOM | 1279 | CD2 | LEU | A | 181 | 15.256 | 3.218 | 19.670 | 1.00 | 20.95 | | A C |
| ANISOU | 1279 | CD2 | LEU | A | 181 | 3788 | 3211 | 3073 | −175 | 35 | −9 | A C |
| SIGUIJ | 1279 | CD2 | LEU | A | 181 | 1 | 0 | 0 | 220 | 80 | 290 | A C |
| ATOM | 1280 | C | LEU | A | 181 | 16.361 | 7.163 | 21.654 | 1.00 | 17.15 | | A C |
| ANISOU | 1280 | C | LEU | A | 181 | 1756 | 1968 | 1299 | 14 | −130 | 7 | A C |
| SIGUIJ | 1280 | C | LEU | A | 181 | 1 | 0 | 0 | 220 | 80 | 290 | A C |
| ATOM | 1281 | O | LEU | A | 181 | 16.578 | 7.556 | 22.811 | 1.00 | 16.13 | | A O |
| ANISOU | 1281 | O | LEU | A | 181 | 2236 | 1939 | 1308 | 50 | −220 | −20 | A O |
| SIGUIJ | 1281 | O | LEU | A | 181 | 1 | 0 | 0 | 221 | 53 | 289 | A O |
| ATOM | 1282 | N | CYS | A | 182 | 15.733 | 7.938 | 20.767 | 1.00 | 15.93 | | A N |
| ANISOU | 1282 | N | CYS | A | 182 | 1636 | 1977 | 1252 | 15 | −62 | 0 | A N |
| SIGUIJ | 1282 | N | CYS | A | 182 | 1 | 0 | 0 | 221 | 59 | 289 | A N |
| ATOM | 1283 | CA | CYS | A | 182 | 14.999 | 9.120 | 21.204 | 1.00 | 15.01 | | A C |
| ANISOU | 1283 | CA | CYS | A | 182 | 1496 | 1914 | 1462 | −93 | 3 | −6 | A C |
| SIGUIJ | 1283 | CA | CYS | A | 182 | 1 | 0 | 0 | 220 | 80 | 290 | A C |
| ATOM | 1284 | C | CYS | A | 182 | 13.521 | 8.880 | 20.989 | 1.00 | 14.28 | | A C |
| ANISOU | 1284 | C | CYS | A | 182 | 1492 | 1609 | 1371 | −26 | 9 | 0 | A C |
| SIGUIJ | 1284 | C | CYS | A | 182 | 1 | 0 | 0 | 220 | 80 | 290 | A C |
| ATOM | 1285 | O | CYS | A | 182 | 13.125 | 7.915 | 20.303 | 1.00 | 13.79 | | A O |
| ANISOU | 1285 | O | CYS | A | 182 | 1842 | 1635 | 1379 | −107 | −69 | 22 | A O |
| SIGUIJ | 1285 | O | CYS | A | 182 | 1 | 0 | 0 | 221 | 53 | 289 | A O |
| ATOM | 1286 | CB | CYS | A | 182 | 15.471 | 10.364 | 20.446 | 1.00 | 15.88 | | A C |
| ANISOU | 1286 | CB | CYS | A | 182 | 1854 | 1974 | 1505 | −259 | 21 | −7 | A C |
| SIGUIJ | 1286 | CB | CYS | A | 182 | 1 | 0 | 0 | 220 | 80 | 290 | A C |
| ATOM | 1287 | SG | CYS | A | 182 | 17.179 | 10.774 | 20.933 | 1.00 | 16.61 | | A S |
| ANISOU | 1287 | SG | CYS | A | 182 | 1886 | 2331 | 1784 | −338 | −44 | −111 | A S |
| SIGUIJ | 1287 | SG | CYS | A | 182 | 1 | 0 | 0 | 221 | 48 | 289 | A S |
| ATOM | 1288 | N | ALA | A | 183 | 12.691 | 9.734 | 21.548 | 1.00 | 13.52 | | A N |
| ANISOU | 1288 | N | ALA | A | 183 | 1501 | 1611 | 1283 | 3 | −50 | 1 | A N |
| SIGUIJ | 1288 | N | ALA | A | 183 | 1 | 0 | 0 | 221 | 59 | 289 | A N |
| ATOM | 1289 | CA | ALA | A | 183 | 11.260 | 9.592 | 21.273 | 1.00 | 13.20 | | A C |
| ANISOU | 1289 | CA | ALA | A | 183 | 1517 | 1668 | 1319 | −31 | −57 | −7 | A C |
| SIGUIJ | 1289 | CA | ALA | A | 183 | 1 | 0 | 0 | 220 | 80 | 290 | A C |
| ATOM | 1290 | CB | ALA | A | 183 | 10.574 | 8.603 | 22.227 | 1.00 | 13.34 | | A C |
| ANISOU | 1290 | CB | ALA | A | 183 | 1571 | 1652 | 1389 | 1 | 13 | 0 | A C |
| SIGUIJ | 1290 | CB | ALA | A | 183 | 1 | 0 | 0 | 220 | 80 | 290 | A C |
| ATOM | 1291 | C | ALA | A | 183 | 10.599 | 10.959 | 21.446 | 1.00 | 13.39 | | A C |
| ANISOU | 1291 | C | ALA | A | 183 | 1651 | 1674 | 1264 | −5 | −1 | 0 | A C |
| SIGUIJ | 1291 | C | ALA | A | 183 | 1 | 0 | 0 | 220 | 80 | 290 | A C |
| ATOM | 1292 | O | ALA | A | 183 | 10.937 | 11.736 | 22.383 | 1.00 | 13.25 | | A O |
| ANISOU | 1292 | O | ALA | A | 183 | 1903 | 1675 | 1270 | −79 | −38 | 8 | A O |
| SIGUIJ | 1292 | O | ALA | A | 183 | 1 | 0 | 0 | 221 | 53 | 289 | A O |
| ATOM | 1293 | N | GLY | A | 184 | 9.634 | 11.249 | 20.592 | 1.00 | 13.85 | | A N |
| ANISOU | 1293 | N | GLY | A | 184 | 1692 | 1596 | 1308 | −57 | −37 | 11 | A N |
| SIGUIJ | 1293 | N | GLY | A | 184 | 1 | 0 | 0 | 221 | 59 | 289 | A N |
| ATOM | 1294 | CA | GLY | A | 184 | 8.925 | 12.512 | 20.673 | 1.00 | 14.85 | | A C |
| ANISOU | 1294 | CA | GLY | A | 184 | 1833 | 1634 | 1631 | 4 | 21 | 0 | A C |
| SIGUIJ | 1294 | CA | GLY | A | 184 | 1 | 0 | 0 | 220 | 79 | 290 | A C |
| ATOM | 1295 | C | GLY | A | 184 | 7.853 | 12.524 | 19.591 | 1.00 | 15.55 | | A C |
| ANISOU | 1295 | C | GLY | A | 184 | 1908 | 1981 | 1696 | 13 | −48 | 4 | A C |
| SIGUIJ | 1295 | C | GLY | A | 184 | 1 | 0 | 0 | 220 | 79 | 290 | A C |
| ATOM | 1296 | O | GLY | A | 184 | 7.673 | 11.534 | 18.865 | 1.00 | 15.41 | | A O |
| ANISOU | 1296 | O | GLY | A | 184 | 2337 | 1985 | 1746 | 5 | −160 | −1 | A O |
| SIGUIJ | 1296 | O | GLY | A | 184 | 1 | 0 | 0 | 221 | 53 | 289 | A O |
| ATOM | 1297 | N | ILE | A | 185 | 7.149 | 13.649 | 19.494 | 1.00 | 16.56 | | A N |
| ANISOU | 1297 | N | ILE | A | 185 | 2464 | 2162 | 1717 | 326 | −463 | −226 | A N |
| SIGUIJ | 1297 | N | ILE | A | 185 | 1 | 0 | 0 | 221 | 59 | 289 | A N |
| ATOM | 1298 | CA | ILE | A | 185 | 6.104 | 13.888 | 18.467 | 1.00 | 17.76 | | A C |
| ANISOU | 1298 | CA | ILE | A | 185 | 2356 | 1838 | 1699 | 2 | −403 | 4 | A C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1298 | CA | ILE | A | 185 | 1 | 0 | 0 | 220 | 79 | 290 | A C |
| ATOM | 1299 | CB | ILE | A | 185 | 4.737 | 14.077 | 19.163 | 1.00 | 18.05 | | A C |
| ANISOU | 1299 | CB | ILE | A | 185 | 2558 | 1913 | 2521 | 8 | 4 | 0 | A C |
| SIGUIJ | 1299 | CB | ILE | A | 185 | 1 | 0 | 0 | 220 | 79 | 290 | A C |
| ATOM | 1300 | CG2 | ILE | A | 185 | 3.671 | 14.450 | 18.160 | 1.00 | 18.41 | | A C |
| ANISOU | 1300 | CG2 | ILE | A | 185 | 2592 | 2147 | 2532 | 91 | −4 | −3 | A C |
| SIGUIJ | 1300 | CG2 | ILE | A | 185 | 1 | 0 | 0 | 220 | 79 | 290 | A C |
| ATOM | 1301 | CG1 | ILE | A | 185 | 4.303 | 12.782 | 19.873 | 1.00 | 18.24 | | A C |
| ANISOU | 1301 | CG1 | ILE | A | 185 | 2702 | 1937 | 2551 | −42 | 10 | −1 | A C |
| SIGUIJ | 1301 | CG1 | ILE | A | 185 | 1 | 0 | 0 | 220 | 79 | 290 | A C |
| ATOM | 1302 | CD1 | ILE | A | 185 | 3.986 | 11.644 | 18.904 | 1.00 | 18.38 | | A C |
| ANISOU | 1302 | CD1 | ILE | A | 185 | 2395 | 1924 | 2566 | 48 | 6 | −1 | A C |
| SIGUIJ | 1302 | CD1 | ILE | A | 185 | 1 | 0 | 0 | 220 | 79 | 290 | A C |
| ATOM | 1303 | C | ILE | A | 185 | 6.528 | 15.183 | 17.749 | 1.00 | 18.58 | | A C |
| ANISOU | 1303 | C | ILE | A | 185 | 2666 | 1856 | 1746 | −36 | −310 | 13 | A C |
| SIGUIJ | 1303 | C | ILE | A | 185 | 1 | 0 | 0 | 220 | 79 | 290 | A C |
| ATOM | 1304 | O | ILE | A | 185 | 6.793 | 16.151 | 18.408 | 1.00 | 18.04 | | A O |
| ANISOU | 1304 | O | ILE | A | 185 | 2616 | 1851 | 1719 | −26 | −305 | 5 | A O |
| SIGUIJ | 1304 | O | ILE | A | 185 | 1 | 0 | 0 | 221 | 53 | 289 | A O |
| ATOM | 1305 | N | PRO | A | 186 | 6.597 | 15.196 | 16.397 | 1.00 | 19.42 | | A N |
| ANISOU | 1305 | N | PRO | A | 186 | 3006 | 2554 | 1750 | −76 | −290 | 29 | A N |
| SIGUIJ | 1305 | N | PRO | A | 186 | 1 | 0 | 0 | 221 | 59 | 289 | A N |
| ATOM | 1306 | CD | PRO | A | 186 | 6.278 | 14.129 | 15.430 | 1.00 | 20.02 | | A C |
| ANISOU | 1306 | CD | PRO | A | 186 | 2736 | 2594 | 1854 | 50 | −335 | −53 | A C |
| SIGUIJ | 1306 | CD | PRO | A | 186 | 1 | 0 | 0 | 220 | 79 | 290 | A C |
| ATOM | 1307 | CA | PRO | A | 186 | 6.974 | 16.437 | 15.725 | 1.00 | 20.07 | | A C |
| ANISOU | 1307 | CA | PRO | A | 186 | 3182 | 2600 | 1801 | −148 | −318 | 58 | A C |
| SIGUIJ | 1307 | CA | PRO | A | 186 | 1 | 0 | 0 | 220 | 79 | 290 | A C |
| ATOM | 1308 | CB | PRO | A | 186 | 6.710 | 16.142 | 14.252 | 1.00 | 20.37 | | A C |
| ANISOU | 1308 | CB | PRO | A | 186 | 3572 | 2807 | 1829 | −63 | −404 | 17 | A C |
| SIGUIJ | 1308 | CB | PRO | A | 186 | 1 | 0 | 0 | 220 | 79 | 290 | A C |
| ATOM | 1309 | CG | PRO | A | 186 | 6.669 | 14.734 | 14.124 | 1.00 | 20.70 | | A C |
| ANISOU | 1309 | CG | PRO | A | 186 | 3533 | 2812 | 1940 | −80 | −155 | 12 | A C |
| SIGUIJ | 1309 | CG | PRO | A | 186 | 1 | 0 | 0 | 220 | 79 | 290 | A C |
| ATOM | 1310 | C | PRO | A | 186 | 6.142 | 17.609 | 16.194 | 1.00 | 20.31 | | A C |
| ANISOU | 1310 | C | PRO | A | 186 | 3182 | 2629 | 1658 | −114 | −395 | 61 | A C |
| SIGUIJ | 1310 | C | PRO | A | 186 | 1 | 0 | 0 | 220 | 79 | 290 | A C |
| ATOM | 1311 | O | PRO | A | 186 | 4.904 | 17.527 | 16.318 | 1.00 | 20.36 | | A O |
| ANISOU | 1311 | O | PRO | A | 186 | 3187 | 2274 | 2361 | −89 | −328 | 31 | A O |
| SIGUIJ | 1311 | O | PRO | A | 186 | 1 | 0 | 0 | 221 | 53 | 289 | A O |
| ATOM | 1312 | N | ASP | A | 186A | 6.835 | 18.715 | 16.417 | 1.00 | 20.72 | | A N |
| ANISOU | 1312 | N | ASP | A | 186A | 2899 | 2555 | 1610 | 28 | −240 | −8 | A N |
| SIGUIJ | 1312 | N | ASP | A | 186A | 1 | 0 | 0 | 221 | 59 | 289 | A N |
| ATOM | 1313 | CA | ASP | A | 186A | 6.237 | 19.998 | 16.786 | 1.00 | 21.18 | | A C |
| ANISOU | 1313 | CA | ASP | A | 186A | 3476 | 2730 | 1801 | 334 | −321 | −97 | A C |
| SIGUIJ | 1313 | CA | ASP | A | 186A | 1 | 0 | 0 | 220 | 79 | 290 | A C |
| ATOM | 1314 | CB | ASP | A | 186A | 5.366 | 20.539 | 15.625 | 1.00 | 22.27 | | A C |
| ANISOU | 1314 | CB | ASP | A | 186A | 3473 | 2376 | 2017 | −90 | −517 | 40 | A C |
| SIGUIJ | 1314 | CB | ASP | A | 186A | 1 | 0 | 0 | 220 | 79 | 290 | A C |
| ATOM | 1315 | CG | ASP | A | 186A | 6.156 | 20.717 | 14.355 | 1.00 | 23.43 | | A C |
| ANISOU | 1315 | CG | ASP | A | 186A | 4196 | 5781 | 2219 | −920 | −183 | −4 | A C |
| SIGUIJ | 1315 | CG | ASP | A | 186A | 1 | 0 | 0 | 220 | 79 | 290 | A C |
| ATOM | 1316 | OD1 | ASP | A | 186A | 7.288 | 21.218 | 14.437 | 1.00 | 24.41 | | A O |
| ANISOU | 1316 | OD1 | ASP | A | 186A | 3792 | 3691 | 2398 | 5 | −194 | −5 | A O |
| SIGUIJ | 1316 | OD1 | ASP | A | 186A | 1 | 0 | 0 | 221 | 53 | 289 | A O |
| ATOM | 1317 | OD2 | ASP | A | 186A | 5.653 | 20.326 | 13.272 | 1.00 | 24.75 | | A O |
| ANISOU | 1317 | OD2 | ASP | A | 186A | 4673 | 6813 | 2176 | −1755 | −103 | 11 | A O |
| SIGUIJ | 1317 | OD2 | ASP | A | 186A | 1 | 0 | 0 | 221 | 53 | 289 | A O |
| ATOM | 1318 | C | ASP | A | 186A | 5.451 | 19.972 | 18.087 | 1.00 | 20.78 | | A C |
| ANISOU | 1318 | C | ASP | A | 186A | 3914 | 2229 | 1960 | 518 | −45 | −12 | A C |
| SIGUIJ | 1318 | C | ASP | A | 186A | 1 | 0 | 0 | 220 | 79 | 290 | A C |
| ATOM | 1319 | O | ASP | A | 186A | 4.604 | 20.805 | 18.310 | 1.00 | 21.16 | | A O |
| ANISOU | 1319 | O | ASP | A | 186A | 4445 | 2561 | 3025 | 917 | 499 | 248 | A O |
| SIGUIJ | 1319 | O | ASP | A | 186A | 1 | 0 | 0 | 221 | 53 | 289 | A O |
| ATOM | 1320 | N | SER | A | 186B | 5.743 | 18.996 | 18.957 | 1.00 | 19.72 | | A N |
| ANISOU | 1320 | N | SER | A | 186B | 2709 | 2092 | 2003 | 20 | −197 | −6 | A N |
| SIGUIJ | 1320 | N | SER | A | 186B | 1 | 0 | 0 | 221 | 59 | 289 | A N |
| ATOM | 1321 | CA | SER | A | 186B | 5.029 | 18.811 | 20.224 | 1.00 | 19.06 | | A C |
| ANISOU | 1321 | CA | SER | A | 186B | 2776 | 2401 | 2023 | −28 | −167 | 9 | A C |
| SIGUIJ | 1321 | CA | SER | A | 186B | 1 | 0 | 0 | 220 | 79 | 290 | A C |
| ATOM | 1322 | CB | SER | A | 186B | 4.333 | 17.456 | 20.205 | 1.00 | 18.95 | | A C |
| ANISOU | 1322 | CB | SER | A | 186B | 2800 | 2411 | 1927 | −39 | −165 | 11 | A C |
| SIGUIJ | 1322 | CB | SER | A | 186B | 1 | 0 | 0 | 220 | 78 | 290 | A C |
| ATOM | 1323 | OG | SER | A | 186B | 3.828 | 17.155 | 21.492 | 1.00 | 18.85 | | A O |
| ANISOU | 1323 | OG | SER | A | 186B | 2384 | 2464 | 1874 | 7 | −315 | 30 | A O |
| SIGUIJ | 1323 | OG | SER | A | 186B | 1 | 0 | 0 | 221 | 53 | 289 | A O |
| ATOM | 1324 | C | SER | A | 186B | 5.994 | 18.854 | 21.391 | 1.00 | 18.39 | | A C |
| ANISOU | 1324 | C | SER | A | 186B | 2588 | 1709 | 1908 | 5 | −14 | 0 | A C |

TABLE 3-continued

Three-dimensional structure of the new binding pocket of kallikrein 7

| Record | Serial | Atom | Res | Chain | SeqNum | X/U11 | Y/U22 | Z/U33 | Occ/U12 | B/U13 | U23 | Chain2 | Element |
|---|---|---|---|---|---|---|---|---|---|---|---|---|---|
| SIGUIJ | 1324 | C | SER | A | 186B | 1 | 0 | 0 | 220 | 78 | 290 | A | C |
| ATOM | 1325 | O | SER | A | 186B | 7.143 | 18.478 | 21.244 | 1.00 | 18.48 | | A | O |
| ANISOU | 1325 | O | SER | A | 186B | 2650 | 2316 | 1988 | 202 | 7 | 3 | A | O |
| SIGUIJ | 1325 | O | SER | A | 186B | 1 | 0 | 0 | 221 | 53 | 289 | A | O |
| ATOM | 1326 | N | ALYS | A | 187 | 5.507 | 19.319 | 22.529 | 0.50 | 17.77 | | A | N |
| ANISOU | 1326 | N | ALYS | A | 187 | 2220 | 1630 | 1851 | −45 | −152 | 14 | A | N |
| SIGUIJ | 1326 | N | ALYS | A | 187 | 1 | 0 | 0 | 221 | 59 | 289 | A | N |
| ATOM | 1327 | N | BLYS | A | 187 | 5.484 | 19.331 | 22.525 | 0.50 | 19.96 | | A | N |
| ANISOU | 1327 | N | BLYS | A | 187 | 2234 | 1592 | 1840 | −71 | −148 | 20 | A | N |
| SIGUIJ | 1327 | N | BLYS | A | 187 | 1 | 0 | 0 | 221 | 59 | 289 | A | N |
| ATOM | 1328 | CA | ALYS | A | 187 | 6.284 | 19.355 | 23.760 | 0.50 | 17.28 | | A | C |
| ANISOU | 1328 | CA | ALYS | A | 187 | 2079 | 1412 | 1804 | −41 | −68 | 9 | A | C |
| SIGUIJ | 1328 | CA | ALYS | A | 187 | 1 | 0 | 0 | 220 | 78 | 290 | A | C |
| ATOM | 1329 | CA | BLYS | A | 187 | 6.185 | 19.396 | 23.809 | 0.50 | 19.47 | | A | C |
| ANISOU | 1329 | CA | BLYS | A | 187 | 2711 | 1446 | 1981 | −143 | −407 | 64 | A | C |
| SIGUIJ | 1329 | CA | BLYS | A | 187 | 1 | 0 | 0 | 220 | 78 | 290 | A | C |
| ATOM | 1330 | CB | ALYS | A | 187 | 5.712 | 20.431 | 24.683 | 0.50 | 18.41 | | A | C |
| ANISOU | 1330 | CB | ALYS | A | 187 | 2400 | 1530 | 1834 | 140 | −77 | −15 | A | C |
| SIGUIJ | 1330 | CB | ALYS | A | 187 | 1 | 0 | 0 | 220 | 78 | 290 | A | C |
| ATOM | 1331 | CB | BLYS | A | 187 | 5.424 | 20.327 | 24.777 | 0.50 | 20.60 | | A | C |
| ANISOU | 1331 | CB | BLYS | A | 187 | 3766 | 1779 | 2431 | 192 | 99 | 11 | A | C |
| SIGUIJ | 1331 | CB | BLYS | A | 187 | 1 | 0 | 0 | 220 | 78 | 290 | A | C |
| ATOM | 1332 | CG | ALYS | A | 187 | 5.737 | 21.819 | 24.058 | 0.50 | 19.76 | | A | C |
| ANISOU | 1332 | CG | ALYS | A | 187 | 3743 | 1555 | 1933 | −99 | −559 | 28 | A | C |
| SIGUIJ | 1332 | CG | ALYS | A | 187 | 1 | 0 | 0 | 220 | 78 | 290 | A | C |
| ATOM | 1333 | CG | BLYS | A | 187 | 5.329 | 21.812 | 24.398 | 0.50 | 21.95 | | A | C |
| ANISOU | 1333 | CG | BLYS | A | 187 | 3097 | 1767 | 2428 | 67 | −200 | −8 | A | C |
| SIGUIJ | 1333 | CG | BLYS | A | 187 | 1 | 0 | 0 | 220 | 78 | 290 | A | C |
| ATOM | 1334 | CD | ALYS | A | 187 | 5.202 | 22.885 | 25.007 | 0.50 | 21.54 | | A | C |
| ANISOU | 1334 | CD | ALYS | A | 187 | 6093 | 1801 | 2387 | 382 | 223 | 21 | A | C |
| SIGUIJ | 1334 | CD | ALYS | A | 187 | 1 | 0 | 0 | 220 | 78 | 290 | A | C |
| ATOM | 1335 | CD | BLYS | A | 187 | 4.571 | 22.614 | 25.506 | 0.50 | 23.73 | | A | C |
| ANISOU | 1335 | CD | BLYS | A | 187 | 5177 | 3591 | 2541 | 1906 | −108 | −75 | A | C |
| SIGUIJ | 1335 | CD | BLYS | A | 187 | 1 | 0 | 0 | 220 | 78 | 290 | A | C |
| ATOM | 1336 | CE | ALYS | A | 187 | 5.691 | 24.276 | 24.602 | 0.50 | 22.22 | | A | C |
| ANISOU | 1336 | CE | ALYS | A | 187 | 9106 | 2124 | 2521 | −591 | 519 | −45 | A | C |
| SIGUIJ | 1336 | CE | ALYS | A | 187 | 1 | 0 | 0 | 220 | 78 | 290 | A | C |
| ATOM | 1337 | CE | BLYS | A | 187 | 4.688 | 24.148 | 25.345 | 0.50 | 24.41 | | A | C |
| ANISOU | 1337 | CE | BLYS | A | 187 | 13777 | 3655 | 5721 | 1369 | 1007 | 152 | A | C |
| SIGUIJ | 1337 | CE | BLYS | A | 187 | 1 | 0 | 0 | 220 | 78 | 290 | A | C |
| ATOM | 1338 | NZ | ALYS | A | 187 | 5.364 | 25.307 | 25.640 | 0.50 | 23.45 | | A | N |
| ANISOU | 1338 | NZ | ALYS | A | 187 | 14140 | 2203 | 3005 | −445 | 1960 | −75 | A | N |
| SIGUIJ | 1338 | NZ | ALYS | A | 187 | 1 | 0 | 0 | 221 | 59 | 289 | A | N |
| ATOM | 1339 | NZ | BLYS | A | 187 | 4.207 | 24.944 | 26.534 | 0.50 | 25.64 | | A | N |
| ANISOU | 1339 | NZ | BLYS | A | 187 | 13596 | 3934 | 5596 | 1778 | 657 | 131 | A | N |
| SIGUIJ | 1339 | NZ | BLYS | A | 187 | 1 | 0 | 0 | 221 | 59 | 289 | A | N |
| ATOM | 1340 | C | ALYS | A | 187 | 6.360 | 18.024 | 24.520 | 0.50 | 16.33 | | A | C |
| ANISOU | 1340 | C | ALYS | A | 187 | 1924 | 1408 | 1780 | −22 | 1 | 0 | A | C |
| SIGUIJ | 1340 | C | ALYS | A | 187 | 1 | 0 | 0 | 220 | 78 | 290 | A | C |
| ATOM | 1341 | C | BLYS | A | 187 | 6.353 | 18.034 | 24.512 | 0.50 | 18.52 | | A | C |
| ANISOU | 1341 | C | BLYS | A | 187 | 1939 | 1424 | 1764 | −37 | −3 | 1 | A | C |
| SIGUIJ | 1341 | C | BLYS | A | 187 | 1 | 0 | 0 | 220 | 78 | 290 | A | C |
| ATOM | 1342 | O | ALYS | A | 187 | 7.132 | 17.917 | 25.480 | 0.50 | 16.34 | | A | O |
| ANISOU | 1342 | O | ALYS | A | 187 | 1933 | 1749 | 1779 | 5 | −3 | 0 | A | O |
| SIGUIJ | 1342 | O | ALYS | A | 187 | 1 | 0 | 0 | 221 | 53 | 289 | A | O |
| ATOM | 1343 | O | BLYS | A | 187 | 7.177 | 17.917 | 25.426 | 0.50 | 18.53 | | A | O |
| ANISOU | 1343 | O | BLYS | A | 187 | 1942 | 1736 | 1762 | 0 | −4 | 0 | A | O |
| SIGUIJ | 1343 | O | BLYS | A | 187 | 1 | 0 | 0 | 221 | 53 | 289 | A | O |
| ATOM | 1344 | N | LYS | A | 188 | 5.557 | 17.033 | 24.125 | 1.00 | 14.96 | | A | N |
| ANISOU | 1344 | N | LYS | A | 188 | 1853 | 1363 | 1774 | 29 | 3 | 1 | A | N |
| SIGUIJ | 1344 | N | LYS | A | 188 | 1 | 0 | 0 | 221 | 59 | 289 | A | N |
| ATOM | 1345 | CA | LYS | A | 188 | 5.442 | 15.771 | 24.874 | 1.00 | 14.02 | | A | C |
| ANISOU | 1345 | CA | LYS | A | 188 | 1589 | 1366 | 1791 | 10 | −67 | 4 | A | C |
| SIGUIJ | 1345 | CA | LYS | A | 188 | 1 | 0 | 0 | 220 | 78 | 290 | A | C |
| ATOM | 1346 | CB | LYS | A | 188 | 4.549 | 14.803 | 24.081 | 1.00 | 14.14 | | A | C |
| ANISOU | 1346 | CB | LYS | A | 188 | 1573 | 1402 | 1780 | −10 | −36 | 0 | A | C |
| SIGUIJ | 1346 | CB | LYS | A | 188 | 1 | 0 | 0 | 220 | 78 | 290 | A | C |
| ATOM | 1347 | CG | LYS | A | 188 | 3.093 | 15.262 | 24.107 | 1.00 | 14.83 | | A | C |
| ANISOU | 1347 | CG | LYS | A | 188 | 1593 | 1677 | 1895 | 69 | −48 | 19 | A | C |
| SIGUIJ | 1347 | CG | LYS | A | 188 | 1 | 0 | 0 | 220 | 78 | 290 | A | C |
| ATOM | 1348 | CD | LYS | A | 188 | 2.268 | 14.487 | 23.118 | 1.00 | 16.07 | | A | C |
| ANISOU | 1348 | CD | LYS | A | 188 | 1835 | 1920 | 2045 | −56 | −162 | −51 | A | C |
| SIGUIJ | 1348 | CD | LYS | A | 188 | 1 | 0 | 0 | 220 | 78 | 290 | A | C |
| ATOM | 1349 | CE | LYS | A | 188 | 0.771 | 14.891 | 23.168 | 1.00 | 16.84 | | A | C |
| ANISOU | 1349 | CE | LYS | A | 188 | 1864 | 2302 | 2691 | 47 | −123 | 10 | A | C |
| SIGUIJ | 1349 | CE | LYS | A | 188 | 1 | 0 | 0 | 220 | 78 | 290 | A | C |
| ATOM | 1350 | NZ | LYS | A | 188 | 0.149 | 14.611 | 24.457 | 1.00 | 18.97 | | A | N |
| ANISOU | 1350 | NZ | LYS | A | 188 | 2285 | 2681 | 2766 | −116 | 36 | 9 | A | N |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1350 | NZ | LYS | A | 188 | 1 | 0 | 0 | 221 | 59 | 289 | A | N |
| ATOM | 1351 | C | LYS | A | 188 | 6.825 | 15.159 | 25.109 | 1.00 | 13.21 | | A | C |
| ANISOU | 1351 | C | LYS | A | 188 | 1592 | 1396 | 1314 | 28 | 3 | 0 | A | C |
| SIGUIJ | 1351 | C | LYS | A | 188 | 1 | 0 | 0 | 220 | 77 | 290 | A | C |
| ATOM | 1352 | O | LYS | A | 188 | 7.611 | 14.950 | 24.182 | 1.00 | 12.89 | | A | O |
| ANISOU | 1352 | O | LYS | A | 188 | 1598 | 1827 | 1295 | 135 | −25 | −1 | A | O |
| SIGUIJ | 1352 | O | LYS | A | 188 | 1 | 0 | 0 | 221 | 53 | 289 | A | O |
| ATOM | 1353 | N | ASN | A | 189 | 7.106 | 14.821 | 26.360 | 1.00 | 12.05 | | A | N |
| ANISOU | 1353 | N | ASN | A | 189 | 1493 | 1287 | 1305 | −33 | 15 | −2 | A | N |
| SIGUIJ | 1353 | N | ASN | A | 189 | 1 | 0 | 0 | 221 | 59 | 289 | A | N |
| ATOM | 1354 | CA | ASN | A | 189 | 8.442 | 14.336 | 26.726 | 1.00 | 11.64 | | A | C |
| ANISOU | 1354 | CA | ASN | A | 189 | 1506 | 1290 | 1360 | −27 | −13 | 2 | A | C |
| SIGUIJ | 1354 | CA | ASN | A | 189 | 1 | 0 | 0 | 220 | 77 | 290 | A | C |
| ATOM | 1355 | CB | ASN | A | 189 | 9.451 | 15.474 | 26.529 | 1.00 | 11.73 | | A | C |
| ANISOU | 1355 | CB | ASN | A | 189 | 1504 | 1272 | 1391 | −11 | −9 | 1 | A | C |
| SIGUIJ | 1355 | CB | ASN | A | 189 | 1 | 0 | 0 | 220 | 77 | 290 | A | C |
| ATOM | 1356 | CG | ASN | A | 189 | 10.808 | 15.004 | 26.122 | 1.00 | 12.45 | | A | C |
| ANISOU | 1356 | CG | ASN | A | 189 | 1520 | 1412 | 1302 | 30 | −41 | −8 | A | C |
| SIGUIJ | 1356 | CG | ASN | A | 189 | 1 | 0 | 0 | 220 | 77 | 290 | A | C |
| ATOM | 1357 | OD1 | ASN | A | 189 | 11.230 | 13.842 | 26.358 | 1.00 | 11.93 | | A | O |
| ANISOU | 1357 | OD1 | ASN | A | 189 | 1572 | 1450 | 1292 | 100 | 121 | 51 | A | O |
| SIGUIJ | 1357 | OD1 | ASN | A | 189 | 1 | 0 | 0 | 221 | 53 | 289 | A | O |
| ATOM | 1358 | ND2 | ASN | A | 189 | 11.548 | 15.934 | 25.501 | 1.00 | 13.28 | | A | N |
| ANISOU | 1358 | ND2 | ASN | A | 189 | 1956 | 1491 | 1618 | −105 | 270 | −58 | A | N |
| SIGUIJ | 1358 | ND2 | ASN | A | 189 | 1 | 0 | 0 | 221 | 59 | 289 | A | N |
| ATOM | 1359 | C | ASN | A | 189 | 8.442 | 13.848 | 28.184 | 1.00 | 11.46 | | A | C |
| ANISOU | 1359 | C | ASN | A | 189 | 1489 | 1279 | 1365 | 57 | 8 | 3 | A | C |
| SIGUIJ | 1359 | C | ASN | A | 189 | 1 | 0 | 0 | 220 | 77 | 290 | A | C |
| ATOM | 1360 | O | ASN | A | 189 | 7.460 | 14.017 | 28.885 | 1.00 | 11.18 | | A | O |
| ANISOU | 1360 | O | ASN | A | 189 | 1475 | 1295 | 1383 | 83 | 3 | 2 | A | O |
| SIGUIJ | 1360 | O | ASN | A | 189 | 1 | 0 | 0 | 221 | 53 | 289 | A | O |
| ATOM | 1361 | N | ALA | A | 190 | 9.588 | 13.320 | 28.631 | 1.00 | 11.38 | | A | N |
| ANISOU | 1361 | N | ALA | A | 190 | 1480 | 1239 | 1397 | 41 | −4 | −1 | A | N |
| SIGUIJ | 1361 | N | ALA | A | 190 | 1 | 0 | 0 | 221 | 59 | 289 | A | N |
| ATOM | 1362 | CA | ALA | A | 190 | 9.839 | 13.028 | 30.026 | 1.00 | 11.34 | | A | C |
| ANISOU | 1362 | CA | ALA | A | 190 | 1428 | 1218 | 1403 | 114 | 4 | 6 | A | C |
| SIGUIJ | 1362 | CA | ALA | A | 190 | 1 | 0 | 0 | 220 | 77 | 290 | A | C |
| ATOM | 1363 | CB | ALA | A | 190 | 10.695 | 11.762 | 30.129 | 1.00 | 11.42 | | A | C |
| ANISOU | 1363 | CB | ALA | A | 190 | 1576 | 1290 | 1506 | 220 | 6 | 7 | A | C |
| SIGUIJ | 1363 | CB | ALA | A | 190 | 1 | 0 | 0 | 220 | 77 | 290 | A | C |
| ATOM | 1364 | C | ALA | A | 190 | 10.590 | 14.233 | 30.624 | 1.00 | 11.69 | | A | C |
| ANISOU | 1364 | C | ALA | A | 190 | 1447 | 1216 | 1552 | 114 | −8 | 4 | A | C |
| SIGUIJ | 1364 | C | ALA | A | 190 | 1 | 0 | 0 | 220 | 77 | 290 | A | C |
| ATOM | 1365 | O | ALA | A | 190 | 11.000 | 15.193 | 29.874 | 1.00 | 12.39 | | A | O |
| ANISOU | 1365 | O | ALA | A | 190 | 1837 | 1276 | 1616 | 5 | 44 | 2 | A | O |
| SIGUIJ | 1365 | O | ALA | A | 190 | 1 | 0 | 0 | 221 | 53 | 289 | A | O |
| ATOM | 1366 | N | CYS | A | 191 | 10.750 | 14.233 | 31.946 | 1.00 | 11.81 | | A | N |
| ANISOU | 1366 | N | CYS | A | 191 | 1490 | 1103 | 1564 | 9 | 2 | 0 | A | N |
| SIGUIJ | 1366 | N | CYS | A | 191 | 1 | 0 | 0 | 221 | 59 | 289 | A | N |
| ATOM | 1367 | CA | CYS | A | 191 | 11.495 | 15.320 | 32.611 | 1.00 | 11.91 | | A | C |
| ANISOU | 1367 | CA | CYS | A | 191 | 1544 | 1111 | 1703 | −2 | −39 | −5 | A | C |
| SIGUIJ | 1367 | CA | CYS | A | 191 | 1 | 0 | 0 | 220 | 77 | 290 | A | C |
| ATOM | 1368 | C | CYS | A | 191 | 12.036 | 14.793 | 33.944 | 1.00 | 11.80 | | A | C |
| ANISOU | 1368 | C | CYS | A | 191 | 1214 | 1167 | 1666 | 0 | 100 | 4 | A | C |
| SIGUIJ | 1368 | C | CYS | A | 191 | 1 | 0 | 0 | 220 | 77 | 290 | A | C |
| ATOM | 1369 | O | CYS | A | 191 | 12.040 | 13.570 | 34.192 | 1.00 | 11.71 | | A | O |
| ANISOU | 1369 | O | CYS | A | 191 | 1357 | 1171 | 1607 | −38 | −73 | 0 | A | O |
| SIGUIJ | 1369 | O | CYS | A | 191 | 1 | 0 | 0 | 221 | 53 | 289 | A | O |
| ATOM | 1370 | CB | CYS | A | 191 | 10.575 | 16.562 | 32.752 | 1.00 | 12.54 | | A | C |
| ANISOU | 1370 | CB | CYS | A | 191 | 1730 | 1191 | 2157 | 120 | 41 | −2 | A | C |
| SIGUIJ | 1370 | CB | CYS | A | 191 | 1 | 0 | 0 | 220 | 77 | 290 | A | C |
| ATOM | 1371 | SG | CYS | A | 191 | 11.386 | 18.128 | 33.252 | 1.00 | 13.85 | | A | S |
| ANISOU | 1371 | SG | CYS | A | 191 | 1970 | 1270 | 1902 | −56 | 194 | 24 | A | S |
| SIGUIJ | 1371 | SG | CYS | A | 191 | 1 | 0 | 0 | 221 | 48 | 289 | A | S |
| ATOM | 1372 | N | AASN | A | 192 | 12.570 | 15.687 | 34.798 | 0.50 | 11.82 | | A | N |
| ANISOU | 1372 | N | AASN | A | 192 | 1408 | 1193 | 1734 | −56 | 26 | −1 | A | N |
| SIGUIJ | 1372 | N | AASN | A | 192 | 1 | 0 | 0 | 221 | 59 | 289 | A | N |
| ATOM | 1373 | N | BASN | A | 192 | 12.568 | 15.696 | 34.795 | 0.50 | 14.01 | | A | N |
| ANISOU | 1373 | N | BASN | A | 192 | 1391 | 1189 | 1728 | −42 | 28 | −1 | A | N |
| SIGUIJ | 1373 | N | BASN | A | 192 | 1 | 0 | 0 | 221 | 59 | 289 | A | N |
| ATOM | 1374 | CA | AASN | A | 192 | 13.201 | 15.266 | 36.067 | 0.50 | 12.62 | | A | C |
| ANISOU | 1374 | CA | AASN | A | 192 | 1420 | 1257 | 1736 | 20 | 48 | 5 | A | C |
| SIGUIJ | 1374 | CA | AASN | A | 192 | 1 | 0 | 0 | 220 | 77 | 290 | A | C |
| ATOM | 1375 | CA | BASN | A | 192 | 13.225 | 15.299 | 36.063 | 0.50 | 14.81 | | A | C |
| ANISOU | 1375 | CA | BASN | A | 192 | 1374 | 1279 | 1725 | 12 | 59 | 5 | A | C |
| SIGUIJ | 1375 | CA | BASN | A | 192 | 1 | 0 | 0 | 220 | 77 | 290 | A | C |
| ATOM | 1376 | CB | AASN | A | 192 | 13.672 | 16.443 | 36.931 | 0.50 | 15.37 | | A | C |
| ANISOU | 1376 | CB | AASN | A | 192 | 2253 | 1352 | 1788 | −236 | −36 | 13 | A | C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1376 | CB | AASN | A | 192 | 1 | 0 | 0 | 220 | 77 | 290 | A C |
| ATOM | 1377 | CB | BASN | A | 192 | 13.644 | 16.494 | 36.969 | 0.50 | 17.56 | | A C |
| ANISOU | 1377 | CB | BASN | A | 192 | 6809 | 1617 | 1888 | −1290 | −736 | 178 | A C |
| SIGUIJ | 1377 | CB | BASN | A | 192 | 1 | 0 | 0 | 220 | 77 | 290 | A C |
| ATOM | 1378 | CG | AASN | A | 192 | 14.769 | 17.215 | 36.280 | 0.50 | 17.74 | | A C |
| ANISOU | 1378 | CG | AASN | A | 192 | 2339 | 1369 | 1933 | −271 | 65 | −28 | A C |
| SIGUIJ | 1378 | CG | AASN | A | 192 | 1 | 0 | 0 | 220 | 77 | 290 | A C |
| ATOM | 1379 | CG | BASN | A | 192 | 13.934 | 17.777 | 36.193 | 0.50 | 19.93 | | A C |
| ANISOU | 1379 | CG | BASN | A | 192 | 3989 | 1283 | 1874 | −239 | −50 | 5 | A C |
| SIGUIJ | 1379 | CG | BASN | A | 192 | 1 | 0 | 0 | 220 | 77 | 290 | A C |
| ATOM | 1380 | OD1 | AASN | A | 192 | 14.522 | 18.106 | 35.442 | 0.50 | 19.81 | | A O |
| ANISOU | 1380 | OD1 | AASN | A | 192 | 3003 | 1423 | 2051 | −256 | −107 | 24 | A O |
| SIGUIJ | 1380 | OD1 | AASN | A | 192 | 1 | 0 | 0 | 221 | 53 | 289 | A O |
| ATOM | 1381 | OD1 | BASN | A | 192 | 15.078 | 18.232 | 36.121 | 0.50 | 22.00 | | A O |
| ANISOU | 1381 | OD1 | BASN | A | 192 | 4514 | 4570 | 2567 | −1549 | 5 | −5 | A O |
| SIGUIJ | 1381 | OD1 | BASN | A | 192 | 1 | 0 | 0 | 221 | 53 | 289 | A O |
| ATOM | 1382 | ND2 | AASN | A | 192 | 16.007 | 16.879 | 36.631 | 0.50 | 19.13 | | A N |
| ANISOU | 1382 | ND2 | AASN | A | 192 | 2368 | 1614 | 2078 | −206 | 19 | −9 | A N |
| SIGUIJ | 1382 | ND2 | AASN | A | 192 | 1 | 0 | 0 | 221 | 59 | 289 | A N |
| ATOM | 1383 | ND2 | BASN | A | 192 | 12.905 | 18.355 | 35.601 | 0.50 | 21.32 | | A N |
| ANISOU | 1383 | ND2 | BASN | A | 192 | 4270 | 1309 | 2842 | −265 | −567 | 76 | A N |
| SIGUIJ | 1383 | ND2 | BASN | A | 192 | 1 | 0 | 0 | 221 | 59 | 289 | A N |
| ATOM | 1384 | C | AASN | A | 192 | 12.264 | 14.462 | 36.903 | 0.50 | 11.77 | | A C |
| ANISOU | 1384 | C | AASN | A | 192 | 1267 | 1262 | 1531 | −1 | −132 | −5 | A C |
| SIGUIJ | 1384 | C | AASN | A | 192 | 1 | 0 | 0 | 220 | 77 | 290 | A C |
| ATOM | 1385 | C | BASN | A | 192 | 12.277 | 14.470 | 36.887 | 0.50 | 13.96 | | A C |
| ANISOU | 1385 | C | BASN | A | 192 | 1223 | 1263 | 1484 | −7 | −135 | −8 | A C |
| SIGUIJ | 1385 | C | BASN | A | 192 | 1 | 0 | 0 | 220 | 77 | 290 | A C |
| ATOM | 1386 | O | AASN | A | 192 | 11.125 | 14.863 | 37.169 | 0.50 | 12.07 | | A O |
| ANISOU | 1386 | O | AASN | A | 192 | 1291 | 1266 | 1846 | 0 | −49 | 0 | A O |
| SIGUIJ | 1386 | O | AASN | A | 192 | 1 | 0 | 0 | 221 | 53 | 289 | A O |
| ATOM | 1387 | O | BASN | A | 192 | 11.130 | 14.866 | 37.118 | 0.50 | 14.26 | | A O |
| ANISOU | 1387 | O | BASN | A | 192 | 1248 | 1266 | 1997 | 1 | −23 | 1 | A O |
| SIGUIJ | 1387 | O | BASN | A | 192 | 1 | 0 | 0 | 221 | 53 | 289 | A O |
| ATOM | 1388 | N | GLY | A | 193 | 12.808 | 13.370 | 37.406 | 1.00 | 10.39 | | A N |
| ANISOU | 1388 | N | GLY | A | 193 | 1144 | 1264 | 1345 | 17 | 6 | −1 | A N |
| SIGUIJ | 1388 | N | GLY | A | 193 | 1 | 0 | 0 | 221 | 59 | 289 | A N |
| ATOM | 1389 | CA | GLY | A | 193 | 12.005 | 12.434 | 38.185 | 1.00 | 10.12 | | A C |
| ANISOU | 1389 | CA | GLY | A | 193 | 1149 | 1288 | 1295 | −17 | −30 | −4 | A C |
| SIGUIJ | 1389 | CA | GLY | A | 193 | 1 | 0 | 0 | 220 | 77 | 290 | A C |
| ATOM | 1390 | C | GLY | A | 193 | 11.536 | 11.260 | 37.368 | 1.00 | 9.29 | | A C |
| ANISOU | 1390 | C | GLY | A | 193 | 966 | 1257 | 1264 | 63 | −38 | 8 | A C |
| SIGUIJ | 1390 | C | GLY | A | 193 | 1 | 0 | 0 | 220 | 76 | 290 | A C |
| ATOM | 1391 | O | GLY | A | 193 | 11.109 | 10.228 | 37.949 | 1.00 | 10.02 | | A O |
| ANISOU | 1391 | O | GLY | A | 193 | 1252 | 1299 | 1302 | −7 | 1 | 0 | A O |
| SIGUIJ | 1391 | O | GLY | A | 193 | 1 | 0 | 0 | 221 | 53 | 289 | A O |
| ATOM | 1392 | N | ASP | A | 194 | 11.609 | 11.355 | 36.050 | 1.00 | 8.82 | | A N |
| ANISOU | 1392 | N | ASP | A | 194 | 1051 | 990 | 1255 | 2 | −37 | −1 | A N |
| SIGUIJ | 1392 | N | ASP | A | 194 | 1 | 0 | 0 | 221 | 59 | 289 | A N |
| ATOM | 1393 | CA | ASP | A | 194 | 11.158 | 10.267 | 35.167 | 1.00 | 9.00 | | A C |
| ANISOU | 1393 | CA | ASP | A | 194 | 1094 | 992 | 1236 | −24 | −6 | 0 | A C |
| SIGUIJ | 1393 | CA | ASP | A | 194 | 1 | 0 | 0 | 220 | 76 | 290 | A C |
| ATOM | 1394 | CB | ASP | A | 194 | 10.554 | 10.842 | 33.894 | 1.00 | 9.29 | | A C |
| ANISOU | 1394 | CB | ASP | A | 194 | 1159 | 1027 | 1245 | 22 | −6 | 0 | A C |
| SIGUIJ | 1394 | CB | ASP | A | 194 | 1 | 0 | 0 | 220 | 76 | 290 | A C |
| ATOM | 1395 | CG | ASP | A | 194 | 9.250 | 11.547 | 34.130 | 1.00 | 9.46 | | A C |
| ANISOU | 1395 | CG | ASP | A | 194 | 1171 | 1042 | 1269 | 32 | −1 | 0 | A C |
| SIGUIJ | 1395 | CG | ASP | A | 194 | 1 | 0 | 0 | 220 | 76 | 290 | A C |
| ATOM | 1396 | OD1 | ASP | A | 194 | 8.417 | 11.087 | 34.969 | 1.00 | 9.59 | | A O |
| ANISOU | 1396 | OD1 | ASP | A | 194 | 1226 | 1150 | 1278 | −16 | 4 | 0 | A O |
| SIGUIJ | 1396 | OD1 | ASP | A | 194 | 1 | 0 | 0 | 221 | 53 | 289 | A O |
| ATOM | 1397 | OD2 | ASP | A | 194 | 8.990 | 12.566 | 33.432 | 1.00 | 10.06 | | A O |
| ANISOU | 1397 | OD2 | ASP | A | 194 | 1204 | 1058 | 1309 | 52 | −5 | 1 | A O |
| SIGUIJ | 1397 | OD2 | ASP | A | 194 | 1 | 0 | 0 | 221 | 53 | 289 | A O |
| ATOM | 1398 | C | ASP | A | 194 | 12.265 | 9.291 | 34.827 | 1.00 | 8.95 | | A C |
| ANISOU | 1398 | C | ASP | A | 194 | 1115 | 1025 | 1181 | 2 | 0 | 0 | A C |
| SIGUIJ | 1398 | C | ASP | A | 194 | 1 | 0 | 0 | 220 | 76 | 290 | A C |
| ATOM | 1399 | O | ASP | A | 194 | 11.930 | 8.200 | 34.314 | 1.00 | 9.47 | | A O |
| ANISOU | 1399 | O | ASP | A | 194 | 1291 | 1042 | 1204 | −33 | −10 | 2 | A O |
| SIGUIJ | 1399 | O | ASP | A | 194 | 1 | 0 | 0 | 221 | 52 | 289 | A O |
| ATOM | 1400 | N | SER | A | 195 | 13.524 | 9.644 | 35.045 | 1.00 | 8.61 | | A N |
| ANISOU | 1400 | N | SER | A | 195 | 1112 | 1039 | 1117 | 1 | 0 | 0 | A N |
| SIGUIJ | 1400 | N | SER | A | 195 | 1 | 0 | 0 | 221 | 59 | 289 | A N |
| ATOM | 1401 | CA | SER | A | 195 | 14.636 | 8.728 | 34.715 | 1.00 | 9.06 | | A C |
| ANISOU | 1401 | CA | SER | A | 195 | 1108 | 1034 | 1200 | −7 | 15 | 0 | A C |
| SIGUIJ | 1401 | CA | SER | A | 195 | 1 | 0 | 0 | 220 | 76 | 290 | A C |
| ATOM | 1402 | CB | SER | A | 195 | 15.932 | 9.226 | 35.339 | 1.00 | 9.26 | | A C |
| ANISOU | 1402 | CB | SER | A | 195 | 1129 | 1029 | 1310 | −11 | −23 | 1 | A C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1402 | CB | SER | A | 195 | 1 | 0 | 0 | 220 | 76 | 290 | A C |
| ATOM | 1403 | OG | SER | A | 195 | 16.952 | 8.239 | 35.258 | 1.00 | 10.77 | | A O |
| ANISOU | 1403 | OG | SER | A | 195 | 1251 | 1131 | 1836 | 94 | 34 | 5 | A O |
| SIGUIJ | 1403 | OG | SER | A | 195 | 1 | 0 | 0 | 221 | 52 | 289 | A O |
| ATOM | 1404 | C | SER | A | 195 | 14.390 | 7.331 | 35.236 | 1.00 | 8.79 | | A C |
| ANISOU | 1404 | C | SER | A | 195 | 1093 | 1037 | 1135 | 5 | −1 | 0 | A C |
| SIGUIJ | 1404 | C | SER | A | 195 | 1 | 0 | 0 | 220 | 76 | 290 | A C |
| ATOM | 1405 | O | SER | A | 195 | 13.928 | 7.140 | 36.359 | 1.00 | 8.77 | | A O |
| ANISOU | 1405 | O | SER | A | 195 | 1141 | 1165 | 1125 | 0 | 0 | 0 | A O |
| SIGUIJ | 1405 | O | SER | A | 195 | 1 | 0 | 0 | 221 | 52 | 289 | A O |
| ATOM | 1406 | N | GLY | A | 196 | 14.731 | 6.344 | 34.397 | 1.00 | 8.96 | | A N |
| ANISOU | 1406 | N | GLY | A | 196 | 1083 | 1037 | 1172 | 8 | 3 | 0 | A N |
| SIGUIJ | 1406 | N | GLY | A | 196 | 1 | 0 | 0 | 221 | 59 | 289 | A N |
| ATOM | 1407 | CA | GLY | A | 196 | 14.603 | 4.955 | 34.824 | 1.00 | 9.79 | | A C |
| ANISOU | 1407 | CA | GLY | A | 196 | 1346 | 1045 | 1251 | −26 | 5 | −1 | A C |
| SIGUIJ | 1407 | CA | GLY | A | 196 | 1 | 0 | 0 | 220 | 76 | 290 | A C |
| ATOM | 1408 | C | GLY | A | 196 | 13.268 | 4.335 | 34.559 | 1.00 | 10.15 | | A C |
| ANISOU | 1408 | C | GLY | A | 196 | 1357 | 1133 | 1279 | −59 | 3 | −2 | A C |
| SIGUIJ | 1408 | C | GLY | A | 196 | 1 | 0 | 0 | 220 | 76 | 290 | A C |
| ATOM | 1409 | O | GLY | A | 196 | 13.122 | 3.077 | 34.625 | 1.00 | 11.37 | | A O |
| ANISOU | 1409 | O | GLY | A | 196 | 1574 | 1138 | 1455 | −86 | 12 | −5 | A O |
| SIGUIJ | 1409 | O | GLY | A | 196 | 1 | 0 | 0 | 221 | 52 | 289 | A O |
| ATOM | 1410 | N | GLY | A | 197 | 12.270 | 5.174 | 34.293 | 1.00 | 10.34 | | A N |
| ANISOU | 1410 | N | GLY | A | 197 | 1390 | 1225 | 1252 | 3 | 0 | 0 | A N |
| SIGUIJ | 1410 | N | GLY | A | 197 | 1 | 0 | 0 | 221 | 59 | 289 | A N |
| ATOM | 1411 | CA | GLY | A | 197 | 10.950 | 4.639 | 34.022 | 1.00 | 10.70 | | A C |
| ANISOU | 1411 | CA | GLY | A | 197 | 1399 | 1258 | 1271 | −14 | −5 | 1 | A C |
| SIGUIJ | 1411 | CA | GLY | A | 197 | 1 | 0 | 0 | 220 | 76 | 290 | A C |
| ATOM | 1412 | C | GLY | A | 197 | 10.775 | 4.179 | 32.572 | 1.00 | 10.49 | | A C |
| ANISOU | 1412 | C | GLY | A | 197 | 1284 | 1160 | 1264 | 32 | 0 | 0 | A C |
| SIGUIJ | 1412 | C | GLY | A | 197 | 1 | 0 | 0 | 220 | 76 | 290 | A C |
| ATOM | 1413 | O | GLY | A | 197 | 11.628 | 4.364 | 31.687 | 1.00 | 10.72 | | A O |
| ANISOU | 1413 | O | GLY | A | 197 | 1301 | 1386 | 1252 | −6 | 3 | 0 | A O |
| SIGUIJ | 1413 | O | GLY | A | 197 | 1 | 0 | 0 | 221 | 52 | 289 | A O |
| ATOM | 1414 | N | PRO | A | 198 | 9.659 | 3.487 | 32.333 | 1.00 | 10.32 | | A N |
| ANISOU | 1414 | N | PRO | A | 198 | 1299 | 1211 | 1147 | −4 | 22 | −1 | A N |
| SIGUIJ | 1414 | N | PRO | A | 198 | 1 | 0 | 0 | 221 | 59 | 289 | A N |
| ATOM | 1415 | CD | PRO | A | 198 | 8.577 | 3.242 | 33.332 | 1.00 | 10.54 | | A C |
| ANISOU | 1415 | CD | PRO | A | 198 | 1332 | 1247 | 1182 | 2 | 56 | 1 | A C |
| SIGUIJ | 1415 | CD | PRO | A | 198 | 1 | 0 | 0 | 220 | 76 | 290 | A C |
| ATOM | 1416 | CA | PRO | A | 198 | 9.493 | 2.681 | 31.115 | 1.00 | 10.29 | | A C |
| ANISOU | 1416 | CA | PRO | A | 198 | 1438 | 1205 | 1158 | 36 | −19 | −3 | A C |
| SIGUIJ | 1416 | CA | PRO | A | 198 | 1 | 0 | 0 | 220 | 76 | 290 | A C |
| ATOM | 1417 | CB | PRO | A | 198 | 8.462 | 1.655 | 31.568 | 1.00 | 10.41 | | A C |
| ANISOU | 1417 | CB | PRO | A | 198 | 1537 | 1278 | 1330 | −35 | 48 | −7 | A C |
| SIGUIJ | 1417 | CB | PRO | A | 198 | 1 | 0 | 0 | 220 | 76 | 290 | A C |
| ATOM | 1418 | CG | PRO | A | 198 | 7.644 | 2.375 | 32.586 | 1.00 | 11.03 | | A C |
| ANISOU | 1418 | CG | PRO | A | 198 | 1439 | 1279 | 1276 | −34 | −28 | 6 | A C |
| SIGUIJ | 1418 | CG | PRO | A | 198 | 1 | 0 | 0 | 220 | 76 | 290 | A C |
| ATOM | 1419 | C | PRO | A | 198 | 8.957 | 3.456 | 29.895 | 1.00 | 10.64 | | A C |
| ANISOU | 1419 | C | PRO | A | 198 | 1350 | 1170 | 1163 | −39 | −14 | 3 | A C |
| SIGUIJ | 1419 | C | PRO | A | 198 | 1 | 0 | 0 | 220 | 76 | 290 | A C |
| ATOM | 1420 | O | PRO | A | 198 | 8.036 | 4.276 | 30.000 | 1.00 | 11.03 | | A O |
| ANISOU | 1420 | O | PRO | A | 198 | 1485 | 1332 | 1335 | 93 | −2 | −1 | A O |
| SIGUIJ | 1420 | O | PRO | A | 198 | 1 | 0 | 0 | 221 | 52 | 289 | A O |
| ATOM | 1421 | N | LEU | A | 199 | 9.511 | 3.089 | 28.732 | 1.00 | 10.69 | | A N |
| ANISOU | 1421 | N | LEU | A | 199 | 1373 | 1162 | 1185 | −100 | 27 | −12 | A N |
| SIGUIJ | 1421 | N | LEU | A | 199 | 1 | 0 | 0 | 221 | 59 | 289 | A N |
| ATOM | 1422 | CA | LEU | A | 199 | 8.960 | 3.416 | 27.418 | 1.00 | 10.99 | | A C |
| ANISOU | 1422 | CA | LEU | A | 199 | 1462 | 1258 | 1196 | −28 | 12 | −1 | A C |
| SIGUIJ | 1422 | CA | LEU | A | 199 | 1 | 0 | 0 | 220 | 76 | 290 | A C |
| ATOM | 1423 | CB | LEU | A | 199 | 10.064 | 4.001 | 26.536 | 1.00 | 11.16 | | A C |
| ANISOU | 1423 | CB | LEU | A | 199 | 1531 | 1357 | 1204 | −105 | 38 | −15 | A C |
| SIGUIJ | 1423 | CB | LEU | A | 199 | 1 | 0 | 0 | 220 | 76 | 290 | A C |
| ATOM | 1424 | CG | LEU | A | 199 | 9.679 | 4.334 | 25.092 | 1.00 | 11.53 | | A C |
| ANISOU | 1424 | CG | LEU | A | 199 | 1678 | 1387 | 1215 | −188 | −4 | 2 | A C |
| SIGUIJ | 1424 | CG | LEU | A | 199 | 1 | 0 | 0 | 220 | 76 | 290 | A C |
| ATOM | 1425 | CD1 | LEU | A | 199 | 8.681 | 5.517 | 25.023 | 1.00 | 12.70 | | A C |
| ANISOU | 1425 | CD1 | LEU | A | 199 | 1922 | 1558 | 2204 | 14 | −71 | 6 | A C |
| SIGUIJ | 1425 | CD1 | LEU | A | 199 | 1 | 0 | 0 | 220 | 76 | 290 | A C |
| ATOM | 1426 | CD2 | LEU | A | 199 | 10.953 | 4.704 | 24.328 | 1.00 | 12.64 | | A C |
| ANISOU | 1426 | CD2 | LEU | A | 199 | 1876 | 3221 | 1286 | −740 | 46 | −32 | A C |
| SIGUIJ | 1426 | CD2 | LEU | A | 199 | 1 | 0 | 0 | 220 | 75 | 290 | A C |
| ATOM | 1427 | C | LEU | A | 199 | 8.489 | 2.055 | 26.870 | 1.00 | 11.49 | | A C |
| ANISOU | 1427 | C | LEU | A | 199 | 1340 | 1248 | 1270 | 14 | 8 | 1 | A C |
| SIGUIJ | 1427 | C | LEU | A | 199 | 1 | 0 | 0 | 220 | 75 | 290 | A C |
| ATOM | 1428 | O | LEU | A | 199 | 9.287 | 1.147 | 26.665 | 1.00 | 11.40 | | A O |
| ANISOU | 1428 | O | LEU | A | 199 | 1339 | 1245 | 1380 | 3 | −3 | 0 | A O |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1428 | O | LEU | A | 199 | 1 | 0 | 0 | 221 | 52 | 289 | A O |
| ATOM | 1429 | N | AVAL | A | 200 | 7.185 | 1.905 | 26.707 | 0.50 | 11.93 | | A N |
| ANISOU | 1429 | N | AVAL | A | 200 | 1338 | 1137 | 1409 | 16 | −1 | 0 | A N |
| SIGUIJ | 1429 | N | AVAL | A | 200 | 1 | 0 | 0 | 221 | 59 | 289 | A N |
| ATOM | 1430 | N | BVAL | A | 200 | 7.186 | 1.915 | 26.680 | 0.50 | 14.12 | | A N |
| ANISOU | 1430 | N | BVAL | A | 200 | 1344 | 1287 | 1383 | 6 | 0 | 0 | A N |
| SIGUIJ | 1430 | N | BVAL | A | 200 | 1 | 0 | 0 | 221 | 59 | 289 | A N |
| ATOM | 1431 | CA | AVAL | A | 200 | 6.624 | 0.630 | 26.281 | 0.50 | 13.23 | | A C |
| ANISOU | 1431 | CA | AVAL | A | 200 | 1574 | 1180 | 1391 | −88 | −36 | 12 | A C |
| SIGUIJ | 1431 | CA | AVAL | A | 200 | 1 | 0 | 0 | 220 | 75 | 290 | A C |
| ATOM | 1432 | CA | BVAL | A | 200 | 6.581 | 0.639 | 26.300 | 0.50 | 15.42 | | A C |
| ANISOU | 1432 | CA | BVAL | A | 200 | 1642 | 1338 | 1400 | −117 | −56 | 23 | A C |
| SIGUIJ | 1432 | CA | BVAL | A | 200 | 1 | 0 | 0 | 220 | 75 | 290 | A C |
| ATOM | 1433 | CB | AVAL | A | 200 | 5.606 | 0.099 | 27.295 | 0.50 | 13.34 | | A C |
| ANISOU | 1433 | CB | AVAL | A | 200 | 1672 | 1757 | 1391 | −334 | −62 | 70 | A C |
| SIGUIJ | 1433 | CB | AVAL | A | 200 | 1 | 0 | 0 | 220 | 75 | 290 | A C |
| ATOM | 1434 | CB | BVAL | A | 200 | 5.488 | 0.249 | 27.312 | 0.50 | 15.53 | | A C |
| ANISOU | 1434 | CB | BVAL | A | 200 | 1838 | 1626 | 1527 | −304 | 82 | −66 | A C |
| SIGUIJ | 1434 | CB | BVAL | A | 200 | 1 | 0 | 0 | 220 | 75 | 290 | A C |
| ATOM | 1435 | CG1 | AVAL | A | 200 | 6.292 | −0.162 | 28.632 | 0.50 | 13.55 | | A C |
| ANISOU | 1435 | CG1 | AVAL | A | 200 | 1665 | 2286 | 1342 | 11 | 5 | 0 | A C |
| SIGUIJ | 1435 | CG1 | AVAL | A | 200 | 1 | 0 | 0 | 220 | 75 | 290 | A C |
| ATOM | 1436 | CG1 | BVAL | A | 200 | 4.723 | −1.017 | 26.843 | 0.50 | 15.74 | | A C |
| ANISOU | 1436 | CG1 | BVAL | A | 200 | 1410 | 1412 | 1576 | 0 | −6 | 0 | A C |
| SIGUIJ | 1436 | CG1 | BVAL | A | 200 | 1 | 0 | 0 | 220 | 75 | 290 | A C |
| ATOM | 1437 | CG2 | AVAL | A | 200 | 4.463 | 1.047 | 27.461 | 0.50 | 14.98 | | A C |
| ANISOU | 1437 | CG2 | AVAL | A | 200 | 1941 | 2131 | 2307 | −33 | 27 | 3 | A C |
| SIGUIJ | 1437 | CG2 | AVAL | A | 200 | 1 | 0 | 0 | 220 | 75 | 290 | A C |
| ATOM | 1438 | CG2 | BVAL | A | 200 | 6.135 | −0.022 | 28.679 | 0.50 | 17.17 | | A C |
| ANISOU | 1438 | CG2 | BVAL | A | 200 | 2144 | 2640 | 1587 | −35 | −16 | 0 | A C |
| SIGUIJ | 1438 | CG2 | BVAL | A | 200 | 1 | 0 | 0 | 220 | 75 | 290 | A C |
| ATOM | 1439 | C | AVAL | A | 200 | 5.981 | 0.752 | 24.908 | 0.50 | 14.07 | | A C |
| ANISOU | 1439 | C | AVAL | A | 200 | 1498 | 1485 | 1367 | 0 | 3 | 0 | A C |
| SIGUIJ | 1439 | C | AVAL | A | 200 | 1 | 0 | 0 | 220 | 75 | 290 | A C |
| ATOM | 1440 | C | BVAL | A | 200 | 5.987 | 0.762 | 24.897 | 0.50 | 16.26 | | A C |
| ANISOU | 1440 | C | BVAL | A | 200 | 1490 | 1495 | 1371 | 0 | 0 | 0 | A C |
| SIGUIJ | 1440 | C | BVAL | A | 200 | 1 | 0 | 0 | 220 | 75 | 290 | A C |
| ATOM | 1441 | O | AVAL | A | 200 | 5.305 | 1.741 | 24.594 | 0.50 | 13.73 | | A O |
| ANISOU | 1441 | O | AVAL | A | 200 | 1646 | 1522 | 1422 | 72 | −118 | −42 | A O |
| SIGUIJ | 1441 | O | AVAL | A | 200 | 1 | 0 | 0 | 221 | 52 | 289 | A O |
| ATOM | 1442 | O | BVAL | A | 200 | 5.352 | 1.768 | 24.551 | 0.50 | 15.92 | | A O |
| ANISOU | 1442 | O | BVAL | A | 200 | 2287 | 1656 | 1640 | 355 | −485 | −204 | A O |
| SIGUIJ | 1442 | O | BVAL | A | 200 | 1 | 0 | 0 | 221 | 52 | 289 | A O |
| ATOM | 1443 | N | CYS | A | 201 | 6.224 | −0.256 | 24.071 | 0.50 | 15.72 | | A N |
| ANISOU | 1443 | N | CYS | A | 201 | 1271 | 1472 | 1352 | −39 | −2 | −1 | A N |
| SIGUIJ | 1443 | N | CYS | A | 201 | 1 | 0 | 0 | 221 | 59 | 289 | A N |
| ATOM | 1444 | CA | CYS | A | 201 | 5.658 | −0.276 | 22.719 | 1.00 | 17.44 | | A C |
| ANISOU | 1444 | CA | CYS | A | 201 | 2518 | 2148 | 1573 | 12 | −528 | −6 | A C |
| SIGUIJ | 1444 | CA | CYS | A | 201 | 1 | 0 | 0 | 220 | 75 | 290 | A C |
| ATOM | 1445 | C | CYS | A | 201 | 5.110 | −1.671 | 22.498 | 1.00 | 18.94 | | A C |
| ANISOU | 1445 | C | CYS | A | 201 | 2602 | 2150 | 2126 | 10 | −638 | −32 | A C |
| SIGUIJ | 1445 | C | CYS | A | 201 | 1 | 0 | 0 | 220 | 75 | 290 | A C |
| ATOM | 1446 | O | CYS | A | 201 | 5.813 | −2.658 | 22.695 | 1.00 | 19.18 | | A O |
| ANISOU | 1446 | O | CYS | A | 201 | 4095 | 2583 | 2869 | 839 | −1856 | −746 | A O |
| SIGUIJ | 1446 | O | CYS | A | 201 | 1 | 0 | 0 | 221 | 52 | 289 | A O |
| ATOM | 1447 | CB | CYS | A | 201 | 6.748 | −0.005 | 21.674 | 1.00 | 17.59 | | A C |
| ANISOU | 1447 | CB | CYS | A | 201 | 3256 | 3970 | 2261 | −353 | 139 | 22 | A C |
| SIGUIJ | 1447 | CB | CYS | A | 201 | 1 | 0 | 0 | 220 | 75 | 290 | A C |
| ATOM | 1448 | SG | CYS | A | 201 | 7.974 | 1.255 | 22.085 | 1.00 | 17.50 | | A S |
| ANISOU | 1448 | SG | CYS | A | 201 | 2224 | 2944 | 1746 | 673 | 162 | 133 | A S |
| SIGUIJ | 1448 | SG | CYS | A | 201 | 1 | 0 | 0 | 221 | 48 | 289 | A S |
| ATOM | 1449 | N | ARG | A | 202 | 3.867 | −1.771 | 22.056 | 1.00 | 20.47 | | A N |
| ANISOU | 1449 | N | ARG | A | 202 | 2697 | 3430 | 2998 | −9 | −918 | −237 | A N |
| SIGUIJ | 1449 | N | ARG | A | 202 | 1 | 0 | 0 | 221 | 59 | 289 | A N |
| ATOM | 1450 | CA | ARG | A | 202 | 3.429 | −3.048 | 21.476 | 1.00 | 21.98 | | A C |
| ANISOU | 1450 | CA | ARG | A | 202 | 3505 | 3546 | 2423 | −510 | −422 | −111 | A C |
| SIGUIJ | 1450 | CA | ARG | A | 202 | 1 | 0 | 0 | 220 | 75 | 290 | A C |
| ATOM | 1451 | CB | ARG | A | 202 | 4.356 | −3.484 | 20.322 | 1.00 | 23.51 | | A C |
| ANISOU | 1451 | CB | ARG | A | 202 | 4708 | 4464 | 3162 | −225 | 458 | −188 | A C |
| SIGUIJ | 1451 | CB | ARG | A | 202 | 1 | 0 | 0 | 220 | 75 | 290 | A C |
| ATOM | 1452 | CG | ARG | A | 202 | 4.054 | −2.872 | 18.967 | 1.00 | 25.72 | | A C |
| ANISOU | 1452 | CG | ARG | A | 202 | 6650 | 4820 | 3356 | −316 | −15 | 2 | A C |
| SIGUIJ | 1452 | CG | ARG | A | 202 | 1 | 0 | 0 | 220 | 75 | 290 | A C |
| ATOM | 1453 | CD | ARG | A | 202 | 4.130 | −3.981 | 17.913 | 1.00 | 27.39 | | A C |
| ANISOU | 1453 | CD | ARG | A | 202 | 15836 | 5050 | 3417 | 1325 | −1073 | −124 | A C |
| SIGUIJ | 1453 | CD | ARG | A | 202 | 1 | 0 | 0 | 220 | 75 | 290 | A C |
| ATOM | 1454 | NE | ARG | A | 202 | 3.147 | −5.039 | 18.198 | 1.00 | 28.89 | | A N |
| ANISOU | 1454 | NE | ARG | A | 202 | 19882 | 7865 | 11675 | −1772 | 1472 | −268 | A N |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1454 | NE | ARG | A | 202 | 1 | 0 | 0 | 221 | 59 | 289 | A | N |
| ATOM | 1455 | CZ | ARG | A | 202 | 3.241 | −6.309 | 17.802 | 1.00 | 29.52 | | A | C |
| ANISOU | 1455 | CZ | ARG | A | 202 | 13635 | 7753 | 10102 | −1680 | −267 | 98 | A | C |
| SIGUIJ | 1455 | CZ | ARG | A | 202 | 1 | 0 | 0 | 220 | 75 | 290 | A | C |
| ATOM | 1456 | NH1 | ARG | A | 202 | 4.279 | −6.722 | 17.087 | 1.00 | 30.11 | | A | N |
| ANISOU | 1456 | NH1 | ARG | A | 202 | 14569 | 12497 | 10591 | 146 | 30 | 2 | A | N |
| SIGUIJ | 1456 | NH1 | ARG | A | 202 | 1 | 0 | 0 | 221 | 59 | 289 | A | N |
| ATOM | 1457 | NH2 | ARG | A | 202 | 2.286 | −7.177 | 18.134 | 1.00 | 30.19 | | A | N |
| ANISOU | 1457 | NH2 | ARG | A | 202 | 14220 | 8203 | 10911 | −2155 | 176 | −83 | A | N |
| SIGUIJ | 1457 | NH2 | ARG | A | 202 | 1 | 0 | 0 | 221 | 59 | 289 | A | N |
| ATOM | 1458 | C | ARG | A | 202 | 3.527 | −4.078 | 22.596 | 1.00 | 21.91 | | A | C |
| ANISOU | 1458 | C | ARG | A | 202 | 3709 | 3701 | 2523 | −1 | 22 | −1 | A | C |
| SIGUIJ | 1458 | C | ARG | A | 202 | 1 | 0 | 0 | 220 | 75 | 290 | A | C |
| ATOM | 1459 | O | ARG | A | 202 | 3.882 | −5.252 | 22.360 | 1.00 | 22.61 | | A | O |
| ANISOU | 1459 | O | ARG | A | 202 | 4400 | 3923 | 2787 | 459 | −1263 | −433 | A | O |
| SIGUIJ | 1459 | O | ARG | A | 202 | 1 | 0 | 0 | 221 | 52 | 289 | A | O |
| ATOM | 1460 | N | GLY | A | 207 | 3.247 | −3.629 | 23.816 | 1.00 | 21.43 | | A | N |
| ANISOU | 1460 | N | GLY | A | 207 | 2943 | 3658 | 2516 | −77 | −115 | −13 | A | N |
| SIGUIJ | 1460 | N | GLY | A | 207 | 1 | 0 | 0 | 221 | 59 | 289 | A | N |
| ATOM | 1461 | CA | GLY | A | 207 | 3.230 | −4.550 | 24.940 | 1.00 | 20.55 | | A | C |
| ANISOU | 1461 | CA | GLY | A | 207 | 2370 | 3677 | 2563 | 54 | −17 | 4 | A | C |
| SIGUIJ | 1461 | CA | GLY | A | 207 | 1 | 0 | 0 | 220 | 75 | 290 | A | C |
| ATOM | 1462 | C | GLY | A | 207 | 4.528 | −4.917 | 25.648 | 1.00 | 19.61 | | A | C |
| ANISOU | 1462 | C | GLY | A | 207 | 2269 | 2796 | 2561 | −214 | 25 | 13 | A | C |
| SIGUIJ | 1462 | C | GLY | A | 207 | 1 | 0 | 0 | 220 | 74 | 290 | A | C |
| ATOM | 1463 | O | GLY | A | 207 | 4.524 | −5.662 | 26.630 | 1.00 | 20.31 | | A | O |
| ANISOU | 1463 | O | GLY | A | 207 | 3111 | 2799 | 2580 | −291 | −10 | 6 | A | O |
| SIGUIJ | 1463 | O | GLY | A | 207 | 1 | 0 | 0 | 221 | 52 | 289 | A | O |
| ATOM | 1464 | N | THR | A | 208 | 5.648 | −4.397 | 25.155 | 1.00 | 18.38 | | A | N |
| ANISOU | 1464 | N | THR | A | 208 | 2147 | 2379 | 2325 | −38 | −69 | −12 | A | N |
| SIGUIJ | 1464 | N | THR | A | 208 | 1 | 0 | 0 | 221 | 59 | 289 | A | N |
| ATOM | 1465 | CA | THR | A | 208 | 6.940 | −4.764 | 25.704 | 1.00 | 17.05 | | A | C |
| ANISOU | 1465 | CA | THR | A | 208 | 2120 | 1671 | 2223 | −212 | −84 | −107 | A | C |
| SIGUIJ | 1465 | CA | THR | A | 208 | 1 | 0 | 0 | 220 | 74 | 290 | A | C |
| ATOM | 1466 | CB | THR | A | 208 | 7.852 | −5.662 | 24.730 | 1.00 | 17.59 | | A | C |
| ANISOU | 1466 | CB | THR | A | 208 | 2326 | 1668 | 2241 | −148 | 21 | −19 | A | C |
| SIGUIJ | 1466 | CB | THR | A | 208 | 1 | 0 | 0 | 220 | 74 | 290 | A | C |
| ATOM | 1467 | OG1 | THR | A | 208 | 8.404 | −4.889 | 23.624 | 1.00 | 18.78 | | A | O |
| ANISOU | 1467 | OG1 | THR | A | 208 | 2979 | 2205 | 2256 | −732 | −64 | 49 | A | O |
| SIGUIJ | 1467 | OG1 | THR | A | 208 | 1 | 0 | 0 | 221 | 52 | 289 | A | O |
| ATOM | 1468 | CG2 | THR | A | 208 | 7.041 | −6.852 | 24.228 | 1.00 | 18.33 | | A | C |
| ANISOU | 1468 | CG2 | THR | A | 208 | 3837 | 2352 | 2244 | −1168 | −3 | 2 | A | C |
| SIGUIJ | 1468 | CG2 | THR | A | 208 | 1 | 0 | 0 | 220 | 74 | 290 | A | C |
| ATOM | 1469 | C | THR | A | 208 | 7.712 | −3.509 | 26.076 | 1.00 | 15.64 | | A | C |
| ANISOU | 1469 | C | THR | A | 208 | 1738 | 1537 | 1589 | −31 | 37 | −6 | A | C |
| SIGUIJ | 1469 | C | THR | A | 208 | 1 | 0 | 0 | 220 | 74 | 290 | A | C |
| ATOM | 1470 | O | THR | A | 208 | 7.567 | −2.413 | 25.438 | 1.00 | 15.24 | | A | O |
| ANISOU | 1470 | O | THR | A | 208 | 1892 | 1544 | 1644 | −30 | −22 | 2 | A | O |
| SIGUIJ | 1470 | O | THR | A | 208 | 1 | 0 | 0 | 221 | 52 | 289 | A | O |
| ATOM | 1471 | N | LEU | A | 209 | 8.579 | −3.704 | 27.046 | 1.00 | 14.47 | | A | N |
| ANISOU | 1471 | N | LEU | A | 209 | 1766 | 1283 | 1616 | −84 | −5 | 2 | A | N |
| SIGUIJ | 1471 | N | LEU | A | 209 | 1 | 0 | 0 | 221 | 59 | 289 | A | N |
| ATOM | 1472 | CA | LEU | A | 209 | 9.498 | −2.670 | 27.440 | 1.00 | 13.39 | | A | C |
| ANISOU | 1472 | CA | LEU | A | 209 | 1771 | 1353 | 1409 | −147 | 84 | −29 | A | C |
| SIGUIJ | 1472 | CA | LEU | A | 209 | 1 | 0 | 0 | 220 | 74 | 290 | A | C |
| ATOM | 1473 | CB | LEU | A | 209 | 10.155 | −3.066 | 28.776 | 1.00 | 13.02 | | A | C |
| ANISOU | 1473 | CB | LEU | A | 209 | 1714 | 1258 | 1427 | −240 | 60 | −34 | A | C |
| SIGUIJ | 1473 | CB | LEU | A | 209 | 1 | 0 | 0 | 220 | 74 | 290 | A | C |
| ATOM | 1474 | CG | LEU | A | 209 | 11.113 | −1.980 | 29.356 | 1.00 | 12.58 | | A | C |
| ANISOU | 1474 | CG | LEU | A | 209 | 1662 | 1214 | 1564 | −188 | 7 | −7 | A | C |
| SIGUIJ | 1474 | CG | LEU | A | 209 | 1 | 0 | 0 | 220 | 74 | 290 | A | C |
| ATOM | 1475 | CD1 | LEU | A | 209 | 10.365 | −0.768 | 29.797 | 1.00 | 13.15 | | A | C |
| ANISOU | 1475 | CD1 | LEU | A | 209 | 1871 | 1300 | 1615 | −55 | −1 | 0 | A | C |
| SIGUIJ | 1475 | CD1 | LEU | A | 209 | 1 | 0 | 0 | 220 | 74 | 290 | A | C |
| ATOM | 1476 | CD2 | LEU | A | 209 | 11.874 | −2.570 | 30.495 | 1.00 | 13.63 | | A | C |
| ANISOU | 1476 | CD2 | LEU | A | 209 | 1888 | 1584 | 1588 | 67 | −12 | −3 | A | C |
| SIGUIJ | 1476 | CD2 | LEU | A | 209 | 1 | 0 | 0 | 220 | 74 | 290 | A | C |
| ATOM | 1477 | C | LEU | A | 209 | 10.546 | −2.453 | 26.352 | 1.00 | 13.39 | | A | C |
| ANISOU | 1477 | C | LEU | A | 209 | 1684 | 1215 | 1320 | −96 | −3 | 1 | A | C |
| SIGUIJ | 1477 | C | LEU | A | 209 | 1 | 0 | 0 | 220 | 74 | 290 | A | C |
| ATOM | 1478 | O | LEU | A | 209 | 11.313 | −3.377 | 26.034 | 1.00 | 14.33 | | A | O |
| ANISOU | 1478 | O | LEU | A | 209 | 2821 | 1643 | 2129 | 572 | 764 | 342 | A | O |
| SIGUIJ | 1478 | O | LEU | A | 209 | 1 | 0 | 0 | 221 | 52 | 289 | A | O |
| ATOM | 1479 | N | GLN | A | 210 | 10.630 | −1.241 | 25.805 | 1.00 | 11.99 | | A | N |
| ANISOU | 1479 | N | GLN | A | 210 | 1456 | 1205 | 1300 | −81 | −2 | 1 | A | N |
| SIGUIJ | 1479 | N | GLN | A | 210 | 1 | 0 | 0 | 221 | 58 | 289 | A | N |
| ATOM | 1480 | CA | GLN | A | 210 | 11.629 | −0.966 | 24.792 | 1.00 | 11.62 | | A | C |
| ANISOU | 1480 | CA | GLN | A | 210 | 1468 | 1260 | 1294 | −94 | 4 | −2 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1480 | CA | GLN | A | 210 | 1 | 0 | 0 | 220 | 74 | 290 | A | C |
| ATOM | 1481 | CB | GLN | A | 210 | 10.930 | −0.471 | 23.528 | 1.00 | 11.73 | | A | C |
| ANISOU | 1481 | CB | GLN | A | 210 | 1575 | 1458 | 1287 | 36 | 2 | 0 | A | C |
| SIGUIJ | 1481 | CB | GLN | A | 210 | 1 | 0 | 0 | 220 | 74 | 290 | A | C |
| ATOM | 1482 | CG | GLN | A | 210 | 10.167 | −1.576 | 22.767 | 1.00 | 11.87 | | A | C |
| ANISOU | 1482 | CG | GLN | A | 210 | 1685 | 1521 | 1267 | −58 | 34 | −8 | A | C |
| SIGUIJ | 1482 | CG | GLN | A | 210 | 1 | 0 | 0 | 220 | 74 | 290 | A | C |
| ATOM | 1483 | CD | GLN | A | 210 | 11.077 | −2.553 | 22.089 | 1.00 | 12.65 | | A | C |
| ANISOU | 1483 | CD | GLN | A | 210 | 1734 | 1594 | 1166 | 31 | −32 | −4 | A | C |
| SIGUIJ | 1483 | CD | GLN | A | 210 | 1 | 0 | 0 | 220 | 74 | 290 | A | C |
| ATOM | 1484 | OE1 | GLN | A | 210 | 12.101 | −2.185 | 21.526 | 1.00 | 12.72 | | A | O |
| ANISOU | 1484 | OE1 | GLN | A | 210 | 1845 | 1744 | 1420 | −28 | 121 | −21 | A | O |
| SIGUIJ | 1484 | OE1 | GLN | A | 210 | 1 | 0 | 0 | 221 | 52 | 289 | A | O |
| ATOM | 1485 | NE2 | GLN | A | 210 | 10.699 | −3.842 | 22.095 | 1.00 | 13.51 | | A | N |
| ANISOU | 1485 | NE2 | GLN | A | 210 | 2158 | 1625 | 1824 | −102 | 6 | −1 | A | N |
| SIGUIJ | 1485 | NE2 | GLN | A | 210 | 1 | 0 | 0 | 221 | 58 | 289 | A | N |
| ATOM | 1486 | C | GLN | A | 210 | 12.663 | 0.084 | 25.228 | 1.00 | 11.48 | | A | C |
| ANISOU | 1486 | C | GLN | A | 210 | 1409 | 1202 | 1310 | −29 | −4 | 1 | A | C |
| SIGUIJ | 1486 | C | GLN | A | 210 | 1 | 0 | 0 | 220 | 74 | 290 | A | C |
| ATOM | 1487 | O | GLN | A | 210 | 13.757 | 0.110 | 24.704 | 1.00 | 11.76 | | A | O |
| ANISOU | 1487 | O | GLN | A | 210 | 1424 | 1533 | 1356 | −12 | 16 | −1 | A | O |
| SIGUIJ | 1487 | O | GLN | A | 210 | 1 | 0 | 0 | 221 | 52 | 289 | A | O |
| ATOM | 1488 | N | GLY | A | 211 | 12.322 | 0.947 | 26.191 | 1.00 | 11.15 | | A | N |
| ANISOU | 1488 | N | GLY | A | 211 | 1398 | 1218 | 1310 | −28 | −8 | 2 | A | N |
| SIGUIJ | 1488 | N | GLY | A | 211 | 1 | 0 | 0 | 221 | 58 | 289 | A | N |
| ATOM | 1489 | CA | GLY | A | 211 | 13.247 | 1.980 | 26.650 | 1.00 | 11.16 | | A | C |
| ANISOU | 1489 | CA | GLY | A | 211 | 1547 | 1392 | 1244 | −207 | 55 | −38 | A | C |
| SIGUIJ | 1489 | CA | GLY | A | 211 | 1 | 0 | 0 | 220 | 74 | 290 | A | C |
| ATOM | 1490 | C | GLY | A | 211 | 13.133 | 2.227 | 28.125 | 1.00 | 10.56 | | A | C |
| ANISOU | 1490 | C | GLY | A | 211 | 1286 | 1259 | 1228 | 0 | 1 | 0 | A | C |
| SIGUIJ | 1490 | C | GLY | A | 211 | 1 | 0 | 0 | 220 | 74 | 290 | A | C |
| ATOM | 1491 | O | GLY | A | 211 | 12.113 | 1.957 | 28.779 | 1.00 | 10.95 | | A | O |
| ANISOU | 1491 | O | GLY | A | 211 | 1278 | 1367 | 1229 | −25 | 0 | 0 | A | O |
| SIGUIJ | 1491 | O | GLY | A | 211 | 1 | 0 | 0 | 221 | 52 | 289 | A | O |
| ATOM | 1492 | N | LEU | A | 212 | 14.212 | 2.793 | 28.658 | 1.00 | 10.43 | | A | N |
| ANISOU | 1492 | N | LEU | A | 212 | 1263 | 1140 | 1161 | 56 | 13 | 6 | A | N |
| SIGUIJ | 1492 | N | LEU | A | 212 | 1 | 0 | 0 | 221 | 58 | 289 | A | N |
| ATOM | 1493 | CA | LEU | A | 212 | 14.224 | 3.418 | 29.993 | 1.00 | 10.26 | | A | C |
| ANISOU | 1493 | CA | LEU | A | 212 | 1398 | 1146 | 1150 | −28 | 42 | −5 | A | C |
| SIGUIJ | 1493 | CA | LEU | A | 212 | 1 | 0 | 0 | 220 | 74 | 290 | A | C |
| ATOM | 1494 | CB | LEU | A | 212 | 15.269 | 2.772 | 30.919 | 1.00 | 11.19 | | A | C |
| ANISOU | 1494 | CB | LEU | A | 212 | 1550 | 1227 | 1285 | 36 | −83 | −10 | A | C |
| SIGUIJ | 1494 | CB | LEU | A | 212 | 1 | 0 | 0 | 220 | 74 | 290 | A | C |
| ATOM | 1495 | CG | LEU | A | 212 | 15.202 | 1.269 | 31.124 | 1.00 | 11.64 | | A | C |
| ANISOU | 1495 | CG | LEU | A | 212 | 2081 | 1226 | 1427 | 10 | −103 | −1 | A | C |
| SIGUIJ | 1495 | CG | LEU | A | 212 | 1 | 0 | 0 | 220 | 74 | 290 | A | C |
| ATOM | 1496 | CD1 | LEU | A | 212 | 16.503 | 0.801 | 31.812 | 1.00 | 13.23 | | A | C |
| ANISOU | 1496 | CD1 | LEU | A | 212 | 2352 | 1816 | 1871 | 325 | −396 | −185 | A | C |
| SIGUIJ | 1496 | CD1 | LEU | A | 212 | 1 | 0 | 0 | 220 | 74 | 290 | A | C |
| ATOM | 1497 | CD2 | LEU | A | 212 | 13.926 | 0.936 | 31.889 | 1.00 | 12.55 | | A | C |
| ANISOU | 1497 | CD2 | LEU | A | 212 | 2166 | 1628 | 1566 | −103 | −15 | 3 | A | C |
| SIGUIJ | 1497 | CD2 | LEU | A | 212 | 1 | 0 | 0 | 220 | 73 | 290 | A | C |
| ATOM | 1498 | C | LEU | A | 212 | 14.578 | 4.861 | 29.800 | 1.00 | 9.76 | | A | C |
| ANISOU | 1498 | C | LEU | A | 212 | 1189 | 1144 | 1004 | 3 | −1 | 0 | A | C |
| SIGUIJ | 1498 | C | LEU | A | 212 | 1 | 0 | 0 | 220 | 73 | 290 | A | C |
| ATOM | 1499 | O | LEU | A | 212 | 15.520 | 5.197 | 29.089 | 1.00 | 9.43 | | A | O |
| ANISOU | 1499 | O | LEU | A | 212 | 1301 | 1173 | 1133 | −33 | 127 | −24 | A | O |
| SIGUIJ | 1499 | O | LEU | A | 212 | 1 | 0 | 0 | 221 | 52 | 289 | A | O |
| ATOM | 1500 | N | VAL | A | 213 | 13.833 | 5.751 | 30.460 | 1.00 | 9.17 | | A | N |
| ANISOU | 1500 | N | VAL | A | 213 | 1209 | 1140 | 1034 | −9 | 27 | −2 | A | N |
| SIGUIJ | 1500 | N | VAL | A | 213 | 1 | 0 | 0 | 221 | 58 | 289 | A | N |
| ATOM | 1501 | CA | VAL | A | 213 | 14.154 | 7.181 | 30.368 | 1.00 | 9.13 | | A | C |
| ANISOU | 1501 | CA | VAL | A | 213 | 1190 | 1139 | 1156 | −3 | −1 | 0 | A | C |
| SIGUIJ | 1501 | CA | VAL | A | 213 | 1 | 0 | 0 | 220 | 73 | 290 | A | C |
| ATOM | 1502 | CB | VAL | A | 213 | 13.218 | 8.032 | 31.250 | 1.00 | 9.23 | | A | C |
| ANISOU | 1502 | CB | VAL | A | 213 | 1182 | 1141 | 1177 | 5 | 0 | 0 | A | C |
| SIGUIJ | 1502 | CB | VAL | A | 213 | 1 | 0 | 0 | 220 | 73 | 290 | A | C |
| ATOM | 1503 | CG1 | VAL | A | 213 | 13.660 | 9.504 | 31.253 | 1.00 | 9.48 | | A | C |
| ANISOU | 1503 | CG1 | VAL | A | 213 | 1439 | 1156 | 1104 | −66 | −12 | 3 | A | C |
| SIGUIJ | 1503 | CG1 | VAL | A | 213 | 1 | 0 | 0 | 220 | 73 | 290 | A | C |
| ATOM | 1504 | CG2 | VAL | A | 213 | 11.775 | 7.899 | 30.744 | 1.00 | 9.96 | | A | C |
| ANISOU | 1504 | CG2 | VAL | A | 213 | 1180 | 1430 | 1270 | −20 | −11 | −2 | A | C |
| SIGUIJ | 1504 | CG2 | VAL | A | 213 | 1 | 0 | 0 | 220 | 73 | 290 | A | C |
| ATOM | 1505 | C | VAL | A | 213 | 15.598 | 7.407 | 30.809 | 1.00 | 9.37 | | A | C |
| ANISOU | 1505 | C | VAL | A | 213 | 1197 | 1166 | 1110 | 0 | −1 | 0 | A | C |
| SIGUIJ | 1505 | C | VAL | A | 213 | 1 | 0 | 0 | 220 | 73 | 290 | A | C |
| ATOM | 1506 | O | VAL | A | 213 | 16.034 | 6.908 | 31.853 | 1.00 | 9.26 | | A | O |
| ANISOU | 1506 | O | VAL | A | 213 | 1222 | 1164 | 1104 | 2 | 5 | 0 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1506 | O | VAL | A | 213 | 1 | 0 | 0 | 221 | 52 | 289 | A | O |
| ATOM | 1507 | N | SER | A | 214 | 16.365 | 8.179 | 30.025 | 1.00 | 9.91 | | A | N |
| ANISOU | 1507 | N | SER | A | 214 | 1230 | 1174 | 1149 | −6 | 6 | −1 | A | N |
| SIGUIJ | 1507 | N | SER | A | 214 | 1 | 0 | 0 | 221 | 58 | 289 | A | N |
| ATOM | 1508 | CA | SER | A | 214 | 17.741 | 8.499 | 30.404 | 1.00 | 10.45 | | A | C |
| ANISOU | 1508 | CA | SER | A | 214 | 1243 | 1218 | 1162 | −3 | −2 | 0 | A | C |
| SIGUIJ | 1508 | CA | SER | A | 214 | 1 | 0 | 0 | 220 | 73 | 290 | A | C |
| ATOM | 1509 | CB | SER | A | 214 | 18.721 | 7.915 | 29.375 | 1.00 | 10.69 | | A | C |
| ANISOU | 1509 | CB | SER | A | 214 | 1287 | 1334 | 1186 | 12 | 17 | −1 | A | C |
| SIGUIJ | 1509 | CB | SER | A | 214 | 1 | 0 | 0 | 220 | 73 | 290 | A | C |
| ATOM | 1510 | OG | SER | A | 214 | 20.052 | 8.252 | 29.751 | 1.00 | 11.37 | | A | O |
| ANISOU | 1510 | OG | SER | A | 214 | 1317 | 1670 | 1351 | −54 | −5 | −5 | A | O |
| SIGUIJ | 1510 | OG | SER | A | 214 | 1 | 0 | 0 | 221 | 52 | 289 | A | O |
| ATOM | 1511 | C | SER | A | 214 | 17.939 | 9.995 | 30.598 | 1.00 | 10.93 | | A | C |
| ANISOU | 1511 | C | SER | A | 214 | 1507 | 1221 | 1162 | −60 | −4 | 1 | A | C |
| SIGUIJ | 1511 | C | SER | A | 214 | 1 | 0 | 0 | 220 | 73 | 290 | A | C |
| ATOM | 1512 | O | SER | A | 214 | 18.233 | 10.427 | 31.739 | 1.00 | 10.97 | | A | O |
| ANISOU | 1512 | O | SER | A | 214 | 1600 | 1266 | 1166 | −112 | −10 | 3 | A | O |
| SIGUIJ | 1512 | O | SER | A | 214 | 1 | 0 | 0 | 221 | 52 | 289 | A | O |
| ATOM | 1513 | N | TRP | A | 215 | 17.818 | 10.827 | 29.547 | 1.00 | 11.11 | | A | N |
| ANISOU | 1513 | N | TRP | A | 215 | 1267 | 1174 | 1161 | −131 | 5 | −5 | A | N |
| SIGUIJ | 1513 | N | TRP | A | 215 | 1 | 0 | 0 | 221 | 58 | 289 | A | N |
| ATOM | 1514 | CA | TRP | A | 215 | 18.158 | 12.208 | 29.728 | 1.00 | 11.48 | | A | C |
| ANISOU | 1514 | CA | TRP | A | 215 | 1487 | 1186 | 1222 | −193 | 9 | −5 | A | C |
| SIGUIJ | 1514 | CA | TRP | A | 215 | 1 | 0 | 0 | 220 | 73 | 290 | A | C |
| ATOM | 1515 | CB | TRP | A | 215 | 19.691 | 12.378 | 29.789 | 1.00 | 12.92 | | A | C |
| ANISOU | 1515 | CB | TRP | A | 215 | 1493 | 1681 | 1625 | −256 | 6 | 7 | A | C |
| SIGUIJ | 1515 | CB | TRP | A | 215 | 1 | 0 | 0 | 220 | 73 | 290 | A | C |
| ATOM | 1516 | CG | TRP | A | 215 | 20.366 | 12.319 | 28.523 | 1.00 | 14.50 | | A | C |
| ANISOU | 1516 | CG | TRP | A | 215 | 1455 | 2674 | 1619 | −221 | −19 | −18 | A | C |
| SIGUIJ | 1516 | CG | TRP | A | 215 | 1 | 0 | 0 | 220 | 73 | 290 | A | C |
| ATOM | 1517 | CD2 | TRP | A | 215 | 20.791 | 13.452 | 27.727 | 1.00 | 15.30 | | A | C |
| ANISOU | 1517 | CD2 | TRP | A | 215 | 2034 | 2839 | 1760 | −470 | −63 | 87 | A | C |
| SIGUIJ | 1517 | CD2 | TRP | A | 215 | 1 | 0 | 0 | 220 | 73 | 290 | A | C |
| ATOM | 1518 | CE2 | TRP | A | 215 | 21.384 | 12.931 | 26.581 | 1.00 | 15.68 | | A | C |
| ANISOU | 1518 | CE2 | TRP | A | 215 | 2230 | 3125 | 1842 | −414 | 6 | −3 | A | C |
| SIGUIJ | 1518 | CE2 | TRP | A | 215 | 1 | 0 | 0 | 220 | 73 | 290 | A | C |
| ATOM | 1519 | CE3 | TRP | A | 215 | 20.722 | 14.850 | 27.882 | 1.00 | 15.92 | | A | C |
| ANISOU | 1519 | CE3 | TRP | A | 215 | 2167 | 2842 | 2272 | −470 | 14 | 20 | A | C |
| SIGUIJ | 1519 | CE3 | TRP | A | 215 | 1 | 0 | 0 | 220 | 73 | 290 | A | C |
| ATOM | 1520 | CD1 | TRP | A | 215 | 20.713 | 11.211 | 27.860 | 1.00 | 14.56 | | A | C |
| ANISOU | 1520 | CD1 | TRP | A | 215 | 1232 | 2691 | 1612 | −237 | −109 | −47 | A | C |
| SIGUIJ | 1520 | CD1 | TRP | A | 215 | 1 | 0 | 0 | 220 | 73 | 290 | A | N |
| ATOM | 1521 | NE1 | TRP | A | 215 | 21.347 | 11.562 | 26.668 | 1.00 | 15.70 | | A | N |
| ANISOU | 1521 | NE1 | TRP | A | 215 | 1537 | 3129 | 1696 | −395 | 8 | 9 | A | N |
| SIGUIJ | 1521 | NE1 | TRP | A | 215 | 1 | 0 | 0 | 221 | 58 | 289 | A | N |
| ATOM | 1522 | CZ2 | TRP | A | 215 | 21.912 | 13.757 | 25.564 | 1.00 | 15.96 | | A | C |
| ANISOU | 1522 | CZ2 | TRP | A | 215 | 1958 | 3076 | 1872 | −263 | −12 | 33 | A | C |
| SIGUIJ | 1522 | CZ2 | TRP | A | 215 | 1 | 0 | 0 | 220 | 73 | 290 | A | C |
| ATOM | 1523 | CZ3 | TRP | A | 215 | 21.252 | 15.664 | 26.885 | 1.00 | 16.39 | | A | C |
| ANISOU | 1523 | CZ3 | TRP | A | 215 | 2166 | 2821 | 2253 | −473 | 2 | 3 | A | C |
| SIGUIJ | 1523 | CZ3 | TRP | A | 215 | 1 | 0 | 0 | 220 | 73 | 290 | A | C |
| ATOM | 1524 | CH2 | TRP | A | 215 | 21.836 | 15.105 | 25.746 | 1.00 | 16.48 | | A | C |
| ANISOU | 1524 | CH2 | TRP | A | 215 | 2473 | 3088 | 2274 | −237 | 28 | −19 | A | C |
| SIGUIJ | 1524 | CH2 | TRP | A | 215 | 1 | 0 | 0 | 220 | 73 | 290 | A | C |
| ATOM | 1525 | C | TRP | A | 215 | 17.590 | 13.041 | 28.594 | 1.00 | 11.26 | | A | C |
| ANISOU | 1525 | C | TRP | A | 215 | 1592 | 1231 | 1237 | −148 | −17 | 6 | A | C |
| SIGUIJ | 1525 | C | TRP | A | 215 | 1 | 0 | 0 | 220 | 73 | 290 | A | C |
| ATOM | 1526 | O | TRP | A | 215 | 17.105 | 12.544 | 27.569 | 1.00 | 11.36 | | A | O |
| ANISOU | 1526 | O | TRP | A | 215 | 1550 | 1239 | 1220 | −123 | 16 | −6 | A | O |
| SIGUIJ | 1526 | O | TRP | A | 215 | 1 | 0 | 0 | 221 | 52 | 289 | A | O |
| ATOM | 1527 | N | GLY | A | 216 | 17.666 | 14.362 | 28.758 | 1.00 | 11.41 | | A | N |
| ANISOU | 1527 | N | GLY | A | 216 | 1612 | 1223 | 1346 | −140 | −1 | 0 | A | N |
| SIGUIJ | 1527 | N | GLY | A | 216 | 1 | 0 | 0 | 221 | 58 | 289 | A | N |
| ATOM | 1528 | CA | GLY | A | 216 | 17.274 | 15.281 | 27.698 | 1.00 | 11.86 | | A | C |
| ANISOU | 1528 | CA | GLY | A | 216 | 1773 | 1255 | 1381 | −102 | −43 | 10 | A | C |
| SIGUIJ | 1528 | CA | GLY | A | 216 | 1 | 0 | 0 | 220 | 73 | 290 | A | C |
| ATOM | 1529 | C | GLY | A | 216 | 17.583 | 16.715 | 28.136 | 1.00 | 12.19 | | A | C |
| ANISOU | 1529 | C | GLY | A | 216 | 1700 | 1263 | 1421 | −100 | −22 | 6 | A | C |
| SIGUIJ | 1529 | C | GLY | A | 216 | 1 | 0 | 0 | 220 | 73 | 290 | A | C |
| ATOM | 1530 | O | GLY | A | 216 | 18.208 | 16.969 | 29.174 | 1.00 | 13.00 | | A | O |
| ANISOU | 1530 | O | GLY | A | 216 | 1985 | 1447 | 1491 | −264 | −143 | 64 | A | O |
| SIGUIJ | 1530 | O | GLY | A | 216 | 1 | 0 | 0 | 221 | 52 | 289 | A | O |
| ATOM | 1531 | N | THR | A | 217 | 17.142 | 17.660 | 27.323 | 1.00 | 12.59 | | A | N |
| ANISOU | 1531 | N | THR | A | 217 | 1784 | 1270 | 1510 | −152 | −123 | 45 | A | N |
| SIGUIJ | 1531 | N | THR | A | 217 | 1 | 0 | 0 | 221 | 58 | 289 | A | N |
| ATOM | 1532 | CA | THR | A | 217 | 17.446 | 19.081 | 27.539 | 1.00 | 12.76 | | A | C |
| ANISOU | 1532 | CA | THR | A | 217 | 1798 | 1290 | 1620 | −179 | 34 | −22 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1532 | CA  | THR | A | 217 | 1      | 0      | 0      | 220   | 73    | 290 | A | C |
| ATOM   | 1533 | CB  | THR | A | 217 | 17.006 | 19.861 | 26.284 | 1.00  | 13.20 |     | A | C |
| ANISOU | 1533 | CB  | THR | A | 217 | 2318   | 1438   | 1753   | −248  | −199  | 72  | A | C |
| SIGUIJ | 1533 | CB  | THR | A | 217 | 1      | 0      | 0      | 220   | 72    | 290 | A | C |
| ATOM   | 1534 | OG1 | THR | A | 217 | 17.663 | 19.279 | 25.147 | 1.00  | 14.39 |     | A | O |
| ANISOU | 1534 | OG1 | THR | A | 217 | 2455   | 1596   | 1805   | −206  | −136  | 36  | A | O |
| SIGUIJ | 1534 | OG1 | THR | A | 217 | 1      | 0      | 0      | 221   | 52    | 289 | A | O |
| ATOM   | 1535 | CG2 | THR | A | 217 | 17.284 | 21.349 | 26.393 | 1.00  | 14.24 |     | A | C |
| ANISOU | 1535 | CG2 | THR | A | 217 | 3800   | 1489   | 2134   | −517  | −236  | 59  | A | C |
| SIGUIJ | 1535 | CG2 | THR | A | 217 | 1      | 0      | 0      | 220   | 72    | 290 | A | C |
| ATOM   | 1536 | C   | THR | A | 217 | 16.691 | 19.625 | 28.751 | 1.00  | 12.38 |     | A | C |
| ANISOU | 1536 | C   | THR | A | 217 | 1688   | 1191   | 1556   | −168  | −40   | 30  | A | C |
| SIGUIJ | 1536 | C   | THR | A | 217 | 1      | 0      | 0      | 220   | 72    | 290 | A | C |
| ATOM   | 1537 | O   | THR | A | 217 | 15.564 | 19.249 | 29.003 | 1.00  | 12.39 |     | A | O |
| ANISOU | 1537 | O   | THR | A | 217 | 1713   | 1362   | 1514   | −232  | −45   | 35  | A | O |
| SIGUIJ | 1537 | O   | THR | A | 217 | 1      | 0      | 0      | 221   | 52    | 289 | A | O |
| ATOM   | 1538 | N   | PHE | A | 218 | 17.334 | 20.559 | 29.465 | 1.00  | 12.21 |     | A | N |
| ANISOU | 1538 | N   | PHE | A | 218 | 1757   | 1254   | 1572   | −226  | −28   | 20  | A | N |
| SIGUIJ | 1538 | N   | PHE | A | 218 | 1      | 0      | 0      | 221   | 58    | 289 | A | N |
| ATOM   | 1539 | CA  | PHE | A | 218 | 16.672 | 21.332 | 30.489 | 1.00  | 11.90 |     | A | C |
| ANISOU | 1539 | CA  | PHE | A | 218 | 1675   | 1246   | 1486   | −208  | −97   | 59  | A | C |
| SIGUIJ | 1539 | CA  | PHE | A | 218 | 1      | 0      | 0      | 220   | 72    | 290 | A | C |
| ATOM   | 1540 | CB  | PHE | A | 218 | 17.356 | 21.058 | 31.829 | 1.00  | 12.66 |     | A | C |
| ANISOU | 1540 | CB  | PHE | A | 218 | 1933   | 1386   | 1551   | −188  | −226  | 79  | A | C |
| SIGUIJ | 1540 | CB  | PHE | A | 218 | 1      | 0      | 0      | 220   | 72    | 290 | A | C |
| ATOM   | 1541 | CG  | PHE | A | 218 | 16.658 | 21.724 | 32.955 | 1.00  | 12.87 |     | A | C |
| ANISOU | 1541 | CG  | PHE | A | 218 | 1730   | 1451   | 1439   | −114  | −385  | 103 | A | C |
| SIGUIJ | 1541 | CG  | PHE | A | 218 | 1      | 0      | 0      | 220   | 72    | 290 | A | C |
| ATOM   | 1542 | CD1 | PHE | A | 218 | 15.709 | 21.011 | 33.658 | 1.00  | 13.77 |     | A | C |
| ANISOU | 1542 | CD1 | PHE | A | 218 | 2172   | 1757   | 1813   | −381  | −61   | 48  | A | C |
| SIGUIJ | 1542 | CD1 | PHE | A | 218 | 1      | 0      | 0      | 220   | 72    | 290 | A | C |
| ATOM   | 1543 | CD2 | PHE | A | 218 | 16.878 | 23.066 | 33.311 | 1.00  | 13.74 |     | A | C |
| ANISOU | 1543 | CD2 | PHE | A | 218 | 1583   | 1452   | 1407   | −86   | −347  | 98  | A | C |
| SIGUIJ | 1543 | CD2 | PHE | A | 218 | 1      | 0      | 0      | 220   | 72    | 290 | A | C |
| ATOM   | 1544 | CE1 | PHE | A | 218 | 14.992 | 21.601 | 34.673 | 1.00  | 15.00 |     | A | C |
| ANISOU | 1544 | CE1 | PHE | A | 218 | 3044   | 2207   | 2268   | −214  | 456   | −105| A | C |
| SIGUIJ | 1544 | CE1 | PHE | A | 218 | 1      | 0      | 0      | 220   | 72    | 290 | A | C |
| ATOM   | 1545 | CE2 | PHE | A | 218 | 16.144 | 23.611 | 34.327 | 1.00  | 13.52 |     | A | C |
| ANISOU | 1545 | CE2 | PHE | A | 218 | 2007   | 1966   | 1633   | 86    | −129  | −59 | A | C |
| SIGUIJ | 1545 | CE2 | PHE | A | 218 | 1      | 0      | 0      | 220   | 72    | 290 | A | C |
| ATOM   | 1546 | CZ  | PHE | A | 218 | 15.221 | 22.887 | 34.986 | 1.00  | 14.44 |     | A | C |
| ANISOU | 1546 | CZ  | PHE | A | 218 | 2309   | 2150   | 2092   | −19   | 167   | −12 | A | C |
| SIGUIJ | 1546 | CZ  | PHE | A | 218 | 1      | 0      | 0      | 220   | 72    | 290 | A | C |
| ATOM   | 1547 | C   | PHE | A | 218 | 16.799 | 22.832 | 30.114 | 1.00  | 11.95 |     | A | C |
| ANISOU | 1547 | C   | PHE | A | 218 | 1447   | 1237   | 1419   | −177  | −9    | 16  | A | C |
| SIGUIJ | 1547 | C   | PHE | A | 218 | 1      | 0      | 0      | 220   | 72    | 290 | A | C |
| ATOM   | 1548 | O   | PHE | A | 218 | 17.888 | 23.293 | 29.760 | 1.00  | 11.79 |     | A | O |
| ANISOU | 1548 | O   | PHE | A | 218 | 1487   | 1509   | 1548   | −289  | −9    | 38  | A | O |
| SIGUIJ | 1548 | O   | PHE | A | 218 | 1      | 0      | 0      | 221   | 52    | 289 | A | O |
| ATOM   | 1549 | N   | PRO | A | 219 | 15.716 | 23.602 | 30.209 | 1.00  | 12.08 |     | A | N |
| ANISOU | 1549 | N   | PRO | A | 219 | 1402   | 1167   | 1545   | −231  | −20   | −31 | A | N |
| SIGUIJ | 1549 | N   | PRO | A | 219 | 1      | 0      | 0      | 221   | 58    | 289 | A | N |
| ATOM   | 1550 | CD  | PRO | A | 219 | 15.818 | 25.074 | 30.059 | 1.00  | 12.42 |     | A | C |
| ANISOU | 1550 | CD  | PRO | A | 219 | 1998   | 1163   | 2680   | −237  | 160   | 47  | A | C |
| SIGUIJ | 1550 | CD  | PRO | A | 219 | 1      | 0      | 0      | 220   | 72    | 290 | A | C |
| ATOM   | 1551 | CA  | PRO | A | 219 | 14.375 | 23.202 | 30.668 | 1.00  | 12.31 |     | A | C |
| ANISOU | 1551 | CA  | PRO | A | 219 | 1418   | 1312   | 1570   | −249  | −1    | −3  | A | C |
| SIGUIJ | 1551 | CA  | PRO | A | 219 | 1      | 0      | 0      | 220   | 72    | 290 | A | C |
| ATOM   | 1552 | CB  | PRO | A | 219 | 13.572 | 24.525 | 30.678 | 1.00  | 12.41 |     | A | C |
| ANISOU | 1552 | CB  | PRO | A | 219 | 1779   | 1449   | 1907   | −23   | 8     | 1   | A | C |
| SIGUIJ | 1552 | CB  | PRO | A | 219 | 1      | 0      | 0      | 220   | 72    | 290 | A | C |
| ATOM   | 1553 | CG  | PRO | A | 219 | 14.642 | 25.560 | 30.920 | 1.00  | 12.69 |     | A | C |
| ANISOU | 1553 | CG  | PRO | A | 219 | 1875   | 1532   | 2386   | −98   | −87   | 1   | A | C |
| SIGUIJ | 1553 | CG  | PRO | A | 219 | 1      | 0      | 0      | 220   | 72    | 290 | A | C |
| ATOM   | 1554 | C   | PRO | A | 219 | 13.726 | 22.195 | 29.731 | 1.00  | 12.75 |     | A | C |
| ANISOU | 1554 | C   | PRO | A | 219 | 1553   | 1349   | 1561   | −312  | 8     | −21 | A | C |
| SIGUIJ | 1554 | C   | PRO | A | 219 | 1      | 0      | 0      | 220   | 72    | 290 | A | C |
| ATOM   | 1555 | O   | PRO | A | 219 | 13.965 | 22.155 | 28.518 | 1.00  | 12.79 |     | A | O |
| ANISOU | 1555 | O   | PRO | A | 219 | 1686   | 1343   | 1555   | −350  | 26    | −33 | A | O |
| SIGUIJ | 1555 | O   | PRO | A | 219 | 1      | 0      | 0      | 221   | 52    | 289 | A | O |
| ATOM   | 1556 | N   | CYS | A | 220 | 12.856 | 21.372 | 30.336 | 1.00  | 12.93 |     | A | N |
| ANISOU | 1556 | N   | CYS | A | 220 | 1508   | 1329   | 1644   | −267  | 9     | 28  | A | N |
| SIGUIJ | 1556 | N   | CYS | A | 220 | 1      | 0      | 0      | 221   | 58    | 289 | A | N |
| ATOM   | 1557 | CA  | CYS | A | 220 | 12.062 | 20.357 | 29.618 | 1.00  | 13.60 |     | A | C |
| ANISOU | 1557 | CA  | CYS | A | 220 | 1546   | 1322   | 1772   | −246  | −24   | −18 | A | C |
| SIGUIJ | 1557 | CA  | CYS | A | 220 | 1      | 0      | 0      | 220   | 72    | 290 | A | C |
| ATOM   | 1558 | C   | CYS | A | 220 | 10.995 | 20.981 | 28.760 | 1.00  | 14.24 |     | A | C |
| ANISOU | 1558 | C   | CYS | A | 220 | 1693   | 1699   | 1739   | 0     | −1    | 0   | A | C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1558 | C | CYS | A | 220 | 1 | 0 | 0 | 220 | 72 | 290 | A | C |
| ATOM | 1559 | O | CYS | A | 220 | 10.615 | 22.141 | 28.942 | 1.00 | 14.47 | | A | O |
| ANISOU | 1559 | O | CYS | A | 220 | 1720 | 1704 | 1837 | 0 | −8 | 0 | A | O |
| SIGUIJ | 1559 | O | CYS | A | 220 | 1 | 0 | 0 | 221 | 52 | 289 | A | O |
| ATOM | 1560 | CB | CYS | A | 220 | 11.388 | 19.442 | 30.614 | 1.00 | 13.73 | | A | C |
| ANISOU | 1560 | CB | CYS | A | 220 | 1754 | 1357 | 1802 | −333 | 3 | −13 | A | C |
| SIGUIJ | 1560 | CB | CYS | A | 220 | 1 | 0 | 0 | 220 | 72 | 290 | A | C |
| ATOM | 1561 | SG | CYS | A | 220 | 12.591 | 18.602 | 31.683 | 1.00 | 13.62 | | A | S |
| ANISOU | 1561 | SG | CYS | A | 220 | 1825 | 1404 | 1757 | −224 | 32 | −41 | A | S |
| SIGUIJ | 1561 | SG | CYS | A | 220 | 1 | 0 | 0 | 221 | 48 | 289 | A | S |
| ATOM | 1562 | N | GLY | A | 220A | 10.397 | 20.125 | 27.903 | 1.00 | 15.11 | | A | N |
| ANISOU | 1562 | N | GLY | A | 220A | 1838 | 1721 | 1732 | −69 | −4 | 2 | A | N |
| SIGUIJ | 1562 | N | GLY | A | 220A | 1 | 0 | 0 | 221 | 58 | 289 | A | N |
| ATOM | 1563 | CA | GLY | A | 220A | 9.164 | 20.493 | 27.261 | 1.00 | 16.18 | | A | C |
| ANISOU | 1563 | CA | GLY | A | 220A | 1866 | 2013 | 1719 | 38 | 10 | 0 | A | C |
| SIGUIJ | 1563 | CA | GLY | A | 220A | 1 | 0 | 0 | 220 | 72 | 290 | A | C |
| ATOM | 1564 | C | GLY | A | 220A | 9.319 | 21.388 | 26.030 | 1.00 | 17.12 | | A | C |
| ANISOU | 1564 | C | GLY | A | 220A | 2445 | 2220 | 1770 | −339 | −171 | 103 | A | C |
| SIGUIJ | 1564 | C | GLY | A | 220A | 1 | 0 | 0 | 220 | 72 | 290 | A | C |
| ATOM | 1565 | O | GLY | A | 220A | 8.307 | 21.865 | 25.599 | 1.00 | 17.88 | | A | O |
| ANISOU | 1565 | O | GLY | A | 220A | 2713 | 2864 | 2256 | 17 | −431 | −23 | A | O |
| SIGUIJ | 1565 | O | GLY | A | 220A | 1 | 0 | 0 | 221 | 52 | 289 | A | O |
| ATOM | 1566 | N | GLN | A | 221 | 10.490 | 21.594 | 25.449 | 1.00 | 18.02 | | A | N |
| ANISOU | 1566 | N | GLN | A | 221 | 2497 | 1863 | 1947 | −323 | −72 | 36 | A | N |
| SIGUIJ | 1566 | N | GLN | A | 221 | 1 | 0 | 0 | 221 | 58 | 289 | A | N |
| ATOM | 1567 | CA | GLN | A | 221 | 10.577 | 22.382 | 24.191 | 1.00 | 18.94 | | A | C |
| ANISOU | 1567 | CA | GLN | A | 221 | 2667 | 1946 | 1980 | −453 | −142 | 78 | A | C |
| SIGUIJ | 1567 | CA | GLN | A | 221 | 1 | 0 | 0 | 220 | 72 | 290 | A | C |
| ATOM | 1568 | CB | GLN | A | 221 | 12.033 | 22.912 | 23.978 | 1.00 | 20.32 | | A | C |
| ANISOU | 1568 | CB | GLN | A | 221 | 2735 | 2120 | 2808 | −542 | 71 | −128 | A | C |
| SIGUIJ | 1568 | CB | GLN | A | 221 | 1 | 0 | 0 | 220 | 72 | 290 | A | C |
| ATOM | 1569 | CG | GLN | A | 221 | 12.698 | 23.650 | 25.232 | 1.00 | 22.63 | | A | C |
| ANISOU | 1569 | CG | GLN | A | 221 | 6266 | 4961 | 2776 | −3750 | 103 | −97 | A | C |
| SIGUIJ | 1569 | CG | GLN | A | 221 | 1 | 0 | 0 | 220 | 71 | 290 | A | C |
| ATOM | 1570 | CD | GLN | A | 221 | 14.309 | 23.668 | 25.301 | 1.00 | 23.50 | | A | C |
| ANISOU | 1570 | CD | GLN | A | 221 | 6269 | 5576 | 2798 | −3749 | 109 | −152 | A | C |
| SIGUIJ | 1570 | CD | GLN | A | 221 | 1 | 0 | 0 | 220 | 71 | 290 | A | C |
| ATOM | 1571 | OE1 | GLN | A | 221 | 15.004 | 23.324 | 24.311 | 1.00 | 24.98 | | A | O |
| ANISOU | 1571 | OE1 | GLN | A | 221 | 6706 | 9542 | 2425 | −1564 | −346 | 0 | A | O |
| SIGUIJ | 1571 | OE1 | GLN | A | 221 | 1 | 0 | 0 | 221 | 52 | 289 | A | O |
| ATOM | 1572 | NE2 | GLN | A | 221 | 14.893 | 24.082 | 26.507 | 1.00 | 24.32 | | A | N |
| ANISOU | 1572 | NE2 | GLN | A | 221 | 4948 | 2602 | 2776 | −1814 | 90 | −60 | A | N |
| SIGUIJ | 1572 | NE2 | GLN | A | 221 | 1 | 0 | 0 | 221 | 58 | 289 | A | N |
| ATOM | 1573 | C | GLN | A | 221 | 10.148 | 21.489 | 23.008 | 1.00 | 18.74 | | A | C |
| ANISOU | 1573 | C | GLN | A | 221 | 2349 | 1846 | 1994 | −295 | −163 | 94 | A | C |
| SIGUIJ | 1573 | C | GLN | A | 221 | 1 | 0 | 0 | 220 | 71 | 290 | A | C |
| ATOM | 1574 | O | GLN | A | 221 | 10.442 | 20.318 | 22.989 | 1.00 | 18.63 | | A | O |
| ANISOU | 1574 | O | GLN | A | 221 | 2832 | 1866 | 1658 | −168 | −431 | 60 | A | O |
| SIGUIJ | 1574 | O | GLN | A | 221 | 1 | 0 | 0 | 221 | 52 | 289 | A | O |
| ATOM | 1575 | N | PRO | A | 222 | 9.442 | 22.036 | 21.994 | 1.00 | 18.66 | | A | N |
| ANISOU | 1575 | N | PRO | A | 222 | 2444 | 2066 | 1903 | −26 | −84 | 5 | A | N |
| SIGUIJ | 1575 | N | PRO | A | 222 | 1 | 0 | 0 | 221 | 58 | 289 | A | N |
| ATOM | 1576 | CD | PRO | A | 222 | 8.907 | 23.396 | 21.813 | 1.00 | 19.06 | | A | C |
| ANISOU | 1576 | CD | PRO | A | 222 | 3241 | 2148 | 2479 | 226 | −555 | −114 | A | C |
| SIGUIJ | 1576 | CD | PRO | A | 222 | 1 | 0 | 0 | 220 | 71 | 290 | A | C |
| ATOM | 1577 | CA | PRO | A | 222 | 9.126 | 21.153 | 20.865 | 1.00 | 18.29 | | A | C |
| ANISOU | 1577 | CA | PRO | A | 222 | 2662 | 2088 | 1906 | −76 | −97 | 11 | A | C |
| SIGUIJ | 1577 | CA | PRO | A | 222 | 1 | 0 | 0 | 220 | 71 | 290 | A | C |
| ATOM | 1578 | CB | PRO | A | 222 | 8.153 | 21.984 | 20.008 | 1.00 | 18.73 | | A | C |
| ANISOU | 1578 | CB | PRO | A | 222 | 3720 | 2824 | 2104 | 768 | −489 | −244 | A | C |
| SIGUIJ | 1578 | CB | PRO | A | 222 | 1 | 0 | 0 | 220 | 71 | 290 | A | C |
| ATOM | 1579 | CG | PRO | A | 222 | 8.573 | 23.377 | 20.316 | 1.00 | 19.22 | | A | C |
| ANISOU | 1579 | CG | PRO | A | 222 | 4653 | 2883 | 2550 | 569 | −865 | −230 | A | C |
| SIGUIJ | 1579 | CG | PRO | A | 222 | 1 | 0 | 0 | 221 | 71 | 290 | A | C |
| ATOM | 1580 | C | PRO | A | 222 | 10.348 | 20.770 | 20.082 | 1.00 | 18.03 | | A | C |
| ANISOU | 1580 | C | PRO | A | 222 | 2412 | 1780 | 1354 | −146 | −451 | 81 | A | C |
| SIGUIJ | 1580 | C | PRO | A | 222 | 1 | 0 | 0 | 221 | 71 | 290 | A | C |
| ATOM | 1581 | O | PRO | A | 222 | 11.340 | 21.500 | 20.052 | 1.00 | 17.67 | | A | O |
| ANISOU | 1581 | O | PRO | A | 222 | 2510 | 1950 | 1890 | −286 | −507 | 188 | A | O |
| SIGUIJ | 1581 | O | PRO | A | 222 | 1 | 0 | 0 | 221 | 52 | 289 | A | O |
| ATOM | 1582 | N | ASN | A | 223 | 10.273 | 19.628 | 19.426 | 1.00 | 17.53 | | A | N |
| ANISOU | 1582 | N | ASN | A | 223 | 2729 | 1793 | 1356 | −225 | −360 | 79 | A | N |
| SIGUIJ | 1582 | N | ASN | A | 223 | 1 | 0 | 0 | 221 | 58 | 289 | A | N |
| ATOM | 1583 | CA | ASN | A | 223 | 11.350 | 19.147 | 18.569 | 1.00 | 17.54 | | A | C |
| ANISOU | 1583 | CA | ASN | A | 223 | 2780 | 1992 | 1428 | −172 | −321 | 52 | A | C |
| SIGUIJ | 1583 | CA | ASN | A | 223 | 1 | 0 | 0 | 221 | 71 | 290 | A | C |
| ATOM | 1584 | CB | ASN | A | 223 | 11.479 | 20.057 | 17.321 | 1.00 | 18.02 | | A | C |
| ANISOU | 1584 | CB | ASN | A | 223 | 3249 | 1976 | 1422 | −171 | −278 | 33 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1584 | CB | ASN | A | 223 | 1 | 0 | 0 | 221 | 71 | 290 | A | C |
| ATOM | 1585 | CG | ASN | A | 223 | 10.215 | 20.035 | 16.501 | 1.00 | 18.59 | | A | C |
| ANISOU | 1585 | CG | ASN | A | 223 | 3261 | 2387 | 1455 | −161 | −297 | 34 | A | C |
| SIGUIJ | 1585 | CG | ASN | A | 223 | 1 | 0 | 0 | 221 | 71 | 290 | A | C |
| ATOM | 1586 | OD1 | ASN | A | 223 | 9.650 | 18.968 | 16.251 | 1.00 | 18.98 | | A | O |
| ANISOU | 1586 | OD1 | ASN | A | 223 | 3166 | 2340 | 1973 | −58 | −523 | 33 | A | O |
| SIGUIJ | 1586 | OD1 | ASN | A | 223 | 1 | 0 | 0 | 221 | 52 | 289 | A | O |
| ATOM | 1587 | ND2 | ASN | A | 223 | 9.739 | 21.206 | 16.088 | 1.00 | 19.13 | | A | N |
| ANISOU | 1587 | ND2 | ASN | A | 223 | 3123 | 2392 | 2721 | −372 | −737 | 299 | A | N |
| SIGUIJ | 1587 | ND2 | ASN | A | 223 | 1 | 0 | 0 | 221 | 58 | 289 | A | N |
| ATOM | 1588 | C | ASN | A | 223 | 12.671 | 19.041 | 19.339 | 1.00 | 17.09 | | A | C |
| ANISOU | 1588 | C | ASN | A | 223 | 2793 | 1697 | 1502 | −204 | −358 | 59 | A | C |
| SIGUIJ | 1588 | C | ASN | A | 223 | 1 | 0 | 0 | 221 | 71 | 290 | A | C |
| ATOM | 1589 | O | ASN | A | 223 | 13.738 | 19.351 | 18.853 | 1.00 | 17.57 | | A | O |
| ANISOU | 1589 | O | ASN | A | 223 | 2923 | 2765 | 1808 | −476 | −247 | 154 | A | O |
| SIGUIJ | 1589 | O | ASN | A | 223 | 1 | 0 | 0 | 221 | 52 | 289 | A | O |
| ATOM | 1590 | N | ASP | A | 224 | 12.575 | 18.521 | 20.560 | 1.00 | 16.25 | | A | N |
| ANISOU | 1590 | N | ASP | A | 224 | 2538 | 1710 | 1506 | −198 | −365 | 72 | A | N |
| SIGUIJ | 1590 | N | ASP | A | 224 | 1 | 0 | 0 | 221 | 58 | 289 | A | N |
| ATOM | 1591 | CA | ASP | A | 224 | 13.720 | 18.394 | 21.449 | 1.00 | 15.80 | | A | C |
| ANISOU | 1591 | CA | ASP | A | 224 | 2495 | 1541 | 1476 | −242 | −327 | 75 | A | C |
| SIGUIJ | 1591 | CA | ASP | A | 224 | 1 | 0 | 0 | 221 | 71 | 290 | A | C |
| ATOM | 1592 | CB | ASP | A | 224 | 13.635 | 19.530 | 22.484 | 1.00 | 16.19 | | A | C |
| ANISOU | 1592 | CB | ASP | A | 224 | 2559 | 1555 | 1532 | −384 | −154 | 54 | A | C |
| SIGUIJ | 1592 | CB | ASP | A | 224 | 1 | 0 | 0 | 221 | 71 | 290 | A | C |
| ATOM | 1593 | CG | ASP | A | 224 | 14.929 | 19.735 | 23.242 | 1.00 | 16.69 | | A | C |
| ANISOU | 1593 | CG | ASP | A | 224 | 2561 | 1777 | 1561 | −421 | −159 | 67 | A | C |
| SIGUIJ | 1593 | CG | ASP | A | 224 | 1 | 0 | 0 | 221 | 71 | 290 | A | C |
| ATOM | 1594 | OD1 | ASP | A | 224 | 15.907 | 19.005 | 22.994 | 1.00 | 17.24 | | A | O |
| ANISOU | 1594 | OD1 | ASP | A | 224 | 2637 | 1866 | 2261 | −364 | −12 | 7 | A | O |
| SIGUIJ | 1594 | OD1 | ASP | A | 224 | 1 | 0 | 0 | 221 | 52 | 289 | A | O |
| ATOM | 1595 | OD2 | ASP | A | 224 | 14.954 | 20.642 | 24.120 | 1.00 | 17.05 | | A | O |
| ANISOU | 1595 | OD2 | ASP | A | 224 | 2851 | 1892 | 1681 | −652 | 75 | −39 | A | O |
| SIGUIJ | 1595 | OD2 | ASP | A | 224 | 1 | 0 | 0 | 221 | 52 | 289 | A | O |
| ATOM | 1596 | C | ASP | A | 224 | 13.581 | 17.040 | 22.170 | 1.00 | 14.99 | | A | C |
| ANISOU | 1596 | C | ASP | A | 224 | 1845 | 1478 | 1361 | −19 | −26 | 1 | A | C |
| SIGUIJ | 1596 | C | ASP | A | 224 | 1 | 0 | 0 | 221 | 71 | 290 | A | C |
| ATOM | 1597 | O | ASP | A | 224 | 13.353 | 16.980 | 23.405 | 1.00 | 15.33 | | A | O |
| ANISOU | 1597 | O | ASP | A | 224 | 1951 | 1733 | 1369 | −154 | 1 | 0 | A | O |
| SIGUIJ | 1597 | O | ASP | A | 224 | 1 | 0 | 0 | 221 | 52 | 289 | A | O |
| ATOM | 1598 | N | PRO | A | 225 | 13.698 | 15.928 | 21.441 | 1.00 | 14.29 | | A | N |
| ANISOU | 1598 | N | PRO | A | 225 | 1966 | 1484 | 1360 | −67 | 54 | −7 | A | N |
| SIGUIJ | 1598 | N | PRO | A | 225 | 1 | 0 | 0 | 221 | 58 | 289 | A | N |
| ATOM | 1599 | CD | PRO | A | 225 | 14.105 | 15.840 | 20.019 | 1.00 | 14.25 | | A | C |
| ANISOU | 1599 | CD | PRO | A | 225 | 2603 | 1703 | 1416 | −202 | 249 | −47 | A | C |
| SIGUIJ | 1599 | CD | PRO | A | 225 | 1 | 0 | 0 | 221 | 71 | 290 | A | C |
| ATOM | 1600 | CA | PRO | A | 225 | 13.222 | 14.644 | 21.984 | 1.00 | 13.59 | | A | C |
| ANISOU | 1600 | CA | PRO | A | 225 | 1693 | 1481 | 1339 | −15 | −61 | 4 | A | C |
| SIGUIJ | 1600 | CA | PRO | A | 225 | 1 | 0 | 0 | 221 | 71 | 290 | A | C |
| ATOM | 1601 | CB | PRO | A | 225 | 13.220 | 13.719 | 20.775 | 1.00 | 14.03 | | A | C |
| ANISOU | 1601 | CB | PRO | A | 225 | 2427 | 1525 | 1340 | −59 | −27 | 2 | A | C |
| SIGUIJ | 1601 | CB | PRO | A | 225 | 1 | 0 | 0 | 221 | 71 | 290 | A | C |
| ATOM | 1602 | CG | PRO | A | 225 | 14.279 | 14.323 | 19.833 | 1.00 | 14.43 | | A | C |
| ANISOU | 1602 | CG | PRO | A | 225 | 2888 | 1702 | 1777 | −198 | 407 | −66 | A | C |
| SIGUIJ | 1602 | CG | PRO | A | 225 | 1 | 0 | 0 | 221 | 71 | 290 | A | C |
| ATOM | 1603 | C | PRO | A | 225 | 14.122 | 14.114 | 23.096 | 1.00 | 12.87 | | A | C |
| ANISOU | 1603 | C | PRO | A | 225 | 1594 | 1510 | 1279 | 15 | 10 | 1 | A | C |
| SIGUIJ | 1603 | C | PRO | A | 225 | 1 | 0 | 0 | 221 | 71 | 290 | A | C |
| ATOM | 1604 | O | PRO | A | 225 | 15.334 | 14.336 | 23.134 | 1.00 | 13.21 | | A | O |
| ANISOU | 1604 | O | PRO | A | 225 | 1601 | 1740 | 1530 | −41 | 2 | 0 | A | O |
| SIGUIJ | 1604 | O | PRO | A | 225 | 1 | 0 | 0 | 221 | 52 | 289 | A | O |
| ATOM | 1605 | N | GLY | A | 226 | 13.489 | 13.433 | 24.047 | 1.00 | 12.02 | | A | N |
| ANISOU | 1605 | N | GLY | A | 226 | 1575 | 1508 | 1262 | −2 | −16 | 0 | A | N |
| SIGUIJ | 1605 | N | GLY | A | 226 | 1 | 0 | 0 | 221 | 58 | 289 | A | N |
| ATOM | 1606 | CA | GLY | A | 226 | 14.217 | 12.778 | 25.138 | 1.00 | 11.76 | | A | C |
| ANISOU | 1606 | CA | GLY | A | 226 | 1492 | 1481 | 1217 | 0 | 44 | 0 | A | C |
| SIGUIJ | 1606 | CA | GLY | A | 226 | 1 | 0 | 0 | 221 | 71 | 290 | A | C |
| ATOM | 1607 | C | GLY | A | 226 | 14.917 | 11.523 | 24.671 | 1.00 | 11.47 | | A | C |
| ANISOU | 1607 | C | GLY | A | 226 | 1455 | 1465 | 1150 | 0 | 11 | 0 | A | C |
| SIGUIJ | 1607 | C | GLY | A | 226 | 1 | 0 | 0 | 221 | 71 | 290 | A | C |
| ATOM | 1608 | O | GLY | A | 226 | 14.568 | 10.914 | 23.642 | 1.00 | 11.78 | | A | O |
| ANISOU | 1608 | O | GLY | A | 226 | 1654 | 1487 | 1159 | −69 | 11 | −3 | A | O |
| SIGUIJ | 1608 | O | GLY | A | 226 | 1 | 0 | 0 | 221 | 52 | 289 | A | O |
| ATOM | 1609 | N | VAL | A | 227 | 15.941 | 11.152 | 25.417 | 1.00 | 11.46 | | A | N |
| ANISOU | 1609 | N | VAL | A | 227 | 1406 | 1234 | 1142 | −76 | 26 | −9 | A | N |
| SIGUIJ | 1609 | N | VAL | A | 227 | 1 | 0 | 0 | 221 | 58 | 289 | A | N |
| ATOM | 1610 | CA | VAL | A | 227 | 16.805 | 10.024 | 25.124 | 1.00 | 11.12 | | A | C |
| ANISOU | 1610 | CA | VAL | A | 227 | 1437 | 1245 | 1153 | −46 | 20 | −4 | A | C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1610 | CA | VAL | A | 227 | 1 | 0 | 0 | 221 | 71 | 290 | A C |
| ATOM | 1611 | CB | VAL | A | 227 | 18.303 | 10.442 | 25.180 | 1.00 | 11.78 | | A C |
| ANISOU | 1611 | CB | VAL | A | 227 | 1441 | 1335 | 1483 | −72 | 0 | 0 | A C |
| SIGUIJ | 1611 | CB | VAL | A | 227 | 1 | 0 | 0 | 221 | 71 | 290 | A C |
| ATOM | 1612 | CG1 | VAL | A | 227 | 19.175 | 9.313 | 24.627 | 1.00 | 12.98 | | A C |
| ANISOU | 1612 | CG1 | VAL | A | 227 | 1874 | 1380 | 2701 | −54 | 678 | −69 | A C |
| SIGUIJ | 1612 | CG1 | VAL | A | 227 | 1 | 0 | 0 | 221 | 71 | 290 | A C |
| ATOM | 1613 | CG2 | VAL | A | 227 | 18.524 | 11.701 | 24.319 | 1.00 | 12.63 | | A C |
| ANISOU | 1613 | CG2 | VAL | A | 227 | 2070 | 1541 | 1692 | −417 | −314 | 203 | A C |
| SIGUIJ | 1613 | CG2 | VAL | A | 227 | 1 | 0 | 0 | 221 | 70 | 290 | A C |
| ATOM | 1614 | C | VAL | A | 227 | 16.555 | 8.910 | 26.127 | 1.00 | 10.85 | | A C |
| ANISOU | 1614 | C | VAL | A | 227 | 1581 | 1223 | 1175 | −4 | 111 | −1 | A C |
| SIGUIJ | 1614 | C | VAL | A | 227 | 1 | 0 | 0 | 221 | 70 | 290 | A C |
| ATOM | 1615 | O | VAL | A | 227 | 16.348 | 9.145 | 27.341 | 1.00 | 10.23 | | A O |
| ANISOU | 1615 | O | VAL | A | 227 | 1443 | 1221 | 1168 | −2 | 94 | −1 | A O |
| SIGUIJ | 1615 | O | VAL | A | 227 | 1 | 0 | 0 | 221 | 52 | 289 | A O |
| ATOM | 1616 | N | TYR | A | 228 | 16.566 | 7.703 | 25.586 | 1.00 | 10.02 | | A N |
| ANISOU | 1616 | N | TYR | A | 228 | 1415 | 1203 | 1169 | 4 | 91 | 2 | A N |
| SIGUIJ | 1616 | N | TYR | A | 228 | 1 | 0 | 0 | 221 | 58 | 289 | A N |
| ATOM | 1617 | CA | TYR | A | 228 | 16.222 | 6.463 | 26.308 | 1.00 | 10.20 | | A C |
| ANISOU | 1617 | CA | TYR | A | 228 | 1328 | 1217 | 1148 | −22 | 6 | −1 | A C |
| SIGUIJ | 1617 | CA | TYR | A | 228 | 1 | 0 | 0 | 221 | 70 | 290 | A C |
| ATOM | 1618 | CB | TYR | A | 228 | 14.913 | 5.863 | 25.811 | 1.00 | 9.96 | | A C |
| ANISOU | 1618 | CB | TYR | A | 228 | 1316 | 1188 | 1210 | 10 | −3 | 0 | A C |
| SIGUIJ | 1618 | CB | TYR | A | 228 | 1 | 0 | 0 | 221 | 70 | 290 | A C |
| ATOM | 1619 | CG | TYR | A | 228 | 13.729 | 6.773 | 26.001 | 1.00 | 9.39 | | A C |
| ANISOU | 1619 | CG | TYR | A | 228 | 1307 | 1182 | 1150 | 2 | −3 | 0 | A C |
| SIGUIJ | 1619 | CG | TYR | A | 228 | 1 | 0 | 0 | 221 | 70 | 290 | A C |
| ATOM | 1620 | CD1 | TYR | A | 228 | 13.533 | 7.897 | 25.185 | 1.00 | 9.77 | | A C |
| ANISOU | 1620 | CD1 | TYR | A | 228 | 1420 | 1198 | 1189 | −35 | −68 | 10 | A C |
| SIGUIJ | 1620 | CD1 | TYR | A | 228 | 1 | 0 | 0 | 221 | 70 | 290 | A C |
| ATOM | 1621 | CE1 | TYR | A | 228 | 12.492 | 8.749 | 25.388 | 1.00 | 10.19 | | A C |
| ANISOU | 1621 | CE1 | TYR | A | 228 | 1413 | 1206 | 1165 | −44 | −56 | 10 | A C |
| SIGUIJ | 1621 | CE1 | TYR | A | 228 | 1 | 0 | 0 | 221 | 70 | 290 | A C |
| ATOM | 1622 | CD2 | TYR | A | 228 | 12.802 | 6.538 | 27.006 | 1.00 | 9.93 | | A C |
| ANISOU | 1622 | CD2 | TYR | A | 228 | 1315 | 1225 | 1146 | −26 | −7 | 1 | A C |
| SIGUIJ | 1622 | CD2 | TYR | A | 228 | 1 | 0 | 0 | 221 | 70 | 290 | A C |
| ATOM | 1623 | CE2 | TYR | A | 228 | 11.746 | 7.360 | 27.192 | 1.00 | 10.22 | | A C |
| ANISOU | 1623 | CE2 | TYR | A | 228 | 1341 | 1289 | 1105 | 4 | −37 | −2 | A C |
| SIGUIJ | 1623 | CE2 | TYR | A | 228 | 1 | 0 | 0 | 221 | 70 | 290 | A C |
| ATOM | 1624 | CZ | TYR | A | 228 | 11.586 | 8.471 | 26.404 | 1.00 | 10.10 | | A C |
| ANISOU | 1624 | CZ | TYR | A | 228 | 1391 | 1309 | 1156 | −46 | −73 | 23 | A C |
| SIGUIJ | 1624 | CZ | TYR | A | 228 | 1 | 0 | 0 | 221 | 70 | 290 | A C |
| ATOM | 1625 | OH | TYR | A | 228 | 10.478 | 9.265 | 26.651 | 1.00 | 11.60 | | A O |
| ANISOU | 1625 | OH | TYR | A | 228 | 1481 | 1416 | 1670 | 19 | 56 | 7 | A O |
| SIGUIJ | 1625 | OH | TYR | A | 228 | 1 | 0 | 0 | 221 | 52 | 289 | A O |
| ATOM | 1626 | C | TYR | A | 228 | 17.290 | 5.436 | 26.099 | 1.00 | 10.30 | | A C |
| ANISOU | 1626 | C | TYR | A | 228 | 1327 | 1224 | 1215 | −20 | 8 | −2 | A C |
| SIGUIJ | 1626 | C | TYR | A | 228 | 1 | 0 | 0 | 221 | 70 | 290 | A C |
| ATOM | 1627 | O | TYR | A | 228 | 17.930 | 5.376 | 25.013 | 1.00 | 10.72 | | A O |
| ANISOU | 1627 | O | TYR | A | 228 | 1534 | 1590 | 1280 | 10 | 137 | −24 | A O |
| SIGUIJ | 1627 | O | TYR | A | 228 | 1 | 0 | 0 | 221 | 52 | 289 | A O |
| ATOM | 1628 | N | THR | A | 229 | 17.535 | 4.608 | 27.117 | 1.00 | 10.63 | | A N |
| ANISOU | 1628 | N | THR | A | 229 | 1353 | 1217 | 1224 | −11 | 7 | −1 | A N |
| SIGUIJ | 1628 | N | THR | A | 229 | 1 | 0 | 0 | 221 | 58 | 289 | A N |
| ATOM | 1629 | CA | THR | A | 229 | 18.329 | 3.402 | 26.944 | 1.00 | 10.92 | | A C |
| ANISOU | 1629 | CA | THR | A | 229 | 1316 | 1211 | 1479 | −30 | 37 | −6 | A C |
| SIGUIJ | 1629 | CA | THR | A | 229 | 1 | 0 | 0 | 221 | 70 | 290 | A C |
| ATOM | 1630 | CB | THR | A | 229 | 18.753 | 2.865 | 28.305 | 1.00 | 11.62 | | A C |
| ANISOU | 1630 | CB | THR | A | 229 | 1564 | 1441 | 1509 | 151 | 9 | 11 | A C |
| SIGUIJ | 1630 | CB | THR | A | 229 | 1 | 0 | 0 | 221 | 70 | 290 | A C |
| ATOM | 1631 | OG1 | THR | A | 229 | 19.487 | 3.872 | 28.948 | 1.00 | 12.39 | | A O |
| ANISOU | 1631 | OG1 | THR | A | 229 | 1810 | 1616 | 1576 | −46 | 9 | −2 | A O |
| SIGUIJ | 1631 | OG1 | THR | A | 229 | 1 | 0 | 0 | 221 | 52 | 289 | A O |
| ATOM | 1632 | CG2 | THR | A | 229 | 19.679 | 1.680 | 28.226 | 1.00 | 12.39 | | A C |
| ANISOU | 1632 | CG2 | THR | A | 229 | 1812 | 1563 | 1817 | 322 | −11 | −29 | A C |
| SIGUIJ | 1632 | CG2 | THR | A | 229 | 1 | 0 | 0 | 221 | 70 | 290 | A C |
| ATOM | 1633 | C | THR | A | 229 | 17.480 | 2.357 | 26.222 | 1.00 | 11.11 | | A C |
| ANISOU | 1633 | C | THR | A | 229 | 1311 | 1182 | 1430 | 1 | 24 | 0 | A C |
| SIGUIJ | 1633 | C | THR | A | 229 | 1 | 0 | 0 | 221 | 70 | 290 | A C |
| ATOM | 1634 | O | THR | A | 229 | 16.345 | 2.041 | 26.627 | 1.00 | 11.43 | | A O |
| ANISOU | 1634 | O | THR | A | 229 | 1374 | 1278 | 1621 | −28 | 140 | −30 | A O |
| SIGUIJ | 1634 | O | THR | A | 229 | 1 | 0 | 0 | 221 | 52 | 289 | A O |
| ATOM | 1635 | N | GLN | A | 230 | 18.056 | 1.751 | 25.172 | 1.00 | 11.04 | | A N |
| ANISOU | 1635 | N | GLN | A | 230 | 1353 | 1214 | 1409 | 70 | 0 | 0 | A N |
| SIGUIJ | 1635 | N | GLN | A | 230 | 1 | 0 | 0 | 221 | 58 | 289 | A N |
| ATOM | 1636 | CA | GLN | A | 230 | 17.336 | 0.791 | 24.322 | 1.00 | 11.88 | | A C |
| ANISOU | 1636 | CA | GLN | A | 230 | 1491 | 1291 | 1412 | −17 | −8 | 1 | A C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1636 | CA | GLN | A | 230 | 1 | 0 | 0 | 221 | 70 | 290 | A C |
| ATOM | 1637 | CB | GLN | A | 230 | 17.919 | 0.838 | 22.899 | 1.00 | 12.79 | | A C |
| ANISOU | 1637 | CB | GLN | A | 230 | 1649 | 1657 | 1435 | 0 | 57 | 1 | A C |
| SIGUIJ | 1637 | CB | GLN | A | 230 | 1 | 0 | 0 | 221 | 70 | 290 | A C |
| ATOM | 1638 | CG | GLN | A | 230 | 17.081 | −0.002 | 21.922 | 1.00 | 13.79 | | A C |
| ANISOU | 1638 | CG | GLN | A | 230 | 1788 | 1661 | 1507 | −12 | −51 | 3 | A C |
| SIGUIJ | 1638 | CG | GLN | A | 230 | 1 | 0 | 0 | 221 | 70 | 290 | A C |
| ATOM | 1639 | CD | GLN | A | 230 | 17.584 | 0.009 | 20.482 | 1.00 | 14.47 | | A C |
| ANISOU | 1639 | CD | GLN | A | 230 | 2306 | 2089 | 1555 | 59 | 122 | 20 | A C |
| SIGUIJ | 1639 | CD | GLN | A | 230 | 1 | 0 | 0 | 221 | 70 | 290 | A C |
| ATOM | 1640 | OE1 | GLN | A | 230 | 16.787 | −0.260 | 19.527 | 1.00 | 16.05 | | A O |
| ANISOU | 1640 | OE1 | GLN | A | 230 | 2732 | 2441 | 1836 | −9 | −214 | −4 | A O |
| SIGUIJ | 1640 | OE1 | GLN | A | 230 | 1 | 0 | 0 | 221 | 52 | 289 | A O |
| ATOM | 1641 | NE2 | GLN | A | 230 | 18.860 | 0.287 | 20.314 | 1.00 | 14.61 | | A N |
| ANISOU | 1641 | NE2 | GLN | A | 230 | 2271 | 1652 | 1107 | 167 | 76 | 13 | A N |
| SIGUIJ | 1641 | NE2 | GLN | A | 230 | 1 | 0 | 0 | 221 | 58 | 289 | A N |
| ATOM | 1642 | C | GLN | A | 230 | 17.450 | −0.613 | 24.913 | 1.00 | 11.68 | | A C |
| ANISOU | 1642 | C | GLN | A | 230 | 1483 | 1291 | 1411 | −9 | −6 | 0 | A C |
| SIGUIJ | 1642 | C | GLN | A | 230 | 1 | 0 | 0 | 221 | 70 | 290 | A C |
| ATOM | 1643 | O | GLN | A | 230 | 18.462 | −1.287 | 24.762 | 1.00 | 11.87 | | A O |
| ANISOU | 1643 | O | GLN | A | 230 | 1507 | 1344 | 1608 | 30 | 15 | −2 | A O |
| SIGUIJ | 1643 | O | GLN | A | 230 | 1 | 0 | 0 | 221 | 52 | 289 | A O |
| ATOM | 1644 | N | VAL | A | 231 | 16.404 | −1.043 | 25.609 | 1.00 | 11.59 | | A N |
| ANISOU | 1644 | N | VAL | A | 231 | 1481 | 1250 | 1408 | 3 | −2 | 0 | A N |
| SIGUIJ | 1644 | N | VAL | A | 231 | 1 | 0 | 0 | 221 | 58 | 289 | A N |
| ATOM | 1645 | CA | VAL | A | 231 | 16.447 | −2.219 | 26.466 | 1.00 | 12.21 | | A C |
| ANISOU | 1645 | CA | VAL | A | 231 | 1612 | 1250 | 1440 | 34 | 29 | 4 | A C |
| SIGUIJ | 1645 | CA | VAL | A | 231 | 1 | 0 | 0 | 221 | 70 | 290 | A C |
| ATOM | 1646 | CB | VAL | A | 231 | 15.087 | −2.347 | 27.266 | 1.00 | 11.61 | | A C |
| ANISOU | 1646 | CB | VAL | A | 231 | 1600 | 1317 | 1383 | 4 | 4 | 0 | A C |
| SIGUIJ | 1646 | CB | VAL | A | 231 | 1 | 0 | 0 | 221 | 70 | 290 | A C |
| ATOM | 1647 | CG1 | VAL | A | 231 | 15.023 | −3.633 | 28.014 | 1.00 | 12.29 | | A C |
| ANISOU | 1647 | CG1 | VAL | A | 231 | 2296 | 1338 | 1493 | 129 | 294 | 41 | A C |
| SIGUIJ | 1647 | CG1 | VAL | A | 231 | 1 | 0 | 0 | 221 | 70 | 290 | A C |
| ATOM | 1648 | CG2 | VAL | A | 231 | 14.982 | −1.162 | 28.257 | 1.00 | 12.18 | | A C |
| ANISOU | 1648 | CG2 | VAL | A | 231 | 1858 | 1317 | 1395 | −39 | 79 | −6 | A C |
| SIGUIJ | 1648 | CG2 | VAL | A | 231 | 1 | 0 | 0 | 221 | 70 | 290 | A C |
| ATOM | 1649 | C | VAL | A | 231 | 16.754 | −3.513 | 25.701 | 1.00 | 12.35 | | A C |
| ANISOU | 1649 | C | VAL | A | 231 | 1608 | 1247 | 1495 | 42 | 25 | 5 | A C |
| SIGUIJ | 1649 | C | VAL | A | 231 | 1 | 0 | 0 | 221 | 70 | 290 | A C |
| ATOM | 1650 | O | VAL | A | 231 | 17.418 | −4.398 | 26.242 | 1.00 | 12.73 | | A O |
| ANISOU | 1650 | O | VAL | A | 231 | 1825 | 1361 | 1477 | 194 | 17 | 8 | A O |
| SIGUIJ | 1650 | O | VAL | A | 231 | 1 | 0 | 0 | 221 | 52 | 289 | A O |
| ATOM | 1651 | N | CYS | A | 232 | 16.270 | −3.612 | 24.464 | 1.00 | 13.22 | | A N |
| ANISOU | 1651 | N | CYS | A | 232 | 1737 | 1327 | 1550 | 76 | −34 | −9 | A N |
| SIGUIJ | 1651 | N | CYS | A | 232 | 1 | 0 | 0 | 221 | 58 | 289 | A N |
| ATOM | 1652 | CA | CYS | A | 232 | 16.490 | −4.834 | 23.661 | 1.00 | 14.33 | | A C |
| ANISOU | 1652 | CA | CYS | A | 232 | 1699 | 1321 | 1642 | 57 | −5 | −3 | A C |
| SIGUIJ | 1652 | CA | CYS | A | 232 | 1 | 0 | 0 | 221 | 70 | 290 | A C |
| ATOM | 1653 | C | CYS | A | 232 | 17.967 | −5.140 | 23.408 | 1.00 | 14.77 | | A C |
| ANISOU | 1653 | C | CYS | A | 232 | 1706 | 1485 | 1870 | 99 | 2 | 0 | A C |
| SIGUIJ | 1653 | C | CYS | A | 232 | 1 | 0 | 0 | 221 | 69 | 290 | A C |
| ATOM | 1654 | O | CYS | A | 232 | 18.307 | −6.249 | 22.935 | 1.00 | 15.41 | | A O |
| ANISOU | 1654 | O | CYS | A | 232 | 2325 | 1606 | 2081 | 356 | −158 | −129 | A O |
| SIGUIJ | 1654 | O | CYS | A | 232 | 1 | 0 | 0 | 221 | 52 | 289 | A O |
| ATOM | 1655 | CB | CYS | A | 232 | 15.736 | −4.752 | 22.312 | 1.00 | 14.90 | | A C |
| ANISOU | 1655 | CB | CYS | A | 232 | 1979 | 1752 | 1751 | 299 | −178 | −142 | A C |
| SIGUIJ | 1655 | CB | CYS | A | 232 | 1 | 0 | 0 | 221 | 69 | 290 | A C |
| ATOM | 1656 | SG | CYS | A | 232 | 16.414 | −3.481 | 21.172 | 1.00 | 15.55 | | A S |
| ANISOU | 1656 | SG | CYS | A | 232 | 2155 | 1860 | 1847 | 211 | −149 | −82 | A S |
| SIGUIJ | 1656 | SG | CYS | A | 232 | 1 | 0 | 0 | 221 | 48 | 289 | A S |
| ATOM | 1657 | N | LYS | A | 233 | 18.841 | −4.183 | 23.661 | 1.00 | 14.58 | | A N |
| ANISOU | 1657 | N | LYS | A | 233 | 1794 | 1605 | 1614 | −18 | 55 | −5 | A N |
| SIGUIJ | 1657 | N | LYS | A | 233 | 1 | 0 | 0 | 221 | 58 | 289 | A N |
| ATOM | 1658 | CA | LYS | A | 233 | 20.281 | −4.345 | 23.441 | 1.00 | 14.96 | | A C |
| ANISOU | 1658 | CA | LYS | A | 233 | 1793 | 1916 | 1589 | 20 | 34 | −1 | A C |
| SIGUIJ | 1658 | CA | LYS | A | 233 | 1 | 0 | 0 | 221 | 69 | 290 | A C |
| ATOM | 1659 | CB | LYS | A | 233 | 20.929 | −3.013 | 23.048 | 1.00 | 15.39 | | A C |
| ANISOU | 1659 | CB | LYS | A | 233 | 1886 | 1930 | 1683 | 0 | 80 | 0 | A C |
| SIGUIJ | 1659 | CB | LYS | A | 233 | 1 | 0 | 0 | 221 | 69 | 290 | A C |
| ATOM | 1660 | CG | LYS | A | 233 | 20.379 | −2.387 | 21.745 | 1.00 | 15.68 | | A C |
| ANISOU | 1660 | CG | LYS | A | 233 | 2041 | 1958 | 1709 | 1 | 15 | 0 | A C |
| SIGUIJ | 1660 | CG | LYS | A | 233 | 1 | 0 | 0 | 221 | 69 | 290 | A C |
| ATOM | 1661 | CD | LYS | A | 233 | 20.467 | −3.337 | 20.517 | 1.00 | 16.47 | | A C |
| ANISOU | 1661 | CD | LYS | A | 233 | 2745 | 1994 | 1706 | 95 | 0 | 0 | A C |
| SIGUIJ | 1661 | CD | LYS | A | 233 | 1 | 0 | 0 | 221 | 69 | 290 | A C |
| ATOM | 1662 | CE | LYS | A | 233 | 19.967 | −2.641 | 19.232 | 1.00 | 17.46 | | A C |
| ANISOU | 1662 | CE | LYS | A | 233 | 2704 | 2172 | 1689 | 228 | 90 | 27 | A C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1662 | CE | LYS | A | 233 | 1 | 0 | 0 | 221 | 69 | 290 | A C |
| ATOM | 1663 | NZ | LYS | A | 233 | 20.709 | −1.429 | 18.892 | 1.00 | 18.10 | | A N |
| ANISOU | 1663 | NZ | LYS | A | 233 | 2910 | 2235 | 2165 | 148 | 274 | 53 | A N |
| SIGUIJ | 1663 | NZ | LYS | A | 233 | 1 | 0 | 0 | 221 | 58 | 289 | A N |
| ATOM | 1664 | C | LYS | A | 233 | 20.980 | −4.904 | 24.701 | 1.00 | 15.08 | | A C |
| ANISOU | 1664 | C | LYS | A | 233 | 1856 | 1893 | 1624 | 9 | −11 | 1 | A C |
| SIGUIJ | 1664 | C | LYS | A | 233 | 1 | 0 | 0 | 221 | 69 | 290 | A C |
| ATOM | 1665 | O | LYS | A | 233 | 22.189 | −5.176 | 24.640 | 1.00 | 15.49 | | A O |
| ANISOU | 1665 | O | LYS | A | 233 | 1892 | 2582 | 1999 | 169 | 14 | −11 | A O |
| SIGUIJ | 1665 | O | LYS | A | 233 | 1 | 0 | 0 | 221 | 52 | 289 | A O |
| ATOM | 1666 | N | PHE | A | 234 | 20.240 | −5.094 | 25.800 | 1.00 | 15.18 | | A N |
| ANISOU | 1666 | N | PHE | A | 234 | 1817 | 1374 | 1619 | 144 | −20 | −10 | A N |
| SIGUIJ | 1666 | N | PHE | A | 234 | 1 | 0 | 0 | 221 | 58 | 289 | A N |
| ATOM | 1667 | CA | PHE | A | 234 | 20.859 | −5.419 | 27.104 | 1.00 | 15.35 | | A C |
| ANISOU | 1667 | CA | PHE | A | 234 | 2261 | 1537 | 1671 | 459 | −178 | −108 | A C |
| SIGUIJ | 1667 | CA | PHE | A | 234 | 1 | 0 | 0 | 221 | 69 | 290 | A C |
| ATOM | 1668 | CB | PHE | A | 234 | 20.684 | −4.191 | 28.069 | 1.00 | 14.40 | | A C |
| ANISOU | 1668 | CB | PHE | A | 234 | 1588 | 1418 | 1521 | 216 | 19 | 26 | A C |
| SIGUIJ | 1668 | CB | PHE | A | 234 | 1 | 0 | 0 | 221 | 69 | 290 | A C |
| ATOM | 1669 | CG | PHE | A | 234 | 21.476 | −3.012 | 27.649 | 1.00 | 13.96 | | A C |
| ANISOU | 1669 | CG | PHE | A | 234 | 1811 | 1528 | 1422 | 48 | 24 | 3 | A C |
| SIGUIJ | 1669 | CG | PHE | A | 234 | 1 | 0 | 0 | 221 | 69 | 290 | A C |
| ATOM | 1670 | CD1 | PHE | A | 234 | 20.887 | −1.978 | 26.983 | 1.00 | 13.80 | | A C |
| ANISOU | 1670 | CD1 | PHE | A | 234 | 1831 | 1597 | 1406 | 126 | 113 | 40 | A C |
| SIGUIJ | 1670 | CD1 | PHE | A | 234 | 1 | 0 | 0 | 221 | 69 | 290 | A C |
| ATOM | 1671 | CD2 | PHE | A | 234 | 22.840 | −2.958 | 27.924 | 1.00 | 13.70 | | A C |
| ANISOU | 1671 | CD2 | PHE | A | 234 | 1813 | 1989 | 1645 | 32 | −18 | 0 | A C |
| SIGUIJ | 1671 | CD2 | PHE | A | 234 | 1 | 0 | 0 | 221 | 69 | 290 | A C |
| ATOM | 1672 | CE1 | PHE | A | 234 | 21.600 | −0.882 | 26.570 | 1.00 | 13.55 | | A C |
| ANISOU | 1672 | CE1 | PHE | A | 234 | 1929 | 1642 | 1311 | 38 | 87 | 8 | A C |
| SIGUIJ | 1672 | CE1 | PHE | A | 234 | 1 | 0 | 0 | 221 | 69 | 290 | A C |
| ATOM | 1673 | CE2 | PHE | A | 234 | 23.558 | −1.868 | 27.521 | 1.00 | 13.95 | | A C |
| ANISOU | 1673 | CE2 | PHE | A | 234 | 1898 | 2016 | 1674 | −10 | 6 | 0 | A C |
| SIGUIJ | 1673 | CE2 | PHE | A | 234 | 1 | 0 | 0 | 221 | 69 | 290 | A C |
| ATOM | 1674 | CZ | PHE | A | 234 | 22.926 | −0.817 | 26.832 | 1.00 | 13.72 | | A C |
| ANISOU | 1674 | CZ | PHE | A | 234 | 1939 | 2021 | 1667 | 5 | 6 | 0 | A C |
| SIGUIJ | 1674 | CZ | PHE | A | 234 | 1 | 0 | 0 | 221 | 69 | 290 | A C |
| ATOM | 1675 | C | PHE | A | 234 | 20.267 | −6.695 | 27.739 | 1.00 | 16.19 | | A C |
| ANISOU | 1675 | C | PHE | A | 234 | 2047 | 1458 | 1584 | 530 | −224 | −168 | A C |
| SIGUIJ | 1675 | C | PHE | A | 234 | 1 | 0 | 0 | 221 | 69 | 290 | A C |
| ATOM | 1676 | O | PHE | A | 234 | 20.407 | −6.952 | 28.914 | 1.00 | 15.82 | | A O |
| ANISOU | 1676 | O | PHE | A | 234 | 2292 | 1605 | 1585 | 596 | −200 | −134 | A O |
| SIGUIJ | 1676 | O | PHE | A | 234 | 1 | 0 | 0 | 221 | 52 | 289 | A O |
| ATOM | 1677 | N | THR | A | 235 | 19.631 | −7.513 | 26.902 | 1.00 | 17.36 | | A N |
| ANISOU | 1677 | N | THR | A | 235 | 3328 | 1614 | 2113 | 297 | −943 | −160 | A N |
| SIGUIJ | 1677 | N | THR | A | 235 | 1 | 0 | 0 | 221 | 58 | 289 | A N |
| ATOM | 1678 | CA | THR | A | 235 | 18.984 | −8.754 | 27.350 | 1.00 | 18.36 | | A C |
| ANISOU | 1678 | CA | THR | A | 235 | 3657 | 1659 | 2822 | 242 | −637 | −74 | A C |
| SIGUIJ | 1678 | CA | THR | A | 235 | 1 | 0 | 0 | 221 | 69 | 290 | A C |
| ATOM | 1679 | CB | THR | A | 235 | 18.554 | −9.620 | 26.125 | 1.00 | 19.04 | | A C |
| ANISOU | 1679 | CB | THR | A | 235 | 3239 | 1769 | 2587 | −218 | −159 | 27 | A C |
| SIGUIJ | 1679 | CB | THR | A | 235 | 1 | 0 | 0 | 221 | 69 | 290 | A C |
| ATOM | 1680 | OG1 | THR | A | 235 | 17.678 | −8.864 | 25.331 | 1.00 | 20.24 | | A O |
| ANISOU | 1680 | OG1 | THR | A | 235 | 3786 | 2237 | 2696 | 253 | −320 | −59 | A O |
| SIGUIJ | 1680 | OG1 | THR | A | 235 | 1 | 0 | 0 | 221 | 52 | 289 | A O |
| ATOM | 1681 | CG2 | THR | A | 235 | 17.874 | −10.902 | 26.570 | 1.00 | 19.96 | | A C |
| ANISOU | 1681 | CG2 | THR | A | 235 | 4745 | 2126 | 2800 | −925 | 101 | −39 | A C |
| SIGUIJ | 1681 | CG2 | THR | A | 235 | 1 | 0 | 0 | 221 | 69 | 290 | A C |
| ATOM | 1682 | C | THR | A | 235 | 19.912 | −9.625 | 28.174 | 1.00 | 18.18 | | A C |
| ANISOU | 1682 | C | THR | A | 235 | 3252 | 1629 | 2358 | 211 | −204 | −35 | A C |
| SIGUIJ | 1682 | C | THR | A | 235 | 1 | 0 | 0 | 221 | 69 | 290 | A C |
| ATOM | 1683 | O | THR | A | 235 | 19.536 | −10.106 | 29.239 | 1.00 | 18.19 | | A O |
| ANISOU | 1683 | O | THR | A | 235 | 3132 | 1497 | 2331 | 257 | −231 | −64 | A O |
| SIGUIJ | 1683 | O | THR | A | 235 | 1 | 0 | 0 | 221 | 52 | 289 | A O |
| ATOM | 1684 | N | LYS | A | 236 | 21.101 | −9.821 | 27.631 | 1.00 | 18.29 | | A N |
| ANISOU | 1684 | N | LYS | A | 236 | 3127 | 1760 | 1798 | 232 | −481 | −77 | A N |
| SIGUIJ | 1684 | N | LYS | A | 236 | 1 | 0 | 0 | 221 | 58 | 289 | A N |
| ATOM | 1685 | CA | LYS | A | 236 | 22.054 | −10.728 | 28.249 | 1.00 | 18.63 | | A C |
| ANISOU | 1685 | CA | LYS | A | 236 | 3363 | 2022 | 1616 | 529 | −414 | −132 | A C |
| SIGUIJ | 1685 | CA | LYS | A | 236 | 1 | 0 | 0 | 221 | 69 | 290 | A C |
| ATOM | 1686 | CB | LYS | A | 236 | 23.253 | −10.968 | 27.340 | 1.00 | 19.90 | | A C |
| ANISOU | 1686 | CB | LYS | A | 236 | 3742 | 2411 | 2145 | 727 | 32 | 14 | A C |
| SIGUIJ | 1686 | CB | LYS | A | 236 | 1 | 0 | 0 | 221 | 69 | 290 | A C |
| ATOM | 1687 | CG | LYS | A | 236 | 24.209 | −11.974 | 27.902 | 1.00 | 21.31 | | A C |
| ANISOU | 1687 | CG | LYS | A | 236 | 4377 | 2728 | 2374 | 1155 | −279 | −150 | A C |
| SIGUIJ | 1687 | CG | LYS | A | 236 | 1 | 0 | 0 | 221 | 69 | 290 | A C |
| ATOM | 1688 | CD | LYS | A | 236 | 25.310 | −12.238 | 26.897 | 1.00 | 22.84 | | A C |
| ANISOU | 1688 | CD | LYS | A | 236 | 6892 | 5054 | 4324 | 3275 | 1915 | 1570 | A C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1688 | CD | LYS | A | 236 | 1 | 0 | 0 | 221 | 69 | 290 | A | C |
| ATOM | 1689 | CE | LYS | A | 236 | 26.216 | −13.345 | 27.370 | 1.00 | 23.64 | | A | C |
| ANISOU | 1689 | CE | LYS | A | 236 | 6392 | 3056 | 4572 | 1820 | −527 | −327 | A | C |
| SIGUIJ | 1689 | CE | LYS | A | 236 | 1 | 0 | 0 | 221 | 69 | 290 | A | C |
| ATOM | 1690 | NZ | LYS | A | 236 | 27.456 | −13.340 | 26.562 | 1.00 | 25.02 | | A | N |
| ANISOU | 1690 | NZ | LYS | A | 236 | 6797 | 13244 | 5535 | 2051 | 95 | 92 | A | N |
| SIGUIJ | 1690 | NZ | LYS | A | 236 | 1 | 0 | 0 | 221 | 58 | 289 | A | N |
| ATOM | 1691 | C | LYS | A | 236 | 22.526 | −10.128 | 29.558 | 1.00 | 17.98 | | A | C |
| ANISOU | 1691 | C | LYS | A | 236 | 2715 | 1993 | 1706 | 1022 | −413 | −322 | A | C |
| SIGUIJ | 1691 | C | LYS | A | 236 | 1 | 0 | 0 | 221 | 69 | 290 | A | C |
| ATOM | 1692 | O | LYS | A | 236 | 22.612 | −10.840 | 30.537 | 1.00 | 17.65 | | A | O |
| ANISOU | 1692 | O | LYS | A | 236 | 3107 | 2053 | 1746 | 1159 | −367 | −267 | A | O |
| SIGUIJ | 1692 | O | LYS | A | 236 | 1 | 0 | 0 | 221 | 52 | 289 | A | O |
| ATOM | 1693 | N | TRP | A | 237 | 22.889 | −8.853 | 29.567 | 1.00 | 17.03 | | A | N |
| ANISOU | 1693 | N | TRP | A | 237 | 2618 | 1993 | 1781 | 1025 | −409 | −346 | A | N |
| SIGUIJ | 1693 | N | TRP | A | 237 | 1 | 0 | 0 | 221 | 58 | 289 | A | N |
| ATOM | 1694 | CA | TRP | A | 237 | 23.384 | −8.251 | 30.810 | 1.00 | 16.42 | | A | C |
| ANISOU | 1694 | CA | TRP | A | 237 | 2455 | 1988 | 1665 | 736 | −256 | −201 | A | C |
| SIGUIJ | 1694 | CA | TRP | A | 237 | 1 | 0 | 0 | 221 | 69 | 290 | A | C |
| ATOM | 1695 | CB | TRP | A | 237 | 23.834 | −6.811 | 30.542 | 1.00 | 16.54 | | A | C |
| ANISOU | 1695 | CB | TRP | A | 237 | 2900 | 2057 | 1693 | 573 | −339 | −161 | A | C |
| SIGUIJ | 1695 | CB | TRP | A | 237 | 1 | 0 | 0 | 221 | 68 | 290 | A | C |
| ATOM | 1696 | CG | TRP | A | 237 | 24.301 | −6.106 | 31.830 | 1.00 | 16.18 | | A | C |
| ANISOU | 1696 | CG | TRP | A | 237 | 2308 | 2005 | 1448 | 199 | 72 | 23 | A | C |
| SIGUIJ | 1696 | CG | TRP | A | 237 | 1 | 0 | 0 | 221 | 68 | 290 | A | C |
| ATOM | 1697 | CD2 | TRP | A | 237 | 23.479 | −5.308 | 32.710 | 1.00 | 16.10 | | A | C |
| ANISOU | 1697 | CD2 | TRP | A | 237 | 2256 | 1884 | 1541 | 68 | 168 | 21 | A | C |
| SIGUIJ | 1697 | CD2 | TRP | A | 237 | 1 | 0 | 0 | 221 | 68 | 290 | A | C |
| ATOM | 1698 | CE2 | TRP | A | 237 | 24.264 | −4.995 | 33.844 | 1.00 | 16.17 | | A | C |
| ANISOU | 1698 | CE2 | TRP | A | 237 | 2715 | 1863 | 1796 | 162 | −178 | −32 | A | C |
| SIGUIJ | 1698 | CE2 | TRP | A | 237 | 1 | 0 | 0 | 221 | 68 | 290 | A | C |
| ATOM | 1699 | CE3 | TRP | A | 237 | 22.168 | −4.852 | 32.648 | 1.00 | 15.70 | | A | C |
| ANISOU | 1699 | CE3 | TRP | A | 237 | 2222 | 1659 | 1712 | −13 | 160 | −4 | A | C |
| SIGUIJ | 1699 | CE3 | TRP | A | 237 | 1 | 0 | 0 | 221 | 68 | 290 | A | C |
| ATOM | 1700 | CD1 | TRP | A | 237 | 25.489 | −6.214 | 32.420 | 1.00 | 16.78 | | A | C |
| ANISOU | 1700 | CD1 | TRP | A | 237 | 2436 | 2182 | 1896 | 260 | −158 | −85 | A | C |
| SIGUIJ | 1700 | CD1 | TRP | A | 237 | 1 | 0 | 0 | 221 | 68 | 290 | A | C |
| ATOM | 1701 | NE1 | TRP | A | 237 | 25.485 | −5.557 | 33.634 | 1.00 | 16.57 | | A | N |
| ANISOU | 1701 | NE1 | TRP | A | 237 | 2778 | 2169 | 1886 | 304 | −182 | −68 | A | N |
| SIGUIJ | 1701 | NE1 | TRP | A | 237 | 1 | 0 | 0 | 221 | 58 | 289 | A | N |
| ATOM | 1702 | CZ2 | TRP | A | 237 | 23.766 | −4.247 | 34.944 | 1.00 | 15.98 | | A | C |
| ANISOU | 1702 | CZ2 | TRP | A | 237 | 2724 | 1596 | 1905 | −228 | 88 | −20 | A | C |
| SIGUIJ | 1702 | CZ2 | TRP | A | 237 | 1 | 0 | 0 | 221 | 68 | 290 | A | C |
| ATOM | 1703 | CZ3 | TRP | A | 237 | 21.680 | −4.106 | 33.762 | 1.00 | 16.00 | | A | C |
| ANISOU | 1703 | CZ3 | TRP | A | 237 | 2333 | 1699 | 1868 | −218 | 354 | −114 | A | C |
| SIGUIJ | 1703 | CZ3 | TRP | A | 237 | 1 | 0 | 0 | 221 | 68 | 290 | A | C |
| ATOM | 1704 | CH2 | TRP | A | 237 | 22.476 | −3.832 | 34.861 | 1.00 | 16.05 | | A | C |
| ANISOU | 1704 | CH2 | TRP | A | 237 | 2714 | 1499 | 2033 | −260 | 87 | −25 | A | C |
| SIGUIJ | 1704 | CH2 | TRP | A | 237 | 1 | 0 | 0 | 221 | 68 | 290 | A | C |
| ATOM | 1705 | C | TRP | A | 237 | 22.294 | −8.322 | 31.896 | 1.00 | 16.26 | | A | C |
| ANISOU | 1705 | C | TRP | A | 237 | 2341 | 1815 | 1571 | 676 | −369 | −261 | A | C |
| SIGUIJ | 1705 | C | TRP | A | 237 | 1 | 0 | 0 | 221 | 68 | 290 | A | C |
| ATOM | 1706 | O | TRP | A | 237 | 22.574 | −8.590 | 33.053 | 1.00 | 15.65 | | A | O |
| ANISOU | 1706 | O | TRP | A | 237 | 2261 | 1882 | 1557 | 952 | −312 | −302 | A | O |
| SIGUIJ | 1706 | O | TRP | A | 237 | 1 | 0 | 0 | 221 | 52 | 289 | A | O |
| ATOM | 1707 | N | ILE | A | 238 | 21.056 | −8.025 | 31.542 | 1.00 | 16.04 | | A | N |
| ANISOU | 1707 | N | ILE | A | 238 | 2313 | 1408 | 1693 | 542 | −360 | −201 | A | N |
| SIGUIJ | 1707 | N | ILE | A | 238 | 1 | 0 | 0 | 221 | 58 | 289 | A | N |
| ATOM | 1708 | CA | ILE | A | 238 | 20.021 | −8.050 | 32.574 | 1.00 | 16.27 | | A | C |
| ANISOU | 1708 | CA | ILE | A | 238 | 2361 | 1425 | 1756 | 531 | −302 | −181 | A | C |
| SIGUIJ | 1708 | CA | ILE | A | 238 | 1 | 0 | 0 | 221 | 68 | 290 | A | C |
| ATOM | 1709 | CB | ILE | A | 238 | 18.660 | −7.606 | 31.953 | 1.00 | 15.62 | | A | C |
| ANISOU | 1709 | CB | ILE | A | 238 | 2330 | 1440 | 1715 | 506 | −265 | −149 | A | C |
| SIGUIJ | 1709 | CB | ILE | A | 238 | 1 | 0 | 0 | 221 | 68 | 290 | A | C |
| ATOM | 1710 | CG2 | ILE | A | 238 | 17.504 | −7.904 | 32.910 | 1.00 | 15.95 | | A | C |
| ANISOU | 1710 | CG2 | ILE | A | 238 | 2542 | 1960 | 2066 | 479 | −14 | −10 | A | C |
| SIGUIJ | 1710 | CG2 | ILE | A | 238 | 1 | 0 | 0 | 221 | 68 | 290 | A | C |
| ATOM | 1711 | CG1 | ILE | A | 238 | 18.744 | −6.118 | 31.573 | 1.00 | 15.59 | | A | C |
| ANISOU | 1711 | CG1 | ILE | A | 238 | 2375 | 1462 | 2087 | 558 | −65 | −65 | A | C |
| SIGUIJ | 1711 | CG1 | ILE | A | 238 | 1 | 0 | 0 | 221 | 68 | 290 | A | C |
| ATOM | 1712 | CD1 | ILE | A | 238 | 17.582 | −5.630 | 30.631 | 1.00 | 16.30 | | A | C |
| ANISOU | 1712 | CD1 | ILE | A | 238 | 2398 | 1805 | 2074 | 675 | −40 | −45 | A | C |
| SIGUIJ | 1712 | CD1 | ILE | A | 238 | 1 | 0 | 0 | 221 | 68 | 290 | A | C |
| ATOM | 1713 | C | ILE | A | 238 | 19.877 | −9.455 | 33.193 | 1.00 | 16.58 | | A | C |
| ANISOU | 1713 | C | ILE | A | 238 | 2917 | 1455 | 1938 | 494 | −247 | −97 | A | C |
| SIGUIJ | 1713 | C | ILE | A | 238 | 1 | 0 | 0 | 221 | 68 | 290 | A | C |
| ATOM | 1714 | O | ILE | A | 238 | 19.856 | −9.658 | 34.435 | 1.00 | 16.17 | | A | O |
| ANISOU | 1714 | O | ILE | A | 238 | 2618 | 1314 | 1932 | 523 | −241 | −124 | A | O |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1714 | O | ILE | A | 238 | 1 | 0 | 0 | 221 | 52 | 289 | A | O |
| ATOM | 1715 | N | ASN | A | 239 | 19.772 | −10.462 | 32.322 | 1.00 | 17.40 | | A | N |
| ANISOU | 1715 | N | ASN | A | 239 | 2720 | 1490 | 2022 | 587 | −317 | −168 | A | N |
| SIGUIJ | 1715 | N | ASN | A | 239 | 1 | 0 | 0 | 221 | 58 | 289 | A | N |
| ATOM | 1716 | CA | ASN | A | 239 | 19.560 | −11.823 | 32.838 | 1.00 | 18.45 | | A | C |
| ANISOU | 1716 | CA | ASN | A | 239 | 3345 | 1520 | 2166 | 463 | −392 | −119 | A | C |
| SIGUIJ | 1716 | CA | ASN | A | 239 | 1 | 0 | 0 | 221 | 68 | 290 | A | C |
| ATOM | 1717 | CB | ASN | A | 239 | 19.189 | −12.774 | 31.691 | 1.00 | 20.04 | | A | C |
| ANISOU | 1717 | CB | ASN | A | 239 | 5980 | 1900 | 1951 | −956 | −63 | 15 | A | C |
| SIGUIJ | 1717 | CB | ASN | A | 239 | 1 | 0 | 0 | 221 | 68 | 290 | A | C |
| ATOM | 1718 | CG | ASN | A | 239 | 17.805 | −12.468 | 31.122 | 1.00 | 21.83 | | A | C |
| ANISOU | 1718 | CG | ASN | A | 239 | 6761 | 7810 | 5084 | 260 | −1304 | 222 | A | C |
| SIGUIJ | 1718 | CG | ASN | A | 239 | 1 | 0 | 0 | 221 | 68 | 290 | A | C |
| ATOM | 1719 | OD1 | ASN | A | 239 | 16.900 | −11.963 | 31.829 | 1.00 | 23.50 | | A | O |
| ANISOU | 1719 | OD1 | ASN | A | 239 | 7722 | 7660 | 7052 | −1 | 110 | −1 | A | O |
| SIGUIJ | 1719 | OD1 | ASN | A | 239 | 1 | 0 | 0 | 221 | 52 | 289 | A | O |
| ATOM | 1720 | ND2 | ASN | A | 239 | 17.616 | −12.779 | 29.837 | 1.00 | 23.10 | | A | N |
| ANISOU | 1720 | ND2 | ASN | A | 239 | 7909 | 9116 | 5160 | −83 | −1388 | −43 | A | N |
| SIGUIJ | 1720 | ND2 | ASN | A | 239 | 1 | 0 | 0 | 221 | 58 | 289 | A | N |
| ATOM | 1721 | C | ASN | A | 239 | 20.751 | −12.322 | 33.624 | 1.00 | 18.28 | | A | C |
| ANISOU | 1721 | C | ASN | A | 239 | 3333 | 1689 | 2087 | 528 | −329 | −114 | A | C |
| SIGUIJ | 1721 | C | ASN | A | 239 | 1 | 0 | 0 | 221 | 68 | 290 | A | C |
| ATOM | 1722 | O | ASN | A | 239 | 20.609 | −12.859 | 34.727 | 1.00 | 18.24 | | A | O |
| ANISOU | 1722 | O | ASN | A | 239 | 3229 | 1606 | 2117 | 838 | −192 | −107 | A | O |
| SIGUIJ | 1722 | O | ASN | A | 239 | 1 | 0 | 0 | 221 | 52 | 289 | A | O |
| ATOM | 1723 | N | ASP | A | 240 | 21.916 | −12.037 | 33.129 | 1.00 | 17.82 | | A | N |
| ANISOU | 1723 | N | ASP | A | 240 | 3295 | 1342 | 1956 | 607 | −371 | −137 | A | N |
| SIGUIJ | 1723 | N | ASP | A | 240 | 1 | 0 | 0 | 221 | 58 | 289 | A | N |
| ATOM | 1724 | CA | ASP | A | 240 | 23.106 | −12.575 | 33.751 | 1.00 | 18.10 | | A | C |
| ANISOU | 1724 | CA | ASP | A | 240 | 3799 | 2334 | 2436 | 1243 | −775 | −496 | A | C |
| SIGUIJ | 1724 | CA | ASP | A | 240 | 1 | 0 | 0 | 221 | 68 | 290 | A | C |
| ATOM | 1725 | CB | ASP | A | 240 | 24.292 | −12.406 | 32.852 | 1.00 | 19.02 | | A | C |
| ANISOU | 1725 | CB | ASP | A | 240 | 4137 | 1964 | 3126 | 1487 | −286 | −241 | A | C |
| SIGUIJ | 1725 | CB | ASP | A | 240 | 1 | 0 | 0 | 221 | 68 | 290 | A | C |
| ATOM | 1726 | CG | ASP | A | 240 | 24.312 | −13.411 | 31.719 | 1.00 | 19.82 | | A | C |
| ANISOU | 1726 | CG | ASP | A | 240 | 4105 | 1550 | 2819 | 841 | 274 | 121 | A | C |
| SIGUIJ | 1726 | CG | ASP | A | 240 | 1 | 0 | 0 | 221 | 68 | 290 | A | C |
| ATOM | 1727 | OD1 | ASP | A | 240 | 23.383 | −14.232 | 31.563 | 1.00 | 20.77 | | A | O |
| ANISOU | 1727 | OD1 | ASP | A | 240 | 4301 | 1803 | 2990 | 618 | 284 | 87 | A | O |
| SIGUIJ | 1727 | OD1 | ASP | A | 240 | 1 | 0 | 0 | 221 | 52 | 289 | A | O |
| ATOM | 1728 | OD2 | ASP | A | 240 | 25.296 | −13.321 | 31.007 | 1.00 | 21.46 | | A | O |
| ANISOU | 1728 | OD2 | ASP | A | 240 | 4280 | 4063 | 3184 | 794 | 513 | 375 | A | O |
| SIGUIJ | 1728 | OD2 | ASP | A | 240 | 1 | 0 | 0 | 221 | 52 | 289 | A | O |
| ATOM | 1729 | C | ASP | A | 240 | 23.423 | −11.897 | 35.057 | 1.00 | 17.51 | | A | C |
| ANISOU | 1729 | C | ASP | A | 240 | 2026 | 1656 | 1996 | 578 | 7 | 15 | A | C |
| SIGUIJ | 1729 | C | ASP | A | 240 | 1 | 0 | 0 | 221 | 68 | 290 | A | C |
| ATOM | 1730 | O | ASP | A | 240 | 23.894 | −12.545 | 35.996 | 1.00 | 17.50 | | A | O |
| ANISOU | 1730 | O | ASP | A | 240 | 3155 | 1656 | 2025 | 974 | −314 | −198 | A | O |
| SIGUIJ | 1730 | O | ASP | A | 240 | 1 | 0 | 0 | 221 | 52 | 289 | A | O |
| ATOM | 1731 | N | THR | A | 241 | 23.229 | −10.574 | 35.130 | 1.00 | 16.51 | | A | N |
| ANISOU | 1731 | N | THR | A | 241 | 1554 | 1642 | 2153 | 499 | −25 | 18 | A | N |
| SIGUIJ | 1731 | N | THR | A | 241 | 1 | 0 | 0 | 221 | 58 | 289 | A | N |
| ATOM | 1732 | CA | THR | A | 241 | 23.519 | −9.853 | 36.374 | 1.00 | 15.98 | | A | C |
| ANISOU | 1732 | CA | THR | A | 241 | 1904 | 1784 | 2151 | 226 | 6 | −4 | A | C |
| SIGUIJ | 1732 | CA | THR | A | 241 | 1 | 0 | 0 | 221 | 68 | 290 | A | C |
| ATOM | 1733 | CB | THR | A | 241 | 23.335 | −8.344 | 36.168 | 1.00 | 15.61 | | A | C |
| ANISOU | 1733 | CB | THR | A | 241 | 2272 | 1779 | 1728 | 242 | −129 | −53 | A | C |
| SIGUIJ | 1733 | CB | THR | A | 241 | 1 | 0 | 0 | 221 | 68 | 290 | A | C |
| ATOM | 1734 | OG1 | THR | A | 241 | 24.246 | −7.924 | 35.136 | 1.00 | 16.03 | | A | O |
| ANISOU | 1734 | OG1 | THR | A | 241 | 2392 | 1887 | 1843 | 240 | −16 | −7 | A | O |
| SIGUIJ | 1734 | OG1 | THR | A | 241 | 1 | 0 | 0 | 221 | 52 | 289 | A | O |
| ATOM | 1735 | CG2 | THR | A | 241 | 23.548 | −7.565 | 37.496 | 1.00 | 15.96 | | A | C |
| ANISOU | 1735 | CG2 | THR | A | 241 | 3006 | 1804 | 1768 | 311 | −300 | −72 | A | C |
| SIGUIJ | 1735 | CG2 | THR | A | 241 | 1 | 0 | 0 | 221 | 68 | 290 | A | C |
| ATOM | 1736 | C | THR | A | 241 | 22.581 | −10.366 | 37.466 | 1.00 | 15.67 | | A | C |
| ANISOU | 1736 | C | THR | A | 241 | 1835 | 1394 | 2154 | 389 | 21 | −17 | A | C |
| SIGUIJ | 1736 | C | THR | A | 241 | 1 | 0 | 0 | 221 | 68 | 290 | A | C |
| ATOM | 1737 | O | THR | A | 241 | 22.981 | −10.530 | 38.632 | 1.00 | 15.41 | | A | O |
| ANISOU | 1737 | O | THR | A | 241 | 1953 | 1460 | 2163 | 397 | −2 | 5 | A | O |
| SIGUIJ | 1737 | O | THR | A | 241 | 1 | 0 | 0 | 221 | 52 | 289 | A | O |
| ATOM | 1738 | N | MET | A | 242 | 21.309 | −10.614 | 37.153 | 1.00 | 15.65 | | A | N |
| ANISOU | 1738 | N | MET | A | 242 | 1830 | 1169 | 2209 | 418 | 21 | −13 | A | N |
| SIGUIJ | 1738 | N | MET | A | 242 | 1 | 0 | 0 | 221 | 58 | 289 | A | N |
| ATOM | 1739 | CA | MET | A | 242 | 20.454 | −11.169 | 38.182 | 1.00 | 16.26 | | A | C |
| ANISOU | 1739 | CA | MET | A | 242 | 1834 | 1352 | 2191 | 308 | −31 | 11 | A | C |
| SIGUIJ | 1739 | CA | MET | A | 242 | 1 | 0 | 0 | 221 | 68 | 290 | A | C |
| ATOM | 1740 | CB | MET | A | 242 | 19.019 | −11.306 | 37.688 | 1.00 | 16.02 | | A | C |
| ANISOU | 1740 | CB | MET | A | 242 | 1872 | 1507 | 2567 | 294 | −153 | 23 | A | C |

TABLE 3-continued

Three-dimensional structure of the new binding pocket of kallikrein 7

| | | | | | | | | | | | | | |
|---|---|---|---|---|---|---|---|---|---|---|---|---|---|
| SIGUIJ | 1740 | CB | MET | A | 242 | 1 | 0 | 0 | 221 | 67 | 290 | A | C |
| ATOM | 1741 | CG | MET | A | 242 | 18.363 | −9.924 | 37.474 | 1.00 | 15.38 | | A | C |
| ANISOU | 1741 | CG | MET | A | 242 | 1839 | 1498 | 1717 | 289 | −44 | −48 | A | C |
| SIGUIJ | 1741 | CG | MET | A | 242 | 1 | 0 | 0 | 221 | 67 | 290 | A | C |
| ATOM | 1742 | SD | MET | A | 242 | 16.600 | −9.974 | 37.099 | 1.00 | 15.58 | | A | S |
| ANISOU | 1742 | SD | MET | A | 242 | 1876 | 1638 | 2298 | 288 | −182 | −86 | A | S |
| SIGUIJ | 1742 | SD | MET | A | 242 | 1 | 0 | 0 | 221 | 48 | 289 | A | S |
| ATOM | 1743 | CE | MET | A | 242 | 16.608 | −10.898 | 35.580 | 1.00 | 16.03 | | A | C |
| ANISOU | 1743 | CE | MET | A | 242 | 2222 | 1519 | 2252 | 29 | −1 | 0 | A | C |
| SIGUIJ | 1743 | CE | MET | A | 242 | 1 | 0 | 0 | 221 | 67 | 290 | A | C |
| ATOM | 1744 | C | MET | A | 242 | 20.951 | −12.552 | 38.622 | 1.00 | 17.07 | | A | C |
| ANISOU | 1744 | C | MET | A | 242 | 2176 | 1393 | 2258 | 422 | 1 | 13 | A | C |
| SIGUIJ | 1744 | C | MET | A | 242 | 1 | 0 | 0 | 221 | 67 | 290 | A | C |
| ATOM | 1745 | O | MET | A | 242 | 20.917 | −12.839 | 39.831 | 1.00 | 17.17 | | A | O |
| ANISOU | 1745 | O | MET | A | 242 | 2211 | 1777 | 2277 | 403 | 5 | 81 | A | O |
| SIGUIJ | 1745 | O | MET | A | 242 | 1 | 0 | 0 | 221 | 52 | 289 | A | O |
| ATOM | 1746 | N | LYS | A | 243 | 21.351 | −13.402 | 37.665 | 1.00 | 18.03 | | A | N |
| ANISOU | 1746 | N | LYS | A | 243 | 2213 | 1425 | 2296 | 434 | 0 | −21 | A | N |
| SIGUIJ | 1746 | N | LYS | A | 243 | 1 | 0 | 0 | 221 | 58 | 289 | A | N |
| ATOM | 1747 | CA | LYS | A | 243 | 21.732 | −14.770 | 38.034 | 1.00 | 19.06 | | A | C |
| ANISOU | 1747 | CA | LYS | A | 243 | 2225 | 1424 | 2431 | 426 | −3 | 6 | A | C |
| SIGUIJ | 1747 | CA | LYS | A | 243 | 1 | 0 | 0 | 221 | 67 | 290 | A | C |
| ATOM | 1748 | CB | LYS | A | 243 | 21.848 | −15.655 | 36.790 | 1.00 | 19.69 | | A | C |
| ANISOU | 1748 | CB | LYS | A | 243 | 4005 | 1401 | 2430 | 522 | 65 | 17 | A | C |
| SIGUIJ | 1748 | CB | LYS | A | 243 | 1 | 0 | 0 | 221 | 67 | 290 | A | C |
| ATOM | 1749 | CG | LYS | A | 243 | 20.535 | −15.890 | 36.035 | 1.00 | 21.32 | | A | C |
| ANISOU | 1749 | CG | LYS | A | 243 | 4461 | 3080 | 3739 | 308 | −657 | −170 | A | C |
| SIGUIJ | 1749 | CG | LYS | A | 243 | 1 | 0 | 0 | 221 | 67 | 290 | A | C |
| ATOM | 1750 | CD | LYS | A | 243 | 20.933 | −16.543 | 34.700 | 1.00 | 22.30 | | A | C |
| ANISOU | 1750 | CD | LYS | A | 243 | 10922 | 2563 | 4249 | 114 | 1364 | 21 | A | C |
| SIGUIJ | 1750 | CD | LYS | A | 243 | 1 | 0 | 0 | 221 | 67 | 290 | A | C |
| ATOM | 1751 | CE | LYS | A | 243 | 19.867 | −17.447 | 34.113 | 1.00 | 22.84 | | A | C |
| ANISOU | 1751 | CE | LYS | A | 243 | 11189 | 2802 | 4638 | −73 | 1171 | −11 | A | C |
| SIGUIJ | 1751 | CE | LYS | A | 243 | 1 | 0 | 0 | 221 | 67 | 290 | A | C |
| ATOM | 1752 | NZ | LYS | A | 243 | 19.720 | −18.657 | 34.959 | 1.00 | 23.58 | | A | N |
| ANISOU | 1752 | NZ | LYS | A | 243 | 3968 | 2803 | 4447 | 8 | 32 | 0 | A | N |
| SIGUIJ | 1752 | NZ | LYS | A | 243 | 1 | 0 | 0 | 221 | 58 | 289 | A | N |
| ATOM | 1753 | C | LYS | A | 243 | 23.036 | −14.780 | 38.811 | 1.00 | 19.41 | | A | C |
| ANISOU | 1753 | C | LYS | A | 243 | 2221 | 1771 | 2421 | 444 | 2 | −6 | A | C |
| SIGUIJ | 1753 | C | LYS | A | 243 | 1 | 0 | 0 | 221 | 67 | 290 | A | C |
| ATOM | 1754 | O | LYS | A | 243 | 23.251 | −15.704 | 39.631 | 1.00 | 19.49 | | A | O |
| ANISOU | 1754 | O | LYS | A | 243 | 2813 | 1899 | 2495 | 659 | 77 | 85 | A | O |
| SIGUIJ | 1754 | O | LYS | A | 243 | 1 | 0 | 0 | 221 | 52 | 289 | A | O |
| ATOM | 1755 | N | LYS | A | 244 | 23.897 | −13.795 | 38.577 | 1.00 | 19.53 | | A | N |
| ANISOU | 1755 | N | LYS | A | 244 | 2133 | 1688 | 2068 | 511 | −36 | −68 | A | N |
| SIGUIJ | 1755 | N | LYS | A | 244 | 1 | 0 | 0 | 221 | 58 | 289 | A | N |
| ATOM | 1756 | CA | LYS | A | 244 | 25.157 | −13.728 | 39.293 | 1.00 | 20.25 | | A | C |
| ANISOU | 1756 | CA | LYS | A | 244 | 2154 | 1775 | 2169 | 541 | −75 | −148 | A | C |
| SIGUIJ | 1756 | CA | LYS | A | 244 | 1 | 0 | 0 | 221 | 67 | 290 | A | C |
| ATOM | 1757 | CB | LYS | A | 244 | 26.178 | −12.970 | 38.454 | 1.00 | 20.71 | | A | C |
| ANISOU | 1757 | CB | LYS | A | 244 | 2628 | 2639 | 2411 | −3 | 4 | 1 | A | C |
| SIGUIJ | 1757 | CB | LYS | A | 244 | 1 | 0 | 0 | 221 | 67 | 290 | A | C |
| ATOM | 1758 | CG | LYS | A | 244 | 26.607 | −13.844 | 37.266 | 1.00 | 21.33 | | A | C |
| ANISOU | 1758 | CG | LYS | A | 244 | 2939 | 2704 | 2415 | 146 | 5 | 2 | A | C |
| SIGUIJ | 1758 | CG | LYS | A | 244 | 1 | 0 | 0 | 221 | 67 | 290 | A | C |
| ATOM | 1759 | CD | LYS | A | 244 | 27.426 | −13.149 | 36.237 | 1.00 | 22.40 | | A | C |
| ANISOU | 1759 | CD | LYS | A | 244 | 3516 | 3005 | 2578 | −172 | 256 | −61 | A | C |
| SIGUIJ | 1759 | CD | LYS | A | 244 | 1 | 0 | 0 | 221 | 67 | 290 | A | C |
| ATOM | 1760 | CE | LYS | A | 244 | 27.046 | −13.689 | 34.891 | 1.00 | 23.00 | | A | C |
| ANISOU | 1760 | CE | LYS | A | 244 | 5164 | 2662 | 2883 | 853 | −627 | −206 | A | C |
| SIGUIJ | 1760 | CE | LYS | A | 244 | 1 | 0 | 0 | 221 | 67 | 290 | A | C |
| ATOM | 1761 | NZ | LYS | A | 244 | 28.051 | −13.198 | 33.885 | 1.00 | 23.58 | | A | N |
| ANISOU | 1761 | NZ | LYS | A | 244 | 6818 | 5829 | 3878 | −592 | 322 | −106 | A | N |
| SIGUIJ | 1761 | NZ | LYS | A | 244 | 1 | 0 | 0 | 221 | 58 | 289 | A | N |
| ATOM | 1762 | C | LYS | A | 244 | 25.059 | −13.148 | 40.701 | 1.00 | 20.44 | | A | C |
| ANISOU | 1762 | C | LYS | A | 244 | 2240 | 1405 | 2114 | 427 | −7 | −9 | A | C |
| SIGUIJ | 1762 | C | LYS | A | 244 | 1 | 0 | 0 | 221 | 67 | 290 | A | C |
| ATOM | 1763 | O | LYS | A | 244 | 26.033 | −13.177 | 41.458 | 1.00 | 20.15 | | A | O |
| ANISOU | 1763 | O | LYS | A | 244 | 2261 | 2172 | 2151 | 487 | −32 | −52 | A | O |
| SIGUIJ | 1763 | O | LYS | A | 244 | 1 | 0 | 0 | 221 | 51 | 289 | A | O |
| ATOM | 1764 | N | HIS | A | 245 | 23.893 | −12.629 | 41.059 | 1.00 | 21.08 | | A | N |
| ANISOU | 1764 | N | HIS | A | 245 | 2292 | 1885 | 1853 | 610 | −111 | −105 | A | N |
| SIGUIJ | 1764 | N | HIS | A | 245 | 1 | 0 | 0 | 221 | 57 | 289 | A | N |
| ATOM | 1765 | CA | HIS | A | 245 | 23.699 | −12.026 | 42.375 | 1.00 | 22.18 | | A | C |
| ANISOU | 1765 | CA | HIS | A | 245 | 2118 | 1610 | 1826 | 331 | −11 | −8 | A | C |
| SIGUIJ | 1765 | CA | HIS | A | 245 | 1 | 0 | 0 | 221 | 67 | 290 | A | C |
| ATOM | 1766 | CB | HIS | A | 245 | 23.528 | −10.498 | 42.280 | 1.00 | 21.47 | | A | C |
| ANISOU | 1766 | CB | HIS | A | 245 | 2113 | 1618 | 2489 | 343 | −60 | 21 | A | C |

TABLE 3-continued

Three-dimensional structure of the new binding pocket of kallikrein 7

| | | | | | | | | | | | | |
|---|---|---|---|---|---|---|---|---|---|---|---|---|
| SIGUIJ | 1766 | CB | HIS | A | 245 | 1 | 0 | 0 | 221 | 67 | 290 | A C |
| ATOM | 1767 | CG | HIS | A | 245 | 24.756 | −9.806 | 41.809 | 1.00 | 21.54 | | A C |
| ANISOU | 1767 | CG | HIS | A | 245 | 2208 | 1683 | 2698 | 274 | 39 | −9 | A C |
| SIGUIJ | 1767 | CG | HIS | A | 245 | 1 | 0 | 0 | 221 | 67 | 290 | A C |
| ATOM | 1768 | CD2 | HIS | A | 245 | 25.094 | −9.348 | 40.592 | 1.00 | 21.75 | | A C |
| ANISOU | 1768 | CD2 | HIS | A | 245 | 2595 | 1985 | 2703 | −38 | 20 | 11 | A C |
| SIGUIJ | 1768 | CD2 | HIS | A | 245 | 1 | 0 | 0 | 221 | 67 | 290 | A C |
| ATOM | 1769 | ND1 | HIS | A | 245 | 25.856 | −9.605 | 42.618 | 1.00 | 22.01 | | A N |
| ANISOU | 1769 | ND1 | HIS | A | 245 | 2583 | 3631 | 3237 | −101 | −356 | −39 | A N |
| SIGUIJ | 1769 | ND1 | HIS | A | 245 | 1 | 0 | 0 | 221 | 57 | 289 | A N |
| ATOM | 1770 | CE1 | HIS | A | 245 | 26.818 | −9.047 | 41.910 | 1.00 | 21.93 | | A C |
| ANISOU | 1770 | CE1 | HIS | A | 245 | 2767 | 3493 | 3671 | 0 | −48 | 0 | A C |
| SIGUIJ | 1770 | CE1 | HIS | A | 245 | 1 | 0 | 0 | 221 | 67 | 290 | A C |
| ATOM | 1771 | NE2 | HIS | A | 245 | 26.379 | −8.876 | 40.682 | 1.00 | 21.98 | | A N |
| ANISOU | 1771 | NE2 | HIS | A | 245 | 2697 | 2672 | 3671 | −298 | −44 | 5 | A N |
| SIGUIJ | 1771 | NE2 | HIS | A | 245 | 1 | 0 | 0 | 221 | 57 | 289 | A N |
| ATOM | 1772 | C | HIS | A | 245 | 22.478 | −12.610 | 43.050 | 1.00 | 23.41 | | A C |
| ANISOU | 1772 | C | HIS | A | 245 | 2277 | 2229 | 1876 | 16 | 4 | 1 | A C |
| SIGUIJ | 1772 | C | HIS | A | 245 | 1 | 0 | 0 | 221 | 67 | 290 | A C |
| ATOM | 1773 | O | HIS | A | 245 | 21.673 | −11.862 | 43.634 | 1.00 | 23.57 | | A O |
| ANISOU | 1773 | O | HIS | A | 245 | 3593 | 2566 | 2676 | 683 | 1018 | 474 | A O |
| SIGUIJ | 1773 | O | HIS | A | 245 | 1 | 0 | 0 | 221 | 51 | 289 | A O |
| ATOM | 1774 | N | ARG | A | 246 | 22.331 | −13.935 | 43.000 | 1.00 | 24.99 | | A N |
| ANISOU | 1774 | N | ARG | A | 246 | 2645 | 2244 | 3081 | −2 | −411 | 11 | A N |
| SIGUIJ | 1774 | N | ARG | A | 246 | 1 | 0 | 0 | 221 | 57 | 289 | A N |
| ATOM | 1775 | CA | ARG | A | 246 | 21.272 | −14.563 | 43.756 | 1.00 | 26.54 | | A C |
| ANISOU | 1775 | CA | ARG | A | 246 | 3755 | 2997 | 5101 | −286 | 913 | 201 | A C |
| SIGUIJ | 1775 | CA | ARG | A | 246 | 1 | 0 | 0 | 221 | 67 | 290 | A C |
| ATOM | 1776 | CB | ARG | A | 246 | 21.219 | −16.057 | 43.462 | 1.00 | 27.41 | | A C |
| ANISOU | 1776 | CB | ARG | A | 246 | 3507 | 3031 | 6293 | −54 | −129 | 9 | A C |
| SIGUIJ | 1776 | CB | ARG | A | 246 | 1 | 0 | 0 | 221 | 67 | 290 | A C |
| ATOM | 1777 | CG | ARG | A | 246 | 21.319 | −16.302 | 42.001 | 1.00 | 28.73 | | A C |
| ANISOU | 1777 | CG | ARG | A | 246 | 8214 | 3342 | 6310 | 616 | 83 | 8 | A C |
| SIGUIJ | 1777 | CG | ARG | A | 246 | 1 | 0 | 0 | 221 | 67 | 290 | A C |
| ATOM | 1778 | CD | ARG | A | 246 | 20.574 | −17.528 | 41.598 | 1.00 | 29.81 | | A C |
| ANISOU | 1778 | CD | ARG | A | 246 | 15256 | 5457 | 7745 | −3138 | −1525 | 513 | A C |
| SIGUIJ | 1778 | CD | ARG | A | 246 | 1 | 0 | 0 | 221 | 67 | 290 | A C |
| ATOM | 1779 | NE | ARG | A | 246 | 19.632 | −17.212 | 40.533 | 1.00 | 30.72 | | A N |
| ANISOU | 1779 | NE | ARG | A | 246 | 13748 | 8730 | 5920 | −1374 | 343 | −74 | A N |
| SIGUIJ | 1779 | NE | ARG | A | 246 | 1 | 0 | 0 | 221 | 57 | 289 | A N |
| ATOM | 1780 | CZ | ARG | A | 246 | 18.420 | −17.731 | 40.467 | 1.00 | 31.19 | | A C |
| ANISOU | 1780 | CZ | ARG | A | 246 | 13449 | 7175 | 6111 | −710 | 314 | −33 | A C |
| SIGUIJ | 1780 | CZ | ARG | A | 246 | 1 | 0 | 0 | 221 | 67 | 290 | A C |
| ATOM | 1781 | NH1 | ARG | A | 246 | 18.022 | −18.576 | 41.414 | 1.00 | 31.95 | | A N |
| ANISOU | 1781 | NH1 | ARG | A | 246 | 8876 | 6548 | 5694 | 477 | −548 | −94 | A N |
| SIGUIJ | 1781 | NH1 | ARG | A | 246 | 1 | 0 | 0 | 221 | 57 | 289 | A N |
| ATOM | 1782 | NH2 | ARG | A | 246 | 17.641 | −17.451 | 39.445 | 1.00 | 31.97 | | A N |
| ANISOU | 1782 | NH2 | ARG | A | 246 | 13844 | 10033 | 6150 | 253 | 282 | 14 | A N |
| SIGUIJ | 1782 | NH2 | ARG | A | 246 | 1 | 0 | 0 | 221 | 57 | 289 | A N |
| ATOM | 1783 | C | ARG | A | 246 | 21.456 | −14.309 | 45.240 | 1.00 | 26.93 | | A C |
| ANISOU | 1783 | C | ARG | A | 246 | 11079 | 4350 | 5249 | −654 | 62 | −6 | A C |
| SIGUIJ | 1783 | C | ARG | A | 246 | 1 | 0 | 0 | 221 | 67 | 290 | A C |
| ATOM | 1784 | O | ARG | A | 246 | 20.426 | −13.976 | 45.883 | 1.00 | 27.58 | | A O |
| ANISOU | 1784 | O | ARG | A | 246 | 11357 | 3254 | 6365 | −1074 | 717 | −122 | A O |
| SIGUIJ | 1784 | O | ARG | A | 246 | 1 | 0 | 0 | 221 | 51 | 289 | A O |
| ATOM | 1785 | OXT | ARG | A | 246 | 22.610 | −14.430 | 45.737 | 1.00 | 27.58 | | A O |
| ANISOU | 1785 | OXT | ARG | A | 246 | 10736 | 6341 | 3324 | −426 | 899 | −68 | A O |
| SIGUIJ | 1785 | OXT | ARG | A | 246 | 1 | 0 | 0 | 221 | 51 | 289 | A O |
| TER | 1 | | ARG | A | 246 | | | | | | | A |
| HETATM | 1786 | OH2 | WAT | S | 1 | 24.781 | −18.805 | 43.324 | 1.00 | 6.43 | | S O |
| ANISOU | 1786 | OH2 | WAT | S | 1 | 1173 | 478 | 1393 | 453 | −95 | 153 | S O |
| SIGUIJ | 1786 | OH2 | WAT | S | 1 | 1 | 0 | 0 | 221 | 51 | 289 | S O |
| HETATM | 1787 | OH2 | WAT | S | 2 | 4.474 | 5.063 | 48.501 | 1.00 | 9.59 | | S O |
| ANISOU | 1787 | OH2 | WAT | S | 2 | 1494 | 1440 | 1186 | −3 | 68 | −4 | S O |
| SIGUIJ | 1787 | OH2 | WAT | S | 2 | 1 | 0 | 0 | 221 | 51 | 289 | S O |
| HETATM | 1788 | OH2 | WAT | S | 3 | 15.552 | 4.965 | 51.375 | 1.00 | 9.82 | | S O |
| ANISOU | 1788 | OH2 | WAT | S | 3 | 1326 | 1720 | 965 | −369 | −36 | 47 | S O |
| SIGUIJ | 1788 | OH2 | WAT | S | 3 | 1 | 0 | 0 | 221 | 51 | 289 | S O |
| HETATM | 1789 | OH2 | WAT | S | 4 | 8.858 | 8.363 | 37.689 | 1.00 | 10.14 | | S O |
| ANISOU | 1789 | OH2 | WAT | S | 4 | 1162 | 1190 | 1480 | −1 | −18 | 0 | S O |
| SIGUIJ | 1789 | OH2 | WAT | S | 4 | 1 | 0 | 0 | 221 | 51 | 289 | S O |
| HETATM | 1790 | OH2 | WAT | S | 5 | 4.835 | 12.969 | 35.509 | 1.00 | 9.64 | | S O |
| ANISOU | 1790 | OH2 | WAT | S | 5 | 1150 | 1216 | 1326 | 6 | 10 | −1 | S O |
| SIGUIJ | 1790 | OH2 | WAT | S | 5 | 1 | 0 | 0 | 221 | 51 | 289 | S O |
| HETATM | 1791 | OH2 | WAT | S | 6 | 9.341 | 7.161 | 35.215 | 1.00 | 10.61 | | S O |
| ANISOU | 1791 | OH2 | WAT | S | 6 | 1360 | 1161 | 1548 | 172 | −2 | 1 | S O |
| SIGUIJ | 1791 | OH2 | WAT | S | 6 | 1 | 0 | 0 | 221 | 51 | 289 | S O |
| HETATM | 1792 | OH2 | WAT | S | 7 | 21.178 | 9.235 | 41.811 | 1.00 | 10.42 | | S O |

TABLE 3-continued

Three-dimensional structure of the new binding pocket of kallikrein 7

| ANISOU | 1792 | OH2 | WAT | S | 7  | 1321    | 1163    | 1465   | −114  | 0    | 0     | S | O |
|--------|------|-----|-----|---|----|---------|---------|--------|-------|------|-------|---|---|
| SIGUIJ | 1792 | OH2 | WAT | S | 7  | 1       | 0       | 0      | 221   | 51   | 289   | S | O |
| HETATM | 1793 | OH2 | WAT | S | 8  | 27.008  | −0.037  | 40.833 | 1.00  | 10.86 |      | S | O |
| ANISOU | 1793 | OH2 | WAT | S | 8  | 1231    | 1546    | 1387   | −17   | −262 | −13   | S | O |
| SIGUIJ | 1793 | OH2 | WAT | S | 8  | 1       | 0       | 0      | 221   | 51   | 289   | S | O |
| HETATM | 1794 | OH2 | WAT | S | 9  | 5.785   | 12.849  | 42.062 | 1.00  | 12.65 |      | S | O |
| ANISOU | 1794 | OH2 | WAT | S | 9  | 1871    | 1478    | 1529   | 256   | 11   | 6     | S | O |
| SIGUIJ | 1794 | OH2 | WAT | S | 9  | 1       | 0       | 0      | 221   | 51   | 289   | S | O |
| HETATM | 1795 | OH2 | WAT | S | 10 | 25.809  | 10.089  | 36.957 | 1.00  | 15.33 |      | S | O |
| ANISOU | 1795 | OH2 | WAT | S | 10 | 1699    | 2881    | 1728   | 75    | −357 | −1336 | S | O |
| SIGUIJ | 1795 | OH2 | WAT | S | 10 | 1       | 0       | 0      | 221   | 51   | 289   | S | O |
| HETATM | 1796 | OH2 | WAT | S | 11 | 2.666   | 19.022  | 31.476 | 1.00  | 12.71 |      | S | O |
| ANISOU | 1796 | OH2 | WAT | S | 11 | 2071    | 1417    | 1720   | 363   | −179 | −112  | S | O |
| SIGUIJ | 1796 | OH2 | WAT | S | 11 | 1       | 0       | 0      | 221   | 51   | 289   | S | O |
| HETATM | 1797 | OH2 | WAT | S | 12 | 4.947   | 3.340   | 30.044 | 1.00  | 15.53 |      | S | O |
| ANISOU | 1797 | OH2 | WAT | S | 12 | 2033    | 1941    | 1721   | −379  | 55   | −55   | S | O |
| SIGUIJ | 1797 | OH2 | WAT | S | 12 | 1       | 0       | 0      | 221   | 51   | 289   | S | O |
| HETATM | 1798 | OH2 | WAT | S | 13 | 13.902  | −0.433  | 19.971 | 1.00  | 15.89 |      | S | O |
| ANISOU | 1798 | OH2 | WAT | S | 13 | 2696    | 1999    | 1557   | −396  | −358 | 132   | S | O |
| SIGUIJ | 1798 | OH2 | WAT | S | 13 | 1       | 0       | 0      | 221   | 51   | 289   | S | O |
| HETATM | 1799 | OH2 | WAT | S | 14 | 21.900  | 4.419   | 27.895 | 1.00  | 14.56 |      | S | O |
| ANISOU | 1799 | OH2 | WAT | S | 14 | 1917    | 1895    | 1557   | −4    | 318  | −35   | S | O |
| SIGUIJ | 1799 | OH2 | WAT | S | 14 | 1       | 0       | 0      | 221   | 51   | 289   | S | O |
| HETATM | 1800 | OH2 | WAT | S | 15 | 4.033   | −1.934  | 40.854 | 1.00  | 13.63 |      | S | O |
| ANISOU | 1800 | OH2 | WAT | S | 15 | 2107    | 1352    | 1711   | −295  | 383  | −146  | S | O |
| SIGUIJ | 1800 | OH2 | WAT | S | 15 | 1       | 0       | 0      | 221   | 51   | 289   | S | O |
| HETATM | 1801 | OH2 | WAT | S | 16 | 22.787  | 8.096   | 47.811 | 1.00  | 13.85 |      | S | O |
| ANISOU | 1801 | OH2 | WAT | S | 16 | 2167    | 1748    | 1779   | −701  | 88   | −98   | S | O |
| SIGUIJ | 1801 | OH2 | WAT | S | 16 | 1       | 0       | 0      | 221   | 51   | 289   | S | O |
| HETATM | 1802 | OH2 | WAT | S | 17 | 19.119  | 8.947   | 33.793 | 1.00  | 11.52 |      | S | O |
| ANISOU | 1802 | OH2 | WAT | S | 17 | 1384    | 1642    | 1345   | 116   | 0    | −1    | S | O |
| SIGUIJ | 1802 | OH2 | WAT | S | 17 | 1       | 0       | 0      | 221   | 51   | 289   | S | O |
| HETATM | 1803 | OH2 | WAT | S | 18 | 19.344  | 12.504  | 33.386 | 1.00  | 16.02 |      | S | O |
| ANISOU | 1803 | OH2 | WAT | S | 18 | 1916    | 2583    | 1861   | −430  | −3   | −19   | S | O |
| SIGUIJ | 1803 | OH2 | WAT | S | 18 | 1       | 0       | 0      | 221   | 51   | 289   | S | O |
| HETATM | 1804 | OH2 | WAT | S | 19 | −0.352  | 11.477  | 24.455 | 1.00  | 18.54 |      | S | O |
| ANISOU | 1804 | OH2 | WAT | S | 19 | 1767    | 2696    | 2887   | 698   | −42  | 24    | S | O |
| SIGUIJ | 1804 | OH2 | WAT | S | 19 | 1       | 0       | 0      | 221   | 51   | 289   | S | O |
| HETATM | 1805 | OH2 | WAT | S | 20 | 2.073   | 15.464  | 31.901 | 1.00  | 14.28 |      | S | O |
| ANISOU | 1805 | OH2 | WAT | S | 20 | 1612    | 1934    | 1675   | 73    | 0    | 0     | S | O |
| SIGUIJ | 1805 | OH2 | WAT | S | 20 | 1       | 0       | 0      | 221   | 51   | 289   | S | O |
| HETATM | 1806 | OH2 | WAT | S | 21 | 1.417   | 20.832  | 35.391 | 1.00  | 14.41 |      | S | O |
| ANISOU | 1806 | OH2 | WAT | S | 21 | 1725    | 1350    | 1965   | 347   | 49   | −56   | S | O |
| SIGUIJ | 1806 | OH2 | WAT | S | 21 | 1       | 0       | 0      | 221   | 51   | 289   | S | O |
| HETATM | 1807 | OH2 | WAT | S | 22 | 0.109   | −4.786  | 46.294 | 1.00  | 24.10 |      | S | O |
| ANISOU | 1807 | OH2 | WAT | S | 22 | 3431    | 2852    | 2764   | 1027  | 639  | 544   | S | O |
| SIGUIJ | 1807 | OH2 | WAT | S | 22 | 1       | 0       | 0      | 221   | 51   | 289   | S | O |
| HETATM | 1808 | OH2 | WAT | S | 23 | 5.790   | −5.960  | 50.260 | 1.00  | 19.83 |      | S | O |
| ANISOU | 1808 | OH2 | WAT | S | 23 | 2406    | 2846    | 1833   | −107  | −54  | −1    | S | O |
| SIGUIJ | 1808 | OH2 | WAT | S | 23 | 1       | 0       | 0      | 221   | 51   | 289   | S | O |
| HETATM | 1809 | OH2 | WAT | S | 24 | 25.312  | −2.553  | 46.116 | 1.00  | 18.04 |      | S | O |
| ANISOU | 1809 | OH2 | WAT | S | 24 | 1597    | 3326    | 2535   | −196  | −79  | −12   | S | O |
| SIGUIJ | 1809 | OH2 | WAT | S | 24 | 1       | 0       | 0      | 221   | 51   | 289   | S | O |
| HETATM | 1810 | OH2 | WAT | S | 25 | 22.872  | 0.557   | 46.323 | 1.00  | 14.62 |      | S | O |
| ANISOU | 1810 | OH2 | WAT | S | 25 | 2126    | 1823    | 1778   | 50    | −471 | −49   | S | O |
| SIGUIJ | 1810 | OH2 | WAT | S | 25 | 1       | 0       | 0      | 221   | 51   | 289   | S | O |
| HETATM | 1811 | OH2 | WAT | S | 26 | 14.410  | −1.902  | 23.124 | 1.00  | 14.14 |      | S | O |
| ANISOU | 1811 | OH2 | WAT | S | 26 | 1804    | 1976    | 1647   | 34    | 12   | 0     | S | O |
| SIGUIJ | 1811 | OH2 | WAT | S | 26 | 1       | 0       | 0      | 221   | 51   | 289   | S | O |
| HETATM | 1812 | OH2 | WAT | S | 27 | 13.755  | 18.203  | 27.222 | 1.00  | 15.46 |      | S | O |
| ANISOU | 1812 | OH2 | WAT | S | 27 | 2007    | 1739    | 1669   | −309  | −51  | 39    | S | O |
| SIGUIJ | 1812 | OH2 | WAT | S | 27 | 1       | 0       | 0      | 221   | 51   | 289   | S | O |
| HETATM | 1813 | OH2 | WAT | S | 28 | 10.386  | 11.514  | 25.133 | 1.00  | 13.16 |      | S | O |
| ANISOU | 1813 | OH2 | WAT | S | 28 | 1921    | 1495    | 1499   | 105   | −40  | −9    | S | O |
| SIGUIJ | 1813 | OH2 | WAT | S | 28 | 1       | 0       | 0      | 221   | 51   | 289   | S | O |
| HETATM | 1814 | OH2 | WAT | S | 29 | 6.031   | 24.167  | 32.208 | 1.00  | 17.37 |      | S | O |
| ANISOU | 1814 | OH2 | WAT | S | 29 | 2381    | 1712    | 2309   | 131   | 7    | 7     | S | O |
| SIGUIJ | 1814 | OH2 | WAT | S | 29 | 1       | 0       | 0      | 221   | 51   | 289   | S | O |
| HETATM | 1815 | OH2 | WAT | S | 30 | 15.062  | 16.500  | 25.595 | 1.00  | 15.15 |      | S | O |
| ANISOU | 1815 | OH2 | WAT | S | 30 | 2188    | 1659    | 1772   | −298  | −402 | 181   | S | O |
| SIGUIJ | 1815 | OH2 | WAT | S | 30 | 1       | 0       | 0      | 221   | 51   | 289   | S | O |
| HETATM | 1816 | OH2 | WAT | S | 31 | 10.624  | 25.090  | 41.301 | 1.00  | 21.60 |      | S | O |
| ANISOU | 1816 | OH2 | WAT | S | 31 | 2700    | 2652    | 3111   | 2     | −47  | −1    | S | O |
| SIGUIJ | 1816 | OH2 | WAT | S | 31 | 1       | 0       | 0      | 221   | 51   | 289   | S | O |
| HETATM | 1817 | OH2 | WAT | S | 32 | 2.808   | 3.760   | 50.728 | 1.00  | 21.37 |      | S | O |
| ANISOU | 1817 | OH2 | WAT | S | 32 | 2182    | 4019    | 2257   | 191   | 2    | −2    | S | O |
| SIGUIJ | 1817 | OH2 | WAT | S | 32 | 1       | 0       | 0      | 221   | 51   | 289   | S | O |
| HETATM | 1818 | OH2 | WAT | S | 33 | 16.530  | 15.962  | 17.042 | 1.00  | 18.16 |      | S | O |

TABLE 3-continued

Three-dimensional structure of the new binding pocket of kallikrein 7

| | | | | | | | | | | | | | |
|---|---|---|---|---|---|---|---|---|---|---|---|---|---|
| ANISOU | 1818 | OH2 | WAT | S | 33 | 2819 | 2566 | 2015 | −16 | 365 | 1 | S | O |
| SIGUIJ | 1818 | OH2 | WAT | S | 33 | 1 | 0 | 0 | 221 | 51 | 289 | S | O |
| HETATM | 1819 | OH2 | WAT | S | 34 | 5.585 | −3.559 | 51.423 | 1.00 | 18.93 | | S | O |
| ANISOU | 1819 | OH2 | WAT | S | 34 | 2586 | 3629 | 1722 | −468 | 25 | −3 | S | O |
| SIGUIJ | 1819 | OH2 | WAT | S | 34 | 1 | 0 | 0 | 221 | 51 | 289 | S | O |
| HETATM | 1820 | OH2 | WAT | S | 35 | 21.770 | 19.513 | 27.539 | 1.00 | 29.03 | | S | O |
| ANISOU | 1820 | OH2 | WAT | S | 35 | 3155 | 4624 | 3657 | −761 | −2 | −1 | S | O |
| SIGUIJ | 1820 | OH2 | WAT | S | 35 | 1 | 0 | 0 | 221 | 51 | 289 | S | O |
| HETATM | 1821 | OH2 | WAT | S | 36 | 13.143 | 20.680 | 26.241 | 1.00 | 16.62 | | S | O |
| ANISOU | 1821 | OH2 | WAT | S | 36 | 1927 | 2059 | 1723 | −15 | −4 | 0 | S | O |
| SIGUIJ | 1821 | OH2 | WAT | S | 36 | 1 | 0 | 0 | 221 | 51 | 289 | S | O |
| HETATM | 1822 | OH2 | WAT | S | 37 | −1.106 | 0.388 | 37.477 | 1.00 | 17.68 | | S | O |
| ANISOU | 1822 | OH2 | WAT | S | 37 | 1816 | 1896 | 2547 | −6 | 132 | 5 | S | O |
| SIGUIJ | 1822 | OH2 | WAT | S | 37 | 1 | 0 | 0 | 221 | 51 | 289 | S | O |
| HETATM | 1823 | OH2 | WAT | S | 38 | 11.350 | 17.436 | 28.280 | 1.00 | 16.01 | | S | O |
| ANISOU | 1823 | OH2 | WAT | S | 38 | 2491 | 1513 | 1556 | −353 | −439 | 141 | S | O |
| SIGUIJ | 1823 | OH2 | WAT | S | 38 | 1 | 0 | 0 | 221 | 51 | 289 | S | O |
| HETATM | 1824 | OH2 | WAT | S | 39 | 23.589 | −7.362 | 27.067 | 1.00 | 19.07 | | S | O |
| ANISOU | 1824 | OH2 | WAT | S | 39 | 2961 | 2213 | 2026 | 1059 | −110 | −97 | S | O |
| SIGUIJ | 1824 | OH2 | WAT | S | 39 | 1 | 0 | 0 | 221 | 51 | 289 | S | O |
| HETATM | 1825 | OH2 | WAT | S | 40 | 19.429 | −5.617 | 48.324 | 1.00 | 17.18 | | S | O |
| ANISOU | 1825 | OH2 | WAT | S | 40 | 1922 | 2364 | 1913 | 272 | −3 | 9 | S | O |
| SIGUIJ | 1825 | OH2 | WAT | S | 40 | 1 | 0 | 0 | 221 | 51 | 289 | S | O |
| HETATM | 1826 | OH2 | WAT | S | 41 | 9.243 | 16.808 | 19.409 | 1.00 | 17.74 | | S | O |
| ANISOU | 1826 | OH2 | WAT | S | 41 | 2768 | 1982 | 2206 | −321 | −314 | 128 | S | O |
| SIGUIJ | 1826 | OH2 | WAT | S | 41 | 1 | 0 | 0 | 221 | 51 | 289 | S | O |
| HETATM | 1827 | OH2 | WAT | S | 42 | 8.159 | −7.341 | 50.894 | 1.00 | 19.75 | | S | O |
| ANISOU | 1827 | OH2 | WAT | S | 42 | 2982 | 2433 | 2025 | −328 | −349 | 137 | S | O |
| SIGUIJ | 1827 | OH2 | WAT | S | 42 | 1 | 0 | 0 | 221 | 51 | 289 | S | O |
| HETATM | 1828 | OH2 | WAT | S | 43 | 24.526 | −15.892 | 42.152 | 1.00 | 19.49 | | S | O |
| ANISOU | 1828 | OH2 | WAT | S | 43 | 3887 | 1662 | 2311 | 514 | −288 | −76 | S | O |
| SIGUIJ | 1828 | OH2 | WAT | S | 43 | 1 | 0 | 0 | 221 | 51 | 289 | S | O |
| HETATM | 1829 | OH2 | WAT | S | 44 | 15.071 | 0.754 | 16.873 | 1.00 | 23.52 | | S | O |
| ANISOU | 1829 | OH2 | WAT | S | 44 | 2962 | 3462 | 2125 | −799 | −23 | 14 | S | O |
| SIGUIJ | 1829 | OH2 | WAT | S | 44 | 1 | 0 | 0 | 221 | 51 | 289 | S | O |
| HETATM | 1830 | OH2 | WAT | S | 45 | 1.623 | 1.863 | 38.928 | 1.00 | 19.00 | | S | O |
| ANISOU | 1830 | OH2 | WAT | S | 45 | 2163 | 2827 | 2281 | 252 | −5 | 5 | S | O |
| SIGUIJ | 1830 | OH2 | WAT | S | 45 | 1 | 0 | 0 | 221 | 51 | 289 | S | O |
| HETATM | 1831 | OH2 | WAT | S | 46 | 1.083 | 11.640 | 21.244 | 1.00 | 20.42 | | S | O |
| ANISOU | 1831 | OH2 | WAT | S | 46 | 2274 | 2112 | 2993 | 9 | −227 | −8 | S | O |
| SIGUIJ | 1831 | OH2 | WAT | S | 46 | 1 | 0 | 0 | 221 | 51 | 289 | S | O |
| HETATM | 1832 | OH2 | WAT | S | 47 | −0.976 | −2.337 | 46.128 | 1.00 | 20.63 | | S | O |
| ANISOU | 1832 | OH2 | WAT | S | 47 | 3091 | 1922 | 2501 | −91 | 62 | −7 | S | O |
| SIGUIJ | 1832 | OH2 | WAT | S | 47 | 1 | 0 | 0 | 221 | 51 | 289 | S | O |
| HETATM | 1833 | OH2 | WAT | S | 48 | −1.532 | 3.190 | 35.408 | 1.00 | 18.27 | | S | O |
| ANISOU | 1833 | OH2 | WAT | S | 48 | 2523 | 2040 | 2240 | 155 | 13 | 5 | S | O |
| SIGUIJ | 1833 | OH2 | WAT | S | 48 | 1 | 0 | 0 | 221 | 51 | 289 | S | O |
| HETATM | 1834 | OH2 | WAT | S | 49 | 10.268 | 17.052 | 21.922 | 1.00 | 15.72 | | S | O |
| ANISOU | 1834 | OH2 | WAT | S | 49 | 2308 | 2056 | 1739 | −85 | −374 | 70 | S | O |
| SIGUIJ | 1834 | OH2 | WAT | S | 49 | 1 | 0 | 0 | 221 | 51 | 289 | S | O |
| HETATM | 1835 | OH2 | WAT | S | 50 | 13.003 | −12.816 | 35.683 | 1.00 | 20.60 | | S | O |
| ANISOU | 1835 | OH2 | WAT | S | 50 | 3574 | 2019 | 2471 | 410 | −281 | −85 | S | O |
| SIGUIJ | 1835 | OH2 | WAT | S | 50 | 1 | 0 | 0 | 221 | 51 | 289 | S | O |
| HETATM | 1836 | OH2 | WAT | S | 51 | 23.454 | 2.971 | 26.072 | 1.00 | 20.51 | | S | O |
| ANISOU | 1836 | OH2 | WAT | S | 51 | 2369 | 2806 | 2279 | 322 | −1 | −9 | S | O |
| SIGUIJ | 1836 | OH2 | WAT | S | 51 | 1 | 0 | 0 | 221 | 51 | 289 | S | O |
| HETATM | 1837 | OH2 | WAT | S | 52 | 20.163 | 20.835 | 28.950 | 1.00 | 19.73 | | S | O |
| ANISOU | 1837 | OH2 | WAT | S | 52 | 1831 | 2320 | 4535 | −156 | −248 | −51 | S | O |
| SIGUIJ | 1837 | OH2 | WAT | S | 52 | 1 | 0 | 0 | 221 | 51 | 289 | S | O |
| HETATM | 1838 | OH2 | WAT | S | 53 | 18.260 | 4.832 | 31.017 | 1.00 | 16.47 | | S | O |
| ANISOU | 1838 | OH2 | WAT | S | 53 | 1722 | 1988 | 1893 | −20 | −25 | −2 | S | O |
| SIGUIJ | 1838 | OH2 | WAT | S | 53 | 1 | 0 | 0 | 221 | 51 | 289 | S | O |
| HETATM | 1839 | OH2 | WAT | S | 54 | 3.473 | 1.488 | 41.250 | 1.00 | 15.36 | | S | O |
| ANISOU | 1839 | OH2 | WAT | S | 54 | 2028 | 1518 | 1768 | 207 | 409 | 148 | S | O |
| SIGUIJ | 1839 | OH2 | WAT | S | 54 | 1 | 0 | 0 | 221 | 51 | 289 | S | O |
| HETATM | 1840 | OH2 | WAT | S | 55 | 15.273 | −6.972 | 16.641 | 1.00 | 26.28 | | S | O |
| ANISOU | 1840 | OH2 | WAT | S | 55 | 4371 | 3181 | 2970 | 325 | 235 | 56 | S | O |
| SIGUIJ | 1840 | OH2 | WAT | S | 55 | 1 | 0 | 0 | 221 | 51 | 289 | S | O |
| HETATM | 1841 | OH2 | WAT | S | 56 | 4.097 | 22.217 | 31.651 | 1.00 | 18.32 | | S | O |
| ANISOU | 1841 | OH2 | WAT | S | 56 | 2455 | 2059 | 2064 | 542 | 92 | 87 | S | O |
| SIGUIJ | 1841 | OH2 | WAT | S | 56 | 1 | 0 | 0 | 221 | 51 | 289 | S | O |
| HETATM | 1842 | OH2 | WAT | S | 57 | 17.859 | 16.386 | 19.498 | 1.00 | 16.54 | | S | O |
| ANISOU | 1842 | OH2 | WAT | S | 57 | 2118 | 2397 | 1880 | 153 | 666 | 686 | S | O |
| SIGUIJ | 1842 | OH2 | WAT | S | 57 | 1 | 0 | 0 | 221 | 51 | 289 | S | O |
| HETATM | 1843 | OH2 | WAT | S | 58 | 3.109 | −4.539 | 29.443 | 1.00 | 23.06 | | S | O |
| ANISOU | 1843 | OH2 | WAT | S | 58 | 4608 | 2423 | 2713 | 35 | 808 | 13 | S | O |
| SIGUIJ | 1843 | OH2 | WAT | S | 58 | 1 | 0 | 0 | 221 | 51 | 289 | S | O |
| HETATM | 1844 | OH2 | WAT | S | 59 | −2.538 | 7.349 | 37.099 | 1.00 | 19.86 | | S | O |

TABLE 3-continued

Three-dimensional structure of the new binding pocket of kallikrein 7

| ANISOU | 1844 | OH2 | WAT | S | 59 | 2079 | 2504 | 2374 | −596 | 170 | 179 | S | O |
|---|---|---|---|---|---|---|---|---|---|---|---|---|---|
| SIGUIJ | 1844 | OH2 | WAT | S | 59 | 1 | 0 | 0 | 221 | 51 | 289 | S | O |
| HETATM | 1845 | OH2 | WAT | S | 60 | 19.442 | 18.113 | 31.002 | 1.00 | 32.60 | | S | O |
| ANISOU | 1845 | OH2 | WAT | S | 60 | 5406 | 6964 | 4243 | 11 | −68 | 0 | S | O |
| SIGUIJ | 1845 | OH2 | WAT | S | 60 | 1 | 0 | 0 | 221 | 51 | 289 | S | O |
| HETATM | 1846 | OH2 | WAT | S | 62 | 4.758 | −5.404 | 30.600 | 1.00 | 24.62 | | S | O |
| ANISOU | 1846 | OH2 | WAT | S | 62 | 2411 | 3146 | 3148 | −140 | 29 | 5 | S | O |
| SIGUIJ | 1846 | OH2 | WAT | S | 62 | 1 | 0 | 0 | 221 | 51 | 289 | S | O |
| HETATM | 1847 | OH2 | WAT | S | 63 | 11.832 | 20.865 | 35.382 | 1.00 | 22.71 | | S | O |
| ANISOU | 1847 | OH2 | WAT | S | 63 | 3516 | 3544 | 2255 | −2153 | −517 | 619 | S | O |
| SIGUIJ | 1847 | OH2 | WAT | S | 63 | 1 | 0 | 0 | 221 | 51 | 289 | S | O |
| HETATM | 1848 | OH2 | WAT | S | 64 | 9.886 | 18.217 | 24.619 | 1.00 | 16.50 | | S | O |
| ANISOU | 1848 | OH2 | WAT | S | 64 | 1996 | 1565 | 2669 | −88 | −22 | 1 | S | O |
| SIGUIJ | 1848 | OH2 | WAT | S | 64 | 1 | 0 | 0 | 221 | 51 | 289 | S | O |
| HETATM | 1849 | OH2 | WAT | S | 65 | 17.902 | 6.647 | 49.778 | 1.00 | 24.11 | | S | O |
| ANISOU | 1849 | OH2 | WAT | S | 65 | 5482 | 2700 | 2275 | 1291 | −322 | −128 | S | O |
| SIGUIJ | 1849 | OH2 | WAT | S | 65 | 1 | 0 | 0 | 221 | 51 | 289 | S | O |
| HETATM | 1850 | OH2 | WAT | S | 66 | 3.910 | −12.994 | 45.112 | 1.00 | 25.58 | | S | O |
| ANISOU | 1850 | OH2 | WAT | S | 66 | 3118 | 1706 | 5270 | 346 | 177 | 10 | S | O |
| SIGUIJ | 1850 | OH2 | WAT | S | 66 | 1 | 0 | 0 | 221 | 51 | 289 | S | O |
| HETATM | 1851 | OH2 | WAT | S | 67 | 22.241 | 18.528 | 23.106 | 1.00 | 36.69 | | S | O |
| ANISOU | 1851 | OH2 | WAT | S | 67 | 3190 | 4405 | 5377 | −5 | 117 | 0 | S | O |
| SIGUIJ | 1851 | OH2 | WAT | S | 67 | 1 | 0 | 0 | 221 | 50 | 289 | S | O |
| HETATM | 1852 | OH2 | WAT | S | 68 | −3.052 | 4.627 | 30.518 | 1.00 | 29.98 | | S | O |
| ANISOU | 1852 | OH2 | WAT | S | 68 | 5803 | 8921 | 4571 | −4535 | −20 | −291 | S | O |
| SIGUIJ | 1852 | OH2 | WAT | S | 68 | 1 | 0 | 0 | 221 | 50 | 289 | S | O |
| HETATM | 1853 | OH2 | WAT | S | 69 | 11.974 | 4.666 | 53.712 | 1.00 | 19.70 | | S | O |
| ANISOU | 1853 | OH2 | WAT | S | 69 | 3516 | 2783 | 2099 | −55 | 627 | −48 | S | O |
| SIGUIJ | 1853 | OH2 | WAT | S | 69 | 1 | 0 | 0 | 221 | 50 | 289 | S | O |
| HETATM | 1854 | OH2 | WAT | S | 70 | 27.570 | −6.698 | 38.544 | 1.00 | 27.70 | | S | O |
| ANISOU | 1854 | OH2 | WAT | S | 70 | 3182 | 4401 | 3470 | 557 | −13 | 13 | S | O |
| SIGUIJ | 1854 | OH2 | WAT | S | 70 | 1 | 0 | 0 | 221 | 50 | 289 | S | O |
| HETATM | 1855 | OH2 | WAT | S | 71 | −4.331 | 5.240 | 42.885 | 1.00 | 28.52 | | S | O |
| ANISOU | 1855 | OH2 | WAT | S | 71 | 2834 | 3803 | 4481 | 311 | 1196 | −245 | S | O |
| SIGUIJ | 1855 | OH2 | WAT | S | 71 | 1 | 0 | 0 | 221 | 50 | 289 | S | O |
| HETATM | 1856 | OH2 | WAT | S | 72 | −1.710 | 13.915 | 40.211 | 1.00 | 20.83 | | S | O |
| ANISOU | 1856 | OH2 | WAT | S | 72 | 2239 | 2670 | 3203 | 92 | −179 | 26 | S | O |
| SIGUIJ | 1856 | OH2 | WAT | S | 72 | 1 | 0 | 0 | 221 | 50 | 289 | S | O |
| HETATM | 1857 | OH2 | WAT | S | 73 | 10.041 | 9.287 | 14.686 | 1.00 | 23.91 | | S | O |
| ANISOU | 1857 | OH2 | WAT | S | 73 | 3206 | 4013 | 2440 | −343 | −149 | 13 | S | O |
| SIGUIJ | 1857 | OH2 | WAT | S | 73 | 1 | 0 | 0 | 221 | 50 | 289 | S | O |
| HETATM | 1858 | OH2 | WAT | S | 74 | 27.415 | −2.814 | 43.051 | 1.00 | 27.21 | | S | O |
| ANISOU | 1858 | OH2 | WAT | S | 74 | 2485 | 2794 | 6783 | 45 | −1456 | 25 | S | O |
| SIGUIJ | 1858 | OH2 | WAT | S | 74 | 1 | 0 | 0 | 221 | 50 | 289 | S | O |
| HETATM | 1859 | OH2 | WAT | S | 75 | 24.225 | −9.992 | 45.971 | 1.00 | 26.90 | | S | O |
| ANISOU | 1859 | OH2 | WAT | S | 75 | 3281 | 2840 | 3048 | 63 | 5 | 1 | S | O |
| SIGUIJ | 1859 | OH2 | WAT | S | 75 | 1 | 0 | 0 | 221 | 50 | 289 | S | O |
| HETATM | 1860 | OH2 | WAT | S | 76 | 7.451 | 15.587 | 21.470 | 1.00 | 18.46 | | S | O |
| ANISOU | 1860 | OH2 | WAT | S | 76 | 3159 | 2145 | 1620 | 190 | 97 | 15 | S | O |
| SIGUIJ | 1860 | OH2 | WAT | S | 76 | 1 | 0 | 0 | 221 | 50 | 289 | S | O |
| HETATM | 1861 | OH2 | WAT | S | 77 | 23.079 | 9.316 | 51.019 | 1.00 | 31.41 | | S | O |
| ANISOU | 1861 | OH2 | WAT | S | 77 | 7206 | 2582 | 3785 | −1401 | 1671 | −513 | S | O |
| SIGUIJ | 1861 | OH2 | WAT | S | 77 | 1 | 0 | 0 | 221 | 50 | 289 | S | O |
| HETATM | 1862 | OH2 | WAT | S | 78 | −3.582 | 2.710 | 41.526 | 1.00 | 23.55 | | S | O |
| ANISOU | 1862 | OH2 | WAT | S | 78 | 1798 | 3072 | 3934 | −311 | 96 | 18 | S | O |
| SIGUIJ | 1862 | OH2 | WAT | S | 78 | 1 | 0 | 0 | 221 | 50 | 289 | S | O |
| HETATM | 1863 | OH2 | WAT | S | 79 | 9.534 | −7.797 | 21.704 | 1.00 | 22.74 | | S | O |
| ANISOU | 1863 | OH2 | WAT | S | 79 | 2763 | 4898 | 1870 | 557 | −89 | −22 | S | O |
| SIGUIJ | 1863 | OH2 | WAT | S | 79 | 1 | 0 | 0 | 221 | 50 | 289 | S | O |
| HETATM | 1864 | OH2 | WAT | S | 80 | 2.971 | 16.345 | 14.945 | 1.00 | 30.00 | | S | O |
| ANISOU | 1864 | OH2 | WAT | S | 80 | 3558 | 4133 | 4282 | 33 | −20 | 1 | S | O |
| SIGUIJ | 1864 | OH2 | WAT | S | 80 | 1 | 0 | 0 | 221 | 50 | 289 | S | O |
| HETATM | 1865 | OH2 | WAT | S | 81 | 20.740 | −0.313 | 53.174 | 1.00 | 22.50 | | S | O |
| ANISOU | 1865 | OH2 | WAT | S | 81 | 3241 | 2437 | 2297 | −463 | −658 | 268 | S | O |
| SIGUIJ | 1865 | OH2 | WAT | S | 81 | 1 | 0 | 0 | 221 | 50 | 289 | S | O |
| HETATM | 1866 | OH2 | WAT | S | 82 | 22.883 | −0.067 | 51.495 | 1.00 | 27.35 | | S | O |
| ANISOU | 1866 | OH2 | WAT | S | 82 | 2443 | 3395 | 2903 | −569 | −66 | −50 | S | O |
| SIGUIJ | 1866 | OH2 | WAT | S | 82 | 1 | 0 | 0 | 221 | 50 | 289 | S | O |
| HETATM | 1867 | OH2 | WAT | S | 84 | −1.171 | 7.724 | 20.366 | 1.00 | 26.92 | | S | O |
| ANISOU | 1867 | OH2 | WAT | S | 84 | 2753 | 5720 | 3097 | 344 | −29 | 15 | S | O |
| SIGUIJ | 1867 | OH2 | WAT | S | 84 | 1 | 0 | 0 | 221 | 50 | 289 | S | O |
| HETATM | 1868 | OH2 | WAT | S | 85 | 3.600 | 5.966 | 14.955 | 1.00 | 25.46 | | S | O |
| ANISOU | 1868 | OH2 | WAT | S | 85 | 3254 | 4647 | 1830 | 1465 | −70 | −46 | S | O |
| SIGUIJ | 1868 | OH2 | WAT | S | 85 | 1 | 0 | 0 | 221 | 50 | 289 | S | O |
| HETATM | 1869 | OH2 | WAT | S | 86 | 32.035 | 8.228 | 33.633 | 1.00 | 27.13 | | S | O |
| ANISOU | 1869 | OH2 | WAT | S | 86 | 3557 | 4229 | 3973 | 10 | −13 | 0 | S | O |
| SIGUIJ | 1869 | OH2 | WAT | S | 86 | 1 | 0 | 0 | 221 | 50 | 289 | S | O |
| HETATM | 1870 | OH2 | WAT | S | 87 | 10.744 | 24.913 | 28.060 | 1.00 | 29.54 | | S | O |

TABLE 3-continued

Three-dimensional structure of the new binding pocket of kallikrein 7

| | | | | | | | | | | | | |
|---|---|---|---|---|---|---|---|---|---|---|---|---|
| ANISOU | 1870 | OH2 | WAT | S | 87 | 5299 | 3251 | 4261 | −984 | −31 | 20 | S | O |
| SIGUIJ | 1870 | OH2 | WAT | S | 87 | 1 | 0 | 0 | 221 | 50 | 289 | S | O |
| HETATM | 1871 | OH2 | WAT | S | 88 | 20.299 | −8.109 | 23.247 | 1.00 | 24.84 | | S | O |
| ANISOU | 1871 | OH2 | WAT | S | 88 | 4326 | 2753 | 2982 | 924 | 61 | 34 | S | O |
| SIGUIJ | 1871 | OH2 | WAT | S | 88 | 1 | 0 | 0 | 221 | 50 | 289 | S | O |
| HETATM | 1872 | OH2 | WAT | S | 89 | 13.944 | 8.215 | 13.170 | 1.00 | 22.01 | | S | O |
| ANISOU | 1872 | OH2 | WAT | S | 89 | 2965 | 4174 | 1733 | −774 | −109 | 8 | S | O |
| SIGUIJ | 1872 | OH2 | WAT | S | 89 | 1 | 0 | 0 | 221 | 50 | 289 | S | O |
| HETATM | 1873 | OH2 | WAT | S | 90 | 18.818 | 15.142 | 31.512 | 1.00 | 19.19 | | S | O |
| ANISOU | 1873 | OH2 | WAT | S | 90 | 2253 | 3049 | 1644 | −56 | 53 | −1 | S | O |
| SIGUIJ | 1873 | OH2 | WAT | S | 90 | 1 | 0 | 0 | 221 | 50 | 289 | S | O |
| HETATM | 1874 | OH2 | WAT | S | 91 | 10.160 | 14.327 | 23.218 | 1.00 | 17.24 | | S | O |
| ANISOU | 1874 | OH2 | WAT | S | 91 | 2285 | 2044 | 2240 | −28 | 0 | 0 | S | O |
| SIGUIJ | 1874 | OH2 | WAT | S | 91 | 1 | 0 | 0 | 221 | 50 | 289 | S | O |
| HETATM | 1875 | OH2 | WAT | S | 92 | 19.051 | 2.536 | 18.790 | 1.00 | 22.31 | | S | O |
| ANISOU | 1875 | OH2 | WAT | S | 92 | 3789 | 2407 | 1997 | −450 | 605 | −159 | S | O |
| SIGUIJ | 1875 | OH2 | WAT | S | 92 | 1 | 0 | 0 | 221 | 50 | 289 | S | O |
| HETATM | 1876 | OH2 | WAT | S | 93 | 18.311 | 15.147 | 36.811 | 1.00 | 23.61 | | S | O |
| ANISOU | 1876 | OH2 | WAT | S | 93 | 2272 | 2201 | 4255 | −624 | −97 | 10 | S | O |
| SIGUIJ | 1876 | OH2 | WAT | S | 93 | 1 | 0 | 0 | 221 | 50 | 289 | S | O |
| HETATM | 1877 | OH2 | WAT | S | 94 | 22.759 | 11.550 | 16.574 | 1.00 | 24.71 | | S | O |
| ANISOU | 1877 | OH2 | WAT | S | 94 | 3729 | 2674 | 3069 | −99 | 46 | −6 | S | O |
| SIGUIJ | 1877 | OH2 | WAT | S | 94 | 1 | 0 | 0 | 221 | 50 | 289 | S | O |
| HETATM | 1878 | OH2 | WAT | S | 95 | 4.625 | −0.920 | 52.854 | 1.00 | 25.59 | | S | O |
| ANISOU | 1878 | OH2 | WAT | S | 95 | 2602 | 6051 | 2740 | 1218 | −27 | 59 | S | O |
| SIGUIJ | 1878 | OH2 | WAT | S | 95 | 1 | 0 | 0 | 221 | 50 | 289 | S | O |
| HETATM | 1879 | OH2 | WAT | S | 96 | 28.207 | −6.456 | 34.713 | 1.00 | 24.66 | | S | O |
| ANISOU | 1879 | OH2 | WAT | S | 96 | 2941 | 4153 | 8749 | 51 | −1299 | 59 | S | O |
| SIGUIJ | 1879 | OH2 | WAT | S | 96 | 1 | 0 | 0 | 221 | 50 | 289 | S | O |
| HETATM | 1880 | OH2 | WAT | S | 97 | 22.260 | −8.621 | 24.974 | 1.00 | 25.76 | | S | O |
| ANISOU | 1880 | OH2 | WAT | S | 97 | 4216 | 2047 | 2584 | 300 | −177 | −28 | S | O |
| SIGUIJ | 1880 | OH2 | WAT | S | 97 | 1 | 0 | 0 | 221 | 50 | 289 | S | O |
| HETATM | 1881 | OH2 | WAT | S | 98 | 29.377 | 1.424 | 35.670 | 1.00 | 28.05 | | S | O |
| ANISOU | 1881 | OH2 | WAT | S | 98 | 2756 | 3143 | 5489 | −29 | −1115 | −15 | S | O |
| SIGUIJ | 1881 | OH2 | WAT | S | 98 | 1 | 0 | 0 | 221 | 50 | 289 | S | O |
| HETATM | 1882 | OH2 | WAT | S | 99 | 7.978 | 26.620 | 35.039 | 1.00 | 27.96 | | S | O |
| ANISOU | 1882 | OH2 | WAT | S | 99 | 4287 | 3004 | 3516 | 776 | 23 | 16 | S | O |
| SIGUIJ | 1882 | OH2 | WAT | S | 99 | 1 | 0 | 0 | 221 | 50 | 289 | S | O |
| HETATM | 1883 | OH2 | WAT | S | 100 | 22.630 | 9.441 | 32.458 | 1.00 | 20.69 | | S | O |
| ANISOU | 1883 | OH2 | WAT | S | 100 | 2311 | 2591 | 2466 | −17 | 0 | 0 | S | O |
| SIGUIJ | 1883 | OH2 | WAT | S | 100 | 1 | 0 | 0 | 221 | 50 | 289 | S | O |
| HETATM | 1884 | OH2 | WAT | S | 101 | 0.044 | −0.604 | 40.115 | 1.00 | 23.48 | | S | O |
| ANISOU | 1884 | OH2 | WAT | S | 101 | 4663 | 1966 | 3220 | 908 | 112 | 51 | S | O |
| SIGUIJ | 1884 | OH2 | WAT | S | 101 | 1 | 0 | 0 | 221 | 50 | 289 | S | O |
| HETATM | 1885 | OH2 | WAT | S | 102 | 10.586 | −14.310 | 36.023 | 1.00 | 32.88 | | S | O |
| ANISOU | 1885 | OH2 | WAT | S | 102 | 3736 | 3334 | 5679 | 13 | 374 | 0 | S | O |
| SIGUIJ | 1885 | OH2 | WAT | S | 102 | 1 | 0 | 0 | 221 | 50 | 289 | S | O |
| HETATM | 1886 | OH2 | WAT | S | 103 | −0.807 | 17.916 | 30.201 | 1.00 | 25.73 | | S | O |
| ANISOU | 1886 | OH2 | WAT | S | 103 | 2592 | 3349 | 4155 | 480 | 117 | −46 | S | O |
| SIGUIJ | 1886 | OH2 | WAT | S | 103 | 1 | 0 | 0 | 221 | 50 | 289 | S | O |
| HETATM | 1887 | OH2 | WAT | S | 104 | 26.760 | −8.913 | 35.163 | 1.00 | 27.66 | | S | O |
| ANISOU | 1887 | OH2 | WAT | S | 104 | 2555 | 3497 | 5031 | 791 | −387 | 171 | S | O |
| SIGUIJ | 1887 | OH2 | WAT | S | 104 | 1 | 0 | 0 | 221 | 50 | 289 | S | O |
| HETATM | 1888 | OH2 | WAT | S | 105 | 3.515 | 9.065 | 11.759 | 1.00 | 30.62 | | S | O |
| ANISOU | 1888 | OH2 | WAT | S | 105 | 3112 | 4092 | 5105 | 142 | 389 | −40 | S | O |
| SIGUIJ | 1888 | OH2 | WAT | S | 105 | 1 | 0 | 0 | 221 | 50 | 289 | S | O |
| HETATM | 1889 | OH2 | WAT | S | 106 | 6.014 | 6.816 | 50.133 | 1.00 | 22.77 | | S | O |
| ANISOU | 1889 | OH2 | WAT | S | 106 | 2984 | 3487 | 2553 | −65 | 64 | −1 | S | O |
| SIGUIJ | 1889 | OH2 | WAT | S | 106 | 1 | 0 | 0 | 221 | 50 | 289 | S | O |
| HETATM | 1890 | OH2 | WAT | S | 107 | 2.535 | 0.919 | 21.717 | 1.00 | 30.69 | | S | O |
| ANISOU | 1890 | OH2 | WAT | S | 107 | 2951 | 3619 | 3870 | 88 | −46 | 5 | S | O |
| SIGUIJ | 1890 | OH2 | WAT | S | 107 | 1 | 0 | 0 | 221 | 50 | 289 | S | O |
| HETATM | 1891 | OH2 | WAT | S | 108 | 8.473 | 5.739 | 51.277 | 1.00 | 27.33 | | S | O |
| ANISOU | 1891 | OH2 | WAT | S | 108 | 3033 | 2855 | 4859 | 3 | 610 | 12 | S | O |
| SIGUIJ | 1891 | OH2 | WAT | S | 108 | 1 | 0 | 0 | 221 | 50 | 289 | S | O |
| HETATM | 1892 | OH2 | WAT | S | 109 | 27.074 | −11.879 | 44.074 | 1.00 | 31.97 | | S | O |
| ANISOU | 1892 | OH2 | WAT | S | 109 | 6557 | 3884 | 8374 | −192 | 1 | 0 | S | O |
| SIGUIJ | 1892 | OH2 | WAT | S | 109 | 1 | 0 | 0 | 221 | 50 | 289 | S | O |
| HETATM | 1893 | OH2 | WAT | S | 110 | 26.737 | −0.258 | 45.534 | 1.00 | 24.30 | | S | O |
| ANISOU | 1893 | OH2 | WAT | S | 110 | 2819 | 3015 | 3951 | 8 | −466 | 17 | S | O |
| SIGUIJ | 1893 | OH2 | WAT | S | 110 | 1 | 0 | 0 | 221 | 50 | 289 | S | O |
| HETATM | 1894 | OH2 | WAT | S | 111 | 23.962 | 16.801 | 23.275 | 1.00 | 30.34 | | S | O |
| ANISOU | 1894 | OH2 | WAT | S | 111 | 4010 | 6257 | 3100 | −2485 | −7 | 57 | S | O |
| SIGUIJ | 1894 | OH2 | WAT | S | 111 | 1 | 0 | 0 | 221 | 50 | 289 | S | O |
| HETATM | 1895 | OH2 | WAT | S | 112 | 16.366 | −14.016 | 33.250 | 1.00 | 31.21 | | S | O |
| ANISOU | 1895 | OH2 | WAT | S | 112 | 6815 | 4084 | 4423 | −1632 | −105 | 59 | S | O |
| SIGUIJ | 1895 | OH2 | WAT | S | 112 | 1 | 0 | 0 | 221 | 50 | 289 | S | O |
| HETATM | 1896 | OH2 | WAT | S | 113 | 31.549 | 3.790 | 28.438 | 1.00 | 29.85 | | S | O |

TABLE 3-continued

Three-dimensional structure of the new binding pocket of kallikrein 7

| | | | | | | | | | | | | |
|---|---|---|---|---|---|---|---|---|---|---|---|---|
| ANISOU | 1896 | OH2 | WAT | S | 113 | 2361 | 5373 | 3457 | −594 | 487 | 160 | S O |
| SIGUIJ | 1896 | OH2 | WAT | S | 113 | 1 | 0 | 0 | 221 | 50 | 289 | S O |
| HETATM | 1897 | OH2 | WAT | S | 114 | 29.814 | 0.473 | 25.485 | 1.00 | 33.55 | | S O |
| ANISOU | 1897 | OH2 | WAT | S | 114 | 3467 | 6416 | 4692 | 1851 | 324 | −280 | S O |
| SIGUIJ | 1897 | OH2 | WAT | S | 114 | 1 | 0 | 0 | 221 | 50 | 289 | S O |
| HETATM | 1898 | OH2 | WAT | S | 115 | 15.127 | 12.287 | 45.057 | 1.00 | 20.18 | | S O |
| ANISOU | 1898 | OH2 | WAT | S | 115 | 2358 | 2101 | 2652 | −13 | −4 | 0 | S O |
| SIGUIJ | 1898 | OH2 | WAT | S | 115 | 1 | 0 | 0 | 221 | 50 | 289 | S O |
| HETATM | 1899 | OH2 | WAT | S | 116 | 25.755 | −5.365 | 27.616 | 1.00 | 27.02 | | S O |
| ANISOU | 1899 | OH2 | WAT | S | 116 | 3859 | 4146 | 2556 | 39 | 281 | −27 | S O |
| SIGUIJ | 1899 | OH2 | WAT | S | 116 | 1 | 0 | 0 | 221 | 50 | 289 | S O |
| HETATM | 1900 | OH2 | WAT | S | 117 | 2.661 | 19.940 | 22.804 | 1.00 | 28.19 | | S O |
| ANISOU | 1900 | OH2 | WAT | S | 117 | 2612 | 4405 | 4384 | 427 | −139 | 32 | S O |
| SIGUIJ | 1900 | OH2 | WAT | S | 117 | 1 | 0 | 0 | 221 | 50 | 289 | S O |
| HETATM | 1901 | OH2 | WAT | S | 118 | 13.816 | 10.501 | 27.860 | 1.00 | 18.47 | | S O |
| ANISOU | 1901 | OH2 | WAT | S | 118 | 2713 | 2171 | 1862 | −163 | 9 | −2 | S O |
| SIGUIJ | 1901 | OH2 | WAT | S | 118 | 1 | 0 | 0 | 221 | 50 | 289 | S O |
| HETATM | 1902 | OH2 | WAT | S | 119 | 26.259 | −0.965 | 25.298 | 1.00 | 33.83 | | S O |
| ANISOU | 1902 | OH2 | WAT | S | 119 | 3054 | 7527 | 4940 | −751 | 504 | 127 | S O |
| SIGUIJ | 1902 | OH2 | WAT | S | 119 | 1 | 0 | 0 | 221 | 50 | 289 | S O |
| HETATM | 1903 | OH2 | WAT | S | 120 | 11.223 | 23.743 | 16.870 | 1.00 | 33.09 | | S O |
| ANISOU | 1903 | OH2 | WAT | S | 120 | 6540 | 2820 | 4675 | −1098 | −79 | 33 | S O |
| SIGUIJ | 1903 | OH2 | WAT | S | 120 | 1 | 0 | 0 | 221 | 50 | 289 | S O |
| HETATM | 1904 | OH2 | WAT | S | 121 | −0.480 | 7.799 | 26.995 | 1.00 | 26.19 | | S O |
| ANISOU | 1904 | OH2 | WAT | S | 121 | 3214 | 4175 | 2071 | 163 | −451 | −7 | S O |
| SIGUIJ | 1904 | OH2 | WAT | S | 121 | 1 | 0 | 0 | 221 | 50 | 289 | S O |
| HETATM | 1905 | OH2 | WAT | S | 122 | 2.362 | 15.205 | 44.578 | 1.00 | 27.82 | | S O |
| ANISOU | 1905 | OH2 | WAT | S | 122 | 5512 | 2305 | 4024 | −230 | 173 | −21 | S O |
| SIGUIJ | 1905 | OH2 | WAT | S | 122 | 1 | 0 | 0 | 221 | 50 | 289 | S O |
| HETATM | 1906 | OH2 | WAT | S | 123 | 19.715 | 7.754 | 50.940 | 1.00 | 25.17 | | S O |
| ANISOU | 1906 | OH2 | WAT | S | 123 | 3519 | 3788 | 2747 | −14 | 107 | 1 | S O |
| SIGUIJ | 1906 | OH2 | WAT | S | 123 | 1 | 0 | 0 | 221 | 50 | 289 | S O |
| HETATM | 1907 | OH2 | WAT | S | 124 | 2.758 | 18.725 | 16.752 | 1.00 | 34.08 | | S O |
| ANISOU | 1907 | OH2 | WAT | S | 124 | 5908 | 6912 | 4121 | 12 | −107 | 1 | S O |
| SIGUIJ | 1907 | OH2 | WAT | S | 124 | 1 | 0 | 0 | 221 | 50 | 289 | S O |
| HETATM | 1908 | OH2 | WAT | S | 125 | −4.642 | −10.188 | 42.639 | 1.00 | 29.52 | | S O |
| ANISOU | 1908 | OH2 | WAT | S | 125 | 2512 | 4249 | 9593 | −641 | 1917 | 396 | S O |
| SIGUIJ | 1908 | OH2 | WAT | S | 125 | 1 | 0 | 0 | 221 | 50 | 289 | S O |
| HETATM | 1909 | OH2 | WAT | S | 126 | 1.240 | 18.510 | 38.272 | 1.00 | 27.99 | | S O |
| ANISOU | 1909 | OH2 | WAT | S | 126 | 4172 | 2933 | 2552 | −57 | 889 | −32 | S O |
| SIGUIJ | 1909 | OH2 | WAT | S | 126 | 1 | 0 | 0 | 221 | 50 | 289 | S O |
| HETATM | 1910 | OH2 | WAT | S | 127 | 3.642 | −7.543 | 31.958 | 1.00 | 27.77 | | S O |
| ANISOU | 1910 | OH2 | WAT | S | 127 | 3242 | 3568 | 3779 | −1225 | −131 | −168 | S O |
| SIGUIJ | 1910 | OH2 | WAT | S | 127 | 1 | 0 | 0 | 221 | 50 | 289 | S O |
| HETATM | 1911 | OH2 | WAT | S | 128 | −2.003 | −7.145 | 36.395 | 1.00 | 36.40 | | S O |
| ANISOU | 1911 | OH2 | WAT | S | 128 | 4151 | 5058 | 5863 | −12 | 49 | 0 | S O |
| SIGUIJ | 1911 | OH2 | WAT | S | 128 | 1 | 0 | 0 | 221 | 50 | 289 | S O |
| HETATM | 1912 | OH2 | WAT | S | 129 | 15.145 | −8.406 | 27.073 | 1.00 | 37.08 | | S O |
| ANISOU | 1912 | OH2 | WAT | S | 129 | 6125 | 6305 | 3951 | 3848 | −145 | −185 | S O |
| SIGUIJ | 1912 | OH2 | WAT | S | 129 | 1 | 0 | 0 | 221 | 50 | 289 | S O |
| HETATM | 1913 | OH2 | WAT | S | 130 | 27.252 | 15.441 | 28.847 | 1.00 | 38.58 | | S O |
| ANISOU | 1913 | OH2 | WAT | S | 130 | 7244 | 4494 | 10213 | 95 | 48 | 0 | S O |
| SIGUIJ | 1913 | OH2 | WAT | S | 130 | 1 | 0 | 0 | 221 | 50 | 289 | S O |
| HETATM | 1914 | OH2 | WAT | S | 131 | 24.590 | −4.578 | 24.926 | 1.00 | 35.10 | | S O |
| ANISOU | 1914 | OH2 | WAT | S | 131 | 3086 | 6214 | 4364 | 997 | 45 | −23 | S O |
| SIGUIJ | 1914 | OH2 | WAT | S | 131 | 1 | 0 | 0 | 221 | 50 | 289 | S O |
| HETATM | 1915 | OH2 | WAT | S | 132 | 26.779 | 10.309 | 19.245 | 1.00 | 31.56 | | S O |
| ANISOU | 1915 | OH2 | WAT | S | 132 | 3055 | 7679 | 5170 | 1664 | 139 | −74 | S O |
| SIGUIJ | 1915 | OH2 | WAT | S | 132 | 1 | 0 | 0 | 221 | 50 | 289 | S O |
| HETATM | 1916 | OH2 | WAT | S | 133 | 0.533 | −7.125 | 45.253 | 1.00 | 27.88 | | S O |
| ANISOU | 1916 | OH2 | WAT | S | 133 | 2994 | 2259 | 3593 | −212 | 48 | 3 | S O |
| SIGUIJ | 1916 | OH2 | WAT | S | 133 | 1 | 0 | 0 | 221 | 50 | 289 | S O |
| HETATM | 1917 | OH2 | WAT | S | 134 | 16.753 | −10.311 | 29.928 | 1.00 | 34.28 | | S O |
| ANISOU | 1917 | OH2 | WAT | S | 134 | 4945 | 7839 | 2779 | −415 | −1740 | −230 | S O |
| SIGUIJ | 1917 | OH2 | WAT | S | 134 | 1 | 0 | 0 | 221 | 50 | 289 | S O |
| HETATM | 1918 | OH2 | WAT | S | 135 | 10.504 | −11.853 | 51.167 | 1.00 | 25.02 | | S O |
| ANISOU | 1918 | OH2 | WAT | S | 135 | 5148 | 2692 | 3373 | −1536 | −817 | 494 | S O |
| SIGUIJ | 1918 | OH2 | WAT | S | 135 | 1 | 0 | 0 | 221 | 50 | 289 | S O |
| HETATM | 1919 | OH2 | WAT | S | 136 | 15.253 | 19.090 | 16.547 | 1.00 | 35.54 | | S O |
| ANISOU | 1919 | OH2 | WAT | S | 136 | 6539 | 6105 | 2770 | 13 | 478 | 5 | S O |
| SIGUIJ | 1919 | OH2 | WAT | S | 136 | 1 | 0 | 0 | 221 | 50 | 289 | S O |
| HETATM | 1920 | OH2 | WAT | S | 137 | 24.070 | 15.576 | 28.300 | 1.00 | 39.96 | | S O |
| ANISOU | 1920 | OH2 | WAT | S | 137 | 6082 | 3159 | 8207 | 150 | −17 | 0 | S O |
| SIGUIJ | 1920 | OH2 | WAT | S | 137 | 1 | 0 | 0 | 221 | 50 | 289 | S O |
| HETATM | 1921 | OH2 | WAT | S | 138 | 19.951 | −7.890 | 49.428 | 1.00 | 37.63 | | S O |
| ANISOU | 1921 | OH2 | WAT | S | 138 | 6820 | 3803 | 3909 | 1919 | 69 | 39 | S O |
| SIGUIJ | 1921 | OH2 | WAT | S | 138 | 1 | 0 | 0 | 221 | 50 | 289 | S O |
| HETATM | 1922 | OH2 | WAT | S | 139 | 9.825 | −10.874 | 30.024 | 1.00 | 24.32 | | S O |

TABLE 3-continued

Three-dimensional structure of the new binding pocket of kallikrein 7

| | | | | | | | | | | | | |
|---|---|---|---|---|---|---|---|---|---|---|---|---|
| ANISOU | 1922 | OH2 | WAT | S | 139 | 4437 | 1727 | 3182 | −42 | 382 | −3 | S O |
| SIGUIJ | 1922 | OH2 | WAT | S | 139 | 1 | 0 | 0 | 221 | 50 | 289 | S O |
| HETATM | 1923 | OH2 | WAT | S | 140 | 14.562 | 14.178 | 16.243 | 1.00 | 30.34 | | S O |
| ANISOU | 1923 | OH2 | WAT | S | 140 | 5368 | 3719 | 3000 | −1110 | 560 | −266 | S O |
| SIGUIJ | 1923 | OH2 | WAT | S | 140 | 1 | 0 | 0 | 221 | 50 | 289 | S O |
| HETATM | 1924 | OH2 | WAT | S | 141 | 9.307 | 13.549 | 16.592 | 1.00 | 30.74 | | S O |
| ANISOU | 1924 | OH2 | WAT | S | 141 | 4656 | 5144 | 4124 | 48 | −3 | 0 | S O |
| SIGUIJ | 1924 | OH2 | WAT | S | 141 | 1 | 0 | 0 | 221 | 49 | 289 | S O |
| HETATM | 1925 | OH2 | WAT | S | 142 | 0.546 | 21.352 | 27.878 | 1.00 | 40.45 | | S O |
| ANISOU | 1925 | OH2 | WAT | S | 142 | 9491 | 3460 | 8370 | 1133 | −6 | −3 | S O |
| SIGUIJ | 1925 | OH2 | WAT | S | 142 | 1 | 0 | 0 | 221 | 49 | 289 | S O |
| HETATM | 1926 | OH2 | WAT | S | 143 | −1.885 | 14.390 | 46.062 | 1.00 | 29.21 | | S O |
| ANISOU | 1926 | OH2 | WAT | S | 143 | 3516 | 3899 | 2996 | 38 | 39 | −1 | S O |
| SIGUIJ | 1926 | OH2 | WAT | S | 143 | 1 | 0 | 0 | 221 | 49 | 289 | S O |
| HETATM | 1927 | OH2 | WAT | S | 144 | 29.346 | −6.151 | 41.426 | 1.00 | 41.53 | | S O |
| ANISOU | 1927 | OH2 | WAT | S | 144 | 3285 | 8590 | 8848 | 929 | 1170 | −193 | S O |
| SIGUIJ | 1927 | OH2 | WAT | S | 144 | 1 | 0 | 0 | 221 | 49 | 289 | S O |
| HETATM | 1928 | OH2 | WAT | S | 145 | 29.449 | −1.201 | 37.125 | 1.00 | 33.69 | | S O |
| ANISOU | 1928 | OH2 | WAT | S | 145 | 2299 | 13945 | 5181 | 1681 | −132 | 46 | S O |
| SIGUIJ | 1928 | OH2 | WAT | S | 145 | 1 | 0 | 0 | 221 | 49 | 289 | S O |
| HETATM | 1929 | OH2 | WAT | S | 146 | 25.252 | 0.908 | 49.035 | 1.00 | 29.41 | | S O |
| ANISOU | 1929 | OH2 | WAT | S | 146 | 2514 | 6062 | 4510 | 1324 | −138 | 67 | S O |
| SIGUIJ | 1929 | OH2 | WAT | S | 146 | 1 | 0 | 0 | 221 | 49 | 289 | S O |
| HETATM | 1930 | OH2 | WAT | S | 147 | 2.465 | 1.781 | 52.221 | 1.00 | 25.79 | | S O |
| ANISOU | 1930 | OH2 | WAT | S | 147 | 4627 | 3968 | 2707 | 6 | −449 | −2 | S O |
| SIGUIJ | 1930 | OH2 | WAT | S | 147 | 1 | 0 | 0 | 221 | 49 | 289 | S O |
| HETATM | 1931 | OH2 | WAT | S | 148 | −4.135 | 10.402 | 43.978 | 1.00 | 33.44 | | S O |
| ANISOU | 1931 | OH2 | WAT | S | 148 | 3655 | 7568 | 7772 | 2975 | −323 | 200 | S O |
| SIGUIJ | 1931 | OH2 | WAT | S | 148 | 1 | 0 | 0 | 221 | 49 | 289 | S O |
| HETATM | 1932 | OH2 | WAT | S | 149 | 17.550 | −1.360 | 16.721 | 1.00 | 26.03 | | S O |
| ANISOU | 1932 | OH2 | WAT | S | 149 | 5814 | 3014 | 2319 | 293 | 1493 | 103 | S O |
| SIGUIJ | 1932 | OH2 | WAT | S | 149 | 1 | 0 | 0 | 221 | 49 | 289 | S O |
| HETATM | 1933 | OH2 | WAT | S | 150 | 10.868 | 14.790 | 18.228 | 1.00 | 26.66 | | S O |
| ANISOU | 1933 | OH2 | WAT | S | 150 | 3764 | 3047 | 2718 | 112 | −180 | −23 | S O |
| SIGUIJ | 1933 | OH2 | WAT | S | 150 | 1 | 0 | 0 | 221 | 49 | 289 | S O |
| HETATM | 1934 | OH2 | WAT | S | 151 | 1.010 | −10.401 | 38.943 | 1.00 | 40.44 | | S O |
| ANISOU | 1934 | OH2 | WAT | S | 151 | 2459 | 2034 | 3405 | −95 | −126 | 4 | S O |
| SIGUIJ | 1934 | OH2 | WAT | S | 151 | 1 | 0 | 0 | 221 | 49 | 289 | S O |
| HETATM | 1935 | OH2 | WAT | S | 152 | 30.616 | −13.418 | 38.615 | 1.00 | 34.81 | | S O |
| ANISOU | 1935 | OH2 | WAT | S | 152 | 8399 | 3393 | 10988 | −717 | −27 | −2 | S O |
| SIGUIJ | 1935 | OH2 | WAT | S | 152 | 1 | 0 | 0 | 221 | 49 | 289 | S O |
| HETATM | 1936 | OH2 | WAT | S | 153 | 24.409 | 3.497 | 23.403 | 1.00 | 40.31 | | S O |
| ANISOU | 1936 | OH2 | WAT | S | 153 | 5220 | 10991 | 3367 | 4730 | −16 | −70 | S O |
| SIGUIJ | 1936 | OH2 | WAT | S | 153 | 1 | 0 | 0 | 221 | 49 | 289 | S O |
| HETATM | 1937 | OH2 | WAT | S | 154 | 21.557 | 7.062 | 27.654 | 1.00 | 28.84 | | S O |
| ANISOU | 1937 | OH2 | WAT | S | 154 | 3016 | 2992 | 2883 | 1 | 5 | 0 | S O |
| SIGUIJ | 1937 | OH2 | WAT | S | 154 | 1 | 0 | 0 | 221 | 49 | 289 | S O |
| HETATM | 1938 | OH2 | WAT | S | 155 | 20.517 | 18.633 | 25.054 | 1.00 | 30.26 | | S O |
| ANISOU | 1938 | OH2 | WAT | S | 155 | 2750 | 4489 | 4630 | −321 | −103 | −18 | S O |
| SIGUIJ | 1938 | OH2 | WAT | S | 155 | 1 | 0 | 0 | 221 | 49 | 289 | S O |
| HETATM | 1939 | OH2 | WAT | S | 156 | 32.648 | 4.297 | 32.274 | 1.00 | 37.94 | | S O |
| ANISOU | 1939 | OH2 | WAT | S | 156 | 3269 | 8129 | 5917 | 181 | −262 | 14 | S O |
| SIGUIJ | 1939 | OH2 | WAT | S | 156 | 1 | 0 | 0 | 221 | 49 | 289 | S O |
| HETATM | 1940 | OH2 | WAT | S | 157 | 21.979 | 13.016 | 14.583 | 1.00 | 35.88 | | S O |
| ANISOU | 1940 | OH2 | WAT | S | 157 | 9146 | 5044 | 3682 | 317 | 1657 | 104 | S O |
| SIGUIJ | 1940 | OH2 | WAT | S | 157 | 1 | 0 | 0 | 221 | 49 | 289 | S O |
| HETATM | 1941 | OH2 | WAT | S | 158 | 6.095 | −7.842 | 18.423 | 1.00 | 34.85 | | S O |
| ANISOU | 1941 | OH2 | WAT | S | 158 | 12566 | 3609 | 4280 | 163 | −318 | −6 | S O |
| SIGUIJ | 1941 | OH2 | WAT | S | 158 | 1 | 0 | 0 | 221 | 49 | 289 | S O |
| HETATM | 1942 | OH2 | WAT | S | 159 | 26.591 | −4.927 | 36.071 | 1.00 | 29.60 | | S O |
| ANISOU | 1942 | OH2 | WAT | S | 159 | 4378 | 4005 | 3346 | −44 | −89 | 7 | S O |
| SIGUIJ | 1942 | OH2 | WAT | S | 159 | 1 | 0 | 0 | 221 | 49 | 289 | S O |
| HETATM | 1943 | OH2 | WAT | S | 160 | 5.561 | 0.764 | 54.769 | 1.00 | 30.77 | | S O |
| ANISOU | 1943 | OH2 | WAT | S | 160 | 2598 | 3822 | 2614 | 932 | −4 | 10 | S O |
| SIGUIJ | 1943 | OH2 | WAT | S | 160 | 1 | 0 | 0 | 221 | 49 | 289 | S O |
| HETATM | 1944 | OH2 | WAT | S | 161 | 10.527 | 25.609 | 25.108 | 1.00 | 34.60 | | S O |
| ANISOU | 1944 | OH2 | WAT | S | 161 | 3770 | 3075 | 7386 | 10 | −1730 | −25 | S O |
| SIGUIJ | 1944 | OH2 | WAT | S | 161 | 1 | 0 | 0 | 221 | 49 | 289 | S O |
| HETATM | 1945 | OH2 | WAT | S | 162 | 3.585 | 27.472 | 24.727 | 1.00 | 37.60 | | S O |
| ANISOU | 1945 | OH2 | WAT | S | 162 | 5160 | 6221 | 7339 | −23 | −124 | −2 | S O |
| SIGUIJ | 1945 | OH2 | WAT | S | 162 | 1 | 0 | 0 | 221 | 49 | 289 | S O |
| HETATM | 1946 | OH2 | WAT | S | 163 | −3.314 | −0.083 | 44.414 | 1.00 | 33.32 | | S O |
| ANISOU | 1946 | OH2 | WAT | S | 163 | 2250 | 7193 | 5469 | 904 | −129 | 29 | S O |
| SIGUIJ | 1946 | OH2 | WAT | S | 163 | 1 | 0 | 0 | 221 | 49 | 289 | S O |
| HETATM | 1947 | OH2 | WAT | S | 165 | 20.321 | 8.942 | 48.820 | 1.00 | 9.64 | | S O |
| ANISOU | 1947 | OH2 | WAT | S | 165 | 3678 | 3212 | 2252 | −60 | 140 | −12 | S O |
| SIGUIJ | 1947 | OH2 | WAT | S | 165 | 1 | 0 | 0 | 221 | 49 | 289 | S O |
| HETATM | 1948 | OH2 | WAT | S | 166 | 16.533 | 7.447 | 53.478 | 1.00 | 9.64 | | S O |

TABLE 3-continued

Three-dimensional structure of the new binding pocket of kallikrein 7

| | | | | | | | | | | | | | |
|---|---|---|---|---|---|---|---|---|---|---|---|---|---|
| ANISOU | 1948 | OH2 | WAT | S | 166 | 3421 | 5345 | 3498 | −1663 | 12 | 27 | S | O |
| SIGUIJ | 1948 | OH2 | WAT | S | 166 | 1 | 0 | 0 | 221 | 49 | 289 | S | O |
| HETATM | 1949 | OH2 | WAT | S | 167 | 6.384 | 13.286 | 44.630 | 1.00 | 9.64 | | S | O |
| ANISOU | 1949 | OH2 | WAT | S | 167 | 4095 | 2912 | 2148 | 1211 | −629 | −376 | S | O |
| SIGUIJ | 1949 | OH2 | WAT | S | 167 | 1 | 0 | 0 | 221 | 49 | 289 | S | O |
| HETATM | 1950 | OH2 | WAT | S | 168 | 15.586 | 14.651 | 46.353 | 1.00 | 9.64 | | S | O |
| ANISOU | 1950 | OH2 | WAT | S | 168 | 5956 | 2789 | 3140 | −1976 | 788 | −443 | S | O |
| SIGUIJ | 1950 | OH2 | WAT | S | 168 | 1 | 0 | 0 | 221 | 49 | 289 | S | O |
| HETATM | 1951 | OH2 | WAT | S | 169 | 17.717 | 14.045 | 44.656 | 1.00 | 9.64 | | S | O |
| ANISOU | 1951 | OH2 | WAT | S | 169 | 2696 | 3803 | 3222 | −469 | −12 | −7 | S | O |
| SIGUIJ | 1951 | OH2 | WAT | S | 169 | 1 | 0 | 0 | 221 | 49 | 289 | S | O |
| HETATM | 1952 | OH2 | WAT | S | 170 | 11.975 | 11.416 | 52.995 | 1.00 | 9.64 | | S | O |
| ANISOU | 1952 | OH2 | WAT | S | 170 | 4141 | 3516 | 3042 | −26 | −61 | 2 | S | O |
| SIGUIJ | 1952 | OH2 | WAT | S | 170 | 1 | 0 | 0 | 221 | 49 | 289 | S | O |
| HETATM | 1953 | OH2 | WAT | S | 171 | −8.832 | 4.580 | 35.128 | 1.00 | 9.64 | | S | O |
| ANISOU | 1953 | OH2 | WAT | S | 171 | 3442 | 5617 | 4705 | 1720 | 401 | −335 | S | O |
| SIGUIJ | 1953 | OH2 | WAT | S | 171 | 1 | 0 | 0 | 221 | 49 | 289 | S | O |
| HETATM | 1954 | OH2 | WAT | S | 172 | −4.277 | −4.060 | 36.933 | 1.00 | 9.64 | | S | O |
| ANISOU | 1954 | OH2 | WAT | S | 172 | 3880 | 2781 | 5563 | −10 | −45 | 0 | S | O |
| SIGUIJ | 1954 | OH2 | WAT | S | 172 | 1 | 0 | 0 | 221 | 49 | 289 | S | O |
| HETATM | 1955 | OH2 | WAT | S | 173 | −0.557 | −0.253 | 30.091 | 1.00 | 9.64 | | S | O |
| ANISOU | 1955 | OH2 | WAT | S | 173 | 4876 | 8675 | 2710 | 779 | −714 | −21 | S | O |
| SIGUIJ | 1955 | OH2 | WAT | S | 173 | 1 | 0 | 0 | 221 | 49 | 289 | S | O |
| HETATM | 1956 | OH2 | WAT | S | 174 | −1.005 | 2.812 | 28.885 | 1.00 | 9.64 | | S | O |
| ANISOU | 1956 | OH2 | WAT | S | 174 | 2929 | 6755 | 3085 | −252 | 3 | 2 | S | O |
| SIGUIJ | 1956 | OH2 | WAT | S | 174 | 1 | 0 | 0 | 221 | 49 | 289 | S | O |
| HETATM | 1957 | OH2 | WAT | S | 175 | 2.618 | 2.639 | 29.286 | 1.00 | 9.64 | | S | O |
| ANISOU | 1957 | OH2 | WAT | S | 175 | 2571 | 3346 | 2427 | −193 | −6 | 4 | S | O |
| SIGUIJ | 1957 | OH2 | WAT | S | 175 | 1 | 0 | 0 | 221 | 49 | 289 | S | O |
| HETATM | 1958 | OH2 | WAT | S | 176 | −6.600 | 7.509 | 35.036 | 1.00 | 9.64 | | S | O |
| ANISOU | 1958 | OH2 | WAT | S | 176 | 2597 | 3342 | 6658 | −80 | 845 | 24 | S | O |
| SIGUIJ | 1958 | OH2 | WAT | S | 176 | 1 | 0 | 0 | 221 | 49 | 289 | S | O |
| HETATM | 1959 | OH2 | WAT | S | 177 | −0.477 | 17.088 | 36.911 | 1.00 | 9.64 | | S | O |
| ANISOU | 1959 | OH2 | WAT | S | 177 | 2189 | 3076 | 4218 | −3 | 153 | 0 | S | O |
| SIGUIJ | 1959 | OH2 | WAT | S | 177 | 1 | 0 | 0 | 221 | 49 | 289 | S | O |
| HETATM | 1960 | OH2 | WAT | S | 178 | −1.260 | 11.427 | 27.528 | 1.00 | 9.64 | | S | O |
| ANISOU | 1960 | OH2 | WAT | S | 178 | 2773 | 4969 | 3125 | 419 | 14 | −9 | S | O |
| SIGUIJ | 1960 | OH2 | WAT | S | 178 | 1 | 0 | 0 | 221 | 49 | 289 | S | O |
| HETATM | 1961 | OH2 | WAT | S | 179 | −0.390 | 18.740 | 34.942 | 1.00 | 9.64 | | S | O |
| ANISOU | 1961 | OH2 | WAT | S | 179 | 2232 | 2541 | 2884 | −14 | 9 | 0 | S | O |
| SIGUIJ | 1961 | OH2 | WAT | S | 179 | 1 | 0 | 0 | 221 | 49 | 289 | S | O |
| HETATM | 1962 | OH2 | WAT | S | 180 | −3.823 | 8.680 | 29.774 | 1.00 | 9.64 | | S | O |
| ANISOU | 1962 | OH2 | WAT | S | 180 | 5318 | 4474 | 2845 | −21 | −757 | 15 | S | O |
| SIGUIJ | 1962 | OH2 | WAT | S | 180 | 1 | 0 | 0 | 221 | 49 | 289 | S | O |
| HETATM | 1963 | OH2 | WAT | S | 181 | −0.781 | 16.019 | 42.114 | 1.00 | 9.64 | | S | O |
| ANISOU | 1963 | OH2 | WAT | S | 181 | 1433 | 1370 | 1665 | 12 | 407 | −109 | S | O |
| SIGUIJ | 1963 | OH2 | WAT | S | 181 | 1 | 0 | 0 | 221 | 49 | 289 | S | O |
| HETATM | 1964 | OH2 | WAT | S | 182 | −1.833 | 14.757 | 37.559 | 1.00 | 9.64 | | S | O |
| ANISOU | 1964 | OH2 | WAT | S | 182 | 2296 | 2695 | 3332 | 99 | −89 | 14 | S | O |
| SIGUIJ | 1964 | OH2 | WAT | S | 182 | 1 | 0 | 0 | 221 | 49 | 289 | S | O |
| HETATM | 1965 | OH2 | WAT | S | 183 | 0.603 | 17.701 | 32.591 | 1.00 | 9.64 | | S | O |
| ANISOU | 1965 | OH2 | WAT | S | 183 | 2203 | 1894 | 3016 | 325 | −284 | −36 | S | O |
| SIGUIJ | 1965 | OH2 | WAT | S | 183 | 1 | 0 | 0 | 221 | 49 | 289 | S | O |
| HETATM | 1966 | OH2 | WAT | S | 184 | 25.865 | 12.353 | 35.363 | 1.00 | 16.02 | | S | O |
| ANISOU | 1966 | OH2 | WAT | S | 184 | 3641 | 5196 | 6549 | 185 | 434 | −39 | S | O |
| SIGUIJ | 1966 | OH2 | WAT | S | 184 | 1 | 0 | 0 | 221 | 49 | 289 | S | O |
| HETATM | 1967 | OH2 | WAT | S | 185 | 21.844 | 14.030 | 33.136 | 1.00 | 16.02 | | S | O |
| ANISOU | 1967 | OH2 | WAT | S | 185 | 4516 | 4386 | 4212 | −31 | 3 | −1 | S | O |
| SIGUIJ | 1967 | OH2 | WAT | S | 185 | 1 | 0 | 0 | 221 | 49 | 289 | S | O |
| HETATM | 1968 | OH2 | WAT | S | 186 | −2.383 | 11.857 | 46.800 | 1.00 | 21.37 | | S | O |
| ANISOU | 1968 | OH2 | WAT | S | 186 | 4014 | 3408 | 2846 | −9 | 1102 | −20 | S | O |
| SIGUIJ | 1968 | OH2 | WAT | S | 186 | 1 | 0 | 0 | 221 | 49 | 289 | S | O |
| HETATM | 1969 | OH2 | WAT | S | 187 | −0.771 | 10.542 | 48.286 | 1.00 | 21.37 | | S | O |
| ANISOU | 1969 | OH2 | WAT | S | 187 | 3450 | 4573 | 5571 | 570 | 2454 | −643 | S | O |
| SIGUIJ | 1969 | OH2 | WAT | S | 187 | 1 | 0 | 0 | 221 | 49 | 289 | S | O |
| HETATM | 1970 | OH2 | WAT | S | 188 | 2.336 | 12.093 | 46.980 | 1.00 | 21.37 | | S | O |
| ANISOU | 1970 | OH2 | WAT | S | 188 | 7535 | 3031 | 4855 | 2228 | 335 | 199 | S | O |
| SIGUIJ | 1970 | OH2 | WAT | S | 188 | 1 | 0 | 0 | 221 | 49 | 289 | S | O |
| HETATM | 1971 | OH2 | WAT | S | 189 | 5.725 | 8.697 | 49.067 | 1.00 | 21.37 | | S | O |
| ANISOU | 1971 | OH2 | WAT | S | 189 | 4279 | 5874 | 5746 | 223 | −22 | 3 | S | O |
| SIGUIJ | 1971 | OH2 | WAT | S | 189 | 1 | 0 | 0 | 221 | 49 | 289 | S | O |
| HETATM | 1972 | OH2 | WAT | S | 190 | 0.753 | 1.655 | 54.193 | 1.00 | 21.37 | | S | O |
| ANISOU | 1972 | OH2 | WAT | S | 190 | 3706 | 5034 | 3101 | 120 | −22 | −1 | S | O |
| SIGUIJ | 1972 | OH2 | WAT | S | 190 | 1 | 0 | 0 | 221 | 49 | 289 | S | O |
| HETATM | 1973 | OH2 | WAT | S | 191 | 19.317 | 3.227 | 56.607 | 1.00 | 17.18 | | S | O |
| ANISOU | 1973 | OH2 | WAT | S | 191 | 7181 | 7861 | 2353 | 7 | 481 | −2 | S | O |
| SIGUIJ | 1973 | OH2 | WAT | S | 191 | 1 | 0 | 0 | 221 | 49 | 289 | S | O |
| HETATM | 1974 | OH2 | WAT | S | 192 | 26.731 | −5.241 | 46.724 | 1.00 | 17.18 | | S | O |

TABLE 3-continued

Three-dimensional structure of the new binding pocket of kallikrein 7

| | | | | | | | | | | | | |
|---|---|---|---|---|---|---|---|---|---|---|---|---|
| ANISOU | 1974 | OH2 | WAT | S | 192 | 2724 | 6561 | 5059 | 995 | −414 | 135 | S O |
| SIGUIJ | 1974 | OH2 | WAT | S | 192 | 1 | 0 | 0 | 221 | 49 | 289 | S O |
| HETATM | 1975 | OH2 | WAT | S | 193 | 18.256 | −2.444 | 55.645 | 1.00 | 17.18 | | S O |
| ANISOU | 1975 | OH2 | WAT | S | 193 | 1320 | 2103 | 1091 | −559 | −7 | 29 | S O |
| SIGUIJ | 1975 | OH2 | WAT | S | 193 | 1 | 0 | 0 | 221 | 49 | 289 | S O |
| HETATM | 1976 | OH2 | WAT | S | 194 | 20.237 | −5.102 | 53.796 | 1.00 | 17.18 | | S O |
| ANISOU | 1976 | OH2 | WAT | S | 194 | 3347 | 3939 | 3483 | −19 | 1 | 0 | S O |
| SIGUIJ | 1976 | OH2 | WAT | S | 194 | 1 | 0 | 0 | 221 | 49 | 289 | S O |
| HETATM | 1977 | OH2 | WAT | S | 195 | 21.094 | −6.781 | 51.353 | 1.00 | 17.18 | | S O |
| ANISOU | 1977 | OH2 | WAT | S | 195 | 7088 | 4678 | 4621 | 334 | −2 | 0 | S O |
| SIGUIJ | 1977 | OH2 | WAT | S | 195 | 1 | 0 | 0 | 221 | 49 | 289 | S O |
| HETATM | 1978 | OH2 | WAT | S | 196 | 21.448 | −10.306 | 48.745 | 1.00 | 17.18 | | S O |
| ANISOU | 1978 | OH2 | WAT | S | 196 | 4343 | 3129 | 4025 | 247 | 1 | 1 | S O |
| SIGUIJ | 1978 | OH2 | WAT | S | 196 | 1 | 0 | 0 | 221 | 49 | 289 | S O |
| HETATM | 1979 | OH2 | WAT | S | 197 | 2.024 | −13.128 | 46.308 | 1.00 | 25.58 | | S O |
| ANISOU | 1979 | OH2 | WAT | S | 197 | 9217 | 4744 | 3533 | −710 | 445 | −62 | S O |
| SIGUIJ | 1979 | OH2 | WAT | S | 197 | 1 | 0 | 0 | 221 | 49 | 289 | S O |
| HETATM | 1980 | OH2 | WAT | S | 198 | −1.668 | −8.796 | 47.162 | 1.00 | 25.58 | | S O |
| ANISOU | 1980 | OH2 | WAT | S | 198 | 6335 | 5284 | 3131 | −6 | −1760 | 8 | S O |
| SIGUIJ | 1980 | OH2 | WAT | S | 198 | 1 | 0 | 0 | 221 | 49 | 289 | S O |
| HETATM | 1981 | OH2 | WAT | S | 199 | 6.598 | −13.515 | 48.535 | 1.00 | 25.58 | | S O |
| ANISOU | 1981 | OH2 | WAT | S | 199 | 5435 | 4232 | 7877 | −124 | 154 | −4 | S O |
| SIGUIJ | 1981 | OH2 | WAT | S | 199 | 1 | 0 | 0 | 221 | 49 | 289 | S O |
| HETATM | 1982 | OH2 | WAT | S | 200 | 6.414 | −10.714 | 49.635 | 1.00 | 25.58 | | S O |
| ANISOU | 1982 | OH2 | WAT | S | 200 | 2698 | 3540 | 4106 | −272 | 387 | 92 | S O |
| SIGUIJ | 1982 | OH2 | WAT | S | 200 | 1 | 0 | 0 | 221 | 49 | 289 | S O |
| HETATM | 1983 | OH2 | WAT | S | 201 | 12.536 | −12.349 | 30.216 | 1.00 | 24.32 | | S O |
| ANISOU | 1983 | OH2 | WAT | S | 201 | 4851 | 4539 | 6835 | 1 | 197 | 0 | S O |
| SIGUIJ | 1983 | OH2 | WAT | S | 201 | 1 | 0 | 0 | 221 | 49 | 289 | S O |
| HETATM | 1984 | OH2 | WAT | S | 202 | 8.989 | −10.878 | 25.331 | 1.00 | 24.32 | | S O |
| ANISOU | 1984 | OH2 | WAT | S | 202 | 4047 | 4487 | 7218 | −34 | −219 | −10 | S O |
| SIGUIJ | 1984 | OH2 | WAT | S | 202 | 1 | 0 | 0 | 221 | 49 | 289 | S O |
| HETATM | 1985 | OH2 | WAT | S | 203 | 12.685 | −11.368 | 33.176 | 1.00 | 24.32 | | S O |
| ANISOU | 1985 | OH2 | WAT | S | 203 | 4501 | 2699 | 4335 | 953 | 19 | 31 | S O |
| SIGUIJ | 1985 | OH2 | WAT | S | 203 | 1 | 0 | 0 | 221 | 49 | 289 | S O |
| HETATM | 1986 | OH2 | WAT | S | 204 | 10.361 | −9.570 | 33.573 | 1.00 | 24.32 | | S O |
| ANISOU | 1986 | OH2 | WAT | S | 204 | 2303 | 2590 | 1842 | 103 | −2 | 0 | S O |
| SIGUIJ | 1986 | OH2 | WAT | S | 204 | 1 | 0 | 0 | 221 | 49 | 289 | S O |
| HETATM | 1987 | OH2 | WAT | S | 205 | 16.739 | 2.916 | 16.744 | 1.00 | 30.34 | | S O |
| ANISOU | 1987 | OH2 | WAT | S | 205 | 3417 | 2295 | 5206 | −90 | −1644 | 120 | S O |
| SIGUIJ | 1987 | OH2 | WAT | S | 205 | 1 | 0 | 0 | 221 | 49 | 289 | S O |
| HETATM | 1988 | OH2 | WAT | S | 206 | 12.807 | 15.979 | 16.650 | 1.00 | 30.34 | | S O |
| ANISOU | 1988 | OH2 | WAT | S | 206 | 4899 | 5487 | 2438 | −2 | −236 | 0 | S O |
| SIGUIJ | 1988 | OH2 | WAT | S | 206 | 1 | 0 | 0 | 221 | 49 | 289 | S O |
| HETATM | 1989 | OH2 | WAT | S | 207 | 13.046 | 13.246 | 13.991 | 1.00 | 30.34 | | S O |
| ANISOU | 1989 | OH2 | WAT | S | 207 | 5929 | 2552 | 3354 | −110 | 278 | −11 | S O |
| SIGUIJ | 1989 | OH2 | WAT | S | 207 | 1 | 0 | 0 | 221 | 49 | 289 | S O |
| HETATM | 1990 | OH2 | WAT | S | 208 | 12.133 | 10.659 | 13.167 | 1.00 | 30.34 | | S O |
| ANISOU | 1990 | OH2 | WAT | S | 208 | 4112 | 4404 | 2364 | −13 | −814 | −37 | S O |
| SIGUIJ | 1990 | OH2 | WAT | S | 208 | 1 | 0 | 0 | 221 | 49 | 289 | S O |
| HETATM | 1991 | OH2 | WAT | S | 209 | −0.469 | 4.967 | 16.910 | 1.00 | 30.69 | | S O |
| ANISOU | 1991 | OH2 | WAT | S | 209 | 3322 | 6694 | 5003 | 811 | −115 | 40 | S O |
| SIGUIJ | 1991 | OH2 | WAT | S | 209 | 1 | 0 | 0 | 221 | 49 | 289 | S O |
| HETATM | 1992 | OH2 | WAT | S | 210 | 1.757 | 3.180 | 22.914 | 1.00 | 30.69 | | S O |
| ANISOU | 1992 | OH2 | WAT | S | 210 | 2424 | 4344 | 2706 | −728 | −30 | −35 | S O |
| SIGUIJ | 1992 | OH2 | WAT | S | 210 | 1 | 0 | 0 | 221 | 49 | 289 | S O |
| HETATM | 1993 | OH2 | WAT | S | 211 | 2.523 | 1.306 | 24.182 | 1.00 | 30.69 | | S O |
| ANISOU | 1993 | OH2 | WAT | S | 211 | 4403 | 4672 | 7372 | −11 | 258 | 5 | S O |
| SIGUIJ | 1993 | OH2 | WAT | S | 211 | 1 | 0 | 0 | 221 | 49 | 289 | S O |
| HETATM | 1994 | OH2 | WAT | S | 212 | 7.074 | −5.418 | 21.373 | 1.00 | 30.69 | | S O |
| ANISOU | 1994 | OH2 | WAT | S | 212 | 4232 | 5911 | 2097 | −598 | −394 | −10 | S O |
| SIGUIJ | 1994 | OH2 | WAT | S | 212 | 1 | 0 | 0 | 221 | 49 | 289 | S O |
| HETATM | 1995 | N1 | INH | I | 1 | 16.972 | 12.024 | 36.885 | 1.00 | 10.95 | | I N |
| ANISOU | 1995 | N1 | INH | I | 1 | 1228 | 1259 | 1389 | −2 | 2 | 0 | I N |
| SIGUIJ | 1995 | N1 | INH | I | 1 | 1 | 0 | 0 | 221 | 57 | 289 | I N |
| HETATM | 1996 | C2 | INH | I | 1 | 16.470 | 11.815 | 38.255 | 1.00 | 10.80 | | I C |
| ANISOU | 1996 | C2 | INH | I | 1 | 1194 | 1175 | 1389 | −1 | −15 | 0 | I C |
| SIGUIJ | 1996 | C2 | INH | I | 1 | 1 | 0 | 0 | 221 | 67 | 290 | I C |
| HETATM | 1997 | C4 | INH | I | 1 | 17.773 | 11.451 | 38.995 | 1.00 | 10.95 | | I C |
| ANISOU | 1997 | C4 | INH | I | 1 | 1273 | 1509 | 1573 | 70 | −120 | 29 | I C |
| SIGUIJ | 1997 | C4 | INH | I | 1 | 1 | 0 | 0 | 221 | 67 | 290 | I C |
| HETATM | 1998 | C7 | INH | I | 1 | 18.620 | 10.789 | 37.920 | 1.00 | 11.54 | | I C |
| ANISOU | 1998 | C7 | INH | I | 1 | 1340 | 1489 | 1655 | 20 | −33 | 3 | I C |
| SIGUIJ | 1998 | C7 | INH | I | 1 | 1 | 0 | 0 | 221 | 67 | 290 | I C |
| HETATM | 1999 | C10 | INH | I | 1 | 18.421 | 11.778 | 36.767 | 1.00 | 11.19 | | I C |
| ANISOU | 1999 | C10 | INH | I | 1 | 1236 | 1496 | 1637 | 47 | 17 | −2 | I C |
| SIGUIJ | 1999 | C10 | INH | I | 1 | 1 | 0 | 0 | 221 | 66 | 290 | I C |
| HETATM | 2000 | C13 | INH | I | 1 | 15.856 | 13.099 | 38.859 | 1.00 | 11.37 | | I C |

TABLE 3-continued

Three-dimensional structure of the new binding pocket of kallikrein 7

| | | | | | | | | | | | | | |
|---|---|---|---|---|---|---|---|---|---|---|---|---|---|
| ANISOU | 2000 | C13 | INH | I | 1 | 1202 | 1164 | 1456 | −2 | −7 | 0 | I | C |
| SIGUIJ | 2000 | C13 | INH | I | 1 | 1 | 0 | 0 | 221 | 66 | 290 | I | C |
| HETATM | 2001 | O14 | INH | I | 1 | 16.080 | 14.251 | 38.328 | 1.00 | 11.37 | | I | O |
| ANISOU | 2001 | O14 | INH | I | 1 | 1368 | 1167 | 1474 | −42 | 12 | 1 | I | O |
| SIGUIJ | 2001 | O14 | INH | I | 1 | 1 | 0 | 0 | 221 | 49 | 289 | I | O |
| HETATM | 2002 | N15 | INH | I | 1 | 15.122 | 12.935 | 39.926 | 1.00 | 11.94 | | I | N |
| ANISOU | 2002 | N15 | INH | I | 1 | 1164 | 1192 | 1434 | 4 | −35 | 3 | I | N |
| SIGUIJ | 2002 | N15 | INH | I | 1 | 1 | 0 | 0 | 221 | 57 | 289 | I | N |
| HETATM | 2003 | C17 | INH | I | 1 | 14.496 | 14.072 | 40.624 | 1.00 | 13.70 | | I | C |
| ANISOU | 2003 | C17 | INH | I | 1 | 1554 | 1302 | 1643 | 137 | 95 | −44 | I | C |
| SIGUIJ | 2003 | C17 | INH | I | 1 | 1 | 0 | 0 | 221 | 66 | 290 | I | C |
| HETATM | 2004 | C20 | INH | I | 1 | 15.528 | 14.722 | 41.570 | 1.00 | 15.91 | | I | C |
| ANISOU | 2004 | C20 | INH | I | 1 | 1958 | 1461 | 2142 | 106 | −328 | −92 | I | C |
| SIGUIJ | 2004 | C20 | INH | I | 1 | 1 | 0 | 0 | 221 | 66 | 290 | I | C |
| HETATM | 2005 | C23 | INH | I | 1 | 14.867 | 15.933 | 42.215 | 1.00 | 17.69 | | I | C |
| ANISOU | 2005 | C23 | INH | I | 1 | 2620 | 1616 | 2462 | 346 | −92 | −131 | I | C |
| SIGUIJ | 2005 | C23 | INH | I | 1 | 1 | 0 | 0 | 221 | 66 | 290 | I | C |
| HETATM | 2006 | C24 | INH | I | 1 | 15.144 | 17.215 | 41.667 | 1.00 | 19.23 | | I | C |
| ANISOU | 2006 | C24 | INH | I | 1 | 4714 | 1737 | 3191 | 128 | 424 | 45 | I | C |
| SIGUIJ | 2006 | C24 | INH | I | 1 | 1 | 0 | 0 | 221 | 66 | 290 | I | C |
| HETATM | 2007 | C26 | INH | I | 1 | 14.536 | 18.418 | 42.262 | 1.00 | 20.20 | | I | C |
| ANISOU | 2007 | C26 | INH | I | 1 | 4777 | 1821 | 3026 | 276 | 191 | 22 | I | C |
| SIGUIJ | 2007 | C26 | INH | I | 1 | 1 | 0 | 0 | 221 | 66 | 290 | I | C |
| HETATM | 2008 | C28 | INH | I | 1 | 13.661 | 18.283 | 43.403 | 1.00 | 20.78 | | I | C |
| ANISOU | 2008 | C28 | INH | I | 1 | 3620 | 3711 | 2333 | 25 | −722 | 47 | I | C |
| SIGUIJ | 2008 | C28 | INH | I | 1 | 1 | 0 | 0 | 221 | 66 | 290 | I | C |
| HETATM | 2009 | C29 | INH | I | 1 | 13.379 | 16.967 | 43.956 | 1.00 | 20.05 | | I | C |
| ANISOU | 2009 | C29 | INH | I | 1 | 3118 | 3598 | 2514 | 417 | −58 | −19 | I | C |
| SIGUIJ | 2009 | C29 | INH | I | 1 | 1 | 0 | 0 | 221 | 66 | 290 | I | C |
| HETATM | 2010 | C31 | INH | I | 1 | 13.993 | 15.794 | 43.341 | 1.00 | 18.98 | | I | C |
| ANISOU | 2010 | C31 | INH | I | 1 | 2740 | 3474 | 2538 | 193 | −9 | −4 | I | C |
| SIGUIJ | 2010 | C31 | INH | I | 1 | 1 | 0 | 0 | 221 | 66 | 290 | I | C |
| HETATM | 2011 | O33 | INH | I | 1 | 13.064 | 19.413 | 44.006 | 1.00 | 22.11 | | I | O |
| ANISOU | 2011 | O33 | INH | I | 1 | 4114 | 3733 | 2949 | 13 | −204 | −7 | I | O |
| SIGUIJ | 2011 | O33 | INH | I | 1 | 1 | 0 | 0 | 221 | 49 | 289 | I | O |
| HETATM | 2012 | C34 | INH | I | 1 | 12.177 | 19.459 | 45.137 | 1.00 | 22.69 | | I | C |
| ANISOU | 2012 | C34 | INH | I | 1 | 4370 | 5531 | 3098 | 125 | −9 | 0 | I | C |
| SIGUIJ | 2012 | C34 | INH | I | 1 | 1 | 0 | 0 | 221 | 66 | 290 | I | C |
| HETATM | 2013 | C38 | INH | I | 1 | 16.126 | 12.284 | 35.849 | 1.00 | 10.52 | | I | C |
| ANISOU | 2013 | C38 | INH | I | 1 | 1219 | 1235 | 1370 | 0 | 14 | 0 | I | C |
| SIGUIJ | 2013 | C38 | INH | I | 1 | 1 | 0 | 0 | 221 | 66 | 290 | I | C |
| HETATM | 2014 | O39 | INH | I | 1 | 14.881 | 12.259 | 36.053 | 1.00 | 10.62 | | I | O |
| ANISOU | 2014 | O39 | INH | I | 1 | 1229 | 1126 | 1282 | 7 | −1 | 0 | I | O |
| SIGUIJ | 2014 | O39 | INH | I | 1 | 1 | 0 | 0 | 221 | 49 | 289 | I | O |
| HETATM | 2015 | N40 | INH | I | 1 | 16.626 | 12.478 | 34.625 | 1.00 | 11.20 | | I | N |
| ANISOU | 2015 | N40 | INH | I | 1 | 1246 | 1379 | 1379 | −35 | 27 | 7 | I | N |
| SIGUIJ | 2015 | N40 | INH | I | 1 | 1 | 0 | 0 | 221 | 57 | 289 | I | N |
| HETATM | 2016 | C42 | INH | I | 1 | 15.778 | 12.641 | 33.479 | 1.00 | 11.10 | | I | C |
| ANISOU | 2016 | C42 | INH | I | 1 | 1317 | 1319 | 1413 | 0 | −13 | −1 | I | C |
| SIGUIJ | 2016 | C42 | INH | I | 1 | 1 | 0 | 0 | 221 | 66 | 290 | I | C |
| HETATM | 2017 | C45 | INH | I | 1 | 15.690 | 14.043 | 32.901 | 1.00 | 11.46 | | I | C |
| ANISOU | 2017 | C45 | INH | I | 1 | 1197 | 1324 | 1481 | −13 | 0 | 0 | I | C |
| SIGUIJ | 2017 | C45 | INH | I | 1 | 1 | 0 | 0 | 221 | 66 | 290 | I | C |
| HETATM | 2018 | C46 | INH | I | 1 | 15.144 | 14.214 | 31.570 | 1.00 | 11.99 | | I | C |
| ANISOU | 2018 | C46 | INH | I | 1 | 1089 | 1484 | 1477 | −6 | 44 | 1 | I | C |
| SIGUIJ | 2018 | C46 | INH | I | 1 | 1 | 0 | 0 | 221 | 66 | 290 | I | C |
| HETATM | 2019 | C47 | INH | I | 1 | 15.066 | 15.581 | 31.002 | 1.00 | 12.32 | | I | C |
| ANISOU | 2019 | C47 | INH | I | 1 | 1379 | 1478 | 1545 | −1 | −1 | 0 | I | C |
| SIGUIJ | 2019 | C47 | INH | I | 1 | 1 | 0 | 0 | 221 | 66 | 290 | I | C |
| HETATM | 2020 | C48 | INH | I | 1 | 15.523 | 16.707 | 31.785 | 1.00 | 12.16 | | I | C |
| ANISOU | 2020 | C48 | INH | I | 1 | 1634 | 1514 | 1574 | −102 | 2 | −2 | I | C |
| SIGUIJ | 2020 | C48 | INH | I | 1 | 1 | 0 | 0 | 221 | 66 | 290 | I | C |
| HETATM | 2021 | C50 | INH | I | 1 | 16.050 | 16.497 | 33.100 | 1.00 | 12.60 | | I | C |
| ANISOU | 2021 | C50 | INH | I | 1 | 1895 | 1427 | 1637 | −229 | −110 | 62 | I | C |
| SIGUIJ | 2021 | C50 | INH | I | 1 | 1 | 0 | 0 | 221 | 66 | 290 | I | C |
| HETATM | 2022 | C52 | INH | I | 1 | 16.141 | 15.172 | 33.661 | 1.00 | 12.30 | | I | C |
| ANISOU | 2022 | C52 | INH | I | 1 | 1628 | 1403 | 1484 | −201 | 3 | −3 | I | C |
| SIGUIJ | 2022 | C52 | INH | I | 1 | 1 | 0 | 0 | 221 | 66 | 290 | I | C |
| HETATM | 2023 | C54 | INH | I | 1 | 14.532 | 15.789 | 29.716 | 1.00 | 12.51 | | I | C |
| ANISOU | 2023 | C54 | INH | I | 1 | 1399 | 1694 | 1538 | 57 | 4 | −1 | I | C |
| SIGUIJ | 2023 | C54 | INH | I | 1 | 1 | 0 | 0 | 221 | 66 | 290 | I | C |
| HETATM | 2024 | C56 | INH | I | 1 | 14.064 | 14.679 | 28.954 | 1.00 | 12.49 | | I | C |
| ANISOU | 2024 | C56 | INH | I | 1 | 1561 | 1708 | 1524 | −7 | 0 | 0 | I | C |
| SIGUIJ | 2024 | C56 | INH | I | 1 | 1 | 0 | 0 | 221 | 66 | 290 | I | C |
| HETATM | 2025 | C58 | INH | I | 1 | 14.145 | 13.345 | 29.492 | 1.00 | 12.43 | | I | C |
| ANISOU | 2025 | C58 | INH | I | 1 | 1302 | 1698 | 1494 | −38 | 7 | 1 | I | C |
| SIGUIJ | 2025 | C58 | INH | I | 1 | 1 | 0 | 0 | 221 | 66 | 290 | I | C |
| HETATM | 2026 | C60 | INH | I | 1 | 14.676 | 13.131 | 30.768 | 1.00 | 12.08 | | I | C |

TABLE 3-continued

| Three-dimensional structure of the new binding pocket of kallikrein 7 | | | | | | | | | | | |
|---|---|---|---|---|---|---|---|---|---|---|---|
| ANISOU | 2026 | C60 | INH | I | 1 | 1315 | 1526 | 1491 | −89 | 6 | 3 I C |
| SIGUIJ | 2026 | C60 | INH | I | 1 | 1 | 0 | 0 | 221 | 66 | 290 I C |
| END | | | | | | | | | | | |

Example 1

(S)-Pyrrolidine-1,2-dicarboxylic acid 1-[(7-ethynyl-naphthalen-1-ylmethyl)-amide] 2-[(2-pyridin-3-yl-ethyl)-amide]

A) 7-Chloro-naphthalene-1-carboxylic acid methyl ester

A mixture of 50 ml of methyl 2-furoate and 400 ml of chlorobenzene is stirred at 0° for 30 minutes, at RT for 1.5 hours and at 100° for 16 hours. 121 g of anhydrous $AlCl_3$ are added by portion at 0°. The solution obtained is cooled, poured in an ice-bath and stirred for 30 minutes before extraction of the aq. phase with ether. The organic phase obtained is washed with aq. 10% $NaHCO_3$ solution and brine, dried and solvent is evaporated. The residue obtained is purified by flash chromatography on silica gel (eluent: cyclohexane/EtOAc 99/1 to 95/5) to obtain the title compound.

B) (7-Chloro-naphthalen-1-yl)-methanol

A 0.7M diisobutylaluminium hydride solution in $CH_2Cl_2$ is added dropwise at −78° to 22 g of 7-chloro-naphthalene-1-carboxylic acid methyl ester in $CH_2Cl_2$. After stirring at −78° for 1 hour, the mixture obtained is warmed up to 0°, quenched with aq. 10% sodium tartrate solution and stirred for further few minutes. The organic phase obtained is separated, washed with brine, dried and solvent is evaporated. The residue obtained is purified by flash chromatography on silica gel (eluent: cyclohexane/EtOAc 8/1 to 4/1) and the title compound is obtained.

MS: 175 [M−H2O+H]+ TLC, Rf (cyclohexane/EtOAc 3/1)=0.3

C) 1-Azidomethyl-7-chloro-naphthalene 1.52 ml of Diphenylphosphoryl azide and 1.10 ml of 1,8-diazabicyclo[5.4.0]undec-7-ene are added to 1.3 g of (7-Chloro-naphthalen-1-yl)-methanol in 18 ml of toluene. The mixture obtained is stirred at rt for 1 hour, washed with brine, the organic phase is dried and solvent is evaporated. The residue obtained is purified by flash chromatography on silica gel (eluent: cyclohexane/EtOAc 99/1) to yield the title compound.

TLC, Rf (cyclohexane/EtOAc 99/1)=0.333

D) C-(7-Chloro-naphthalen-1-yl)-methylamine hydrochloride 1.24 g of Triphenylphosphine and 410 µl of H2O are added to 998 mg of 1-azidomethyl-7-chloro-naphthalene in 20 ml of THF. The mixture obtained is stirred at 50° for 5 hours and solvent is evaporated. The residue obtained is acidified with aq. 1N HCl solution and extracted with EtOAc. The aq. phase obtained is basified with aq. 10% $NaHCO_3$ solution and extracted with EtOAc. The organic phase obtained is dried and solvent is evaporated. The title compound is obtained as the free amine compound and converted to the hydrochloride salt by addition of 4M HCl solution in dioxane. Solvent is evaporated and the residue obtained is stirred with ether, the mixture obtained is filtered and the filtrate obtained is dried to yield the title compound.

MS: 192 [M+H]+ TLC, Rf ($CH_2Cl_2$/MeOH/$NH_4OH$ 95/5/0.01)=0.25

E) C-(7-Triethylsilanylethynyl-naphthalen-1-yl)-methylamine

A solution of 500 mg of C-(7-Chloro-naphthalen-1-yl)-methylamine hydrochloride, 5.4 mg of bis(acetonitrile)palladium (II) chloride, 29.8 mg of 2-dicyclohexylphosphino-2',4',6'-triisopropyl-1,1'-biphenyl and 1.7 g of cesium carbonate in 7.5 ml of acetonitrile is stirred at rt for 25 minutes. After adding 495 µl of (triethylsilyl)acetylene, the mixture obtained is stirred at 90° for 2 hours, quenched with $H_2O$ and extracted with EtOAc. The organic phase obtained is washed with brine, dried and solvent is evaporated. The residue obtained is purified by flash chromatography on silica gel (eluent: $CH_2Cl_2$/MeOH/$NH_4OH$ 99/1/0.01 to 95/5/0.01) the title compound is obtained.

MS: 279 [M−NH3+H]+ TLC, Rf ($CH_2Cl_2$/MeOH/$NH_4OH$ 98/2/0.01)=0.22

F) (S)-1-[(7-Triethylsilanylethynyl-naphthalen-1-ylmethyl)-carbamoyl]-pyrrolidine-2-carboxylic acid A 20% phosgene solution in 8 ml of toluene is added to 500 mg of C-(7-triethylsilanylethynyl-naphthalen-1-yl)-methylamine and 479 µl of diisopropylethylamine in 40 ml of toluene. The solution obtained is stirred at reflux for 3 hours and another portion of a 20% phosgene solution in 8 ml of toluene is added and stirred at reflux another hour. Solvent is evaporated. To the evaporation residue obtained 559 µl of diisopropylethylamine in 40 ml of THF and 213 mg of (S)-pyrrolidine-2-carboxylic acid are added. The mixture obtained is stirred for 1 hour and solvent is evaporated. The residue obtained is purified by preparative HPLC (Waters Sun Fire C18 column, gradient water/acetonitrile 95/5 to 0/100) to yield the title compound.

MS: 437 [M+H]+ HPLC (method B): 4.366 minutes

G) (S)-1-[(7-Ethynyl-naphthalen-1-ylmethyl)-carbamoyl]-pyrrolidine-2-carboxylic acid A solution of 250 mg of (S)-1-[(7-Triethylsilanylethynyl-naphthalen-1-ylmethyl)-carbamoyl]-pyrrolidine-2-carboxylic acid in 14 ml of THF is stirred at rt for 1 hour. Solvent is evaporated and the residue obtained is purified by preparative HPLC (Waters Sun Fire C18 column, gradient water/acetonitrile 95/5 to 0/100) to yield the title compound.

MS: 323 [M+H]+ TLC, Rf (EtOAc/AcOH 50/1)=0.16

H) (S)-Pyrrolidine-1,2-dicarboxylic acid 1-[(7-ethynyl-naphthalen-1-ylmethyl)-amide] 2-[(2-pyridin-3-yl-ethyl)-amide]

11.6 mg of 3-(2-aminoethyl)pyridine, 4.05 µl of diisopropylethylamine, 13.1 mg of 1-hydroxybenzotriazole and 18.8 mg of N-(Ethyl-N'-(3-dimethylaminopropyl)carbodiimide hydrochloride are added to 20 mg of (S)-1-[(7-ethynyl-naphthalen-1-ylmethyl)-carbamoyl]-pyrrolidine-2-carboxylic acid in 1 ml of $CH_2Cl_2$. The reaction mixture obtained is stirred at rt for 16 hours, solvent is evaporated and the residue obtained is purified by preparative HPLC (Waters Sun Fire C18 column, gradient water/acetonitrile 95/5 to 0/100) to yield the title compound.
MS: 427 [M+H]+ TLC, Rf ($CH_2Cl_2$/MeOH/$NH_4OH$ 95/5/0.01)=0.37.

Example 2

(S)-Pyrrolidine-1,2-dicarboxylic acid 2-[(2-dimethylamino-ethyl)-amide] 1-[(7-ethynyl-naphthalen-1-ylmethyl)-amide]

The title compound is prepared analogously as described in example 1 using N,N-dimethylethylenediamine instead of 3-(2-aminoethyl)pyridine.
MS: 393 [M+H]+ TLC, Rf ($CH_2Cl_2$/MeOH/$NH_4OH$ 95/5/0.01)=0.07

Example 3

(S)-Pyrrolidine-1,2-dicarboxylic acid 1-[(7-ethynyl-naphthalen-1-ylmethyl)-amide] 2-[(2-pyridin-4-yl-ethyl)-amide]

The title compound is prepared analogously as described in example 1 using 4-(2-aminoethyl)pyridine instead of 3-(2-aminoethyl)pyridine.
MS: 427 [M+H]+ TLC, Rf ($CH_2Cl_2$/MeOH/$NH_4OH$ 95/5/0.01)=0.10

Example 4

(S)-Pyrrolidine-1,2-dicarboxylic acid 1-[(7-ethynyl-naphthalen-1-ylmethyl)-amide] 2-[(6-methoxy-pyridin-3-ylmethyl)-amide]

The title compound is prepared analogously as described in example 1 using C-(6-Methoxy-pyridin-3-yl)-methylamine instead of 3-(2-aminoethyl)pyridine.
MS: 443 [M+H]+ TLC, Rf ($CH_2Cl_2$/MeOH/$NH_4OH$ 95/5/0.01)=0.275

Example 5

(S)-Pyrrolidine-1,2-dicarboxylic acid 1-[(7-ethynyl-naphthalen-1-ylmethyl)-amide] 2-[(1-methyl-piperidin-4-ylmethyl)-amide]

The title compound is prepared analogously as described in example 1 using 1-(methylpiperidin-4-yl)methylamine instead of 3-(2-aminoethyl)pyridine.
MS: 433 [M+H]+ TLC, Rf ($CH_2Cl_2$/MeOH/NH4OH 95/5/0.01)=0.072

Example 6

(S)-Pyrrolidine-1,2-dicarboxylic acid 1-[(7-ethynyl-naphthalen-1-ylmethyl)-amide] 2-[4-(4-methyl-piperazin-1-yl)-benzylamide]

The title compound is prepared analogously as described in example 1 using 4-(4-methylpiperazino)benzylamine instead of 3-(2-aminoethyl)pyridine.
MS: 510 [M+H]+ TLC, Rf ($CH_2Cl_2$/MeOH/$NH_4OH$ 95/5/0.01)=0.1

Example 7

(S)-Pyrrolidine-1,2-dicarboxylic acid 1-[(7-ethynyl-naphthalen-1-ylmethyl)-amide] 2-(4-morpholin-4-ylmethyl-benzylamide)

The title compound is prepared analogously as described in example 1 using 4-(morpholinomethyl)benzylamine instead of 3-(2-aminoethyl)pyridine.
MS: 511 [M+H]+ TLC, Rf ($CH_2Cl_2$/MeOH/$NH_4OH$ 98/2/0.01)=0.26

Example 8

(S)-Pyrrolidine-1,2-dicarboxylic acid 1-[(7-ethynyl-naphthalen-1-ylmethyl)-amide] 2-methylamide The title compound is prepared analogously as described in example 1 using methylamine hydrochloride instead of 3-(2-aminoethyl)pyridine.
MS: 336 [M+H]+ TLC, Rf (ethylacetate)=0.1

Example 9

(S)-Pyrrolidine-1,2-dicarboxylic acid 2-{[2-(4-benzyl-piperazin-1-yl)-ethyl]-amide} 1-[(7-ethynyl-naphthalen-1-ylmethyl)-amide]

The title compound is prepared analogously as described in example 1 using 2-(4-Benzyl-piperazin-1-yl)-ethylamine instead of 3-(2-aminoethyl)pyridine.
MS: 524 [M+H]+ TLC, Rf ($CH_2Cl_2$/MeOH/$NH_4OH$ 95/5/0.01)=0.32

Example 10

(S)-Pyrrolidine-1,2-dicarboxylic acid 1-[(7-ethynyl-naphthalen-1-ylmethyl)-amide] 2-[(2-methoxy-ethyl)-amide]

The title compound is prepared analogously as described in example 1 using 2-methoxyethylamine instead of 3-(2-aminoethyl)pyridine.
MS: 380 [M+H]+ TLC, Rf ($CH_2Cl_2$/MeOH/$NR_4OH$ 95/5/0.01)=0.276

Example 11

(S)-Pyrrolidine-1,2-dicarboxylic acid 1-[(7-ethynyl-naphthalen-1-ylmethyl)-amide] 2-[(pyridin-3-ylmethyl)-amide]

The title compound is prepared analogously as described in example 1 using 3-picolylamine instead of 3-(2-aminoethyl)pyridine.
MS: 413 [M+H]+ TLC, Rf ($CH_2Cl_2$/MeOH/$NH_4OH$ 95/5/0.01)=0.17

Example 12

(S)-Pyrrolidine-1,2-dicarboxylic acid 1-[(7-ethynyl-naphthalen-1-ylmethyl)-amide] 2-[(pyridin-4-ylmethyl)-amide]

The title compound is prepared analogously as described in example 1 using 4-picolylamine instead of 3-(2-aminoethyl)pyridine.

MS: 413 [M+H]+ TLC, Rf (CH$_2$Cl$_2$/MeOH/NH$_4$OH 95/5/0.01)=0.215

Example 13

(S)-Pyrrolidine-1,2-dicarboxylic acid 1-[(7-ethynyl-naphthalen-1-ylmethyl)-amide] 2-{[2-(4-methyl-piperazin-1-yl)-ethyl]-amide}

The title compound is prepared analogously as described in example 1 using 1-(2-aminoethyl)4-methylpiperazine instead of 3-(2-aminoethyl)pyridine.

MS: 448 [M+H]+ TLC, Rf (CH$_2$Cl$_2$/MeOH/NH$_4$OH 95/5/0.01)=0.088

Example 14

(S)-Pyrrolidine-1,2-dicarboxylic acid 1-[(6-chloro-naphthalen-1-ylmethyl)-amide] 2-{[2-(4-methoxy-phenyl)-ethyl]-amide}

A) C-(6-Chloro-naphthalen-1-yl)-methylamine trifluoroacetic acid salt

The title compound is prepared analogously as described in example 1 step C and D using (6-Chloro-naphthalen-1-yl)-methanol instead of (7-Chloro-naphthalen-1-yl)-methanol.

MS: 175 [M-NH3+H]+ HPLC (method B): 1.935 min

B) (S)-2-[2-(4-Methoxy-phenyl)-ethylcarbamoyl]-pyrrolidine-1-carboxylic acid tert-butyl ester 18.9 g of N-(Ethyl-N'-(3-dimethylaminopropyl)carbodiimide hydrochloride are added to a cooled solution of 20.04 g of (S)-Pyrrolidine-1,2-dicarboxylic acid 1-tert-butyl ester, 14.9 g of 4-methoxyphenethylamine, 16.9 ml of diisopropylethylamine and 13.2 g of 1-hydroxy-benzotriazole in 250 ml of CH$_2$Cl$_2$. The reaction mixture obtained is stirred at rt for 16 hours, the reaction is quenched with aq. 2N HCl solution and the aq. phase obtained is extracted with CH$_2$Cl$_2$. The combined organic phases obtained are washed with aq. 2N HCl solution, brine and aq. saturated NaHCO$_3$ solution, dried and solvent is evaporated. The residue obtained is purified by recrystallisation with EtOAc/hexane (1/3) to afford the title compound.

MS: 349 [M+H]+ TLC, Rf (ethylacetate/hexane 1/1)=0.21

C) (S)-Pyrrolidine-2-carboxylic acid [2-(4-methoxy-phenyl)-ethyl]-amide

4N HCl solution in 41 ml of dioxane is added to a fine suspension of 16.78 g of (S)-2-[2-(4-Methoxy-phenyl)-ethylcarbamoyl]-pyrrolidine-1-carboxylic acid tert-butyl ester in 40 ml of dioxane. After stirring under poor cooling with an ice-bath for 2.5 hours, solvent is evaporated, the residue obtained is cooled over night at 0° and resulting crystals are stirred with 150 ml of tert-butylmethylether, filtered and dried to yield the title compound.

MS: 249 [M+H]+ TLC, Rf (CH$_2$Cl$_2$/MeOH/NH$_4$OH 90/9/1)=0.35

D) (S)-Pyrrolidine-1,2-dicarboxylic acid 1-[(6-chloro-naphthalen-1-ylmethyl)-amide] 2-{[2-(4-methoxy-phenyl)-ethyl]-amide}

A solution of 33 mg of C-(6-Chloro-naphthalen-1-yl)-methylamine trifluoroacetic acid salt, 22 mg of 4-nitrophenyl-chloroformate and 25 µl of pyridine in 3 ml of CH$_2$Cl$_2$ is stirring at rt for 1 hour. 30 mg of (S)-Pyrrolidine-2-carboxylic acid [2-(4-methoxy-phenyl)-ethyl]-amide and 37 µl of diisopropylethylamine are added. The reaction mixture obtained is stirred at it for 16 hours, solvent is evaporated and the residue obtained is purified by preparative HPLC (Waters Sun Fire C18 column, gradient water/acetonitrile 95/5 to 0/100) to yield the title compound.

MS: 466 [M+H]+ TLC, Rf (EtOAc)=0.363

Example 15

(S)-Pyrrolidine-1,2-dicarboxylic acid 1-[(7-chloro-naphthalen-1-ylmethyl)-amide] 2-{[2-(4-methoxy-phenyl)-ethyl]-amide}

The title compound is prepared analogously as described in example 14 using C-(7-Chloro-naphthalen-1-yl)-methylamine trifluoroacetic acid salt instead of C-(6-Chloro-naphthalen-1-yl)-methylamine trifluoroacetic acid salt.

MS: 466 [M+H]+ TLC, Rf (EtOAc)=0.45

Example 16

(S)-Pyrrolidine-1,2-dicarboxylic acid 1-[(5-bromo-benzo[b]thiophen-3-ylmethyl)-amide] 2-{[2-(4-methoxy-phenyl)-ethyl]-amide}

The title compound is prepared analogously as described in example 14 using C-(5-Bromo-benzo[b]thiophen-3-yl)-methylamine instead of C-(6-Chloro-naphthalen-1-yl)methylamine trifluoroacetic acid salt.

MS: 518 [M+H]+ TLC, Rf (EtOAc/cyclohexyane 2/1)=0.1

Example 17

(S)-Pyrrolidine-1,2-dicarboxylic acid 1-[(5-chloro-benzo[b]thiophen-3-ylmethyl)-amide] 2-{[2-(4-methoxy-phenyl)-ethyl]-amide}

The title compound is prepared analogously as described in example 14 using C-(5-chloro-benzo[b]thiophen-3-yl)-methylamine hydrochloride instead of C-(6-Chloro-naphthalen-1-yl)-methylamine trifluoroacetic acid salt.

MS: 472 [M+H]+ TLC, Rf (EtOAc/cyclohexyane 2/1)=0.209

Example 18

(S)-Pyrrolidine-1,2-dicarboxylic acid 1-[(7-ethynyl-naphthalen-1-ylmethyl)-amide] 2-{[2-(4-methoxy-phenyl)-ethyl]-amide}

A) (S)-Pyrrolidine-1,2-dicarboxylic acid 2-{[2-(4-methoxy-phenyl)-ethyl]-amide} 1-[(7-triethylsilanyl-ethynyl-naphthalen-1-ylmethyl)-amide]

The title compound is prepared analogously as described in example 14 using C-(7-Triethylsilanylethynyl-naphthalen-1-yl)-methylamine instead of C-(6-Chloro-naphthalen-1-yl)-methylamine trifluoroacetic acid salt.

MS: 570 [M+H]+

B) (S)-Pyrrolidine-1,2-dicarboxylic acid 1-[(7-ethynyl-naphthalen-1-ylmethyl)-amide] 2-{[2-(4-methoxy-phenyl)-ethyl]-amide}

The title compound is prepared analogously as described in example 1 part G using (S)-Pyrrolidine-1,2-dicarboxylic acid 2-{[2-(4-methoxy-phenyl)-ethyl]-amide} 1-[(7-triethylsilanylethynyl-naphthalen-1-ylmethyl)-amide] instead of (S)-1-[(7-Triethylsilanylethynyl-naphthalen-1-ylmethyl)-carbamoyl]-pyrrolidine-2-carboxylic acid.
MS: 456 [M+H]+ TLC, Rf (EtOAc/cyclohexane 2/1)=0.15

Example 19

(2S,4R)-4-Methoxy-pyrrolidine-1,2-dicarboxylic acid 1-[(7-ethynyl-naphthalen-1-ylmethyl)-amide] 2-[(pyridin-3-ylmethyl)-amide]

A) (2S,4R)-4-Methoxy-2-[(pyridin-3-ylmethyl)-carbamoyl]-pyrrolidine-1-carboxylic acid tert-butyl ester The title compound is prepared analogously as described in example 14 step B using (2S,4R)-4-Methoxy-pyrrolidine-1,2-dicarboxylic acid 1-tert-butyl ester instead of (S)-Pyrrolidine-1,2-dicarboxylic acid 1-tert-butyl ester and 3-picolylamine instead of 4-methoxyphenethylamine.
MS: 336 [M+H]+ TLC, Rf (CH$_2$Cl$_2$/MeOH/NH$_4$OH 90/9/1)=0.36

B) ((2S,4R)-4-Methoxy-pyrrolidine-2-carboxylic acid (pyridin-3-ylmethyl)-amide

The title compound is prepared analogously as described in example 14 step C using (2S,4R)-4-Methoxy-2-[(pyridin-3-ylmethyl)-carbamoyl]-pyrrolidine-1-carboxylic acid tert-butyl ester instead of (S)-2-[2-(4-Methoxy-phenyl)-ethylcarbamoyl]-pyrrolidine-1-carboxylic acid tert-butyl ester.
MS: 236 [M+H]+ TLC, Rf (CH$_2$Cl$_2$/MeOH/NH$_4$OH 90/9/1)=0.31

C) (2S,4R)-4-Methoxy-pyrrolidine-1,2-dicarboxylic acid 2-[(pyridin-3-ylmethyl)-amide] 1-[(7-triethylsilanylethynyl-naphthalen-1-ylmethyl)-amide]

The title compound is prepared analogously as described in example 1 part F using ((2S,4R)-4-Methoxy-pyrrolidine-2-carboxylic acid (pyridin-3-ylmethyl)-amide instead of (S)-pyrrolidine-2-carboxylic acid.
MS: 557 [M+H]+ TLC, Rf (CH$_2$Cl$_2$/MeOH/NH$_4$OH 90/9/1)=0.44

D) (2S,4R)-4-Methoxy-pyrrolidine-1,2-dicarboxylic acid 1-[(7-ethynyl-naphthalen-1-ylmethyl)-amide] 2-[(pyridin-3-ylmethyl)-amide]

The title compound is prepared analogously as described in example 18 part B using (2S,4R)-4-Methoxy-pyrrolidine-1,2-dicarboxylic acid 2-[(pyridin-3-ylmethyl)-amide] 1-[(7-triethylsilanylethynyl-naphthalen-1-ylmethyl)-amide] instead of (S)-Pyrrolidine-1,2-dicarboxylic acid 2-{[2-(4-methoxy-phenyl)-ethyl]-amide} 1-[(7-triethylsilanylethynyl-naphthalen-1-ylmethyl)-amide].
MS: 443 [M+H]+ TLC, Rf (CH$_2$Cl$_2$/MeOH/NH$_4$OH 90/9/1)=0.23

Example 20

(S)-Piperidine-1,2-dicarboxylic acid 1-[(7-ethynyl-naphthalen-1-ylmethyl)-amide] 2-[(pyridin-3-ylmethyl)-amide]

The title compound is prepared analogously as described in example 19 using (S)-Piperidine-1,2-dicarboxylic acid 1-tert-butyl ester instead of (2S,4R)-4-Methoxy-pyrrolidine-1,2-dicarboxylic acid 1-tert-butyl ester.
MS: 427 [M+H]+ TLC, Rf (CH$_2$Cl$_2$/MeOH/NH$_4$OH 90/9/1)=0.36

Example 21

(S)-Hexahydro-cyclopenta[c]pyrrole-1,2-dicarboxylic acid 2-[(7-ethynyl-naphthalen-1-ylmethyl)-amide] 1-[(pyridin-3-ylmethyl)-amide]

A) (S)-Hexahydro-cyclopenta[c]pyrrole-1,2-dicarboxylic acid 2-tert-butyl ester 1-ethyl ester 2.36 g of Di(tert-butyl)dicarbonate are added in 3-times to a mixture of 1.65 g of (S)-octahydro-cyclopenta[c]pyrrole-1-carboxylic acid ethyl ester and 1.45 g of NaCO$_3$ in 20 ml of dioxane and 10 ml of H$_2$O. The reaction mixture obtained is stirred at rt for 4 hours, the reaction is quenched with brine and the residue obtained is extracted with EtOAc. The organic phase obtained is washed with brine, dried and solvent is evaporated before purification by flash chromatography on silica gel is carried out (eluent: cyclohexane/EtOAc 9/1) to yield the title compound.
MS: 228 [M-isobutene+H]+ TLC, Rf (cyclohexane/EtOAc 4/1)=0.353

B) (S)-Hexahydro-cyclopenta[c]pyrrole-1,2-dicarboxylic acid 2-tert-butyl ester

A mixture of 2 g of (S)-Hexahydro-cyclopenta[c]pyrrole-1,2-dicarboxylic acid 2-tert-butyl ester 1-ethyl ester and 449 mg of LiOH in 30 ml of THF and 10 ml of H$_2$O is stirred at rt for 16 hours. The reaction is quenched with brine, acidified to pH 2 with aq. 2N HCl solution and extracted with EtOAc. The combined organic phases obtained are washed with brine, dried and solvent is evaporated to afford the title compound.
MS: 200 [M+H]+ TLC, Rf (hexane/EtOAc/AcOH 3/6/1) =0.71

C) (S)-1-[(Pyridin-3-ylmethyl)-carbamoyl]-hexahydro-cyclopenta[c]pyrrole-2-carboxylic acid tert-butyl ester 50% propylphosphonic anhydride solution in 650 µl of DMF is added to a solution of 200 mg of (S)-Hexahydro-cyclopenta[c]pyrrole-1,2-dicarboxylic acid 2-tert-butyl ester, 7.42 mg of 4-dimethylaminopyridine and 650 µl of diisopropylethylamine in CH$_2$Cl$_2$. After stirring at rt for 16 hours, the reaction is quenched with aq. 2N NaOH solution, eluted through a Chem Elut extraction with CH$_2$Cl$_2$ and solvent is evaporated before purification by preparative HPLC is carried out (Waters Sun Fire C18 column, gradient water/acetonitrile 95/5 to 0/100) to yield the title compound.
MS: 346 [M+H]+ TLC, Rf (CH$_2$Cl$_2$/MeOH/NH$_4$OH 90/9/1)=0.42

D) (S)-Hexahydro-cyclopenta[c]pyrrole-1,2-dicarboxylic acid 2-[(7-ethynyl-naphthalen-1-ylmethyl)-amide] 1-[(pyridin-3-ylmethyl)-amide]

The title compound is prepared analogously as described in example 19 using (S)-1-[(Pyridin-3-ylmethyl)-carbamoyl]-hexahydro-cyclopenta[c]pyrrole-2-carboxylic acid tert-butyl ester instead of (2S,4R)-4-Methoxy-2-[(pyridin-3-ylmethyl)-carbamoyl]-pyrrolidine-1-carboxylic acid tert-butyl ester.

MS: 453 [M+H]+ TLC, Rf (CH$_2$Cl$_2$/MeOH/NH$_4$OH 90/9/1)=0.29

Example 22

(S)-2,3-Dihydro-indole-1,2-dicarboxylic acid 1-[(7-ethynyl-naphthalen-1-ylmethyl)-amide] 2-[(pyridin-3-ylmethyl)-amide]

The title compound is prepared analogously as described in example 21 using (S)-2,3-Dihydro-indole-1,2-dicarboxylic acid 1-tert-butyl ester instead of (S)-Hexahydro-cyclopenta[c]pyrrole-1,2-dicarboxylic acid 2-tert-butyl ester.
MS: 461 [M+H]+ TLC, Rf (CH$_2$Cl$_2$/MeOH/NH$_4$OH 90/9/1)=0.42

Example 23

(S)-1,3-Dihydro-isoindole-1,2-dicarboxylic acid 2-[(7-ethynyl-naphthalen-1-ylmethyl)-amide] 1-[(pyridin-3-ylmethyl)-amide]

The title compound is prepared analogously as described in example 21 using 1,3-Dihydro-isoindole-1,2-dicarboxylic acid 2-tert-butyl ester instead of (S)-Hexahydro-cyclopenta[c]pyrrole-1,2-dicarboxylic acid 2-tert-butyl ester.
MS: 461 [M+H]+ TLC, Rf (CH$_2$Cl$_2$/MeOH/NH$_4$OH 90/9/1)=0.34

Example 24

(1R,2S,5S)-3-Aza-bicyclo[3.1.0]hexane-2,3-dicarboxylic acid 3-[(7-ethynyl-naphthalen-1-ylmethyl)-amide] 2-[(Pyridin-3-ylmethyl)-amide]

The title compound is prepared analogously as described in example 21 using (1R,2S,5S)-3-aza-bicyclo[3.1.0]hexane-2,3-dicarboxylic acid 3-tert-butyl ester instead of (S)-Hexahydro-cyclopenta[c]pyrrole-1,2-dicarboxylic acid 2-tert-butyl ester.
MS: 425 [M+H]+ TLC, Rf (CH$_2$Cl$_2$/MeOH/NH$_4$OH 90/9/1)=0.32

Example 25

(1S,2S,5R)-3-Aza-bicyclo[3.1.0]hexane-2,3-dicarboxylic acid 3-[(7-ethynyl-naphthalen-1-ylmethyl)-amide] 2-[(pyridin-3-ylmethyl)-amide]

The title compound is prepared analogously as described in example 21 using (1S,2S,5R)-3-aza-bicyclo[3.1.0]hexane-2,3-dicarboxylic acid 3-tert-butyl ester instead of (S)-Hexahydro-cyclopenta[c]pyrrole-1,2-dicarboxylic acid 2-tert-butyl ester.
MS: 425 [M+H]+ TLC, Rf (CH$_2$Cl$_2$/MeOH/NH$_4$OH 90/9/1)=0.36

Example 26

(S)-Pyrrolidine-1,2-dicarboxylic acid 1-[(naphthalen-1-ylmethyl)-amide] 2-(phenethyl-amide)

A) (4-Polystyryloxy-2,6-dimethoxy-benzyl)-phenethyl-amine 25 g of commercially available 2-(3,5-dimethoxy-4-formylphenoxy)ethoxymethyl polystyrene is washed 4 times with a 10/3 mixture of DCE and TMOF (150 ml). The resin obtained is suspended in the above 10/3 mixture of DCE and TMOF (150 ml) again and treated with 15.1 g of phenethylamine. The slurry obtained is shaken on an orbital shaker at it for 16 hours, the resin obtained is drained and washed successively with DMA, THF and CH$_2$Cl$_2$. A preformed solution of 5.1 ml of MeOH, 7.2 ml of AcOH and 125 mmol borane-pyridine complex in CH$_2$Cl$_2$ is added to the resin and shaking is resumed for 4 hours at rt. The resin obtained is drained and washed successively with DMA, AcOH/DMA (1/19), DMA, THF/H$_2$O (9/1), THF, CH$_2$Cl$_2$, MeOH, THF, MeOH. The title compound is thoroughly dried under vacuum to constant weight.

B) (6)-2-[(4-Polystyryloxy-2,6-dimethoxy-benzyl)-phenethyl-carbamoyl]-pyrrolidine-1-carboxylic acid 9H-fluoren-9-ylmethyl ester 122 mg of (S)-pyrrolidine-1,2-dicarboxylic acid 1-(9H-fluoren-9-ylmethyl) ester followed by 126 µl of DIPEA are added to a solution of 140 mg of HATU in 1.20 ml of NMP. The solution obtained is added onto 200 mg of the (4-polystyryloxy-2,6-dimethoxy-benzyl)-phenethyl-amine resin (loading approximated as 0.6 mmol/g, 0.12 mmol) and the slurry obtained is shaken for 2 hours at 60°. The resin obtained is washed successively with DMA, MeOH, CH$_2$Cl$_2$, and treated for one hour at it with a 1M solution of Ac$_2$O and 2M DIPEA in 5 ml of CH$_2$Cl$_2$. The resin obtained is drained and washed 3 consecutive times using the above solvent sequence of DMA, MeOH and CH$_2$Cl$_2$.

C) (S)-Pyrrolidine-2-carboxylic acid (4-polystyryloxy-2,6-dimethoxy-benzyl)-phenethyl-amide The resin (S)-2-[(4-Polystyryloxy-2,6-dimethoxy-benzyl)-phenethyl-carbamoyl]-pyrrolidine-1-carboxylic acid 9H-fluoren-9-ylmethyl ester obtained in step B (0.12 mmol of bound species) is suspended in a mixture of piperidine and DMA (1/4, 3 ml) and shaken on an orbital shaker for 20 minutes before draining and washing successively with DMA, MeOH, and CH$_2$Cl$_2$. The resin obtained is submitted one additional time to the piperidine and DMA solution for 20 minutes before final washing with DMA, MeOH, and CH$_2$Cl$_2$ to give the title compound.

D) (S)-Pyrrolidine-1,2-dicarboxylic acid 2-[(4-polystyryloxy-2,6-dimethoxy-benzyl)-phenethyl-amide] 1-[(naphthalen-1-ylmethyl)-amide]

210 mg of 1-(aminomethyl)naphthalene followed by 210 µl of DIPEA are cautialy added to a solution of 249 mg of 4-nitrophenylchloroformate in 2.60 ml of DCE. The solution obtained is stirred for 2.5 hours at it and added to the resin (0.12 mmol of bound species) obtained in step C. The slurry of resin obtained is shaken at it for 17 hours on an orbital shaker. The resin obtained is drained and washed 3 consecutive times using a sequence of DMA, MeOH and CH$_2$Cl$_2$ to give the title compound.

E) (S)-Pyrrolidine-1,2-dicarboxylic acid 1-[(naphthalen-1-ylmethyl)-amide] 2-(phenethyl-amide)

The resin of step D) (0.12 mmol of bound species) is treated with a solution of 20% TFA in 2 ml of $CH_2Cl_2$ for 1 hour at rt. The resin obtained is filtered and washed 3 times with 2 ml of $CH_2Cl_2$. The combined filtrates obtained are concentrated and the residue obtained is dissolved in MeOH and submitted to purification by preparative HPLC to give the title compound.

MS: 402 [M+H]+, 424 [M+Na]+ HPLC: 4.44 min, 100% UV purity

Example 27

(2S,4S)-4-Phenyl-pyrrolidine-1,2-dicarboxylic acid 1-[(naphthalen-1-ylmethyl)-amide] 2-(phenethyl-amide)

The title compound is prepared analogously as described in example 26 using (2S,4S)-4-phenyl-pyrrolidine-1,2-dicarboxylic acid 1-(9H-fluoren-9-ylmethyl) ester instead of (S)-pyrrolidine-1,2-dicarboxylic acid 1-(9H-fluoren-9-ylmethyl) ester in step B.

MS: 478 [M+H]+, 500 [M+Na]+ HPLC: 5.22 minutes

Example 28

(2S,4R)-4-Phenyl-pyrrolidine-1,2-dicarboxylic acid 1-[(naphthalen-1-ylmethyl)-amide] 2-(phenethyl-amide)

The title compound is prepared analogously as described in example 26 using (2S,4R)-4-phenyl-pyrrolidine-1,2-dicarboxylic acid 1-(9H-fluoren-9-ylmethyl) ester instead of (S)-pyrrolidine-1,2-dicarboxylic acid 1-(9H-fluoren-9-ylmethyl) ester in step B.

MS: 478 [M+H]+, 500 [M+Na]+ HPLC: 5.13 minutes

Example 29

(S)-3,4-Dihydro-1H-isoquinoline-2,3-dicarboxylic acid 2-[(naphthalen-1-ylmethyl)-amide] 3-(phenethyl-amide)

The title compound is prepared analogously as described in example 26 using (S)-3,4-dihydro-1H-isoquinoline-2,3-dicarboxylic acid 2-(9H-fluoren-9-ylmethyl) ester instead of (S)-pyrrolidine-1,2-dicarboxylic acid 1-(9H-fluoren-9-ylmethyl) ester in step B.

MS: 464 [M+H]+, 486 [M+Na]+ HPLC: 5.04 minutes

Example 30

(S)-Piperidine-1,2-dicarboxylic acid 1-[(naphthalen-1-ylmethyl)-amide] 2-(phenethyl-amide)

The title compound is prepared analogously as described in example 26 using (S)-piperidine-1,2-dicarboxylic acid 1-(9H-fluoren-9-ylmethyl) ester instead of (S)-pyrrolidine-1,2-dicarboxylic acid 1-(9H-fluoren-9-ylmethyl) ester in step B.

MS: 438 [M+Na]+ HPLC: 4.77 minutes

Example 31

(S)-Pyrrolidine-1,2-dicarboxylic acid 2-{[2-(4-methoxy-phenyl)-ethyl]-amide} 1-[(naphthalen-1-ylmethyl)-amide]

The title compound is prepared analogously as described in example 26 using 2-(4-Methoxy-phenyl)-ethylamine instead of phenethylamine in step A.

MS: 432 [M+H]+, 454 [M+Na]+ HPLC: 4.23 minutes

Example 32

(S)-Pyrrolidine-1,2-dicarboxylic acid 2-benzylamide 1-[(naphthalen-1-ylmethyl)-amide]

The title compound is prepared analogously as described in example 26 using benzylamine instead of phenethylamine in step A.

MS: 388 [M+H]+, 410 [M+Na]+ HPLC: 4.11 minutes

Example 33

(S)-Pyrrolidine-1,2-dicarboxylic acid 2-cyclohexyl-methyl-amide 1-[(naphthalen-1-ylmethyl)-amide]

The title compound is prepared analogously as described in example 26 using C-cyclohexyl-methylamine instead of phenethylamine in step A.

MS: 394 [M+H]+, 416 [M+Na]+ HPLC: 4.68 minutes

Example 34

(S)-Pyrrolidine-1,2-dicarboxylic acid 2-[(3-methyl-butyl)-amide] 1-[(naphthalen-1-ylmethyl)-amide]

The title compound is prepared analogously as described in example 26 using 3-methyl-butylamine instead of phenethylamine in step A.

MS: 368 [M+H]+, 390 [M+Na]+ HPLC: 4.34 minutes

Example 35

(S)-Pyrrolidine-1,2-dicarboxylic acid 1-[(naphthalen-1-ylmethyl)-amide] 2-[(tetrahydro-furan-2-ylmethyl)-amide]

The title compound is prepared analogously as described in example 26 using C-(tetrahydro-furan-2-yl)-methylamine instead of phenethylamine in step A.

MS: 382 [M+H]+, 404 [M+Na]+ HPLC: 3.47 minutes

Example 36

(1S,2S,5R)-3-aza-bicyclo[3.1.0]hexane-2,3-dicarboxylic acid 3-[(7-chloro-naphthalen-1-ylmethyl)-amide] 2-[(pyridin-3-ylmethyl)-amide]

The title compound is prepared analogously as described in example 1 step F using (1S,2S,5R)-3-aza-bicyclo[3.1.0]hexane-2-carboxylic acid (pyridin-3-ylmethyl)-amide instead of (S)-pyrrolidine-2-carboxylic acid and C-(7-chloro-naphthalen-1-yl)-methylamine instead of C-(7-triethylsilanyleethynylnaphthalen-1-yl)-methylamine. The title compound is dissolved in CH₂Cl₂ and treated with polymer bound benzylamine.

MS: 434.9 [M+H]+, 432.8 [M−H]− TLC, Rf (CH₂Cl₂/MeOH/NH₄OH 95/5/0.5) 0.10

Example 37

(1S,2S,5R)-3-aza-bicycic[3.1.0]hexane-2,3-dicarboxylic acid 3-[(7-chloro-naphthalen-1-ylmethyl)-amide] 2-{[2-(4-methoxy-phenyl)-ethyl]-amide}

The title compound is prepared analogously as described in example 1 step F using (1S,2S,5R)-3-aza-bicyclo[3.1.0]hexane-2-carboxylic acid [2-(4-methoxy-phenyl)-ethyl]-amide instead of (S)-pyrrolidine-2-carboxylic acid and C-(7-chloronaphthalen-1-yl)-methylamine instead of C-(7-triethylsilanyleethynylnaphthalen-1-yl)-methylamine. The title compound is dissolved in CH₂Cl₂ and treated with polymer bound benzylamine.

MS: 477.9 [M+H]+, 475.8 [M−H]− TLC, Rf (CH₂Cl₂/MeOH/NH₄OH 95/5/0.5) 0.40

TABLE 1

A compound of formula

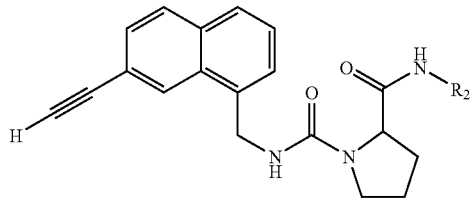

wherein R₂ is as defined in Table 1.

| Example No. | R₂ |
|---|---|
| 1 | 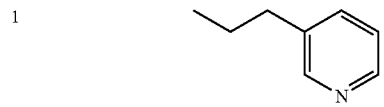 |
| 2 | 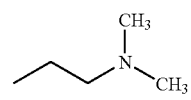 |
| 3 | 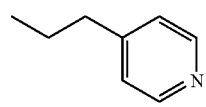 |
| 4 | 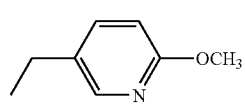 |

TABLE 1-continued

A compound of formula wherein R₂ is as defined in Table 1.

| Example No. | R₂ |
|---|---|
| 5 | N-CH₃ piperidine with ethyl |
| 6 | ethyl-phenyl-piperazine-N-CH₃ |
| 7 | ethyl-phenyl-CH₂-morpholine |
| 8 | —CH₃ |
| 9 | propyl-piperazine-benzyl |
| 10 | propyl-O-CH₃ |
| 11 | ethyl-pyridin-3-yl |
| 12 | ethyl-pyridin-4-yl |
| 13 | propyl-piperazine-N—CH₃ |

TABLE 1-continued
A compound of formula
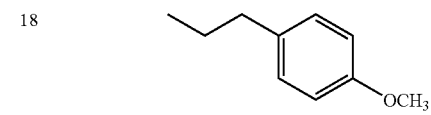
wherein R₂ is as defined in Table 1.
| Example No. | R₂ |
|---|---|
| 18 | 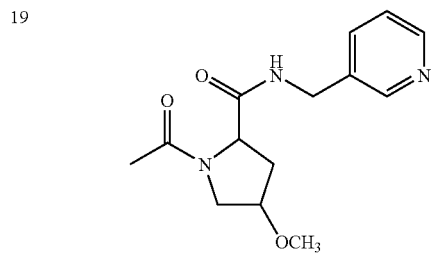 |
TABLE 2
A compound of formula
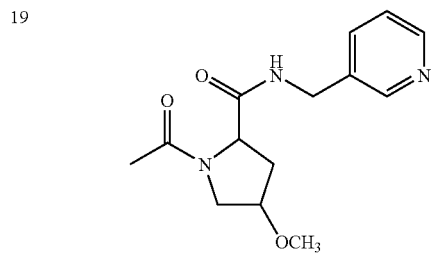
wherein Y is as defined in Table 2.
| Example No. | Y |
|---|---|
| 19 | 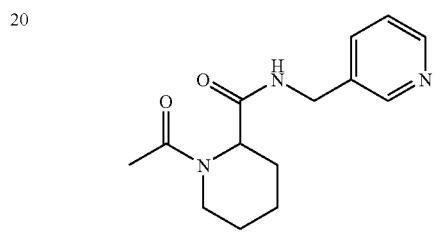 |
| 20 | 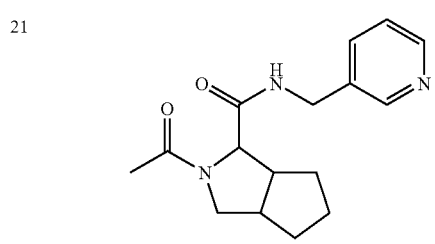 |
| 21 | 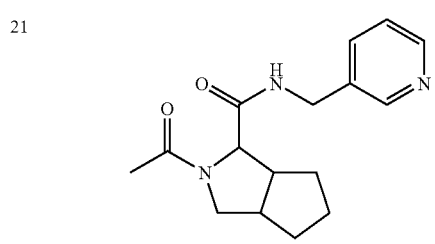 |
TABLE 2-continued
A compound of formula
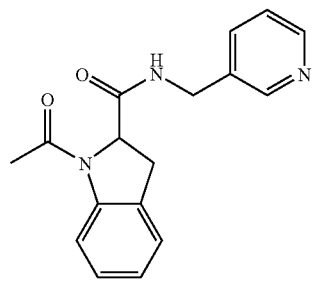
wherein Y is as defined in Table 2.
| Example No. | Y |
|---|---|
| 22 | 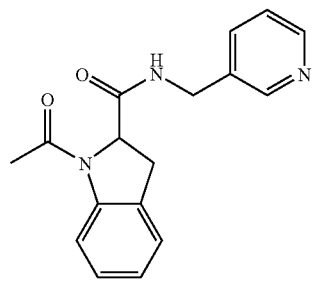 |
| 23 | 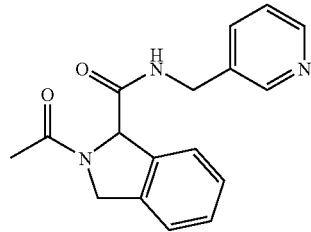 |
| 24 | 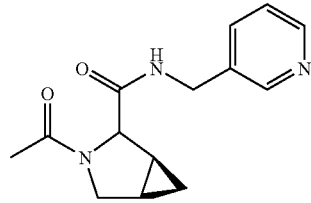 |
| 25 | 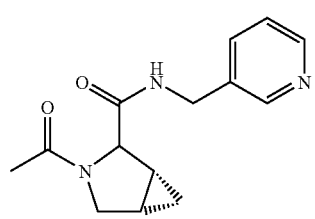 |

TABLE 3
A compound of formula
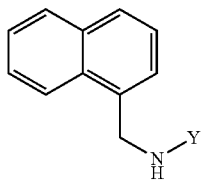
wherein Y is as defined in Table 3.
| Example No. | Y |
|---|---|
| 26 | 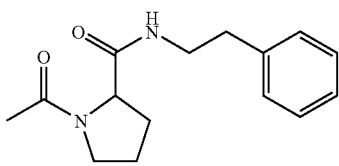 |
| 27 | 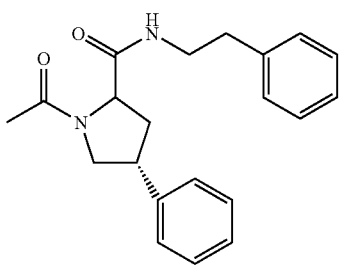 |
| 28 | 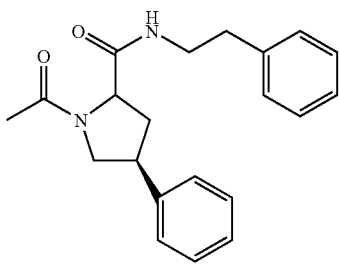 |
| 29 | 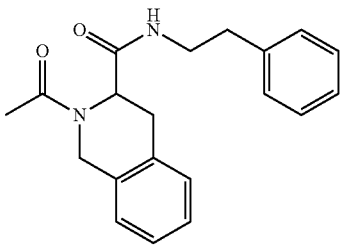 |
| 30 | 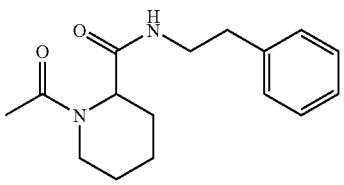 |
| 31 | 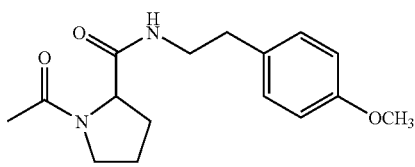 |

TABLE 3-continued
A compound of formula
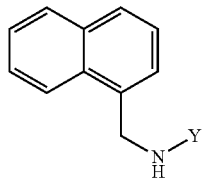
wherein Y is as defined in Table 3.
| Example No. | Y |
|---|---|
| 32 | 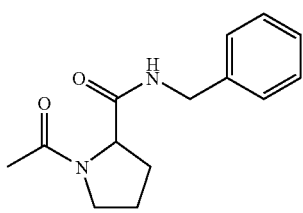 |
| 33 | 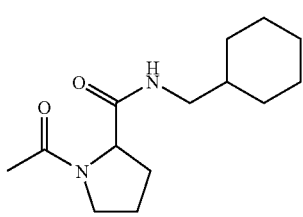 |
| 34 | 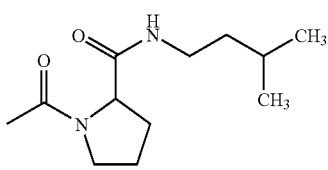 |
| 35 | 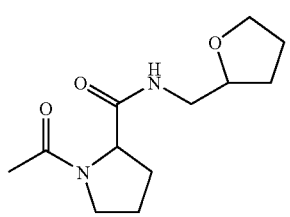 |
Example No. 14 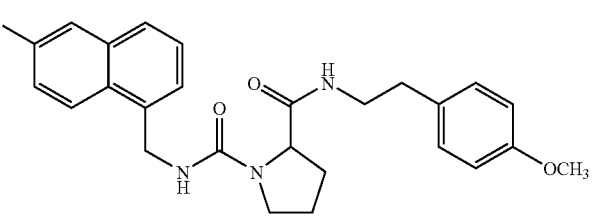
Example No. 15 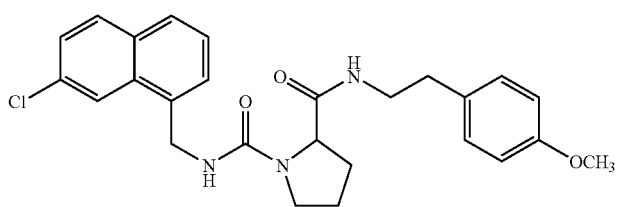

TABLE 3-continued
A compound of formula
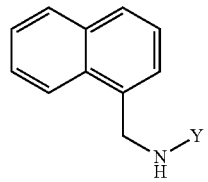
wherein Y is as defined in Table 3.
| Example No. | Y |
|---|---|
| Example No. 16 | 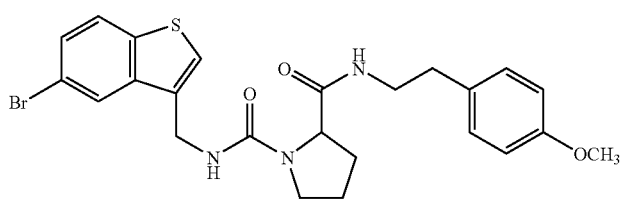 |
| Example No. 17 | 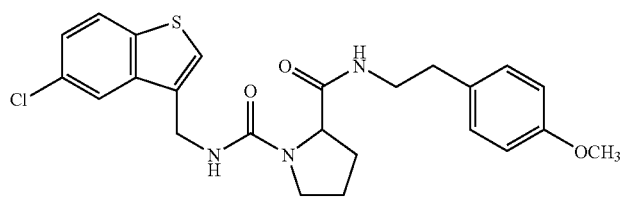 |
| Example No. 36 | 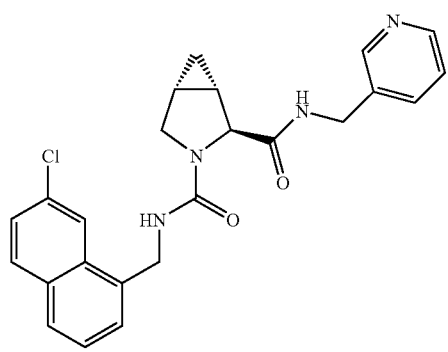 |
| Example No. 37 | 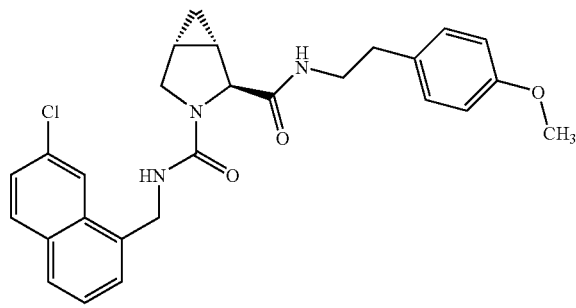 |

Example 38

A) Test on Recovery of Skin Barrier Disruption in Mice

Method: Skin barrier disruption is achieved in groups of hairless SKH1 mice with repeated stripping of the skin with S-Sqame® skin sampling disks. The procedure is completed when transepidermal water loss (TEWL) achieved ≧40 mg/cm²/h. TEWL is assessed with a Tewameter TM210 (Courage Khazaka, Cologne, Del.). Immediately after barrier disruption 30 µl of the compound of example 37(=Test compound 1) is applied at 10 mM concentration. Controls animals are treated similarly with the solvent (EtOH/propylene glycol, 3/7 (v/v)) alone. TEWL is measured before, immediately after, and at 3 hrs after barrier disruption. In each animal, the percentage recovery is calculated using the formula: (1−[TEWL at 3 hrs−base line TEWL]/[TEWL immediately after stripping−base line TEWL])×100%.

Table 1 shows that a single application of the Test compound 1 accelerates barrier repair by 65-76% compared to repair in mice treated with the solvent alone (p<0.001).

TABLE 1

| Animals | % Recovery in barrier disruption Mean (SD values), n: 8 or 12 animals per group) |
|---|---|
| Treated with Test compound 1 at 10 mM | 76 (3.3)*** |
| Treated with solvent alone | 56 (7.1) |

**p < 0.001 vs solvent control

B) Test on Anti-Inflammatory Activity in Murine Model of Irritant Contact Dermatitis (ICD)

Method: Crl:NMRI mice are challenged with 10 µl 0.005% phorbol 12-myristat-13-acetate (TPA) on the inner surface of the right ear. The unchallenged left ears serve as normal controls and dermatitis is evaluated from the difference in auricular weight (taken as a measure of inflammatory swelling) 6 hours after the challenge. The animals are treated topically with 10 µl of the test compound 1 or the solvent 30 minutes prior to the challenge. The efficacy of the treatment is calculated as the percentage inhibition of inflammatory auricular swelling relative to animals treated with the vehicle alone.

Table 2 shows that TPA-induced irritant dermatitis is concentration-dependently inhibited. The inflammatory swelling is inhibited by 54-73% at 20 mM concentrations; no statistically significant inhibition was observed at 3 mM.

TABLE 2

| Concentration | % Inhibition inflammatory swelling [Mean ± SEM values$^{(n\ animals)}$] Test compound 1 |
|---|---|
| 30 mM | 73 ± 7.0***$^{24}$ |
| 10 mM | 41 ± 5.3***$^{24}$ |
| 3 mM | 13 ± 6.1$^{ns24}$ |

***p < 0.001,
**p < 0.01 vs controls,
$^{ns}$not statistically significant (p > 0.05)

C) Test on Anti-Inflammatory Activity in Swine Model of Allergic Contact Dermatitis (ACD)

Eight days before the elicitation of the ACD, 500 µl of 10% 2,4-dinitrofluorobenzene (DNFB, dissolved in DMSO/acetone/olive oil [1/5/3, v/v/v]) are applied epicutaneously in divided volumes onto the basis of both ears and onto both groins (100 µl/site) for sensitization. The challenge reactions are elicited with 15 µl of DNFB (1.0%) on contralateral test sites (each 7 cm² in size) of the shaved dorsolateral back. For treatment, the compound of example 11 (=Test compound 2) and the placebo (solvent only) are applied contralaterally to 2 test sites in each animal 0.5 and 6 hours after the challenge. The test sites are clinically examined 24 hours after the challenge when inflammation peaks. The changes are scored on a scale from 0 to 4 (Table XY), allowing a combined maximal score of 12 per designated site. Skin reddening is measured reflectometrically using a* values (see Table 3)

TABLE 3

Scoring of clinical signs of test sites affected with ACD

| Score | Erythema/Intensity | Erythema/Extent | Induration |
|---|---|---|---|
| 0 | absent | absent | absent |
| 1 | scarcely visible | small spotted | scarcely palpable |
| 2 | mild | large spotted | mild hardening |
| 3 | pronounced | confluent | pronounced hardening |
| 4 | severe (or livid discoloring) | homogenous redness | pronounced and elevated hardening |

Table 4 summarizes the results of the treatment of test sites affected with ACD: A 1% solution of the Test compound 2 inhibits clinical inflammatory changes by 42% (p<0.01) and measured skin redness by 32 (p<0.05)

TABLE 4

| Test sites | Clinical score (Mean, SD, n: 8+) | A* value (Mean, SD, n: 8+) |
|---|---|---|
| Treated with 1% Test compound 2 | 4.1 (1.3) | 7.7 (1.6) |
| Treated with placebo (solvent) | 7.1 (1.8) | 11.7 (2.3) |
| Inhibition vs placebo-treated sites | 42.4 (11.1) | 31.9 (18.4) |

+: 2 test sites each in 4 animals

REFERENCES

1 Skytt A., Stromqvist M. and Egelrud T. (1995) Primary substrate specificity of recombinant human stratum corneum chymotryptic enzyme. *Biochem Biophys Res Commun* 211, 586-589.

2 Egelrud T. (1993) Purification and preliminary characterization of stratum corneum chymotryptic enzyme: a proteinase that may be involved in desquamation. *J. Invest. Dermatol.* 101, 200-204.

3 Yousef G. M., Scorilas A., Magklara A., Soosaipillai A. and Diamandis E. P. (2000) The KLK7 (PRSS6) gene, encoding for the stratum corneum chymotryptic enzyme is a new member of the human kallikrein gene family—genomic characterization, mapping, tissue expression and hormonal regulation. *Gene* 254, 119-128.

4 Simon M., Jonca N., Guerrin M., Haftek M., Bernard D., Caubet C., Egelrud T., Schmidt R. and Serre G. (2001) Refined characterization of corneodesmosin proteolysis during terminal differentiation of human epidermis and its relationship to desquamation. *J. Biol. Chem.* 276(23), 20292-20299.

5 Caubet C., Jonca N., Brattsand M., Guerrin M., Bernard D., Schmidt R., Egelrud T., Simon M. and Serre G. (2004)

Degradation of corneodesmosome proteins by two serine proteases of the kallikrein family, SCTE/KLK5/hK5 and SCCE/KLK7/hK7. *J. Invest. Dermatol.* 122, 1235-1244.

6 Brattsand M., Stefansson K., Lundh C., Haasum Y. and Egelrud T. (2005) A proteolytic cascade of kallikreins in the stratum corneum. *J. Invest. Dermatol.* 124(1), 198-203.

7 Hachem J. P., Man M. Q., Crumrine D., Uchida Y., Brown B. E., Rogiers V., Roseeuw D., Feingold K. R. and Elias P. M. (2005) Sustained serine proteases activity by prolonged increase in pH leads to degradation of lipid processing enzymes and profound alterations of barrier function and stratum corneum integrity. *J. Invest. Dermatol.* 125(3), 510-520.

8 Nylander-Lundqvist E. and Egelrud T. (1997) Formation of active IL-1β from pro-IL-1β catalyzed by stratum corneum chymotryptic enzyme in vitro. *Acta Derm. Venereol.* 77(3), 203-206.

9 Vasilopoulos Y., Cork M. J., Murphy R., Williams H. C., Robinson D. A., Duff G. W., Ward S. J. and Tazi-Ahnini R. (2004) Genetic association between an AACC insertion in the 3'UTR of the stratum corneum chymotryptic enzyme gene and atopic dermatitis. *J. Invest. Dermatol.* 123, 62-66.

10 Schechter N. M., Choi E. J., Wang Z. M., Hanakawa Y., Stanley J. R., Kang Y., Clayman G. L. and Jayakumar A. (2005) Inhibition of human kallikreins 5 and 7 by the serine protease inhibitor lympho-epithelial Kazal-type inhibitor (LEKTI). *Biol. Chem.* 386, 1173-1184.

11 Franzke C. W., Baici A., Bartels J., Christophers E. and Wiedow O. (1996) Antileukoprotease inhibits stratum corneum chymotryptic enzyme—Evidence for a regulative function in desquamation. *J. Biol. Chem.* 271, 21886-21890.

12 Descargues P., Deraison C., Bonnart C., Kreft M., Kishibe M., Ishida-Yamamoto A., Elias P., Barrandon Y., Zambruno G., Sonnenberg A. and Hovnanian A. (2005) Spink5-deficient mice mimic Netherton syndrome through degradation of desmoglein 1 by epidermal protease hyperactivity. *Nat. Genet.* 37(1), 56-65.

13 Walley A. J., Chavanas S., Moffatt M. F., Esnouf R. M., Ubhi B., Lawrence R., Wong K., Abecasis G. R., Jones E. Y., Harper J. I., Hovnanian A. and Cookson W. O. (2001) Gene polymorphism in Netherton and common atopic disease. *Nat. Genet.* 29(2), 175-178.

14 Nishio Y., Noguchi E., Shibasaki M., Kamioka M., Ichikawa E., Ichikawa K., Umebayashi Y., Otsuka F. and Arinami T. (2003) Association between polymorphisms in the SPINK5 gene and atopic dermatitis in the Japanese. *Genes Immun.* 4(7), 515-517.

15 Descargues P., Deraison C., Prost C., Fraitag S., Mazereeuw-Hautier J., D'Alessio M., Ishida-Yamamoto A., Bodemer C., Zambruno G. and Hovnanian A. (2006) Corneodesmosomal cadherins are preferential targets of stratum corneum trypsin- and chymotrypsin-like hyperactivity in Netherton syndrome. *J. Invest. Dermatol.* 126(7), 1622-1632.

16 Hachem J. P., Wagberg F., Schmuth M., Crumrine D., Lissens W., Jayakumar A., Houben E., Mauro T. M., Leonardsson G., Brattsand M., Egelrud T., Roseeuw D., Clayman G. L., Feingold K. R., Williams M. L., Elias P. M. (2006) Serine protease activity and residual LEKTI expression determine phenotype in Netherton syndrome. *J. Invest. Dermatol.* 126(7), 1609-1621.

17 Hansson L., Baeckman A., Ny A., Edlund M., Ekholm E., Hammarstroem B. E., Toernell J., Wallbrandt P., Wennbo H., and Egelrud T. (2002) Epidermal Overexpression of Stratum Corneum Chymotryptic Enzyme in Mice: A Model for Chronic Itchy Dermatitis, *J. Invest. Dermatol.* 118, 444-449.

18 Ny A. and Egelrud T. (2003) Transgenic mice over-expressing a serine protease in the skin: evidence of interferon gamma-independent MHC II expression by epidermal keratinocytes. *Acta Derm. Venereol.* 83, 322-327.

19 Ny A. and Egelrud T. (2004) Epidermal hyperproliferation and decreased skin barrier function in mice overexpressing stratum corneum chymotryptic enzyme. *Acta Derm. Venereol.* 84, 18-22.

20 Ekholm E. and Egelrud T. (1999) Stratum corneum chymotryptic enzyme in psoriasis. *Arch. Dermatol. Res.* 291 (4), 195-200.

21 Otwinowski, Z. and Minor, W. (1997) Processing of X-ray diffraction data collected in oscillation mode. *Methods in Enzymology*, 276, C. W. Carter, Jr. and R. M. Sweet, Eds., Academic Press.

22 Kabsch W. (1993) Automatic Processing of Rotation Diffraction Data from Crystals of Initially Unknown Symmetry and Cell Constants. *J. App. Cryst.* 26, 795-800.

23 Kroemer M., Dreyer M. K. and Wendt K. U. (2004) APRV—a program for automated data processing, refinement and visualization. *Acta Cryst.* D60, 1679-82.

24 Vagin A., and Teplyakov A. (1997) MOLREP: an automated program for molecular replacement. *J. Appl. Cryst.* 30, 1022-1025.

25 Laxmikanthan G., Blaber S. I., Bernett M. J., Scarisbrick I. A., Juliano M. A. and Blaber M. (2005) 1.70 Å X-ray structure of human apo kallikrein 1: structural changes upon peptide inhibitor/substrate binding. *Proteins* 58(4), 802-814.

26 Brünger A. T., Adams P. D., Clore G. M., DeLano W. L., Gros P., Grosse-Kunstleve R. W., Jiang J.-S., Kuszewski J., Nigles M., Pannu N. S., Read R. J., Rice L. M., Simonson T. and Warren G. L. (1998) Crystallography & NMR System: A new software suite for macromolecular structure determination. *Acta Cryst*, D54, 905-921.

27 Johns T. A., Zou J. Y., Cowan S. W. and Kjeldgaard M. (1991) Improved methods for building protein models in electron density maps and the location of errors in these models. *Acta Cryst.*, A47, 110-119.

28 Engh R. A. and Huber R. (1991) Accurate bond and angle parameters for X-ray protein structure refinement. *Acta Cryst.* A47, 392-400.

29 Laskowski R. A., MacArthur M. W., Moss D. S. and Thornton J. M. (1993) PROCHECK: a program to check the stereochemical quality of protein structures. *J. Appl. Cryst.* 26, 238-291.

30 Birktoft J. J., Kraut J. and Freer S. T. (1976) A detailed structural comparison between the charge relay system in chymotrypsinogen and in alpha-chymotrypsin. *Biochemistry* 15(20), 4481-5.

31 Bernett M. J., Blaber S. I., Scarisbrick I. A., Dhanarajan P., Thompson S. M. and Blaber M. (2002) Crystal structure and biochemical characterization of human kallikrein 6 reveals that a trypsin-like kallikrein is expressed in the central nervous system. *J. Biol. Chem.* 277(27), 24562-24570.

32 Kishi T., Kato M., Shimizu T., Kato K., Matsumoto K., Yoshida S., Shiosaka S., Hakoshima T. (1999) Crystal structure of neuropsin, a hippocampal protease involved in kindling epileptogenesis. *J. Biol. Chem.* 274, 4220-4224.

33 Debela M., Magdolen V., Schechter N., Valachova M., Lottspeich F., Craik C. S., Choe Y., Bode W. and Goettig P. (2006) Specificity profiling of seven human tissue kallikreins reveals individual subsite preferences. *J. Biol. Chem.* E-PUB.

34 Yamasaki K., Schauber J., Coda A., Lin H., Dorschner R. A., Schechter N. M., Bonnart C., Descargues P., Hovnanian A. and Gallo R. L. (2006) Kallikrein-mediated proteolysis regulates the antimicrobial effects of cathelicidins in skin. *FASEB J.* 2006 October; 20(12):2068-80.

The invention claimed is:

1. A modulator of kallikrein 7 which is a compound of formula

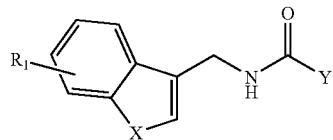

(I)

Or a salt thereof wherein
$R_1$ is cyano, $(C_{1-8})$alkyl, $(C_{2-8})$alkenyl, $(C_{2-8})$alkynyl, halogen, $(C_{1-8})$alkylamino, $(C_{1-8})$alkylamino$(C_{1-8})$alkyl, $(C_{1-8})$alkoxy, or halo$(C_{1-8})$alkyl,
X is CH=CH, NH, N=CH, O or S,
Y is a group of formula

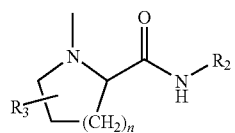

(II)

wherein
the N-containing ring system is optionally annelated with $(C_{3-8})$cycloalkyl, $(C_{6-18})$aryl or heterocyclyl having 5 to 6 ring members and 1 to 4 heteroatoms selected from N, O, S,
n is 1, 2 or 3,
$R_2$ is
$(C_{1-8})$alkyl, $(C_{1-8})$alkylamino, $(C_{1-8})$alkylamino$(C_{1-8})$alkyl, di$(C_{1-8})$alkylamino$(C_{1-8})$alkyl, halo$(C_{1-8})$alkyl, $(C_{1-8})$alkoxy, $(C_{1-8})$alkoxy$(C_{1-8})$alkyl, or
$(CH_2)_m$—Z, wherein Z is unsubstituted or substituted $(C_{3-8})$cycloalkyl, $(C_{6-18})$aryl or heterocyclyl having 5 to 6 ring members and 1 to 4 heteroatoms selected from N, O, S; and
m is 1 or 2,
$R_3$ is hydrogen, $(C_{1-8})$alkyl, $(C_{1-8})$alkoxy, $(C_{6-18})$aryl or heterocyclyl having 5 to 6 ring members and 1 to 4 heteroatoms selected from N, O, S.

2. A compound according to claim 1, wherein
$R_1$ is ethynyl, chloro or bromo,
X is CH=CH or S,
Y is a group of formula (II), wherein
the N-containing ring system is optionally annelated with cyclopropyl, cyclopentyl or phenyl,
n is 1 or 2,
$R_2$ is $(C_{1-8})$alkyl, $(C_{1-4})$alkylamino, di$(C_{1-4})$alkylamino$(C_{1-4})$alkyl, $(C_{1-4})$alkoxy, $(C_{1-4})$alkoxy$(C_{1-4})$alkyl or
a group $(CH_2)_m$—Z, wherein Z is unsubstituted cyclohexyl, unsubstituted phenyl, phenyl substituted by $(C_{1-4})$alkoxy, phenyl substituted by heterocyclyl having 6 ring members and 1 or 2 heteroatoms selected from N, O, or
unsubstituted or substituted heterocyclyl having 6 ring members and 1 or 2 heteroatoms selected from N, O;
m is 1 or 2,
$R_3$ is hydrogen or $(C_{1-4})$alkoxy.

3. A compound of claim 1, wherein
Y is a group of formula (II), wherein
the N-containing ring system is optionally annelated with cyclopropyl, cyclopentyl or phenyl,
$R_2$ is methyl, dimethylaminoethyl, methoxyethyl, or
a group $(CH_2)_m$—Z, wherein Z is unsubstituted cyclohexyl, unsubstituted phenyl, phenyl substituted by methoxy, piperazinyl or morpholinyl;
pyridinyl, piperidinyl, tetrahydrofuranyl, unsubstituted piperazinyl or piperazinyl substituted by methyl or phenyl,
and m, n, $R_1$, $R_3$ and X are as defined in claim 1.

4. A compound of claim 1 in the form of a salt.

5. A pharmaceutical composition comprising a compound of claim 1 in association with at least one pharmaceutical excipient.

6. A method of treating, with the exception of prophylaxis, a disorder mediated by kallikrein-7 activity, which treatment comprises administering to a subject in need of such treatment an effective amount of a compound of claim 1 wherein said disorder which is mediated by kallikrein-7 activity is selected from the group consisting of keloids, hypertrophic scars, acne, atopic dermatitis, psoriasis, pustular psoriasis, rosacea, Netherton's syndrome or other pruritic dermatoses such as prurigo nodularis, unspecified itch of the elderly, aged skin, inflammatory bowel disease, Crohn's disease, and pancreatitis.

* * * * *